US007582475B2

(12) United States Patent
Horanyi et al.

(10) Patent No.: US 7,582,475 B2
(45) Date of Patent: Sep. 1, 2009

(54) VECTORS AND METHODS FOR HIGH THROUGHPUT CO-EXPRESSION

(75) Inventors: Peter S. Horanyi, Athens, GA (US); James Griffith, Watkinsville, GA (US); Bi-Cheng Wang, Athens, GA (US); Francis E. Jenney, Jr., Hoschton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 235 days.

(21) Appl. No.: 11/327,200

(22) Filed: Jan. 6, 2006

(65) Prior Publication Data

US 2006/0183193 A1 Aug. 17, 2006

Related U.S. Application Data

(60) Provisional application No. 60/756,028, filed on Jan. 4, 2006, provisional application No. 60/642,310, filed on Jan. 7, 2005, provisional application No. 60/642,309, filed on Jan. 7, 2005.

(51) Int. Cl.
*C12Q 1/68* (2006.01)
*C12P 19/34* (2006.01)
*C12N 15/00* (2006.01)
*C07H 21/02* (2006.01)
*C07H 21/04* (2006.01)

(52) U.S. Cl. .................. 435/320.1; 435/6; 435/91.1; 435/252.3; 435/455; 536/23.1; 536/23.7; 536/24.5

(58) Field of Classification Search .................. 435/6, 435/91.1, 91.31, 455, 462, 320.1, 252.3; 536/23.1, 23.7, 24.5
See application file for complete search history.

(56) References Cited

U.S. PATENT DOCUMENTS

| | | | |
|---|---|---|---|
| 4,952,496 | A | 8/1990 | Studier et al. |
| 5,021,344 | A | 6/1991 | Armau et al. |
| 5,118,620 | A | 6/1992 | Armau et al. |
| 5,284,933 | A | 2/1994 | Döbeli et al. |
| 5,310,663 | A | 5/1994 | Döbeli et al. |
| 5,693,489 | A | 12/1997 | Studier et al. |
| 5,869,320 | A | 2/1999 | Studier et al. |
| 5,888,732 | A | 3/1999 | Hartley et al. |
| 6,143,557 | A | 11/2000 | Hartley et al. |
| 6,171,861 | B1 | 1/2001 | Hartley et al. |
| 6,270,969 | B1 | 8/2001 | Hartley et al. |
| 6,277,608 | B1 | 8/2001 | Hartley et al. |
| 6,720,140 | B1 | 4/2004 | Hartley et al. |
| 2005/0069929 | A1* | 3/2005 | Chesnut et al. ............. 435/6 |
| 2007/0196838 | A1* | 8/2007 | Chesnut et al. ............. 435/6 |

FOREIGN PATENT DOCUMENTS

EP 282042 9/1988

OTHER PUBLICATIONS

Ambion, the RNA Company. Ambion's Online Appendix. The mechanism of RNA Interference (RNAi). Retrieved from the Internet on Jan. 6, 2006. Retrieved from http://www.ambion.com/techlib/append/RNAi_mechanism.html, 1 page.

Ambion, the RNA Company. "RNA Interference and Gene Silencing—History and Overview," Retrieved from the Internet on Jan. 6, 2006. Retrieved from http://www.ambion.com/techlib/hot-topics/mai/mai_may2002_print.html 8 pages.

Ambion, the RNA Company. "RNAi: A "How To" for New Users," Retrieved from the internet on Jan. 6, 2006. Retrieved from http://www.ambion.com/techlib/tn/115/11.html 5 pages.

Apfeld et al., "Cell Nonautonomy of *C. elegans* daf-2 Function in the Regulation of Diapause and Life Span," 1998. *Cell.* 95:199-210.

Ausubel et al., eds, (Current Protocols in Molecular Biology, Green Publishing Assoc., Inc., John Wiley & Sons, Inc., NY 1994). 12 pages.

Bass, B., "The Short Answer," 2001. *Nature*, 411:428-429.

Benakis. "Artemisin and derivatives: recent progress in malaria treatment," Indian Medlars Centre. Laboratory of Drug Metabolism, Dept. of Pharm., Univ. Medical Centre, Geneva, Switzerland. Journal of Parasitic Diseases. 1996. 10(1):65. Retrieved from the Internet on Mar. 9, 2006. Retrieved from http://medind.nic.in/imvw/imvw13236.html 1 page.

Bernard et al., "The F plasmid CcdB protein induces efficient ATP-dependent DNA cleavage by gyrase," 1993. *J. Mol. Biol.* 234:534-541.

Bernard et al., "The 41 Carboxy-terminal Residues of the Mini-F Plasmid CcdA Protein are sufficient to Antagonize the Killer Activity of the CcdB protein," 1991. *Mol. Gen. Genet.* 226:297-304.

Brenner, "Target Selection for Structural Genomics," 2000. *Nat Struct Biol.* 7 Suppl:967-969.

Brenner et al., "Expectations from Structural Genomics," 2000. *Protein Sci.* 9:197-200.

Burley, "An Overview of Structural Genomics," 2000. *Nat Struct Biol.* 7 Suppl:932-934.

Campbell et al., "A monomeric red fluorescent protein," 2002. *Proc. Natl. Acad. Sci. USA*, 99:7877-7882.

Cayla Transferring genes. Product Data Sheet for Zeocin™. Catalog #ZEOCL0001, ZEOCL0005, ZEOCP0001, ZEOCP0005. 1 page.

Cayla, Zeocin/Phleomycin Resistance. Retrieved from the internet on Mar. 11, 2005. Retrieved from http://www.cayla.com/support/datasheets/shble.htm. 2 pages.

Cayla, Transferring genes. Phleomycin. Catalog #PHLEP0250, PHLEP0500, PHLEP0001, PHLEL0100, PHLEL0500. 2 pages.

Celestino et al., "Update of microbial genome programs for bacteria and archaea," 2004. *Gen Mol.* Res. 3:421-431.

Chance et al., "Structural genomics: A pipeline for providing structures for the biologist," 2002. *Protein Science*, 11:723-738.

(Continued)

*Primary Examiner*—Jane Zara
(74) *Attorney, Agent, or Firm*—Mueting Raasch & Gebhardt, P.A.

(57) ABSTRACT

The present invention includes vectors and methods for high throughput co-expression.

21 Claims, 129 Drawing Sheets

OTHER PUBLICATIONS

Chayen, "Protein crystallization for genomics: throughput versus output," 2003. *J. Struct Funct Genomics*, 4:115-120.

Cherry et al., "Genetic and physical maps of *Saccharomyces cerevisiae*," 1997. *Nature*, 387(6632 Suppl):67-73.

Christendat et al., "Structural proteomics of an archaeon," 2000. *Nat Struct Biol*, 7:903-909.

Clontech. Innovative Tools to Accelerate Discovery. Living Colors® User Manual. PT2040-1 (PR1Y691). Published Nov. 26, 2001. 47 pages.

Collins et al., "A Vision for the Future of Genomics Research, *A blueprint for the genomic era*," 2003. *Nature*, 422:835-847.

Cormack et al., "FACS-optimized mutants of the green fluorescent protein (GFP)," 1996, *Gene*, 173:33-38.

Crabtree et al., "Facile and Gentle Method for Quantitative Lysis of *Escherichia coli* and *Salmonella typhimurium*," 1984. *J. Bact.*, 158:354-356.

Cuff et al., "Jpred: a consensus secondary structure prediction server," 1998. *Bioinformatics Applications Note*, 14:892-893.

Dolinski et al., "Changing perspectives in yeast research nearly a decade after the genome sequence," 2005. *Genome Research*, 15(12):1611-1619.

Drocourt et al., "Cassettes of the *Streptoalloteichus hindustanus* ble gene for transformation of lower and hiogher eukaryotes to phleomycin resistance," 1990. *Nucleic Acids Res.*, 18:4009.

Elshorst et al., "NMR solution structure of a complex of calmodulin with a binding peptide of the Ca2+ pump," 1999. *Biochemistry*, 38(38):12320-12332.

Facts on Acts. Artemisinin-Based Combination Therapies. Jan. 2006 Update. World Health Organization. 4 pages.

Falconer et al., "Chemical Treatment of *Escherichia coli*: 1. Extraction of Intracellular Protein from Uninduced Cells," 1997. *Biotechnol. Bioengin.* 53:453-458.

Ferreira et al., "Distribution of Artemisinin in *Artemisia annua*," 1996. Distribution of artemisinin in *Artemisia annua*. p. 579-584. J. Janick (ed.), Progress in New Crops. ASHS Press, Arlington, VA. Retrieved from the internet on Mar. 9, 2006. Retrieved from http://www.hort/purdue.edu/newcrop/proceedings1996/v3-578.html. 12 pages.

Fire et al., "Potent and specific genetic interference by double-stranded RNA in *Caenorhabditis elegans*," 1998. *Nature.* 391:806-811.

Gateway Technology Manual, Version E, updated Sep. 22, 2003; available on the wordwide web at invitrogen.com/content/sfs/manuals/gatewayman.pdf.

Gonczy et al., "Functional genomic analysis of cell division in *C. elegans* using RNAi of genes on chromosome III," 2000. *Nature*, 408(6810):331-336.

Hartley et al., "DNA Cloning Using In Vitro Site-Specific Recombination," 2000. *Genome Res.* 10:1788-1795.

Henricksen et al., "Recombinant Replication Protein A: Expression, Complex Formation, and Functional Characterization," 1994. *J. Biol. Chem*, 269:11121-11132.

Invitrogen. "Invitrogen Provides the NIH Mammalian Gene Collection with Open Access to Gateway and Other Cloning Technologies: Innovative Move will Benefit Researchers Worldwide," Retrieved from the internet on Mar. 11, 2005. Retrieved from http://phx.corporate-ir.net/phoenix.zhtml?c=61498&p=irol-newsArticle_print&ID=523210. 2 pages.

Invitrogen. "Overview of Gateway® Technology," Retrieved from the Internet on Jul. 7, 2005. Retrieved from https://catalog.invitrogen.com/index.cfm?fuseaction=viewCatalog.viewProductDetails &product description. 2 pages.

Invitrogen life technologies. Letter to Global Life Science Research Community. Re: "Gateway® Clone Distribution Policy," Oct. 29, 2003. 4 pages.

Invitrogen life technologies. "Champion™ pET104 BioEase™ Gateway® Expression System, For Cloning and Expression of biotinylated fusion proteins in *E. coli*," Catalog No. K104-01, Version C, Mar. 15, 2004, 25-0472. 36 pages.

Invitrogen Catalog # 11828-029. "Gateway® Vector Conversion System with One Shot® ccdB Survival™ Competent Cells," Accessible at www.invitrogen.com/content/sfs/manuals/gatewayvectorconversion_ccdbsurvival_man.pdf Invitrogen Life Technologies Instruction Manual. Version A. Jun. 14, 2004.

Kamath et al., "Genome-wide RNAi screening in *Carnorhabditis elegans*," 2003. *Methods*. 30:313-321.

Kessler et al., "Study of Calmodulin Binding to the Alternatively Spliced C-Terminal Domain of the Plasma Membrane $Ca^{2+}$ Pump," 1992. *Biochemistry*, 31:11785-11792.

Landy, "Dynamic, Structural, and Regulatory Aspects of λ Site-Specific Recombination," 1989. *Annu Rev Biochem*, 58:913-949.

Lesley et al., "Structural genomics of the Thermotoga maritima proteome implemented in a high-throughput structure determination pipeline," 2002. *Proc. Natl. Acad. Sci. USA* 99:11664-11669.

Li et al., "Coexpression of nuclear receptor partners increses their solubility and biological activities," 1997. *Proc Natl Acad Sci*, USA, 94:2278-2283.

Lindblad-Toh et al., "Genome sequence, comparative analysis and haplotype structure of the domestic dog," 2005. *Nature*, 438:803-819.

Liu et al., "The high-throughput protein-to-structure pipeline at SECSG," Acta Cryst., 2005, 61:679-684.

Machalek, "From Genes to Proteins: NIGMS Catalogs the Shapes of Life,"NIH Record, Feb. 2001. Retrieved from the wordlwide web at nigms.nih.gov/psi/ and resb.org/pdb/strucgen.html#Wordwide.

Matz et al., "Fluroescent proteins from nonbioluminescent Anthozoa species," 1999. *Nat. Biotechnol*. 17:969-973.

Nagai et al., "A variant of yellow fluorescent protein with fast and efficient maturation for cell-biological applications," 2002. *Nat. Biotechnol.* 20:87-90.

National Human Genome Research Institute. News Release. "International Consortium Completes Human Genome Project," Apr. 14, 2003. Retrieved from the Internet on Dec. 14, 2005. Retrieved from http://www.genome.gov.pfv.cfm?pageID=11006929 5 pages.

"The map-based sequence of the rice genome," 2005. *Nature*, 436:793-800.

Novagen 2004/2005 Catalog. Title page, Table of Contents. Protein Expression, Prokaryotic Expression: Coexpression. p. 207.

"Novagen: TB392: pCDF-1b Vector Map," 3 pages.

"Novagen: TB336: pACYC Duet™-1 Vector Map," Retrieved from the Internet on May 10, 2006. Retrieved from http://www.emdbiosciences.com/product/print/TB336?x=7&y=8. 3 pages.

"Novagen: TB401:pRSF-1 And pCDF-1 Vectors for Coexpression." Retrieved from the Internet on May 10, 2006. Retrieved from http://www.emdbiosciences.com/product/print/TB401?x=7&y=9. 11 pages.

Novina et al., "The RNAi revolution," 2004. *Nature*. 430:161-164.

Norvell et al., "Structural genomics programs at the US National Institute of General Medical Sciences," 2000. *Nat. Struct. Biol.* 7 Suppl:931.

"Protein Structure Initiative—*Better Tools and Better Knowledge for Structural Genomics*" Retrieved from the Internet on Dec. 6, 2005. Retrieved from http://www.nigms.nih.gov/Initiatives/PSI/.1 page.

Rost, "Marrying structure and genomics," 1998. *Structure*, 6:259-263.

Rual et al., "Toward improving *Caenorhabditis elegans* Phenome Mapping with and ORFeome-based RNAi Library," 2004. *Genome Res.* 14:2162-2168.

Rual et al., "ORFeome projects: gateway between genomics and omics," 2004. *Curr Opin Chem Biol*. 8(1):20-5, 2004.

Salmon et al., "The antidote and autoregulatory functions of the F plasmid CcdA protein: a genetic and biochemical survey," 1994. *Mol. Gen. Genet*. 244:530-538.

Salwinski et al., "The Database of Interacting Proteins: 2004 update," 2004. *Nucleic Acids Research*, vol. 32, Database Issue D449-D451.

Sambrook et al., *Molecular Cloning: A Laboratory Manual*, 2001. Cold Spring Harbor Laboratory Press, Cold Spring Harbor, NY. 22 pages.

Sasaki et al., "Evidence for high specificity and efficiency of multiple recombination signals in mixed DNA cloning by the multisite gateway system," 2004. *J. Biotechnol*. 107:233-243.

Sasaki et al., "Multi-gene gateway clone design for expression of multiple heterologous genes in living cells: Eukaryotic clones containing two and three ORF multigene cassettes expressed from a single promotoer," 2005. *J. Biotechnol.*, doi:10.1016/j.jbiotec.2005.02.022.

Sharp., "RNA Interference—2001" 2001. *Genes Dev.* 15:485-490.

Silva et al., "RNA-interference-based functional genomics in mammalian cells: reverse genetics coming of age," 2004. *Oncogene.* 23:8401-8409.

Sone et al., "Multi-gene gateway clone design for expression of multiple heterologous genes in living cells: Modular construction of multiple cDNA expression elements using recombinant cloning," 2005. *J. Biotechnol.* Jun. 24 (doi: 10,1016/jbiotec.2005.02.021).

Sorenson et al., "Advanced genetic strategies for recombinant protein expression in *Escherichia coli*," 2005. *J. Biotechnol.* 115(2):113-128.

Stevens et al., "Global Efforts in Structural Genomics," 2001. *Science*, 194:89-92.

Structural Genomics. Protein Data Bank (PDB), Retrieved from the Internet on Dec. 6, 2005. Retrieved from http://www.rcsb.org/pdb/strucgen.html. 3 pages.

Terskikh et al., "Analysis of DsRed Mutants, Space around the fluorophore accelerates fluorescence development," 2002. *J. Biol. Chem.* 277:7633-7636.

Timmons et al., "Specific interference by ingested dsRNA," 1998. *Nature.* 395:854.

Tsien. "Rosy Dawn for Fluorescent Proteins," 1999. *Nature Biotech.*, 17:956-957.

Uetsuki et al., "Isolation and characterization of the human chromosomal gene for polypeptide chain elongation factor-I alpha," 1989. *J. Biol. Chem.* 264:5791-5798.

Van Haaften et al., "Genomic instability and cancer: scanning the *Caenorhabditis elegans* genome for tumor suppressors," 2004. *Oncogene.* 23:8366-8375.

Vincze et al., "NEBcutter: a program to cleave DNA with restriction enzymes," 2003. *Nucleic Acids Res.* 31:3688-3691.

Walhout et al., "Gateway recombinational cloning: application to the cloning of large numbers of open reading frames or ORFeomes," 2000. *Methods Enzymol.* 328:575-592.

Wang et al., "Visualization of coupled protein folding and binding in bacteria and purification of the heterodimeric complex," 2003. *Proc Natl Acad Sci USA* 100:478-483.

Wang. "Southeast Collaboratory for Structural Genomics (SECSG)." Retrieved from the Internet on Dec. 6, 2005. Retrieved from http://www.nigms.nih.gov/Initiatives/PSI/Centers/SECSG.htm. 2 pages.

Wianny et al., "Specific interference with gene function by double-stranded RNA in early mouse development," 2000. *Nature Cell Biology*, 2:70-75.

Willingham et al., "RNAi and HTS:exploring cancer by systematic loss-of-function," 2004. *Oncogene.* 23:8392-9400.

Yahata et al., "Multi-gene gateway clone design for expression of multiple heterologous genes in living cells: Conditionial gene expression at near physiological levels," 2005. *J. Biotechnol.* 118(2):123-134. Doi:10.1016/j.jbiotec.2005.02.020.

Zhang et al., "Genetically encoded reporters of protein kinase A activity reveal impact of substrate tethering," 2001. *PNAS*, 98:26:14497-15002.

Zhang et al., "An enhanced green fluroescent protein allows sensitive detection of gene transfer in mammalian cells," 1996. *Biochem. Biophys. Res. Commun.* 227:707-711.

Adams et al., "The Southeast Collaboratory for Structural Genomics: A High-Throughput Gene to Structure Factor," 2003. *Acc Chem Res.* 36:191-198.

\* cited by examiner

| Reading Frame Cassette: | A (1711 bp) | B (1713bp) | C.1 (1714 bp) |
|---|---|---|---|
| attR1 site | 4-128 | 5-129 | 6-130 |
| Primer 1 | 163-185 | 164-186 | 165-187 |
| Chloramphenicol resistance gene | 237-896 | 238-897 | 239-919 |
| ccdB gene | 1238-1543 | 1239-1544 | 1239-1544 |
| Primer 2 | 1444-1466 | 1445-1467 | 1445-1467 |
| attR2 site | 1584-1708 | 1585-1709 | 1585-1709 |

| Fig. 3₁ |
|---------|
| Fig. 3₂ |
| Fig. 3₃ |

Fig. 3 pDEST-C1 sequence

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                     NcoI
                    ~~~~~~~
  61 GAGATATACC ATGGCACATC ACCACCACCA TCACGTGGGT ACCGGTTCGA ATGATGACGA
     CTCTATATGG TACCGTGTAG TGGTGGTGGT AGTGCACCCA TGGCCAAGCT TACTACTGCT
 121 CGACAAATCA ACAAGTTTGT ACAAAAAAGC TGAACGAGAA ACGTAAAATG ATATAAATAT
     GCTGTTTAGT TGTTCAAACA TGTTTTTTCG ACTTGCTCTT TGCATTTTAC TATATTTATA
 181 CAATATATTA AATTAGATTT TGCATAAAAA ACAGACTACA TAATACTGTA AAACACAACA
     GTTATATAAT TTAATCTAAA ACGTATTTTT TGTCTGATGT ATTATGACAT TTTGTGTTGT
                            NotI
                           ~~~~~~~~
 241 TATCCAGTCA TATTGGCGGC CGCATTAGGC ACCCCAGGCT TTACACTTTA TGCTTCCGGC
     ATAGGTCAGT ATAACCGCCG GCGTAATCCG TGGGGTCCGA AATGTGAAAT ACGAAGGCCG
                                                  BamHI
                                                 ~~~~~~~
 301 TCGTATAATG TGTGGATTTT GAGTTAGGAT CCGTCGAGAT TTTCAGGAGC TAAGGAAGCT
     AGCATATTAC ACACCTAAAA CTCAATCCTA GGCAGCTCTA AAAGTCCTCG ATTCCTTCGA
 361 AAAATGGAGA AAAAAATCAC TGGATATACC ACCGTTGATA TATCCCAATG GCATCGTAAA
     TTTTACCTCT TTTTTTAGTG ACCTATATGG TGGCAACTAT ATAGGGTTAC CGTAGCATTT
 421 GAACATTTTG AGGCATTTCA GTCAGTTGCT CAATGTACCT ATAACCAGAC CGTTCAGCTG
     CTTGTAAAAC TCCGTAAAGT CAGTCAACGA GTTACATGGA TATTGGTCTG GCAAGTCGAC
 481 GATATTACGG CCTTTTTAAA GACCGTAAAG AAAAATAAGC ACAAGTTTTA TCCGGCCTTT
     CTATAATGCC GGAAAAATTT CTGGCATTTC TTTTTATTCG TGTTCAAAAT AGGCCGGAAA
                                                     EcoRI
                                                    ~~~~~~~
 541 ATTCACATTC TTGCCCGCCT GATGAATGCT CATCCGGAAT TCCGTATGGC AATGAAAGAC
     TAAGTGTAAG AACGGGCGGA CTACTTACGA GTAGGCCTTA AGGCATACCG TTACTTTCTG
 601 GGTGAGCTGG TGATATGGGA TAGTGTTCAC CCTTGTTACA CCGTTTTCCA TGAGCAAACT
     CCACTCGACC ACTATACCCT ATCACAAGTG GGAACAATGT GGCAAAAGGT ACTCGTTTGA
 661 GAAACGTTTT CATCGCTCTG GAGTGAATAC CACGACGATT TCCGGCAGTT TCTACACATA
     CTTTGCAAAA GTAGCGAGAC CTCACTTATG GTGCTGCTAA AGGCCGTCAA AGATGTGTAT
 721 TATTCGCAAG ATGTGGCGTG TTACGGTGAA AACCTGGCCT ATTTCCCTAA AGGGTTTATT
     ATAAGCGTTC TACACCGCAC AATGCCACTT TTGGACCGGA TAAAGGGATT TCCCAAATAA
 781 GAGAATATGT TTTTCGTCTC AGCCAATCCC TGGGTGAGTT TCACCAGTTT TGATTTAAAC
     CTCTTATACA AAAAGCAGAG TCGGTTAGGG ACCCACTCAA AGTGGTCAAA ACTAAATTTG
                                                          NcoI
                                                         ~~~~~~~
 841 GTGGCCAATA TGGACAACTT CTTCGCCCCC GTTTTCACCA TGGGCAAATA TTATACGCAA
     CACCGGTTAT ACCTGTTGAA GAAGCGGGGG CAAAAGTGGT ACCCGTTTAT AATATGCGTT
 901 GGCGACAAGG TGCTGATGCC GCTGGCGATT CAGGTTCATC ATGCCGTTTG TGATGGCTTC
     CCGCTGTTCC ACGACTACGG CGACCGCTAA GTCCAAGTAG TACGGCAAAC ACTACCGAAG
 961 CATGTCGGCA GAATGCTTAA TGAATTACAA CAGTACTGCG ATGAGTGCA GGGCGGGGCG
     GTACAGCCGT CTTACGAATT ACTTAATGTT GTCATGACGC TACTCACCGT CCCGCCCCGC
                                BamHI
                               ~~~~~~~
1021 TAAAGATCTG GATCCGGCTT ACTAAAAGCC AGATAACAGT ATGCGTATTT GCGCGCTGAT
     ATTTCTAGAC CTAGGCCGAA TGATTTTCGG TCTATTGTCA TACGCATAAA CGCGCGACTA
1081 TTTTGCGGTA TAAGAATATA TACTGATATG TACCCGAA GTATGTCAAA AAGAGGTATG
     AAAACGCCAT ATTCTTATAT ATGACTATAC ATATGGGCTT CATACAGTTT TTCTCCATAC
1141 CTATGAAGCA GCGTATTACA GTGACAGTTG ACAGCGACAG CTATCAGTTG CTCAAGGCAT
     GATACTTCGT CGCATAATGT CACTGTCAAC TGTCGCTGTC GATAGTCAAC GAGTTCCGTA
1201 ATATGATGTC AATATCTCCG GTCTGGTAAG CACAACCATG CAGAATGAAG CCCGTCGTCT
     TATACTACAG TTATAGAGGC CAGACCATTC GTGTTGGTAC GTCTTACTTC GGGCAGCAGA
1261 GCGTGCCGAA CGCTGGAAAG CGGAAAATCA GGAAGGGATG GCTGAGGTCG CCCGGTTTAT
     CGCACGGCTT GCGACCTTTC GCCTTTTAGT CCTTCCCTAC CGACTCCAGC GGGCCAAATA
1321 TGAAATGAAC GGCTCTTTTG CTGACGAGAA CAGGGGCTGG TGAAATGCAG TTTAAGGTTT
     ACTTTACTTG CCGAGAAAAC GACTGCTCTT GTCCCCGACC ACTTTACGTC AAATTCCAAA
1381 ACACCTATAA AAGAGAGAGC CGTTATCGTC TGTTTGTGGA TGTACAGAGT GATATTATTG
     TGTGGATATT TTCTCTCTCG GCAATAGCAG ACAAACACCT ACATGTCTCA CTATAATAAC
         SmaI
        ~~~~~~~
         XmaI
        ~~~~~~~
         AvaI                                      ApaLI
        ~~~~~~~                                   ~~~~~~~
1441 ACACGCCCGG GCGACGGATG GTGATCCCCC TGGCCAGTGC ACGTCTGCTG TCAGATAAAG
```

Fig. 3₁

```
       TGTGCGGGCC CGCTGCCTAC CACTAGGGGG ACCGGTCACG TGCAGACGAC AGTCTATTTC
1501   TCTCCCGTGA ACTTTACCCG GTGGTGCATA TCGGGGATGA AAGCTGGCGC ATGATGACCA
       AGAGGGCACT TGAAATGGGC CACCACGTAT AGCCCCTACT TTCGACCGCG TACTACTGGT
1561   CCGATATGGC CAGTGTGCCG GTCTCCGTTA TCGGGGAAGA AGTGGCTGAT CTCAGCCACC
       GGCTATACCG GTCACACGGC CAGAGGCAAT AGCCCCTTCT TCACCGACTA GAGTCGGTGG
1621   GCGAAAATGA CATCAAAAAC GCCATTAACC TGATGTTCTG GGGAATATAA ATGTCAGGCT
       CGCTTTTACT GTAGTTTTTG CGGTAATTGG ACTACAAGAC CCCTTATATT TACAGTCCGA
                                                   PstI
                                                   ~~~~~~~
1681   CCCTTATACA CAGCCAGTCT GCAGGTCGAC CATAGTGACT GGATATGTTG TGTTTTACAG
       GGGAATATGT GTCGGTCAGA CGTCCAGCTG GTATCACTGA CCTATACAAC ACAAAATGTC
1741   TATTATGTAG TCTGTTTTTT ATGCAAAATC TAATTTAATA TATTGATATT TATATCATTT
       ATAATACATC AGACAAAAAA TACGTTTTAG ATTAAATTAT ATAACTATAA ATATAGTAAA
                                                         BamHI       SacI
                                                         ~~~~~~~     ~~
1801   TACGTTTCTC GTTCAGCTTT CTTGTACAAA GTGGTTGATG AGTCCGGATC CCAATTGGGA
       ATGCAAAGAG CAAGTCGAAA GAACATGTTT CACCAACTAC TCAGGCCTAG GGTTAACCCT
                                                          NotI
       SacI             PstI        HindIII      AvaI
       ~~~~             ~~~~~~~     ~~~~~~       ~~~~~~~
1861   GCTCGTGTAC ACGGCGCGCC TGCAGGTCGA CAAGCTTGCG GCCGCACTCG AGTCTGGTAA
       CGAGCACATG TGCCGCGCGG ACGTCCAGCT GTTCGAACGC CGGCGTGAGC TCAGACCATT
1921   AGAAACCGCT GCTGCGAAAT TTGAACGCCA GCACATGGAC TCGTCTACTA GCGCAGCTTA
       TCTTTGGCGA CGACGCTTTA AACTTGCGGT CGTGTACCTG AGCAGATGAT CGCGTCGAAT
1981   ATTAACCTAG GCTGCTGCCA CCGCTGAGCA ATAACTAGCA TAACCCCTTG GGGCCTCTAA
       TAATTGGATC CGACGACGGT GGCGACTCGT TATTGATCGT ATTGGGGAAC CCCGGAGATT
2041   ACGGGTCTTG AGGGGTTTTT TGCTGAAACC TCAGGCATTT GAGAAGCACA CGGTCACACT
       TGCCCAGAAC TCCCCAAAAA ACGACTTTGG AGTCCGTAAA CTCTTCGTGT GCCAGTGTGA
2101   GCTTCCGGTA GTCAATAAAC CGGTAAACCA GCAATAGACA TAAGCGGCTA TTTAACGACC
       CGAAGGCCAT CAGTTATTTG GCCATTTGGT CGTTATCTGT ATTCGCCGAT AAATTGCTGG
2161   CTGCCCTGAA CCCGACGACC GGTCATCGTG GCCGGCCCTC GGCTTGAACG
       GACGGGACTT GGCTGCTGGC CCAGTAGCAC CGGCCGGGAG CCGAACTTGC
2221   AATTGTTAGA CATTATTTGC CGACTACCTT GGTGATCTCG CCTTTCACGT AGTGGACAAA
       TTAACAATCT GTAATAAACG GCTGATGGAA CCACTAGAGC GGAAAGTGCA TCACCTGTTT
2281   TTCTTCCAAC TGATCTGCGC GCGAGGCCAA GCGATCTTCT TCTTGTCCAA GATAAGCCTG
       AAGAAGGTTG ACTAGACGCG CGCTCCGGTT CGCTAGAAGA AGAACAGGTT CTATTCGGAC
2341   TCTAGCTTCA AGTATGACGG GCTGATACTG GGCCGGCAGG CGCTCCATTG CCCAGTCGGC
       AGATCGAAGT TCATACTGCC CGACTATGAC CCGGCCGTCC GCGAGGTAAC GGGTCAGCCG
2401   AGCGACATCC TTCGGCGCGA TTTTGCCGGT TACTGCGCTG TACCAAATGC GGGACAACGT
       TCGCTGTAGG AAGCCGCGCT AAAACGGCCA ATGAGCGAC ATGGTTTACG CCCTGTTGCA
2461   AAGCACTACA TTTCGCTCAT CGCCAGCCCA GTCGGGCGGC GAGTTCCATA GCGTTAAGGT
       TTCGTGATGT AAAGCGAGTA GCGGTCGGGT CAGCCCGCCG CTCAAGGTAT CGCAATTCCA
2521   TTCATTTAGC GCCTCAAATA GATCCTGTTC AGGAACCGGA TCAAAGAGTT CCTCCGCCGC
       AAGTAAATCG CGGAGTTTAT CTAGGACAAG TCCTTGGCCT AGTTTCTCAA GGAGGCGGCG
2581   TGGACCTACC AAGGCAACGC TATGTTCTCT TGCTTTTGTC AGCAAGATAG CCAGATCAAT
       ACCTGGATGG TTCCGTTGCG ATACAAGAGA ACGAAAACAG TCGTTCTATC GGTCTAGTTA
2641   GTCGATCGTG GCTGGCTCGA AGATACCTGC AAGAATGTCA TTGCGCTGCC ATTCTCCAAA
       CAGCTAGCAC CGACCGAGCT TCTATGGACG TTCTTACAGT AACGCGACGG TAAGAGGTTT
                                                         ApaLI
                                                         ~~~~~~~
2701   TTGCAGTTCG CGCTTAGCTG GATAACGCCA CGGAATGATG TCGTCGTGCA CAACAATGGT
       AACGTCAAGC GCGAATCGAC CTATTGCGGT GCCTTACTAC AGCAGCACGT GTTGTTACCA
2761   GACTTCTACA GCGCGGAGAA TCTCGCTCTC TCCAGGGGAA GCCGAAGTTT CCAAAAGGTC
       CTGAAGATGT CGCGCCTCTT AGAGCGAGAG AGGTCCCCTT CGGCTTCAAA GGTTTTCCAG
2821   GTTGATCAAA GCTCGCCGCG TTGTTTCATC AAGCCCTTACG GTCACCGTAA CCAGCAAATC
       CAACTAGTTT CGAGCGGCGC AACAAAGTAG TTCGGAATGC CAGTGGCATT GGTCGTTTAG
2881   AATATCACTG TGTGGCTTCA GGCCGCCATC CACTGCGGAG CCGTACAAAT GTACGGCCAG
       TTATAGTGAC ACACCGAAGT CCGGCGGTAG GTGACGCCTC GGCATGTTTA CATGCCGGTC
2941   CAACGTCGGT TCGAGATGGC GCTCGATGAC GCCAACTACC TCTGATAGTT GAGTCGATAC
       GTTGCAGCCA AGCTCTACCG CGAGCTACTG CGGTTGATGG AGACTATCAA CTCAGCTATG
3001   TTCGGCGATC ACCGCTTCCC TCATACTCTT CCTTTTTCAA TATTATTGAA GCATTTATCA
       AAGCCGCTAG TGGCGAAGGG AGTATGAGAA GGAAAAAGTT ATAATAACTT CGTAAATAGT
3061   GGGTTATTGT CTCATGAGCG ATATTACATA TGAATGTATT TAGAAAAATA AACAAATAGC
       CCCAATAACA GAGTACTCGC CTATGTATAA ACTTACATAA ATCTTTTTAT TTGTTTATCG
3121   TAGCTCACTC GGTCGCTACG CTCCGGGCGT GAGACTGCGG CGGGCGCTGC GGACACATAC
       ATCGAGTGAG CCAGCGATGC GAGGCCCGCA CTCTGACGCC GCCCGCGACG CCTGTGTATG
3181   AAAGTTACCC ACAGATTCCG TGGATAAGCA GGGGACTAAC ATGTGAGGCA AACAGCAGG
       TTTCAATGGG TGTCTAAGGC ACCTATTCGT CCCCTGATTG TACACTCCGT TTTGTCGTCC
3241   GCCGCGCCGG TGGCGTTTTT CCATAGGCTC CGCCCTCCTG CCAGAGTTCA CATAAACAGA
       CGGCGCGGCC ACCGCAAAAA GGTATCCGAG GCGGGAGGAC GGTCTCAAGT GTATTTGTCT
```

Fig. 3$_2$

```
3301  CGCTTTTCCG GTGCATCTGT GGGAGCCGTG AGGCTCAACC ATGAATCTGA CAGTACGGGC
      GCGAAAAGGC CACGTAGACA CCCTCGGCAC TCCGAGTTGG TACTTAGACT GTCATGCCCG
3361  GAAACCCGAC AGGACTTAAA GATCCCCACC GTTTCCGGCG GGTCGCTCCC TCTTGCGCTC
      CTTTGGGCTG TCCTGAATTT CTAGGGGTGG CAAAGGCCGC CCAGCGAGGG AGAACGCGAG
3421  TCCTGTTCCG ACCCTGCCGT TTACCGGATA CCTGTTCCGC CTTTCTCCCT TACGGGAAGT
      AGGACAAGGC TGGGACGGCA AATGGCCTAT GGACAAGGCG GAAAGAGGGA ATGCCCTTCA
3481  GTGGCGCTTT CTCATAGCTC ACACACTGGT ATCTCGGCTC GGTGTAGGTC GTTCGCTCCA
      CACCGCGAAA GAGTATCGAG TGTGTGACCA TAGAGCCGAG CCACATCCAG CAAGCGAGGT
3541  AGCTGGGCTG TAAGCAAGAA CTCCCCGTTC AGCCCGACTG CTGCGCCTTA TCCGGTAACT
      TCGACCCGAC ATTCGTTCTT GAGGGGCAAG TCGGGCTGAC GACGCGGAAT AGGCCATTGA
3601  GTTCACTTGA GTCCAACCCG GAAAAGCACG GTAAAACGCC ACTGGCAGCA GCCATTGGTA
      CAAGTGAACT CAGGTTGGGC CTTTTCGTGC CATTTTGCGT TGACCGTCGT CGGTAACCAT
3661  ACTGGGAGTT CGCAGAGGAT TTGTTTAGCT AAACACGCGG TTGCTCTTGA AGTGTGCGCC
      TGACCCTCAA GCGTCTCCTA AACAAATCGA TTTGTGCGCC AACGAGAACT TCACACGCGG
3721  AAAGTCCGGC TACACTGAA GGACAGATTT GGTTGCTGTG CTCTGCGAAA GCCAGTTACC
      TTTCAGGCCG ATGTGACCTT CCTGTCTAAA CCAACGACAC GAGACGCTTT CGGTCAATGG
3781  ACGGTTAAGC AGTTCCCCAA CTGACTTAAC CTTCGATCAA ACCACCTCCC CAGGTGGTTT
      TGCCAATTCG TCAAGGGGTT GACTGAATTG GAAGCTAGTT TGGTGGAGGG GTCCACCAAA
3841  TTTCGTTTAC AGGGCAAAAG ATTACGCGCA GAAAAAAGG ATCTCAAGAA GATCCTTTGA
      AAAGCAAATG TCCCGTTTTC TAATGCGCGT CTTTTTTTCC TAGAGTTCTT CTAGGAAACT
3901  TCTTTTCTAC TGAACCGCTC TAGATTTCAG TGCAATTTAT CTCTTCAAAT GTAGCACCTG
      AGAAAAGATG ACTTGGCGAG ATCTAAAGTC ACGTTAAATA GAGAAGTTTA CATCGTGGAC
3961  AAGTCAGCCC CATACGATAT AAGTTGTAAT TCTCATGTTA GTCATGCCCC GCGCCCACCG
      TTCAGTCGGG GTATGCTATA TTCAACATTA AGAGTACAAT CAGTACGGGG CGCGGGTGGC
4021  GAAGGAGCTG ACTGGGTTGA AGGCTCTCAA GGGCATCGGT CGAGATCCCG GTGCCTAATG
      CTTCCTCGAC TGACCCAACT TCCGAGAGTT CCCGTAGCCA GCTCTAGGGC CACGGATTAC
4081  AGTGAGCTAA CTTACATTAA TTGCGTTGCG CTCACTGCCC GCTTTCCAGT CGGGAAACCT
      TCACTCGATT GAATGTAATT AACGCAACGC GAGTGACGGG CGAAAGGTCA GCCCTTTGGA
4141  GTCGTGCCAG CTGCATTAAT GAATCGGCCA ACGCGCGGGG AGAGGCGGTT TGCGTATTGG
      CAGCACGGTC GACGTAATTA CTTAGCCGGT TGCGCGCCCC TCTCCGCCAA ACGCATAACC
4201  GCGCCAGGGT GGTTTTTCTT TTCACCAGTG AGACGGGCAA CAGCTGATTG CCCTTCACCG
      CGCGGTCCCA CCAAAAAGAA AAGTGGTCAC TCTGCCCGTT GTCGACTAAC GGGAAGTGGC
4261  CCTGGCCCTG AGAGAGTTGC AGCAAGCGGT CCACGCTGGT TTGCCCCAGC AGGCGAAAAT
      GGACCGGGAC TCTCTCAACG TCGTTCGCCA GGTGCGACCA AACGGGGTCG TCCGCTTTTA
4321  CCTGTTTGAT GGTGGTTAAC GGCGGGATAT AACATGAGCT GTCTTCGGTA TCGTCGTATC
      GGACAAACTA CCACCAATTG CCGCCCTATA TTGTACTCGA CAGAAGCCAT AGCAGCATAG
4381  CCACTACCGA GATGTCCGCA CCAACGCGCA GCCCGGACTC GGTAATGGCG CGCATTGCGC
      GGTGATGGCT CTACAGGCGT GGTTGCGCGT CGGGCCTGAG CCATTACCGC GCGTAACGCG
4441  CCAGCGCCAT CTGATCGTTG GCAACCAGCA TCGCAGTGGG AACGATGCCC TCATTCAGCA
      GGTCGCGGTA GACTAGCAAC CGTTGGTCGT AGCGTCACCC TTGCTACGGG AGTAAGTCGT
4501  TTTGCATGGT TTGTTGAAAA CCGGACATGG CACTCCAGTC GCCTTCCCGT TCCGCTATCG
      AAACGTACCA AACAACTTTT GGCCTGTACC GTGAGGTCAG CGGAAGGGCA AGGCGATAGC
4561  GCTGAATTTG ATTGCGAGTG AGATATTTAT GCCAGCCAGC CAGACGCAGA CGCGCCGAGA
      CGACTTAAAC TAACGCTCAC TCTATAAATA CGGTCGGTCG GTCTGCGTCT GCGCGGCTCT
4621  CAGAACTTAA TGGGCCCGCT AACAGCGCGA TTTGCTGGTG ACCCAATGCG ACCAGATGCT
      GTCTTGAATT ACCCGGGCGA TTGTCGCGCT AAACGACCAC TGGGTTACGC TGGTCTACGA
4681  CCACGCCCAG TCGCGTACCG TCTTCATGGG AGAAAATAAT ACTGTTGATG GGTGTCTGGT
      GGTGCGGGTC AGCGCATGGC AGAAGTACCC TCTTTTATTA TGACAACTAC CCACAGACCA
4741  CAGAGACATC AAGAAATAAC GCCGGAACAT TAGTGCAGGC AGCTTCCACA GCAATGGCAT
      GTCTCTGTAG TTCTTTATTG CGGCCTTGTA ATCACGTCCG TCGAAGGTGT CGTTACCGTA
                                                                    ApaLI
                                                                    ~~
4801  CCTGGTCATC CAGCGGATAG TTAATGATCA GCCCACTGAC GCGTTGCGCG AGAAGATTGT
      GGACCAGTAG GTCGCCTATC AATTACTAGT CGGGTGACTG CGCAACGCGC TCTTCTAACA
      ApaLI
      ~~~~
4861  GCACCGCCGC TTTACAGGCT TCGACGCCGC TTCGTTCTAC CATCGACACC ACCACGCTGG
      CGTGGCGGCG AAATGTCCGA AGCTGCGGCG AAGCAAGATG GTAGCTGTGG TGGTGCGACC
4921  CACCCAGTTG ATCGGCGCGA GATTTAATCG CCGCGACAAT TGCGACGGC GCGTGCAGGG
      GTGGGTCAAC TAGCCGCGCT CTAAATTAGC GGCGCTGTTA AACGCTGCCG CGCACGTCCC
4981  CCAGACTGGA GGTGGCAACG CCAATCAGCA ACGACTGTTT GCCCGCCAGT TGTTGTGCCA
      GGTCTGACCT CCACCGTTGC GGTTAGTCGT TGCTGACAAA CGGGCGGTCA ACAACACGGT
5041  CGCGGTTGGG AATGTAATTC AGCTCCGCCA TCGCCGCTTC CACTTTTTCC CGCGTTTTCG
      GCGCCAACCC TTACATTAAG TCGAGGCGGT AGCGGCGAAG GTGAAAAAGG GCGCAAAAGC
5101  CAGAAACGTG GCTGGCCTGG TTCACCACGC GGGAAACGGT CTGATAAGAG ACACCGGCAT
      GTCTTTGCAC CGACCGGACC AAGTGGTGCG CCCTTTGCCA GACTATTCTC TGTGGCCGTA
5161  ACTCTGCGAC ATCGTATAAC GTTACTGGTT TCACATTCAC CACCCTGAAT TGACTCTCTT
      TGAGACGCTG TAGCATATTG CAATGACCAA AGTGTAAGTG GTGGGACTTA ACTGAGAGAA
5221  CCGGGCGCTA TCATGCCATA CCGCGAAAGG TTTTGCGCCA TTCGATGGTG TCCGGGATCT
      GGCCCGCGAT AGTACGGTAT GGCGCTTTCC AAAACGCGGT AAGCTACCAC AGGCCCTAGA
5281  CGACGCTCTC CCTTATGCGA CTCCTGCATT AGGAAATTAA TACGACTCAC TATA
      GCTGCGAGAG GGAATACGCT GAGGACGTAA TCCTTTAATT ATGCTGAGTG ATAT
```

Fig. 5 pDEST-C2 sequence

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
               NcoI
               ~~~~~~~
  61 GAGATATACC ATGGCACATC ACCACCACCA TCACGTGGGT ACCGGTTCGA ATGATGACGA
     CTCTATATGG TACCGTGTAG TGGTGGTGGT AGTGCACCCA TGGCCAAGCT TACTACTGCT
               SacI
               ~~~~~~~
 121 CGACAAGAGC TCGATCACAA GTTTGTACAA AAAAGCTGAA CGAGAAACGT AAAATGATAT
     GCTGTTCTCG AGCTAGTGTT CAAACATGTT TTTTCGACTT GCTCTTTGCA TTTTACTATA
 181 AAATATCAAT ATATTAAATT AGATTTTGCA TAAAAAACAG ACTACATAAT ACTGTAAAAC
     TTTATAGTTA TATAATTTAA TCTAAAACGT ATTTTTTGTC TGATGTATTA TGACATTTTG
 241 ACAACATATC CAGTCACTAT GGCGGCCGCC ACGTTAAGGG ATTTTGGTCA TGATCAGCAC
     TGTTGTATAG GTCAGTGATA CCGCCGGCGG TGCAATTCCC TAAAACCAGT ACTAGTCGTG
 301 GTGTTGACAA TTAATCATCG GCATAGTATA TCGGCATAGT ATAATACGAC AAGGTGAGGA
     CACAACTGTT AATTAGTAGC CGTATCATAT AGCCGTATCA TATTATGCTG TTCCACTCCT
               NcoI
               ~~~~~~~
 361 ACTAAACCAT GGCCAAGTTG ACCAGTGCCG TTCCGGTGCT CACCGCGCGC GACGTCGCCG
     TGATTTGGTA CCGGTTCAAC TGGTCACGGC AAGGCCACGA GTGGCGCGCG CTGCAGCGGC
                                                       SmaI
                                                       ~~~~~~~
                                                        XmaI
                                                        ~~~~~~~
                                              AvaI      AvaI
                                              ~~~~~~~   ~~~~~~~
 421 GAGCGGTCGA GTTCTGGACC GACCGGCTCG GGTTCTCCCG GGACTTCGTG GAGGACGACT
     CTCGCCAGCT CAAGACCTGG CTGGCCGAGC CCAAGAGGGC CCTGAAGCAC CTCCTGCTGA
 481 TCGCCGGTGT GGTCCGGGAC GACGTGACCC TGTTCATCAG CGCGGTCCAG GACCAGGTGG
     AGCGGCCACA CCAGGCCCTG CTGCACTGGG ACAAGTAGTC GCGCCAGGTC CTGGTCCACC
 541 TGCCGGACAA CACCCTGGCC TGGGTGTGGG TGCGCGGCCT GGACGAGCTG TACGCCGAGT
     ACGGCCTGTT GTGGGACCGG ACCCACACCC ACGCGCCGGA CCTGCTCGAC ATGCGGCTCA
 601 GGTCGGAGGT CGTGTCCACG AACTTCCGGG ACGCCTCCGG GCCGGCCATG ACCCGAGATCG
     CCAGCCTCCA GCACAGGTGC TTGAAGGCCC TGCGGAGGCC CGGCCGGTAC TGGCTCTAGC
                                                              ApaLI
                                                              ~~~~~~
 661 GCGAGCAGCC GTGGGGGCGG GAGTTCGCCC TGCGCGACCC GGCCGGCAAC TGCGTGCACT
     CGCTCGTCGG CACCCCCGCC CTCAAGCGGG ACGCGCTGGG CCGGCCGTTG ACGCACGTGA
 721 TCGTGGCCGA GGAGCAGGAC TGATCATGAT GATATTATTT TATCTTGTGC AATGTAACAT
     AGCACCGGCT CCTCGTCCTG ACTAGTACTA CTATAATAAA ATAGAACACG TTACATTGTA
 781 CAGAGATTTT GAGACACGGG CCAGAGCTGC AGGAAACAG CTATGACCAT GTAATACGAC
     GTCTCTAAAA CTCTGTGCCC GGTCTCGACG GTCCTTTGTC GATACTGGTA CATTATGCTG
 841 TCACTATAGG GGATATCAGC TGGATGGCAA ATAATGATTT TATTTTGACT GATAGTGACC
     AGTGATATCC CCTATAGTCG ACCTACCGTT TATTACTAAA ATAAAACTGA CTATCACTGG
 901 TGTTCGTTGC AACACCGGTG CTAGCGTATA CCCGAAGTAT GTCAAAAAGA GGTGTGCTAT
     ACAAGCAACG TTGTGGCCAC GATCGCATAT GGGCTTCATA CAGTTTTTCT CCACACGATA
 961 GAAGCAGCGT ATTACAGTGA CAGTTGACAG CGACAGCTAT CAGTTGCTCA AGGCATATAT
     CTTCGTCGCA TAATGTCACT GTCAACTGTC GCTGTCGATA GTCAACGAGT TCCGTATATA
1021 GATGTCAATA TCTCCGGTCT GGTAAGCACA ACCATGCAGA ATGAAGCCCG TCGTCTGCGT
     CTACAGTTAT AGAGGCCAGA CCATTCGTGT TGGTACGTCT TACTTCGGGC AGCAGACGCA
1081 GCCGAACGCT GGAAAGCGGA AAATCAGGAA GGGATGGCTG AGGTCGCCCG GTTTATTGAA
     CGGCTTGCGA CCTTTCGCCT TTTAGTCCTT CCCTACCGAC TCCAGCGGGC CAAATAACTT
1141 ATGAACGGCT CTTTTGCTGA CGAGAACAGG GACTGGTGAA ATGCAGTTTA AGGTTTACAC
     TACTTGCCGA GAAAACGACT GCTCTTGTCC CTGACCACTT TACGTCAAAT TCCAAATGTG
1201 CTATAAAAGA GAGAGCCGTT ATCGTCTGTT TGTGGATGTA CAGAGTGATA TTATTGACAC
     GATATTTTCT CTCTCGGCAA TAGCAGACAA ACACCTACAT GTCTCACTAT AATAACTGTG
     SmaI
     ~~~~~~~
     XmaI
     ~~~~~~
     AvaI                                       ApaLI
     ~~~~~~                                     ~~~~~~
1261 GCCCGGGCGA CGGATGGTGA TCCCCCTGGC CAGTGCACGT CTGCTGTCAG ATAAAGTCTC
     CGGGCCCGCT GCCTACCACT AGGGGGACCG GTCACGTGCA GACGACAGTC TATTTCAGAG
1321 CCGTGAACTT TACCCGGTGG TGCATATCGG GGATGAAAGC TGGCGCATGA TGACCACCGA
     GGCACTTGAA ATGGGCCACC ACGTATAGCC CCTACTTTCG ACCGCGTACT ACTGGTGGCT
1381 TATGGCCAGT GTGCCGGTCT CCGTTATCGG GGAAGAAGTG GCTGATCTCA GCCGGCGCGA
     ATACCGGTCA CACGGCCAGA GGCAATAGCC CCTTCTTCAC CGACTAGAGT CGGCCGCGCT
1441 AAATGACATC AAAAACGCCA TTAACCTGAT GTTCTGGGGA ATATAAATGT CAGGCTCCCT
     TTTACTGTAG TTTTTGCGGT AATTGGACTA CAAGACCCCT TATATTTACA GTCCGAGGGA
```

Fig. 5₁

```
                    PstI
                   ~~~~~~~
1501   TATACACAGC CAGTCTGCAG GTCGACCATA GTGACTGGAT ATGTTGTGTT TTACAGTATT
       ATATGTGTCG GTCAGACGTC CAGCTGGTAT CACTGACCTA TACAACACAA AATGTCATAA
1561   ATGTAGTCTG TTTTTTATGC AAAATCTAAT TTAATATATT GATATTTATA TCATTTTACG
       TACATCAGAC AAAAAATACG TTTTAGATTA AATTATATAA CTATAAATAT AGTAAAATGC
1621   TTTCTCGTTC AGCTTTCTTG TACAAAGTGG TGATAATTAA TTAAGATCAG ATCCGGCTGC
       AAAGAGCAAG TCGAAAGAAC ATGTTTCACC ACTATTAATT AATTCTAGTC TAGGCCGACG
                                                                  PstI
                                                                 ~~~~~~~
       HindIII    BamHI      SacI                                HindIII
       ~~~~~~     ~~~~~~     ~~~~~~~                             ~
1681   TAAGCTTGAG TCCGGATCCC AATTGGGAGC TCGTGTACAC GGCGCGCCTG CAGGTCGACA
       ATTCGAACTC AGGCCTAGGG TTAACCCTCG AGCACATGTG CCGCGCGGAC GTCCAGCTGT
       HindIII    AvaI
       ~~~~~      ~~~~~~~
1741   AGCTTGCGGC CGCACTCGAG TCTGGTAAAG AAACCGCTGC TGCGAAATTT GAACGCCAGC
       TCGAACGCCG GCGTGAGCTC AGACCATTTC TTTGGCGACG ACGCTTTAAA CTTGCGGTCG
1801   ACATGGACTC GTCTACTAGC GCAGCTTAAT TAACCTAGGC TGCTGCCACC GCTGAGCAAT
       TGTACCTGAG CAGATGATCG CGTCGAATTA ATTGGATCCG ACGACGGTGG CGACTCGTTA
1861   AACTAGCATA ACCCCTTGGG GCCTCTAAAC GGGTCTTGAG GGGTTTTTTG CTGAAACCTC
       TTGATCGTAT TGGGGAACCC CGGAGATTTG CCCAGAACTC CCCAAAAAAC GACTTTGGAG
1921   AGGCATTTGA GAAGCACACG GTCACACTGC TTCCGGTAGT CAATAAACCG GTAAACCAGC
       TCCGTAAACT CTTCGTGTGC CAGTGTGACG AAGGCCATCA GTTATTTGGC CATTTGGTCG
1981   AATAGACATA AGCGGCTATT TAACGACCCT GCCCTGAACC GACGACAAGC TGACGACCGG
       TTATCTGTAT TCGCCGATAA ATTGCTGGGA CGGGACTTGG CTGCTGTTCG ACTGCTGGCC
2041   GTCTCCGCAA GTGGCACTTT TCGGGGAAAT GTGCGCGGAA CCCCTATTTG TTTATTTTTC
       CAGAGGCGTT CACCGTGAAA AGCCCCTTTA CACGCGCCTT GGGGATAAAC AAATAAAAAG
2101   TAAATACATT CAAATATGTA TCCGCTCATG AATTAATTCT TAGAAAAACT CATCGAGCAT
       ATTTATGTAA GTTTATACAT AGGCGAGTAC TTAATTAAGA ATCTTTTTGA GTAGCTCGTA
2161   CAAATGAAAC TGCAATTTAT TCATATCAGG ATTATCAATA CCATATTTTT GAAAAAGCCG
       GTTTACTTTG ACGTTAAATA AGTATAGTCC TAATAGTTAT GGTATAAAAA CTTTTTCGGC
2221   TTTCTGTAAT GAAGGAGAAA ACTCACCGAG GCAGTTCCAT AGGATGGCAA GATCCTGGTA
       AAAGACATTA CTTCCTCTTT TGAGTGGCTC CGTCAAGGTA TCCTACCGTT CTAGGACCAT
2281   TCGGTCTGCG ATTCCGACTC GTCCAACATC AATACAACCT ATTAATTTCC CCTCGTCAAA
       AGCCAGACGC TAAGGCTGAG CAGGTTGTAG TTATGTTGGA TAATTAAAGG GGAGCAGTTT
2341   AATAAGGTTA TCAAGTGAGA AATCACCATG AGTGACGACT GAATCCGGTG AGAATGCAA
       TTATTCCAAT AGTTCACTCT TTAGTGGTAC TCACTGCTGA CTTAGGCCAC TCTTACCGTT
2401   AAGTTTATGC ATTTCTTTCC AGACTTGTTC AACAGGCCAG CCATTACGCT CGTCATCAAA
       TTCAAATACG TAAAGAAAGG TCTGAACAAG TTGTCCGGTC GGTAATGCGA GCAGTAGTTT
2461   ATCACTCGCA TCAACCAAAC CGTTATTCAT TCGTGATTGC GCCTGAGCGA GACGAAATAC
       TAGTGAGCGT AGTTGGTTTG GCAATAAGTA AGCACTAACG CGGACTCGCT CTGCTTTATG
2521   GCGGTCGCTG TTAAAAGGAC AATTACAAAC AGGAATCGAA TGCAACCGGC GCAGGAACAC
       CGCCAGCGAC AATTTTCCTG TTAATGTTTG TCCTTAGCTT ACGTTGGCCG CGTCCTTGTG
2581   TGCCAGCGCA TCAACAATAT TTCACCTGA ATCAGGATAT TCTTCTAATA CCTGGAATGC
       ACGGTCGCGT AGTTGTTATA AAGTGGACT TAGTCCTATA AGAAGATTAT GGACCTTACG
              SmaI
              ~~~~~~~
              XmaI
              ~~~~~~~
              AvaI
              ~~~~~~~
2641   TGTTTTCCCG GGGATCGCAG TGGTGAGTAA CCATGCATCA TCAGGAGTAC GGATAAAATG
       ACAAAAGGGC CCCTAGCGTC ACCACTCATT GGTACGTAGT AGTCCTCATG CCTATTTTAC
2701   CTTGATGGTC GGAAGAGGCA TAAATTCCGT CAGCCAGTTT AGTCTGACCA TCTCATCGT
       GAACTACCAG CCTTCTCCGT ATTTAAGGCA GTCGGTCAAA TCAGACTGGT AGAGTAGACA
2761   AACATCATTG GCAACGCTAC CTTTGCCATG TTTCAGAAAC AACTCTGGCG CATCGGGCTT
       TTGTAGTAAC CGTTGCGATG GAAACGGTAC AAAGTCTTTG TTGAGACCGC GTAGCCCGAA
                  ClaI
                  ~~~~~~~
2821   CCCATACAAT CGATAGATTG TCGCACCTGA TTGCCCGACA TTATCGCGAG CCCATTTATA
       GGGTATGTTA GCTATCTAAC AGCGTGGACT AACGGGCTGT AATAGCGCTC GGGTAAATAT
2881   CCCATATAAA TCAGCATCCA TGTTGGAATT TAATCGCGGC CTAGAGCAAG ACGTTTCCCG
       GGGTATATTT AGTCGTAGGT ACAACCTTAA ATTAGCGCCG GATCTCGTTC TGCAAAGGGC
2941   TTGAATATGG CTCATATTCT TCCTTTTTCA ATATTATTGA AGCATTTATC AGGGTTATTG
       AACTTATACC GAGTATGAGA AGGAAAAAGT TATAATAACT TCGTAAATAG TCCCAATAAC
3001   TCTCATGAGC GGATACATAT TTGAATGTAT TTAGAAAAAT AAACAAATAG GCATGCAGCG
       AGAGTACTCG CCTATGTATA AACTTACATA AATCTTTTTA TTTGTTTATC CGTACGTCGC
3061   CTCTTCCGCT TCCTCGCTCA CTGACTCGCT ACGCTCGGTC GTTCGACTGC GGCGAGCGGT
       GAGAAGGCGA AGGAGCGAGT GACTGAGCGA TGCGAGCCAG CAAGCTGACG CCGCTCGCCA
3121   GTCAGCTCAC TCAAAGCGG TAATACGGTT ATCCACAGAA TCAGGGGATA AGCCGGAAA
       CAGTCGAGTG AGTTTCGCC ATTATGCCAA TAGGTGTCTT AGTCCCCTAT TCGGCCTTT
3181   GAACATGTGA GCAAAAAGCA AGCACCGGA AGAAGCCAAC GCCGCAGGCG TTTTTCCATA
```

Fig. 5₂

```
              CTTGTACACT CGTTTTTCGT TTCGTGGCCT TCTTCGGTTG CGGCGTCCGC AAAAAGGTAT
      3241    GGCTCCGCCC CCCTGACGAG CATCACAAAA ATCGACGCTC AAGCCAGAGG TGGCGAAACC
              CCGAGGCGGG GGGACTGCTC GTAGTGTTTT TAGCTGCGAG TTCGGTCTCC ACCGCTTTGG
      3301    CGACAGGACT ATAAAGATAC CAGGCGTTTC CCCCTGGAAG CTCCCTGCTG CGCTCTCCTG
              GCTGTCCTGA TATTTCTATG GTCCGCAAAG GGGGACCTTC GAGGGAGCAC GCGAGAGGAC
      3361    TTCCGACCCT GCCGCTTACC GGATACCTGT CCGCCTTTCT CCCTTCGGGA AGCGTGGCGC
              AAGGCTGGGA CGGCGAATGG CCTATGGACA GCCGGAAAGA GGGAAGCCCT TCGCACCGCG
      3421    TTTCTCATAG CTCACGCTGT TGGTATCTCA GTTCGGTGTA GGTCGTTCGC TCCAAGCTGG
              AAAGAGTATC GAGTGCGACA ACCATAGAGT CAAGCCACAT CCAGCAAGCG AGGTTCGACC
                                                    ApaLI
                                                    ~~~~~~~
      3481    GCTGTGTGCA CGAACCCCCC GTTCAGCCCG ACCGCTGCGC CTTATCCGGT AACTATCGTC
              CGACACACGT GCTTGGGGGG CAAGTCGGGC TGGCGACGCG GAATAGGCCA TTGATAGCAG
      3541    TTGAGTCCAA CCCGGTAAGA CACGACTTAT CGCCACTGGC AGCAGCCATT GGTAACTGAT
              AACTCAGGTT GGGCCATTCT GTGCTGAATA GCGGTGACCG TCGTCGGTAA CCATTGACTA
      3601    TTAGAGGACT TTGTCTTGAA GTTATGCACC TGTTAAGGCT AAACTGAAAG AACAGATTTT
              AATCTCCTGA AACAGAACTT CAATACGTGG ACAATTCCGA TTTGACTTTC TTGTCTAAAA
      3661    GGTGAGTGCG GTCCTCCAAC CCACTTACCT TGGTTCAAAG AGTTGGTAGC TCAGCGAACC
              CCACTCACGC CAGGAGGTTG GGTGAATGGA ACCAAGTTTC TCAACCATCG AGTCGCTTGG
      3721    TTGAGAAAAC CACCGTTGGT AGCGGTGGTT TTTCTTTATT TATGAGATGA TGAATCAATC
              AACTCTTTTG GTGGCAACCA TCGCCACCAA AAAGAAATAA ATACTCTACT ACTTAGTTAG
      3781    GGTCTATCAA GTCAACGAAC AGCTATTCCG TTACTCTAGA TTTCAGTGCA ATTTATCTCT
              CCAGATAGTT CAGTTGCTTG TCGATAAGGC AATGAGATCT AAAGTCACGT TAAATAGAGA
      3841    TCAAATGTAG CACCTGAAGT CAGCCCCATA CGATATAGTT TGTAATTCTC ATGTTAGTCA
              AGTTTACATC GTGGACTTCA GTCGGGGTAT GCTATATTCA ACATTAAGAG TACAATCAGT
      3901    TGCCCCGCGC CCACCGGAAG GAGCTGACTG GGTTGAAGGC TCTCAAGGGC ATCGGTCGAG
              ACGGGGCGCG GGTGGCCTTC CTCGACTGAC CCAACTTCCG AGAGTTCCCG TAGCCAGCTC
      3961    ATCCCGGTGC CTAATGAGTG AGCTAACTTA CATTAATTGC GTTGCGCTCA CTGCCCGCTT
              TAGGGCCACG GATTACTCAC TCGATTGAAT GTAATTAACG CAACGCGAGT GACGGGCGAA
      4021    TCCAGTCGGG AAACCTGTCG TGCCAGCTGC ATTAATGAAT CGGCCAACGC GCGGGGAGAG
              AGGTCAGCCC TTTGGACAGC ACGGTCGACG TAATTACTTA GCCGGTTGCG CGCCCCTCTC
      4081    GCGGTTTGCG TATTGGGCGC CAGGGTGGTT TTTCTTTTCA CCAGTGAGAC GGGCAACAGC
              CGCCAAACGC ATAACCCGCG GTCCCACCAA AAAGAAAAGT GGTCACTCTG CCCGTTGTCG
      4141    TGATTGCCCT TCACCGCCTG GCCCTGAGAG AGTTGCAGCA AGCGGTCCAC GCTGGTTTGC
              ACTAACGGGA AGTGGCGGAC CGGGACTCTC TCAACGTCGT TCGCCAGGTG CGACCAAACG
      4201    CCCAGCAGGC GAAAATCCTG TTTGATGGTG GTTAACGGCG GGATATAACA TGAGCTGTCT
              GGGTCGTCCG CTTTTAGGAC AAACTACCAC CAATTGCCGC CCTATATTGT ACTCGACAGA
      4261    TCGGTATCGT CGTATCCCAC TACCGAGATG TCCGCACCAA CGCGCAGCCC GGACTCGGTA
              AGCCATAGCA GCATAGGGTG ATGGCTCTAC AGGCGTGGTT GCGCGTCGGG CCTGAGCCAT
      4321    ATGGCGCGCA TTGCGCCCAG CGCCATCGA TCGTTGGCAA CCAGCATCGC AGTGGGAACG
              TACCGCGCGT AACGCGGGTC GCGGTAGACT AGCAACCGTT GGTCGTAGCG TCACCCTTGC
      4381    ATGCCCTCAT TCAGCATTTG CATGGTTTGT TGAAAACCGG ACATGGCACT CCAGTCGCCT
              TACGGGAGTA AGTCGTAAAC GTACCAAACA ACTTTTGGCC TGTACCGTGA GGTCAGCGGA
      4441    TCCCGTTCCG CTATCGGCTG AATTTGATTG CGAGTGAGAT ATTTATGCCA GCCAGCCAGA
              AGGGCAAGGC GATAGCCGAC TTAAACTAAC GCTCACTCTA TAAATACGGT CGGTCGGTCT
      4501    CGCAGACGCG CCGAGACAGA ACTTAATGGG CCCGCTAACA GCGCGATTTG CTGGTGACCC
              GCGTCTGCGC GGCTCTGTCT TGAATTACCC GGGCGATTGT CGCGCTAAAC GACCACTGGG
      4561    AATGCGACCA GATGCTCCAC GCCCAGTCGC GTACCGTCTT CATGGGAGAA AATAATACTG
              TTACGCTGGT CTACGAGGTG CGGGTCAGCG CATGGCAGAA GTACCCTCTT TTATTATGAC
      4621    TTGATGGGTG TCTGGTCAGA GACATCAAGA AATAACGCCG GAACATTAGT GCAGGCAGCT
              AACTACCCAC AGACCAGTCT CTGTAGTTCT TTATTGCGGC CTTGTAATCA CGTCCGTCGA
      4681    TCCACAGCAA TGGCATCCTG GTCATCCAGC GGATAGTTAA TGATCAGCCC ACTGACGCGT
              AGGTGTCGTT ACCGTAGGAC CAGTAGGTCG CCTATCAATT ACTAGTCGGG TGACTGCGCA
                                                    ApaLI
                                                    ~~~~~~~
      4741    TGCGCGAGAA GATTGTGCAC CGCCGCTTTA CAGGCTTCGA CGCCGCTTCG TTCTACCATC
              ACGCGCTCTT CTAACACGTG GCGGCGAAAT GTCCGAAGCT GCGGCGAAGC AAGATGGTAG
      4801    GACACCACCA CGCTGGCACC CAGTTGATCG GCGCGAGATT TAATCGCCGC GACAATTTGC
              CTGTGGTGGT GCGACCGTGG GTCAACTAGC CGCGCTCTAA ATTAGCGGCG CTGTTAAACG
      4861    GACGGCGCGT GCAGGGCCAG ACTGGAGGTG GCAACGCCAA TCAGCAACGA CTGTTTGCCC
              CTGCCGCGCA CGTCCCGGTC TGACCTCCAC CGTTGCGGTT AGTCGTTGCT GACAAACGGG
      4921    GCCAGTTGTT GTGCCACGCG GTTGGGAATG TAATTCAGCT CCGCCATCGC CGCTTCCACT
              CGGTCAACAA CACGGTGCGC CAACCCTTAC ATTAAGTCGA GGCGGTAGCG GCGAAGGTGA
      4981    TTTTCCCGCG TTTTCGCAGA AACGTGGCTG GCCTGGTTCA CCACGCGGGA AACGGTCTGA
              AAAAGGGCGC AAAAGCGTCT TTGCACCGAC CGGACCAAGT GGTGCGCCCT TTGCCAGACT
      5041    TAAGAGACAC CGGCATACTC TGCGACATCG TATAACGTTA CTGGTTTCAC ATTCACCACC
              ATTCTCTGTG GCCGTATGAG ACGCTGTAGC ATATTGCAAT GACCAAAGTG TAAGTGGTGG
      5101    CTGAATTGAC TCTCTTCCGG GCGCTATCAT GCCATACCGC GAAAGGTTTT GCGCCATTCG
              GACTTAACTG AGAGAAGGCC CGCGATAGTA CGGTATGGCG CTTTCCAAAA CGCGGTAAGC
      5161    ATGGTGTCCG GATCTCGAC GCTCTCCCTT ATGCGACTCC TGCATTAGGA AATTAATACG
              TACCACAGGC CCTAGAGCTG CGAGAGGGAA TACGCTGAGG ACGTAATCCT TTAATTATGC
      5221    ACTCACTATA
              TGAGTGATAT
```

Fig. 5₃

| Fig. 7$_1$ |
|---|
| Fig. 7$_2$ |
| Fig. 7$_3$ |

Fig. 7 pDEST-C3 nucleotide

```
                                                                              EcoRI
                                                                              ~~~~~~
             NcoI                                          BamHI       SacI
             ~~~~~~~                                       ~~~~~~      ~~~
  61  GAGATATACC ATGGGCAGCA GCCATCACCA TCATCACCAC AGCCAGGATC CGAATTCGAG
      CTCTATATGG TACCCGTCGT CGGTAGTGGT AGTAGTGGTG TCGGTCCTAG GCTTAAGCTC
      SacI
      ~~~
 121  CTCGATCACA AGTTTGTACA AAAAAGCTGA ACGAGAAACG TAAAATGATA TAAATATCAA
      GAGCTAGTGT TCAAACATGT TTTTTCGACT TGCTCTTTGC ATTTTACTAT ATTTATAGTT
 181  TATATTAAAT TAGATTTTGC ATAAAAAACA GACTACATAA TACTGTAAAA CACAACATAT
      ATATAATTTA ATCTAAAACG TATTTTTTGT CTGATGTATT ATGACATTTT GTGTTGTATA
                       NotI
                       ~~~~~~~~~~
 241  CCAGTCACTA TGGCGGCCGC CACGTTAAGG GATTTTGGTC ATGATCAGCA CGTGTTGACA
      GGTCAGTGAT ACCGCCGGCG GTGCAATTCC CTAAAACCAG TACTAGTCGT GCACAACTGT
                                                                   NcoI
                                                                   ~~~ .
 301  ATTAATCATC GGCATAGTAT ATCGGCATAG TATAATACGA CAAGGTGAGG AACTAAACCA
      TAATTAGTAG CCGTATCATA TAGCCGTATC ATATTATGCT GTTCCACTCC TTGATTTGGT
      NcoI
      ~~~
 361  TGGCCAAGTT GACCAGTGCC GTTCCGGTGC TCACCGCGCG CGACGTCGCC GGAGCGGTCG
      ACCGGTTCAA CTGGTCACGG CAAGGCCACG AGTGGCGCGC GCTGCAGCGG CCTCGCCAGC
 421  AGTTCTGGAC CGACCGGCTC GGGTTCTCCC GGGACTTCGT GGAGGACGAC TTCGCCGGTG
      TCAAGACCTG GCTGGCCGAG CCCAAGAGGG CCCTGAAGCA CCTCCTGCTG AAGCGGCCAC
 481  TGGTCCGGGA CGACGTGACC CTGTTCATCA GCGCGGTCCA GGACCAGGTG GTGCCGGACA
      ACCAGGCCCT GCTGCACTGG GACAAGTAGT CGCGCCAGGT CCTGGTCCAC CACGGCCTGT
 541  ACACCCTGGC CTGGGTGTGG GTGCGCGCC TGGACGAGCT GTACGCCGAG TGGTCGGAGG
      TGTGGGACCG GACCCACACC CACGCGCGG ACCTGCTCGA CATGCGGCTC ACCAGCCTCC
 601  TCGTGTCCAC GAACTTCCGG GACGCCTCCG GGCCGGCCAT GACCGAGATC GGCGAGCAGC
      AGCACAGGTG CTTGAAGGCC CTGCGGAGGC CCGGCCGGTA CTGGCTCTAG CCGCTCGTCG
 661  CGTGGGGGCG GGAGTTCGCC CTGCGCGACC CGGCCGGCAA CTGCGTGCAC TTCGTGGCCG
      GCACCCCCGC CCTCAAGCGG GACGCGCTGG GCCGGCCGTT GACGCACGTG AAGCACCGGC
 721  AGGAGCAGGA CTGATCATGA TGAATGTAACA TCAGAGATTT
      TCCTCGTCCT GACTAGTACT ACTATAATAA AATAGAACAC GTTACATTGT AGTCTCTAAA
 781  TGAGACACGG GCCAGAGCTG CCAGGAAACA GCTATGACCA TGTAATACGA CTCACTATAG
      ACTCTGTGCC CGGTCTCGAC GGTCCTTTGT CGATACTGGT ACATTATGCT GAGTGATATC
 841  GGGATATCAG CTGGATGGCA ATAATGATT TTATTTTGAC TGATAGTGAC CTGTTCGTTG
      CCCTATAGTC GACCTACCGT TTATTACTAA AATAAAACTG ACTATCACTG GACAAGCAAC
 901  CAACACCGGT GCTAGCGTAT ACCCGAAGTA TGTCAAAAAG AGGTGTGCTA TGAAGCAGCG
      GTTGTGGCCA CGATCGCATA TGGGCTTCAT ACAGTTTTTC TCCACACGAT ACTTCGTCGC
 961  TATTACAGTG ACAGTTGACA GCGACAGCTA TCAGTTGCTC AAGGCATATA TGATGTCAAT
      ATAATGTCAC TGTCAACTGT CGCTGTCGAT AGTCAACGAG TTCCGTATAT ACTACAGTTA
1021  ATCTCCGGTC TGGTAAGCAC AACCATGCAG AATGAAGCCC GTCGTCTGCG TGCCGAACGC
      TAGAGGCCAG ACCATTCGTG TTGGTACGTC TTACTTCGGG CAGCAGACGC ACGGCTTGCG
1081  TGGAAAGCGG AAAATCAGGA AGGGATGGCT GAGGTCGCCC GGTTTATTGA AATGAACGGC
      ACCTTTCGCC TTTTAGTCCT TCCCTACCGA CTCCAGCGGG CCAAATAACT TTACTTGCCG
1141  TCTTTTGCTG ACGAGAACAG GGACTGGTGA AATGCAGTTT AAGGTTTACA CCTATAAAAG
      AGAAAACGAC TGCTCTTGTC CCTGACCACT TTACGTCAAA TTCCAAATGT GGATATTTTC
1201  AGACGACCGT TATCGTCTGT TTGTGGATGT ACAGAGTGAT ATTATTGACA CGCCCGGGCG
      TCTGCTGGCA ATAGCAGACA AACACCTACA TGTCTCACTA TAATAACTGT GCGGGCCCGC
1261  ACGGATGGTG ATCCCCCTGG CCAGTGCACG TCTGCTGTCA GATAAAGTCT CCCGTGAACT
      TGCCTACCAC TAGGGGGACC GGTCACGTGC AGACGACAGT CTATTTCAGA GGGCACTTGA
1321  TTACCCGGTG GTGCATATCG GGGATGAAAG CTGGCGCATG ATGACCACCG ATATGGCCAG
      AATGGGCCAC CACGTATAGC CCCTACTTTC GACCGCGTAC TACTGGTGGC TATACCGGTC
1381  TGTGCCGGTC TCCGTTATCG GGGAAGAAGT GGCTGATCTC AGCCGCCGCG AAAATGACAT
      ACACGGCCAG AGGCAATAGC CCCTTCTTCA CCGACTAGAG TCGGCGGCGC TTTTACTGTA
1441  CAAAAACGCC ATTAACCTGA TGTTCTGGGG AATATAAATG TCAGGCTCCC TTATACACAG
      GTTTTTGCGG TAATTGGACT ACAAGACCCC TTATATTTAC AGTCCGAGGG AATATGTGTC
      PstI
      ~~~~~~~
1501  CCAGTCTGCA GGTCGACCAT AGTGACTGGA TATGTTGTGT TTTACAGTAT TATGTAGTCT
      GGTCAGACGT CCAGCTGGTA TCACTGACCT ATACAACACA AAATGTCATA ATACATCAGA
1561  GTTTTTTATG CAAAAATCTAA TTTAATATAT TGATATTTAT ATCATTTTAC GTTTCTCGTT
      CAAAAAATAC GTTTTAGATT AAATTATATA ACTATAAATA TAGTAAAATG CAAAGAGCAA
                                                                  NotI
                                                                  ~~
```

Fig. 7₁

```
                                                        HindIII
                                                        ~~~~~~
1621 CAGCTTTCTT GTACAAAGTG GTGATAATTA ATTAAGATCA GATCCGGCTG CTAAGCTTGC
     GTCGAAAGAA CATGTTTCAC CACTATTAAT TAATTCTAGT CTAGGCCGAC GATTCGAACG
     NotI
     ~~~~~~
1681 GGCCGCATAA TGCTTAAGTC GAACAGAAAG TAATCGTATT GTACACGGCC GCATAATCGA
     CCGGCGTATT ACGAATTCAG CTTGTCTTTC ATTAGCATAA CATGTGCCGG CGTATTAGCT
1741 AATTAATACG ACTCACTATA GGGGAATTGT GAGCGGATAA CAATTCCCCA TCTTAGTATA
     TTAATTATGC TGAGTGATAT CCCCTTAACA CTCGCCTATT GTTAAGGGGT AGAATCATAT
1801 TTAGTTAAGT ATAAGAAGGA GATATACATA TGGCAGATCT CAATTGGATA TCGGCCGGCC
     AATCAATTCA TATTCTTCCT CTATATGTAT ACCGTCTAGA GTTAACCTAT AGCCGGCCGG
1861 ACGCGATCGC TGACGTCGGT ACCCTCGAGT CTGGTAAAGA AACCGCTGCT GCGAAATTTG
     TGCGCTAGCG ACTGCAGCCA TGGGAGCTCA GACCATTTCT TTGGCGACGA CGCTTTAAAC
1921 AACGCCAGCA CATGGACTCG TCTACTAGCG CAGCTTAATT AACCTAGGCT GCTGCCACCG
     TTGCGGTCGT GTACCTGAGC AGATGATCGC GTCGAATTAA TTGGATCCGA CGACGGTGGC
1981 CTGAGCAATA ACTAGCATAA CCCCTTGGGG CCTCTAAACG GGTCTTGAGG GGTTTTTTGC
     GACTCGTTAT TGATCGTATT GGGGAACCCC GGAGATTTGC CCAGAACTCC CCAAAAAACG
2041 TGAAACCTCA GGCATTTGAG AAGCACACGG TCACACTGCT TCCGGTAGTC AATAAACCGG
     ACTTTGGAGT CCGTAAACTC TTCGTGTGCC AGTGTGACGA AGGCCATCAG TTATTTGGCC
2101 TAAACCAGCA ATAGACATAA GCGGCTATTT AACGACCCTG CCCTGAACCG ACGACCGGGT
     ATTTGGTCGT TATCTGTATT CGCCGATAAA TTGCTGGGAC GGGACTTGGC TGCTGGCCCA
2161 CGAATTTGCT TTCGAATTTC TGCCATTCAT CCGCTTATTA TCACTTATTC AGGCGTAGCA
     GCTTAAACGA AAGCTTAAAG ACGGTAAGTA GGCGAATAAT AGTGAATAAG TCCGCATCGT
2221 CCAGGCGTTT AAGGGCACCA ATAACTGCCT TAAAAAAATT ACGCCCCGCC CTGCCACTCA
     GGTCCGCAAA TTCCCGTGGT TATTGACGGA ATTTTTTTAA TGCGGGGCGG GACGGTGAGT
2281 TCGCAGTACT GTTGTAATTC ATTAAGCATT CTGCCGACAT GGAAGCCATC ACAGACGGCA
     AGCGTCATGA CAACATTAAG TAATTCGTAA GACGGCTGTA CCTTCGGTAG TGTCTGCCGT
2341 TGATGAACCT GAATCGCCAG CGGCATCAGC ACCTTGTCGC CTTGCGTATA ATATTTGCCC
     ACTACTTGGA CTTAGCGGTC GCCGTAGTCG TGGAACAGCG GAACGCATAT TATAAACGGG
2401 ATAGTGAAAA CGGGGGCGAA GAAGTTGTCC ATATTGGCCA CGTTTAAATC AAAACTGGTG
     TATCACTTTT GCCCCCGCTT CTTCAACAGG TATAACCGGT GCAAATTTAG TTTTGACCAC
2461 AAACTCACCC AGGGATTGGC TGAGACGAAA AACATATTCT CAATAAACCC TTTAGGGAAA
     TTTGAGTGGG TCCCTAACCG ACTCTGCTTT TTGTATAAGA GTTATTTGGG AAATCCCTTT
2521 TAGGCCAGGT TTTCACCGTA ACACGCCACA TCTTGCGAAT ATATGTGTAG AAACTGCCGG
     ATCCGGTCCA AAAGTGGCAT TGTGCGGTGT AGAACGCTTA TATACACATC TTTGACGGCC
2581 AAATCGTCGT GGTATTCACT CCAGAGCGAT GAAAACGTTT CAGTTTGCTC ATGGAAAACG
     TTTAGCAGCA CCATAAGTGA GGTCTCGCTA CTTTTGCAAA GTCAAACGAG TACCTTTTGC
2641 GTGTAACAAG GGTGAACACT ATCCCATATC ACCAGCTCAC CGTCTTTCAT TGCCATACGG
     CACATTGTTC CCACTTGTGA TAGGGTATAG TGGTCGAGTG GCAGAAAGTA ACGGTATGCC
2701 AACTCCGGAT GAGCATTCAT CAGGCGGGCA AGAATGTGAA TAAAGGCCGG ATAAAACTTG
     TTGAGGCCTA CTCGTAAGTA GTCCGCCCGT TCTTACACTT ATTTCCGGCC TATTTTGAAC
2761 TGCTTATTTT TCTTTACGGT CTTTAAAAAG GCCGTAATAT CCAGCTGAAC GGTCTGGTTA
     ACGAATAAAA AGAAATGCCA GAAATTTTTC CGGCATTATA GGTCGACTTG CCAGACCAAT
2821 TAGGTACATT GAGCAACTGA CTGAAATGCC TCAAAATGTT CTTTACGATG CCATTGGGAT
     ATCCATGTAA CTCGTTGACT GACTTTACGG AGTTTTACAA GAAATGCTAC GGTAACCCTA
2881 ATATCAACGG TGGTATATCC AGTGATTTTT TCTCCATTTT AGCTTCCTT AGCTCCTGAA
     TATAGTTGCC ACCATATAGG TCACTAAAAA AAGAGGTAAA ATCGAAGGAA TCGAGGACTT
2941 AATCTCGATA ACTCAAAAAA TACGCCCGGT AGTGATCTTA TTTCATTATG GTGAAAGTTG
     TTAGAGCTAT TGAGTTTTTT ATGCGGGCCA TCACTAGAAT AAAGTAATAC CACTTTCAAC
3001 GAACCTCTTA CGTGCCGATC AACGTCTCAT TTCGCCAAA AGTTGGCCCA GGGCTTCCCG
     CTTGGAGAAT GCACGGCTAG TTGCAGAGTA AAAGCGGTTT TCAACCGGGT CCCGAAGGGC
3061 GTATCAACAG GGACACCAGG ATTTATTTAT TCTGCGAAGT GATCTTCCGT CACAGGTATT
     CATAGTTGTC CCTGTGGTCC TAAATAAATA AGACGCTTCA CTAGAAGGCA GTGTCCATAA
3121 TATTCGGCGC AAAGTGCGTC GGGTGATGCT GCCAACTTAC TGATTTAGTG TATGATGGTG
     ATAAGCCGCG TTTCACGCAG CCCACTACGA CGGTTGAATG ACTAAATCAC ATACTACCAC
3181 TTTTTGAGGT GCTCCAGTGG CTTCTGTTTC TATCAGCTGT CCCTCCTGTT CAGCTACTGA
     AAAAACTCCA CGAGGTCACC GAAGACAAAG ATAGTCGACA GGGAGGACAA GTCGATGACT
3241 CGGGGTGGTG CGTAACGGCA AAAGCACCGC CGGACATCAG CGCTAGCGGA GTGTATACTG
     GCCCCACCAC GCATTGCCGT TTTCGTGGCG GCCTGTAGTC GCGATCGCCT CACATATGAC
3301 GCTTACTATG TTGCCACTGA TGAGGGTGTC AGTGAAGTGC TTCATGTGGC AGGAGAAAA
     CGAATGATAC AACCGTGACT ACTCCCACAG TCACTTCACG AAGTACACCG TCCTCTTTTT
3361 AGGCTGCACC GGTGCGTCAG CAGAATATGT GATACAGGAT ATATTCCGCT TCCTCGCTCA
     TCCGACGTGG CCACGCAGTC GTCTTATACA CTATGTCCTA TATAAGGCGA AGGAGCGAGT
3421 CTGACTCGCT ACGCTCGGTC GTTCGACTGC GGCGAGCGGA AATGGCTTAC GAACGGGGCG
     GACTGAGCGA TGCGAGCCAG CAAGCTGACG CCGCTCGCCT TTACCGAATG CTTGCCCCGC
3481 GAGATTTCCT GGAAGATGCC AGGAAGATAC TTAACAGGGA AGTGAGAGGG CCGCGGCAAA
     CTCTAAAGGA CCTTCTACGG TCCTTCTATG AATTGTCCCT TCACTCTCCC GGCGCCGTTT
3541 GCCGTTTTTC CATAGGCTCC GCCCCCCTGA CAAGCATCAC GAAATCTGAC GCTCAAATCA
     CGGCAAAAAG GTATCCGAGG CGGGGGGACT GTTCGTAGTG CTTTAGACTG CGAGTTTAGT
3601 GTGGTGGCGA AACCCGACAG GACTATAAAG ATACCAGGCG TTTCCCCTGG CGGCTCCCTC
```

Fig. 7$_2$

```
       CACCACCGCT TTGGGCTGTC CTGATATTTC TATGGTCCGC AAAGGGGACC GCCGAGGGAG
 3661  GTGCGCTCTC CTGTTCCTGC CTTTCGGTTT ACCGGTGTCA TTCCGCTGTT ATGGCCGCGT
       CACGCGAGAG GACAAGGACG GAAAGCCAAA TGGCCACAGT AAGGCGACAA TACCGGCGCA
 3721  TTGTCTCATT CCACGCCTGA CACTCAGTTC CGGGTAGGCA GTTCGCTCCA AGCTGGACTG
       AACAGAGTAA GGTGCGGACT GTGAGTCAAG GCCCATCCGT CAAGCGAGGT TCGACCTGAC
 3781  TATGCACGAA CCCCCCGTTC AGTCCGACCG CTGCGCCTTA TCCGGTAACT ATCGTCTTGA
       ATACGTGCTT GGGGGGCAAG TCAGGCTGGC GACGCGGAAT AGGCCATTGA TAGCAGAACT
 3841  GTCCAACCCG GAAAGACATG CAAAAGCACC ACTGGCAGCA GCCACTGGTA ATTGATTTAG
       CAGGTTGGGC CTTTCTGTAC GTTTTCGTGG TGACCGTCGT CGGTGACCAT TAACTAAATC
 3901  AGGAGTTAGT CTTGAAGTCA TGCGCCGGTT AAGGCTAAAC TGAAAGGACA AGTTTTGGTG
       TCCTCAATCA GAACTTCAGT ACGCGGCCAA TTCCGATTTG ACTTTCCTGT TCAAAACCAC
 3961  ACTGCGCTCC TCCAAGCCAG TTACCTCGGT TCAAAGAGTT GGTAGCTCAG AGAACTTCG
       TGACGCGAGG AGGTTCGGTC AATGGAGCCA AGTTTCTCAA CCATCGAGTC TCTTGGAAGC
 4021  AAAAACCGCC CTGCAAGGCG GTTTTTTCGT TTTCAGAGCA AGAGATTACG CGCAGACCAA
       TTTTTGGCGG GACGTTCCGC CAAAAAAGCA AAAGTCTCGT TCTCTAATGC GCGTCTGTT
 4081  AACGATCTCA AGAAGATCAT CTTATTAATC AGATAAAATA TTTCTAGATT TCAGTGCAAT
       TTGCTAGAGT TCTTCTAGTA GAATAATTAG TCTATTTTAT AAAGATCTAA AGTCACGTTA
 4141  TTATCTCTTC AAATGTAGCA CCTGAAGTCA GCCCCATACG ATATAAGTTG TAATTCTCAT
       AATAGAGAAG TTTACATCGT GGACTTCAGT CGGGGTATGC TATATTCAAC ATTAAGAGTA
 4201  GTTAGTCATG CCCCGCGCCC ACCGGAAGGA GCTGACTGGG TTGAAGGCTC TCAAGGGCAT
       CAATCAGTAC GGGGCGCGGG TGGCCTTCCT CGACTGACCC AACTTCCGAG AGTTCCCGTA
 4261  CGGTCGAGAT CCCGGTGCCT AATGAGTGAG CTAACTTACA TTAATTGCGT TGCGCTCACT
       GCCAGCTCTA GGGCCACGGA TTACTCACTC GATTGAATGT AATTAACGCA ACGCGAGTGA
 4321  GCCCGCTTTC CAGTCGGGAA ACCTGTCGTG CCAGCTGCAT TAATGAATCG GCCAACGCGC
       CGGGCGAAAG GTCAGCCCTT TGGACAGCAC GGTCGACGTA ATTACTTAGC CGGTTGCGCG
 4381  GGGGAGAGGC GGTTTGCGTA TTGGGCGCCA GGGTGGTTTT TCTTTTCACC AGTGAGACGG
       CCCCTCTCCG CCAAACGCAT AACCCGCGGT CCCACCAAAA AGAAAAGTGG TCACTCTGCC
 4441  GCAACAGCTG ATTGCCCTTC ACCGCCTGGC CCTGAGAGAG TTGCAGCAAG CGGTCCACGC
       CGTTGTCGAC TAACGGGAAG TGGCGGACCG GGACTCTCTC AACGTCGTTC GCCAGGTGCG
 4501  TGGTTTGCCC CAGCAGGCGA AAATCCTGTT TGATGGTGGT TAACGGCGGG ATATAACATG
       ACCAAACGGG TCGTCCGCT TTTAGGACAA ACTACCACCA ATTGCCGCCC TATATTGTAC
 4561  AGCTGTCTTC GGTATCGTCG TATCCCACTA CCGAGATGTC CGCACCAACG CGCAGCCCGG
       TCGACAGAAG CCATAGCAGC ATAGGGTGAT GGCTCTACAG GCGTGGTTGC GCGTCGGGCC
 4621  ACTCGGTAAT GGCGCGCATT GCGCCCAGCG CCATCTGATC GTTGGCAACC AGCATCGCAG
       TGAGCCATTA CCGCGCGTAA CGCGGGTCGC GGTAGACTAG CAACCGTTGG TCGTAGCGTC
 4681  TGGGAACGAT GCCCTCATTC AGCATTTGCA TGGTTTGTTG AAAACCGGAC ATGGCACTCC
       ACCCTTGCTA CGGGAGTAAG TCGTAAACGT ACCAAACAAC TTTTGGCCTG TACCGTGAGG
 4741  AGTCGCCTTC CCGTTCCGCT ATCGGCTGAA TTTGATTGCG AGTGAGATAT TTATGCCAGC
       TCAGCGGAAG GGCAAGGCGA TAGCCGACTT AAACTAACGC TCACTCTATA AATACGGTCG
 4801  CAGCCAGACG CAGACGCGCC GAGACAGAAC TTAATGGGCC CGCTAACAGC GCGATTTGCT
       GTCGGTCTGC GTCTGCGCGG CTCTGTCTTG AATTACCCGG GCGATTGTCG CGCTAAACGA
 4861  GGTGACCCAA TGCGACCAGA TGCTCCACGC CCAGTCGCGT ACCGTCTTCA TGGGAGAAAA
       CCACTGGGTT ACGCTGGTCT ACGAGGTGCG GGTCAGCGCA TGGCAGAAGT ACCCTCTTTT
 4921  TAATACTGTT GATGGGTGTC TGGTCAGAGA CATCAAGAAA TAACGCCGGA ACATTAGTGC
       ATTATGACAA CTACCCACAG ACCAGTCTCT GTAGTTCTTT ATTGCGGCCT TGTAATCACG
 4981  AGGCAGCTTC CACAGCAATG GCATCCTGGT CATCCAGCGG ATAGTTAATG ATCAGCCCAC
       TCCGTCGAAG GTGTCGTTAC CGTAGGACCA GTAGGTCGCC TATCAATTAC TAGTCGGGTG
 5041  TGACCGTTG CGCGAGAAGA TTGTGCACCG CCGCTTTACA GGCTTCGACG CCGCTTCGTT
       ACTGCGCAAC GCGCTCTTCT AACACGTGGC GGCGAAATGT CCGAAGCTGC GGCGAAGCAA
 5101  CTACCATCGA CACCACCACG CTGGCACCCA GTTGATCGGC GCGAGATTTA ATCGCCGCGA
       GATGGTAGCT GTGGTGGTGC GACCGTGGGT CAACTAGCCG CGCTCTAAAT TAGCGGCGCT
 5161  CAATTTGCGA CGGCGCGTGC AGGGCCAGAC TGGAGGTGGC AACGCCAATC AGCAACGACT
       GTTAAACGCT GCCGCGCACG TCCCGGTCTG ACCTCCACCG TTGCGGTTAG TCGTTGCTGA
 5221  GTTTGCCCGC CAGTTGTTGT GCCACGCGGT TGGGAATGTA ATTCAGCTCC GCCATCGCCA
       CAAACGGGCG GTCAACAACA CGGTGCGCCA ACCCTTACAT TAAGTCGAGG CGGTAGCGGC
 5281  CTTCCACTTT TTCCCGCGTT TTCGCAGAAA CGTGGCTGGC CTGGTTCACC ACGCGGGAAA
       GAAGGTGAAA AAGGGCGCAA AAGCGTCTTT GCACCGACCG GACCAAGTGG TGCGCCCTTT
 5341  CGGTCTGATA AGAGACACCG GCATACTCTG CGACATCGTA TAACGTTACT GGTTTCACAT
       GCCAGACTAT TCTCTGTGGC CGTATGAGAC GCTGTAGCAT ATTGCAATGA CCAAAGTGTA
 5401  TCACCACCCT GAATTGACTC TCTTCCGGGC GCTATCATGC CATACCGCGA AAGGTTTTGC
       AGTGGTGGGA CTTAACTGAG AGAAGGCCCG CGATAGTACG GTATGCGCT TTCCAAAACG
 5461  GCCATTCGAT GGTGTCCGGG ATCTCGACGC TCTCCCTTAT GCGACTCCTG CATTAGGAAA
       CGGTAAGCTA CCACAGGCCC TAGAGCTGCG AGAGGGAATA CGCTGAGGAC GTAATCCTTT
 5521  TTAATACGAC TCACTATA
       AATTATGCTG AGTGATAT
```

Fig. 7₃

G144704 Cassette

| Fig. 9₁ |
|---------|
| Fig. 9₂ |

Fig. 9

G144704 sequence attR1 and attR2

```
        SacI
     ~~~~~~
   1 GAGCTCGATC ACAAGTTTGT ACAAAAAAGC TGAACGAGAA ACGTAAAATC ATATAAATAT
     CTCGAGCTAG TGTTCAAACA TGTTTTTTCG ACTTGCTCTT TGCATTTTAC TATATTTATA

61 GAATATATTA AATTAGATTT TGCATAAAAA ACAGACTACA TAATACTGTA AAACACAACA
     GTTATATAAT TTAATCTAAA ACGTATTTTT TGTCTGATGT ATTATGACAT TTTGTGTTGT
                     NotI
                 ~~~~~~~~~
 121 TATCCAGTCA CTATGGCGGC CGCCACGTTA AGGGATTTTG GTCATGATCA GCACGTGTTG
     ATAGGTCAGT GATACCGCCG GCGGTGCAAT TCCCTAAAAC CAGTACTAGT CGTGCACAAC

181 ACAATTAATC ATCGGCATAG TATATCGGCA TAGTATAATA CGACAAGGTG AGGAACTAAA
     TGTTAATTAG TAGCCGTATC ATATAGCCGT ATCATATTAT GCTGTTCCAC TCCTTGATTT
                     NcoI
                     ~~~~~~
         MetAlaLys LeuThrSer AlaValProVal LeuThrAla ArgAspVal AlaGlyAlaVal·
 241 CCATGGCCAA GTTGACCAGT GCCGTTCCGG TGCTCACCGC GCGCGACGTC GCCGGAGCGG
     GGTACCGGTT CAACTGGTCA CGGCAAGGCC ACGAGTGGCG CGCGCTGCAG CGGCCTCGCC

·VGluPheTrp ThrAspArg LeuGlyPheSer ArgAspPhe ValGluAsp AspPheAlaGly·
 301 TCGAGTTCTG GACCGACCGG CTCGGGTTCT CCCGGGACTT CGTGGAGGAC GACTTCGCCG
     AGCTCAAGAC CTGGCTGGCC GAGCCCAAGA GGGCCCTGAA GCACCTCCTG CTGAAGCGGC

·GValValArg AspAspVal ThrLeuPheIle SerAlaVal GlnAspGln ValValProAsp·
 361 GTGTGGTCCG GGACGACGTG ACCCTGTTCA TCAGCGCGGT CCAGGACCAG GTGGTGCCGG
     CACACCAGGC CCTGCTGCAC TGGGACAAGT AGTCGCGCCA GGTCCTGGTC CACCACGGCC

·AAsnThrLeu AlaTrpVal TrpValArgGly LeuAspGlu LeuTyrAla GluTrpSerGlu·
 421 ACAACACCCT GGCCTGGGTG TGGGTGCGCG GCCTGGACGA GCTGTACGCC GAGTGGTCGG
     TGTTGTGGGA CCGGACCCAC ACCCACGCGC CGGACCTGCT CGACATGCGG CTCACCAGCC

·GValValSer ThrAsnPhe ArgAspAlaSer GlyProAla MetThrGlu IleGlyGluGln·
 481 AGGTCGTGTC CACGAACTTC CGGGACGCCT CCGGGCCGGC CATGACCGAG ATCGGCGAGC
     TCCAGCACAG GTGCTTGAAG GCCCTGCGGA GGCCCGGCCG GTACTGGCTC TAGCCGCTCG
         BglI                                              ApaLI
     ~~~~~~~~~~~~                                        ~~~~~~~~
     ·GProTrpGly ArgGluPhe AlaLeuArgAsp ProAlaGly AsnCysVal HisPheValAla·
 541 AGCCGTGGGG GCGGGAGTTC GCCCTGCGCG ACCCGGCCGG CAACTGCGTG CACTTCGTGG
     TCGGCACCCC CGCCCTCAAG CGGGACGCGC TGGGCCGGCC GTTGACGCAC GTGAAGCACC

·AGluGluGln Asp***
 601 CCGAGGAGCA GGACTGATCA TGATGATATT ATTTTATCTT GTGCAATGTA ACATCAGAGA
     GGCTCCTCGT CCTGACTAGT ACTACTATAA TAAAATAGAA CACGTTACAT TGTAGTCTCT

661 TTTTGAGACA CGGGCCAGAG CTGCCAGGAA ACAGCTATGA CCATGTAATA CGACTCACTA
     AAAACTCTGT GCCCGGTCTC GACGGTCCTT TGTCGATACT GGTACATTAT GCTGAGTGAT

721 TAGGGGATAT CAGCTGGATG GCAAATAATG ATTTTATTTT GACTGATAGT GACCTGTTCG
     ATCCCCTATA GTCGACCTAC CGTTTATTAC TAAAATAAAA CTGACTATCA CTGGACAAGC
                 AgeI
               ~~~~~~~
 781 TTGCAACACC GGTGCTAGCG TATACCCGAA GTATGTCAAA AGAGGTGTG CTATGAAGCA
     AACGTTGTGG CCACGATCGC ATATGGGCTT CATACAGTTT TCTCCACAC GATACTTCGT

841 GCGTATTACA GTGACAGTTG ACAGCGACAG CTATCAGTTG CTCAAGGCAT ATATGATGTC
     CGCATAATGT CACTGTCAAC TGTCGCTGTC GATAGTCAAC GAGTTCCGTA TATACTACAG

901 AATATCTCCG GTCTGGTAAG CACAACCATG CAGAATGAAG CCCGTCGTCT GCGTGCCGAA
     TTATAGAGGC CAGACCATTC GTGTTGGTAC GTCTTACTTC GGGCAGCAGA CGCACGGCTT

961 CGCTGGAAAG CGGAAAATCA GGAAGGGATG GCTGAGGTCG CCCGGTTTAT TGAAATGAAC
     GCGACCTTTC GCCTTTTAGT CCTTCCCTAC CGACTCCAGC GGGCCAAATA ACTTTACTTG
```

Fig. 9₁

```
                              MetGln PheLysValTyr ThrTyrLys·
1021 GGCTCTTTTG CTGACGAGAA CAGGGACTGG TGAAATGCAG TTTAAGGTTT ACACCTATAA
     CCGAGAAAAC GACTGCTCTT GTCCCTGACC ACTTTACGTC AAATTCCAAA TGTGGATATT

·ArgGluSer ArgTyrArgLeu PheValAsp ValGlnSer AspIleIleAsp ThrProGly·
1081 AAGAGAGAGC CGTTATCGTC TGTTTGTGGA TGTACAGAGT GATATTATTG ACACGCCCGG
     TTCTCTCTCG GCAATAGCAG ACAAACACCT ACATGTCTCA CTATAATAAC TGTGCGGGCC
                                                ApaLI
                                                ~~~~~~~
     ·ArgArgMet ValIleProLeu AlaSerAla ArgLeuLeu SerAspLysVal SerArgGlu·
1141 GCGACGGATG GTGATCCCCC TGGCCAGTGC ACGTCTGCTG TCAGATAAAG TCTCCCGTGA
     CGCTGCCTAC CACTAGGGGG ACCGGTCACG TGCAGACGAC AGTCTATTTC AGAGGGCACT

·LeuTyrPro ValValHisIle GlyAspGlu SerTrpArg MetMetThrThr AspMetAla·
1201 ACTTTACCCG GTGGTGCATA TCGGGGATGA AAGCTGGCGC ATGATGACCA CCGATATGGC
     TGAAATGGGC CACCACGTAT AGCCCCTACT TTCGACCGCG TACTACTGGT GGCTATACCG

·SerValPro ValSerValIle GlyGluGlu ValAlaAsp LeuSerArgArg GluAsnAsp·
1261 CAGTGTGCCG GTCTCCGTTA TCGGGGAAGA AGTGGCTGAT CTCAGCCGCC GCGAAAATGA
     GTCACACGGC CAGAGGCAAT AGCCCCTTCT TCACCGACTA GAGTCGGCGG CGCTTTTACT

·IleLysAsn AlaIleAsnLeu MetPheTrp GlyIle***
1321 CATCAAAAAC GCCATTAACC TGATGTTCTG GGGAATATAA ATGTCAGGCT CCCTTATACA
     GTAGTTTTTG CGGTAATTGG ACTACAAGAC CCCTTATATT TACAGTCCGA GGGAATATGT
             PstI
             ~~~~~~~
1381 CAGCCAGTCT GCAGGTCGAC CATAGTGACT GGATATGTTG TGTTTTACAG TATTATGTAG
     GTCGGTCAGA CGTCCAGCTG GTATCACTGA CCTATACAAC ACAAAATGTC ATAATACATC

1441 TCTGTTTTTT ATGCAAAATC TAATTTAATA TATTGATATT TATATCATTT TACGTTTCTC
     AGACAAAAAA TACGTTTTAG ATTAAATTAT ATAACTATAA ATATAGTAAA ATGCAAAGAG
                                                                HindIII
                                                                ~~~~~
1501 GTTCAGCTTT CTTGTACAAA GTGGTGATAA TTAATTAAGA TCAGATCCGG CTGCTAAGCT
     CAAGTCGAAA GAACATGTTT CACCACTATT AATTAATTCT AGTCTAGGCC GACGATTCGA HindIII
     ~
1561 T
     A
```

Fig. 17 pDEST-CM1 sequence

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                                SacI
                                                                ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGGACCAT GATTACGCCA AGCTATCAAC TTTGTATAGA AAAGTTGAAC GAGAAACGTA
     GAGCCTGGTA CTAATGCGGT TCGATAGTTG AAACATATCT TTTCAACTTG CTCTTTGCAT
 181 AAATGATATA AATATCAATA TATTAAATTA GATTTTGCAT AAAAAACAGA CTACATAATA
     TTTACTATAT TTATAGTTAT ATAATTTAAT CTAAAACGTA TTTTTTGTCT GATGTATTAT
                                               PstI
                                               ~~~~~~~
 241 CTGTAAAACA CAACATATCC AGTCACTATG GTCGACCTGC AGACTGGCTG TGTATAAGGG
     GACATTTTGT GTTGTATAGG TCAGTGATAC CAGCTGGACG TCTGACCGAC ACATATTCCC
 301 AGCCTGACAT TTATATTCCC CAGAACATCA GGTTAATGGC GTTTTTGATG TCATTTTCGC
     TCGGACTGTA AATATAAGGG GTCTTGTAGT CCAATTACCG CAAAAACTAC AGTAAAAGCG
 361 GGTGGCTGAG ATCAGCCACT TCTTCCCCGA TAACGGAGAC CGGCACACTG GCCATATCGG
     CCACCGACTC TAGTCGGTGA AGAAGGGGCT ATTGCCTCTG GCCGTGTGAC CGGTATAGCC
 421 TGGTCATCAT GCGCCAGCTT TCATCCCCGA TATGCACCAC CGGGTAAAGT TCACGGGGGA
     ACCAGTAGTA CGCGGTCGAA AGTAGGGGCT ATACGTGGTG GCCCATTTCA AGTGCCCCCT
                                                         XmaI
                                                         ~~~~~~~
                                                          SmaI
                                                          ~~~~~~~
 481 CTTTATCTGA CAGCAGACGT GCACTGGCCA GGGGGATCAC CATCCGTCGC CCGGGCGTGT
     GAAATAGACT GTCGTCTGCA CGTGACCGGT CCCCCTAGTG GTAGGCAGCG GGCCCGCACA
 541 CAATAATATC ACTCTGTACA TCCACAAACA GACGATAACG GCTCTCTCTT TTATAGGTGT
     GTTATTATAG TGAGACATGT AGGTGTTTGT CTGCTATTGC CGAGAGAGAA AATATCCACA
 601 AAACCTTAAA CTGCATTTCA CCAGCCCCTG TTCTCGTCGG CAAAAGAGCC GTTCATTTCA
     TTTGGAATTT GACGTAAAGT GGTCGGGGAC AAGACGAGCC GTTTTCTCGG CAAGTAAAGT
 661 ATAAACCGGG CGACCTCAGC CATCCCTTCC TGATTTTCCG CTTTCCAGCG TTCGGCACGC
     TATTTGGCCC GCTGGAGTCG GTAGGGAAGG ACTAAAAGGC GAAAGGTCGC AAGCCGTGCG
 721 AGACGACGGG CTTCATTCTG CATGGTTGTG CTTACCGAAC CGGAGATATT GACATCATAT
     TCTGCTGCCC GAAGTAAGAC GTACCAACAC GAATGGCTTG GCCTCTATAA CTGTAGTATA
 781 ATGCCTTGAG CAACTGATAG CTGTCGCTGT CAACTGTCAC TGTAATACGC TGCTTCATAG
     TACGGAACTC GTTGACTATC GACAGCGACA GTTGACAGTG ACATTATGCG ACGAAGTATC
 841 CATACCTCTT TTTGACATAC TTCGGGTATA CATATCAGTA TATATTCTTA TACCGCAAAA
     GTATGGAGAA AAACTGTATG AAGCCCATAT GTATAGTCAT ATATAAGAAT ATGGCGTTTT
 901 ATCAGCGCGC AAATACGCAT ACTGTTATCT GGCTTTTAGT AAGCCGGATC CTCTAGATTA
     TAGTCGCGCG TTTATGCGTA TGACAATAGA CCGAAAATCA TTCGGCCTAG GAGATCTAAT
 961 CGCCCCGCCC TGCCACTCAT CGCAGTACTG TTGTAATTCA TTAAGCATTC TGCCGACATG
     GCGGGGCGGG ACGGTGAGTA GCGTCATGAC AACATTAAGT AATTCGTAAG ACGGCTGTAC
1021 GAAGCCATCA CAAACGGCAT GATGAACCTG AATCGCCAGC GGCATCAGCA CCTTGTCGCC
     CTTCGGTAGT GTTTGCCGTA CTACTTGGAC TTAGCGGTCG CCGTAGTCGT GGAACAGCGG
1081 TTGCGTATAA TATTTGCCCA TGGTGAAAAC GGGGGCGAAG AAGTTGTCCA TATTGGCCAC
     AACGCATATT ATAAACGGGT ACCACTTTTG CCCCCGCTTC TTCAACAGGT ATAACCGGTG
1141 GTTTAAATCA AAACTGGTGA AACTCACCCA GGGATTGGCT GAGACGAAAA ACATATTCTC
     CAAATTTAGT TTTGACCACT TTGAGTGGGT CCCTAACGA CTCTGCTTTT TGTATAAGAG
1201 AATAAACCCT TTAGGGAAAT AGGCCAGGTT TTCACCGTAA CACGCCACAT CTTGCGAATA
     TTATTTGGGA AATCCCTTTA TCCGGTCCAA AAGTGGCATT GTGCGGTGTA GAACGCTTAT
1261 TATGTGTAGA AACTGCCGGA AATCGTCGTG GTATTCACTC CAGAGCGATG AAAACGTTTC
     ATACACATCT TTGACGGCCT TTAGCAGCAC CATAAGTGAG GTCTCGCTAC TTTTGCAAAG
1321 AGTTTGCTCA TGGAAAACGG TGTAACAAGG GTGAACACTA TCCCATATCA CCAGCTCACC
     TCAAACGAGT ACCTTTTGCC ACATTGTTCC CACTTGTGAT AGGGTATAGT GGTCGAGTGG
1381 GTCTTTCATT GCCATACGGA ATTCCGGATG AGCATTCATC AGGCGGGCAA GAATGTGAAT
     CAGAAAGTAA CGGTATGCCT TAAGGCCTAC TCGTAAGTAG TCCGCCCGTT CTTACACTTA
1441 AAAGGCCGGA TAAAACTTGT GCTTATTTTT CTTTACGGTC TTTAAAAAGG CCGTAATATC
     TTTCCGGCCT ATTTTGAACA CGAATAAAAA GAAATGCCAG AAATTTTTCC GGCATTATAG
1501 CAGCTGAACG GTCTGGTTAT AGGTACATTG AGCAACTGAC TGAAATGCCT CAAAATGTTC
     GTCGACTTGC CAGACCAATA TCCATGTAAC TCGTTGACTG ACTTTACGGA GTTTTACAAG
1561 TTTACGATGC CATTGGGATA TATCAACGGT GGTATATCCA GTGATTTTTT CTCCATTTT
     AAATGCTACG GTAACCCTAT ATAGTTGCCA CCATATAGGT CACTAAAAAA GAGGTAAAA
1621 AGCTTCCTTA GCTCCTGAAA ATCTCGACGG ATCCTAACTC AAAATCCACA CATTATACGA
     TCGAAGGAAT CGAGGACTTT TAGAGCTGCC TAGGATTGAG TTTTAGGTGT GTAATATGCT
1681 GCCGGAAGCA TAAAGTGTAA AGCCTGGGGG TGCCTAATGC GGCCGCCATA GTGACTGGAT
     CGGCCTTCGT ATTTCACATT TCGGACCCCC ACGGATTACG CCGGCGGTAT CACTGACCTA
```

Fig. 17₁

```
1741 ATGTTGTGTT TTACAGTATT ATGTAGTCTG TTTTTTATGC AAAATCTAAT TTAATATATT
     TACAACACAA AATGTCATAA TACATCAGAC AAAAAATACG TTTTAGATTA AATTATATAA
1801 GATATTTATA TCATTTTACG TTTCTCGTTC AACTTTATTA TACATAGTTG ATAATTCACT
     CTATAAATAT AGTAAAATGC AAAGAGCAAG TTGAAATAAT ATGTATCAAC TATTAAGTGA
1861 GGCCGTCGTT TTACAACGTC GTGACTGGGA AAACCCTGGC GTTACCCAAC TTAATCGCCT
     CCGGCAGCAA AATGTTGCAG CACTGACCCT TTTGGGACCG CAATGGGTTG AATTAGCGGA
              HindIII
              ~~~~~~~
1921 TGCAGCACAA GCTTGCGGCC GCATAATGCT TAAGTCGAAC AGAAAGTAAT CGTATTGTAC
     ACGTCGTGTT CGAACGCCGG CGTATTACGA ATTCAGCTTG TCTTTCATTA GCATAACATG
1981 ACGGCCGCAT AATCGAAATT AATACGACTC ACTATAGGGG AATTGTGAGC GGATAACAAT
     TGCCGGCGTA TTAGCTTTAA TTATGCTGAG TGATATCCCC TTAACACTCG CCTATTGTTA
2041 TCCCCATCTT AGTATATTAG TTAAGTATAA GAAGGAGATA TACATATGGC AGATCTCAAT
     AGGGGTAGAA TCATATAATC AATTCATATT CTTCCTCTAT ATGTATACCG TCTAGAGTTA
2101 TGGATATCGG CCGCCACGC GATCGCTGAC GTCGGTACCC TCGAGTCTGG TAAAGAAACC
     ACCTATAGCC GGCCGGTGCG CTAGCGACTG CAGCCATGGG AGCTCAGACC ATTTCTTTGG
                                                              AvrII
                                                              ~~
2161 GCTGCTGCGA AATTTGAACG CCAGCACATG GACTCGTCTA CTAGCGCAGC TTAATTAACC
     CGACGACGCT TTAAACTTGC GGTCGTGTAC CTGAGCAGAT GATCGCGTCG AATTAATTGG
     AvrII
     ~~~~
2221 TAGGCTGCTG CCACCGCTGA GCAATAACTA GCATAACCCC TTGGGGCCTC TAAACGGGTC
     ATCCGACGAC GGTGGCGACT CGTTATTGAT CGTATTGGGG AACCCCGGAG ATTTGCCCAG
2281 TTGAGGGGTT TTTTGCTGAA ACCTCAGGCA TTTGAGAAGC ACACGGTCAC ACTGCTTCCG
     AACTCCCCAA AAAACGACTT TGGAGTCCGT AAACTCTTCG TGTGCCAGTG TGACGAAGGC
2341 GTAGTCAATA AACCGGTAAA CCAGCAATAG ACATAAGCGG CTATTTAACG ACCCTGCCCT
     CATCAGTTAT TTGGCCATTT GGTCGTTATC TGTATTCGCC GATAAATTGC TGGGACGGGA
2401 GAACCGACGA CCGGTCATC GTGGCCGGAT CTTGCGGCCC CTCGGCTTGA ACGAATTGTT
     CTTGGCTGCT GGCCCAGTAG CACCGGCCTA GAACGCCGGG GAGCCGAACT TGCTTAACAA
2461 AGACATTATT TGCCGACTAC CTTGGTGATC TCGCCTTTCA CGTAGTGGAC AAAATTCTTCC
     TCTGTAATAA ACGGCTGATG GAACCACTAG AGCGGAAAGT GCATCACCTG TTTAAGAAGG
2521 AACTGATCTG CGCGCGAGGC CAAGCGATCT TCTTCTTGTC CAAGATAAGC CTGTCTAGCT
     TTGACTAGAC GCGCGCTCCG GTTCGCTAGA AGAAGAACAG GTTCTATTCG GACAGATCGA
2581 TCAAGTATGA CGGGCTGATA CTGGGCCGGC AGGCGCTCCA TTGCCCAGTC GGCAGCGACA
     AGTTCATACT GCCCGACTAT GACCCGGCCG TCCGCGAGGT AACGGGTCAG CCGTCGCTGT
2641 TCCTTCGGCG CGATTTTGCC GGTTACTGCG CTGTACCAAA TGCGGGACAA CGTAAGCACT
     AGGAAGCCGC GCTAAAACGG CCAATGACGG GACATGGTTT ACGCCCTGTT GCATTCGTGA
2701 ACATTTCGCT CATCGCCAGC CCAGTCGGGC GGCGAGTTCC ATAGCGTTAA GGTTTCATTT
     TGTAAAGCGA GTAGCGGTCG GGTCAGCCCG CCGCTCAAGG TATCGCAATT CCAAAGTAAA
2761 AGCGCCTCAA ATAGATCCTG TTCAGGAACC GGATCAAAGA GTTCCTCCGC CGCTGGACCT
     TCGCGGAGTT TATCTAGGAC AAGTCCTTGG CCTAGTTTCT CAAGGAGGCG GCGACCTGGA
2821 ACCAAGGCAA CGCTATGTTC TCTTGCTTTT GTCAGCAAGA TAGCCAGATC AATGTCGATC
     TGGTTCCGTT GCGATACAAG AGAACGAAAA CAGTCGTTCT ATCGGTCTAG TTACAGCTAG
2881 GTGGCTGGCT CGAAGATACC TGCAAGAATG TCATTGCGCT GCCATTCTCC AAATTGCAGT
     CACCGACCGA GCTTCTATGG ACGTTCTTAC AGTAACGCGA CGGTAAGAGG TTTAACGTCA
2941 TCGCGCTTAG CTGGATAACG CCACGGAATG ATGTCGTCGT GCACAACAAT GGTGACTTCT
     AGCGCGAATC GACCTATTGC GGTGCCTTAC TACAGCAGCA CGTGTTGTTA CCACTGAAGA
3001 ACAGCGCGGA GAATCTCGCT CTCTCCAAGG GAAGCCGAAG TTTCCAAAAG GTCGTTGATC
     TGTCGCGCCT CTTAGAGCGA GAGAGGTCCC CTTCGGCTTC AAAGGTTTTC CAGCAACTAG
3061 AAAGCTCGCC GCGTTGTTTC ATCAAGCTTT ACGGTCACCG TAACCAGCAA ATCAATATCA
     TTTCGAGCGG CGCAACAAAG TAGTTCGGAA TGCCAGTGGC ATTGGTCGTT TAGTTATAGT
3121 CTGTGTGGCT TCAGGCCGCC ATCCACTGCG GAGCCGTACA AATGTACGGC CAGCAACGTC
     GACACACCGA AGTCCGGCGG TAGGTGACGC CTCGGCATGT TTACATGCCG GTCGTTGCAG
3181 GGTTCGAGAT GGCGCTCGAT GACGCCAACT ACCTCTGATA GTTGAGTCGA TACTTCGGCG
     CCAAGCTCTA CCGCGAGCTA CTGCGGTTGA TGGAGACTAT CAACTCAGCT ATGAAGCCGC
3241 ATCACCGCTT CCCTCATACT CTTCCTTTTT CAATATTATT GAAGCATTTA TCAGGGTTAT
     TAGTGGCGAA GGGAGTATGA GAAGGAAAAA GTTATAATAA CTTCGTAAAT AGTCCCAATA
3301 TGTCTCATGA GCGGATACAT ATTTGAATGT ATTTAGAAAA ATAAACAAAT AGCTAGCTCA
     ACAGAGTACT CGCCTATGTA TAAACTTACA TAAATCTTTT TATTTGTTTA TCGATCGAGT
3361 CTCGGTCGCT ACGCTCCGGG CGTGAGACTG CGGCGGCGC TGCGGACACA TACAAAGTTA
     GAGCCAGCGA TGCGAGGCCC GCACTCTGAC GCCGCCCGCG ACGCCTGTGT ATGTTTCAAT
3421 CCCACAGATT CCGTGGATAA GCAGGGGACT AACATGTGAG GCAAAACAGC AGGGCCGCGC
     GGGTGTCTAA GGCACCTATT CGTCCCCTGA TTGTACACTC CGTTTTGTCG TCCCGGCGCG
3481 CGGTGCCGTT TTTCCATAGG CTCCGCCCTC CTGCCAGAGT TCACATAAAC AGACGCTTTT
     GCCACCGCAA AAAGGTATCC GAGGCGGGAG GACGGTCTCA AGTGTATTTG TCTGCGAAAA
3541 CCGGTGCATC TGTGGGAGCC GTGAGGCTCA ACCATGAATC TGACAGTACG GGCGAAACCC
     GGCCACGTAG ACACCCTCGG CACTCCGAGT TGGTACTTAG ACTGTCATGC CCGCTTTGGG
3601 GACAGACTT AAAGATCCCC GCGGGTCGCT GCGGGTGCGC CCCTCCTTGC CTCTCCTGTT
     CTGTCCTGAA TTTCTAGGGG TGGCAAAGGC CGCCCAGCGA GGGAGAACGC GAGAGGACAA
3661 CCGACCCTGC CGTTTACCGG ATACCTGTTC CGCCTTTCTC CCTTACGGGA AGTGTGGCGC
```

Fig. 17₂

```
      GGCTGGGACG GCAAATGGCC TATGGACAAG GCGGAAAGAG GGAATGCCCT TCACACCGCG
3721  TTTCTCATAG CTCACACACT GGTATCTCGG CTCGGTGTAG GTCGTTCGCT CCAAGCTGGG
      AAAGAGTATC GAGTGTGTGA CCATAGAGCC GAGCCACATC CAGCAAGCGA GGTTCGACCC
3781  CTGTAAGCAA GAACTCCCCG TTCAGCCCGA CTGCTGCGCC TTATCCGGTA ACTGTTCACT
      GACATTCGTT CTTGAGGGGC AAGTCGGGCT GACGACGCGG AATAGGCCAT TGACAAGTGA
3841  TGAGTCCAAC CCGGAAAAGC ACGGTAAAAC GCCACTGGCA GCAGCCATTG GTAACTGGGA
      ACTCAGGTTG GGCCTTTTCG TGCCATTTTG CGGTGACCGT CGTCGGTAAC CATTGACCCT
3901  GTTCGCAGAG GATTTGTTTA GCTAAACACG CGGTTGCTCT TGAAGTGTGC GCCAAAGTCC
      CAAGCGTCTC CTAAACAAAT CGATTTGTGC GCCAACGAGA ACTTCACACG CGGTTTCAGG
3961  GGCTACACTG GAAGGACAGA TTTGGTTGCT GTGCTCTGCG AAAGCCAGTT ACCACGGTTA
      CCGATGTGAC CTTCCTGTCT AAACCAACGA CACGAGACGC TTTCGGTCAA TGGTGCCAAT
4021  AGCAGTTCCC CAACTGACTT AACCTTCGAT CAAACCACCT CCCCAGGTGG TTTTTTCGTT
      TCGTCAAGGG GTTGACTGAA TTGGAAGCTA GTTTGGTGGA GGGGTCCACC AAAAAAGCAA
4081  TACAGGGCAA AAGATTACGC GCAGAAAAAA AGGATCTCAA GAAGATCCTT TGATCTTTTC
      ATGTCCCGTT TTCTAATGCG CGTCTTTTTT TCCTAGAGTT CTTCTAGGAA ACTAGAAAAG
4141  TACTGAACCG CTCTAGATTT CAGTGCAATT TATCTCTTCA AATGTAGCAC CTGAAGTCAG
      ATGACTTGGC GAGATCTAAA GTCACGTTAA ATAGAGAAGT TTACATCGTG GACTTCAGTC
4201  CCCCATACGA TATAAGTTGT AATTCTCATG TTAGTCATGC CCCGCGCCCA CCGGAAGGAG
      GGGGTATGCT ATATTCAACA TTAAGAGTAC AATCAGTACG GGGCGCGGGT GGCCTTCCTC
4261  CTGACTGGGT TGAAGGCTCT CAAGGGCATC GGTCGAGATC CCGGTGCCTA ATGAGTGAGC
      GACTGACCCA ACTTCCGAGA GTTCCCGTAG CCAGCTCTAG GGCCACGGAT TACTCACTCG
4321  TAACTTACAT TAATTGCGTT GCGCTCACTG CCCGCTTTCC AGTCGGGAAA CCTGTCGTGC
      ATTGAATGTA ATTAACGCAA CGCGAGTGAC GGGCGAAAGG TCAGCCCTTT GGACAGCACG
4381  CAGCTGCATT AATGAATCGG CCAACGCGCG GGGAGAGGCG GTTTGCGTAT TGGGCGCCAG
      GTCGACGTAA TTACTTAGCC GGTTGCGCGC CCCTCTCCGC CAAACGCATA ACCCGCGGTC
4441  GGTGGTTTTT CTTTTCACCA GTGAGACGGG CAACAGCTGA TTGCCCTTCA CCGCCTGGCC
      CCACCAAAAA GAAAAGTGGT CACTCTGCCC GTTGTCGACT AACGGGAAGT GGCGGACCGG
4501  CTGAGAGAGT TGCAGCAAGC GGTCCACGCT GGTTTGCCCC AGCAGGCGAA AATCCTGTTT
      GACTCTCTCA ACGTCGTTCG CCAGGTGCGA CCAAACGGGG TCGTCCGCTT TTAGGACAAA
4561  GATGGTGGTT AACGGCGGGA TATAACATGA GCTGTCTTCG GTATCGTCGT ATCCCACTAC
      CTACCACCAA TTGCCGCCCT ATATTGTACT CGACAGAAGC CATAGCAGCA TAGGGTGATG
4621  CGAGATGTCC GCACCAACGC GCAGCCCGGA CTCGGTAATG GCGCGCATTG CGCCCAGCGC
      GCTCTACAGG CGTGGTTGCG CGTCGGGCCT GAGCCATTAC CGCGCGTAAC GCGGGTCGCG
4681  CATCTGATCG TTGGCAACCA GCATCGCAGT GGGAACGATG CCCTCATTCA GCATTTGCAT
      GTAGACTAGC AACCGTTGGT CGTAGCGTCA CCCTTGCTAC GGGAGTAAGT CGTAAACGTA
4741  GGTTTGTTGA AAACCGGACA TGGCACTCCA GTCGCCTTCC CGTTCCGCTA TCGGCTGAAT
      CCAAACAACT TTTGGCCTGT ACCGTGAGGT CAGCGGAAGG GCAAGGCGAT AGCCGACTTA
4801  TTGATTGCGA GTGAGATATT TATGCCAGCC AGCCAGACGC AGACGCGCCG AGACAGAACT
      AACTAACGCT CACTCTATAA ATACGGTCGG TCGGTCTGCG TCTGCGCGGC TCTGTCTTGA
4861  TAATGGGCCC GCTAACAGCG CGATTTGCTG GTGACCCAAT GCGACCAGAT GCTCCACGCC
      ATTACCCGGG CGATTGTCGC GCTAAACGAC CACTGGGTTA CGCTGGTCTA CGAGGTGCGG
4921  CAGTGCCGTA CCGTCTTCAT GGGAGAAAAT AATACTGTTG ATGGGTGTCT GGTCAGAGAC
      GTCAGCGCAT GGCAGAAGTA CCCTCTTTTA TTATGACAAC TACCCACAGA CCAGTCTCTG
4981  ATCAAGAAAT AACGCCGGAA CATTAGTGCA GGCAGCTTCC ACAGCAATGG CATCCTGGTC
      TAGTTCTTTA TTGCGGCCTT GTAATCACGT CCGTCGAAGG TGTCGTTACC GTAGGACCAG
5041  ATCCAGCGGA TAGTTAATGA TCAGCCCACT GACGCGTTGC GCGAGAAGAT TGTGCACCGC
      TAGGTCGCCT ATCAATTACT AGTCGGGTGA CTGCGCAACG CGCTCTTCTA ACACGTGGCG
5101  CGCTTTACAG GCTTCGACGC CGCTTCGTTC TACCATCGAC ACCACCACGC TGGCACCCAG
      GCGAAATGTC CGAAGCTGCG GCGAAGCAAG ATGGTAGCTG TGGTGGTGCG ACCGTGGGTC
5161  TTGATCGGCG CGAGATTTAA TCGCCGCGAC AATTTGCGAC GGCGCGTGCA GGGCCAGACT
      AACTAGCCGC GCTCTAAATT AGCGGCGCTG TTAAACGCTG CCGCGCACGT CCCGGTCTGA
5221  GGAGGTGGCA ACGCCAATCA GCAACGACTG TTTGCCCGCC AGTTGTTGTG CCACGCGGTT
      CCTCCACCGT TGCGGTTAGT CGTTGCTGAC AAACGGGCGG TCAACAACAC GGTGCGCCAA
5281  GGGAATGTAA TTCAGCTCCG CCATCGCCGC TTCCACTTTT TCCCGCGTTT TCGCAGAAAC
      CCCTTACATT AAGTCGAGGC GGTAGCGGCG AAGGTGAAAA AGGGCGCAAA AGCGTCTTTG
5341  GTGGCTGGCC TGGTTCACCA CGCGGGAAAC GGTCTGATAA GAGACACCGG CATACTCTGC
      CACCGACCGG ACCAAGTGGT GCGCCCTTTG CCAGACTATT CTCTGTGGCC GTATGAGACG
5401  GACATCGTAT AACGTTACTG GTTTCACATT CACCACCCTG AATTGACTCT CTTCCGGGCG
      CTGTAGCATA TTGCAATGAC CAAAGTGTAA GTGGTGGGAC TTAACTGAGA GAAGGCCCGC
5461  CTATCATGCC ATACCGCGAA AGGTTTTGCG CCATTCGATG GTGTCCGGGA TCTCGACGCT
      GATAGTACGG TATGGCGCTT TCCAAAACGC GGTAAGCTAC CACAGGCCCT AGAGCTGCGA
5521  CTCCCTTATG CGACTCCTGC ATTAGGAAAT TAATACGACT CACTATA
      GAGGGAATAC GCTGAGGACG TAATCCTTTA ATTATGCTGA GTGATAT
```

Fig. 17₃

| Fig. 19₁ |
|---|
| Fig. 19₂ |
| Fig. 19₃ |

Fig. 19 pDEST-CM2 sequence

```
   1  GGGGAATTGT GAGCGGATAA CAATTCCCCT GTAGAAATAA TTTTGTTTAA CTTTAATAAG
      CCCCTTAACA CTCGCCTATT GTTAAGGGGA CATCTTTATT AAAACAAATT GAAATTATTC
                                                                EcoRI
                                                                ~~~~~~
               NcoI                              BamHI        SacI
               ~~~~~~~                           ~~~~~~       ~~~
  61  GAGATATACC ATGGGCAGCA GCCATCACCA TCATCACCAC AGCCAGGATC CGAATTCGAG
      CTCTATATGG TACCCGTCGT CGGTAGTGGT AGTAGTGGTG TCGGTCCTAG GCTTAAGCTC
      SacI
      ~~~
 121  CTCGGACCAT GATTACGCCA AGCTATCAAC TTTGTATAGA AAAGTTGAAC GAGAAACGTA
      GAGCCTGGTA CTAATGCGGT TCGATAGTTG AAACATATCT TTTCAACTTG CTCTTTGCAT
 181  AAATGATATA AATATCAATA TATTAAATTA GATTTTGCAT AAAAAACAGA CTACATAATA
      TTTACTATAT TTATAGTTAT ATAATTTAAT CTAAAACGTA TTTTTTGTCT GATGTATTAT
                                                 PstI
                                                 ~~~~~~~
 241  CTGTAAAACA CAACATATCC AGTCACTATG GTCGACCTGC AGACTGGCTG TGTATAAGGG
      GACATTTTGT GTTGTATAGG TCAGTGATAC CAGCTGGACG TCTGACCGAC ACATATTCCC
 301  AGCCTGACAT TTATATTCCC CAGAACATCA GGTTAATGGC GTTTTTGATG TCATTTTCGC
      TCGGACTGTA AATATAAGGG GTCTTGTAGT CCAATTACCG CAAAAACTAC AGTAAAAGCG
 361  GGTGGCTGAG ATCAGCCACT TCTTCCCCGA TAACGGAGAC CGGCACACTG GCCATATGCG
      CCACCGACTC TAGTCGGTGA AGAAGGGGCT ATTGCCTCTG GCCGTGTGAC CGGTATAGCG
 421  TGGTCATCAT GCGCCAGCTT TCATCCCCGA TATGCACCAC CGGGTAAAGT TCACGGGGGA
      ACCAGTAGTA CGCGGTCGAA AGTAGGGGCT ATACGTGGTG GCCCATTTCA AGTGCCCCCT
                                                           XmaI
                                                           ~~~~~~
                                                           SmaI
                                                           ~~~~~~~
 481  CTTTATCTGA CAGCAGACGT GCACTGGCCA GGGGGATCAC CATCCGTCGC CCGGGCGTGT
      GAAATAGACT GTCGTCTGCA CGTGACCGGT CCCCCTAGTG GTAGGCAGCG GGCCCGCACA
 541  CAATAATATC ACTCTGTACA TCCACAAACA GACGATAACG GCTCTCTCTT TTATAGGTGT
      GTTATTATAG TGAGACATGT AGGTGTTTGT CTGCTATTGC CGAGAGAGAA AATATCCACA
 601  AAACCTTAAA CTGCATTTCA CCAGCCCCTG TTCTCGTCGG CAAAAGAGCC GTTCATTTCA
      TTTGGAATTT GACGTAAAGT GGTCGGGGAC AAGAGCAGCC GTTTTCTCGG CAAGTAAAGT
 661  ATAAACCGGG CGACCTCAGC CATCCCTTCC TGATTTTCCG CTTTCCAGCG TTCGGCACGC
      TATTTGGCCC GCTGGAGTCG GTAGGGAAGG ACTAAAAGGC GAAAGGTCGC AAGCCGTGCG
 721  AGACGACGGG CTTCATTCTG CATGGTTGTG CTTACCGAAC CGGAGATATT GACATCATAT
      TCTGCTGCCC GAAGTAAGAC GTACCAACAC GAATGGCTTG GCCTCTATAA CTGTAGTATA
 781  ATGCCTTGAG CAACTGATAG CTGTCGCTGT CAACTGTCAC TGTAATACGC TGCTTCATAG
      TACGGAACTC GTTGACTATC GACAGCGACA GTTGACAGTG ACATTATGCG ACGAAGTATC
 841  CATACCTCTT TTTGACATAC TTCGGGTATA CATATCAGTA TATATTCTTA TACCGCAAAA
      GTATGGAGAA AAACTGTATG AAGCCCATAT GTATAGTCAT ATATAAGAAT ATGGCGTTTT
                                                           BamHI
                                                           ~~~~~~~
 901  ATCAGCGCGC AAATACGCAT ACTGTTATCT GGCTTTTAGT AAGCCGGATC CTCTAGATTA
      TAGTCGCGCG TTTATGCGTA TGACAATAGA CCGAAAATCA TTCGGCCTAG GAGATCTAAT
 961  CGCCCCGCCC TGCCACTCAT CGCAGTACTG TTGTAATTCA TTAAGCATTC TGCCGACATG
      GCGGGGCGGG ACGGTGAGTA GCGTCATGAC AACATTAAGT AATTCGTAAG ACGGCTGTAC
1021  GAAGCCATCA CAAACGGCAT GATGAACCTG AATCGCCAGC GGCATCAGCA CCTTGTCGCC
      CTTCGGTAGT GTTTGCCGTA CTACTTGGAC TTAGCGGTCG CCGTAGTCGT GGAACAGCGG
                          NcoI
                          ~~~~~~~
1081  TTGCGTATAA TATTTGCCCA TGGTGAAAAC GGGGGCGAAG AAGTTGTCCA TATTGGCCAC
      AACGCATATT ATAAACGGGT ACCACTTTTG CCCCCGCTTC TTCAACAGGT ATAACCGGTG
1141  GTTTAAATCA AAACTGGTGA AACTCACCCA GGGATTGGCT GAGACGAAAA ACATATTCTC
      CAAATTTAGT TTTGACCACT TTGAGTGGGT CCCTAACCGA CTCTGCTTTT TGTATAAGAG
1201  AATAAACCCT TAGGGAAAT AGGCCAGGTT TCACCGTAA CACGCCACAT CTTGCGAATA
      TTATTTGGGA AATCCCTTTA TCCGGTCCAA AGTGGCATT GTGCGGTGTA GAACGCTTAT
1261  TATGTGTAGA AACTGCCGGA AATCGTCGTG GTATTCATTC CAGAGCGATG AAAACGTTTC
      ATACACATCT TTGACGGCCT TTAGCAGCAC CATAAGTAAG GTCTCGCTAC TTTTGCAAAG
1321  AGTTTGCTCA TGGAAAACGG TGTAACAAGG GTGAACACTA TCCCATATCA CCAGCTCACC
      TCAAACGAGT ACCTTTTGCC ACATTGTTCC CACTTGTGAT AGGGTATAGT GGTCGAGTGG
                          EcoRI
                          ~~~~~~~
1381  GTCTTTCATT GCCATACGGA ATTCCGGATG AGCATTCATC AGGCGGGCAA GAATGTGAAT
      CAGAAAGTAA CGGTATGCCT TAAGGCCTAC TCGTAAGTAG TCCGCCCGTT CTTACACTTA
1441  AAAGGCCGGA TAAAACTTGT GCTTATTTTT CTTTACGGTC TTTAAAAGG CCGTAATATC
      TTTCCGGCCT ATTTTGAACA CGAATAAAAA GAAATGCCAG AAATTTTTCC GGCATTATAG
1501  CAGCTGAACG GTCTGGTTAT AGGTACATTG AGCAACTGAC TGAAATGCCT CAAATGTTC
      GTCGACTTGC CAGACCAATA TCCATGTAAC TCGTTGACTG ACTTTACGGA GTTTTACAAG
1561  TTTACGATGC CATTGGGATA TATCAACGGT GGTATATCCA GTGATTTTTT TCTCCATTTT
```

Fig. 19₁

```
              AAATGCTACG GTAACCCTAT ATAGTTGCCA CCATATAGGT CACTAAAAAA AGAGGTAAAA
                                              BamHI
                                              ~~~~~~~
      1621    AGCTTCCTTA GCTCCTGAAA ATCTCGACGG ATCCTAACTC AAAATCCACA CATTATACGA
              TCGAAGGAAT CGAGGACTTT TAGAGCTGCC TAGGATTGAG TTTTAGGTGT GTAATATGCT
      1681    GCCCGAAGCA TAAAGTGTAA AGCCTGGGGG TGCCTAATGC GGCCGCCATA GTGACTGGAT
              CGGCCTTCGT ATTTCACATT TCGGACCCCC ACGGATTACG CCGGCGGTAT CACTGACCTA
      1741    ATGTTGTGTT TTACAGTATT ATGTAGTCTG TTTTTTATGC AAAATCTAAT TTAATATATT
              TACAACACAA AATGTCATAA TACATCAGAC AAAAAATACG TTTTAGATTA AATTATATAA
      1801    GATATTTATA TCATTTTACG TTTCTCGTTC AACTTTATTA TACATAGTTG ATAATTCACT
              CTATAAATAT AGTAAAATGC AAAGAGCAAG TTGAAATAAT ATGTATCAAC TATTAAGTGA
      1861    GGCCGTCGTT TTACAACGTC GTGACTGGGA AAACCCTGGC GTTACCCAAC TTAATCGCCT
              CCGGCAGCAA AATGTTGCAG CACTGACCCT TTTGGGACCG CAATGGGTTG AATTAGCGGA
                      HindIII
                      ~~~~~~~
      1921    TGCAGCACAA GCTTGCGGCC GCATAATGCT TAAGTCGAAC AGAAAGTAAT CGTATTGTAC
              ACGTCGTGTT CGAACGCCGG CGTATTACGA ATTCAGCTTG TCTTTCATTA GCATAACATG
      1981    ACGGCCGCAT AATCGAAATT AATACGACTC ACTATAGGGG AATTGTGAGC GGATAACAAT
              TGCCGGCGTA TTAGCTTTAA TTATGCTGAG TGATATCCCC TTAACACTCG CCTATTGTTA
      2041    TCCCCATCTT AGTATATTAG TTAAGTATAA GAAGGAGATA TACATATGGC AGATCTCAAT
              AGGGGTAGAA TCATATAATC AATTCATATT CTTCCTCTAT ATGTATACCG TCTAGAGTTA
      2101    TGGATATCGG CCGGCCACGC GATCGCTGAC GTCGGTACCC TCGAGTCTGG TAAAGAAACC
              ACCTATAGCC GGCCGGTGCG CTAGCGACTG CAGCCATGGG AGCTCAGACC ATTTCTTTGG
      2161    GCTGCTGCGA AATTTGAACG CCAGCACATG GACTCGTCTA CTAGCGCAGC TTAATTAACC
              CGACGACGCT TTAAACTTGC GGTCGTGTAC CTGAGCAGAT GATCGCGTCG AATTAATTGG
      2221    TAGGCTGCTG CCACCGCTGA GCAATAACTA GCATAACCCC TTGGGGCCTC TAAACGGGTC
              ATCCGACGAC GGTGGCGACT CGTTATTGAT CGTATTGGGG AACCCCGGAG ATTTGCCCAG
      2281    TTGAGGGGTT TTTTGCTGAA ACCTCAGGCA TTTGAGAAGC ACACGGTCAC ACTGCTTCCG
              AACTCCCCAA AAAACGACTT TGGAGTCCGT AAACTCTTCG TGTGCCAGTG TGACGAAGGC
      2341    GTAGTCAATA AACCGGTAAA CCAGCAATAG ACATAAGCGG CTATTTAACG ACCCTGCCCT
              CATCAGTTAT TTGGCCATTT GGTCGTTATC TGTATTCGCC GATAAATTGC TGGGACGGGA
      2401    GAACCGACGA CAAGCTGACG ACCGGGTCTC CGCAAGTGGC ACTTTTCGGG GAAATGTGCG
              CTTGGCTGCT GTTCGACTGC TGGCCCAGAG GCGTTCACCG TGAAAAGCCC CTTTACACGC
      2461    CGGAACCCCT ATTTGTTTAT TTTTCTAAAT ACATTCAAAT ATGTATCCGC TCATGAATTA
              GCCTTGGGGA TAAACAAATA AAAAGATTTA TGTAAGTTTA TACATAGGCG AGTACTTAAT
      2521    ATTCTTAGAA AAACTCATCG AGCATCAAAT GAAACTGCAA TTTATTCATA TCAGGATTAT
              TAAGAATCTT TTTGAGTAGC TCGTAGTTTA CTTTGACGTT AAATAAGTAT AGTCCTAATA
      2581    CAATACCATA TTTTTGAAAA AGCCGTTTCT GTAATGAAGG AGAAAACTCA CCGAGGCAGT
              GTTATGGTAT AAAAACTTTT TCGGCAAAGA CATTACTTCC TCTTTTGAGT GGCTCCGTCA
      2641    TCCATAGGAT GGCAAGATCC TGGTATCGGT CTGCGATTCC GACTCGTCCA ACATCAATAC
              AGGTATCCTA CCGTTCTAGG ACCATAGCCA GACGCTAAGG CTGAGCAGGT TGTAGTTATG
      2701    AACCTATTAA TTTCCCCTCG TCAAAAATAA GGTTATCAAG TGAGAAATCA CCATGAGTGA
              TTGGATAATT AAAGGGGAGC AGTTTTTATT CCAATAGTTC ACTCTTTAGT GGTACTCACT
      2761    CGACTGAATC CGGTGAGAAT GGCAAAAGTT TATGCATTTC TTTCCAGACT TGTTCAACAG
              GCTGACTTAG GCCACTCTTA CCGTTTTCAA ATACGTAAAG AAAGGTCTGA ACAAGTTGTC
      2821    GCCAGCCATT ACGCTCGTCA TCAAAATCAC TCGCATCAAC CAAACCGTTA TTCATTCGTG
              CGGTCGGTAA TGCGAGCAGT AGTTTTAGTG AAGCGTAGTTG GTTTGGCAAT AAGTAAGCAC
      2881    ATTGCGCCTG AGCGAGACGA AATACGCGGT CGCTGTTAAA AGGACAATTA CAAACAGGAA
              TAACGCGGAC TCGCTCTGCT TTATGCGCCA GCGACAATTT TCCTGTTAAT GTTTGTCCTT
      2941    TCGAATGCAA CCGGCGCAGG AACACTGCCA GCGCATCAAC AATATTTTCA CCTGAATCAG
              AGCTTACGTT GGCCGCGTCC TTGTGACGGT CGCGTAGTTG TTATAAAAGT GGACTTAGTC
                                                                    XmaI
                                                                    ~~~~~~
                                                                    SmaI
                                                                    ~~~~~~
      3001    GATATTCTTC TAATACCTGG AATGCTGTTT TCCCGGGGAT CGCAGTGGTG AGTAACCATG
              CTATAAGAAG ATTATGGACC TTACGACAAA AGGGCCCCTA GCGTCACCAC TCATTGGTAC
      3061    CATCATCAGG AGTACGGATA AAATGCTTGA TGGTCGGAAG AGGCATAAAT TCCGTCAGCC
              GTAGTAGTCC TCATGCCTAT TTTACGAACT ACCAGCCTTC TCCGTATTTA AGGCAGTCGG
      3121    AGTTTAGTCT GACCATCTCA TCTGTAACAT CATTGGCAAC GCTACCTTTG CCATGTTTCA
              TCAAATCAGA CTGGTAGAGT AGACATTGTA GTAACCGTTG CGATGGAAAC GGTACAAAGT
                                                                    ClaI
                                                                    ~~~~~~
      3181    GAAACAACTC TGGCGCATCG GGCTTCCCAT ACAATCGATA GATTGTCGCA CCTGATTGCC
              CTTTGTTGAG ACCGCGTAGC CCGAAGGGTA TGTTAGCTAT CTAACAGCGT GGACTAACGG
      3241    CGACATTATC GCGAGCCCAT TTATACCCAT ATAAATCGAC ATCATGTTG GAATTTAATC
              GCTGTAATAG CGCTCGGGTA AATATGGGTA TATTTAGTCG TAGGTACAAC CTTAAATTAG
      3301    GCGGCCTAGA GCAAGACGTT TCCCGTTGAA TATGGCTCAT ACTCTTCCTT TTTCAATATT
              CGCCGGATCT CGTTCTGCAA AGGGCAACTT ATACCGAGTA TGAGAAGGAA AAAGTTATAA
      3361    ATTGAAGCAT TTATCAGGGT TATTGTCTCA TGAGCGGATA CATATTTGAA TGTATTTAGA
              TAACTTCGTA AATAGTCCCA ATAACAGAGT ACTCGCCTAT GTATAAACTT ACATAAATCT
      3421    AAAATAAACA AATAGGCATG CAGCGCTCTT CCGCTTCCTC GCTCACTGAC TCGCTACGCT
              TTTTATTTGT TTATCCGTAC GTCGCGAGAA GGCGAAGGAG CGAGTGACTG AGCGATGCGA
```

Fig. 19₂

```
3481  CGGTCGTTCG ACTGCGGCGA GCGGTGTCAG CTCACTCAAA AGCGGTAATA CGGTTATCCA
      GCCAGCAAGC TGACGCCGCT CGCCACAGTC GAGTGAGTTT TCGCCATTAT GCCAATAGGT
3541  CAGAATCAGG GGATAAAGCC GGAAAGAACA TGTGAGCAAA AAGCAAAGCA CCGGAAGAAG
      GTCTTAGTCC CCTATTTCGG CCTTTCTTGT ACACTCGTTT TTCGTTTCGT GGCCTTCTTC
3601  CCAACGCCGC AGGCGTTTTT CCATAGGCTC CGCCCCCCTG ACGAGCATCA CAAAAATCGA
      GGTTGCGGCG TCCGCAAAAA GGTATCCGAG GCGGGGGGAC TGCTCGTAGT GTTTTTAGCT
3661  CGCTCAAGCC AGAGGTGGCG AAACCCGACA GGACTATAAA GATACCAGGC GTTTCCCCCT
      GCGAGTTCGG TCTCCACCGC TTTGGGCTGT CCTGATATTT CTATGGTCCG CAAAGGGGGA
3721  GGAAGCTCCC TCGTGCGCTC TCCTGTTCCG ACCCTGCCGC TTACCGGATA CCTGTCCGCC
      CCTTCGAGGG AGCACGCGAG AGGACAAGGC TGGGACGGCG AATGGCCTAT GGACAGGCGG
3781  TTTCTCCCTT CGGGAAGCGT GGCGCTTTCT CATAGCTCAC GCTGTTGGTA TCTCAGTTCG
      AAAGAGGGAA GCCCTTCGCA CCGCGAAAGA GTATCGAGTG CGACAACCAT AGAGTCAAGC
3841  GTGTAGGTCG TTCGCTCCAA GCTGGGCTGT GTGCACGAAC CCCCCGTTCA GCCCGACCGC
      CACATCCAGC AAGCGAGGTT CGACCCGACA CACGTGCTTG GGGGGCAAGT CGGGCTGGCG
3901  TGCGCCTTAT CCGGTAACTA TCGTCTTGAG TCCAACCCGG TAAGACACGA CTTATCGCCA
      ACGCGGAATA GGCCATTGAT AGCAGAACTC AGGTTGGGCC ATTCTGTGCT GAATAGCGGT
3961  CTGGCAGCAG CCATTGGTAA CTGATTTAGA GGACTTTGTC TTGAAGTTAT GCACCTGTTA
      GACCGTCGTC GGTAACCATT GACTAAATCT CCTGAAACAG AACTTCAATA CGTGGACAAT
4021  AGGCTAAACT GAAAGAACAG ATTTTGGTGA GTGCGGTCCT CCAACCCACT TACCTTGGTT
      TCCGATTTGA CTTTCTTGTC TAAAACCACT CACGCCAGGA GGTTGGGTGA ATGGAACCAA
4081  CAAAGAGTTG GTAGCTCAGC GAACCTTGAG AAAACCACCG TTGGTAGCGG TGGTTTTTCT
      GTTTCTCAAC CATCGAGTCG CTTGGAACTC TTTTGGTGGC AACCATCGCC ACCAAAAGA
4141  TTATTTATGA GATGATGAAT CAATCGGTCT ATCAAGTCAA CGAACAGTCA TTCCGTTACT
      AATAAATACT CTACTACTTA GTTAGCCAGA TAGTTCAGTT GCTTGTCGAT AAGGCAATGA
4201  CTAGATTTCA GTGCAATTTA TCTCTTCAAA TGTAGCACCT GAAGTCAGCC CCATACGATA
      GATCTAAAGT CACGTTAAAT AGAGAAGTTT ACATCGTGGA CTTCAGTCGG GGTATGCTAT
4261  TAAGTTGTAA TTCTCATGTT AGTCATGCCC CGCGCCCACC GGAAGGAGCT GACTGGGTTG
      ATTCAACATT AAGAGTACAA TCAGTACGGG GCGCGGGTGG CCTTCCTCGA CTGACCCAAC
4321  AAGGCTCTCA AGGGCATCGG TCGAGATCCC GGTGCCTAAT GAGTGAGCTA ACTTACATTA
      TTCCGAGAGT TCCCGTAGCC AGCTCTAGGG CCACGGATTA CTCACTCGAT TGAATGTAAT
4381  ATTGCGTTGC GCTCACTGCC CGCTTTCCAG TCGGGAAACC TGTCGTGCCA GCTGCATTAA
      TAACGCAACG CGAGTGACGG GCGAAAGGTC AGCCCTTTGG ACAGCACGGT CGACGTAATT
4441  TGAATCGGCC AACGCGCGGG GAGAGGCGGT TTGCGTATTG GGCGCCAGGG TGGTTTTTCT
      ACTTAGCCGG TTGCGCGCCC CTCTCCGCCA AACGCATAAC CCGCGGTCCC ACCAAAAAGA
4501  TTTCACCAGT GAGACGGGCA ACAGCTGATT GCCCTTCACC GCCTGGCCCT GAGAGAGTTG
      AAAGTGGTCA CTCTGCCCGT TGTCGACTAA CGGGAAGTGG CGGACCGGGA CTCTCTCAAC
4561  CAGCAGCGG TCCACGCTGG TTTGCCCCAG CAGGCGAAAA TCCTGTTTGA TGGTGGTTAA
      GTCGTTCGCC AGGTGCGACC AAAACGGGGTC GTCCGCTTTT AGGACAAACT ACCACCAATT
4621  CGGCGGGATA TAACATGAGC TGTCTTCGGT ATCGTCGTAT CCCACTACCG AGATGTCCGC
      GCCGCCCTAT ATTGTACTCG ACAGAAGCCA TAGCAGCATA GGGTGATGGC TCTACAGGCG
4681  ACCAACGCGC AGCCCGGACT CGGTAATGGC GCGCATTGCG CCCAGCGCCA TCTGATCGTT
      TGGTTGCGCG TCGGGCCTGA GCCATTACCG CGCGTAACGC GGGTCGCGGT AGACTAGCAA
4741  GGCAACCAGC ATCGCAGTGG GAACGATGCC CTCATTCAGC ATTTGCATGG TTTGTTGAAA
      CCGTTGGTCG TAGCGTCACC CTTGCTACGG GAGTAAGTCG TAAACGTACC AAACAACTTT
4801  ACCGGACATG GCACTCCAGT CGCCTTCCCG TTCCGCTATC GGCTGAATTT GATTGCGAGT
      TGGCCTGTAC CGTGAGGTCA GCGGAAGGGC AAGGCGATAG CCGACTTAAA CTAACGCTCA
4861  GAGATATTTA TGCCAGCCAG CCAGAACGCAG ACGCGCCGAG ACAGAACTTA ATGGGCCCGC
      CTCTATAAAT ACGGTCGGTC GGTCTGCGTC TGCGCGGCTC TGTCTTGAAT TACCCGGGCG
4921  TAACAGCGCG ATTTGCTGGT GACCCAATGC GACCAGATGC TCCACGCCCA GTCGCGTACC
      ATTGTCGCGC TAAACGACCA CTGGGTTACG CTGGTCTACG AGGTGCGGGT CAGCGCATGG
4981  GTCTTCATGG GAGAAAATAA TACTGTTGAT GGGTGTCTGG TCAGAGACAT CAAGAAATAA
      CAGAAGTACC CTCTTTTATT ATGACAACTA CCCACAGACC AGTCTCTGTA GTTCTTTATT
5041  CGCCGGAACA TTAGTGCAGG CAGCTTCAC AGCAATGGCA TCCTGGTCAT CCAGCGGATA
      GCGGCCTTGT AATCACGTCC GTCGAAGGTG TCGTTACCGT AGGACCAGTA GGTCGCCTAT
5101  GTTAATGATC AGCCCACTGA CGCGTTGCGC GAGAAGATTG TGCACCGCCG CTTTACAGGC
      CAATTACTAG TCGGGTGACT GCGCAACGCG CTCTTCTAAC ACGTGGCGGC GAAATGTCCG
5161  TTCGACGCCG CTTCGTTCTA CCATCGACAC CACCACGCTG GCACCCAGTT GATCGGCGCG
      AAGCTGCGGC GAAGCAAGAT GGTAGCTGTG GTGGTGCGAC CGTGGGTCAA CTAGCCGCGC
5221  AGATTTAATC GCCGCGACAA TTTGCGACGG CGCGTGCAGG GCCAGACTGG AGGTGGCAAC
      TCTAAATTAG CGGCGCTGTT AAACGCTGCC GCGCACGTCC CGGTCTGACC TCCACCGTTG
5281  GCCAATCAGC AACGACTGTT TGCCCGCCAG TTGTTGTGCC ACGCGGTTGG GAATGTAATT
      CGGTTAGTCG TTGCTGACAA ACGGGCGGTC AACAACACGG TGCGCCAACC CTTACATTAA
5341  CAGCTCCGCC ATCGCCGCTT CCACTTTTTC CCGCGTTTTC GCAGAAACGT GGCTGGCCTG
      GTCGAGGCGG TAGCGGCGAA GGTGAAAAAG GGCGCAAAAG CGTCTTTGCA CCGACCGGAC
5401  GTTCACCACG CGGGAAACGG TCTGATAAGA GACACCGGCA TACTCTGCGA CATCGTATAA
      CAAGTGGTGC GCCCTTTGCC AGACTATTCT CTGTGGCCGT ATGAGACGCT GTAGCATATT
5461  CGTTACTGGT TTCACATTCA CCACCCTGAA TTGACTCTCT TCCGGGCGCT ATCATGCCAT
      GCAATGACCA AAGTGTAAGT GGTGGGACTT AACTGAGAGA AGGCCCGCGA TAGTACGGTA
5521  ACCGCGAAAG GTTTTGCGCC ATTCGATGGT GTCCGGGATC TCGACGCTCT CCCTTATGCG
      TGGCGCTTTC CAAAACGCGG TAAGCTACCA CAGGCCCTAG AGCTGCGAGA GGGAATACGC
5581  ACTCCTGCAT TAGGAAAATTA ATACGACTCA CTATA
      TGAGGACGTA ATCCTTTAAT TATGCTGAGT GATAT
```

Multisite TetR cassette sequence:

```
        SacI
        ~~~~~~
   1  GAGCTCGACC ATGATTACGC CAAGCTATCA ACTTTGTATA GAAAAGTTGA ACGAGAAACG
      CTCGAGCTGG TACTAATGCG GTTCGATAGT TGAAACATAT CTTTTCAACT TGCTCTTTGC
  61  TAAAATGATA TAAATATCAA TATATTAAAT TAGATTTTGC ATAAAAAACA GACTACATAA
      ATTTTACTAT ATTTATAGTT ATATAATTTA ATCTAAAACG TATTTTTTGT CTGATGTATT
                                                       PstI
                                                       ~~~~~~~
 121  TACTGTAAAA CACAACATAT CCAGTCACTA TGGTCGACCT GCAGACTGGC TGTGTATAAG
      ATGACATTTT GTGTTGTATA GGTCAGTGAT ACCAGCTGGA CGTCTGACCG ACACATATTC
 181  GGAGCCTGAC ATTTATATTC CCCAGAACAT CAGGTTAATG GCGTTTTTGA TGTCATTTTC
      CCTCGGACTG TAAATATAAG GGGTCTTGTA GTCCAATTAC CGCAAAAACT ACAGTAAAAG
 241  GCGGTGGCTG AGATCAGCCA CTTCTTCCCC GATAACGGAG ACCGGCACAC TGGCCATATC
      CGCCACCGAC TCTAGTCGGT GAAGAAGGGG CTATTGCCTC TGGCCGTGTG ACCGGTATAG
 301  GGTGGTCATC ATGCGCCAGC TTTCATCCCC GATATGCACC ACCGGGTAAA GTTCACGGGG
      CCACCAGTAG TACGCGGTCG AAAGTAGGGG CTATACGTGG TGGCCCATTT CAAGTGCCCC
                                                               SmaI
                                                               ~~~~~~
                                                               XmaI
                                                               ~~~~~~
                           ApaLI                               AvaI
                           ~~~~~~                              ~~~~~~
 361  GACTTTATCT GACAGCAGAC GTGCACTGGC CAGGGGGATC ACCATCCGTC GCCCGGGCGT
      CTGAAATAGA CTGTCGTCTG CACGTGACCG GTCCCCCTAG TGGTAGGCAG CGGGCCCGCA
 421  GTCAATAATA TCACTCTGTA CATCCACAAA CAGACGATAA CGGCTCTCTC TTTTATAGGT
      CAGTTATTAT AGTGAGACAT GTAGGTGTTT GTCTGCTATT GCCGAGAGAG AAAATATCCA
 481  GTAAACCTTA AACTGCATTT CACCAGCCCC TGTTCTCGTC GGCAAAAGAG CCGTTCATTT
      CATTTGGAAT TTGACGTAAA GTGGTCGGGG ACAAGAGCAG CCGTTTTCTC GGCAAGTAAA
 541  CAATAAACCG GGCGACCTCA GCCATCCCTT CCTGATTTTC CGCTTTCCAG CGTTCGGCAC
      GTTATTTGGC CCGCTGGAGT CGGTAGGGAA GGACTAAAAG GCGAAAGGTC GCAAGCCGTG
 601  GCAGACGACG GGCTTCATTC TGCATGGTTG TGCTTACCGA ACCGGAGATA TTGACATCAT
      CGTCTGCTGC CCGAAGTAAG ACGTACCAAC ACGAATGGCT TGGCCTCTAT AACTGTAGTA
 661  ATATGCCTTG AGCAACTGAT AGCTGTCGCT GTCAACTGTC ACTGTAATAC GCTGCTTCAT
      TATACGGAAC TCGTTGACTA TCGACAGCGA CAGTTGACAG TGACATTATG CGACGAAGTA
 721  AGCATACCTC TTTTTGACAT ACTTCGGGTA TACATATCAG TATATATTCT TATACCGCAA
      TCGTATGGAG AAAAACTGTA TGAAGCCCAT ATGTATAGTC ATATATAAGA ATATGGCGTT
                                                               XbaI
                                                               ~~~~~~
                                                       BamHI
                                                       ~~~~~~~
 781  AAATCAGCGC GCAAATACGC ATACTGTTAT CTGGCTTTTA GTAAGCCGGA TCCTCTAGAG
      TTTAGTCGCG CGTTTATGCG TATGACAATA GACCGAAAAT CATTCGGCCT AGGAGATCTC
 841  ACGCGATGGA TATGTTCTGC CAAGGGTTGG TTTGCGCATT CACAGTTCTC CGCAAGAATT
      TGCGCTACCT ATACAAGACG GTTCCCAACC AAACGCGTAA GTGTCAAGAG GCGTTCTTAA
 901  GATTGGCTCC AATTCTTGGA GTGGTGAATC CGTTAGCGAG GTGCCGCCGG CTTCCATTCA
      CTAACCGAGG TTAAGAACCT CACCACTTAG GCAATCGCTC CACGGCGGCC GAAGGTAAGT
 961  GGTCGAGGTG GCCCGGCTCC ATGCACCGCG ACGCAACGCG GGGAGGCAGA CAAGGTATAG
      CCAGCTCCAC CGGGCCGAGG TACGTGGCGC TGCGTTGCGC CCCTCCGTCT GTTCCATATC
1021  GGCGGCGCCT ACAATCCATG CCAACCCGTT CCATGTGCTC GCCGAGGCGG CATAAATCGC
      CCGCCGCGGA TGTTAGGTAC GGTTGGGCAA GGTACACGAG CGGCTCCGCC GTATTTAGCG
1081  CGTGACGATC AGCGGTCCAG TGATCGAAGT TAGGCTGGTA AGAGCCGCGA GCGATCCTTG
      GCACTGCTAG TCGCCAGGTC ACTAGCTTCA ATCCGACCAT TCTCGGCGCT CGCTAGGAAC
1141  AAGCTGTCCC TGATGGTCGT CATCTACCTG CCTGGACAGC ATGGCCTGCA ACGCGGGCAT
      TTCGACAGGG ACTACCAGCA GTAGATGGAC GGACCTGTCG TACCGGACGT TGCGCCCGTA
1201  CCCGATGCCG CCGGAAGCGA GAAGAATCAT AATGGGGAAG GCCATCCAGC CTCGCGTCGC
      GGGCTACGGC GGCCTTCGCT CTTCTTAGTA TTACCCCTTC CGGTAGGTCG GAGCGCAGCG
1261  GAACGCCAGC AAGACGTAGC CCAGCGCGTC GGCCGCCATG CCGGCGATAA TGGCCTGCTT
      CTTGCGGTCG TTCTGCATCG GGTCGCGCAG CCGGCGGTAC GGCCGCTATT ACCGGACGAA
1321  CTCGCCGAAA CGTTTGGTGG CGGGACCAGT GACGAAGGCT TGAGCGAGGG CGTGCAAGAT
      GAGCGGCTTT GCAAACCACC GCCCTGGTCA CTGCTTCCGA ACTCGCTCCC GCACGTTCTA
1381  TCCGAATACC GCAAGCGACA GGCCGATCAT CGTCGCGCTC CAGCGAAAGC GGTCCTCGCC
      AGGCTTATGG CGTTCGCTGT CCGGCTAGTA GCAGCGCGAG GTCGCTTTCG CCAGGAGCGG
1441  GAAAATGACC CAGAGCGCTG CCGGCACCTG TCCTACGAGT TGCATGATAA AGAAGACAGT
      CTTTTACTGG GTCTCGCGAC GGCCGTGGAC AGGATGCTCA ACGTACTATT TCTTCTGTCA
1501  CATAAGTGCG GCGACGATAG TCATGCCCCG CGCCCACCGG AAGGAGCTGA CTGGGTTGAA
      GTATTCACGC CGCTGCTATC AGTACGGGGC GCGGGTGGCC TTCCTCGACT GACCCAACTT
                                                        EcoNI
                                                        ~~~~~~~~~~~
```

Fig. 21₁

```
1561  GGCTCTCAAG GGCATCGGTC GACGCTCTCC CTTATGCGAC TCCTGCATTA GGAAGCAGCC
      CCGAGAGTTC CCGTAGCCAG CTGCGAGAGG GAATACGCTG AGGACGTAAT CCTTCGTCGG
1621  CAGTAGTAGG TTGAGGCCGT TGAGCACCGC CGCCGCAAGG AATGGTGCAT GCAAGGAGAT
      GTCATCATCC AACTCCGGCA ACTCGTGGCG GCGGCGTTCC TTACCACGTA CGTTCCTCTA
1681  GGCGCCCAAC AGTCCCCCGG CCACGGGGCC TGCCACCATA CCCACGCCGA ACAAGCGCT
      CCGCGGGTTG TCAGGGGGCC GGTGCCCCGG ACGGTGGTAT GGGTGCGGCT TTGTTCGCGA
1741  CATGAGCCCG AAGTGGCGAG CCCGATCTTC CCCATCGGTG ATGTCGGCGA TATAGGCGCC
      GTACTCGGGC TTCACCGCTC GGGCTAGAAG GGGTAGCCAC TACAGCCGCT ATATCCGCGG
                                                                BamHI
                                                                ~~~~~~
1801  AGCAACCGCA CCTGTGGCGC CGGTGATGCC GGCCACGATG CGTCCGGCGT AGAGGATCCA
      TCGTTGGCGT GGACACCGCG GCCACTACGG CCGGTGCTAC GCAGGCCGCA TCTCCTAGGT
1861  CAGGACGGGT GTGGTCGCCA TGATCGCGTA GTCGATAGTG GCTCCAAGTA GCGAAGCGAG
      GTCCTGCCCA CACCAGCGGT ACTAGCGCAT CAGCTATCAC CGAGGTTCAT CGCTTCGCTC
1921  CAGGACTGGG CGGCGGCCAA AGCGGTCGGA CAGTGCTCCG AGAACGGGTG CGCATAGAAA
      GTCCTGACCC GCCGCCGGTT TCGCCAGCCT GTCACGAGGC TCTTGCCCAC GCGTATCTTT
1981  TTGCATCAAC GCATATAGCG CTAGCAGCAC GCCATAGTGA CTGGCGATGC TGTCGGAATG
      AACGTAGTTG CGTATATCGC GATCGTCGTG CGGTATCACT GACCGCTACG ACAGCCTTAC
2041  GACGATATCC CGCAAGAGGC CCGGCAGTAC CGGCATAACC AAGCCTATGC CTACAGCATC
      CTGCTATAGG GCGTTCTCCG GGCCGTCATG GCCGTATTGG TTCGGATACG GATGTCGTAG
2101  CAGGGTGACG GTGCCGAGGA TGACGATGAG CGCATTGTTA GATTTCATAC ACGGTGCCTG
      GTCCCACTGC CACGGCTCCT ACTGCTACTC GCGTAACAAT CTAAAGTATG TGCCACGGAC
                                                 HindIII
                                                 ~~~~~~~
                                                        ClaI
                                                        ~~~~~~
2161  ACTGCGTTAG CAATTTAACT GTGATAAACT ACCGCATTAA AGCTTATCGA TGATAAGCTG
      TGACGCAATC GTTAAATTGA CACTATTTGA TGGCGTAATT TCGAATAGCT ACTATTCGAC
                      NotI
                      ~~~~~~~~
2221  TCAAACATGA GAAGCGGCCG CCATAGTGAC TGGATATGTT GTGTTTTACA GTATTATGTA
      AGTTTGTACT CTTCGCCGGC GGTATCACTG ACCTATACAA CACAAAATGT CATAATACAT
2281  GTCTGTTTTT TATGCAAAAT CTAATTTAAT ATATTGATAT TTATATCATT TTACGTTTCT
      CAGACAAAAA ATACGTTTTA GATTAAATTA TATAACTATA AATATAGTAA AATGCAAAGA
2341  CGTTCAACTT TATTATACAT AGTTGATAAT TCACTGGCCG TCGTTTTACA ACGTCGTGAC
      GCAAGTTGAA ATAATATGTA TCAACTATTA AGTGACCGGC AGCAAAATGT TGCAGCACTG
                                                                HindIII
                                                                ~~~~~~
2401  TGGGAAAACC CTGGCGTTAC CCAACTTAAT CGCCTTGCAG CACAAGCTT
      ACCCTTTTGG GACCGCAATG GGTTGAATTA GCGGAACGTC GTGTTCGAA
```

Fig. 21$_2$

| Fig. 23$_1$ |
|:---:|
| Fig. 23$_2$ |
| Fig. 23$_3$ |
| Fig. 23$_4$ |

Fig. 23 pDEST-CM3 sequence

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                                 EcoRI
                                                                 ~~~~~~
              NcoI                              BamHI        SacI
              ~~~~~~                            ~~~~~~       ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGACCATG ATTACGCCAA GCTATCAACT TTGTATAGAA AAGTTGAACG AGAAACGTAA
     GAGCTGGTAC TAATGCGGTT CGATAGTTGA AACATATCTT TTCAACTTGC TCTTTGCATT
 181 AATGATATAA ATATCAATAT ATTAAATTAG ATTTTGCATA AAAAACAGAC TACATAATAC
     TTACTATATT TATAGTTATA TAATTTAATC TAAAACGTAT TTTTTGTCTG ATGTATTATG
                                                PstI
                                                ~~~~~~~
 241 TGTAAAACAC AACATATCCA GTCACTATGG TCGACCTGCA GACTGGCTGT GTATAAGGGA
     ACATTTTGTG TTGTATAGGT CAGTGATACC AGCTGGACGT CTGACCGACA CATATTCCCT
 301 GCCTGACATT TATATTCCCC AGAACATCAG GTTAATGGCG TTTTTGATGT CATTTTCGCG
     CGGACTGTAA ATATAAGGGG TCTTGTAGTC CAATTACCGC AAAAACTACA GTAAAAGCGC
 361 GTGGCTGAGA TCAGCCACTT CTTCCCCGAT AACGGAGACC GGCACACTGG CCATATCGGT
     CACCGACTCT AGTCGGTGAA GAAGGGGCTA TTGCCTCTGG CCGTGTGACC GGTATAGCCA
 421 GGTCATCATG CGCCAGCTTT CATCCCCGAT ATGCACCACC GGGTAAAGTT CACGGGGGAC
     CCAGTAGTAC GCGGTCGAAA GTAGGGGCTA TACGTGGTGG CCCATTTCAA GTGCCCCCTG
 481 TTTATCTGAC AGCAGACGTG CACTGGCCAG GGGGATCACC ATCCGTCGCC CGGGCGTGTC
     AAATAGACTG TCGTCTGCAC GTGACCGGTC CCCCTAGTGG TAGGCAGCGG GCCCGCACAG
 541 AATAATATCA CTCTGTACAT CCACAAACAG ACGATAACGG CTCTCTCTTT TATAGGTGTA
     TTATTATAGT GAGACATGTA GGTGTTTGTC TGCTATTGCC GAGAGAGAAA ATATCCACAT
 601 AACCTTAAAC TGCATTTCAC CCCCCTGT TCTCGTCGGC AAAAGAGCCG TTCATTTCAA
     TTGGAATTTG ACGTAAAGTG GTCGGGACA AGAGCAGCCG TTTTCTCGGC AAGTAAAGTT
 661 TAAACCGGGC GACCTCAGCC ATCCCTTCCT GATTTTCCGC TTTCCAGCGT TCGGCACGCA
     ATTTGGCCCG CTGGAGTCGG TAGGGAAGGA CTAAAAGGCG AAAGGTCGCA AGCCGTGCGT
 721 GACGACGGGC TTCATTCTGC ATGGTTGTGC TTACCGAACC GGAGATATTG ACATCATATA
     CTGCTGCCCG AAGTAAGACG TACCAACACG AATGGCTTGG CCTCTATAAC TGTAGTATAT
 781 TGCCTTGAGC AACTGATAGC TGTCGCTGTC AACTGTCACT GTAATACGCT GCTTCATAGC
     ACGGAACTCG TTGACTATCG ACAGCGACAG TTGACAGTGA CATTATGCGA CGAAGTATCG
 841 ATACCTCTTT TTGACATACT TCGGGTATAC ATATCAGTAT ATATTCTTAT ACCGCAAAAA
     TATGGAGAAA AACTGTATGA AGCCCATATG TATAGTCATA TATAAGAATA TGGCGTTTTT
                                                         BamHI
                                                         ~~~~~~~~
 901 TCAGCGCGCA AATACGCATA CTGTTATCTG GCTTTTAGTA AGCCGGATCC TCTAGAGACG
     AGTCGCGCGT TTATGCGTAT GACAATAGAC CGAAAATCAT TCGGCCTAGG AGATCTCTGC
 961 CGATGGATAT GTTCTGCCAA GGGTTGGTTT GCGCATTCAC AGTTCTCCGC AAGAATTGAT
     GCTACCTATA CAAGACGGTT CCCAACCAAA CGCGTAAGTG TCAAGAGGCG TTCTTAACTA
1021 TGGCTCCAAT TCTTGGAGTG GTGAATCCGT TAGCGAGGTG CCGCCGGCTT CCATTCAGGT
     ACCGAGGTTA AGAACCTCAC CACTTAGGCA ATCGCTCCAC GGCGGCCGAA GGTAAGTCCA
1081 CGAGGTGGCC CGGCTCCATG CACCGCGACG CAACGCGGGG AGGCAGACAA GGTATAGGGC
     GCTCCACCGG GCCGAGGTAC GTGGCGCTGC GTTGCGCCCC TCCGTCTGTT CCATATCCCG
1141 GGCGCCTACA ATCCATGCCA ACCCGTTCCA TGTGCTCGCC GAGGCGGCAT AAATCGCCGT
     CCGCGGATGT TAGGTACGGT TGGGCAAGGT ACACGAGCGG CTCCGCCGTA TTTAGCGGCA
1201 GACGATCAGC GGTCCAGTGA TCGAAGTTAG GCTGGTAAGA GCCGCGAGCG ATCCTTGAAG
     CTGCTAGTCG CCAGGTCACT AGCTTCAATC CGACCATTCT CGGCGCTCGC TAGGAACTTC
1261 CTGTCCCTGA TGGTCGTCAT CTACCTGCCT GGACAGCATG GCCTGCAACG CGGGCATCCC
     GACAGGGACT ACCAGCAGTA GATGGACGGA CCTGTCGTAC CGGACGTTGC GCCCGTAGGG
1321 GATGCCGCCG GAAGCGAGAA GAATCATAAT GGGGAAGGCC ATCCAGCCTC GCGTCGCGAA
     CTACGGCGGC CTTCGCTCTT CTTAGTATTA CCCCTTCCGG TAGGTCGGAG CGCAGCGCTT
1381 CGCCAGCAAG ACGTAGCCCA GCGCGTCGGC CGCCATGCCG GCGATAATGG CCTGCTTCTC
     GCGGTCGTTC TGCATCGGGT CGCGCAGCCG GCGGTACGGC CGCTATTACC GGACGAAGAG
1441 GCCGAAACGT TTGGTGGCGG ACCAGTGAC GAAGGCTTGA GCGAGGGCGT GCAAGATTCC
     CGGCTTTGCA AACCACCGCC CTGGTCACTG CTTCCGAACT CGCTCCCGCA CGTTCTAAGG
1501 GAATACCGCA AGCGACAGGC CGCGCTCCAG CGAAGAGCGG CGAAACGGGT CCTCGCCGAA
     CTTATGGCGT TCGCTGTCCG GCGCGAGGTC GCTTCTCGCC GCTTTGCCCA GGAGCGGCTT
1561 AATGACCCAG AGCGCTGCCG GCACCTGTCC TACGAGTTGC ATGATAAAGA AGACAGTCAT
     TTACTGGGTC TCGCGACGGC CGTGGACAGG ATGCTCAACG TACTATTTCT TCTGTCAGTA
1621 AAGTGCGGCG ACGATAGTCA TGCCCCGCGC CCACCGGAAG GAGCTGACTG GGTTGAAGGC
     TTCACGCCGC TGCTATCAGT ACGGGGCGCG GGTGGCCTTC CTCGACTGAC CCAACTTCCG
                                                         EcoNI
                                                         ~~~~~~~~~~~~
1681 TCTCAAGGGC ATCGGTCGAC GCTCTCCCTT ATGCGACTCC TGCATTAGGA AGCAGCCCAG
     AGAGTTCCCG TAGCCAGCTG CGAGAGGGAA TACGCTGAGG ACGTAATCCT TCGTCGGGTC
```

Fig. 23₁

```
1741  TAGTAGGTTG AGGCCGTTGA GCACCGCCGC CGCAAGGAAT GGTGCATGCA AGGAGATGGC
      ATCATCCAAC TCCGGCAACT CGTGGCGGCG GCGTTCCTTA CCACGTACGT TCCTCTACCG
1801  GCCCAACAGT CCCCCGGCCA CGGGGCCTGC CACCATACCC ACGCCGAAAC AAGCGCTCAT
      CGGGTTGTCA GGGGGCCGGT GCCCCGGACG GTGGTATGGG TGCGGCTTTG TTCGCGAGTA
1861  GAGCCCGAAG TGGCGAGCCC GATCTTCCCC ATCGGTGATG TCGGCGATAT AGGCGCCAGC
      CTCGGGCTTC ACCGCTCGGG CTAGAAGGGG TAGCCACTAC AGCCGCTATA TCCGCGGTCG
                                                                 BamHI
                                                                 ~~~~~~
1921  AACCGCACCT GTGGCGCCGG TGATGCCGGC CACGATGCGT CCGGCGTAGA GGATCCACAG
      TTGGCGTGGA CACCGCGGCC ACTACGGCCG GTGCTACGCA GGCCGCATCT CCTAGGTGTC
1981  GACGGGTGTG GTCGCCATGA TCGCGTAGTC GATAGTGGCT CCAAGTAGCG AAGCGAGCAG
      CTGCCCACAC CAGCGGTACT AGCGCATCAG CTATCACCGA GGTTCATCGC TTCGCTCGTC
2041  GACTGGGCGG CGGCCAAAGC GGTCGGACAG TGCTCCGAGA ACGGGTGCGC ATAGAAATTG
      CTGACCCGCC GCCGGTTTCG CCAGCCTGTC ACGAGGCTCT TGCCCACGCG TATCTTTAAC
2101  CATCAACGCA TATAGCGCTA GCAGCACGCC ATAGTGACTG GCGATGCTGT CGGAATGGAC
      GTAGTTGCGT ATATCGCGAT CGTCGTGCGG TATCACTGAC CGCTACGACA GCCTTACCTG
2161  GATATCCCGC AAGAGGCCCG GCAGTACCGG CATAACCAAG CCTATGCCTA CAGCATCCAG
      CTATAGGGCG TTCTCCGGGC CGTCATGGCC GTATTGGTTC GGATACGGAT GTCGTAGGTC
2221  GGTGACGGTG CCGAGGATGA CGATGAGCGC ATTGTTAGAT TTCATACACG GTGCCTGACT
      CCACTGCCAC GGCTCCTACT GCTACTCGCG TAACAATCTA AAGTATGTGC CACGGACTGA
                                                    HindIII
                                                    ~~~~~~~
2281  GCGTTAGCAA TTTAACTGTG ATAAACTACC GCATTAAAGC TTATCGATGA TAAGCTGTCA
      CGCAATCGTT AAATTGACAC TATTTGATGG CGTAATTTCG AATAGCTACT ATTCGACAGT
2341  AACATGAGAA GCGGCCGCCA TAGTGACTGG ATATGTTGTG TTTTACAGTA TTATGTAGTC
      TTGTACTCTT CGCCGGCGGT ATCACTGACC TATACAACAC AAAATGTCAT AATACATCAG
2401  TGTTTTTTAT GCAAAATCTA ATTTAATATA TTGATATTTA TATCATTTTA CGTTTCTCGT
      ACAAAAAATA CGTTTTAGAT TAAATTATAT AACTATAAAT ATAGTAAAAT GCAAAGACTA
2461  TCAACTTTAT TATACATAGT TGATAATTCA CTGGCCGTCG TTTTACAACG TCGTGACTGG
      AGTTGAAATA ATATGTATCA ACTATTAAGT GACCGGCAGC AAAATGTTGC AGCACTGACC
                                                        HindIII
                                                        ~~~~~~
2521  GAAAACCCTG GCGTTACCCA ACTTAATCGC CTTGCAGCAC AAGCTTGCGG CCGCATAATG
      CTTTTGGGAC CGCAATGGGT TGAATTAGCG GAACGTCGTG TTCGAACGCC GGCGTATTAC
2581  CTTAAGTCGA ACAGAAAGTA ATCGTATTGT ACACGGCCGC ATAATCGAAA TTAATACGAC
      GAATTCAGCT TGTCTTTCAT TAGCATAACA TGTGCCGGCG TATTAGCTTT AATTATGCTG
2641  TCACTATAGG GGAATTGTGA GCGGATAACA ATTCCCCATC TTAGTATATT AGTTAAGTAT
      AGTGATATCC CCTTAACACT CGCCTATTGT TAAGGGGTAG AATCATATAA TCAATTCATA
2701  AAGAAGGAGA TATACATATG GCAGATCTCA ATTGGATATC GGCCGGCCAC GCGATCGCTG
      TTCTTCCTCT ATATGTATAC CGTCTAGAGT TAACCTATAG CCGGCCGGTG CGCTAGCGAC
2761  ACGTCGGTAC CCTCGAGTCT GGTAAAGAAA CCGCTGCTGC GAAATTTGAA CGCCAGCACA
      TGCAGCCATG GGAGCTCAGA CCATTTCTTT GGCGACGACG CTTTAAACTT GCGGTCGTGT
2821  TGGACTCGTC TACTAGCGCA GCTTAATTAA CCTAGGCTGC TGCCACCGCT GAGCAATAAC
      ACCTGAGCAG ATGATCGCGT CGAATTAATT GGATCCGACG ACGGTGGCGA CTCGTTATTG
2881  TAGCATAACC CCTTGGGGCC TCTAAACGGG TCTTGAGGGG TTTTTTGCTG AAACCTCAGG
      ATCGTATTGG GGAACCCCGG AGATTTGCCC AGAACTCCCC AAAAAACGAC TTTGGAGTCC
2941  CATTTGAGAA GCACACGGTC ACACTGCTTC CGGTAGTCAA TAAACCGGTA AACCAGCAAT
      GTAAACTCTT CGTGTGCCAG TGTGACGAAG GCCATCAGTT ATTTGGCCAT TTGGTCGTTA
3001  AGACATAAGC GGCTATTTAA CGACCCTGCC CTGAACCGAC GACCGGGTCG AATTTGCTTT
      TCTGTATTCG CCGATAAATT GCTGGGACGG GACTTGGCTG CTGGCCCAGC TTAAACGAAA
3061  CGAATTTCTG CCATTCATCC GCTTATTATC ACTTATTCAG GCGTAGCACC AGGCGTTTAA
      GCTTAAAGAC GGTAAGTAGG CGAATAATAG TGAATAAGTC CGCATCGTGG TCCGCAAATT
3121  GGGCACCAAT AACTGCCTTA AAAAAATTAC GCCCCGCCCT GCCACTCATC GCAGTACTGT
      CCCGTGGTTA TTGACGGAAT TTTTTTAATG CGGGGCGGGA CGGTGAGTAG CGTCATGACA
3181  TGTAATTCAT TAAGCATTCT GCCGACATGG AAGCCATCAC AGACGGCATG ATGAACCTGA
      ACATTAAGTA ATTCGTAAGA CGGCTGTACC TTCGGTAGTG TCTGCCGTAC TACTTGGACT
3241  ATCGCCAGCG GCATCAGCAC CTTGTCGCCT TGCGTATAAT ATTTGCCCAT AGTGAAAACG
      TAGCGGTCGC CGTAGTCGTG GAACAGCGGA ACGCATATTA TAAACGGGTA TCACTTTTGC
3301  GGGGCGAAGA AGTTGTCCAT ATTGGCCACG TTTAAATCAA AACTGGTGAA ACTCACCCAG
      CCCCGCTTCT TCAACAGGTA TAACCGGTGC AAATTTAGTT TTGACCACTT TGAGTGGGTC
3361  GGATTGGCTG AGACGAAAAA CATATTCTCA ATAAACCCTT TAGGGAAATA GGCCAGGTTT
      CCTAACCGAC TCTGCTTTTT GTATAAGAGT TATTTGGGAA ATCCCTTTAT CCGGTCCAAA
3421  TCACCGTAAC ACGCCACATC TTGCGAATAT ATGTGTAGAA ACTGCCGGAA ATCGTCGTGG
      AGTGGCATTG TGCGGTGTAG AACGCTTATA TACACATCTT TGACGGCCTT TAGCAGCACC
3481  TATTCACTCC AGAGCGATGA AAACGTTTCA GTTTGCTCAT GGAAAACGGT GTAACAAGGG
      ATAAGTGAGG TCTCGCTACT TTTGCAAAGT CAAACAGAGTA CCTTTTGCCA CATTGTTCCC
3541  TGAACACTAT CCCATATCAC CAGCTCACCG TCTTCATTG CCATACGGAA CTCCGGATGA
      ACTTGTGATA GGGTATAGTG GTCGAGTGGC AGAAAGTAAC GGTATGCCTT GAGGCCTACT
3601  GCATTCATCA GGCGGGCAAG AATGTGAATA AAGGCCGGAT AAAACTTGTG CTTATTTTTC
      CGTAAGTAGT CCGCCCGTTC TTACACTTAT TTCCGGCCTA TTTTGAACAC GAATAAAAAG
3661  TTTACGGTCT TTAAAAAGGC CGTAATATCC AGCTGAACGG TCTGGTTATA GGTACATTGA
      AAATGCCAGA AATTTTTCCG GCATTATAGG TCGACTTGCC AGACCAATAT CCATGTAACT
3721  GCAACTGACT GAAATGCCTC AAAATGTTCT TTACGATGCC ATTGGGATAT ATCAACGGTG
```

Fig. 23$_2$

```
           CGTTGACTGA CTTTACGGAG TTTTACAAGA AATGCTACGG TAACCCTATA TAGTTGCCAC
     3781  GTATATCCAG TGATTTTTTT CTCCATTTTA GCTTCCTTAG CTCCTGAAAA TCTCGATAAC
           CATATAGGTC ACTAAAAAAA GAGGTAAAAT CGAAGGAATC GAGGACTTTT AGAGCTATTG
     3841  TCAAAAAATA CGCCCGGTAG TGATCTTATT TCATTATGGT GAAAGTTGGA ACCTCTTACG
           AGTTTTTTAT GCGGGCCATC ACTAGAATAA AGTAATACCA CTTTCAACCT TGGAGAATGC
     3901  TGCCGATCAA CGTCTCATTT TCGCCAAAAG TTGGCCCAGG GCTTCCCGGT ATCAACAGGG
           ACGGCTAGTT GCAGAGTAAA AGCGGTTTTC AACCGGGTCC CGAAGGGCCA TAGTTGTCCC
     3961  ACACCAGGAT TTATTTATTC TGCGAAGTGA TCTTCCGTCA CAGGTATTTA TTCGGCGCAA
           TGTGGTCCTA AATAAATAAG ACGCTTCACT AGAAGGCAGT GTCCATAAAT AAGCCGCGTT
     4021  AGTGCGTCGG GTGATGCTGC CAACTTACTG ATTTAGTGTA TGATGGTGTT TTTGAGGTGC
           TCACGCAGCC CACTACGACG GTTGAATGAC TAAATCACAT ACTACCACAA AAACTCCACG
     4081  TCCAGTGGCT TCTGTTTCTA TCAGCTGTCC CTCCTGTTCA GCTACTGACG GGGTGGTGCG
           AGGTCACCGA AGACAAAGAT AGTCGACAGG GAGGACAAGT CGATGACTGC CCCACCACGC
     4141  TAACGGCAAA AGCACCGCCG GACATCAGCG CTAGCGGAGT GTATACTGGC TTACTATGTT
           ATTGCCGTTT TCGTGGCGGC CTGTAGTCGC GATCGCCTCA CATATGACCG AATGATACAA
     4201  GGCACTGATG AGGGTGTCAG TGAAGTGCTT CATGTGGCAG GAGAAAAAAG GCTGCACCGG
           CCGTGACTAC TCCCACAGTC ACTTCACGAA GTACACCGTC CTCTTTTTTC CGACGTGGCC
     4261  TGCCTCAGCA GAATATGTGA TACAGGATAT ATTCCGCTTC CTCGCTCACT GACTCGCTAC
           ACGCAGTCGT CTTATACACT ATGTCCTATA TAAGGCGAAG GAGCGAGTGA CTGAGCGATG
     4321  GCTCGGTCGT TCGACTGCGG CGAGCGGAAA TGGCTTACGA ACGGGGCGGA GATTTCCTGG
           CGAGCCAGCA AGCTGACGCC GCTCGCCTTT ACCGAATGCT TGCCCCGCCT CTAAAGGACC
     4381  AAGATGCCAG GAAGATACTT AACAGGGAAG TGAGAGGGCC GCGGCAAAGC CGTTTTTCCA
           TTCTACGGTC CTTCTATGAA TTGTCCCTTC ACTCTACCGG CGCCGTTTCG GCAAAAAGGT
     4441  TAGGCTCCGC CCCCCTGACA AGCATCACGA AATCTGACGC TCAAATCAGT GGTGGCGAAA
           ATCCGAGGCG GGGGGACTGT TCGTAGTGCT TTAGACTGCG AGTTTAGTCA CCACCGCTTT
     4501  CCCGACAGGA CTATAAAGAT ACCAGGCGTT TCCCCTGGCG GCTCCCTCGT GCGCTCTCCT
           GGGCTGTCCT GATATTTCTA TGGTCCGCAA AGGGGACCGC CGAGGGAGCA CGCGAGAGGA
     4561  GTTCCTGCCT TTCGGTTTAC CGGTGTCATT CCGCTGTTAT GGCCGCGTTT GTCTCATTCC
           CAAGGACGGA AAGCCAAATG GCCACAGTAA GGCGACAATA CCGGCGCAAA CAGAGTAAGG
     4621  ACGCCTGACA CTCAGTTCCG GGTAGGCAGT TCGCTCCAAG CTGGACTGTA TGCACGAACC
           TGCGGACTGT GAGTCAAGGC CCATCCGTCA AGCGAGGTTC GACCTGACAT ACGTGCTTGG
     4681  CCCCGTTCAG TCCGACCGCT GCGCCTTATC CGGTAACTAT CGTCTTGAGT CCAACCCGGA
           GGGGCAAGTC AGGCTGGCGA CGCGGAATAG GCCATTGATA GCAGAACTCA GGTTGGGCCT
     4741  AAGACATGCA AAAGCACCAC TGGCAGCAGC CACTGGTAAT TGATTTAGAG GAGTTAGTCT
           TTCTGTACGT TTTCGTGGTG ACCGTCGTCG GTGACCATTA ACTAAATCTC CTCAATCAGA
     4801  TGAAGTCATG CGCCGGTTAA GGCTAAACTG AAAGGACAAG TTTTGGTGAC TGCGCTCCTC
           ACTTCAGTAC GCGGCCAATT CCGATTTGAC TTTCCTGTTC AAAACCACTG ACGCGAGGAG
     4861  CAAGCCAGTT ACCTCGGTTC AAAGAGTTGG TAGCTCAGAG AACCTTCGAA AAACCGCCCT
           GTTCGGTCAA TGGAGCCAAG TTTCTCAACC ATCGAGTCTC TTGGAAGCTT TTTGGCGGGA
     4921  GCAAGGCGGT TTTTTCGTTT TCAGAGCAAG AGATTACGCG CAGACCAAAA CGATCTCAAG
           CGTTCCGCCA AAAAAGCAAA AGTCTCGTTC TCTAATGCGC GTCTGGTTTT GCTAGAGTTC
     4981  AAGATCATCT TATTAATCAG ATAAAATATT TCTAGATTTC AGTGCAATTT ATCTCTTCAA
           TTCTAGTAGA ATAATTAGTC TATTTTATAA AGATCTAAAG TCACGTTAAA TAGAGAAGTT
     5041  ATGTAGCACC TGAAGTCAGC CCCATACGAT ATAAGTTGTA ATTCTCATGT TAGTCATGCC
           TACATCGTGG ACTTCAGTCG GGGTATGCTA TATTCAACAT TAAGAGTACA ATCAGTACGG
     5101  CCCGCGCCCAC CGGAAGGAGC TGACTGGGTT GAAGGCTCTC AAGGGCATCG GTCGAGATCC
           GGGCGCGGGTG GCCTTCCTCG ACTGACCCAA CTTCCGAGAG TTCCCGTAGC CAGCTCTAGG
     5161  CGGTGCCTAA TGAGTGAGCT AACTTACATT AATTGCGTTG CGCTCACTGC CCGCTTTCCA
           GCCACGGATT ACTCACTCGA TTGAATGTAA TTAACGCAAC GCGAGTGACG GGCGAAAGGT
     5221  GTCGGGAAAC CTGTCGTGCC AGCTGCATTA ATGAATCGGC CAACGCGCGG GGAGAGGCGG
           CAGCCCTTTG GACAGCACGG TCGACGTAAT TACTTAGCCG GTTGCGCGCC CCTCTCCGCC
     5281  TTTGCGTATT GGGCGCCAGG GTGGTTTTTC TTTTCACCAG TGAGACGGGC AACAGCTGAT
           AAACGCATAA CCCGCGGTCC CACCAAAAAG AAAAGTGGTC ACTCTGCCCG TTGTCGACTA
     5341  TGCCCTTCAC CGCCTGGCCC TGAGAGAGTT GCAGCAAGCG GTCCACGCTG GTTTGCCCCA
           ACGGGAAGTG GCGGACCGGG ACTCTCTCAA CGTCGTTCGC CAGGTGCGAC CAAACGGGGT
     5401  GCAGGCGAAA ATCCTGTTTG ATGGTGGTTA ACGGCGGGAT ATAACATGAG CTGTCTTCGG
           CGTCCGCTTT TAGGACAAAC TACCACCAAT TGCCGCCCTA TATTGTACTC GACAGAAGCC
     5461  TATCGTCGTA TCCCACTACC GAGATGTCCG CACCAACGCG CAGCCCGGAC TCGGTAATGG
           ATAGCAGCAT AGGGTGATGG CTCTACAGGC GTGGTTGCGC GTCGGGCCTG AGCCATTACC
     5521  CGCGCATTGC GCCCAGCGCC ATCTGATCGT TGGCAACCAG CATCGCAGTG GAACGATGC
           GCGCGTAACG CGGGTCGCGG TAGACTAGCA ACCGTTGGTC GTAGCGTCAC CCTTGCTACG
     5581  CCTCATTCAG CATTTGCATG GTTTGTTGAA AACCGACAT GGCACTCGAG TCGCCTTCCC
           GGAGTAAGTC GTAAACGTAC CAAACAACTT TTGGCCTGTA CCGTGAGGTC AGCGGAAGGG
     5641  GTTCCGCTAT CGGCTGAATT TGATTGCGAG TGAGATATTT ATGCCAGCCA GCCAGACGCA
           CAAGGCGATA GCCGACTTAA ACTAACGCTC ACTCTATAAA TACGGTCGGT CGGTCTGCGT
     5701  GACGCGCCGA GACAGAACTT AATGGGCCCG CTAACAGCGC GATTTGCTGG TGACCCAATG
           CTGCGCGGCT CTGTCTTGAA TTACCCGGGC GATTGTCGCG CTAAACGACC ACTGGGTTAC
     5761  CGACCAGATG CTCCACGCCC AGTCGCGTAC CGTCTTCATG GGAGAAAATA ATACTGTTGA
           GCTGGTCTAC GAGGTGCGGG TCAGCGCATG GCAGAAGTAC CCTCTTTTAT TATGACAACT
     5821  TGGGTGTCTG GTCAGAGACA TCAAGAAATA ACGCCGGAAC ATTAGTGCAG GCAGCTTCCA
           ACCCACAGAC CAGTCTCTGT AGTTCTTTAT TGCGGCCTTG TAATCACGTC CGTCGAAGGT
     5881  CAGCAATGGC ATCCTGGTCA TCCAGCGGAT AGTTAATGAT CAGCCCACTG ACGCGTTGCG
           GTCGTTACCG TAGGACCAGT AGGTCGCCTA TCAATTACTA GTCGGGTGAC TGCGCAACGC
```

Fig. 23₃

```
5941  CGAGAAGATT GTGCACCGCC GCTTTACAGG CTTCGACGCC GCTTCGTTCT ACCATCGACA
      GCTCTTCTAA CACGTGGCGG CGAAATGTCC GAAGCTGCGG CGAAGCAAGA TGGTAGCTGT
6001  CCACCACGCT GGCACCCAGT TGATCGGCGC GAGATTTAAT CGCCGCGACA ATTTGCGACG
      GGTGGTGCGA CCGTGGGTCA ACTAGCCGCG CTCTAAATTA GCGGCGCTGT TAAACGCTGC
6061  GCGCGTGCAG GGCCAGACTG GAGGTGGCAA CGCCAATCAG CAACGACTGT TTGCCCGCCA
      CGCGCACGTC CCGGTCTGAC CTCCACCGTT GCGGTTAGTC GTTGCTGACA AACGGGCGGT
6121  GTTGTTGTGC CACGCGGTTG GGAATGTAAT TCAGCTCCGC CATCGCCGCT TCCACTTTTT
      CAACAACACG GTGCGCCAAC CCTTACATTA AGTCGAGGCG GTAGCGGCGA AGGTGAAAAA
6181  CCCGCGTTTT CGCAGAAACG TGGCTGGCCT GGTTCACCAC GCGGGAAACG GTCTGATAAG
      GGGCGCAAAA GCGTCTTTGC ACCGACCGGA CCAAGTGGTG CGCCCTTTGC CAGACTATTC
6241  AGACACCGGC ATACTCTGCG ACATCGTATA ACGTTACTGG TTTCACATTC ACCACCCTGA
      TCTGTGGCCG TATGAGACGC TGTAGCATAT TGCAATGACC AAAGTGTAAG TGGTGGGACT
6301  ATTGACTCTC TTCCGGGCGC TATCATGCCA TACCGCGAAA GGTTTTGCGC CATTCGATGG
      TAACTGAGAG AAGGCCCGCG ATAGTACGGT ATGGCGCTTT CCAAAACGCG GTAAGCTACC
                                                              EcoNI
                                                       ~~~~~~~~~~~~
6361  TGTCCGGGAT CTCGACGCTC TCCCTTATGC GACTCCTGCA TTAGGAAATT AATACGACTC
      ACAGGCCCTA GAGCTGCGAG AGGGAATACG CTGAGGACGT AATCCTTTAA TTATGCTGAG
6421  ACTATA
      TGATAT
```

Fig. 23₄

| Fig. $25_1$ |
|---|
| Fig. $25_2$ |
| Fig. $25_3$ |
| Fig. $25_4$ |

Fig. 25 pDEST-CM4 sequence

```
   1 GGGGAATTGT GAGCGGATAA CAATTCCCCT CTAGAAATAA TTTTGTTTAA CTTTAAGAAG
     CCCCTTAACA CTCGCCTATT GTTAAGGGGA GATCTTTATT AAAACAAATT GAAATTCTTC
                                                                SacI
                                                                ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGGACCAT GATTACGCCA AGCTATCAAC TTTGTATAGA AAAGTTGAAC GAGAAACGTA
     GAGCCTGGTA CTAATGCGGT TCGATAGTTG AAACATATCT TTTCAACTTG CTCTTTGCAT
 181 AAATGATATA AATATCAATA TATTAAATTA GATTTTGCAT AAAAAACAGA CTACATAATA
     TTTACTATAT TTATAGTTAT ATAATTTAAT CTAAAACGTA TTTTTTGTCT GATGTATTAT
                                              PstI
                                              ~~~~~~~
 241 CTGTAAAACA CAACATATCC AGTCACTATG GTCGACCTGC AGACTGGCTG TGTATAAGGG
     GACATTTTGT GTTGTATAGG TCAGTGATAC CAGCTGGACG TCTGACCGAC ACATATTCCC
 301 AGCCTGACAT TTATATTCCC CAGAACATCA GGTTAATGGC GTTTTTGATG TCATTTTCGC
     TCGGACTGTA AATATAAGGG GTCTTGTAGT CCAATTACCG CAAAAACTAC AGTAAAAGCG
 361 GGTGGCTGAG ATCAGCCACT TCTTCCCCGA TAACGGAGAC CGGCACACTG GCCATATCGG
     CCACCGACTC TAGTCGGTGA AGAAGGGGCT ATTGCCTCTG GCCGTGTGAC CGGTATAGCC
 421 TGGTCATCAT GCGCCAGCTT TCATCCCCGA TATGCACCAC CGGGTAAAGT TCACGGGGGA
     ACCAGTAGTA CGCGGTCGAA AGTAGGGGCT ATACGTGGTG GCCCATTTCA AGTGCCCCCT
 481 CTTTATCTGA CAGCAGACGT GCACTGGCCA GGGGGATCAC CATCCGTCGC CCGGGCGTGT
     GAAATAGACT GTCGTCTGCA CGTGACCGGT CCCCCTAGTG GTAGGCAGCG GGCCCGCACA
 541 CAATAATATC ACTCTGTACA TCCACAAACA GACGATAACG GCTCTCTCTT TTATAGGTGT
     GTTATTATAG TGAGACATGT AGGTGTTTGT CTGCTATTGC CGAGAGAGAA AATATCCACA
 601 AAACCTTAAA CTGCATTTCA CCAGCCCCTG TTCTCGTCGG CAAAAGAGCC GTTCATTTCA
     TTTGGAATTT GACGTAAAGT GGTCGGGGAC AAGAGCAGCC GTTTTCTCGG CAAGTAAAGT
 661 ATAAACCGGG CGACCTCAGC CATCCCTTCC TGATTTTCCG CTTTCCAGCG TTCGGCACGC
     TATTTGGCCC GCTGGAGTCG GTAGGGAAGG ACTAAAAGGC GAAAGGTCGC AAGCCGTGCG
 721 AGACGACGGG CTTCATTCTG CATGGTTGTG CTTACCGAAC CGGAGATATT GACATCATAT
     TCTGCTGCCC GAAGTAAGAC GTACCAACAC GAATGGCTTG GCCTCTATAA CTGTAGTATA
 781 ATGCCTTGAG GACTGATAG CTGTCGCTGT CAACTGTCAC TGTAATACGC TGCTTCATAG
     TACGGAACTC GTTGACTATC GACAGCGACA GTTGACAGTG ACATTATGCG ACGAAGTATC
 841 CATACCTCTT TTTGACATAC TTCGGGTATA CATATCAGTA TATATTCTTA TACCGCAAAA
     GTATGGAGAA AAACTGTATG AAGCCCATAT GTATAGTCAT ATATAAGAAT ATGGCGTTTT
 901 ATCAGCGCGC AAATACGCAT ACTGTTATCT GGCTTTTAGT AAGCCGGATC CTCTAGATTA
     TAGTCGCGCG TTTATGCGTA TGACAATAGA CCGAAAATCA TTCGGCCTAG GAGATCTAAT
 961 CGCCCCGCCC TGCCACTCAT CGCAGTACTG TTGTAATTCA TTAAGCATTC TGCCGACATG
     GCGGGGCGGG ACGGTGAGTA GCGTCATGAC AACATTAAGT AATTCGTAAG ACGGCTGTAC
1021 GAAGCCATCA CAAACGGCAT GATGAACCTG AATCGCCAGC GGCATCAGCA CCTTGTCGCC
     CTTCGGTAGT GTTTGCCGTA CTACTTGGAC TTAGCGGTCG CCGTAGTCGT GGAACAGCGG
1081 TTGCGTATAA TATTTGCCCA TGGTGAAAAC GGGGGCGAAG AAGTTGTCCA TATTGGCCAC
     AACGCATATT ATAAACGGGT ACCACTTTTG CCCCCGCTTC TTCAACAGGT ATAACCGGTG
1141 GTTTAAATCA AAACTGGTGA AACTCACCCA GGGATTGGCT GAGACGAAAA ACATATTCTC
     CAAATTTAGT TTTGACCACT TTGAGTGGGT CCCTAACCGA CTCTGCTTTT TGTATAAGAG
1201 AATAAACCCT TTAGGGAAAT AGGCCAGGTT TTCACCGTAA CACGCCACAT CTTGCGAATA
     TTATTTGGGA AATCCCTTTA TCCGGTCCAA AAGTGGCATT GTGCGGTGTA GAACGCTTAT
1261 TATGTGTAGA AACTGCCGGA AATCGTCGTG GTATTCACTC CAGAGCGATG AAAACGTTTC
     ATACACATCT TTGACGGCCT TTAGCAGCAC CATAAGTGAG GTCTCGCTAC TTTTGCAAAG
1321 AGTTTGCTCA TGGAAAACGG TGTAACAAGG GTGAACACTA TCCCATATCA CCAGCTCACC
     TCAAACGAGT ACCTTTTGCC ACATTGTTCC CACTTGTGAT AGGGTATAGT GGTCGAGTGG
1381 GTCTTTCATT GCCATACGGA ATTCCGGATG AGCATTCATC AGGCGGGCAA GAATGTGAAT
     CAGAAAGTAA CGGTATGCCT TAAGGCCTAC TCGTAAGTAG TCCGCCCGTT CTTACACTTA
1441 AAAGGCCGGA TAAAACTTGT GCTTATTTTT CTTTACGGTC TTTAAAAAGG CCGTAATATC
     TTTCCGGCCT ATTTTGAACA CGAATAAAAA GAAATGCCAG AAATTTTTCC GGCATTATAG
1501 CAGCTGAACG GTCTGGTTAT AGGTACATTG AGCAACTGAC TGAAATGCCT CAAAATGTTC
     GTCGACTTGC CAGACCAATA TCCATGTAAC TCGTTGACTG ACTTTACGGA GTTTTACAAG
1561 TTTACGATGC CATTGGGATA TATCAACGGT GGTATATCCA GTGATTTTTT CTCCATTTT
     AAATGCTACG GTAACCCTAT ATAGTTGCCA CCATATAGGT CACTAAAAAA AGAGGTAAAA
1621 AGCTTCCTTA GCTCCTGAAA ATCTCGACGG ATCCTAACTC AAAATCCACA CATTATACGA
     TCGAAGGAAT CGAGGACTTT TAGAGCTGCC TAGGATTGAG TTTTAGGTGT GTAATATGCT
1681 GCCGGAAGCA TAAAGTGTAA AGCCTGGGGG TGCCTAATGC GGCCGCCATA GTGACTGGAT
     CGGCCTTCGT ATTTCACATT TCGGACCCCC ACGGATTACG CCGGCGGTAT CACTGACCTA
1741 ATGTTGTGTT TTACAGTATT ATGTAGTCTG TTTTTTATGC AAAATCTAAT TTAATATATT
     TACAACACAA AATGTCATAA TACATCAGAC AAAAAATACG TTTTAGATTA AATTATATAA
```

Fig. 25₁

```
1801  GATATTTATA TCATTTTACG TTTCTCGTTC AACTTTATTA TACATAGTTG ATAATTCACT
      CTATAAATAT AGTAAAATGC AAAGAGCAAG TTGAAATAAT ATGTATCAAC TATTAAGTGA
1861  GGCCGTCGTT TTACAACGTC GTGACTGGGA AAACCCTGGC GTTACCCAAC TTAATCGCCT
      CCGGCAGCAA AATGTTGCAG CACTGACCCT TTTGGGACCG CAATGGGTTG AATTAGCGGA
               HindIII
               ~~~~~~~
1921  TGCAGCACAA GCTTGCGGCC GCATAATGCT TAAGTCGAAC AGAAAGTAAT CGTATTGTAC
      ACGTCGTGTT CGAACGCCGG CGTATTACGA ATTCAGCTTG TCTTTCATTA GCATAACATG
1981  ACGGCCGCAT AATCGAAATT AATACGACTC ACTATAGGGG AATTGTGAGC GGATAACAAT
      TGCCGGCGTA TTAGCTTTAA TTATGCTGAG TGATATCCCC TTAACACTCG CCTATTGTTA
2041  TCCCCATCTT AGTATATTAG TTAAGTATAA GAAGGAGATA TACATATGGC AGATCTCAAT
      AGGGGTAGAA TCATATAATC AATTCATATT CTTCCTCTAT ATGTATACCG TCTAGAGTTA
2101  TGGATATCGG CCGGCCACGC GATCGCTGAC GTCGGTACCC TCGAGTCTGG TAAAGAAACC
      ACCTATAGCC GGCCGGTGCG CTAGCGACTG CAGCCATGGG AGCTCAGACC ATTTCTTTGG
                                                                  AvrII
                                                                  ~~
2161  GCTGCTGCGA AATTTGAACG CCAGCACATG GACTCGTCTA CTAGCGCAGC TTAATTAACC
      CGACGACGCT TTAAACTTGC GGTCGTGTAC CTGAGCAGAT GATCGCGTCG AATTAATTGG
      AvrII
      ~~~~
2221  TAGGCTGCTG CCACCGCTGA GCAATAACTA GCATAACCCC TTGGGGCCTC TAAACGGGTC
      ATCCGACGAC GGTGGCGACT CGTTATTGAT CGTATTGGGG AACCCCGGAG ATTTGCCCAG
2281  TTGAGGGGTT TTTTGCTGAA AGGAGGAACT ATATCCGGAT TGGCGAATGG GACGCGCCCT
      AACTCCCCAA AAAACGACTT TCCTCCTTGA TATAGGCCTA ACCGCTTACC CTGCGCGGGA
2341  GTAGCGGCGC ATTAAGCGCG GCGGGTGTGG TGGTTACGCG CAGCGTGACC GCTACACTTG
      CATCGCCGCG TAATTCGCGC CGCCCACACC ACCAATGCGC GTCGCACTGG CGATGTGAAC
2401  CCAGCGCCCT AGCGCCCGCT CCTTTCGCTT TCTTCCCTTC CTTTCTCGCC ACGTTCGCCG
      GGTCGCGGGA TCGCGGGCGA GGAAAGCGAA AGAAGGGAAG GAAAGAGCGG TGCAAGCGGC
2461  GCTTTCCCCG TCAAGCTCTA AATCGGGGGC TCCCTTTAGG GTTCCGATTT AGTGCTTTAC
      CGAAAGGGGC AGTTCGAGAT TTAGCCCCCG AGGGAAATCC CAAGGCTAAA TCACGAAATG
2521  GGCCACCTCGA CCCCAAAAAA CTTGATTAGG GTGATGGTTC ACGTAGTGGG CCATCGCCCT
      CCGTGGAGCT GGGGTTTTTT GAACTAATCC CACTACCAAG TGCATCACCC GGTAGCGGGA
2581  GATAGACGGT TTTTCGCCCT TTGACGTTGG AGTCCACGTT CTTTAATAGT GGACTCTTGT
      CTATCTGCCA AAAAGCGGGA AACTGCAACC TCAGGTGCAA GAAATTATCA CCTGAGAACA
2641  TCCAAACTGG AACAACACTC AACCCTATCT CGGTCTATTC TTTTGATTTA TAAGGGATTT
      AGGTTTGACC TTGTTGTGAG TTGGGATAGA GCCAGATAAG AAAACTAAAT ATTCCCTAAA
2701  TGCCGATTTC GGCCTATTGG TTAAAAAATG AGCTGATTTA ACAAAAATTT AACGCGAATT
      ACGGCTAAAG CCGGATAACC AATTTTTTAC TCGACTAAAT TGTTTTTAAA TTGCGCTTAA
2761  TTAACAAAAT ATTAACGTTT ACAATTTCTG GCGGCACGAT GGCATGAGAT TATCAAAAAG
      AATTGTTTTA TAATTGCAAA TGTTAAAGAC CGCCGTGCTA CCGTACTCTA ATAGTTTTTC
2821  GATCTTCACC TAGATCCTTT TAAATTAAAA ATGAAGTTTT AAATCAATCT AAAGTATATA
      CTAGAAGTGG ATCTAGGAAA ATTTAATTTT TACTTCAAAA TTTAGTTAGA TTTCATATAT
2881  TGAGTAAACT TGGTCTGACA GTTACCAATG CTTAATCAGT GAGGCACCTA TCTCAGCGAT
      ACTCATTTGA ACCAGACTGT CAATGGTTAC GAATTAGTCA CTCCGTGGAT AGAGTCGCTA
2941  CTGTCTATTT CGTTCATCCA TAGTTGCCTG ACTCCCCGTC GTGTAGATAA CTACGATACG
      GACAGATAAA GCAAGTAGGT ATCAACGGAC TGAGGGGCAG CACATCTATT GATGCTATGC
3001  GGAGGGCTTA CCATCTGGCC CCAGTGCTGC AATGATACCG CGAGACCCAC GCTCACCGGC
      CCTCCCGAAT GGTAGACCGG GGTCACGACG TTACTATGGC GCTCTGGGTG CGAGTGGCCG
3061  TCCAGATTTA TCAGCAATAA ACCAGCCAGC CGGAAGGGCC GAGCGCAGAA GTGGTCCTGC
      AGGTCTAAAT AGTCGTTATT TGGTCGGTCG GCCTTCCCGG CTCGCGTCTT CACCAGGACG
3121  AACTTTATCC GCCTCCATCC AGTCTATTAA TTGTTGCCGG GAAGCTAGAG TAAGTAGTTC
      TTGAAATAGG CGGAGGTAGG TCAGATAATT AACAACGGCC CTTCGATCTC ATTCATCAAG
3181  GCCAGTTAAT AGTTTGCGCA ACGTTGTTGC CATTGCTACA GGCATCGTGG TGTCACGCTC
      CGGTCAATTA TCAAACGCGT TGCAACAACG GTAACGATGT CCGTAGCACA ACAGTGCGAG
3241  GTCGTTTGGT ATGGCTTCAT TCAGCTCCGG TTCCCAACGA TCAAGGCGAG TTACATGATC
      CAGCAAACCA TACCGAAGTA AGTCGAGGCC AAGGGTTGCT AGTTCCGCTC AATGTACTAG
3301  CCCCATGTTG TGCAAAAAAG CGGTTAGCTC CTTCGGTCCT CCGATCGTTG TCAGAAGTAA
      GGGGTACAAC ACGTTTTTTC GCCAATCGAG GAAGCCAGGA GGCTAGCAAC AGTCTTCATT
3361  GTTGCCGCA GTGTTATCAC TCATGGTTAT GGCAGCACTG CATAATTCTC TTACTGTCAT
      CAACCGGCGT CACAATAGTG AGTACCAATA CCGTCGTGAC GTATTAAGAG AATGACAGTA
3421  GCCATCCGTA AGATGCTTTT CTGTGACTGG TGAGTACTCA ACCAAGTCAT TCTGAGAATA
      CGGTAGGCAT TCTACGAAAA GACACTGACC ACTCATGAGT TGGTTCAGTA AGACTCTTAT
3481  GTGTATGCGG CGACCGAGTT GCTCTTGCCC GGCGTCAATA CGGGATAATA CCGCGCCACA
      CACATACGCC GCTGGCTCAA CGAGAACGGG CCGCAGTTAT GCCCTATTAT GGCGCGGTGT
3541  TAGCAGAACT TTAAAAGTGC TCATCATTGG AAAACGTTCT TCGGGGCGAA AACTCTCAAG
      ATCGTCTTGA AATTTTCACG AGTAGTAACC TTTTGCAAGA AGCCCCGCTT TTGAGAGTTC
3601  GATCTTACCG CTGTTGAGAT CCAGTTCGAT GTAACCCACT CGTGCACCCA ACTGATCTTC
      CTAGAATGGC GACAACTCTA GGTCAAGCTA CATTGGGTGA GCACGTGGGT TGACTAGAAG
3661  AGCATCTTTT ACTTTCACCA GCGTTTCTGG GTGAGCAAAA ACAGGAAGGC AAAATGCCGC
      TCGTAGAAAA TGAAAGTGGT CGCAAAGACC CACTCGTTTT TGTCCTTCCG TTTTACGGCG
3721  AAAAAGGGA ATAAGGGCGA CACGGAAATG TTGAATACTC ATACTCTTCC TTTTTCAATC
```

Fig. 25₂

```
          TTTTTTCCCT TATTCCCGCT GTGCCTTTAC AACTTATGAG TATGAGAAGG AAAAAGTTAG
    3781  ATGATTGAAG CATTTATCAG GGTTATTGTC TCATGAGCGG ATACATATTT GAATGTATTT
          TACTAACTTC GTAAATAGTC CCAATAACAG AGTACTCGCC TATGTATAAA CTTACATAAA
    3841  AGAAAAATAA ACAAATAGGT CATGACCAAA ATCCCTTAAC GTGAGTTTTC GTTCCACTGA
          TCTTTTTATT TGTTTATCCA GTACTGGTTT TAGGGAATTG CACTCAAAAG CAAGGTGACT
    3901  GCGTCAGACC CCGTAGAAAA GATCAAAGGA TCTTCTTGAG ATCCTTTTTT TCTGCGCGTA
          CGCAGTCTGG GGCATCTTTT CTAGTTTCCT AGAAGAACTC TAGGAAAAAA AGACGCGCAT
    3961  ATCTGCTGCT TGCAAACAAA AAACCACCG CTACCAGCGG TGGTTTGTTT GCCGGATCAA
          TAGACGACGA ACGTTTGTTT TTTTGGTGGC GATGGTCGCC ACCAAACAAA CGGCCTAGTT
    4021  GAGCTACCAA CTCTTTTTCC GAAGGTAACT GGCTTCAGCA GAGCGCAGAT ACCAAATACT
          CTCGATGGTT GAGAAAAAGG CTTCCATTGA CCGAAGTCGT CTCGCGTCTA TGGTTTATGA
    4081  GTCCTTCTAG TGTAGCCGTA GTTAGGCCAC CACTTCAAGA ACTCTGTAGC ACCGCCTACA
          CAGGAAGATC ACATCGGCAT CAATCCGGTG GTGAAGTTCT TGAGACATCG TGGCGGATGT
    4141  TACCTCGCTC TGCTAATCCT GTTACCAGTG GCTGCTGCCA GTGGCGATAA GTCGTGTCTT
          ATGGAGCGAG ACGATTAGGA CAATGGTCAC CGACGACGGT CACCGCTATT CAGCACAGAA
    4201  ACCGGGTTGG ACTCAAGACG ATAGTTACCG GATAAGGCGC AGCGGTCGGG CTGAACGGGG
          TGGCCCAACC TGAGTTCTGC TATCAATGGC CTATTCCGCG TCGCCAGCCC GACTTGCCCC
    4261  GGTTCGTGCA CACAGCCCAG CTTGGAGCGA ACGACCTACA CCGAACTGAG ATACCTACAG
          CCAAGCACGT GTGTCGGGTC GAACCTCGCT TGCTGGATGT GGCTTGACTC TATGGATGTC
    4321  CGTGAGCTAT GAGAAAGCGC CACGCTTCCC GAAGGGAGAA AGGCGGACAG GTATCCGGTA
          GCACTCGATA CTCTTTCGCG GTGCGAAGGG CTTCCCTCTT TCCGCCTGTC CATAGGCCAT
    4381  AGCGGCAGGG TCGGAACAGG AGAGCGCACG AGGGAGCTTC CAGGGGGAAA CGCCTGGTAT
          TCGCCGTCCC AGCCTTGTCC TCTCGCGTGC TCCCTCGAAG GTCCCCCTTT GCGGACCATA
    4441  CTTTATAGTC CTGTCGGGTT TCGCCACCTC TGACTTGAGC GTCGATTTTT GTGATGCTCG
          GAAATATCAG GACAGCCCAA AGCGGTGGAG ACTGAACTCG CAGCTAAAAA CACTACGAGC
    4501  TCAGGGGGC GGAGCCTATG GAAAAACGCC AGCAACGCGG CCTTTTTACG GTTCCTGGCC
          AGTCCCCCCG CCTCGGATAC CTTTTTGCGG TCGTTGCGCC GGAAAAATGC CAAGGACCGG
    4561  TTTTGCTGGC CTTTTGCTCA CATGTTCTTT CCTGCGTTAT CCCCTGATTC TGTGGATAAC
          AAAACGACCG GAAAACGAGT GTACAAGAAA GGACGCAATA GGGGACTAAG ACACCTATTG
    4621  CGTATTACCG CCTTTGAGTG AGCTGATACC GCTCGCCGCA GCCGAACGAC CGAGCGCAGC
          GCATAATGGC GGAAACTCAC TCGACTATGG CGAGCGGCGT CGGCTTGCTG GCTCGCGTCG
    4681  GAGTCAGTGA GCGAGGAAGC GGAAGAGCGC CTGATGCGGT ATTTTCTCCT TACGCATCTG
          CTCAGTCACT CGCTCCTTCG CCTTCTCGCG GACTACGCCA TAAAGAGGA ATGCGTAGAC
    4741  TGCGGTATTT CACACCGCAT ATATGGTGCA CTCTCAGTAC AATCTGCTCT GATGCCGCAT
          ACGCCATAAA GTGTGGCGTA TATACCACGT GAGAGTCATG TTAGACGAGA CTACGGCGTA
    4801  AGTTAAGCCA GTATACACTC CGCTATCGCT ACGTGACTGG GTCATGGCTG CGCCCCGACA
          TCAATTCGGT CATATGTGAG GCGATAGCGA TGCACTGACC CAGTACCGAC GCGGGGCTGT
    4861  CCCGCCAACA CCCGCTGACG CGCCCTGACG GCTTGTCTG CTCCCGGCAT CCGCTTACAG
          GGGCGGTTGT GGGCGACTGC GCGGGACTGC CCGAACAGAC GAGGGCCGTA GGCGAATGTC
    4921  ACAAGCTGTG ACCGTCTCCG GGAGCTGCAT GTGTCAGAGG TTTTCACCGT CATCACCGAA
          TGTTCGACAC TGGCAGAGGC CCTCGACGTA CACAGTCTCC AAAAGTGGCA GTAGTGGCTT
    4981  ACGCGCGAGG CAGCTGCGGT AAAGCTCATC AGCGTGGTCG TGAAGCGATT CACAGATGTC
          TGCGCGCTCC GTCGACGCCA TTTCGAGTAG TCGCACCAGC ACTTGCTAA GTGTCTACAG
    5041  TGCCTGTTCA TCCGCGTCCA GCTCGTTGAG TTTCTCCAGA AGCGTTAATG TCTGGCTTCT
          ACGGACAAGT AGGCGCAGGT CGAGCAACTC AAAGAGGTCT TCGCAATTAC AGACCGAAGA
    5101  GATAAAGCGG GCCATGTTAA GGGCGGTTTT TTCCTGTTTG GTCACTGATG CCTCCGTGTA
          CTATTTCGCC CGGTACAATT CCCGCCAAAA AAGGACAAAC CAGTGACTAC GGAGGCACAT
    5161  AGGGGGATTT CTGTTCATGG GGTAATGAT ACCGATGAAA CGAGAGAGGA TGCTCACGAT
          TCCCCCTAAA GACAAGTACC CCATTACTA TGGCTACTTT GCTCTCTCCT ACGAGTGCTA
    5221  ACGGGTTACT GATGATGAAC ATGCCCGGTT ACTGGAACGT TGTGAGGGTA AACAACTGGC
          TGCCCAATGA CTACTACTTG TACGGGCCAT ACACTCCCAT TTGTTGACCG
    5281  GGTATGGATG CGGCGGGACC AGAGAAAAAT CACTCAGGGT CAATGCCAGC GCTTCGTTAA
          CCATACCTAC GCCGCCCTGG TCTCTTTTTA GTGAGTCCCA GTTACGGTCG CGAAGCAATT
    5341  TACAGATGTA GGTGTTCCAC AGGGTAGCCA GCAGCATCCT GCGATGCAGA TCCGGAACAT
          ATGTCTACAT CCACAAGGTG TCCCATCGGT CGTCGTAGGA CGCTACGTCT AGGCCTTGTA
    5401  AATGGTCAG GGCGCTGACT TCCGCGTTTC CAGACTTTAC GAAACAGGA AACCGAAGAC
          TTACCACGTC CCGCGACTGA AGGCGCAAAG GTCTGAAATG CTTTGTGCCT TTGGCTTCTG
    5461  CATTCATGTT GTTGCTCAGG TCGCAGACGT TTTGCAGCAG CAGTCGCTTC ACGTTCGCTC
          GTAAGTACAA CAACGAGTCC AGCGTCTGCA AAACGTCGTC GTCAGCGAAG TGCAAGCGAG
    5521  GCGTATCGGT GATTCATTCT GCTAACCAGT AAGGCAACCC CGCCAGCCTA GCCGGGTCCT
          CGCATAGCCA CTAAGTAAGA CGATTGGTCA TTCCGTTGGG GCGGTCGGAT CGGCCCAGGA
    5581  CAACGACAGG AGCACGATCA TGCTAGTCAT GCCCCGCGCC CACCGGAAGG AGCTGACTGG
          GTTGCTGTCC TCGTGCTAGT ACGATCAGTA CGGGGCGCGG GTGGCCTTCC TCGACTGACC
    5641  GTTGAAGGCT CTCAAGGGCA TCGGTCGAGA TCCCGGTGCC TAATGAGTGA GCTAACTTAC
          CAACTTCCGA GAGTTCCCGT AGCCAGCTCT AGGGCCACGG ATTACTCACT CGATTGAATG
    5701  ATTAATTGCG TTGCGCTCAC TGCCCGCTTT CCAGTCGGGA AACCTGTCGT GCCAGCTGCA
          TAATTAACGC AACGCGAGTG ACGGGCGAAA GGTCAGCCCT TTGGACAGCA CGGTCGACGT
    5761  TTAATGAATC GGCCAACGCG CGGGGAGAGG CGGTTTGCGT ATTGGGCGCC AGGGTGGTTT
          AATTACTTAG CCGGTTGCGC GCCCCTCTCC GCCAAACGCA TAACCCGCGG TCCCACCAAA
    5821  TTCTTTTCAC CAGTGAGACG GGCAACAGCT GATTGCCCTT CACCGCCTGG CCCTGAGAGA
```

Fig. 25₃

```
            AAGAAAAGTG GTCACTCTGC CCGTTGTCGA CTAACGGGAA GTGGCGGACC GGGACTCTCT
      5881  GTTGCAGCAA GCGGTCCACG CTGGTTTGCC CCAGCAGGCG AAAATCCTGT TGATGGTGG
            CAACGTCGTT CGCCAGGTGC GACCAAACGG GGTCGTCCGC TTTTAGGACA AACTACCACC
      5941  TTAACGGCGG GATATAACAT GAGCTGTCTT CGGTATCGTC GTATCCCACT ACCGAGATGT
            AATTGCCGCC CTATATTGTA CTCGACAGAA GCCATAGCAG CATAGGGTGA TGGCTCTACA
      6001  CCGCACCAAC GCGCAGCCCG GACTCGGTAA TGGCGCGCAT GCGCCCAGC GCCATCTGAT
            GGCGTGGTTG CGCGTCGGGC CTGAGCCATT ACCGCGCGTA ACGCGGGTCG CGGTAGACTA
      6061  CGTTGGCAAC CAGCATCGCA GTGGGAACGA TGCCCTCATT CAGCATTTGC ATGGTTTGTT
            GCAACCGTTG GTCGTAGCGT CACCCTTGCT ACGGGAGTAA GTCGTAAACG TACCAAACAA
      6121  GAAAACCGGA CATGGCACTC CAGTCGCCTT CCCGTTCCGC TATCGGCTGA ATTTGATTGC
            CTTTTGGCCT GTACCGTGAG GTCAGCGGAA GGGCAAGGCG ATAGCCGACT TAAACTAACG
      6181  GAGTGAGATA TTTATGCCAG CCAGCCAGAC GCAGACGCGC CGAGACAGAA CTTAATGGGC
            CTCACTCTAT AAATACGGTC GGTCGGTCTG CGTCTGCGCG GCTCTGTCTT GAATTACCCG
      6241  CCGCTAACAG CGCGATTTGC TGGTGACCCA ATGCGACCAG ATGCTCCACG CCCAGTCGCG
            GGCGATTGTC GCGCTAAACG ACCACTGGGT TACGCTGGTC TACGAGGTGC GGGTCAGCGC
      6301  TACCGTCTTC ATGGGAGAAA ATAATACTGT TGATGGGTGT CTGGTCAGAG ACATCAAGAA
            ATGGCAGAAG TACCCTCTTT TATTATGACA ACTACCCACA GACCAGTCTC TGTAGTTCTT
      6361  ATAACGCCGG AACATTAGTG CAGGCAGCTT CCACAGCAAT GGCATCCTGG TCATCCAGCG
            TATTGCGGCC TTGTAATCAC GTCCGTCGAA GGTGTCGTTA CCGTAGGACC AGTAGGTCGC
      6421  GATAGTTAAT GATCAGCCCA CTGACGCGTT GCGCGAGAAG ATTGTGCACC GCCGCTTTAC
            CTATCAATTA CTAGTCGGGT GACTGCGCAA CGCGCTCTTC TAACACGTGG CGGCGAAATG
      6481  AGGCTTCGAC GCCGCTTCGT TCTACCATCG ACACCACCAC GCTGGCACCC AGTTGATCGG
            TCCGAAGCTG CGGCGAAGCA AGATGGTAGC TGTGGTGGTG CGACCGTGGG TCAACTAGCC
      6541  CGCGAGATTT AATCGCCGCG ACAATTTGCG ACGGCGCGTG CAGGGCCAGA CTGGAGGTGG
            GCGCTCTAAA TTAGCGGCGC TGTTAAACGC TGCCGCGCAC GTCCCGGTCT GACCTCCACC
      6601  CAACGCCAAT CAGCAACGAC TGTTTGCCCG CCAGTTGTTG TGCCACGCGG TTGGGAATGT
            GTTGCGGTTA GTCGTTGCTG ACAAACGGGC GGTCAACAAC ACGGTGCGCC AACCCTTACA
      6661  AATTCAGCTC CGCCATCGCC GCTTCCACTT TTTCCCGCGT TTTCGCAGAA ACGTGGCTGG
            TTAAGTCGAG GCGGTAGCGG CGAAGGTGAA AAAGGGCGCA AAAGCGTCTT TGCACCGACC
      6721  CCTGGTTCAC CACGCGGGAA ACGGTCTGAT AAGAGACACC GGCATACTCT GCGACATCGT
            GGACCAAGTG GTGCGCCCTT TGCCAGACTA TTCTCTGTGG CCGTATGAGA CGCTGTAGCA
      6781  ATAACGTTAC TGGTTTCACA TTCACCACCC TGAATTGACT CTCTTCCGGG CGCTATCATG
            TATTGCAATG ACCAAAGTGT AAGTGGTGGG ACTTAACTGA GAGAAGGCCC GCGATAGTAC
      6841  CCATACCGCG AAAGGTTTTG CGCCATTCGA TGGTGTCCGG GATCTCGACG CTCTCCCTTA
            GGTATGGCGC TTTCCAAAAC GCGGTAAGCT ACCACAGGCC CTAGAGCTGC GAGAGGGAAT
      6901  TGCGACTCCT GCATTAGGAA GCAGCCCAGT AGTAGGTTGA GGCCGTTGAG CACCGCCGCC
            ACGCTGAGGA CGTAATCCTT CGTCGGGTCA TCATCCAACT CCGGCAACTC GTGGCGGCGG
      6961  GCAAGGAATG GTGCATGCAA GGAGATGGCG CCCAACAGTC CCCCGGCCAC GGGGCCTGCC
            CGTTCCTTAC CACGTACGTT CCTCTACCGC GGGTTGTCAG GGGGCCGGTG CCCCGGACGG
      7021  ACCATACCCA CGCCGAAACA AGCGCTCATG AGCCCGAAGT GGCGAGCCCG ATCTTCCCCA
            TGGTATGGGT GCGGCTTTGT TCGCGAGTAC TCGGGCTTCA CCGCTCGGGC TAGAAGGGGT
      7081  TCGGTGATGT CGGCGATATA GGCGCCAGCA ACCGCACCTG TGGCGCCGGT GATGCCGGCC
            AGCCACTACA GCCGCTATAT CCGCGGTCGT TGGCGTGGAC ACCGCGGCCA CTACGGCCGG
                                                      ClaI
                                                     ~~~~~~~
      7141  ACGATGCGTC CGGCGTAGAG GATCGAGATC GATCTCGATC CGCGAAATT AATACGACTC
            TGCTACGCAG GCCGCATCTC CTAGCTCTAG CTAGAGCTAG GGCGCTTTAA TTATGCTGAG
      7201  ACTATA
            TGATAT
```

Fig. 25₄

| Fig. 28$_1$ |
|---|
| Fig. 28$_2$ |
| Fig. 28$_3$ |

Fig. 28

```
  1 GGGGAATTGT GAGCGGATAA CAATTCCCCT GTAGAAATAA TTTTGTTTAA CTTTAATAAG
    CCCCTTAACA CTCGCCTATT GTTAAGGGGA CATCTTTATT AAAACAAATT GAAATTATTC
                                                          EcoRI
                                                          ~~~~~~
            NcoI                                 BamHI        SacI
            ~~~~~~~                              ~~~~~~~      ~~~
 61 GAGATATACC ATGGGCAGCA GCCATCACCA TCATCACCAC AGCCAGGATC CGAATTCGAG
    CTCTATATGG TACCCGTCGT CGGTAGTGGT AGTAGTGGTG TCGGTCCTAG GCTTAAGCTC
    SacI
    ~~~
121 CTCGATCACA AGTTTGTACA AAAAAGCTGA ACGAGAAACG TAAAATGATA TAAATATCAA
    GAGCTAGTGT TCAAACATGT TTTTTCGACT TGCTCTTTGC ATTTTACTAT ATTTATAGTT
181 TATATTAAAT TAGATTTTGC ATAAAAAACA GACTACATAA TACTGTAAAA CACAACATAT
    ATATAATTTA ATCTAAAACG TATTTTTTGT CTGATGTATT ATGACATTTT GTGTTGTATA
                    NotI
                    ~~~~~~~~~
241 CCAGTCACTA TGGCGGCCGC CACGTTAAGG GATTTTGGTC ATGATCAGCA CGTGTTGACA
    GGTCAGTGAT ACCGCCGGCG GTGCAATTCC CTAAAACCAG TACTAGTCGT GCACAACTGT
                                                             NcoI
                                                             ~~~
301 ATTAATCATC GGCATAGTAT ATCGGCATAG TATAATACGA CAAGGTGAGG AACTAAACCA
    TAATTAGTAG CCGTATCATA TAGCCGTATC ATATTATGCT GTTCCACTCC TTGATTTGGT
    NcoI
    ~~~
361 TGGCCAAGTT GACCAGTGCC GTTCCGGTGC TCACCGCGCG CGACGTCGCC GGAGCGGTCG
    ACCGGTTCAA CTGGTCACGG CAAGGCCACG AGTGGCGCGC GCTGCAGCGG CCTCGCCAGC
421 AGTTCTGGAC CGACCGGCTC GGGTTCTCCC GGGACTTCGT GGAGGACGAC TTCGCCGGTG
    TCAAGACCTG GCTGGCCGAG CCCAAGAGGG CCCTGAAGCA CCTCCTGCTG AAGCGGCCAC
481 TGGTCCGGGA CGACGTGACC CTGTTCATCA GCGCGGTCCA GGACCAGGTG GTGCCGGACA
    ACCAGGCCCT GCTGCACTGG GACAAGTAGT CGCGCCAGGT CCTGGTCCAC CACGGCCTGT
541 ACACCCTGGC CTGGGTGTGG GTGCGCGGCC TGGACGAGCT GTACGCCGAG TGGTCGGAGG
    TGTGGGACCG GACCCACACC CACGCGCCGG ACCTGCTCGA CATGCGGCTC ACCAGCCTCC
601 TCGTGTCCAC GAACTTCCGG GACGCCTCCG GGCCGGCCAT GACCGAGATC GGCGAGCAGC
    AGCACAGGTG CTTGAAGGCC CTGCGGAGGC CCGGCCGGTA CTGGCTCTAG CCGCTCGTCG
661 CGTGGGGGCG GGAGTTCGCC CTGCCGCACC CGGCCGGCAA CTGCGTGCAC TTCGTGGCCG
    GCACCCCCGC CCTCAAGCGG GACGCGCTGG GCCGGCCGTT GACGCACGTG AAGCACCGGC
721 AGGAGCAGGA CTGATCATGA TGATATTATT TTATCTTGTG CAATGTAACA TCAGAGATTT
    TCCTCGTCCT GACTAGTACT ACTATAATAA AATAGAACAC GTTACATTGT AGTCTCTAAA
781 TGAGACACGG GCCAGAGCTG CCAGGAAACA GCTATGACCA TGTAATACGA CTCACTATAG
    ACTCTGTGCC CGGTCTCGAC GGTCCTTTGT CGATACTGGT ACATTATGCT GAGTGATATC
841 GGGATATCAG CTGGATGGCA AATAATGATT TATTTTGAC TGATAGTGAC CTGTTCGTTG
    CCCTATAGTC GACCTACCGT TTATTACTAA AATAAAACTG ACTATCACTG GACAAGCAAC
901 CAACACCGGT GCTAGCGTAT ACCCGAAGTA TGTCAAAAAG AGGTGTGCTA TGAAGCAGCG
    GTTGTGGCCA CGATCGCATA TGGGCTTCAT ACAGTTTTTC TCCACACGAT ACTTCGTCGC
961 TATTACAGTG ACAGTTGACA GCGACAGCTA TCAGTTGCTC AAGGCATATA TGATGTCAAT
    ATAATGTCAC TGTCAACTGT CGCTGTCGAT AGTCAACGAG TTCCGTATAT ACTACAGTTA
1021 ATCTCCGGTC TGGTAAGCAC AACCATGCAG AATGAAGCCC GTCGTCTGCG TGCCGAACGC
     TAGAGGCCAG ACCATTCGTG TTGGTACGTC TTACTTCGGG CAGCAGACGC ACGGCTTGCG
1081 TGGAAAGCGG AAAATCAGGA AGGGATGGCT GAGGTCGCCC GGTTTATTGA AATGAACGGC
     ACCTTTCGCC TTTTAGTCCT TCCCTACCGA CTCCAGCGGG CCAAATAACT TTACTTGCCG
1141 TCTTTTGCTG ACGAGAACAG GGACTGGTGA ATGCAGTTT AAGGTTTACA CCTATAAAAG
     AGAAAACGAC TGCTCTTGTC CCTGACCACT TTACGTCAAA TTCCAAATGT GGATATTTTC
1201 AGAGAGCCGT TATCGTCTGT TTGTGGATGT ACAGATGAT ATTATTGACA CGCCCGGGCG
     TCTCTCGGCA ATAGCAGACA AACACCTACA TGTCTCACTA TAATAACTGT GCGGGCCCGC
1261 ACGGATGGTG ATCCCCCTGG CCAGTGCACG TCTGCTGTCA GATAAAGTCT CCCGTGAACT
     TGCCTACCAC TAGGGGGACC GGTCACGTGC AGACGACAGT CTATTTCAGA GGGCACTTGA
1321 TTACCCGGTG GTGCATATCG GGGATGAAAG CTGGCGCATG ATGACCACCG ATATGGCCAG
     AATGGGCCAC CACGTATAGC CCCTACTTTC GACCGCGTAC TACTGGTGGC TATACCGGTC
1381 TGTGCCGGTC TCCGTTATCG GGGAAGAAGT GGCTGATCTC AGCCGCCGCG AAAATGACAT
     ACACGGCCAG AGGCAATAGC CCCTTCTTCA CCGACTAGAG TCGGCGGCGC TTTTACTGTA
1441 CAAAAACGCC ATTAACCTGA TGTTCTGGGG AATATAAATG TCAGGCTCCC TTATACACAG
     GTTTTTGCGG TAATTGGACT ACAAGACCCC TTATATTTAC AGTCCGAGGG AATATGTGTC
          PstI
          ~~~~~~~
1501 CCAGTCTGCA GGTCGACCAT AGTGACTGGA TATGTTGTGT TTTACAGTAT TATGTAGTCT
     GGTCAGACGT CCAGCTGGTA TCACTGACCT ATACAACACA AAATGTCATA ATACATCAGA
```

Fig. 28₁

```
1561    GTTTTTTATG CAAAATCTAA TTTAATATAT TGATATTTAT ATCATTTTAC GTTTCTCGTT
        CAAAAAATAC GTTTTAGATT AAATTATATA ACTATAAATA TAGTAAAATG CAAAGAGCAA
                                                                HindIII
                                                                ~~~~~~
1621    CAGCTTTCTT GTACAAAGTG GTGATAATTA ATTAAGATCA GATCCGGCTG CTAAGCTTGG
        GTCGAAAGAA CATGTTTCAC CACTATTAAT TAATTCTAGT CTAGGCCGAC GATTCGAACC
                                                   AvrII
                                                   ~~~~~~
1681    AATTGTTATC CGCTCACAAT TCCTATAGTG AGTCGTATTA CCTAGGCTGC TGCCACCGCT
        TTAACAATAG GCGAGTGTTA AGGATATCAC TCAGCATAAT GGATCCGACG ACGGTGGCGA
1741    GAGCAATAAC TAGCATAACC CCTTGGGGCC TCTAAACGGG TCTTGAGGGG TTTTTTGCTG
        CTCGTTATTG ATCGTATTGG GGAACCCCGG AGATTTGCCC AGAACTCCCC AAAAAACGAC
1801    AAACCTCAGG CATTTGAGAA GCACACGGTC ACACTGCTTC CGGTAGTCAA TAAACCGGTA
        TTTGGAGTCC GTAAACTCTT CGTGTGCCAG TGTGACGAAG GCCATCAGTT ATTTGGCCAT
1861    AACCAGCAAT AGACATAAGC GGCTATTTAA CGACCCTGCC CTGAACCGAC GACCGGGTCG
        TTGGTCGTTA TCTGTATTCG CCGATAAATT GCTGGGACGG GACTTGGCTG CTGGCCCAGC
1921    AATTTGCTTT CGAATTTCTG CCATTCATCC GCTTATTATC ACTTATTCAG GCGTAGCACC
        TTAAACGAAA GCTTAAAGAC GGTAAGTAGG CGAATAATAG TGAATAAGTC CGCATCGTGG
1981    AGGCGTTTAA GGGCACCAAT AACTGCCTTA AAAAAATTAC GCCCCGCCCT GCCACTCATC
        TCCGCAAATT CCCGTGGTTA TTGACGGAAT TTTTTTAATG CGGGGCGGGA CGGTGAGTAG
2041    GCAGTACTGT TGTAATTCAT TAAGCATTCT GCCGACATGG AAGCCATCAC AGACGGCATG
        CGTCATGACA ACATTAAGTA ATTCGTAAGA CGGCTGTACC TTCGGTAGTG TCTGCCGTAC
2101    ATGAACCTGA ATCGCCAGCG GCATCAGCAC CTTGTCGCCT TGCGTATAAT ATTTGCCCAT
        TACTTGGACT TAGCGGTCGC CGTAGTCGTG GAACAGCGGA ACGCATATTA TAAACGGGTA
2161    AGTGAAAACG GGGGCGAAGA AGTTGTCCAT ATTGGCCACG TTTAAATCAA AACTGGTGAA
        TCACTTTTGC CCCCGCTTCT TCAACAGGTA TAACCGGTGC AAATTTAGTT TTGACCACTT
2221    ACTCACCCAG GGATTGGCTG AGACGAAAAA CATATTCTCA ATAAACCCTT TAGGGAAATA
        TGAGTGGGTC CCTAACCGAC TCTGCTTTTT GTATAAGAGT TATTTGGGAA ATCCCTTTAT
2281    GGCCAGGTTT TCACCGTAAC ACGCCACATC TTGCGAATAT ATGTGTAGAA ACTGCCGGAA
        CCGGTCCAAA AGTGGCATTG TGCGGTGTAG AACGCTTATA TACACATCTT TGACGGCCTT
2341    ATCGTCGTGG TATTCACTCC AGAGCGATGA AAACGTTTCA GTTTGCTCAT GGAAAACGGT
        TAGCAGCACC ATAAGTGAGG TCTCGCTACT TTTGCAAAGT CAAACGAGTA CCTTTTGCCA
2401    GTAACAAGGG TGAACACTAT CCCATATCAC CAGCTCACCG TCTTTCATTG CCATACGGAA
        CATTGTTCCC ACTTGTGATA GGGTATAGTG GTCGAGTGGC AGAAAGTAAC GGTATGCCTT
2461    CTCCGGATGA GCATTCATCA GGCGGGCAAG AATGTGAATA AAGGCCGGAT AAAACTTGTG
        GAGGCCTACT CGTAAGTAGT CCGCCCGTTC TTACACTTAT TTCCGGCCTA TTTTGAACAC
2521    CTTATTTTTC TTTACGGTCT TTAAAAAGGC CGTAATATCC AGCTGAACGG TCTGGTTATA
        GAATAAAAAG AAATGCCAGA AATTTTTCCG GCATTATAGG TCGACTTGCC AGACCAATAT
2581    GGTACATTGA GCAACTGACT GAAATGCCTC AAAATGTTCT TTACGATGCC ATTGGGATAT
        CCATGTAACT CGTTGACTGA CTTTACGGAG TTTTACAAGA AATGCTACGG TAACCCTATA
2641    ATCAACGGTG TATATCCAG TGATTTTTTT CTCCATTTTA GCTTCCTTAG CTCCTGAAAA
        TAGTTGCCAC CATATAGGTC ACTAAAAAAA GAGGTAAAAT CGAAGGAATC GAGGACTTTT
2701    TCTCGATAAC TCAAAAAATA CGCCCGGTAG TGATCTTATT TCATTATGGT GAAAGTTGGA
        AGAGCTATTG AGTTTTTTAT GCGGGCCATC ACTAGAATAA AGTAATACCA CTTTCAACCT
2761    ACCTCTTACG TGCCGATCAA CGTCTCATTT TCGCCAAAAG TTGGCCCAGG GCTTCCCGGT
        TGGAGAATGC ACGGCTAGTT GCAGAGTAAA AGCGGTTTTC AACCGGGTCC CGAAGGGCCA
2821    ATCAACAGGG ACACCAGGAT TTATTTATTC TGCGAAGTGA TCTTCCGTCA CAGGTATTTA
        TAGTTGTCCC TGTGGTCCTA AATAAATAAG ACGCTTCACT AGAAGGCAGT GTCCATAAAT
2881    TTCGCGCAA AGTGCGTCGG GTGATGCTGC CAACTTACTG ATTTAGTGTA TGATGGTGTT
        AAGCCGCGTT TCACGCAGCC CACTACGACG GTTGAATGAC TAAATCACAT ACTACCACAA
2941    TTTGAGGTGC TCCAGTGGCT TCTGTTTCTA TCAGCTGTCC CTCCTGTTCA GCTACTGACG
        AAACTCCACG AGGTCACCGA AGACAAAGAT AGTCGACAGG GAGGACAAGT CGATGACTGC
3001    GGGTGGTGCG TAACGGCAAA AGCACCGCCG GACATCAGCG CTAGCGGAGT GTATACTGGC
        CCCACCACGC ATTGCCGTTT TCGTGGCGGC CTGTAGTCGC GATCGCCTCA CATATGACCG
3061    TTACTATGTT GGCACTGATG AGGGTGTCAG TGAAGTGCTT CATGTGGCAG GAGAAAAAAG
        AATGATACAA CCGTGACTAC TCCCACAGTC ACTTCACGAA GTACACCGTC CTCTTTTTTC
3121    GCTGCACCGG TGCGTCAGCA GAATATGTGA TACAGGATAT ATTCCGCTTC CTCGCTCACT
        CGACGTGGCC ACGCAGTCGT CTTATACACT ATGTCCTATA TAAGGCGAAG GAGCGAGTGA
3181    GACTCGCTAC GCTCGGTCGT TCGACTGCGG CGAGCGGAAA TGGCTTACGA ACGGGGCGGA
        CTGAGCGATG CGAGCCAGCA AGCTGACGCC GCTCGCCTTT ACCGAATGCT TGCCCCGCCT
3241    GATTTCCTGG AAGATGCCAG GAAGATACTT AACAGGGAAG TGAGAGGGCC GCGGCAAAGC
        CTAAAGGACC TTCTACGGTC CTTCTATGAA TTGTCCCTTC ACTCTCCCGG CGCCGTTTCG
3301    CGTTTTTCCA TAGGCTCCGC CCCCCTGACA AGCATCACGA AATCTGACGC TCAAATCAGT
        GCAAAAAGGT ATCCGAGGCG GGGGGACTGT TCGTAGTGCT TTAGACTGCG AGTTTAGTCA
3361    GGTGGCGAAA CCCGACAGGA CTATAAAGAT ACCAGGCGTT TCCCCTGGCG GCTCCCTCGT
        CCACCGCTTT GGGCTGTCCT GATATTTCTA TGGTCCGCAA AGGGGACCGC CGAGGGAGCA
3421    GCGCTCTCCT GTTCCTGCCT TTCGGTTTAC CGGTGTCATT CCGCTGTTAT GGCCGCGTTT
        CGCGAGAGGA CAAGGACGGA AAGCCAAATA GGCGACAATA CCGGCGCAAA CCGGCGCAAA
3481    GTCTCATTCC ACGCCTGACA CTCAGTTCCG GGTAGGCAGT TCGCTCCAAG CTGGACTGTA
        CAGAGTAAGG TGCGGACTGT GAGTCAAGGC CCATCCGTCA AGCGAGGTTC GACCTGACAT
3541    TGCACGAACC CCCCGTTCAG TCCGACCGCT GCGCCTTATC CGGTAACTAT CGTCTTGAGT
```

Fig. 28$_2$

```
      ACGTGCTTGG GGGGCAAGTC AGGCTGGCGA CGCGGAATAG GCCATTGATA GCAGAACTCA
3601  CCAACCCGGA AAGACATGCA AAAGCACCAC TGGCAGCAGC CACTGGTAAT TGATTTAGAG
      GGTTGGGCCT TTCTGTACGT TTTCGTGGTG ACCGTCGTCG GTGACCATTA ACTAAATCTC
3661  GAGTTAGTCT TGAAGTCATG CGCGGTTAA GGCTAAACTG AAAGGACAAG TTTTGGTGAC
      CTCAATCAGA ACTTCAGTAC GCGGCCAATT CCGATTTGAC TTTCCTGTTC AAAACCACTG
3721  TGCGCTCCTC CAAGCCAGTT ACCTCGGTTC AAAGAGTTGG TAGCTCAGAG AACCTTCGAA
      ACGCGAGGAG GTTCGGTCAA TGGAGCCAAG TTTCTCAACC ATCGAGTCTC TTGGAAGCTT
3781  AAACCGCCCT GCAAGGCGGT TTTTTCGTTT TCAGAGCAAG AGATTACGCG CAGACCAAAA
      TTTGGCGGGA CGTTCCGCCA AAAAGCAAA AGTCTCGTTC TCTAATGCGC GTCTGGTTTT
3841  CGATCTCAAG AAGATCATCT TATTAATCAG ATAAAATATT TCTAGATTTC AGTGCAATTT
      GCTAGAGTTC TTCTAGTAGA ATAATTAGTC TATTTTATAA AGATCTAAAG TCACGTTAAA
3901  ATCTCTTCAA ATGTAGCACC TGAAGTCAGC CCCATACGAT ATAAGTTGTA ATTCTCATGT
      TAGAGAAGTT TACATCGTGG ACTTCAGTCG GGGTATGCTA TATTCAACAT TAAGAGTACA
3961  TAGTCATGCC CCGCGCCCAC CGGAAGGAGC TGACTGGGTT GAAGGCTCTC AAGGGCATCG
      ATCAGTACGG GGCGCGGGTG GCCTTCCTCG ACTGACCCAA CTTCCGAGAG TTCCCGTAGC
4021  GTCGAGATCC CGGTGCCTAA TGAGTGAGCT AACTTACATT AATTGCGTTG CGCTCACTGC
      CAGCTCTAGG GCCACGGATT ACTCACTCGA TTGAATGTAA TTAACGCAAC GCGAGTGACG
4081  CCGCTTTCCA GTCGGGAAAC CTGTCGTGCC AGCTGCATTA ATGAATCGGC CAACGCGCGG
      GGCGAAAGGT CAGCCCTTTG GACAGCACGG TCGACGTAAT TACTTAGCCG GTTGCGCGCC
4141  GGAGAGGCGG TTTGCGTATT GGGCGCCAGG GTGGTTTTTC TTTTCACCAG TGAGACGGGC
      CCTCTCCGCC AAACGCATAA CCCGCGGTCC CACCAAAAAG AAAAGTGGTC ACTCTGCCCG
4201  AACAGCTGAT TGCCCTTCAC CGCCTGGCCC TGAGAGAGTT GCAGCAAGCG GTCCACGCTG
      TTGTCGACTA ACGGGAAGTG GCGGACCGGG ACTCTCTCAA CGTCGTTCGC CAGGTGCGAC
4261  GTTTGCCCCA GCAGGCGAAA AATCCGTTTG ATGGTGGTTA ACGGCGGGAT ATAACATGAG
      CAAACGGGGT CGTCCGCTTT TAGGACAAAC TACCACCAAT TGCCGCCCTA TATTGTACTC
4321  CTGTCTTCGG TATCGTCGTA TCCCACTACC GAGATGTCCG CACCAACGCG CAGCCCGGAC
      GACAGAAGCC ATAGCAGCAT AGGGTGATGG CTCTACAGGC GTGGTTGCGC GTCGGGCCTG
4381  TCGGTAATGG CGCGCATTGC GCCCAGCGCC ATCTGATCGT TGGCAACCAG CATCGCAGTG
      AGCCATTACC GCGCGTAACG CGGGTCGCGG TAGACTAGCA ACCGTTGGTC GTAGCGTCAC
4441  GGAACGATGC CCTCATTCAG CATTTGCATG GTTTGTTGAA AACCGGACAT GGCACTCCAG
      CCTTGCTACG GGAGTAAGTC GTAAACGTAC CAAACAACTT TTGGCCTGTA CCGTGAGGTC
4501  TCGCCTTCCC GTTCCGCTAT CGGCTGAATT TGATTGCGAG TGAGATATTT ATGCCAGCCA
      AGCGGAAGGG CAAGGCGATA GCCGACTTAA CTAACGCTC ACTCTATAAA TACGGTCGGT
4561  GCCAGACGCA GACGCGCCGA GACAGAACTT AATGGGCCCG CTAACAGCGC GATTTGCTGG
      CGGTCTGCGT CTGCGCGGCT CTGTCTTGAA TTACCCGGGC GATTGTCGCG CTAAACGACC
4621  TGACCCAATG CGACCAGATG CTCCACGCCC AGTCGCGTAC CGTCTTCATG GGAGAAAATA
      ACTGGGTTAC GCTGGTCTAC GAGGTGCGGG TCAGCGCATG GCAGAAGTAC CCTCTTTTAT
4681  ATACTGTTGA TGGGTGTCTG GTCAGAGACA TCAAGAAATA ACGCCGGAAC ATTAGTGCAG
      TATGACAACT ACCCACAGAC CAGTCTCTGT AGTTCTTTAT TGCGGCCTTG TAATCACGTC
4741  GCAGCTTCCA CAGCAATGGC ATCCTGGTCA TCCAGCGGAT AGTTAATGAT CAGCCCACTG
      CGTCGAAGGT GTCGTTACCG TAGGACCAGT AGGTCGCCTA TCAATTACTA GTCGGGTGAC
4801  ACGCGTTGCG CGAGAAGATT GTGCACCGCC GCTTTACAGG CTTCGACGCC GCTTCGTTCT
      TGCGCAACGC GCTCTTCTAA CACGTGGCGG CGAAATGTCC GAAGCTGCGG CGAAGCAAGA
4861  ACCATCGACA CCACCACGCT GGCACCCAGT TGATCGGCGC GAGATTTAAT CGCCGCGACA
      TGGTAGCTGT GGTGGTGCGA CCGTGGGTCA ACTAGCCGCG CTCTAAATTA GCGGCGCTGT
4921  ATTTGCGACG GCGCGTGCAG GGCCAGACTG GAGGTGGCAA CGCCAATCAG CAACGACTGT
      TAAACGCTGC CGCGCACGTC CCGGTCTGAC CTCCACCGTT GCGGTTAGTC GTTGCTGACA
4981  TTGCCCGCCA GTTGTTGTGC CACGCGGTTG GGAATGTAAT TCAGCTCCGC CATCGCCGCT
      AACGGGCGGT CAACAACACG GTGCGCCAAC CCTTACATTA AGTCGAGGCG GTAGCGGCGA
5041  TCCACTTTTT CCCGCGTTTT CGCAGAAACG TGGCTGGCCT GGTTCACCAC GCGGGAAACG
      AGGTGAAAAA GGGCGCAAAA GCGTCTTTGC ACCGACCGGA CCAAGTGGTG CGCCCTTTGC
5101  GTCTGATAAG AGACACCGGC ATACTCTGCG ACATCGTATA ACGTTACTGG TTTCACATTC
      CAGACTATTC TCTGTGGCCG TATGAGACGT TGTAGCATAT TGCAATGACC AAAGTGTAAG
5161  ACCACCCTGA ATTGACTCTC TTCCGGGCGC TATCATGCCA TACCGCGAAA GGTTTTGCGC
      TGGTGGGACT TAACTGAGAG AAGGCCCGCG ATAGTACGGT ATGGCGCTTT CCAAAACGCG
5221  CATTCGATGG TGTCCGGGAT CTCGACGCTC TCCCTTATGC GACTCCTGCA TTAGGAAATT
      GTAAGCTACC ACAGGCCCTA GAGCTGCGAG AGGGAATACG CTGAGGACGT AATCCTTTAA
5281  AATACGACTC ACTATA
      TTATGCTGAG TGATAT
```

Fig. 28₃

| Fig. 30₁ |
|---|
| Fig. 30₂ |
| Fig. 30₃ |

Fig. 30

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                            EcoRI
                                                            ~~~~~~
                                              BamHI          SacI
                                              ~~~~~~~        ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGATCACA AGTTTGTACA AAAAAGCTGA ACGAGAAACG TAAAATGATA TAAATATCAA
     GAGCTAGTGT TCAAACATGT TTTTTCGACT TGCTCTTTGC ATTTTACTAT ATTTATAGTT
 181 TATATTAAAT TAGATTTTGC ATAAAAAACA GACTACATAA TACTGTAAAA CACAACATAT
     ATATAATTTA ATCTAAAACG TATTTTTTGT CTGATGTATT ATGACATTTT GTGTTGTATA
 241 CCAGTCACTA TGGCGGCCGC CACGTTAAGG GATTTTGGTC ATGATCAGCA CGTGTTGACA
     GGTCAGTGAT ACCGCCGGCG GTGCAATTCC CTAAAACCAG TACTAGTCGT GCACAACTGT
 301 ATTAATCATC GGCATAGTAT ATCGGCATAG TATAATACGA CAAGGTGAGG AACTAAACCA
     TAATTAGTAG CCGTATCATA TAGCCGTATC ATATTATGCT GTTCCACTCC TTGATTTGGT
 361 TGGCCAAGTT GACCAGTGCC GTTCCGGTGC TCACCGCGCG CGACGTCGCC GGAGCGGTCG
     ACCGGTTCAA CTGGTCACGG CAAGGCCACG AGTGGCGCGC GCTGCAGCGG CCTCGCCAGC
 421 AGTTCTGGAC CGACCGGCTC GGGTTCTCCC GGGACTTCGT GGAGGACGAC TTCGCCGGTG
     TCAAGACCTG GCTGGCCGAG CCCAAGAGGG CCCTGAAGCA CCTCCTGCTG AAGCGGCCAC
 481 TGGTCCGGGA CGACGTGACC CTGTTCATCA GCGCGGTCCA GGACCAGGTG GTGCCGGACA
     ACCAGGCCCT GCTGCACTGG GACAAGTAGT CGCGCCAGGT CCTGGTCCAC CACGGCCTGT
 541 ACACCCTGGC CTGGGTGTGG GTGCGCGGCC TGGACGAGCT GTACGCCGAG TGGTCGGAGG
     TGTGGGACCG GACCCACACC CACGCGCCGG ACCTGCTCGA CATGCGGCTC ACCAGCCTCC
 601 TCGTGTCCAC GAACTTCCGG GACGCCTCCG GGCCGGCCAT GACCGAGATC GGCGAGCAGC
     AGCACAGGTG CTTGAAGGCC CTGCGGAGGC CCGGCCGGTA CTGGCTCTAG CCGCTCGTCG
 661 CGTGGGGGCG GGAGTTCGCC CTGCGCGACC CGGCCGGCAA CTGCGTGCAC TTCGTGGCCG
     GCACCCCCGC CCTCAAGCGG GACGCGCTGG GCCGGCCGTT GACGCACGTG AAGCACCGGC
 721 AGGAGCAGGA CTGATCATGA TGATATTATT TTATCTTGTG CAATGTAACA TCAGAGATTT
     TCCTCGTCCT GACTAGTACT ACTATAATAA AATAGAACGA GTTACATTGT AGTCTCTAAA
 781 TGAGACACGG GCCAGAGCTG CCAGGAAACA GCTATGACCA TGTAATACGA CTCACTATAG
     ACTCTGTGCC CGGTCTCGAC GGTCCTTTGT CGATACTGGT ACATTATGCT GAGTGATATC
 841 GGGATATCAG CTGGATGGCA AATAATGATT TTATTTTGAC TGATAGTGAC CTGTTCGTTG
     CCCTATAGTC GACCTACCGT TTATTACTAA AATAAACTG ACTATCACTG GACAAGCAAC
 901 CAACACCGGT GCTAGCGTAT ACCCGAAGTA TGTCAAAAAG AGGTGTGCTA TGAAGCAGCG
     GTTGTGGCCA CGATCGCATA TGGGCTTCAT ACAGTTTTTC TCCACACGAT ACTTCGTCGC
 961 TATTACAGTG ACAGTTGACA GCGACAGCTA TCAGTTGCTC AAGGCATATA TGATGTCAAT
     ATAATGTCAC TGTCAACTGT CGCTGTCGAT AGTCAACGAG TTCCGTATAT ACTACAGTTA
1021 ATCTCCGGTC TGGTAAGCAC AACCATGCGC AATGAAGCCC GTCGTCTGCA TGCCGAACGC
     TAGAGGCCAG ACCATTCGTG TTGGTACGTC TTACTTCGGG CAGCAGACGC ACGGCTTGCG
1081 TGGAAAGCGG AAAATCAGGA AGGGATGGCT GAGGTCGCCC GGTTTATTGA AATGAACGGC
     ACCTTTCGCC TTTTAGTCCT TCCCTACCGA CTCCAGCGGG CCAAATAACT TTACTTGCCG
1141 TCTTTTGCTG ACGAGAACAG GGACTGGTGA AATGCAGTTT AAGGTTTACA CCTATAAAAG
     AGAAAACGAC TGCTCTTGTC CCTGACCACT TTACGTCAAA TTCCAAATGT GGATATTTTC
1201 AGAGACCCGT TATCGTCTGT TTGTGGATGT ACAGAGTGAT ATTATTGACA CGCCCGGGCG
     TCTCTCGGCA ATAGCAGACA AACACCTACA TGTCTCACTA TAATAACTGT GCGGGCCCGC
1261 ACGGATGGTG ATCCCCCTGG CCAGTGCACG TCTGCTGTCA GATAAAGTCT CCCGTGAACT
     TGCCTACCAC TAGGGGGACC GGTCACGTGC AGACGACAGT CTATTTCAGA GGGCACTTGA
1321 TTACCCGGTG GTGCATATCG GGGATGAAAG CTGGCGCATG ATGACCACCG ATATGGCCAG
     AATGGGCCAC CACGTATAGC CCCTACTTTC GACCGCGTAC TACTGGTGGC TATACCGGTC
1381 TGTGCCGGTC TCCGTTATCG GGAAGAAGT GGCTGATCTC AGCCGCCGCG AAAATGACAT
     ACACGGCCAG AGGCAATAGC CCCTTCTTCA CCGACTAGAG TCGGCGGCGC TTTTACTGTA
1441 CAAAAACGCC ATTAACCTGA TGTTCTGGGG AATATAAATG TCAGGCTCCC TTATACACAG
     GTTTTTGCGG TAATTGGACT ACAAGACCCC TTATATTTAC AGTCCGAGGG AATATGTGTC
     PstI
     ~~~~~~~
1501 CCAGTCTGCA GGTCGACCAT AGTGACTGGA TATGTTGTGT TTTACAGTAT TATGTAGTCT
     GGTCAGACGT CCAGCTGGTA TCACTGACCT ATACAACACA AAATGTCATA ATACATCAGA
1561 GTTTTTTATG CAAATCTAA TTTAATATAT TGATATTTAT ATCATTTTAC GTTTCTCGTT
     CAAAAAATAC GTTTTAGATT AAATTATATA ACTATAAATA TAGTAAAATG CAAAGAGCAA
                                                               HindIII
                                                               ~~~~~~
1621 CAGCTTTCTT GTACAAAGTG GTGATAATTA ATTAAGATCA GATCCGGCTG CTAAGCTTGG
     GTCGAAAGAA CATGTTTCAC CACTATTAAT TAATTCTAGT CTAGGCCGAC GATTCGAACC
                                                     AvrII
                                                     ~~~~~
1681 AATTGTTATC CGCTCACAAT TCCTATAGTG AGTCGTATTA CCTAGGCTGC TGCCACCGCT
     TTAACAATAG GCGAGTGTTA AGGATATCAC TCAGCATAAT GGATCCGACG ACGGTGGCGA
```

Fig. 30₁

```
1741  GAGCAATAAC TAGCATAACC CCTTGGGGCC TCTAAACGGG TCTTGAGGGG TTTTTTGCTG
      CTCGTTATTG ATCGTATTGG GGAACCCCGG AGATTTGCCC AGAACTCCCC AAAAAACGAC
1801  AAACCTCAGG CATTTGAGAA GCACACGGTC ACACTGCTTC CGGTAGTCAA TAAACCGGTA
      TTTGGAGTCC GTAAACTCTT CGTGTGCCAG TGTGACGAAG GCCATCAGTT ATTTGGCCAT
1861  AACCAGCAAT AGACATAAGC GGCTATTTAA CGACCCTGCC CTGAACCGAC GACCGGGTCA
      TTGGTCGTTA TCTGTATTCG CCGATAAATT GCTGGGACGG GACTTGGCTG CTGGCCCAGT
1921  TCGTGGCCGG ATCTTGCGGC CCCTCGGCTT GAACGAATTG TTAGACATTA TTTGCCGACT
      AGCACCGGCC TAGAACGCCG GGGAGCCGAA CTTGCTTAAC AATCTGTAAT AAACGGCTGA
1981  ACCTTGGTGA TCTCGCCTTT CACGTAGTGG ACAAATTCTT CCAACTGATC TGCGCGCGAG
      TGGAACCACT AGAGCGGAAA GTGCATCACC TGTTTAAGAA GGTTGACTAG ACGCGCGCTC
2041  GCCAAGCGAT CTTCTTCTTG TCCAAGATAA GCCTGTCTAG CTTCAAGTAT GACGGGCTGA
      CGGTTCGCTA GAAGAAGAAC AGGTTCTATT CGGACAGATC GAAGTTCATA CTGCCCGACT
2101  TACTGGGCCG GCAGGCGCTC CATTGCCCAG TCGGCAGCGA CATCCTTCGG CGCGATTTTG
      ATGACCCGGC CGTCCGCGAG GTAACGGGTC AGCCGTCGCT GTAGGAAGCC GCGCTAAAAC
2161  CCGGTTACTG CGCTGTACCA AATGCGGGAC AACGTAAGCA CTACATTTCG CTCATCGCCA
      GGCCAATGAC GCGACATGGT TTACGCCCTG TTGCATTCGT GATGTAAAGC GAGTAGCGGT
2221  GCCCAGTCGG GCGGCGAGTT CCATAGCGTT AAGGTTTCAT TTAGCGCCTC AAATAGATCC
      CGGGTCAGCC CGCCGCTCAA GGTATCGCAA TTCCAAAGTA AATCGCGGAG TTTATCTAGG
2281  TGTTCAGGAA CCGGATCAAA GAGTTCCTCC GCCGCTGGAC CTACCAAGGC AACGCTATGT
      ACAAGTCCTT GGCCTAGTTT CTCAAGGAGG CGGCGACCTG GATGGTTCCG TTGCGATACA
2341  TCTCTTGCTT TTGTCAGCAA GATAGCCAGA TCAATGTCGA TCGTGGCTGG CTCGAAGATA
      AGAGAACGAA ACAGTCGTT CTATCGGTCT AGTTACAGCT AGCACCGACC GAGCTTCTAT
2401  CCTGCAAGAA TGTCATTGCG CTGCCATTCT CCAAATTGCA GTTCGCGCTT AGCTGGATAA
      GGACGTTCTT ACAGTAACGC GACGGTAAGA GGTTTAACGT CAAGCGCGAA TCGACCTATT
2461  CGCCACGAAA TGATGTCGTC GTGCACAACA ATGGTGACTT CTACAGCGCG GAGAATCTCG
      GCGGTGCCTT ACTACAGCAG CACGTGTTGT TACCACTGAA GATGTCGCGC CTCTTAGAGC
2521  CTCTCTCCAG GGGAAGCCGA AGTTTCCAAA AGGTCGTTGA TCAAAGCTCG CCGCGTTGTT
      GAGAGAGGTC CCCTTCGGCT TCAAAGGTTT TCCAGCAACT AGTTTCGAGC GGCGCAACAA
2581  TCATCAAGCC TTACGGTCAC CGTAACCAGC AAATCATAT CACTGTGTGG CTTCAGGCCG
      AGTAGTTCGG AATGCCAGTG GCATTGGTCG TTTAGTTATA GTGACACACC GAAGTCCGGC
2641  CCATCCACTG CGGAGCCGTA CAAATGTACG GCCAGCAACG TCGGTTCGAG ATGGCGCTCG
      GGTAGGTGAC GCCTCGGCAT GTTTACATGC CGGTCGTTGC AGCCAAGCTC TACCGCGAGC
2701  ATGACGCCAA CTACCTCTGA TAGTTGAGTC GATACTTCGG CGATCACCGC TTCCCTCATA
      TACTGCGGTT GATGGAGACT ATCAACTCAG CTATGAAGCC GCTAGTGCCG AAGGGAGTAT
2761  CTCTTCCTTT TTCAATATTA TTGAAGCATT TATCAGGGTT ATTGTCTCAT GAGCGGATAC
      GAGAAGGAAA AAGTTATAAT AACTTCGTAA ATAGTCCCAA TAACAGAGTA CTCGCCTATG
2821  ATATTTGAAT GTATTTAGAA AAATAAACAA ATAGCTAGCT CACTCGGTCG CTACGCTCCG
      TATAAACTTA CATAAATCTT TTTATTTGTT TATCGATCGA GTGAGCCAGC GATGCGAGGC
2881  GGCGTGAGAC TGCGGCGGGC GCTGCGGACA CATACAAAGT TACCCACAGA TTCCGTGGAT
      CCGCACTCTG ACGCCGCCCG CGACGCCTGT GTATGTTTCA ATGGGTGTCT AAGGCACCTA
2941  AAGCAGGGGA CTAACATGTG AGGCAAAACA GCAGGGCCGG GCCGGTGGCG TTTTTCCATA
      TTCGTCCCCT GATTGTACAC TCCGTTTTGT CGTCCCGGCC CGGCCACCGC AAAAAGGTAT
3001  GGCTCCGCCC TCCTGCCAGA GTTCACATAA ACAGACGCTT TTCCGGTGCA TCTGTGGGAG
      CCGAGGCGGG AGGACGGTCT CAAGTGTATT TGTCTGCGAA AAGGCCACGT AGACACCCTC
3061  CCGTGAGGCT CAACCATGAA TCTGACAGTA CGGGCGAAAC CCGACAGGAC TTAAAGATCC
      GGCACTCCGA GTTGGTACTT AGACTGTCAT GCCCGCTTTG GGCTGTCCTG AATTTCTAGG
3121  CCACCGTTTC CGGCGGGTCG CTCCCTCTTG CGCTCTCCTG TTCCGACCCT GCCGTTTACC
      GGTGGCAAAG GCCGCCCAGC GAGGGAGAAC GCGAGAGGAC AAGGCTGGGA CGGCAAATGG
3181  GGATACCTGT TCCGCCTTTC TCCCTTACGG GAAGTGTGGC GCTTTCTCAT AGCTCACACA
      CCTATGGACA AGGCGGAAAG AGGGAATGCC CTTCACACCG CGAAAGAGTA TCGAGTGTGT
3241  CTGGTATCTC GGCTCGGTGT AGGTCGTTCG CTCCAAGCTG GGCTGTAAGC AAGAACTCCC
      GACCATAGAG CCGAGCCACA TCCAGCAAGC GAGGTTCGAC CCGACATTCG TTCTTGAGGG
3301  CGTTCAGCCC GACTGCTGCG CCTTATCCGG TAACTGTTCA CTTGAGTCCA ACCCGGAAAA
      GCAAGTCGGG CTGACGACGC GGAATAGGCC ATTGACAAGT GAACTCAGGT TGGGCCTTTT
3361  GCACGGTAAA ACGCCACTGG CAGCAGCCAT TGGTAACTGG GAGTTCGCAG AGGATTGTT
      CGTGCCATTT TGCGGTGACC GTCGTCGGTA ACCATTGACC CTCAAGCGTC TCCTAAACAA
3421  TAGCTAAACA CGCGGTTGCT CTTGAAGTGT GCGCCAAAGT CCGGCTACAC TGGAAGGACA
      ATCGATTTGT GCGCCAACGA GAACTTCACA CGCGGTTTCA GGCCGATGTG ACCTTCCTGT
3481  GATTTGGTTG CTGTGCTCTG CGAAAGCCAG TTACCACGGT TAAGCAGTTC CCCAACTGAC
      CTAAACCAAC GACACGAGAC GCTTTCGGTC AATGGTGCCA ATTCGTCAAG GGGTTGACTG
3541  TTAACCTTCG ATCAAACCAC CTCCCCAGGT GGTTTTTTCG TTTACAGGGC AAAAGATTAC
      AATTGGAAGC TAGTTTGGTG GAGGGGTCCA CCAAAAAAGC AAATGTCCCG TTTTCTAATG
3601  GCGCAGAAAA AAAGGATCTC AAGAAGATCC TTTGATCTTT TCTACTGAAC CGCTCTAGAT
      CGCGTCTTTT TTTCCTAGAG TTCTTCTAGG AAACTAGAAA AGATGACTTG GCGAGATCTA
3661  TTCAGTGCAA TTTATCTCTT CAAATGTAGC ACCTGAAGTC AGCCCCATAC GATATAAGTT
      AAGTCACGTT AAATAGAGAA GTTTACATCG TGGACTTCAG TCGGGGTATG CTATATTCAA
3721  GTAATTCTCA TGTTAGTCAT GCCCCGCGCC CACCGGAAGG AGCTGACTGG GTTGAAGGCT
      CATTAAGAGT ACAATCAGTA CGGGGCGCGG GTGGCCTTCC TCGACTGACC CAACTTCCGA
3781  CTCAAGGGCA TCGGTCGAGA TCCCGGTGCC TAATGAGTGA GCTAACTTAC ATTAATTGCG
```

Fig. 30₂

```
      GAGTTCCCGT AGCCAGCTCT AGGGCCACGG ATTACTCACT CGATTGAATG TAATTAACGC
3841  TTGCGCTCAC TGCCCGCTTT CCAGTCGGGA AACCTGTCGT GCCAGCTGCA TTAATGAATC
      AACGCGAGTG ACGGGCGAAA GGTCAGCCCT TTGGACAGCA CGGTCGACGT AATTACTTAG
3901  GGCCAACGCG CGGGGAGAGG CGGTTTGCGT ATTGGGCGCC AGGGTGGTTT TTCTTTTCAC
      CCGGTTGCGC GCCCCTCTCC GCCAAACGCA TAACCCGCGG TCCCACCAAA AAGAAAAGTG
3961  CAGTGAGACG GGCAACAGCT GATTGCCCTT CACCGCCTGG CCCTGAGAGA GTTGCAGCAA
      GTCACTCTGC CCGTTGTCGA CTAACGGGAA GTGGCGGACC GGGACTCTCT CAACGTCGTT
4021  GCGGTCCACG CTGGTTTGCC CCAGCAGGCG AAAATCCTGT TTGATGGTGG TTAACGGCGG
      CGCCAGGTGC GACCAAACGG GGTCGTCCGC TTTTAGGACA AACTACCACC AATTGCCGCC
4081  GATATAACAT GAGCTGTCTT CGGTATCGTC GTATCCCACT ACCGAGATGT CCGCACCAAC
      CTATATTGTA CTCGACAGAA GCCATAGCAG CATAGGGTGA TGGCTCTACA GGCGTGGTTG
4141  GCGCAGCCCG GACTCGGTAA TGGCGCGCAT TGCGCCCAGC GCCATCTGAT CGTTGGCAAC
      CGCGTCGGGC CTGAGCCATT ACCGCGCGTA ACGCGGGTCG CGGTAGACTA GCAACCGTTG
4201  CAGCATCGCA GTGGGAACGA TGCCCTCATT CAGCATTTGC ATGGTTTGTT GAAAACCGGA
      GTCGTAGCGT CACCCTTGCT ACGGGAGTAA GTCGTAAACG TACCAAACAA CTTTTGGCCT
4261  CATGGCACTC CAGTCGCCTT CCCGTTCCGC TATCGGCTGA ATTTGATTGC GAGTGAGATA
      GTACCGTGAG GTCAGCGGAA GGGCAAGGCG ATAGCCGACT TAAACTAACG CTCACTCTAT
4321  TTTATGCCAG CCAGCCAGAC GCAGACGCGC CGAGACAGAA CTTAATGGGC CCGCTAACAG
      AAATACGGTC GGTCGGTCTG CGTCTGCGCG GCTCTGTCTT GAATTACCCG GGCGATTGTC
4381  CGCGATTTGC TGGTGACCCA ATGCGACCAG ATGCTCCACG CCCAGTCGCG TACCGTCTTC
      GCGCTAAACG ACCACTGGGT TACGCTGGTC TACGAGGTGC GGGTCAGCGC ATGGCAGAAG
4441  ATGGGAGAAA ATAATACTGT TGATGGGTGT CTGGTCAGAG ACATCAAGAA ATAACGCCGG
      TACCCTCTTT TATTATGACA ACTACCCACA GACCAGTCTC TGTAGTTCTT TATTGCGGCC
4501  AACATTAGTG CAGGCAGCTT CCACAGCAAT GGCATCCTGG TCATCCAGCG GATAGTTAAT
      TTGTAATCAC GTCCGTCGAA GGTGTCGTTA CCGTAGGACC AGTAGGTCGC CTATCAATTA
4561  GATCAGCCCA CTGACGCGTT GCGCGAGAAG ATTGTGCACC GCCGCTTTAC AGGCTTCGAC
      CTAGTCGGGT GACTGCGCAA CGCGCTCTTC TAACACGTGG CGGCGAAATG TCCGAAGCTG
4621  GCCGCTTCGT TCTACCATCG ACACCACCAC GCTGGCACCC AGTTGATCGG CGCGAGATTT
      CGGCGAAGCA AGATGGTAGC TGTGGTGGTG CGACCGTGGG TCAACTAGCC GCGCTCTAAA
4681  AATCGCCGCG ACAATTTGCG ACGGCGCGTG CAGGGCCAGA CTGGAGGTGG CAACGCCAAT
      TTAGCGGCGC TGTTAAACGC TGCCGCGCAC GTCCCGGTCT GACCTCCACC GTTGCGGTTA
4741  CAGCAACGAC TGTTTGCCCG CCAGTTGTTG TGCCACGCGG TTGGGAATGT AATTCAGCTC
      GTCGTTGCTG ACAAACGGGC GGTCAACAAC ACGGTGCGCC AACCCTTACA TTAAGTCGAG
4801  CGCCATCGCC GCTTCCACTT TTTCCCGCGT TTTCGCAGAA ACGTGGCTGG CCTGGTTCAC
      GCGGTAGCGG CGAAGGTGAA AAAGGGCGCA AAAGCGTCTT TGCACCGACC GGACCAAGTG
4861  CACGCGGGAA ACGGTCTGAT AAGAGACACC GGCATACTCT GCGACATCGT ATAACGTTAC
      GTGCGCCCTT TGCCAGACTA TTCTCTGTGG CCGTATGAGA CGCTGTAGCA TATTGCAATG
4921  TGGTTTCACA TTCACCACCC TGAATTGACT CTCTTCCGGG CGCTATCATG CCATACCGCG
      ACCAAAGTGT AAGTGGTGGG ACTTAACTGA GAGAAGGCCC GCGATAGTAC GGTATGGCGC
4981  AAAGGTTTTG CGCCATTCGA TGGTGTCCGG GATCTCGACG CTCTCCCTTA TGCGACTCCT
      TTTCCAAAAC GCGGTAAGCT ACCACAGGCC CTAGAGCTGC GAGAGGGAAT ACGCTGAGGA
5041  GCATTAGGAA ATTAATACGA CTCACTATA
      CGTAATCCTT TAATTATGCT GAGTGATAT
```

Fig. 30$_3$

| Fig. 32$_1$ |
|---|
| Fig. 32$_2$ |
| Fig. 32$_3$ |

Fig. 32

```
   1  GGGGAATTGT GAGCGGATAA CAATTCCCCT GTAGAAATAA TTTTGTTTAA CTTTAATAAG
      CCCCTTAACA CTCGCCTATT GTTAAGGGGA CATCTTTATT AAAACAAATT GAAATTATTC
                                                                 EcoRI
                                                                 ~~~~~~
           NcoI                                      BamHI       SacI
           ~~~~~~~                                   ~~~~~~~     ~~~
  61  GAGATATACC ATGGGCAGCA GCCATCACCA TCATCACCAC AGCCAGGATC CGAATTCGAG
      CTCTATATGG TACCCGTCGT CGGTAGTGGT AGTAGTGGTG TCGGTCCTAG GCTTAAGCTC
      SacI
      ~~~
 121  CTCGATCACA AGTTTGTACA AAAAAGCTGA ACGAGAAACG TAAAATGATA TAAATATCAA
      GAGCTAGTGT TCAAACATGT TTTTTCGACT TGCTCTTTGC ATTTTACTAT ATTTATAGTT
 181  TATATTAAAT TAGATTTTGC ATAAAAAACA GACTACATAA TACTGTAAAA CACAACATAT
      ATATAATTTA ATCTAAAACG TATTTTTTGT CTGATGTATT ATGACATTTT GTGTTGTATA
 241  CCAGTCACTA TGGCGGCCGC CACGTTAAGG GATTTTGGTC ATGATCAGCA CGTGTTGACA
      GGTCAGTGAT ACCGCCGGCG GTGCAATTCC CTAAAACCAG TACTAGTCGT GCACAACTGT
                                                                  NcoI
                                                                  ~~~
 301  ATTAATCATC GGCATAGTAT ATCGGCATAG TATAATACGA CAAGGTGAGG AACTAAACCA
      TAATTAGTAG CCGTATCATA TAGCCGTATC ATATTATGCT GTTCCACTCC TTGATTTGGT
      NcoI
      ~~~
 361  TGGCCAAGTT GACCAGTGCC GTTCCGGTGC TCACCGCGCG CGACGTCGCC GGAGCGGTCG
      ACCGGTTCAA CTGGTCACGG CAAGGCCACG AGTGGCGCGC GCTGCAGCGG CCTCGCCAGC
 421  AGTTCTGGAC CGACCGGCTC GGGTTCTCCC GGACTTCGT GGAGGACGAC TTCGCCGGTG
      TCAAGACCTG GCTGGCCGAG CCCAAGAGGG CCCTGAAGCA CCTCCTGCTG AAGCGGCCAC
 481  TGGTCCGGGA CGACGTGACC CTGTTCATCA GCGCGGTCCA GGACCAGGTG GTGCCGGACA
      ACCAGGCCCT GCTGCACTGG GACAAGTAGT CGCGCCAGGT CCTGGTCCAC CACGGCCTGT
 541  ACACCCTGGC CTGGGTGTGG GTGCGCGGCC TGGACGAGCT GTACGCCGAG TGGTCGGAGG
      TGTGGGACCG GACCCACACC CACGCGCCGG ACCTGCTCGA CATGCGGCTC ACCAGCCTCC
 601  TCGTGTCCAC GAACTTCCGG GACGCCTCCG GGCCGGCCAT GACCGAGATC GGCGAGCAGC
      AGCACAGGTG CTTGAAGGCC CTGCGGAGGC CCGGCCGGTA CTGGCTCTAG CCGCTCGTCG
 661  CGTGGGGGCG GGAGTTCGCC CTGCGCGACC CGGCCGGCAA CTGCGTGCAC TTCGTGGCCG
      GCACCCCCGC CCTCAAGCGG GACGCGCTGG GCCGGCCGTT GACGCACGTG AAGCACCGGC
 721  AGGAGCAGGA CTGATCATGA TGATATTATT TTATCTTGTG CAATGTAACA TCAGAGATTT
      TCCTCGTCCT GACTAGTACT ACTATAATAA AATAGAACAC GTTACATTGT AGTCTCTAAA
 781  TGAGACACGG GCCAGAGCTG CCAGGAAACA GCTATGACCA TGTAATACGA CTCACTATAG
      ACTCTGTGCC CGGTCTCGAC GGTCCTTTGT CGATACTGGT ACATTATGCT GAGTGATATC
 841  GGGATATCAG CTGGATGGCA ATAATGATT TTATTTTGAC TGATAGTGAC CTGTTCGTTG
      CCCTATAGTC GACCTACCGT TTATTACTAA AATAAAACTG ACTATCACTG GACAAGCAAC
 901  CAACACCGGT GCTAGCGTAT ACCCGAAGTA TGTCAAAAAG AGGTGTGCTA TGAAGCAGCG
      GTTGTGGCCA CGATCGCATA TGGGCTTCAT ACAGTTTTTC TCCACACGAT ACTTCGTCGC
 961  TATTACAGTG ACAGTTGACA GCGACAGCTA TCAGTTGCTC AAGGCATATA TGATGTCAAT
      ATAATGTCAC TGTCAACTGT CGCTGTCGAT AGTCAACGAG TTCCGTATAT ACTACAGTTA
1021  ATCTCCGGTC TGGTAAGCAC AACCATGCAG AATGAAGCCC GTCGTCTGCG TGCCGAACGC
      TAGAGGCCAG ACCATTCGTG TTGGTACGTC TTACTTCGGG CAGCAGACGC ACGGCTTGCG
1081  TGGAAAGCGG AAAATCAGGA AGGGATGGCT GAGGTCGCCC GGTTTATTGA AATGAACGGC
      ACCTTTCGCC TTTTAGTCCT TCCCTACCGA CTCCAGCGGG CCAAATAACT TTACTTGCCG
1141  TCTTTTGCTG ACGAGAACAG GGACTGGTGA AATGCAGTTT AAGGTTTACA CCTATAAAAG
      AGAAAACGAC TGCTCTTGTC CCTGACCACT TTACGTCAAA TTCCAAATGT GGATATTTTC
1201  AGAGAGCCGT TATCGTCTGT TTGTGGATGT ACAGAGTGAT ATTATTGACA CGCCCGGGCG
      TCTCTCGGCA ATAGCAGACA AACACCTACA TGTCTCACTA TAATAACTGT GCGGGCCCGC
1261  ACGGATGGTG ATCCCCCTGG CCAGTGCACG TCTGCTGTCA GATAAAGTCT CCCGTGAACT
      TGCCTACCAC TAGGGGGACC GGTCACGTGC AGACGACAGT CTATTTCAGA GGGCACTTGA
1321  TTACCCGGTG GTGCATATCG GGGATGAAAG CTGGCGCATG ATGACCACCG ATATGGCCAG
      AATGGGCCAC CACGTATAGC CCCTACTTTC GACCGCGTAC TACTGGTGGC TATACCGGTC
1381  TGTGCCGGTC TCCGTTATCG GGAAGAAGT GGCTGATCTC AGCCGCCGCG AAAATGACAT
      ACACGGCCAG AGGCAATAGC CCCTTCTTCA CCGACTAGAG TCGGCGGCGC TTTTACTGTA
1441  CAAAAACGCC ATTAACCTGA TGTTCTGGGG AATATAAATG TCAGGCTCCC TTATACACAG
      GTTTTTGCGG TAATTGGACT ACAAGACCCC TTATATTTAC AGTCCGAGGG AATATGTGTC
      PstI
      ~~~~~~~
1501  CCAGTCTGCA GGTCGACCAT AGTGACTGGA TATGTTGTGT TTTACAGTAT TATGTAGTCT
      GGTCAGACGT CCAGCTGGTA TCACTGACCT ATACAACACA AAATGTCATA ATACATCAGA
1561  GTTTTTTATG CAAAATCTAA TTTAATATAT TGATATTTAT ATCATTTTAC GTTTCTCGTT
      CAAAAAATAC GTTTTAGATT AAATTATATA ACTATAAATA TAGTAAAATG CAAAGAGCAA
```

Fig. 32$_1$

```
                                                                HindIII
                                                                ~~~~~~
1621  CAGCTTTCTT GTACAAAGTG GTGATAATTA ATTAAGATCA GATCCGGCTG CTAAGCTTGG
      GTCGAAAGAA CATGTTTCAC CACTATTAAT TAATTCTAGT CTAGGCCGAC GATTCGAACC
                                                  AvrII
                                                  ~~~~~~
1681  AATTGTTATC CGCTCACAAT TCCTATAGTG AGTCGTATTA CCTAGGCTGC TGCCACCGCT
      TTAACAATAG GCGAGTGTTA AGGATATCAC TCAGCATAAT GGATCCGACG ACGGTGGCGA
1741  GAGCAATAAC TAGCATAACC CCTTGGGGCC TCTAAACGGG TCTTGAGGGG TTTTTTGCTG
      CTCGTTATTG ATCGTATTGG GGAACCCCGG AGATTTGCCC AGAACTCCCC AAAAAACGAC
1801  AAACCTCAGG CATTTGAGAA GCACACGGTC ACACTGCTTC CGGTAGTCAA TAAACCGGTA
      TTTGGAGTCC GTAAACTCTT CGTGTGCCAG TGTGACGAAG GCCATCAGTT ATTTGGCCAT
1861  AACCAGCAAT AGACATAAGC GGCTATTTAA CGACCCTGCC CTGAACCGAC GACAAGCTGA
      TTGGTCGTTA TCTGTATTCG CCGATAAATT GCTGGGACGG GACTTGGCTG CTGTTCGACT
1921  CGACCGGGTC TCCGCAAGTG GCACTTTTCG GGGAAATGTG CGCGGAACCC CTATTTGTTT
      GCTGGCCCAG AGGCGTTCAC CGTGAAAAGC CCCTTTACAC GCGCCTTGGG GATAAACAAA
1981  ATTTTTCTAA ATACATTCAA ATATGTATCC GCTCATGAAT TAATTCTTAG AAAAACTCAT
      TAAAAAGATT TATGTAAGTT TATACATAGG CGAGTACTTA ATTAAGAATC TTTTTGAGTA
2041  CGAGCATCAA ATGAAACTGC AATTTATTCA TATCAGGATT ATCAATACCA TATTTTTGAA
      GCTCGTAGTT TACTTTGACG TTAAATAAGT ATAGTCCTAA TAGTTATGGT ATAAAAACTT
2101  AAAGCCGTTT CTGTAATGAA GGAGAAAACT CACCGAGGCA GTTCCATAGG ATGGCAAGAT
      TTTCGGCAAA GACATTACTT CCTCTTTTGA GTGGCTCCGT CAAGGTATCC TACCGTTCTA
2161  CCTGGTATCG GTCTGCGATT CCGACTCGTC CAACATCAAT ACAACCTATT AATTTCCCCT
      GGACCATAGC CAGACGCTAA GGCTGAGCAG GTTGTAGTTA TGTTGGATAA TTAAAGGGGA
2221  CGTCAAAAAT AAGGTTATCA AGTGAGAAAT CACCATGAGT GACGACTGAA TCCGGTGAGA
      GCAGTTTTTA TTCCAATAGT TCACTCTTTA GTGGTACTCA CTGCTGACTT AGGCCACTCT
2281  ATGGCAAAAG TTTATGCATT TCTTTCCAGA CTTGTTCAAC AGGCCAGCCA TTACGCTCGT
      TACCGTTTTC AAATACGTAA AGAAAGGTCT GAACAAGTTG TCCGGTCGGT AATGCGAGCA
2341  CATCAAAATC ACTCGCATCA ACCAAACCGT TATTCATTCG TGATTGCGCC TGAGCGAGAC
      GTAGTTTTAG TGAGCGTAGT TGGTTTGGCA ATAAGTAAGC ACTAACGCGG ACTCGCTCTG
2401  GAAATACGCG GTCGCTGTTA AAAGGACAAT TACAAACAGG AATCGAATGC AACCGGCGCA
      CTTTATGCGC CAGCGACAAT TTTCCTGTTA ATGTTTGTCC TTAGCTTACG TTGGCCGCGT
2461  GGAACACTGC CAGCGCATCA ACAATATTTT CACCTGAATC AGGATATTCT TCTAATACCT
      CCTTGTGACG GTCGCGTAGT TGTTATAAAA GTGGACTTAG TCCTATAAGA AGATTATGGA
2521  GGAATGCTGT TTTCCCGGGG ATCGCAGTGG TGAGTAACCA TGCATCATCA GGAGTACGGA
      CCTTACGACA AAAGGGCCCC TAGCGTCACC ACTCATTGGT ACGTAGTAGT CCTCATGCCT
2581  TAAAATGCTT GATGGTCGGA AGAGGCATAA ATTCCGTCAG CCAGTTTAGT CTGACCATCT
      ATTTTACGAA CTACCAGCCT TCTCCGTATT TAAGGCAGTC GGTCAAATCA GACTGGTAGA
2641  CATCTGTAAC ATCATTGGCA ACGCTACCTT TGCCATGTTT CAGAAACAAC TCTGGCGCAT
      GTAGACATTG TAGTAACCGT TGCGATGGAA ACGGTACAAA GTCTTTGTTG AGACCGCGTA
                        ClaI
                        ~~~~~~~
2701  CGGGCTTCCC ATACAATCGA TAGATTGTCG CACCTGATTG CCCGACATTA TCGCGAGCCC
      GCCCGAAGGG TATGTTAGCT ATCTAACAGC GTGGACTAAC GGGCTGTAAT AGCGCTCGGG
2761  ATTTATACCC ATATAAATCA GCATCCATGT TGGAATTTAA TCGCGGCCTA GAGCAAGACG
      TAAATATGGG TATATTTAGT CGTAGGTACA ACCTTAAATT AGCGCCGGAT CTCGTTCTGC
2821  TTTCCCGTTG AATATGGCTC ATACTCTTCC TTTTTCAATA TTATTGAAGC ATTTATCAGG
      AAAGGGCAAC TTATACCGAG TATGAGAAGG AAAAAGTTAT AATAACTTCG TAAATAGTCC
2881  GTTATTGTCT CATGAGCGGA TACATATTTG AATGTATTTA GAAAAATAAA CAAATAGGCA
      CAATAACAGA GTACTCGCCT ATGTATAAAC TTACATAAAT CTTTTTATTT GTTTATCCGT
2941  TGCAGCGCTC TTCCGCTTCC TCGCTCACTG ACTCGCTACG CTCGGTCGTT CGACTGCGGC
      ACGTCGCGAG AAGGCGAAGG AGCGAGTGAC TGAGCGATGC GAGCCAGCAA GCTGACGCCG
3001  GAGCGGTGTC AGCTCACTCA AAAGCGGTAA TACGGTTATC CACAGAATCA GGGGATAAAG
      CTCGCCACAG TCGAGTGAGT TTTCGCCATT ATGCCAATAG GTGTCTTAGT CCCCTATTTC
3061  CCGGAAAGAA CATGTGAGCA AAAAGCAAAG CACCGGAAGA AGCCAACGCC GCAGGCGTTT
      GGCCTTTCTT GTACACTCGT TTTTCGTTTC GTGGCCTTCT TCGGTTGCGG CGTCCGCAAA
3121  TTCCATAGGC TCCGCCCCCC TGACGAGCAT CACAAAAATC GACGCTCAAG TGGAGAGGTG
      AAGGTATCCG AGGCGGGGGG ACTGCTCGTA GTGTTTTTAG CTGCGAGTTC GGTCTCCACC
3181  CGAAACCCGA CAGGACTATA AAGATACCAG GCGTTTCCCC TGGAAGCTC CCTCGTGCGC
      GCTTTGGGCT GTCCTGATAT TTCTATGGTC CGCAAAGGGG GACCTTCGAG GGAGCACGCG
3241  TCTCCTGTTC CGACCCTGCC GCTTACCGGA TACCTGTCCG CCTTTCTCCC TTCGGGAAGC
      AGAGGACAAG GCTGGGACGG CGAATGGCCT ATGGACAGGC GGAAAGAGGG AAGCCCTTCG
3301  GTGGCGCTTT CTCATAGCTC ACGCTGTTGG TATCTCAGTT CGGTGTAGGT CGTTCGCTCC
      CACCGCGAAA GAGTATCGAG TGCGACAACC ATAGAGTCAA GCCACATCCA GCAAGCGAGG
3361  AAGCTGGGCT GTGTGCACGA ACCCCCCGTT CAGCCCGACC GCTGCGCCTT ATCCGGTAAC
      TTCGACCCGA CACACGTGCT TGGGGGGCAA GTCGGGCTGG CGACGCGGAA TAGGCCATTG
3421  TATCGTCTTG AGTCCAACCC GGTAAGACAC GACTTATCGC CACTGGCAGC AGCCATTGGT
      ATAGCAGAAC TCAGGTTGGG CCATTCTGTG CTGAATAGCG GTGACCGTCG TCGGTAACCA
```

Fig. 32₂

```
3481 AACTGATTTA GAGGACTTTG TCTTGAAGTT ATGCACCTGT TAAGGCTAAA CTGAAAGAAC
     TTGACTAAAT CTCCTGAAAC AGAACTTCAA TACGTGGACA ATTCCGATTT GACTTCTTG
3541 AGATTTTGGT GAGTGCGGTC CTCCAACCCA CTTACCTTGG TTCAAAGAGT TGGTAGCTCA
     TCTAAAACCA CTCACGCCAG GAGGTTGGGT GAATGGAACC AAGTTTCTCA ACCATCGAGT
3601 GCGAACCTTG AGAAAACCAC CGTTGGTAGC GGTGGTTTTT CTTTATTTAT GAGATGATGA
     CGCTTGGAAC TCTTTTGGTG GCAACCATCG CCACCAAAAA GAAATAAATA CTCTACTACT
3661 ATCAATCGGT CTATCAAGTC AACGAACAGC TATTCCGTTA CTCTAGATTT CAGTGCAATT
     TAGTTAGCCA GATAGTTCAG TTGCTTGTCG ATAAGGCAAT GAGATCTAAA GTCACGTTAA
3721 TATCTCTTCA AATGTAGCAC CTGAAGTCAG CCCCATACGA TATAAGTTGT AATTCTCATG
     ATAGAGAAGT TTACATCGTG GACTTCAGTC GGGGTATGCT ATATTCAACA TTAAGAGTAC
3781 TTAGTCATGC CCCGCGCCCA CCGGAAGGAG CTGACTGGGT TGAAGGCTCT CAAGGGCATC
     AATCAGTACG GGGCGCGGGT GGCCTTCCTC GACTGACCCA ACTTCCGAGA GTTCCCGTAG
3841 GGTCGAGATC CCGGTGCCTA ATGAGTGAGC TAACTTACAT TAATTGCGTT GCGCTCACTG
     CCAGCTCTAG GGCCACGGAT TACTCACTCG ATTGAATGTA ATTAACGCAA CGCGAGTGAC
3901 CCCGCTTTCC AGTCGGGAAA CCTGTCGTGC CAGCTGCATT AATGAATCGG CCAACGCGCG
     GGGCGAAAGG TCAGCCCTTT GGACAGCACG GTCGACGTAA TTACTTAGCC GGTTGCGCGC
3961 GGGAGAGGCG GTTTGCGTAT TGGGCGCCAG GGTGGTTTTT CTTTTCACCA GTGAGACGGG
     CCCTCTCCGC CAAACGCATA ACCCGCGGTC CCACCAAAAA GAAAAGTGGT CACTCTGCCC
4021 CAACAGCTGA TTGCCCTTCA CCGCCTGGCC CTGAGAGAGT TGCAGCAAGC GGTCCACGCT
     GTTGTCGACT AACGGGAAGT GGCGGACCGG GACTCTCTCA ACGTCGTTCG CCAGGTGCGA
4081 GGTTTGCCCC AGCAGGCGAA AATCCTGTTT GATGGTGGTT AACGGCGGGA TATAACATGA
     CCAAACGGGG TCGTCCGCTT TTAGGACAAA CTACCACCAA TTGCCGCCCT ATATTGTACT
4141 GCTGTCTTCG GTATCGTCGT ATCCCACTAC CGAGATGTCC GCACCAACGC GCAGCCCGGA
     CGACAGAAGC CATAGCAGCA TAGGGTGATG GCTCTACAGG CGTGGTTGCG CGTCGGGCCT
4201 CTCGGTAATG GCGCGCATTG CGCCCAGCGC CATCTGATCG TTGGCAACCA GCATCGCAGT
     GAGCCATTAC CGCGCGTAAC GCGGGTCGCG GTAGACTAGC AACCGTTGGT CGTAGCGTCA
4261 GGGAACGATG CCCTCATTCA GCATTTGCAT GGTTTGTTGA AAACCGGACA TGGCACTCCA
     CCCTTGCTAC GGGAGTAAGT CGTAAACGTA CCAAACAACT TTTGGCCTGT ACCGTGAGGT
4321 GTCGCCTTCC CGTTCCGCTA TCGGCTGAAT TTGATTGCGA GTGAGATATT TATGCCAGCC
     CAGCGGAAGG GCAAGGCGAT AGCCGACTTA AACTAACGCT CACTCTATAA ATACGGTCGG
4381 AGCCAGACGC AGACGCGCCG AGACAGAACT TAATGGGCCC GCTAACAGCG CGATTTGCTG
     TCGGTCTGCG TCTGCGCGGC TCTGTCTTGA ATTACCCGGG CGATTGTCGC GCTAAACGAC
4441 GTGACCCAAT GCGACCAGAT GCTCCACGCC CAGTCGCGTA CCGTCTTCAT GGGAGAAAAT
     CACTGGGTTA CGCTGGTCTA CGAGGTGCGG GTCAGCGCAT GGCAGAAGTA CCCTCTTTTA
4501 AATACTGTTG ATGGGTGTCT GGTCAGAGAC ATCAAGAAAT AACGCCGGAA CATTAGTGCA
     TTATGACAAC TACCCACAGA CCAGTCTCTG TAGTTCTTTA TTGCGGCCTT GTAATCACGT
4561 GGCAGCTTCC ACAGCAATGG CATCCTGGTC ATCCAGCGGA TAGTTAATGA TCAGCCCACT
     CCGTCGAAGG TGTCGTTACC GTAGGACCAG TAGGTCGCCT ATCAATTACT AGTCGGGTGA
4621 GACGCGTTGC GCGAGAAGAT TGTGCACCGC CGCTTTACAG GCTTCGACGC CGCTTCGTTC
     CTGCGCAACG CGCTCTTCTA ACACGTGGCG GCGAAATGTC CGAAGCTGCG GCGAAGCAAG
4681 TACCATCGAC ACCACCACGC TGGCACCCAG TTGATCGGCG CGAGATTTAA TCGCCGCGAC
     ATGGTAGCTG TGGTGGTGCG ACCGTGGGTC AACTAGCCGC GCTCTAAATT AGCGGCGCTG
4741 AATTTGCGAC GGCGCGTGCA GGGCCAGACT GGAGGTGGCA ACGCCAATCA GCAACGACTG
     TTAAACGCTG CCGCGCACGT CCCGGTCTGA CCTCCACCGT TGCGGTTAGT CGTTGCTGAC
4801 TTTGCCCGCC AGTTGTTGTG CCACGCGGTT GGGAATGTAA TTCAGCTCCG CCATCGCCGC
     AAACGGGCGG TCAACAACAC GGTGCGCCAA CCCTTACATT AAGTCGAGGC GGTAGCGGCG
4861 TTCCACTTTT TCCCGCGTTT TCGCAGAAAC GTGGCTGGCC TGGTTCACCA CGCGGGAAAC
     AAGGTGAAAA AGGGCGCAAA AGCGTCTTTG CACCGACCGG ACCAAGTGGT GCGCCCTTTG
4921 GGTCTGATAA GAGACACCGG CATACTCTGC GACATCGTAT AACGTTACTG GTTTCACATT
     CCAGACTATT CTCTGTGGCC GTATGAGACG CTGTAGCATA TTGCAATGAC CAAAGTGTAA
4981 CACCACCCTG AATTGACTCT CTTCCGGGCG CTATCATGCC ATACCGCGAA AGGTTTTGCG
     GTGGTGGGAC TTAACTGAGA GAAGGCCCGC GATAGTACGG TATGGCGCTT TCCAAACGC
5041 CCATTCGATG GTGTCCGGGA TCTCGACGCT CTCCCTTATG CGACTCCTGC ATTAGGAAAT
     GGTAAGCTAC CACAGGCCCT AGAGCTGCGA GAGGGAATAC GCTGAGGACG TAATCCTTTA
5101 TAATACGACT CACTATA
     ATTATGCTGA GTGATAT
```

Fig. 32₃

| Fig. 34₁ |
|---|
| Fig. 34₂ |
| Fig. 34₃ |
| Fig. 34₄ |

Fig. 34

```
   1    GGGGAATTGT GAGCGGATAA CAATTCCCCT CTAGAAATAA TTTTGTTTAA CTTTAAGAAG
        CCCCTTAACA CTCGCCTATT GTTAAGGGGA GATCTTTATT AAAACAAATT GAAATTCTTC
                                                               EcoRI
                                                               ~~~~~~

NcoI                                    BamHI        SacI
             ~~~~~~                                  ~~~~~~~      ~~~
   61   GAGATATACC ATGGGCAGCA GCCATCACCA TCATCACCAC AGCCAGGATC CGAATTCGAG
        CTCTATATGG TACCCGTCGT CGGTAGTGGT AGTAGTGGTG TCGGTCCTAG GCTTAAGCTC
        SacI
        ~~~
  121   CTCGATCACA AGTTTGTACA AAAAAGCTGA ACGAGAAACG TAAAATGATA TAAATATCAA
        GAGCTAGTGT TCAAACATGT TTTTTCGACT TGCTCTTTGC ATTTTACTAT ATTTATAGTT
  181   TATATTAAAT TAGATTTTGC ATAAAAAACA GACTACATAA TACTGTAAAA CACAACATAT
        ATATAATTTA ATCTAAAACG TATTTTTTGT CTGATGTATT ATGACATTTT GTGTTGTATA
  241   CCAGTCACTA TGGCGGCCGC CACGTTAAGG GATTTTGGTC ATGATCAGCA CGTGTTGACA
        GGTCAGTGAT ACCGCCGGCG GTGCAATTCC CTAAAACCAG TACTAGTCGT GCACAACTGT
                                                                    NcoI
                                                                    ~~~
  301   ATTAATCATC GGCATAGTAT ATCGGCATAG TATAATACGA CAAGGTGAGG AACTAAACCA
        TAATTAGTAG CCGTATCATA TAGCCGTATC ATATTATGCT GTTCCACTCC TTGATTTGGT
        NcoI
        ~~~
  361   TGGCCAAGTT GACCAGTGCC GTTCCGGTGC TCACCGCGCG CGACGTCGCC GGAGCGGTCG
        ACCGGTTCAA CTGGTCACGG CAAGGCCACG AGTGGCGCGC GCTGCAGCGG CCTCGCCAGC
  421   AGTTCTGGAC CGACCGGCTC GGGTTCTCCC GGGACTTCGT GGAGGACGAC TTCGCCGGTG
        TCAAGACCTG GCTGGCCGAG CCCAAGAGGG CCCTGAAGCA CCTCCTGCTG AAGCGGCCAC
  481   TGGTCCGGGA CGACGTGACC CTGTTCATCA GCGCGGTCCA GGACCAGGTG GTGCCGGACA
        ACCAGGCCCT GCTGCACTGG GACAAGTAGT CGCGCCAGGT CCTGGTCCAC CACGGCCTGT
  541   ACACCCTGGC CTGGGTGTGG GTGCGCGGCC TGGACGAGCT GTACGCCGAG TGGTCGGAGG
        TGTGGGACCG GACCCACACC CACGCGCCGG ACCTGCTCGA CATGCGGCTC ACCAGCCTCC
  601   TCGTGTCCAC GAACTTCCGG GACGCCTCCG GGCCGGCCAT GACCGAGATC GGCGAGCAGC
        AGCACAGGTG CTTGAAGGCC CTGCGGAGGC CCGGCCGGTA CTGGCTCTAG CCGCTCGTCG
  661   CGTGGGGGCC GGAGTTCGCC CTGCGCGACC CGGCCGGCAA CTGCGTGCAC TTCGTGGCCG
        GCACCCCCGC CCTCAAGCGG GACGCGCTGG GCCGGCCGTT GACGCACGTG AAGCACCGGC
  721   AGGAGCAGGA CTGATCATGA TGATATTATT TTATCTTGTG CAATGTAACA TCAGAGATTT
        TCCTCGTCCT GACTAGTACT ACTATAATAA AATAGAACAC GTTACATTGT AGTCTCTAAA
  781   TGAGACACGG GCCAGAGCTG CCAGGAAACA GCTATGACCA TGTAATACGA CTCACTATAG
        ACTCTGTGCC CGGTCTCGAC GGTCCTTTGT CGATACTGGT ACATTATGCT GAGTGATATC
  841   GGGATATCAG CTGGATGGCA AATAATGATT TTATTTTGAC TGATAGTGAC CTGTTCGTTG
        CCCTATAGTC GACCTACCGT TTATTACTAA AATAAAACTG ACTATCACTG GACAAGCAAC
  901   CAACACCGGT GCTAGCGTAT ACCCGAAGTA TGTCAAAAAG AGGTGTGCTA TGAAGCAGCG
        GTTGTGGCCA CGATCGCATA TGGGCTTCAT ACAGTTTTTC TCCACACGAT ACTTCGTCGC
  961   TATTACAGTG ACAGTTGACA GCGACAGCTA TCAGTTGCTC AAGGCATATA TGATGTCAAT
        ATAATGTCAC TGTCAACTGT CGCTGTCGAT AGTCAACGAG TTCCGTATAT ACTACAGTTA
 1021   ATCTCCGGTC TGGTAAGCAC AACCATGCAG AATGAAGCCC GTCGTCTGCG TGCCGAACGC
        TAGAGGCCAG ACCATTCGTG TTGGTACGTC TTACTTCGGG CAGCAGACGC ACGGCTTGCG
 1081   TGGAAAGCGG AAAATCAGGA AGGGATGGCT GAGGTCGCCC GGTTTATTGA AATGAACGGC
        ACCTTTCGCC TTTTAGTCCT TCCCTACCGA CTCCAGCGGG CCAAATAACT TTACTTGCCG
 1141   TCTTTTGCTG ACGAGAACAG GGACTGGTGA AATGCAGTTT AAGGTTTACA CCTATAAAAG
        AGAAAACGAC TGCTCTTGTC CCTGACCACT TTACGTCAAA TTCCAAATGT GGATATTTTC
 1201   AGAGAGCCGT TATCGTCTGT TTGTGGATGT ACAGAGTGAT ATTATTGACA CGCCCGGGCG
        TCTCTCGGCA ATAGCAGACA AACACCTACA TGTCTCACTA TAATAACTGT GCGGGCCCGC
 1261   ACGGATGGTG ATCCCCCTGG CCAGTGCACG TCTGCTGTCA GATAAAGTCT CCCGTGAACT
        TGCCTACCAC TAGGGGGACC GGTCACGTGC AGACGACAGT CTATTTCAGA GGGCACTTGA
 1321   TTACCCGGTG GTGCATATCG GGGATGAAAG CTGGCGCATG ATGACCACCG ATATGGCCAG
        AATGGGCCAC CACGTATAGC CCCTACTTTC GACCGCGTAC TACTGGTGGC TATACCGGTC
 1381   TGTGCCGGTC TCCGTTATCG GGGAAGAAGT GGCTGATCTC AGCCGCCGCG AAAATGACAT
        ACACGGCCAG AGGCAATAGC CCCTTCTTCA CCGACTAGAG TCGGCGGCGC TTTTACTGTA
 1441   CAAAAACGCC ATTAACCTGA TGTTCTGGGG AATATAAATG TCAGGCTCCC TTATACACAG
        GTTTTTGCGG TAATTGGACT ACAAGACCCC TTATATTTAC AGTCCGAGGG AATATGTGTC
             PstI
             ~~~~~~~
 1501   CCAGTCTGCA GGTCGACCAT AGTGACTGGA TATGTTGTGT TTTACAGTAT TATGTAGTCT
        GGTCAGACGT CCAGCTGGTA TCACTGACCT ATACAACACA AAATGTCATA ATACATCAGA
 1561   GTTTTTTATG CAAAATCTAA TTTAATATAT TGATATTTAT ATCATTTTAC GTTTCTCGTT
        CAAAAAATAC GTTTTAGATT AAATTATATA ACTATAAATA TAGTAAAATG CAAAGAGCAA
                                                                  HindIII
                                                                  ~~~~~~~
 1621   CAGCTTTCTT GTACAAAGTG GTGATAATTA ATTAAGATCA GATCCGGCTG CTAAGCTTGG
```

Fig. 34₁

```
                GTCGAAAGAA CATGTTTCAC CACTATTAAT TAATTCTAGT CTAGGCCGAC GATTCGAACC
                                                                     AvrII
                                                                     ~~~~~~
     1681  AATTGTTATC CGCTCACAAT TCCTATAGTG AGTCGTATTA CCTAGGCTGC TGCCACCGCT
           TTAACAATAG GCGAGTGTTA AGGATATCAC TCAGCATAAT GGATCCGACG ACGGTGGCGA
     1741  GAGCAATAAC TAGCATAACC CCTTGGGGCC TCTAAACGGG TCTTGAGGGG TTTTTTGCTG
           CTCGTTATTG ATCGTATTGG GGAACCCCGG AGATTTGCCC AGAACTCCCC AAAAAACGAC
     1801  AAAGGAGGAA CTATATCCGG ATTGGCGAAT GGGACGCGCC CTGTAGCGGC GCATTAAGCG
           TTTCCTCCTT GATATAGGCC TAACCGCTTA CCCTGCGCGG GACATCGCCG CGTAATTCGC
     1861  CGGCGGGTGT GGTGGTTACG CGCAGCGTGA CCGCTACACT TGCCAGCGCC CTAGCGCCCG
           GCCGCCCACA CCACCAATGC GCGTCGCACT GGCGATGTGA ACGGTCGCGG GATCGCGGGC
     1921  CTCCTTTCGC TTTCTTCCCT TCCTTTCTCG CCACGTTCGC CGGCTTTCCC CGTCAAGCTC
           GAGGAAAGCG AAAGAAGGGA AGGAAAGAGC GGTGCAAGCG GCCGAAAGGG GCAGTTCGAG
     1981  TAAATCGGGG GCTCCCTTTA GGGTTCCGAT TTAGTGCTTT ACGGCACCTC GACCCCAAAA
           ATTTAGCCCC CGAGGGAAAT CCCAAGGCTA AATCACGAAA TGCCGTGGAG CTGGGGTTTT
     2041  AACTTGATTA GGGTGATGGT TCACGTAGTG GGCCATCGCC CTGATAGACG GTTTTTCGCC
           TTGAACTAAT CCCACTACCA AGTGCATCAC CCGGTAGCGG GACTATCTGC CAAAAAGCGG
     2101  CTTTGACGTT GGAGTCCACG TTCTTTAATA GTGGACTCTT GTTCCAAACT GGAACAACAC
           GAAACTGCAA CCTCAGGTGC AAGAAATTAT CACCTGAGAA CAAGGTTTGA CCTTGTTGTG
     2161  TCAACCCTAT CTCGGTCTAT TCTTTTGATT TATAAGGGAT TTTGCCGATT TCGGCCTATT
           AGTTGGGATA GAGCCAGATA AGAAAACTAA ATATTCCCTA AAACGGCTAA AGCCGGATAA
     2221  GGTTAAAAAA TGAGCTGATT TAACAAAAAT TTAACGCGAA TTTTAACAAA ATATTAACGT
           CCAATTTTTT ACTCGACTAA ATTGTTTTTA AATTGCGCTT AAAATTGTTT TATAATTGCA
     2281  TTACAATTTC TGGCGGCACG ATGGCATGAG ATTATCAAAA AGGATCTTCA CCTAGATCCT
           AATGTTAAAG ACCGCCGTGC TACCGTACTC TAATAGTTTT TCCTAGAAGT GGATCTAGGA
     2341  TTTAAATTAA AAATGAAGTT TTAAATCAAT CTAAAGTATA TATGAGTAAA CTTGGTCTGA
           AAATTTAATT TTTACTTCAA AATTTAGTTA GATTTCATAT ATACTCATTT GAACCAGACT
     2401  CAGTTACCAA TGCTTAATCA GTGAGGCACC TATCTCAGCG ATCTGTCTAT TTCGTTCATC
           GTCAATGGTT ACGAATTAGT CACTCCGTGG ATAGAGTCGC TAGACAGATA AAGCAAGTAG
     2461  CATAGTTGCC TGACTCCCCG TCGTGTAGAT AACTACGATA CGGGAGGGCT TACCATCTGG
           GTATCAACGG ACTGAGGGGC AGCACATCTA TTGATGCTAT GCCCTCCCGA ATGGTAGACC
     2521  CCCCAGTGCT GCAATGATAC CGCGAGACCC ACGCTCACCG GCTCCAGATT TATCAGCAAT
           GGGGTCACGA CGTTACTATG GCGCTCTGGG TGCGAGTGGC CGAGGTCTAA ATAGTCGTTA
     2581  AAACCAGCCA GCCGGAAGGG CCGAGCGCAG AAGTGGTCCT GCAACTTTAT CGCCCTCCAT
           TTTGGTCGGT CGGCCTTCCC GGCTCGCGTC TTCACCAGGA CGTTGAAATA GCGGGAGGTA
     2641  CCAGTCTATT AATTGTTGCC GGGAAGCTAG AGTAAGTAGT TCGCCAGTTA ATAGTTTGCG
           GGTCAGATAA TTAACAACGG CCCTTCGATC TCATTCATCA AGCGGTCAAT TATCAAACGC
     2701  CAACGTTGTT GCCATTGCTA CAGGCATCGT GGTGTCACGC TCGTCGTTTG GTATGGCTTC
           GTTGCAACAA CGGTAACGAT GTCCGTAGCA CCACAGTGCG AGCAGCAAAC CATACCGAAG
     2761  ATTCAGCTCC GGTTCCCAAC GATCAAGGCG AGTTACATGA TCCCCCATGT TGTGCAAAAA
           TAAGTCGAGG CCAAGGGTTG CTAGTTCCGC TCAATGTACT AGGGGGTACA ACACGTTTTT
     2821  AGCGGTTAGC TCCTTCGGTC CTCCGATCGT TGTCAGAAGT AAGTTGGCCG CAGTGTTATC
           TCGCCAATCG AGGAAGCCAG GAGGCTAGCA ACAGTCTTCA TTCAACCGGC GTCACAATAG
     2881  ACTCATGGTT ATGGCAGCAC TGCATAATTC TCTTACTGTC ATGCCATCCG TAAGATGCTT
           TGAGTACCAA TACCGTCGTG ACGTATTAAG AGAATGACAG TACGGTAGGC ATTCTACGAA
     2941  TTCTGTGACT GGTGAGTACT CAACCAAGTC ATTCTGAGAA TAGTGTATGC GGCGACCGAG
           AAGACACTGA CCACTCATGA GTTGGTTCAG TAAGACTCTT ATCACATACG CCGCTGGCTC
     3001  TTGCTCTTGC CCGGCGTCAA TACGGGATAA CATAGCAGAA CTTTAAAAGT
           AACGAGAACG GGCCGCAGTT ATGCCCTATT ATGGCGCGGT GTATCGTCTT GAAATTTTCA
     3061  GCTCATCATT GGAAAACGTT CTTCGGGGCG AAAACTCTCA AGGATCTTAC CGCTGTTGAG
           CGAGTAGTAA CCTTTTGCAA GAAGCCCCGC TTTTGAGAGT TCCTAGAATG GCGACAACTC
     3121  ATCCAGTTCG ATGTAACCCA CTCGTGCACC CAACTGATCT TCAGCATCTT TTACTTTCAC
           TAGGTCAAGC TACATTGGGT GAGCACGTGG GTTGACTAGA AGTCGTAGAA AATGAAAGTG
     3181  CAGCGTTTCT GGGTGAGCAA AAACAGGAAG GCAAAATGCC GCAAAAAAGG GAATAAGGGC
           GTCGCAAAGA CCCACTCGTT TTTGTCCTTC CGTTTTACGG CGTTTTTTCC CTTATTCCCG
     3241  GACACGGAAA TGTTGAATAC TCATACTCTT CCTTTTTCAA TCATGATTGA AGCATTTATC
           CTGTGCCTTT ACAACTTATG AGTATGAGAA GGAAAAAGTT AGTACTAACT TCGTAAATAG
     3301  AGGGTTATTG TCTCATGAGC GGATACATAT TTGAATGTAT TTAGAAAAAT AAACAAATAG
           TCCCAATAAC AGAGTACTCG CCTATGTATA AACTTACATA AATCTTTTTA TTTGTTTATC
     3361  GTCATGACCA AAATCCCTTA ACGTGAGTTT TCGTTCCACT GAGCGTCAGA CCCCGTAGAA
           CAGTACTGGT TTTAGGGAAT TGCACTCAAA AGCAAGGTGA CTCGCAGTCT GGGGCATCTT
     3421  AAGATCAAAG GATCTTCTTG AGATCCTTTT TTTCTGCGCG TAATCTGCTG CTTGCAAACA
           TTCTAGTTTC CTAGAAGAAC TCTAGGAAAA AAAGACGCGC ATTAGACGAC GAACGTTTGT
     3481  AAAAAACCAC CGCTACCAGC GGTGGTTTGT TTGCCGGATC AAGAGCTACC AACTCTTTTT
           TTTTTTGGTG GCGATGGTCG CCACCAAACA AACGGCCTAG TTCTCGATGG TTGAGAAAAA
     3541  CCGAAGGTAA CTGGCTTCAG CAGAGCGCAG ATACCAAATA CTGTCCTTCT AGTGTAGCCG
           GGCTTCCATT GACCGAAGTC GTCTCGCGTC TATGGTTTAT GACAGGAAGA TCACATCGGC
     3601  TAGTTAGGCC ACCACTTCAA GAACTCTGTA GCACCGCCTA CATACCTCGC TCTGCTAATC
           ATCAATCCGG TGGTGAAGTT CTTGAGACAT CGTGGCGGAT GTATGGAGCG AGACGATTAG
     3661  CTGTTACCAG TGGCTGCTGC CAGTGGCGAT AAGTCGTGTC TTACCGGGTT GGACTCAAGA
           GACAATGGTC ACCGACGACG GTCACCGCTA TTCAGCACAG AATGGCCCAA CCTGAGTTCT
     3721  CGATAGTTAC CGGATAAGGC GCAGCGGTCG GGCTGAACGG GGGGTTCGTG CACACAGCCC
```

Fig. 34₂

```
      GCTATCAATG GCCTATTCCG CGTCGCCAGC CCGACTTGCC CCCCAAGCAC GTGTGTCGGG
3781  AGCTTGGAGC GAACGACCTA CACCGAACTG AGATACCTAC AGCGTGAGCT ATGAGAAAGC
      TCGAACCTCG CTTGCTGGAT GTGGCTTGAC TCTATGGATG TCGCACTCGA TACTCTTTCG
3841  GCCACGCTTC CCGAAGGGAG AAAGGCGGAC AGGTATCCGG TAAGCGGCAG GGTCGGAACA
      CGGTGCGAAG GGCTTCCCTC TTTCCGCCTG TCCATAGGCC ATTCGCCGTC CCAGCCTTGT
3901  GGAGAGCGCA CGAGGGAGCT TCCAGGGGGA AACGCCTGGT ATCTTTATAG TCCTGTCGGG
      CCTCTCGCGT GCTCCCTCGA AGGTCCCCCT TTGCGGACCA TAGAAATATC AGGACAGCCC
3961  TTTCGCCACC TCTGACTTGA GCGTCGATTT TTGTGATGCT CGTCAGGGGG GCGGAGCCTA
      AAAGCGGTGG AGACTGAACT CGCAGCTAAA AACACTACGA GCAGTCCCCC CGCCTCGGAT
4021  TGGAAAAACG CCAGCAACGC GGCCTTTTTA CGGTTCCTGG CCTTTTGCTG GCCTTTTGCT
      ACCTTTTTGC GGTCGTTGCG CCGGAAAAAT GCCAAGGACC GGAAAACGAC CGGAAAACGA
4081  CACATGTTCT TTCCTGCGTT ATCCCCTGAT TCTGTGGATA ACCGTATTAC CGCCTTTGAG
      GTGTACAAGA AAGGACGCAA TAGGGGACTA AGACACCTAT TGGCATAATG GCGGAAACTC
4141  TGAGCTGATA CCGCTCGCCC CAGCCGAACG ACCGAGCGCA GCGAGTCAGT GAGCGAGGAA
      ACTCGACTAT GGCGAGCGGC GTCGGCTTGC TGGCTCGCGT CGCTCAGTCA CTCGCTCCTT
4201  GCGGAAGAGC GCCTGATCG GTATTTTCTC CTTACGCATC TGTGCGGTAT TTCACACCGC
      CGCCTTCTCG CGGACTACGC CATAAAAGAG GAATGCGTAG ACACGCCATA AAGTGTGGCG
4261  ATATATGGTG CACTCTCAGT ACAATCTGCT CTGATGCCGC ATAGTTAAGC CAGTATACAC
      TATATACCAC GTGAGAGTCA TGTTAGACGA GACTACGGCG TATCAATTCG GTCATATGTG
4321  TCCGCTATCG CTACGTGACT GGGTCATGGC TGCGCCCCGA CACCCGCCAA CACCCGCTGA
      AGGCGATAGC GATGCACTGA CCCAGTACCG ACGCGGGGCT GTGGGCGGTT GTGGGCGACT
4381  CGCGCCCTGA CGGGCTTGTC TGCTCCCGGC ATCCGCTTAC AGACAAGCTG TGACCGTCTC
      GCGCGGGACT GCCCGAACAG ACGAGGGCCG TAGGCGAATG TCTGTTCGAC ACTGGCAGAG
4441  CGGGAGCTGC ATGTGTCAGA GGTTTTCACC GTCATCACCG AAACGCGCGA GGCAGCTGCG
      GCCCTCGACG TACACAGTCT CCAAAAGTGG CAGTAGTGGC TTTGCGCGCT CCGTCGACGC
4501  GTAAAGCTCA TCAGCGTGGT CGTGAAGCGA TTCAGATGG TCTGCCTGTT CATCCGCGTC
      CATTTCGAGT AGTCGCACCA GCACTTGCT AAGTGTCTAC AGACGGACAA GTAGGCGCAG
4561  CAGCTCGTTG AGTTTCTCCA GAAGCGTTAA TGTCTGGCTT CTGATAAAGC GGGCCATGTT
      GTCGAGCAAC TCAAAGAGGT CTTCGCAATT ACAGACCGAA GACTATTTCG CCCGGTACAA
4621  AAGGGCGGTT TTTTCCTGTT TGGTCACTGA TGCCTCCGTG TAAGGGGGAT TTCTGTTCAT
      TTCCCGCCAA AAAAGGACAA ACCAGTGACT ACGGAGGCAC ATTCCCCCTA AAGACAAGTA
4681  GGGGGTAATG ATACCGATGA AACGAGAGAG GATGCTCACG ATACGGGTTA CTGATGATGA
      CCCCCATTAC TATGGCTACT TTGCTCTCTC CTACGAGTGC TATGCCCAAT GACTACTACT
4741  ACATGCCCGG TTACTGGAAC GTTGTGAGGG TAAACAACTG GCGGTATGGA TGCGGCGGGA
      TGTACGGGCC AATGACCTTG CAACACTCCC ATTTGTTGAC CGCCATACCT ACGCCGCCCT
4801  CCAGAGAAAA ATCACTCAGG GTCAATGCCA GCGCTTCGTT AATACAGATG TAGGTGTTCC
      GGTCTCTTTT TAGTGAGTCC CAGTTACGGT CGCGAAGCAA TTATGTCTAC ATCCACAAGG
4861  ACAGGGTAGC CAGCAGCATC CTGCGATGCA GATCCGGAAC ATAATGGTGC AGGGCGCTGA
      TGTCCCATCG GTCGTCGTAG GACGCTACGT CTAGGCCTTG TATTACCACG TCCCGCGACT
4921  CTTCCGCGTT TCCAGACTTT ACGAAACACG GAAACCGAAG ACCATTCATG TTGTTGCTCA
      GAAGGCGCAA AGGTCTGAAA TGCTTTGTGC CTTTGGCTTC TGGTAAGTAC AACAACGAGT
4981  GGTCGACGAC GTTTTGCAGC AGCAGTCGCT TCACGTTCGC TCGCGTATCG GTGATTCATT
      CCAGCGTCTG CAAAACGTCG TCGTCAGCGA AGTGCAAGCG AGCGCATAGC CACTAAGTAA
5041  CTGCTAACCA GTAAGGCAAC CCCGCCAGCC TAGCCGGGTC CTCAACGACA GGAGCACGAT
      GACGATTGGT CATTCCGTTG GGGCGGTCGG ATCGGCCCAG GAGTTGCTGT CCTCGTGCTA
5101  CATGCTAGTC ATGCCCCGCG CCCACCGGAA GGAGCTGACT GGGTTGAAGG CTCTCAAGGG
      GTACGATCAG TACGGGGCGC GGGTGGCCTT CCTCGACTGA CCCAACTTCC GAGAGTTCCC
5161  CATCGGTCGA GATCCCGGTG CCTAATGAGT GAGCTAACTT ACATTAATTG CGTTGCGCTC
      GTAGCCAGCT CTAGGGCCAC GGATTACTCA CTCGATTGAA TGTAATTAAC GCAACGCGAG
5221  ACTGCCCGCT TTCCAGTCGG GAAACCTGTC GTGCCAGCTG CATTAATGAA TCGGCCAACG
      TGACGGGCGA AAGGTCAGCC CTTTGGACAG CACGGTCGAC GTAATTACTT AGCCGGTTGC
5281  CGCGGGGAGA GGCGGTTTGC GTATTGGGCG CCAGGGTGGT TTTTCTTTTC ACCAGTGAGA
      GCGCCCCTCT CCGCCAAACG CATAACCCGC GGTCCCACCA AAAAGAAAAG TGGTCACTCT
5341  CGGGCAACAG CTGATTGCCC TTCACCGCCT GGCCCTGAGA GAGTTGCAGC AAGCGGTCCA
      GCCCGTTGTC GACTAACGGG AAGTGGCGGA CCGGGACTCT CTCAACGTCG TTCGCCAGGT
5401  CGCTGGTTTG CCCCAGCAGG CGAAAATCCT GTTTGATGGT GGTTAACGGC GGGATATAAC
      GCGACCAAAC GGGGTCGTCC GCTTTTAGGA CAAACTACCA CCAATTGCCG CCCTATATTG
5461  ATGAGCTGTC TTCGGTATCG TCGTATCCCA CTACCGAGAT GTCCGCACCA ACGCGCAGCC
      TACTCGACAG AAGCCATAGC AGCATAGGGT GATGGCTCTA CAGGCGTGGT TGCGCGTCGG
5521  CGGACTCGGT AATGGCGCGC ATTGCGCCCA GCGCCATCTG ATCGTTGGCA ACCAGCATCG
      GCCTGAGCCA TTACCGCGCG TAACGCGGGT CGCGGTAGAC TAGCAACCGT TGGTCGTAGC
5581  CAGTGGGAAC GATGCCCTCA TTCAGCATTT GCATGGTTTG TTGAAAACCG GACATGGCAC
      GTCACCCTTG CTACGGGAGT AAGTCGTAAA CGTACCAAAC AACTTTTGGC CTGTACCGTG
5641  TCCAGTCGCC TTCCCGTTCC GCTATCGGCT GAATTTGATT GCGAGTGAGA TATTTATGCC
      AGGTCAGCGG AAGGGCAAGG CGATAGCCGA CTTAAACTAA CGCTCACTCT ATAAATACGG
5701  AGCCAGCCAG ACGCAGACGC GCCGAGACAG AACTTAATGG GCCCGCTAAC AGCGCGATTT
      TCGGTCGGTC TGCGTCTGCG CGGCTCTGTC TTGAATTACC CGGGCGATTG TCGCGCTAAA
5761  GCTGGTGACC CAATGCGACC AGATGCTCCA CGCCCAGTCG CGTACCGTCT TCATGGGAGA
      CGACCACTGG GTTACGCTGG TCTACGAGGT GCGGGTCAGC GCATGGCAGA AGTACCCTCT
```

Fig. 34₃

```
5821  AAATAATACT GTTGATGGGT GTCTGGTCAG AGACATCAAG AAATAACGCC GGAACATTAG
      TTTATTATGA CAACTACCCA CAGACCAGTC TCTGTAGTTC TTTATTGCGG CCTTGTAATC
5881  TGCAGGCAGC TTCCACAGCA ATGGCATCCT GGTCATCCAG CGGATAGTTA ATGATCAGCC
      ACGTCCGTCG AAGGTGTCGT TACCGTAGGA CCAGTAGGTC GCCTATCAAT TACTAGTCGG
5941  CACTGACGCG TTGCGCGAGA AGATTGTGCA CCGCCGCTTT ACAGGCTTCG ACGCCGCTTC
      GTGACTGCGC AACGCGCTCT TCTAACACGT GGCGGCGAAA TGTCCGAAGC TGCGGCGAAG
6001  GTTCTACCAT CGACACCACC ACGCTGGCAC CCAGTTGATC GGCGCGAGAT TTAATCGCCG
      CAAGATGGTA GCTGTGGTGG TGCGACCGTG GGTCAACTAG CCGCGCTCTA AATTAGCGGC
6061  CGACAATTTG CGACGGCGCG TGCAGGGCCA GACTGGAGGT GGCAACGCCA ATCAGCAACG
      GCTGTTAAAC GCTGCCGCGC ACGTCCCGGT CTGACCTCCA CCGTTGCGGT TAGTCGTTGC
6121  ACTGTTTGCC CGCCAGTTGT TGTGCCACGC GGTTGGGAAT GTAATTCAGC TCCGCCATCG
      TGACAAACGG GCGGTCAACA ACACGGTGCG CCAACCCTTA CATTAAGTCG AGGCGGTAGC
6181  CCGCTTCCAC TTTTTCCCGC GTTTTCGCAG AAACGTGGCT GGCCTGGTTC ACCACGCGGG
      GGCGAAGGTG AAAAAGGGCG CAAAAGCGTC TTTGCACCGA CCGGACCAAG TGGTGCGCCC
6241  AAACGGTCTG ATAAGAGACA CCGGCATACT CTGCGACATC GTATAACGTT ACTGGTTTCA
      TTTGCCAGAC TATTCTCTGT GGCCGTATGA GACGCTGTAG CATATTGCAA TGACCAAAGT
6301  CATTCACCAC CCTGAATTGA CTCTCTTCCG GGCGCTATCA TGCCATACCG CGAAAGGTTT
      GTAAGTGGTG GGACTTAACT GAGAGAAGGC CCGCGATAGT ACGGTATGGC GCTTTCCAAA
6361  TGCGCCATTC GATGGTGTCC GGGATCTCGA CGCTCTCCCT TATGCGACTC CTGCATTAGG
      ACGCGGTAAG CTACCACAGG CCCTAGAGCT GCGAGAGGGA ATACGCTGAG GACGTAATCC
6421  AAGCAGCCCA GTAGTAGGTT GAGGCCGTTG AGCACCGCCG CCGCAAGGAA TGGTGCATGC
      TTCGTCGGGT CATCATCCAA CTCCGGCAAC TCGTGGCGGC GGCGTTCCTT ACCACGTACG
6481  AAGGAGATGG CGCCCAACAG TCCCCCGCC ACGGGCCTG CCACCATACC CACGCCGAAA
      TTCCTCTACC GCGGGTTGTC AGGGGGCCGG TGCCCCGGAC GGTGGTATGG GTGCGGCTTT
6541  CAAGCGCTCA TGACCCCGAA GTGGCGAGCC CGATCTTCCC CATCGGTGAT GTCGGCGATA
      GTTCGCGAGT ACTCGGGCTT CACCGCTCGG GCTAGAAGGG GTAGCCACTA CAGCCGCTAT
6601  TAGGCGCCAG CAACCGCACC TGTGGCGCCG GTGATGCCGG CCACGATGCG TCCGGCGTAG
      ATCCGCGGTC GTTGGCGTGG ACACCGCGGC CACTACGGCC GGTGCTACGC AGGCCGCATC
                     ClaI
                     ~~~~~~~
6661  AGGATCGAGA TCGATCTCGA TCCCGCGAAA TTAATACGAC TCACTATA
      TCCTAGCTCT AGCTAGAGCT AGGGCGCTTT AATTATGCTG AGTGATAT
```

Fig. 34₄

| Fig. 36₁ |
|---|
| Fig. 36₂ |
| Fig. 36₃ |

Fig. 36

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                                SacI
                                                                ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGGACCAT GATTACGCCA AGCTATCAAC TTTGTATAGA AAAGTTGAAC GAGAAACGTA
     GAGCCTGGTA CTAATGCGGT TCGATAGTTG AAACATATCT TTTCAACTTG CTCTTTGCAT
 181 AAATGATATA AATATCAATA TATTAAATTA GATTTTGCAT AAAAAACAGA CTACATAATA
     TTTACTATAT TTATAGTTAT ATAATTTAAT CTAAAACGTA TTTTTTGTCT GATGTATTAT
                                                PstI
                                                ~~~~~~~
 241 CTGTAAAACA CAACATATCC AGTCACTATG GTCGACCTGC AGACTGGCTG TGTATAAGGG
     GACATTTTGT GTTGTATAGG TCAGTGATAC CAGCTGGACG TCTGACCGAC ACATATTCCC
 301 AGCCTGACAT TTATATTCCC CAGAACATCA GGTTAATGGC GTTTTTGATG TCATTTTCGC
     TCGGACTGTA AATATAAGGG GTCTTGTAGT CCAATTACCG CAAAAACTAC AGTAAAAGCG
 361 GGTGGCTGAG ATCAGCCACT TCTTCCCCGA TAACGGAGAC CGGCACACTG GCCATATCGG
     CCACCGACTC TAGTCGGTGA AGAAGGGGCT ATTGCCTCTG GCCGTGTGAC CGGTATAGCC
 421 TGGTCATCAT GCGCCAGCTT TCATCCCCGA TATGCACCAC CGGGTAAAGT TCACGGGGGA
     ACCAGTAGTA CGCGGTCGAA AGTAGGGGCT ATACGTGGTG GCCCATTTCA AGTGCCCCCT
                                                          XmaI
                                                          ~~~~~~~
                                                           SmaI
                                                           ~~~~~~~
 481 CTTTATCTGA CAGCAGACGT GCACTGGCCA GGGGGATCAC CATCCGTCGC CCGGGCGTGT
     GAAATAGACT GTCGTCTGCA CGTGACCGGT CCCCCTAGTG GTAGGCAGCG GGCCCGCACA
 541 CAATAATATC ACTCTGTACA TCCACAAACA GACGATAACG GCTCTCTCTT TTATAGGTGT
     GTTATTATAG TGAGACATGT AGGTGTTTGT CTGCTATTGC CGAGAGAGAA AATATCCACA
 601 AAACCTTAAA CTGCATTTCA CCAGCCCCTG TTCTCGTCGG CAAAAGAGCC GTTCATTTCA
     TTTGGAATTT GACGTAAAGT GGTCGGGGAC AAGAGCAGCC GTTTTCTCGG CAAGTAAAGT
 661 ATAAACCGGG CGACCTCAGC CATCCCTTCC TGATTTTCCG CTTTCCAGCG TTCGGCACGC
     TATTTGGCCC GCTGGAGTCG GTAGGGAAGG ACTAAAAGGC GAAAGGTCGC AAGCCGTGCG
 721 AGACGAGCGG CTTCATTCTG CATGGTTGTG CTTACCGAAC CGGAGATATT GACATCATAT
     TCTGCTGCCC GAAGTAAGAC GTACCAACAC GAATGGCTTG GCCTCTATAA CTGTAGTATA
 781 ATGCCTTGAG CAACTGATAG CTGTCGCTGT CAACTGTCAC TGTAATACGC TGCTTCATAG
     TACGGAACTC GTTGACTATC GACAGCGACA GTTGACAGTG ACATTATGCG ACGAAGTATC
 841 CATACCTCTT TTTGACATAC TTCGGGTATA CATATCAGTA TATATTCTTA TACCGCAAAA
     GTATGGAGAA AAACTGTATG AAGCCCATAT GTATAGTCAT ATATAAGAAT ATGGCGTTTT
 901 ATCAGCGCGC AAATACGCAT ACTGTTATCT GGCTTTTAGT AAGCCGGATC CTCTAGATTA
     TAGTCGCGCG TTTATGCGTA TGACAATAGA CCGAAAATCA TTCGGCCTAG GAGATCTAAT
 961 CGCCCCGCCC TGCCACTCAT CGCAGTACTG TTGTAATTCA TTAAGCATTC TGCCGACATG
     GCGGGGCGGG ACGGTGAGTA GCGTCATGAC AACATTAAGT AATTCGTAAG ACGGCTGTAC
1021 GAAGCCATCA CAAACGGCAT GATGAACCTG AATCGCCAGC GGCATCAGCA CCTTGTCGCC
     CTTCGGTAGT GTTTGCCGTA CTACTTGGAC TTAGCGGTCG CCGTAGTCGT GGAACAGCGG
1081 TTGCGTATAA TATTTGCCCA TGGTGAAAAC GGGGGCGAAG AAGTTGTCCA TATTGGCCAC
     AACGCATATT ATAAACGGGT ACCACTTTTG CCCCCGCTTC TTCAACAGGT ATAACCGGTG
1141 GTTTAAATCA AAACTGGTGA AACTCACCCA GGGATTGGCT GAGACGAAAA ACATATTCTC
     CAAATTTAGT TTTGACCACT TTGAGTGGGT CCCTAACCGA CTCTGCTTTT TGTATAAGAG
1201 AATAAACCCT TTAGGGAAAT AGGCCAGGTT TTCACCGTAA CACGCCACAT CTTGCGAATA
     TTATTTGGGA AATCCCTTTA TCCGGTCCAA AAGTGGCATT GTGCGGTGTA GAACGCTTAT
1261 TATGTGTACA AACTGCCGGA AATCGTCGTG GTATTCACTC CAGAGCGATG AAAACGTTTC
     ATACACATGT TTGACGGCCT TTAGCAGCAC CATAAGTGAG GTCTCGCTAC TTTTGCAAAG
1321 AGTTTGCTCA TGGAAAACGG TGTAACAAGG GTGAACACTA TCCCATATCA CCAGCTCACC
     TCAAACGAGT ACCTTTTGCC ACATTGTTCC CACTTGTGAT AGGGTATAGT GGTCGAGTGG
1381 GTCTTTCATT GCCATACGGA ATTCCGGATG AGCATTCATC AGGCGGGCAA GAATGTGAAT
     CAGAAAGTAA CGGTATGCCT TAAGGCCTAC TCGTAAGTAG TCCGCCCGTT CTTACACTTA
1441 AAAGGCCGGA TAAAACTTGT GCTTATTTTT CTTTACGGTC TTTAAAAAGG CCGTAATATC
     TTTCCGGCCT ATTTTGAACA CGAATAAAAA GAAATGCCAG AAATTTTTCC GGCATTATAG
1501 CAGCTGAACG GTCTGGTTAT AGGTACATTG AGCAACTGAC TGAAATGCCT CAAAATGTTC
     GTCGACTTGC CAGACCAATA TCCATGTAAC TCGTTGACTG ACTTTACGGA GTTTTACAAG
1561 TTTACGATGC CATTGGGATA TATCAACGGT GGTATATCCA GTGATTTTTT CTCCATTTT
     AAATGCTACG GTAACCCTAT ATAGTTGCCA CCATATAGGT CACTAAAAAA AGAGGTAAAA
1621 AGCTTCCTTA GCTCCTGAAA ATCTCGACGG ATCCTAGCTC AAATCCACA CATTATACGA
     TCGAAGGAAT CGAGGACTTT TAGAGCTGCC TAGGATTGAG TTTTAGGTGT GTAATATGCT
1681 GCCGGAAGCA TAAAGTGTAA AGCCTGGGGG TGCCTAATGC GGCCGCCATA GTGACTGGAT
     CGGCCTTCGT ATTTCACATT TCGGACCCCC ACGGATTACG CCGGCGGTAT CACTGACCTA
1741 ATGTTGTGTT TTACAGTATT ATGTAGTCTG TTTTTTATGC AAAATCTAAT TTAATATATT
     TACAACACAA AATGTCATAA TACATCAGAC AAAAAATACG TTTTAGATTA AATTATATAA
```

Fig. 36₁

```
1801 GATATTTATA TCATTTTACG TTTCTCGTTC AACTTTATTA TACATAGTTG ATAATTCACT
     CTATAAATAT AGTAAAATGC AAAGAGCAAG TTGAAATAAT ATGTATCAAC TATTAAGTGA
1861 GGCCGTCGTT TTACAACGTC GTGACTGGGA AAACCCTGGC GTTACCCAAC TTAATCGCCT
     CCGGCAGCAA AATGTTGCAG CACTGACCCT TTTGGGACCG CAATGGGTTG AATTAGCGGA
              HindIII                                            AvrII
              ~~~~~~~                                            ~~~~
1921 TGCAGCACAA GCTTGGAATT GTTATCCGCT CACAATTCCT ATAGTGAGTC GTATTACCTA
     ACGTCGTGTT CGAACCTTAA CAATAGGCGA GTGTTAAGGA TATCACTCAG CATAATGGAT
     AvrII
     ~~
1981 GGCTGCTGCC ACCGCTGAGC AATAACTAGC ATAACCCCTT GGGGCCTCTA AACGGGTCTT
     CCGACGACGG TGGCGACTCG TTATTGATCG TATTGGGGAA CCCCGGAGAT TTGCCCAGAA
2041 GAGGGGTTTT TTGCTGAAAC CTCAGGCATT TGAGAAGCAC ACGGTCACAC TGCCTTCCGGT
     CTCCCCAAAA AACGACTTTG GAGTCCGTAA ACTCTTCGTG TGCCAGTGTG ACGAAGGCCA
2101 AGTCAATAAA CCGGTAAACC AGCAATAGAC ATAAGCGGCT ATTTAACGAC CCTGCCCTGA
     TCAGTTATTT GGCCATTTGG TCGTTATCTG TATTCGCCGA TAAATTGCTG GGACGGGACT
2161 ACCGACGACC GGGTCATCGT GGCCGGATCT TGCGGCCCCT CGGCTTGAAC GAATTGTTAG
     TGGCTGCTGG CCCAGTAGCA CCGGCCTAGA ACGCCGGGGA GCCGAACTTG CTTAACAATC
2221 ACATTATTTG CCGACTACCT TGGTGATCTC GCCTTTCACG TAGTGGACAA ATTCTTCCAA
     TGTAATAAAC GGCTGATGGA ACCACTAGAG CGGAAAGTGC ATCACCTGTT TAAGAAGGTT
2281 CTGATCTGCG CGCGAGGCCA AGCGATCTTC TTCTTGTCCA AGATAAGCCT GTCTAGCTTC
     GACTAGACGC GCGCTCCGGT TCGCTAGAAG AAGAACAGGT TCTATTCGGA CAGATCGAAG
2341 AAGTATGACG GGCTGATACT GGGCCGGCAG GCGCTCCATT GCCCAGTCGG CAGCGACATC
     TTCATACTGC CCGACTATGA CCCGGCCGTC CGCGAGGTAA CGGGTCAGCC GTCGCTGTAG
2401 CTTCGGCGCG ATTTTGCCGG TTACTGCGCT GTACCAAATG CGGGACAACG TAAGCACTAC
     GAAGCCGCGC TAAAACGGCC AATGACGCGA CATGGTTTAC GCCCTGTTGC ATTCGTGATG
2461 ATTTCGCTCA TCGCCAGCCC AGTCGGGCGG CGAGTTCCAT AGCGTTAAGG TTTCATTTAG
     TAAAGCGAGT AGCGGTCGGG TCAGCCCGCC GCTCAAGGTA TCGCAATTCC AAAGTAAATC
2521 CGCCTCAAAT AGATCCTGTT CAGGAACCGG ATCAAAGAGT TCCTCCGCCG CTGGACCTAC
     GCGGAGTTTA TCTAGGACAA GTCCTTGGCC TAGTTTCTCA AGGAGGCGGC GACCTGGATG
2581 CAAGGCAACG CTATGTTCTC TTGCTTTTGT CAGCAAGATA GCCAGATCAA TGTCGATCGT
     GTTCCGTTGC GATACAAGAG AACGAAAACA GTCGTTCTAT CGGTCTAGTT ACAGCTAGCA
2641 GGCTGGCTCG AAGATACCTG CAAGAATGTC ATTGCGCTGC CATTCTCCAA ATTGCAGTTC
     CCGACCGAGC TTCTATGGAC GTTCTTACAG TAACGCGACG GTAAGAGGTT TAACGTCAAG
2701 GCGCTTAGCT GGATAACGCC ACGGAATGAT GTCGTCGTGC ACAACAATGG TGACTTCTAC
     CGCGAATCGA CCTATTGCGG TGCCTTACTA CAGCAGCACG TGTTGTTACC ACTGAAGATG
2761 AGCGCGGAGA ATCTCGCTCT CTCCAGGGGA AGCCGAAGTT TCCAAAAGGT CGTTGATCAA
     TCGCGCCTCT TAGAGCGAGA GAGGTCCCCT TCGGCTTCAA AGGTTTTCCA GCAACTAGTT
2821 AGCTCGCCGC GTTGTTTCAT CAAGCCTTAC GGTCACCGTA ACCAGCAAAT CAATATCACT
     TCGAGCGGCG CAACAAAGTA GTTCGGAATG CCAGTGGCAT TGGTCGTTTA GTTATAGTGA
2881 GTGTGGCTTC AGGCCGCCAT CCACTGCGGA GCCGTACAAA TGTACGGCCA GCAACGTCGG
     CACACCGAAG TCCGGCGGTA GGTGACGCCT CGGCATGTTT ACATGCCGGT CGTTGCAGCC
2941 TTCGAGATGG CGCTCGATGA CGCCAACTAC CTCTGATAGT TGAGTCGATA CTTCGGCGAT
     AAGCTCTACC GCGAGCTACT GCGGTTGATG GAGACTATCA ACTCAGCTAT GAAGCCGCTA
3001 CACCGCTTCC CTCATACTCT TCCTTTTTCA ATATTATTGA AGCATTTATC AGGGTTATTG
     GTGGCGAAGG GAGTATGAGA AGGAAAAAGT TATAATAACT TCGTAAATAG TCCCAATAAC
3061 TCTCATGAGC GGATACATAT TTGAATGTAT TTAGAAAAAT AAACAAATAG CTAGCTCACT
     AGAGTACTCG CCTATGTATA AACTTACATA AATCTTTTTA TTTGTTTATC GATCGAGTGA
3121 CGGTCGCTAC GCTCCGGGCG TGAGACTGCG GCGGGCGCTG CGGACACATA CAAAGTTACC
     GCCAGCGATG CGAGGCCCGC ACTCTGACGC CGCCCGCGAC GCCTGTGTAT GTTTCAATGG
3181 CACAGATTCC GTGGATAAGC AGGGGACTAA CATGTGAGGC AAAACAGCAG GGCCGCGCCG
     GTGTCTAAGG CACCTATTCG TCCCCTGATT GTACACTCCG TTTTGTCGTC CCGGCGCGGC
3241 GTGGCGTTTT TCCATAGGCT CCGCCCTCCT GCCAGGCGGT ACATAAACAG ACGCTTTTCC
     CACCGCAAAA AGGTATCCGA GGCGGGAGGA CGGTCTCAAG TGTATTTGTC TGCGAAAAGG
3301 GGTGCATCTG TGGGAGCCGT GAGGCTCAAC CATGAATCTG ACAGTACGGG CGAAACCCGA
     CCACGTAGAC ACCCTCGGCA CTCCGAGTTG GTACTTAGAC TGTCATGCCC GCTTTGGGCT
3361 CAGGACTTAA AGATCCCCAC CGTTTCCGGC GGGTCGCTCC CTCTTGCGCT CTCCTGTTCC
     GTCCTGAATT TCTAGGGGTG GCAAAGGCCG CCCAGCGAGG GAGAACGCGA GAGGACAAGG
3421 GACCCTGCCG TTTACCGGAT ACCTGTTCCG CCTTTCTCCC TTACGGGAAG TGTGGCGCTT
     CTGGGACGGC AAATGGCCTA TGGACAAGGC GGAAAGAGGG AATGCCCTTC ACACCGCGAA
3481 TCTCATAGCT CACACACTGG TATCTCGGCT CGGTGTAGGT CGTTCGCTCC AAGCTGGGCT
     AGAGTATCGA GTGTGTGACC ATAGAGCCGA GCCACATCCA GCAAGCGAGG TTCGACCCGA
3541 GTAAGCAAGA ACTCCCCGTT CAGCCCGACT GCTGCGCCTT ATCCGGTAAC TGTTCACTTG
     CATTCGTTCT TGAGGGGCAA GTCGGGCTGA CGACGCGGAA TAGGCCATTG ACAAGTGAAC
3601 AGTCCAACCC GGAAAAGCAC GGTAAAACGC CACTGGCAGC AGCCATTGGT AACTGGGAGT
     TCAGGTTGGG CCTTTTCGTG CCATTTTGCG GTGACCGTCG TCGGTAACCA TTGACCCTCA
3661 TCGCAGAGGA TTTGTTTAGC TAAACACGCG GTTGCTCTTG AAGTGTGCGC CAAAGTCCGG
     AGCGTCTCCT AAACAAATCG ATTTGTGCGC CAACGAGAAC TTCACACGCG GTTTCAGGCC
3721 CTACACTGGA AGGACAGATT TGGTTGCTGT GCTCTGCGAA AGCCAGTTAC CACGGTTAAG
```

```
      GATGTGACCT TCCTGTCTAA ACCAACGACA CGAGACGCTT TCGGTCAATG GTGCCAATTC
3781  CAGTTCCCCA ACTGACTTAA CCTTCGATCA AACCACCTCC CCAGGTGGTT TTTTCGTTTA
      GTCAAGGGGT TGACTGAATT GGAAGCTAGT TTGGTGGAGG GGTCCACCAA AAAAGCAAAT
3841  CAGGGCAAAA GATTACGCGC AGAAAAAAAG GATCTCAAGA AGATCCTTTG ATCTTTTCTA
      GTCCCGTTTT CTAATGCGCG TCTTTTTTTC CTAGAGTTCT TCTAGGAAAC TAGAAAAGAT
3901  CTGAACCGCT CTAGATTTCA GTGCAATTTA TCTCTTCAAA TGTAGCACCT GAAGTCAGCC
      GACTTGGCGA GATCTAAAGT CACGTTAAAT AGAGAAGTTT ACATCGTGGA CTTCAGTCGG
3961  CCATACGATA TAAGTTGTAA TTCTCATGTT AGTCATGCCC CGCGCCCACC GGAAGGAGCT
      GGTATGCTAT ATTCAACATT AAGAGTACAA TCAGTACGGG GCGCGGGTGG CCTTCCTCGA
4021  GACTGGGTTG AAGGCTCTCA AGGGCATCGG TCGAGATCCC GGTGCCTAAT GAGTGAGCTA
      CTGACCCAAC TTCCGAGAGT TCCCGTAGCC AGCTCTAGGG CCACGGATTA CTCACTCGAT
4081  ACTTACATTA ATTGCGTTGC GCTCACTGCC CGCTTTCCAG TCGGGAAACC TGTCGTGCCA
      TGAATGTAAT TAACGCAACG CGAGTGACGG GCGAAAGGTC AGCCCTTTGG ACAGCACGGT
4141  GCTGCATTAA TGAATCGGCC AACGCGCGGG GAGAGGCGGT TTGCGTATTG GGCGCCAGGG
      CGACGTAATT ACTTAGCCGG TTGCGCGCCC CTCTCCGCCA AACGCATAAC CCGCGGTCCC
4201  TGGTTTTTCT TTTCACCAGT GAGACGGGCA ACAGCTGATT GCCCTTCACC GCCTGGCCCT
      ACCAAAAAGA AAAGTGGTCA CTCTGCCCGT TGTCGACTAA CGGGAAGTGG CGGACCGGGA
4261  GAGAGAGTTG CAGCAAGCGG TCCACGCTGG TTTGCCCCAG CAGGCGAAAA TCCTGTTTGA
      CTCTCTCAAC GTCGTTCGCC AGGTGCGACC AAACGGGGTC GTCCGCTTTT AGGACAAACT
4321  TGGTGGTTAA CGGCGGGATA TAACATGAGC TGTCTTCGGT ATCGTCGTAT CCCACTACCG
      ACCACCAATT GCCGCCCTAT ATTGTACTCG ACAGAAGCCA TAGCAGCATA GGGTGATGGC
4381  AGATGTCCGC ACCAACGCGC AGCCCGGACT CGGTAATGGC GCGCATTGCG CCCAGCGCCA
      TCTACAGGCG TGGTTGCGCG TCGGGCCTGA GCCATTACCG CGCGTAACGC GGGTCGCGGT
4441  TCTGATCGTT GGCAACCAGC ATCGCAGTGG GAACGATGCC CTCATTCAGC ATTTGCATGG
      AGACTAGCAA CCGTTGGTCG TAGCGTCACC CTTGCTACGG GAGTAAGTCG TAAACGTACC
4501  TTTGTTGAAA ACCGGACATG GCACTCCAGT CGCCTTCCCG TTCCGCTATC GGCTGAATTT
      AAACAACTTT TGGCCTGTAC CGTGAGGTCA GCGGAAGGGC AAGGCGATAG CCGACTTAAA
4561  GATTGCGAGT GAGATATTTA TGCCAGCCAG CCAGACGCAG ACGCGCCGAG ACAGAACTTA
      CTAACGCTCA CTCTATAAAT ACGGTCGGTC GGTCTGCGTC TGCGCGGCTC TGTCTTGAAT
4621  ATGGGCCCGC TAACAGCGCG ATTTGCTGGT GACCCAATGC GACCAGATGC TCCACGCCCA
      TACCCGGGCG ATTGTCGCGC TAAACGACCA CTGGGTTACG CTGGTCTACG AGGTGCGGGT
4681  GTCGCGTACC GTCTTCATGG GAGAAAATAA TACTGTTGAT GGGTGTCTGG TCAGAGACAT
      CAGCGCATGG CAGAAGTACC CTCTTTTATT ATGACAACTA CCCACAGACC AGTCTCTGTA
4741  CAAGAAATAA CGCCGGAACA TTAGTGCAGG CAGCTTCCAC AGCAATGGCA TCCTGGTCAT
      GTTCTTTATT GCGGCCTTGT AATCACGTCC GTCGAAGGTG TCGTTACCGT AGGACCAGTA
4801  CCAGCGGATA GTTAATGATC AGCCCACTGA CGCGTTGCGC GAGAAGATTG TGCACCGCCG
      GGTCGCCTAT CAATTACTAG TCGGGTGACT GCGCAACGCG CTCTTCTAAC ACGTGGCGGC
4861  CTTTACAGGC TTCACGCCG CTTCGTTCTA CCATCGACAC CACCACGCTG GCACCCAGTT
      GAAATGTCCG AAGCTGCGGC GAAGCAAGAT GGTAGCTGTG GTGGTGCGAC CGTGGGTCAA
4921  GATCGGCGCG AGATTTAATC GCCGCGACAA TTTGCGACGG CGCGTGCAGG GCCAGACTGG
      CTAGCCGCGC TCTAAATTAG CGGCGCTGTT AAACGCTGCC GCGCACGTCC CGGTCTGACC
4981  AGGTGGCAAC GCCAATCAGC AACGACTGTT TGCCCGCCAG TTGTTGTGCC ACGCGGTTGG
      TCCACCGTTG CGGTTAGTCG TTGCTGACAA ACGGGCGGTC AACAACACGG TGCGCCAACC
5041  GAATGTAATT CAGCTCCGCC ATCGCCGCTT CCACTTTTTC CCGCGTTTTC GCAGAAACGT
      CTTACATTAA GTCGAGGCGG TAGCGGCGAA GGTGAAAAAG GGCGCAAAAG CGTCTTTGCA
5101  GGCTGGCCTG GTTCACCACG CGGGAAACGG TCTGATAAGA GACACCGGCA TACTCTGCGA
      CCGACCGGAC CAAGTGGTGC GCCCTTTGCC AGACTATTCT CTGTGGCCGT ATGAGACGCT
5161  CATCGTATAA CGTTACTGGT TTCACATTCA CCACCCTGAA TTGACTCTCT TCCGGGCGCT
      GTAGCATATT GCAATGACCA AAGTGTAAGT GGTGGGACTT AACTGAGAGA AGGCCCGCGA
5221  ATCATGCCAT ACCGCGAAAG GTTTTGCGCC ATTCGATGGT GTCCGGGATC TCGACGCTCT
      TAGTACGGTA TGGCGCTTTC CAAAACGCGG TAAGCTACCA CAGGCCCTAG AGCTGCGAGA
5281  CCCTTATGCG ACTCCTGCAT TAGGAAATTA ATACGACTCA CTATA
      GGGAATACGC TGAGGACGTA ATCCTTTAAT TATGCTGAGT GATAT
```

```
   1 GGGGAATTGT GAGCGGATAA CAATTCCCCT GTAGAAATAA TTTTGTTTAA CTTTAATAAG
     CCCCTTAACA CTCGCCTATT GTTAAGGGGA CATCTTTATT AAAACAAATT GAAATTATTC
                                                                 SacI
                                                                 ~~~
               NcoI                                          EcoRI
               ~~~~~~~                                       ~~~~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGGACCAT GATTACGCCA AGCTATCAAC TTTGTATAGA AAAGTTGAAC GAGAAACGTA
     GAGCCTGGTA CTAATGCGGT TCGATAGTTG AAACATATCT TTTCAACTTG CTCTTTGCAT
 181 AAATGATATA AATATCAATA TATTAAATTA GATTTTGCAT AAAAAACAGA CTACATAATA
     TTTACTATAT TTATAGTTAT ATAATTTAAT CTAAAACGTA TTTTTTGTCT GATGTATTAT
                                               PstI
                                               ~~~~~~~
 241 CTGTAAAACA CAACATATCC AGTCACTATG GTCGACCTGC AGACTGGCTG TGTATAAGGG
     GACATTTTGT GTTGTATAGG TCAGTGATAC CAGCTGGACG TCTGACCGAC ACATATTCCC
 301 AGCCTGACAT TTATATTCCC CAGAACATCA GGTTAATGGC GTTTTTGATG TCATTTTCGC
     TCGGACTGTA AATATAAGGG GTCTTGTAGT CCAATTACCG CAAAAACTAC AGTAAAAGCG
 361 GGTGGCTGAG ATCAGCCACT TCTTCCCCGA TAACGGAGAC CGGCACACTG GCCATATCGG
     CCACCGACTC TAGTCGGTGA AGAAGGGGCT ATTGCCTCTG GCCGTGTGAC CGGTATAGCC
 421 TGGTCATCAT GCGCCAGCTT TCATCCCCGA TATGCACCAC CGGGTAAAGT TCACGGGGGA
     ACCAGTAGTA CGCGGTCGAA AGTAGGGGCT ATACGTGGTG GCCCATTTCA AGTGCCCCCT
 481 CTTTATCTGA CAGCAGACGT GCACTGGCCA GGGGGATCAC CATCCGTCGC CCGGGCGTGT
     GAAATAGACT GTCGTCTGCA CGTGACCGGT CCCCCTAGTG GTAGGCAGCG GGCCCGCACA
 541 CAATAATATC ACTCTGTACA TCCACAAACA GACGATAACG CTCTCTCTT TTATAGGTGT
     GTTATTATAG TGAGACATGT AGGTGTTTGT CTGCTATTGC GAGAGAGAA AATATCCACA
 601 AAACCTTAAA CTGCATTTCA CAAACCCCTG TTCTCGTCGG CAAAAGACGC GTTCATTTCA
     TTTGGAATTT GACGTAAAGT GGTCGGGGAC AAGAGCAGCC GTTTTCTCGG CAAGTAAAGT
 661 ATAAACCGGG CGACCTCAGC CATCCCTTCC TGATTTTCCG CTTTCCAGCG TTCGGCACGC
     TATTTGGCCC GCTGGAGTCG GTAGGGAAGG ACTAAAAGGC GAAAGGTCGC AAGCCGTGCG
 721 AGACGACGGG CTTCATTCTG CATGGTTGTG CTTACCGAAC CGGAGATATT GACATCATAT
     TCTGCTGCCC GAAGTAAGAC GTACCAACAC GAATGGCTTG GCCTCTATAA CTGTAGTATA
 781 ATGCCTTGAG CAACTGATAG CTGTCGCTGT CAACTGTCAC TGTAATACGC TGCTTCATAG
     TACGGAACTC GTTGACTATC GACAGCGACA GTTGACAGTG ACATTATGCG ACGAAGTATC
 841 CATACCTCTT TTTGACATAC TTCGGGTATA CATATCAGTA TATATTCTTA TACCGCAAAA
     GTATGGAGAA AAACTGTATG AAGCCCATAT GTATAGTCAT ATATAAGAAT ATGGCGTTTT
 901 ATCAGCGCGC AAATACGCAT ACTGTTATCT GGCTTTTAGT AAGCCGGGTC CTCTAGATTA
     TAGTCGCGCG TTTATGCGTA TGACAATAGA CCGAAAATCA TTCGGCCCAG GAGATCTAAT
 961 CGCCCCGCCC TGCCACTCAT CGCAGTACTG TTGTAATTCA TTAAGCATTC TGCCGACATG
     GCGGGGCGGG ACGGTGAGTA GCGTCATGAC AACATTAAGT AATTCGTAAG ACGGCTGTAC
1021 GAAGCCATCA CAAACGGCAT GATGAACCTG AATCGCCAGC GGCATCAGCA CCTTGTCGCC
     CTTCGGTAGT GTTTGCCGTA CTACTTGGAC TTAGCGGTCG CCGTAGTCGT GGAACAGCGG
                                     NcoI
                                     ~~~~~~~
1081 TTGCGTATAA TATTTGCCCA TGGTGAAAAC GGGGGCGAAG AAGTTGTCCA TATTGGCCAC
     AACGCATATT ATAAACGGGT ACCACTTTTG CCCCCGCTTC TTCAACAGGT ATAACCGGTG
1141 GTTTAAATCA AAACTGGTGA AACTCACCCA GGGATTGGCT GAGACGAAAA ACATATTCTC
     CAAATTTAGT TTTGACCACT TTGAGTGGGT CCCTAACCGA CTCTGCTTTT TGTATAAGAG
1201 AATAAACCCT TTAGGGAAAT AGGCCAGGTT TTCACCGTAA CACGCCACAT CTTGCGAATA
     TTATTTGGGA AATCCCTTTA TCCGGTCCAA AAGTGGCATT GTGCGGTGTA GAACGCTTAT
1261 TATGTGTAGA AACTGCCGGA AATCGTCGTG GTATTCACTC CAGAGCGATG AAAACGTTTC
     ATACACATCT TTGACGGCCT TTAGCAGCAC CATAAGTGAG GTCTCGCTAC TTTTGCAAAG
1321 AGTTTGCTCA TGGAAAACGG TGTAACAAGG GTGAACACTA TCCCATATCA CCAGCTCACC
     TCAAACGAGT ACCTTTTGCC ACATTGTTCC CACTTGTGAT AGGGTATAGT GGTCGAGTGG
                                           EcoRI
                                           ~~~~~~~
1381 GTCTTTCATT GCCATACGGA ATTCCGGATG AGCATTCATC AGGCGGGCAA GAATGTGAAT
     CAGAAAGTAA CGGTATGCCT TAAGGCCTAC TCGTAAGTAG TCCGCCCGTT CTTACACTTA
1441 AAAGGCCGGA TAAACTTGT GCTTATTTTT CTTTACGGTC TTTAAAAAGG CCGTAATATC
     TTTCCGGCCT ATTTTGAACA CGAATAAAAA GAAATGCCAG AAATTTTTCC GGCATTATAG
1501 CAGCTGAACG GTCTGGTTAT AGGTACATTG AGCAACTGAC TGAAATGCCT CAAAATGTTC
     GTCGACTTGC CAGACCAATA TCCATGTAAC TCGTTGACTG ACTTTACGGA GTTTTACAAG
1561 TTTACGATGC CATTGGGATA TATCAACGGT GGTATATCCA GTGATTTTTT TCTCCCATTTT
     AAATGCTACG GTAACCTAT ATAGTTGCCA CCATATAGGT CACTAAAAA AGAGGTAAAA
1621 AGCTTCCTTA GCTCCTGAAA ATCTCGACGG ATCCTAACTC AAAATCCACA CATTATACGA
     TCGAAGGAAT CGAGGACTTT TAGAGCTGCC TAGGATTGAG TTTTAGGTGT GTAATATGCT
1681 GCCGGAAGCA TAAAGTGTAA AGCCTGGGGG TGCCTAATGC GGCCGCCATA GTGACTGGAT
```

Fig. 38₁

```
            CGGCCTTCGT ATTTCACATT TCGGACCCCC ACGGATTACG CCGGCGGTAT CACTGACCTA
      1741  ATGTTGTGTT TTACAGTATT ATGTAGTCTG TTTTTTATGC AAAATCTAAT TTAATATATT
            TACAACACAA AATGTCATAA TACATCAGAC AAAAAATACG TTTTAGATTA AATTATATAA
      1801  GATATTTATA TCATTTTACG TTTCTCGTTC AACTTTATTA TACATAGTTG ATAATTCACT
            CTATAAATAT AGTAAAATGC AAAGAGCAAG TTGAAATAAT ATGTATCAAC TATTAAGTGA
      1861  GGCCGTCGTT TTACAACGTC GTGACTGGGA AAACCCTGGC GTTACCCAAC TTAATCGCCT
            CCGGCAGCAA AATGTTGCAG CACTGACCCT TTTGGGACCG CAATGGGTTG AATTAGCGGA
                HindIII                                                AvrII
                ~~~~~~~                                                ~~~~
      1921  TGCAGCACAA GCTTGGAATT GTTATCCGCT CACAATTCCT ATAGTGAGTC GTATTACCTA
            ACGTCGTGTT CGAACCTTAA CAATAGGCGA GTGTTAAGGA TATCACTCAG CATAATGGAT
                AvrII
                ~~
      1981  GGCTGCTGCC ACCGCTGAGC AATAACTAGC ATAACCCCTT GGGGCCTCTA AACGGGTCTT
            CCGACGACGG TGGCGACTCG TTATTGATCG TATTGGGGAA CCCCGGAGAT TTGCCCAGAA
      2041  GAGGGGTTTT TTGCTGAAAC CTCAGGCATT TGAGAAGCAC ACGGTCACAC TGCTTCCGGT
            CTCCCCAAAA AACGACTTTG GAGTCCGTAA ACTCTTCGTG TGCCAGTGTG ACGAAGGCCA
      2101  AGTCAATAAA CCGGTAAACC AGCAATAGAC ATAAGCGGCT ATTTAACGAC CCTGCCCTGA
            TCAGTTATTT GGCCATTTGG TCGTTATCTG TATTCGCCGA TAAATTGCTG GGACGGGACT
      2161  ACCGACGACA AGCTGACGAC CGGGTCTCCG CAAGTGGCAC TTTTCGGGGA AATGTGCGCG
            TGGCTGCTGT TCGACTGCTG GCCCAGAGGC GTTCACCGTG AAAAGCCCCT TTACACGCGC
      2221  GAACCCCTAT TTGTTTATTT TTCTAAATAC ATTCAAATAT GTATCCGCTC ATGAATTAAT
            CTTGGGGATA AACAAATAAA AAGATTTATG TAAGTTTATA CATAGGCGAG TACTTAATTA
      2281  TCTTAGAAAA ACTCATCGAG CATCAAATGA AACTGCAATT TATTCATATC AGGATTATCA
            AGAATCTTTT TGAGTAGCTC GTAGTTTACT TTGACGTTAA ATAAGTATAG TCCTAATAGT
      2341  ATACCATATT TTTGAAAAAG CCGTTTCTGT AATGAAGGAG AAAACTCACC GAGGCAGTTC
            TATGGTATAA AAACTTTTTC GGCAAAGACA TTACTTCCTC TTTTGAGTGG CTCCGTCAAG
      2401  CATAGGATGG CAAGATCCTG GTATCGGTCT GCGATTCCGA CTCGTCCAAC ATCAATACAA
            GTATCCTACC GTTCTAGGAC CATAGCCAGA CGCTAAGGCT GAGCAGGTTG TAGTTATGTT
      2461  CCTATTAATT TCCCCTCGTC AAAAATAAGG TTATCAAGTG AGAAATCACC ATGAGTGACG
            GGATAATTAA AGGGGAGCAG TTTTTATTCC AATAGTTCAC TCTTTAGTGG TACTCACTGC
      2521  ACTGAATCCG GTGAGAATGG CAAAAGTTTA TGCATTTCTT TCCAGACTTG TTCAACAGGC
            TGACTTAGGC CACTCTTACC GTTTTCAAAT ACGTAAAGAA AGGTCTGAAC AAGTTGTCCG
      2581  CAGCCATTAC GCTCGTCATC AAAATCACTC GCATCAACCA AACCGTTATT CATTCGTGAT
            GTCGGTAATG CGAGCAGTAG TTTTAGTGAG CGTAGTTGGT TTGGCAATAA GTAAGCACTA
      2641  TGCGCCTGAG CGAGACGAAA TACGCGGTCG CTGTTAAAAG GACAATTACA AACAGGAATC
            ACGCGGACTC GCTCTGCTTT ATGCGCCAGC GACAATTTTC CTGTTAATGT TTGTCCTTAG
      2701  GAATGCAACC GGCGCAGGAA CACTGCCAGC GCATCAACAA TATTTTCACC TGAATCAGGA
            CTTACGTTGG CCGCGTCCTT GTGACGGTCG CGTAGTTGTT ATAAAAGTGG ACTTAGTCCT
      2761  TATTCTTCTA ATACCTGGAA TGCTGTTTTC CCGGGGATCG CAGTGGTGAG TAACCATGCA
            ATAAGAAGAT TATGGACCTT ACGACAAAAG GGCCCCTAGC GTCACCACTC ATTGGTACGT
      2821  TCATCAGGAG TACGGATAAA ATGCTTGATG GTCGGAAGAG GCATAAATTC CGTCAGCCAG
            AGTAGTCCTC ATGCCTATTT TACGAACTAC CAGCCTTCTC CGTATTTAAG GCAGTCGGTC
      2881  TTTAGTCTGA CCATCTCATC TGTAACATCA TTGGCAACGC TACCTTTGCC ATGTTTCAGA
            AAATCAGACT GGTAGAGTAG ACATTGTAGT AACCGTTGCG ATGGAAACGG TACAAAGTCT
                                                   ClaI
                                                   ~~~~~~
      2941  AACAACTCTG GCGCATCGGG CTTCCCATAC AATCGATAGA TTGTCGCACC TGATTGCCCG
            TTGTTGAGAC CGCGTAGCCC GAAGGGTATG TTAGCTATCT AACAGCGTGG ACTAACGGGC
      3001  ACATTATCGC GAGCCCATTT ATACCCATAT AAATCAGCAT CCATGTTGGA ATTTAATCGC
            TGTAATAGCG CTCGGGTAAA TATGGGTATA TTTAGTCGTA GGTACAACCT TAAATTAGCG
      3061  GGCCTAGAGC AAGACGTTTC CCGTTGAATA TGGCTCATAA CACCCCTTGT TTGCCTGGCG
            CCGGATCTCG TTCTGCAAAG GGCAACTTAT ACCGAGTATT GTGGGGAACA AACGGACCGC
      3121  TGAAGCATTT ATCAGGGTTA TTGTCTCATG AGCGGATACA TATTTGAATG TATTTAGAAA
            ACTTCGTAAA TAGTCCCAAT AACAGAGTAC TCGCCTATGT ATAAACTTAC ATAAATCTTT
      3181  AATAAACAAA TAGGCATGCA GCGCTCTTCC GCTTCCTCGC TCACTGACTC GCTACGCTCG
            TTATTTGTTT ATCCGTACGT CGCGAGAAGG CGAAGGAGCG AGTGACTGAG CGATGCGAGC
      3241  GTCGTTCGAC TGCGGCGAGC GGTGTCAGCT CACTCAAAAG CGGTAATACG GTTATCCACA
            CAGCAAGCTG ACGCCGCTCG CCACAGTCGA GTGAGTTTTC GCCATTATGC CAATAGGTGT
      3301  GAATCAGGGG ATAAAGCCGG AAAGAACATG TGAGCAAAAA GCAAAGCACC GGAAGAAGCC
            CTTAGTCCCC TATTTCGGCC TTTCTTGTAC ACTCGTTTTT CGTTTCGTGG CCTTCTTCGG
      3361  AACGCCGCAG GCGTTTTTCC ATAGGCTCCG CCCCCCTGAC GAGCATCACA AAAATCGACG
            TTGCGGCGTC CGCAAAAAGG TATCCGAGGC GGGGGGACTG CTCGTAGTGT TTTTAGCTGC
      3421  CTCAAGCCAG AGGTGGCGAA ACCCGACAGG ACTATAAAGA TACCAGGCGT TTCCCCCTGG
            GAGTTCGGTC TCCACCGCTT TGGGCTGTCC TGATATTTCT ATGGTCCGCA AAGGGGGACC
      3481  AAGCTCCCTC GTGCGCTCTC CTGTTCCGAC CCTGCCGCTT ACCGGATACC TGTCCGCCTT
            TTCGAGGGAG CACGCGAGAG GACAAGGCTG GGACGGCGAA TGGCCTATGG ACAGGCGGAA
      3541  TCTCCCTTCG GGAAGCGTGG CGCTTTCTCA TAGCTCACGC TGTTGGTATC TCAGTTCGGT
            AGAGGGAAGC CCTTCGCACC GCGAAAGAGT ATCGAGTGCG ACAACCATAG AGTCAAGCCA
```

Fig. 38₂

```
3601 GTAGGTCGTT CGCTCCAAGC TGGGCTGTGT GCACGAACCC CCCGTTCAGC CCGACCGCTG
     CATCCAGCAA GCGAGGTTCG ACCCGACACA CGTGCTTGGG GGGCAAGTCG GGCTGGCGAC
3661 CGCCTTATCC GGTAACTATC GTCTTGAGTC CAACCCGGTA AGACACGACT TATCGCCACT
     GCGGAATAGG CCATTGATGA CAGAACTCAG GTTGGGCCAT TCTGTGCTGA ATAGCGGTGA
3721 GGCAGCAGCC ATTGGTAACT GATTTAGAGG ACTTTGTCTT GAAGTTATGC ACCTGTTAAG
     CCGTCGTCGG TAACCATTGA CTAAATCTCC TGAAACAGAA CTTCAATACG TGGACAATTC
3781 GCTAAACTGA AAGAACAGAT TTTGGTGAGT GCGGTCCTCC AACCCACTTA CCTTGGTTCA
     CGATTTGACT TTCTTGTCTA AAACCACTCA CGCCAGGAGG TTGGGTGAAT GGAACCAAGT
3841 AAGAGTTGGT AGCTCAGCGA ACCTTGAGAA AACCACCGTT GGTAGCGGTG GTTTTTCTTT
     TTCTCAACCA TCGAGTCGCT TGGAACTCTT TTGGTGGCAA CCATCGCCAC CAAAAAGAAA
3901 ATTTATGAGA TGATGAATCA ATCGGTCTAT CAAGTCAACG AACAGCTATT CCGTTACTCT
     TAAATACTCT ACTACTTAGT TAGCCAGATA GTTCAGTTGC TTGTCGATAA GGCAATGAGA
3961 AGATTTCAGT GCAATTTATC TCTTCAAATG TAGCACCTGA AGTCAGCCCC ATACGATATA
     TCTAAAGTCA CGTTAAATAG AGAAGTTTAC ATCGTGGACT TCAGTCGGGG TATGCTATAT
4021 AGTTGTAATT CTCATGTTAG TCATGCCCCG CGCCCACCGG AAGGAGCTGA CTGGGTTGAA
     TCAACATTAA GAGTACAATC AGTACGGGGC GCGGGTGGCC TTCCTCGACT GACCCAACTT
4081 GGCTCTCAAG GGCATCGGTC GAGATCCCGG TGCCTAATGA GTGAGCTAAC TTACATTAAT
     CCGAGAGTTC CCGTAGCCAG CTCTAGGGCC ACGGATTACT CACTCGATTG AATGTAATTA
4141 TGCGTTGCGC TCACTGCCCG CTTTCCAGTC GGGAAACCTG TCGTGCCAGC TGCATTAATG
     ACGCAACGCG AGTGACGGGC GAAAGGTCAG CCCTTTGGAC AGCACGGTCG ACGTAATTAC
4201 AATCGGCCAA CGCGCGGGGA GAGGCGGTTT GCGTATTGGG CGCCAGGGTG GTTTTTCTTT
     TTAGCCGGTT GCGCGCCCCT CTCCGCCAAA CGCATAACCC GCGGTCCCAC CAAAAAGAAA
4261 TCACCAGTGA GACGGGCAAC AGCTGATTGC CCTTCACGGC CCTGGCCCTGA GAGAGTTGCA
     AGTGGTCACT CTGCCCGTTG TCGACTAACG GGAAGTGGCG GACCGGGACT CTCTCAACGT
4321 GCAAGCGGTC CACGCTGGTT TGCCCCAGCA GGCGAAAATC CTGTTTGATG GTGGTTAACG
     CGTTCGCCAG GTGCGACCAA ACGGGGTCGT CCGCTTTTAG GACAAACTAC CACCAATTGC
4381 GCGGGATATA ACATGAGCTG TCTTCGGTAT CGTCGTATCC CACTACCGAG ATGTCCGCAC
     CGCCCTATAT TGTACTCGAC AGAAGCCATA GCAGCATAGG GTGATGGCTC TACAGGCGTG
4441 CAACGCGCAG CCCGGACTCG GTAATGGCGC GCATTGCGCC CAGCGCCATC TGATCGTTGG
     GTTGCGCGTC GGGCCTGAGC CATTACCGCG GTAACGCGG GTCGCGGTAG ACTAGCAACC
4501 CAACCAGCAT CGCAGTGGGA ACGATGCCCT CATTCAGCAT TTGCATGGTT TGTTGAAAAC
     GTTGGTCGTA GCGTCACCCT TGCTACGGGA GTAAGTCGTA AACGTACCAA ACAACTTTTG
4561 CGGACATGGC ACTCCAGTCG CCTTCCCGTT CCGCTATCGG CTGAATTTGA TTGCGAGTGA
     GCCTGTACCG TGAGGTCAGC GGAAGGGCAA GGCGATAGCC GACTTAAACT AACGCTCACT
4621 GATATTTATG CCAGCCAGCC AGACGCAGAC GCGCCGAGAC AGAACTTAAT GGGCCCGCTA
     CTATAAATAC GGTCGGTCGG TCTGCGTCTG CGCGGCTCTG TCTTGAATTA CCCGGGCGAT
4681 ACAGCGCGAT TTGCTGGTGA CCCAATGCGA CCAGATGCTC CACGCCCAGT CGCGTACCGT
     TGTCGCGCTA AACGACCACT GGGTTACGCG GGTCTACGAG GTGCGGGTCA GCGCATGGCA
4741 CTTCATGGGA GAAAATAATA CTGTTGATGG GTGTCTGGTC AGAGACATCA AGAAATAACG
     GAAGTACCCT CTTTTATTAT GACAACTACC CACAGACCAG TCTCTGTAGT TCTTTATTGC
4801 CCGGAACATT AGTGCAGGCA GCTTCCACAG CAATGGCATC CTGGTCATCC AGCGGATAGT
     GGCCTTGTAA TCACGTCCGT CGAAGGTGTC GTTACCGTAG GACCAGTAGG TCGCCTATCA
4861 TAATGATCAG CCCACTGACG CGTTGCGCGA GAAGATTGTG CACCGCCGCT TTACAGGCTT
     ATTACTAGTC GGGTGACTGC GCAACGCGCT CTTCTACAC GTGGCGGCGA AATGTCCGAA
4921 CGACGCCGCT TCGTTCTACC ATCGACACCA CCACGCTGGC ACCCAGTTGA TCGGCGCGAG
     GCTGCGGCGA AGCAAGATGG TAGCTGTGGT GGTGCGACCG TGGGTCAACT AGCCGCGCTC
4981 ATTTAATCGC CGCGACAATT TGCGACGGCG CGTGCAGGGC CAGACTGGAG GTGGCAACGC
     TAAATTAGCG GCGCTGTTAA ACGCTGCCGC GCACGTCCCG GTCTGACCTC CACCGTTGCG
5041 CAATCAGCAA CGACTGTTTG CCCGCCAGTT GTTGTGCCAC GCGGTTGGGA ATGTAATTCA
     GTTAGTCGTT GCTGACAAAC GGGCGGTCAA CAACACGGTG CGCCAACCCT TACATTAAGT
5101 GCTCCGCCAT CGCCGCTTCC ACTTTTTCCC GCGTTTTCGC AGAAACGTGG CTGGCCTGGT
     CGAGGCGGTA GCGGCGAAGG TGAAAAAGGG CGCAAAAGCG TCTTTGCACC GACCGGACCA
5161 TCACCACGCG GGAAACGGTC TGATAAGAGA CACCGGCATA CTCTGCGACA TCGTATAACG
     AGTGGTGCGC CCTTTGCCAG ACTATTCTCT GTGGCCGTAT GAGACGCTGT AGCATATTGC
5221 TTACTGGTTT CACATTCACC ACCCTGAATT GACTCTCTTC CGGGCGCTAT CATGCCATAC
     AATGACCAAA GTGTAAGTGG TGGGACTTAA CTGAGAGAAG GCCCGCGATA GTACGGTATG
5281 CGCGAAAGGT TTTGCGCCAT TCGATGGTGT CCGGGATCTC GACGCTCTCC CTTATGCGAC
     GCGCTTTCCA AAACGCGGTA AGCTACCACA GGCCCTAGAG CTGCGAGAGG GAATACGCTG
5341 TCCTGCATTA GGAAATTAAT ACGACTCACT ATA
     AGGACGTAAT CCTTTAATTA TGCTGAGTGA TAT
```

```
   1 GGGGAATTGT GAGCGGATAA CAATTCCCCT CTAGAAATAA TTTTGTTTAA CTTTAAGAAG
     CCCCTTAACA CTCGCCTATT GTTAAGGGGA GATCTTTATT AAAACAAATT GAAATTCTTC
                                                                 SacI
                                                                 ~~~
  61 GAGATATACC ATGGGCAGCA GCCATCACCA TCATCACCAC AGCCAGGATC CGAATTCGAG
     CTCTATATGG TACCCGTCGT CGGTAGTGGT AGTAGTGGTG TCGGTCCTAG GCTTAAGCTC
     SacI
     ~~~
 121 CTCGGACCAT GATTACGCCA AGCTATCAAC TTTGTATAGA AAAGTTGAAC GAGAAACGTA
     GAGCCTGGTA CTAATGCGGT TCGATAGTTG AAACATATCT TTTCAACTTG CTCTTTGCAT
 181 AAATGATATA AATATCAATA TATTAAATTA GATTTTGCAT AAAAAACAGA CTACATAATA
     TTTACTATAT TTATAGTTAT ATAATTTAAT CTAAAACGTA TTTTTTGTCT GATGTATTAT
                                                PstI
                                                ~~~~~~~~
 241 CTGTAAAACA CAACATATCC AGTCACTATG GTCGACCTGC AGACTGGCTG TGTATAAGGG
     GACATTTTGT GTTGTATAGG TCAGTGATAC CAGCTGGACG TCTGACCGAC ACATATTCCC
 301 AGCCTGACAT TTATATTCCC CAGAACATCA GGTTAATGGC GTTTTTGATG TCATTTTCGC
     TCGGACTGTA AATATAAGGG GTCTTGTAGT CCAATTACCG CAAAAACTAC AGTAAAAGCG
 361 GGTGGCTGAG ATCAGCCACT TCTTCCCCGA TAACGGAGAC CGGCACACTG GCCATATCGG
     CCACCGACTC TAGTCGGTGA AGAAGGGGCT ATTGCCTCTG GCCGTGTGAC CGGTATAGCC
 421 TGGTCATCAT GCGCCAGCTT TCATCCCCGA TATGCACCAC CGGGTAAAGT TCACGGGGGA
     ACCAGTAGTA CGCGGTCGAA AGTAGGGGCT ATACGGTGGT GCCCATTTCA AGTGCCCCCT
 481 CTTTATCTGA CAGCAGACGT GCACTGGCCA GGGGGATCAC CATCCGTCGC CCGGGCGTGT
     GAAATAGACT GTCGTCTGCA CGTGACCGGT CCCCCTAGTG GTAGGCAGCG GGCCCGCACA
 541 CAATAATATC ACTCTGTACA TCCACAAACA GACGATAACG GCTCTCTCTT TTATAGGTGT
     GTTATTATAG TGAGACATGT AGGTGTTTGT CTGCTATTGC CGAGAGAGAA AATATCCACA
 601 AAACCTTAAA CTGCATTTCA CCAGCCCCTG TTCTCGTCGG CAAAAGAGCC GTTCATTTCA
     TTTGGAATTT GACGTAAAGT GGTCGGGGAC AAGAGCAGCC GTTTTCTCGG CAAGTAAAGT
 661 ATAAACCGGG CGACCTCAGC CATCCCTTCC TGATTTTCCG CTTTCCAGCG TTCGGCACGC
     TATTTGGCCC GCTGGAGTCG GTAGGGAAGG ACTAAAAGGC GAAAGGTCGC AAGCCGTGCG
 721 AGACGACGGG CTTCATTCTG CATGGTTGTG CTTACCGAAC CGGAGATATT GACATCATAT
     TCTGCTGCCC GAAGTAAGAC GTACCAACAC GAATGGCTTG GCCTCTATAA CTGTAGTATA
 781 ATGCCTTGAG CAACTGATAG CTGTCGCTGT CAACTGTCAC TGTAATACGC TGCTTCATAG
     TACGGAACTC GTTGACTATC GACAGCGACA GTTGACAGTG ACATTATGCG ACGAAGTATC
 841 CATACCTCTT TTTGACATAC TTCGGGTATA CATATCAGTA TATATTCTTA TACCGCAAAA
     GTATGGAGAA AAACTGTATG AAGCCCATAT GTATAGTCAT ATATAAGAAT ATGGCGTTTT
 901 ATCAGCGCGC AAATACGCAT ACTGTTATCT GGCTTTTAGT AAGCCGGATC CTCTAGATTA
     TAGTCGCGCG TTTATGCGTA TGACAATAGA CCGAAAATCA TTCGGCCTAG GAGATCTAAT
 961 CGCCCCGCCC TGCCACTCAT CGCAGTACTG TTGTAATTCA TTAAGCATTC TGCCGACATG
     GCGGGGCGGG ACGGTGAGTA GCGTCATGAC AACATTAAGT AATTCGTAAG ACGGCTGTAC
1021 GAAGCCATCA CAAACGGCAT GATGAACCTG AATCGCCAGC GGCATCAGCA CCTTGTCGCC
     CTTCGGTAGT GTTTGCCGTA CTACTTGGAC TTAGCGGTCG CCGTAGTCGT GGAACAGCGG
1081 TTGCGTATAA TATTTGCCCA TGGTGAAAAC GGGGGCGAAG AAGTTGTCCA TATTGGCCAC
     AACGCATATT ATAAACGGGT ACCACTTTTG CCCCCGCTTC TTCAACAGGT ATAACCGGTG
1141 GTTTAAATCA AAACTGGTGA AACTCACCCA GGGATTGGCT GAGACGAAAA ACATATTCTC
     CAAATTTAGT TTTGACCACT TTGAGTGGGT CCCTAACCGA CTCTGCTTTT TGTATAAGAG
1201 AATAAACCCT TTAGGGAAAT AGGCCAGGTT TTCACCGTAA CACGCCACAT CTTGCGAATA
     TTATTTGGGA AATCCCTTTA TCCGGTCCAA AAGTGGCATT GTGCGGTGTA GAACGCTTAT
1261 TATGTGTAGA AACTGCCGGA AATCGTCGTG GTATTCACTC CAGAGCGATG AAAACGTTTC
     ATACACATCT TTGACGGCCT TTAGCAGCAC CATAAGTGAG GTCTCGCTAC TTTTGCAAAG
1321 AGTTTGCTCA TGGAAAACGG TGTAACAAGG GTGAACACTA TCCCATATCA CCAGCTCACC
     TCAAACGAGT ACCTTTTGCC ACATTGTTCC CACTTGTGAT AGGGTATAGT GGTCGAGTGG
1381 GTCTTTCATT GCCATACGGA ATTCCGGATG AGCATTCATC AGGCGGGCAA GAATGTGAAT
     CAGAAAGTAA CGGTATGCCT TAAGGCCTAC TCGTAAGTAG TCCGCCCGTT CTTACACTTA
1441 AAAGGCCGGA TAAAACTTGT GCTTATTTTT CTTTACGGTC TTTAAAAAGG CCGTAATATC
     TTTCCGGCCT ATTTTGAACA CGAATAAAAA GAAATGCCAG AAATTTTTCC GGCATTATAG
1501 CAGCTGAACG GTCTGGTTAT AGGTACATTG AGCAACTGAC TGAAATGCCT CAAAATGTTC
     GTCGACTTGC CAGACCAATA TCCATGTAAC TCGTTGACTG ACTTTACGGA GTTTTACAAG
1561 TTTACGATGC CATTGGGATA TATCAACGGT GGTATATCCA GTGATTTTTT CTCCATTTT
     AAATGCTACG GTAACCCTAT ATAGTTGCCA CCATAAAGGT CACTAAAAAA GAGGTAAAA
1621 AGCTTCCTTA GCTCCTGAAA ATCTCGACGG ATCCTAACTC AAAATCCACA CATTATACGA
     TCGAAGGAAT CGAGGACTTT TAGAGCTGCC TAGGATTGAG TTTTAGGTGT GTAATATGCT
1681 GCCCGGAAGCA TAAAGTGTAA AGCCTGGGGG TGCCTAATGC GGCCGCCATA GTGACTGGAT
     CGGCCTTCGT ATTTCACATT TCGGACCCCC ACGGATTACG CCGGCGGTAT CACTGACCTA
1741 ATGTTGTGTT TTACAGTATT ATGTAGTCTG TTTTTTATGC AAAATCTAAT TTAATATATT
     TACAACACAA AATGTCATAA TACATCAGAC AAAAAATACG TTTTAGATTA AATTATATAA
1801 GATATTTATA TCATTTTACG TTTCTCGTTC AACTTTATTA TACATAGTTG ATAATTCACT
     CTATAAATAT AGTAAAATGC AAAGAGCAAG TTGAAATAAT ATGTATCAAC TATTAAGTGA
```

Fig. 40₁

```
1861  GGCCGTCGTT TTACAACGTC GTGACTGGGA AAACCCTGGC GTTACCCAAC TTAATCGCCT
      CCGGCAGCAA AATGTTGCAG CACTGACCCT TTTGGGACCG CAATGGGTTG AATTAGCGGA
               HindIII                                              AvrII
               ~~~~~~~                                               ~~~~
1921  TGCAGCACAA GCTTGGAATT GTTATCCGCT CACAATTCCT ATAGTGAGTC GTATTACCTA
      ACGTCGTGTT CGAACCTTAA CAATAGGCGA GTGTTAAGGA TATCACTCAG CATAATGGAT
      AvrII
      ~~
1981  GGCTGCTGCC ACCGCTGAGC AATAACTAGC ATAACCCCTT GGGGCCTCTA AACGGGTCTT
      CCGACGACGG TGGCGACTCG TTATTGATCG TATTGGGGAA CCCCGGAGAT TTGCCCAGAA
2041  GAGGGGTTTT TTGCTGAAAG GAGGAACTAT ATCCGGATTG GCGAATGGGA CGCGCCCTGT
      CTCCCCAAAA AACGACTTTC CTCCTTGATA TAGGCCTAAC CGCTTACCCT GCGCGGGACA
2101  AGCGGCGCAT TAAGCGCGGC GGGTGTGGTG GTTACGCGCA GCGTGACCGC TACACTTGCC
      TCGCCGCGTA ATTCGCGCCG CCCACACCAC CAATGCGCGT CGCACTGGCG ATGTGAACGG
2161  AGCGCCCTAG CGCCCGCTCC TTTCGCTTTC TTCCCTTCCT TTCTCGCCAC GTTCGCCGGC
      TCGCGGGATC GCGGGCGAGG AAAGCGAAAG AAGGGAAGGA AAGAGCGGTG CAAGCGGCCG
2221  TTTCCCCGTC AAGCTCTAAA TCGGGGGCTC CCTTTAGGGT TCCGATTTAG TGCTTTACGG
      AAAGGGGCAG TTCGAGATTT AGCCCCCGAG GGAAATCCCA AGGCTAAATC ACGAAATGCC
2281  CACCTCGACC CCAAAAAACT TGATTAGGGT GATGGTTCAC GTAGTGGGCC ATCGCCCTGA
      GTGGAGCTGG GGTTTTTTGA ACTAATCCCA CTACCAAGTG CATCACCCGG TAGCGGGACT
2341  TAGACGGTTT TTCGCCCTTT GACGTTGGAG TCCACGTTCT TTAATAGTGG ACTCTTGTTC
      ATCTGCCAAA AAGCGGGAAA CTGCAACCTC AGGTGCAAGA AATTATCACC TGAGAACAAG
2401  CAAACTGGAA CAACACTCAA CCCTATCTCG GTCTATTCTT TTGATTATA AGGGATTTTG
      GTTTGACCTT GTTGTGAGTT GGGATAGAGC CAGATAAGAA AACTAAATAT TCCCTAAAAC
2461  CCGATTTCGG CCTATTGGTT AAAAAATGAG CTGATTTAAC AAAAATTTAA CGCGAATTTT
      GGCTAAAGCC GGATAACCAA TTTTTTACTC GACTAAATTG TTTTTAAATT GCGCTTAAAA
2521  AACAAAATAT TAACGTTTAC AATTTCTGGC GGCACGATGG CATGAGATTA TCAAAAAGGA
      TTGTTTTATA ATTGCAAATG TTAAAGACCG CCGTGCTACC GTACTCTAAT AGTTTTTCCT
2581  TCTTCACCTA GATCCTTTTA AATTAAAAAT GAAGTTTTAA ATCAATCTAA AGTATATATG
      AGAAGTGGAT CTAGGAAAAT TTAATTTTTA CTTCAAAATT TAGTTAGATT TCATATATAC
2641  AGTAAACTTG GTCTGACAGT TACCAATGCT TAATCAGTGA GGCACCTATC TCAGCGATCT
      TCATTTGAAC CAGACTGTCA ATGGTTACGA ATTAGTCACT CCGTGGATAG AGTCGCTAGA
2701  GTCTATTTCG TTCATCCATA GTTGCCTGAC TCCCCGTCGT GTAGATAACT ACGATACGGG
      CAGATAAAGC AAGTAGGTAT CAACGGACTG AGGGGCAGCA CATCTATTGA TGCTATGCCC
2761  AGGGCTTACC ATCTGGCCCC AGTGCTGCAA TGATACCGCG AGACCCACGC TCACCGGCTC
      TCCCGAATGG TAGACCGGGG TCACGACGTT ACTATGGCGC TCTGGGTGCG AGTGGCCGAG
2821  CAGATTTATC AGCAATAAAC CAGCCAGCCG GAAGGGCCGA GCGCAGAAGT GGTCCTGCAA
      GTCTAAATAG TCGTTATTTG GTCGGTCGGC CTTCCCGGCT CGCGTCTTCA CCAGGACGTT
2881  CTTTATCCGC CTCCATCCAG TCTATTAATT GTTGCCGGGA AGCTAGAGTA AGTAGTTCGC
      GAAATAGGCG GAGGTAGGTC AGATAATTAA CAACGGCCCT TCGATCTCAT TCATCAAGCG
2941  CAGTTAATAG TTTGCGCAAC GTTGTTGCCA TTGCTACAGG CATCGTGGTG TCACGCTCGT
      GTCAATTATC AAACGCGTTG CAACAACGGT AACGATGTCC GTAGCACCAC AGTGCGAGCA
3001  CGTTTGGTAT GGCTTCATTC AGCTCCGGTT CCCAACGATC AAGGCGAGTT ACATGATCCC
      GCAAACCATA CCGAAGTAAG TCGAGGCCAA GGGTTGCTAG TTCCGCTCAA TGTACTAGGG
3061  CCATGTTGTG CAAAAAAGCG GTTAGCTCCT TCGGTCCTCC GATCGTTGTC AGAAGTAAGT
      GGTACAACAC GTTTTTTCGC CAATCGAGGA AGCCAGGAGG CTAGCAACAG TCTTCATTCA
3121  TGGCCGCAGT GTTATCACTC ATGGTTATGG CAGCACTGCA TAATTCTCTT ACTGTCATGC
      ACCGGCGTCA CAATAGTGAG TACCAATACC GTCGTGACGT ATTAAGAGAA TGACAGTACG
3181  CATCCGTAAG ATGCTTTTCT GTGACTGGTG AGTACTCAAC CAAGTCATTC TGAGAATAGT
      GTAGGCATTC TACGAAAAGA CACTGACCAC TCATGAGTTG GTTCAGTAAG ACTCTTATCA
3241  GTATGCGGCG ACCGAGTTGC TCTTGCCCGG CGTCAATACG GGATAATACC GCGCCACATA
      CATACGCCGC TGGCTCAACG AGAACGGGCC GCAGTTATGC CCTATTATGG CGCGGTGTAT
3301  GCAGAACTTT AAAAGTGCTC ATCATTGGAA AACGTTCTTC GGGGCGAAAA CTCTCAAGGA
      CGTCTTGAAA TTTTCACGAG TAGTAACCTT TTGCAAGAAG CCCCGCTTTT GAGAGTTCCT
3361  TCTTACCGCT GTTGAGATCC AGTTCGATGT AACCCACTCG TGCACCCAAC TGATCTTCAG
      AGAATGGCGA CAACTCTAGG TCAAGCTACA TTGGGTGAGC ACGTGGGTTG ACTAGAAGTC
3421  CATCTTTTAC TTTCACCAGC GTTTCTGGGT GAGCAAAAAC AGGAAGGCAA AATGCCGCAA
      GTAGAAAATG AAAGTGGTCG CAAAGACCCA CTCGTTTTTG TCCTTCCGTT TTACGGCGTT
3481  AAAAGGGAAT AAGGGCGACA CGGAAATGTT GAATACTCAT ACTCTTCCTT TTTCAATCAT
      TTTTCCCTTA TTCCCGCTGT GCCTTTACAA CTTATGAGTA TGAGAAGGAA AAAGTTAGTA
3541  GATTGAAGCA TTTATCAGGG TTATTGTCTC ATGAGCGGAT ACATATTTGA ATGTATTTAG
      CTAACTTCGT AAATAGTCCC ATAACAGAG TACTCGCCTA TGTATAAACT TACATAAATC
3601  AAAAATAAAC AAATAGGTCA TGACCAAAAT CCCTTAACGT GAGTTTTCGT TCCACTGAGC
      TTTTTATTTG TTTATCCAGT ACTGGTTTTA GGGAATTGCA CTCAAAAGCA AGGTGACTCG
3661  GTCAGACCCC GTAGAAAAGA TCAAAGGATC TTCTTGAGAT CCTTTTTTTC TGCGCGTAAT
      CAGTCTGGGG CATCTTTTCT AGTTTCCTAG AAGAACTCTA GGAAAAAAAG ACGCGCATTA
3721  CTGCTGCTTG CAAACAAAAA AACCACCGCT ACCAGCGGTG GTTTGTTTGC CGGATCAAGA
      GACGACGAAC GTTTGTTTTT TTGGTGGCGA TGGTCGCCAC CAAACAAACG GCCTAGTTCT
3781  GCTACCAACT CTTTTTTCCGA AGGTAACTGG CTTCAGCAGA GCGCAGATAC CAAATACTGT
      CGATGGTTGA GAAAAAGGCT TCCATTGACC GAAGTCGTCT CGCGTCTATG GTTTATGACA
3841  CCTTCTAGTG TAGCCGTAGT TAGGCCACCA CTTCAAGAAC TCTGTAGCAC CGCCTACATA
```

Fig. 40₂

```
      GGAAGATCAC ATCGGCATCA ATCCGGTGGT GAAGTTCTTG AGACATCGTG GCGGATGTAT
3901  CCTCGCTCTG CTAATCCTGT TACCAGTGGC TGCTGCCAGT GGCGATAAGT CGTGTCTTAC
      GGAGCGAGAC GATTAGGACA ATGGTCACCG ACGACGGTCA CCGCTATTCA GCACAGAATG
3961  CGGGTTGGAC TCAAGACGAT AGTTACCGGA TAAGGCGCAG CGGTCGGGCT GAACGGGGGG
      GCCCAACCTG AGTTCTGCTA TCAATGGCCT ATTCCGCGTC GCCAGCCCGA CTTGCCCCCC
4021  TTCGTGCACA CAGCCCAGCT TGGAGCGAAC GACCTACACC GAACTGAGAT ACCTACAGCG
      AAGCACGTGT GTCGGGTCGA ACCTCGCTTG CTGGATGTGG CTTGACTCTA TGGATGTCGC
4081  TGAGCTATGA GAAAGCGCCA CGCTTCCCGA AGGGAGAAAG GCGGACAGGT ATCCGGTAAG
      ACTCGATACT CTTTCGCGGT GCGAAGGGCT TCCCTCTTTC CGCCTGTCCA TAGGCCATTC
4141  CGGCAGGGTC GGAACAGGAG AGCGCACGAG GGAGCTTCCA GGGGGAAACG CCTGGTATCT
      GCCGTCCCAG CCTTGTCCTC TCGCGTGCTC CCTCGAAGGT CCCCCTTTGC GGACCATAGA
4201  TTATAGTCCT GTCGGGTTTC GCCACCTCTG ACTTGAGCGT CGATTTTTGT GATGCTCGTC
      AATATCAGGA CAGCCCAAAG CGGTGGAGAC TGAACTCGCA GCTAAAAACA CTACGAGCAG
4261  AGGGGGGCGG AGCCTATGGA AAAACGCCAG CAACGCGGCC TTTTTACGGT TCCTGGCCTT
      TCCCCCCGCC TCGGATACCT TTTTGCGGTC GTTGCGCCGG AAAAATGCCA AGGACCGGAA
4321  TTGCTGGCCT TTTGCTCACA TGTTCTTTCC TGCGTTATCC CCTGATTCTG TGGATAACCG
      AACGACCGGA AAACGAGTGT ACAAGAAAGG ACGCAATAGG GGACTAAGAC ACCTATTGGC
4381  TATTACCGCC TTTGAGTGAG CTGATACCGC TCGCCGCAGC CGAACGACCG AGCGCAGCGA
      ATAATGGCGG AAACTCACTC GACTATGGCG AGCGGCGTCG GCTTGCTGGC TCGCGTCGCT
4441  GTCAGTGAGC GAGGAAGCGG AAGAGCGCCT GATGCGGTAT TTTCTCCTTA CGCATCTGTG
      CAGTCACTCG CTCCTTCGCC TTCTCGCGGA CTACGCCATA AAAGAGGAAT GCGTAGACAC
4501  CGGTATTTCA CACCGCATAT ATGGTGCACT CTCAGTACAA TCTGCTCTGA TGCCGCATAG
      GCCATAAAGT GTGGCGTATA TACCACGTGA GAGTCATGTT AGACGAGACT ACGGCGTATC
4561  TTAAGCCAGT ATACACTCCG CTATCGCTAC GTGACTGGGT CATGGCTGCG CCCCGACACC
      AATTCGGTCA TATGTGAGGC GATAGCGATG CACTGACCCA GTACCGACGC GGGGCTGTGG
4621  CGCCAACACC CGCTGACGCG CCCTGACGGG CTTGTCTGCT CCCGGCATCC GCTTACGAC
      GCGGTTGTGG GCGACTGCGC GGGACTGCCC GAACAGACGA GGGCCGTAGG CGAATGTCTG
4681  AAGCTGTGAC CGTCTCCGGG AGCTGCATGT GTCAGAGGTT TCACCGTCA TCACCGAAAC
      TTCGACACTG GCAGAGGCCC TCGACGTACA CAGTCTCCAA AAGTGGCAGT AGTGGCTTTG
4741  GCGCGAGGCA GCTGCGGTAA AGCTCATCAG CGTGGTCGTG AAGCGATTCA CAGATGTCTG
      CGCGCTCCGT CGACGCCATT TCGAGTAGTC GCACCAGCAC TTCGCTAAGT GTCTACAGAC
4801  CCTGTTCATC CGCGTCCAGC TCGTTGAGTT TCTCCAGAAG CGTTAATGTC TGGCTTCTGA
      GGACAAGTAG GCGCAGGTCG AGCAACTCAA AGAGGTCTTC GCAATTACAG ACCGAAGACT
4861  TAAAGCGGGC CATGTTAAGG GCGGTTTTTT CCTGTTTGGT CACTGATGCC TCCGTGTAAG
      ATTTCGCCCG GTACAATTCC CGCCAAAAAA GGACAAACCA GTGACTACGG AGGCACATTC
4921  GGGGATTTCT GTTCATGGGG GTAATGATAC CGATGAAACG AGAGAGGATG CTCACGATAC
      CCCCTAAAGA CAAGTACCCC CATTACTATG GCTACTTTGC TCTCTCCTAC GAGTGCTATG
4981  GGGTTACTGA TGATGAACAT GCCCGGTTAC TGGAACGTTG TGAGGGTAAA CAACTGGCGG
      CCCAATGACT ACTACTTGTA CGGGCCAATG ACCTTGCAAC ACTCCCATTT GTTGACCGCC
5041  TATGGATGCG GCGGGACCAG AGAAAAATCA CTCAGGGTCA ATGCCAGCGC TTCGTTAATA
      ATACCTACGC CGCCCTGGTC TCTTTTTAGT GAGTCCCAGT TACGGTCGCG AAGCAATTAT
5101  CAGATGTAGG TGTTCCACAG GGTAGCCAGC AGCATCCTGC GATGCAGATC CGGAACATAA
      GTCTACATCC ACAAGGTGTC CCATCGGTCG TCGTAGGACG CTACGTCTAG GCCTTGTATT
5161  TGGTGCAGGG CGCTGACTTC CGCGTTTCCA GACTTTACGA AACACGGAAA CCGAAGACCA
      ACCACGTCCC GCGACTGAAG GCGCAAAGGT CTGAAATGCT TTGTGCCTTT GGCTTCTGGT
5221  TTCATGTTGT TGCTCAGGTC GCAGACGTTT TGCAGCAGCA GTCGCTTCAC GTTCGCTCGC
      AAGTACAACA ACGAGTCCAG CGTCTGCAAA ACGTCGTCGT CAGCGAAGTG CAAGCGAGCG
5281  GTATCGGTGA TTCATTCTGC TAACCAGTAA GGCAACCCCG CCAGCCTAGC CGGGTCCTCA
      CATAGCCACT AAGTAAGACG ATTGGTCATT CCGTTGGGGC GGTCGGATCG GCCCAGGAGT
5341  ACGACAGGAG CACGATCATG CTAGTCATGC CCCGCGCCCA CCGGAAGGAG CTGACTGGGT
      TGCTGTCCTC GTGCTAGTAC GATCAGTACG GGGCGCGGGT GGCCTTCCTC GACTGACCCA
5401  TGAAGGCTCT CAAGGGCATC GGTCGAGATC CCGGTGCCTA ATGAGTGAGC TAACTTACAT
      ACTTCCGAGA GTTCCCGTAG CCAGCTCTAG GGCCACGGAT TACTCACTCG ATTGAATGTA
5461  TAATTGCGTT GCGCTCACTG CCCGCTTTCC AGTCGGGAAA CCTGTCGTGC CAGCTGCATT
      ATTAACGCAA CGCGAGTGAC GGGCGAAAGG TCAGCCCTTT GGACAGCACG GTCGACGTAA
5521  AATGAATCGG CCAACGCGCG GGGAGAGGCG GTTTGCGTAT TGGGCGCCAG GGTGGTTTTT
      TTACTTAGCC GGTTGCGCGC CCCTCTCCGC CAAACGCATA ACCCGCGGTC CCACCAAAAA
5581  CTTTTCACCA GTGAGACGGG CAACAGCTGA TTGCCCTTCA CCGCCTGGCC CTGAGAGAGT
      GAAAAGTGGT CACTCTGCCC GTTGTCGACT AACGGGAAGT GGCGGACCGG GACTCTCTCA
5641  TGCAGCAAGC GGTCCACGCT GGTTTGCCCC AGCAGGCGAA AATCCTGTTT GATGGTGGTT
      ACGTCGTTCG CCAGGTGCGA CCAAACGGGG TCGTCCGCTT TTAGGACAAA CTACCACCAA
5701  AACGGCGGGA TATAACATGA GCTGTCTTCG GTATCGTCGT ATCCCACTAC CGAGATGTCC
      TTGCCGCCCT ATATTGTACT CGACAGAAGC CATAGCAGCA TAGGGTGATG GCTCTACAGG
5761  GCACCAACGC GCAGCCCGGA CTCGGTAATG GCGCGCATTG CGCCCAGCGC CATCTGATCG
      CGTGGTTGCG CGTCGGGCCT GAGCCATTAC CGCGCGTAAC GCGGGTCGCG GTAGACTAGC
5821  TTGGCAACCA GCATCGCAGT GGGAACGATG CCCTCATTCA GCATTTGCAT GGTTTGTTGA
      AACCGTTGGT CGTAGCGTCA CCCTTGCTAC GGGAGTAAGT CGTAAACGTA CCAAACAACT
```

Fig. 40₃

```
5881  AAACCGGACA TGGCACTCCA GTCGCCTTCC CGTTCCGCTA TCGGCTGAAT TTGATTGCGA
      TTTGGCCTGT ACCGTGAGGT CAGCGGAAGG GCAAGGCGAT AGCCGACTTA AACTAACGCT
5941  GTGAGATATT TATGCCAGCC AGCCAGACGC AGACGCGCCG AGACAGAACT TAATGGGCCC
      CACTCTATAA ATACGGTCGG TCGGTCTGCG TCTGCGCGGC TCTGTCTTGA ATTACCCGGG
6001  GCTAACAGCG CGATTTGCTG GTGACCCAAT GCGACCAGAT GCTCCACGCC CAGTCGCGTA
      CGATTGTCGC GCTAAACGAC CACTGGGTTA CGCTGGTCTA CGAGGTGCGG GTCAGCGCAT
6061  CCGTCTTCAT GGGAGAAAAT AATACTGTTG ATGGGTGTCT GGTCAGAGAC ATCAAGAAAT
      GGCAGAAGTA CCCTCTTTTA TTATGACAAC TACCCACAGA CCAGTCTCTG TAGTTCTTTA
6121  AACGCCGGAA CATTAGTGCA GGCAGCTTCC ACAGCAATGG CATCCTGGTC ATCCAGCGGA
      TTGCGGCCTT GTAATCACGT CCGTCGAAGG TGTCGTTACC GTAGGACCAG TAGGTCGCCT
6181  TAGTTAATGA TCAGCCCACT GACGCGTTGC GCGAGAAGAT TGTGCACCGC CGCTTTACAG
      ATCAATTACT AGTCGGGTGA CTGCGCAACG CGCTCTTCTA ACACGTGGCG GCGAAATGTC
6241  GCTTCGACGC CGCTTCGTTC TACCATCGAC ACCACCACGC TGGCACCCAG TTGATCGGCG
      CGAAGCTGCG GCGAAGCAAG ATGGTAGCTG TGGTGGTGCG ACCGTGGGTC AACTAGCCGC
6301  CGAGATTTAA TCGCCGCGAC AATTTGCGAC GGCGCGTGCA GGGCCAGACT GGAGGTGGCA
      GCTCTAAATT AGCGGCGCTG TTAAACGCTG CCGCGCACGT CCCGGTCTGA CCTCCACCGT
6361  ACGCCAATCA GCAACGACTG TTTGCCCGCC AGTTGTTGTG CCACGCGGTT GGGAATGTAA
      TGCGGTTAGT CGTTGCTGAC AAACGGGCGG TCAACAACAC GGTGCGCCAA CCCTTACATT
6421  TTCAGCTCCG CCATCGCCGC TTCCACTTTT TCCCGCGTTT TCGCAGAAAC GTGGCTGGCC
      AAGTCGAGGC GGTAGCGGCG AAGGTGAAAA AGGGCGCAAA AGCGTCTTTG CACCGACCGG
6481  TGGTTCACCA CGCGGGAAAC GGTCTGATAA GAGACACCGG CATACTCTGC GACATCGTAT
      ACCAAGTGGT GCGCCCTTTG CCAGACTATT CTCTGTGGCC GTATGAGACG CTGTAGCATA
6541  AACGTTACTG GTTTCACATT CACCACCCTG AATTGACTCT CTTCCGGGCG CTATCATGCC
      TTGCAATGAC CAAAGTGTAA GTGGTGGGAC TTAACTGAGA GAAGGCCCGC GATAGTACGG
6601  ATACCGCGAA AGGTTTTGCG CCATTCGATG GTGTCCGGGA TCTCGACGCT CTCCCTTATG
      TATGGCGCTT TCCAAAACGC GGTAAGCTAC CACAGGCCCT AGAGCTGCGA GAGGGAATAC
6661  CGACTCCTGC ATTAGGAAGC AGCCCAGTAG TAGGTTGAGG CCGTTGAGCA CCGCCGCCGC
      GCTGAGGACG TAATCCTTCG TCGGGTCATC ATCCAACTCC GGCAACTCGT GGCGGCGGCG
6721  AAGGAATGGT GCATGCAAGG AGATGGCGCC CAACAGTCCC CCGGCCACGG GGCCTGCCAC
      TTCCTTACCA CGTACGTTCC TCTACCGCGG GTTGTCAGGG GGCCGGTGCC CCGGACGGTG
6781  CATACCCACG CCGAACAAG CGCTCATGAG CCCGAAGTGG CGAGCCCGAT CTTCCCCATC
      GTATGGGTGC GGCTTTGTTC GCGAGTACTC GGGCTTACC GCTCGGGCTA GAAGGGGTAG
6841  GGTGATGTCG GCGATATAGG CGCCAGCAAC CGCACCTGTG GCGCCGGTGA TGCCGGCCAC
      CCACTACAGC CGCTATATCC GCGGTCGTTG GCGTGGACAC CGCGGCCACT ACGGCCGGTG
                                                     ClaI
                                                    ~~~~~~~
6901  GATGCGTCCG GCGTAGAGGA TCGAGATCGA TCTCGATCCC GCGAAATTAA TACGACTCAC
      CTACGCAGGC CGCATCTCCT AGCTCTAGCT AGAGCTAGGG CGCTTTAATT ATGCTGAGTG
6961  TATA
      ATAT
```

Fig. 40$_4$

| Fig. $42_1$ |
|---|
| Fig. $42_2$ |
| Fig. $42_3$ |
| Fig. $42_4$ |

Fig. 42

```
   1 ATCCGGATAT AGTTCCTCCT TTCAGCAAAA AACCCCTCAA GACCCGTTTA GAGGCCCCAA
     TAGGCCTATA TCAAGGAGGA AAGTCGTTTT TTGGGGAGTT CTGGGCAAAT CTCCGGGGTT
  61 GGGGTTATGC TAGTTATTGC TCAGCGGTGG CAGCAGCCAA CTCAGCTTCC TTTCGGGCTT
     CCCCAATACG ATCAATAACG AGTCGCCACC GTCGTCGGTT GAGTCGAAGG AAAGCCCGAA
                                                            HindIII
                                                            ~~~~~~
 121 TGTTAGCAGC CGGATCTCAG TGGTGGTGGT GGTGGTGCTC GAGTGCGGCC GCAAGCTTAG
     ACAATCGTCG GCCTAGAGTC ACCACCACCA CCACCACGAG CTCACGCCGG CGTTCGAATC
                          ~~~~~~~~~~~~~~~~~~                ~~~
                                His tag
 181 CAGCCGGATC TGATCTTAAT TAATTATCAC CACTTTGTAC AAGAAAGCTG AACGAGAAAC
     GTCGGCCTAG ACTAGAATTA ATTAATAGTG GTGAAACATG TTCTTTCGAC TTGCTCTTTG
 241 GTAAAATGAT ATAAATATCA ATATATTAAA TTAGATTTTG CATAAAAAAC AGACTACATA
     CATTTTACTA TATTTATAGT TATATAATTT AATCTAAAAC GTATTTTTTG TCTGATGTAT
                                                           PstI
                                                           ~~~~~~
 301 ATACTGTAAA ACACAACATA TCCAGTCACT ATGGTCGACC TGCAGACTGG CTGTGTATAA
     TATGACATTT TGTGTTGTAT AGGTCAGTGA TACCAGCTGG ACGTCTGACC GACACATATT
 361 GGGAGCCTGA CATTTATATT CCCCAGAACA TCAGGTTAAT GGCGTTTTTG ATGTCATTTT
     CCCTCGGACT GTAAATATAA GGGGTCTTGT AGTCCAATTA CCGCAAAAAC TACAGTAAAA
 421 CGCGGCGGCT GAGATCAGCC ACTTCTTCCC CGATAACGGA GACCGGCACA CTGGCCATAT
     GCGCCGCCGA CTCTAGTCGG TGAAGAAGGG GCTATTGCCT CTGGCCGTGT GACCGGTATA
 481 CGGTGGTCAT CATGCGCCAG CTTTCATCCC CGATATGCAC CACCGGGTAA AGTTCACGGG
     GCCACCAGTA GTACGCGGTC GAAAGTAGGG GCTATACGTG GTGGCCCATT TCAAGTGCCC
                                                              XmaI
                                                              ~~~~~~
                                                              SmaI
                                                              ~~~~~~
 541 AGACTTTATC TGACAGCAGA CGTGCACTGG CCAGGGGGAT CACCATCCGT CGCCCGGGCG
     TCTGAAATAG ACTGTCGTCT GCACGTGACC GGTCCCCCTA GTGGTAGGCA GCGGGCCCGC
 601 TGTCAATAAT ATCACTCTGT ACATCCACAA ACAGACGATA ACGGCTCTCT CTTTTATAGG
     ACAGTTATTA TAGTGAGACA TGTAGGTGTT TGTCTGCTAT TGCCGAGAGA GAAAATATCC
 661 TGTAAACCTT AAACTGCATT TCACCAGTCC CTGTTCTCGT CAGCAAAAGA GCCGTTCATT
     ACATTTGGAA TTTGACGTAA AGTGGTCAGG GACAAGAGCA GTCGTTTTCT CGGCAAGTAA
 721 TCAATAAACC GGGCGACCTC AGCCATCCCT TCCTGATTTT CCGCTTTCCA GCGTTCGGCA
     AGTTATTTGG CCCGCTGGAG TCGGTAGGGA AGGACTAAAA GGCGAAAGGT CGCAAGCCGT
 781 CGCAGACGAC GGGCTTCATT CTGCATGGTT GTGCTTACCA GACCGGAGAT ATTGACATCA
     GCGTCTGCTG CCCGAAGTAA GACGTACCAA CACGAATGGT CTGGCCTCTA TAACTGTAGT
 841 TATATGCCTT GAGCAACTGA TAGCTGTCGC TGTCAATACT CACTGTAATA CGCTGCTTCA
     ATATACGGAA CTCGTTGACT ATCGACAGCG ACAGTTGACA GTGACATTAT GCGACGAAGT
 901 TAGCACACCT CTTTTTGACA TACTTCGGGT ATACGCTAGC ACCGGTGTTG CAACGAACAG
     ATCGTGTGGA GAAAAACTGT ATGAAGCCCA TATGCGATCG TGGCCACAAC GTTGCTTGTC
 961 GTCACTATCA GTCAAAATAA AATCATTATT TGCCATCCAG CTGATATCCC CTATAGTGAG
     CAGTGATAGT CAGTTTTATT TTAGTAATAA ACGGTAGGTC GACTATAGGG GATATCACTC
1021 TCGTATTACA TGGTCATAGC TGTTTCCTGG CAGCTCTGGC CCGTGTCTCA AAATCTCTGA
     AGCATAATGT ACCAGTATCG ACAAAGGACC GTCGAGACCG GGCACAGAGT TTTAGAGACT
1081 TGTTACATTG CACAAGATAA AATAATATCA TCATGATCAG TCCTGCTCCT CGGCCACGAA
     ACAATGTAAC GTGTTCTATT TTATTATAGT AGTACTAGTC AGGACGAGGA GCCGGTGCTT
1141 GTGCACGCAG TTGCCGGCCG GGTCGCGCAG GGCGAACTCC CGCCCCCACG GCTGCTCGCC
     CACGTGCGTC AACGGCCGGC CCAGCGCGTC CCGCTTGAGG GCGGGGGTGC CGACGAGCGG
1201 GATCTCGGTC ATGGCCGGCC GGAGGCGTC CCGGAAGTTC GTGGACACGA CCTCCGACCA
     CTAGAGCCAG TACCGGCCGG GCCTCCGCAG GGCCTTCAAG CACCTGTGCT GGAGGCTGGT
1261 CTCGGCGTAC AGCTCGTCCA GGCCGCGCAC CCACACCCAG GCCAGGGTGT TGTCCGGCAC
     GAGCCGCATG TCGAGCAGGT CCGGCGCGTG GGTGTGGGTC CGGTCCCACA ACAGGCCGTG
1321 CACCTGGTCC TGGACCGCGC TGATGAACAG GGTCACGTCG TCCCGGACCA CACCGGCGAA
     GTGGACCAGG ACCTGGCGCG ACTACTTGTC CCAGTGCAGC AGGGCCTGGT GTGGCCGCTT
                  XmaI
                  ~~~~~~
                  SmaI
                  ~~~~~~
1381 GTCGTCCTCC ACGAAGTCCC GGGAGAACCC GAGCCGGTCG GTCCAGAACT CGACCGCTCC
     CAGCAGGAGG TGCTTCAGGG CCCTCTTGGG CTCGGCCAGC CAGGTCTTGA GCTGGCGAGG
                                                              NcoI
                                                              ~~~~~~
1441 GGCGACGTCG CGCGCGGTGA GCACCGGAAC GGCACTGGTC AACTTGGCCA TGGTTTAGTT
     CCGCTGCAGC GCGCGCCACT CGTGGCCTTG CCGTGACCAG TTGAACCGGT ACCAAATCAA
1501 CCTCACCTTG TCGTATTATA CTATGCCGAT ATACTATGCC GATGATTAAT TGTCAACACG
     GGAGTGGAAC AGCATAATAT GATACGGCTA TATGATACGG CTACTAATTA ACAGTTGTGC
1561 TGCTGATCAT GACCAAAATC CCTTAACGTG GCGGCCGCCA TAGTGACTGG ATATGTTGTG
     ACGACTAGTA CTGGTTTTAG GGAATTGCAC CGCCGGCGGT ATCACTGACC TATACAACAC
```

Fig. 42₁

```
                                                                           EcoRI
                                                                           ~~~~~
                                        SacI              BamHI
                                        ~~~~~~~           ~
1681   TATCATTTTA CGTTTCTCGT TCAGCTTTTT TGTACAAACT TGTGATCGAG CTCGAATTCG
       ATAGTAAAAT GCAAAGAGCA AGTCGAAAAA ACATGTTTGA ACACTAGCTC GAGCTTAAGC
       BamHI                 NcoI
       ~~~~~                 ~~~~~~
1741   GATCCGAATT AATTCCGATA TCCATGGCCA TCGCCGGCTG GGCAGCGAGG AGCAGCAGAC
       CTAGGCTTAA TTAAGGCTAT AGGTACCGGT AGCGGCCGAC CCGTCGCTCC TCGTCGTCTG
1801   CAGCAGCAGC GGTCGGCAGC AGGTATTTCA TATGTATATC TCCTTCTTAA AGTTAAACAA
       GTCGTCGTCG CCAGCCGTCG TCCATAAAGT ATACATATAG AGGAAGAATT TCAATTTGTT
1861   AATTATTTCT AGAGGGGAAT TGTTATCCGC TCACAATTCC CCTATAGTGA GTCGTATTAA
       TTAATAAAGA TCTCCCCTTA ACAATAGGCG AGTGTTAAGG GGATATCACT CAGCATAATT
1921   TTTCGCGGGA TCGAGATCTC GATCCTCTAC GCCGGACGCA TCGTGGCCGG CATCACCGGC
       AAAGCGCCCT AGCTCTAGAG CTAGGAGATG CGGCCTGCGT AGCACCGGCC GTAGTGGCCG
1981   GCCACAGGTG CGGTTGCTGG CGCCTATATC GCCGACATCA CCGATGGGGA AGATCGGGCT
       CGGTGTCCAC GCCAACGACC GCGGATATAG CGGCTGTAGT GGCTACCCCT TCTAGCCCGA
2041   CGCCACTTCG GGCTCATGAG CGCTTGTTTC GGCGTGGGTA TGGTGGCAGG CCCCGTGGCC
       GCGGTGAAGC CCGAGTACTC GCGAACAAAG CCGCACCCAT ACCACCGTCC GGGGCACCGG
2101   GGGGGACTGT TGGGCGCCAT CTCCTTGCAT GCACCATTCC TTGCGGCGGC GGTGCTCAAC
       CCCCCTGACA ACCCGCGGTA GAGGAACGTA CGTGGTAAGG AACGCCGCCG CCACGAGTTG
                                     EcoNI
                                     ~~~~~~~~~~~~~
2161   GGCCTCAACC TACTACTGGG CTGCTTCCTA ATGCAGGAGT CGCATAAGGG AGAGCGTCGA
       CCGGAGTTGG ATGATGACCC GACGAAGGAT TACGTCCTCA GCGTATTCCC TCTCGCAGCT
2221   GATCCCGGAC ACCATCGAAT GGCGCAAAAC CTTTCGCGGT ATGGCATGAT AGCGCCCGGA
       CTAGGGCCTG TGGTAGCTTA CCGCGTTTTG GAAAGCGCCA TACCGTACTA TCGCGGGCCT
2281   AGAGACGAGA TTCAGGGTGG TGAATGTGAA ACCAGTAACG TTATACGATG TCGCAGAGTA
       TCTCTCAGTT AAGTCCCACC ACTTACACTT TGGTCATTGC AATATGCTAC AGCGTCTCAT
2341   TGCCGGTGTC TCTTATCAGA CCGTTTCCCG CGTGGTGAAC CAGGCCAGCC ACGTTTCTGC
       ACGGCCACAG AGAATAGTCT GGCAAAGGGC GCACCACTTG GTCCGGTCGG TGCAAAGACG
2401   GAAAACGCGG GAAAAAGTGG AAGCGGCGAT GGCGGAGCTG AATTACATTC CCAACCGCGT
       CTTTTGCGCC CTTTTTCACC TTCGCCGCTA CCGCCGCTAC TTAATGTAAG GGTTGGCGCA
2461   GGCACAACAA CTGGCGGGCA AACAGTCGTT GCTGATTGGC GTTGCCACCT CCAGTCTGGC
       CCGTGTTGTT GACCGCCCGT TTGTCAGCAA CGACTAACCG CAACGGTGGA GGTCAGACCG
2521   CCTGCACGCG CCGTCGCAAA TTGTCGCGGC GATTAAATCT CGCGCCGATC AACTGGGTGC
       GGACGTGCGC GGCAGCGTTT AACAGCGCCG CTAATTTAGA GCGCGGCTAG TTGACCCACG
2581   CAGCGTGGTG GTGTCGATGG TAGAACGAAG CGGCGTCGAA GCCTGTAAAG CGGCGGTGCA
       GTCGCACCAC CACAGCTACC ATCTTGCTTC GCCGCAGCTT CGGACATTTC GCCGCCACGT
2641   CAATCTTCTC GCGCAACGCG TCAGTGGGCT GATCATTAAC TATCCGCTGG ATGACCAGGA
       GTTAGAAGAG CGCGTTGCGC AGTCACCCGA CTAGTAATTG ATAGGCGACC TACTGGTCCT
2701   TGCCATTGCT GTGGAAGCTG CCTGCACTAA TGTTCCGGCG TTATTTCTTG ATGTCTCTGA
       ACGGTAACGA CACCTTCGAC GGACGTGATT ACAAGGCCGC AATAAAGAAC TACAGAGACT
2761   CCAGACACCC ATCAACAGTA TTATTTTCTC CCATGAAGAC GGTACGCGAC TGGGCGTGGA
       GGTCTGTGGG TAGTTGTCAT AATAAAAGAG GGTACTTCTG CCATGCGCTG ACCCGCACCT
2821   GCATCTGGTC GCATTGGGTC ACCAGCAAAT CGCGCTGTTA GCGGGCCCAT TAAGTTCTGT
       CGTAGACCAG CGTAACCCAG TGGTCGTTTA GCGCGACAAT CGCCCGGGTA ATTCAAGACA
2881   CTCGGCGCGT CTGCGTCTGG CTGGCTGGCA TAAATATCTC ACTCGCAATC AAATTCAGCC
       GAGCCGCGCA GACGCAGACC GACCGACCGT ATTTATAGAG TGAGCGTTAG TTTAAGTCGG
2941   GATAGCGGAA CGGGAAGGCG ACTGGAGTGC CATGTCCGGT TTTCAACAAA CCATGCAAAT
       CTATCGCCTT GCCCTTCCGC TGACCTCACG GTACAGGCCA AAAGTTGTTT GGTACGTTTA
3001   GCTGAATGAG GGCATCGTTC CCACTGCGAT GCTGGTTGCC AACGATCAGA TGGCGCTGGG
       CGACTTACTC CCGTAGCAAG GGTGACGCTA CGACCAACGG TTGCTAGTCT ACCGCGACCC
3061   CGCAATGCGC GCCATTACCG AGTCCGGGCT GCGCGTTGGT GCGGATATCT CGGTAGTGGG
       GCGTTACGCG CGGTAATGGC TCAGGCCCGA CGCGCAACCA CGCCTATAGA GCCATCACCC
3121   ATACGACGAT ACCGAAGACA GCTCATGTTA TATCCCGCCG TTAACCACCA TCAAACAGGA
       TATGCTGCTA TGGCTTCTGT CGAGTACAAT ATAGGGCGGC AATTGGTGGT AGTTTGTCCT
3181   TTTTCGCCTG CTGGGGCAAA CCAGCGTGGA CCGCTTGCTG CAACTCTCTC AGGGCCAGGC
       AAAAGCGGAC GACCCCGTTT GGTCGCACCT GGCGAACGAC GTTGAGAGAG TCCCGGTCCG
3241   GGTGAGGGC AATCAGCTGT TGCCCGTCTC ACTGGTGAAA AGAAAAACCA CCCTGGCGCC
       CCACTTCCCG TTAGTCGACA ACGGGCAGAG TGACCACTTT TCTTTTTGGT GGGACCGCGG
3301   CAATACGCAA ACCGCCTCTC CCCGCGCGTT GGCCGATTCA TTAATGCAGC TGGCACGACA
       GTTATGCGTT TGGCGGAGAG GGGCGCGCAA CCGGCTAAGT AATTACGTCG ACCGTGCTGT
3361   GGTTTCCCGA CTGGAAAGCG GGCAGTGAGC GCAACGCAAT TAATGTAAGT TAGCTCACTC
       CCAAAGGGCT GACCTTTCGC CCGTCACTCG CGTTGCGTTA ATTACATTCA ATCGAGTGAG
3421   ATTAGGCACC GGGATCTCGA CCGATGCCCT TGAGAGCCTT CAACCCAGTC AGCTCCTTCC
```

Fig. 42₂

```
              TAATCCGTGG CCCTAGAGCT GGCTACGGGA ACTCTCGGAA GTTGGGTCAG TCGAGGAAGG
      3481    GGTGGGCGCG GGGCATGACT ATCGTCGCCG CACTTATGAC TGTCTTCTTT ATCATGCAAC
              CCACCCGCGC CCCGTACTGA TAGCAGCGGC GTGAATACTG ACAGAAGAAA TAGTACGTTG
      3541    TCGTAGGACA GGTGCCGGCA GCGCTCTGGG TCATTTTCGG CGAGGACCGC TTTCGCTGGA
              AGCATCCTGT CCACGGCCGT CGCGAGACCC AGTAAAAGCC GCTCCTGGCG AAAGCGACCT
      3601    GCGCGACGAT GATCGGCCTG TCGCTTGCGG TATTCGGAAT CTTGCACGCC CTCGCTCAAG
              CGCGCTGCTA CTAGCCGGAC AGCGAACGCC ATAAGCCTTA GAACGTGCGG GAGCGAGTTC
      3661    CCTTCGTCAC TGGTCCCGCC ACCAAACGTT TCGGCGAGAA GCAGGCCATT ATCGCCGGCA
              GGAAGCAGTG ACCAGGGCGG TGGTTTGCAA AGCCGCTCTT CGTCGGTAA TAGCGGCCGT
      3721    TGGCGGCCCC ACGGGTGCGC ATGATCGTGC TCCTGTCGTT GAGGACCCGG CTAGGCTGGC
              ACCGCCGGGG TGCCCACGCG TACTAGCACG AGGACAGCAA CTCCTGGGCC GATCCGACCG
      3781    GGGGTTGCCT TACTGGTTAG CAGAATGAAT CACCGATACG CGAGCGAACG TGAAGCGACT
              CCCCAACGGA ATGACCAATC GTCTTACTTA GTGGCTATGC GCTCGCTTGC ACTTCGCTGA
      3841    GCTGCTGCAA AACGTCTGCG ACCTGAGCAA CAACATGAAT GGTCTTCGGT TTCCGTGTTT
              CGACGACGTT TTGCAGACGC TGGACTCGTT GTTGTACTTA CCAGAAGCCA AAGGCACAAA
      3901    CGTAAAGTCT GGAAACGCGG AAGTCAGCGC CCTGCACCAT TATGTTCCGG ATCTGCATCG
              GCATTTCAGA CCTTTGCGCC TTCAGTCGCG GGACGTGGTA ATACAAGGCC TAGACGTAGC
      3961    CAGGATGCTG CTGGCTACCC TGTGGAACAC CTACATCTGT ATTAACGAAG CGCTGGCATT
              GTCCTACGAC GACCGATGGG ACACCTTGTG GATGTAGACA TAATTGCTTC GCGACCGTAA
      4021    GACCCTGAGT GATTTTTCTC TGGTCCCGCC GCATCCATAC CGCCAGTTGT TTACCCTCAC
              CTGGGACTCA CTAAAAAGAG ACCAGGGCGG CGTAGGTATG GCGGTCAACA AATGGGAGTG
      4081    AACGTTCCAG TAACCGGGCA TGTTCATCAT CAGTAACCCG TATCGTGAGC ATCCTCTCTC
              TTGCAAGGTC ATTGGCCCGT ACAAGTAGTA GTCATTGGGC ATAGCACTCG TAGGAGAGAG
      4141    GTTTCATCGG TATCATTACC CCCATGAACA GAAATCCCCC TTACACGGAG GCATCAGTGA
              CAAAGTAGCC ATAGTAATGG GGGTACTTGT CTTTAGGGGG AATGTGCCTC CGTAGTCACT
      4201    CCAAACAGGA AAAAACCGCC CTTAACATGG CCCGCTTTAT CAGAAGCCAG ACATTAACGC
              GGTTTGTCCT TTTTTGGCGG GAATTGTACC GGGCGAAATA GTCTTCGGTC TGTAATTGCG
      4261    TTCTGGAGAA ACTCAACGGC CTGGACGCGG ATGAACAGGC AGACATCTGT GAATCGCTTC
              AAGACCTCTT TGAGTTGCTC GACCTGCGCC TACTTGTCCG TCTGTAGACA CTTAGCGAAG
      4321    ACGACCACGC TGATGAGCTT TACCGCAGCT GCCTCGCGCG TTTCGGTGAT GACGGTGAAA
              TGCTGGTGCG ACTACTCGAA ATGGCGTCGA CGGAGCGCGC AAAGCCACTA CTGCCACTTT
      4381    ACCTCTGACA CATGCAGCTC CCGGAGACGG TCACAGCTTG TCTGTAAGCG GATGCCGGGA
              TGGAGACTGT GTACGTCGAG GGCCTCTGCC AGTGTCGAAC AGACATTCGC CTACGGCCCT
      4441    GCAGACAAGC CCGTCAGGGC GCGTCAGCGG GTGTTGGCGG GTGTCGGGGC GCAGCCATGA
              CGTCTGTTCG GGCAGTCCCG CGCAGTCGCC CACAACCGCC CACAGCCCCG CGTCGGTACT
      4501    CCCAGTCACG TAGCGATAGC GGAGTGTATA CTGGCTTAAC TATGCGGCAT CAGAGCAGAT
              GGGTCAGTGC ATCGCTATCG CCTCACATAT GACCGAATTG ATACGCCGTA GTCTCGTCTA
      4561    TGTACTGAGA GTGCACCATA TATGCGGTGT GAAATACCGC ACAGATGCGT AAGGAGAAAA
              ACATGCTCT CACGTGGTAT ATACGCCACA CTTTATGGCG TGTCTACGCA TTCCTCTTTT
      4621    TACCGCATCA GGCGCTCTTC CGCTTCCTCG CTCACTGACT CGCTGCGCTC GGTCGTTCGG
              ATGGCGTAGT CCGCGAGAAG GCGAAGGAGC GAGTGACTGA GCGACGCGAG CCAGCAAGCC
      4681    CTGCGGCGAG CGGTATCAGC TCACTCAAAG GCGGTAATAC GGTTATCCAC AGAATCAGGG
              GACGCCGCTC GCCATAGTCG AGTGAGTTTC CGCCATTATG CCAATAGGTG TCTTAGTCCC
      4741    GATAACGCAG GAAAGAACAT GTGAGCAAAA GGCCAGCAAA AGGCCAGGAA CCGTAAAAAG
              CTATTGCGTC CTTTCTTGTA CACTCGTTTT CCGGTCGTTT TCCGGTCCTT GGCATTTTTC
      4801    GCCGCGTTGC TGGCGTTTTT CCATAGGCTC CGCCCCCCTG ACGAGCATCA CAAAAATCGA
              CGGCGCAACG ACCGCAAAAA GGTATCCGAG GCGGGGGGAC TGCTCGTAGT GTTTTTAGCT
      4861    CGCTCAAGTC AGAGGTGGCG AAACCCGACA GGACTATAAA GATACCAGGC GTTTCCCCCT
              GCGAGTTCAG TCTCCACCGC TTTGGGCTGT CCTGATATTT CTATGGTCCG CAAAGGGGGA
      4921    GGAAGCTCCC TCGTGCGCTC TCCTGTTCCG ACCCTGCCGC TTACCGGATA CCTGTCCGCC
              CCTTCGAGGG AGCACGCGAG AGGACAAGGC TGGGACGGCG AATGGCCTAT GGACAGGCGG
      4981    TTTCTCCCTT CGGGAAGCGT GGCGCTTTCT CATAGCTCAC GCTGTAGGTA TCTCAGTTCG
              AAAGAGGGAA GCCCTTCGCA CCGCGAAAGA GTATCGAGTG CGACATCCAT AGAGTCAAGC
      5041    GTGTAGGTCG TTCGCTCCAA GCTGGGCTGT GTGCACGAAC CCCCCGTTCA GCCCGACCGC
              CACATCCAGC AAGCGAGGTT CGACCCGACA CACGTGCTTG GGGGGCAAGT CGGGCTGGCG
      5101    TGCGCCTTAT CCGGTAACTA TCGTCTTGAG TCCAACCCGG TAAGACACGA CTTATCGCCA
              ACGCGGAATA GGCCATTGAT AGCAGAACTA AGGTTGGGCC ATTCTGTGCT GAATAGCGGT
      5161    CTGGCAGCAG CCACTGGTAA CAGGATTAGC AGAGCGAGGT ATGTAGGCGG TGCTACAGAG
              GACCGTCGTC GGTGACCATT GTCCTAATCG TCTCGCTCCA TACATCCGCC ACGATGTCTC
      5221    TTCTTGAAGT GGTGGCCTAA CTACGGCTAC ACTAGAAGGA CAGTATTTGG TATCTGCGCT
              AAGAACTTCA CCACCGGATT GATGCCGATG TGATCTTCCT GTCATAAACC ATAGACGCGA
      5281    CTGCTGAAGC CAGTTACCTT CGGAAAAAGA GTTGGTAGCT CTTGATCCGG CAAACAAACC
              GACGACTTCG GTCAATGGAA GCCTTTTTCT CAACCATCGA GAACTAGGCC GTTTGTTTGG
      5341    ACCGCTGGTA GCGGTGGTTT TTTTGTTTGC AAGCAGCAGA TTACGCGCAG AAAAAAAGGA
              TGGCGACCAT CGCCACCAAA AAAACAAACG TTCGTCGTCT AATGCGCGTC TTTTTTTCCT
      5401    TCTCAAGAAG ATCCTTTGAT CTTTTCTACG GGGTCTGACG CTCAGTGGAA CGAAAACTCA
              AGAGTTCTTC TAGGAAACTA GAAAAGATGC CCCAGACTGC GAGTCACCTT GCTTTTGAGT
      5461    CGTTAAGGGA TTTTGGTCAT GAACAATAAA ACTGTCTGCT TACATAAACA GTAATACAAG
              GCAATTCCCT AAAACCAGTA CTTGTTATTT TGACAGACGA ATGTATTTGT CATTATGTTC
```

Fig. 42₃

```
5521 GGGTGTTATG AGCCATATTC AACGGGAAAC GTCTTGCTCT AGGCCGCGAT TAAATTCCAA
     CCCACAATAC TCGGTATAAG TTGCCCTTTG CAGAACGAGA TCCGGCGCTA ATTTAAGGTT
5581 CATGGATGCT GATTTATATG GGTATAAATG GGCTCGCGAT AATGTCGGGC AATCAGGTGC
     GTACCTACGA CTAAATATAC CCATATTTAC CCGAGCGCTA TTACAGCCCG TTAGTCCACG
             ClaI
             ~~~~~~
5641 GACAATCTAT CGATTGTATG GGAAGCCCGA TGCGCCAGAG TTGTTTCTGA AACATGGCAA
     CTGTTAGATA GCTAACATAC CCTTCGGGCT ACGCGGTCTC AACAAAGACT TTGTACCGTT
5701 AGGTAGCGTT GCCAATGATG TTACAGATGA GATGGTCAGA CTAAACTGGC TGACGGAATT
     TCCATCGCAA CGGTTACTAC AATGTCTACT CTACCAGTCT GATTTGACCG ACTGCCTTAA
5761 TATGCCTCTT CCGACCATCA AGCATTTTAT CCGTACTCCT GATGATGCAT GGTTACTCAC
     ATACGGAGAA GGCTGGTAGT TCGTAAAATA GGCATGAGGA CTACTACGTA CCAATGAGTG
             XmaI
             ~~~~~~
             SmaI                                              EcoNI
             ~~~~~~                                            ~~~~~~~~~~~~
5821 CACTGCGATC CCCGGGAAAA CAGCATTCCA GGTATTAGAA GAATATCCTG ATTCAGGTGA
     GTGACGCTAG GGGCCCTTTT GTCGTAAGGT CCATAATCTT CTTATAGGAC TAAGTCCACT
5881 AAATATTGTT GATGCGCTGG CAGTGTTCCT GCGCCGGTTG CATTCGATTC CTGTTTGTAA
     TTTATAACAA CTACGCGACC GTCACAAGGA CGCGGCCAAC GTAAGCTAAG GACAAACATT
5941 TTGTCCTTTT AACAGCGATC GCGTATTTCG TCTCGCTCAG GCGCAATCAC GAATGAATAA
     AACAGGAAAA TTGTCGCTAG CGCATAAAGC AGAGCGAGTC CGCGTTAGTG CTTACTTATT
6001 CGGTTTGGTT GATGCGAGTG ATTTTGATGA CGAGCGTAAT GGCTGGCCTG TTGAACAAGT
     GCCAAACCAA CTACGCTCAC TAAAACTACT GCTCGCATTA CCGACCGGAC AACTTGTTCA
6061 CTGGAAAGAA ATGCATAAAC TTTTGCCATT CTCACCGGAT TCAGTCGTCA CTCATGGTGA
     GACCTTTCTT TACGTATTTG AAAACGGTAA GAGTGGCCTA AGTCAGCAGT GAGTACCACT
6121 TTTCTCACTT GATAACCTTA TTTTTGACGA GGGGAAATTA ATAGGTTGTA TTGATGTTGG
     AAAGAGTGAA CTATTGGAAT AAAAACTGCT CCCCTTTAAT TATCCAACAT AACTACAACC
6181 ACGAGTCGGA ATCGCAGACC GATACCAGGA TCTTGCCATC CTATGGAACT GCCTCGGTGA
     TGCTCAGCCT TAGCGTCTGG CTATGGTCCT AGAACGGTAG GATACCTTGA CGGAGCCACT
6241 GTTTTCTCCT TCATTACAGA AACGGCTTTT TCAAAAATAT GGTATTGATA ATCCTGATAT
     CAAAAGAGGA AGTAATGTCT TTGCCGAAAA AGTTTTTATA CCATAACTAT TAGGACTATA
6301 GAATAAATTG CAGTTTCATT TGATGCTCGA TGAGTTTTTC TAAGAATTAA TTCATGAGCG
     CTTATTTAAC GTCAAAGTAA ACTACGAGCT ACTCAAAAAG ATTCTTAATT AAGTACTCGC
6361 GATACATATT TGAATGTATT TAGAAAAATA AACAAATAGG GGTTCCGCGC ACATTTCCCC
     CTATGTATAA ACTTACATAA ATCTTTTTAT TTGTTTATCC CCAAGGCGCG TGTAAAGGGG
6421 GAAAAGTGCC ACCTGAAATT GTAACGTTA ATATTTTGTT AAAATTCGCG TTAAATTTTT
     CTTTTCACGG TGGACTTTAA CATTTGCAAT TATAAAACAA TTTTAAGCGC AATTTAAAAA
6481 GTTAAATCAG CTCATTTTTT AACCAATAGG CCGAAATCGG CAAAATCCCT TATAAATCAA
     CAATTTAGTC GAGTAAAAAA TTGGTTATCC GGCTTTAGCC GTTTTAGGGA ATATTTAGTT
6541 AAGAATAGAC CGAGATAGGG TTGAGTGTTG TTCCAGTTTG GAACAAGAGT CCACTATTAA
     TTCTTATCTG GCTCTATCCC AACTCACAAC AAGGTCAAAC CTTGTTCTCA GGTGATAATT
6601 AGAACGTGGA CTCCAACGTC AAAGGGCGAA AAACCGTCTA TCAGGGCGAT GGCCCACTAC
     TCTTGCACCT GAGGTTGCAG TTTCCCGCTT TTTGGCAGAT AGTCCCGCTA CCGGGTGATG
6661 GTGAACCATC ACCCTAATCA AGTTTTTTGG GGTCGAGGTG CCGTAAAGCA CTAAATCGGA
     CACTTGGTAG TGGGATTAGT TCAAAAAACC CCAGCTCCAC GGCATTTCGT GATTTAGCCT
6721 ACCCTAAAGG GAGCCCCCGA TTTAGAGCTT GACGGGGAAA GCCGGCGAAC GTGGCGAGAA
     TGGGATTTCC CTCGGGGGCT AAATCTCGAA CTGCCCCTTT CGGCCGCTTG CACCGCTCTT
6781 AGGAAGGGAA GAAAGCGAAA GGAGCGGGCG CTAGGGCGCT GGCAAGTGTA GCGGTCACGC
     TCCTTCCCTT CTTTCGCTTT CCTCGCCCGC GATCCCGCGA CCGTTCACAT CGCCAGTGCG
6841 TGCGCGTAAC CACCACACCC GCCGCGCTTA ATGCGCCGCT ACAGGGCGCG TCCCATTCGC
     ACGCGCATTG GTGGTGTGGG CGGCGCGAAT TACGCGGCGA TGTCCCGCGC AGGGTAAGCG
6901 CA
     GT
```

```
        EcoNI
     ~~~~~~~~~~~
   1 CCTGCATTAG GAAGCAGCCC AGTAGTAGGT TGAGGCCGTT GAGCACCGCC GCCGCAAGGA
     GGACGTAATC CTTCGTCGGG TCATCATCCA ACTCCGGCAA CTCGTGGCGG CGGCGTTCCT
  61 ATGGTGCATG CAAGGAGATG GCGCCCAACA GTCCCCCGGC CACGGGGCCT GCCACCATAC
     TACCACGTAC GTTCCTCTAC CGCGGGTTGT CAGGGGGCCG GTGCCCCGGA CGGTGGTATG
 121 CCACGCCGAA ACAAGCGCTC ATGACCCGA AGTGGCGAGC CCGATCTTCC CCATCGGTGA
     GGTGCGGCTT TGTTCGCGAG TACTCGGGCT TCACCGCTCG GGCTAGAAGG GGTAGCCACT
 181 TGTCGGCGAT ATAGGCGCCA GCAACCGCAC CTGTGGCGCC GGTGATGCCG GCCACGATGC
     ACAGCCGCTA TATCCGCGGT CGTTGGCGTG GACACCGCGG CCACTACGGC CGGTGCTACG
 241 GTCCGGCGTA GAGGATCGAG ATCTCGATCC CGCGAAATTA ATACGACTCA CTATAGGGA
     CAGGCCGCAT CTCCTAGCTC TAGAGCTAGG GCGCTTTAAT TATGCTGAGT GATATCCCCT
 301 ATTGTGAGCG GATAACAATT CCCCTCTAGA AATAATTTTG TTTAACTTTA AGAAGGAGAT
     TAACACTCGC CTATTGTTAA GGGGAGATCT TTATTAAAAC AAATTGAAAT TCTTCCTCTA
 361 ATACATATGA AATACCTGCT GCCGACCGCT GCTGCTGGTC TGCTGCTCCT CGCTGCCCAG
     TATGTATACT TTATGGACGA CGGCTGGCGA CGACGACCAG ACGACGAGGA GCGACGGGTC
                                                     EcoRI
                                                    ~~~~~~~
          NcoI                    BamHI     SacI
        ~~~~~~                   ~~~~~~    ~~~~~~~
 421 CCGGCGATGG CCATGGATAT CGGAATTAAT TCGGATCCGA ATTCGAGCTC GATCACAAGT
     GGCCGCTACC GGTACCTATA GCCTTAATTA AGCCTAGGCT TAAGCTCGAG CTAGTGTTCA
 481 TTGTACAAAA AAGCTGAACG AGAAACGTAA AATGATATAA ATATCAATAT ATTAAATTAG
     AACATGTTTT TTCGACTTGC TCTTTGCATT TTACTATATT TATAGTTATA TAATTTAATC
 541 ATTTTGCATA AAAAACAGAC TACATAATCC TGTAAAACAC AACATATCCA GTCACTATGG
     TAAAACGTAT TTTTTGTCTG ATGTATTATG ACATTTTGTG TTGTATAGGT CAGTGATACC
 601 CGGCCGCCAC GTTAAGGGAT TTTGGTCATG ATCAGCACGT GTTGACAATT AATCATCGGC
     GCCGGCGGTG CAATTCCCTA AAACCAGTAC TAGTCGTGCA CAACTGTTAA TTAGTAGCCG
                                                                    NcoI
                                                                   ~~~~~~~
 661 ATAGTATATC GGCATAGTAT AATACGACAA GGTGAGGAAC TAAACCATGG CCAAGTTGAC
     TATCATATAG CCGTATCATA TTATGCTGTT CCACTCCTTG ATTTGGTACC GGTTCAACTG
 721 CAGTGCCGTT CCGGTGCTCA CCGCGCGCGA CGTCGCCGGA GCGGTCGAGT TCTGGACCGA
     GTCACGGCAA GGCCACGAGT GGCGCGCGCT GCAGCGGCCT CGCCAGCTCA AGACCTGGCT
 781 CCGGCTCGGG TTCTCCCGGG ACTTCGTGGA GGACGACTTC GCCGGTGTGG TCCGGGACGA
     GGCCGAGCCC AAGAGGGCCC TGAAGCACCT CCTGCTGAAG CGGCCACACC AGGCCCTGCT
 841 CGTGACCCTG TTCATCAGCG CGGTCCAGGA CCAGGTGGTG CCGGACAACA CCCTGGCCTG
     GCACTGGGAC AAGTAGTCGC GCCAGGTCCT GGTCCACCAC GGCCTGTTGT GGGACCGGAC
 901 GGTGTGGGTG CGCGGCCTGG ACGAGCTGTA CGCCGAGTGG TCGGAGGTCG TGTCCACGAA
     CCACACCCAC GCGCCGGACC TGCTCGACAT GCGGCTCACC AGCCTCCAGC ACAGGTGCTT
 961 CTTCCGGGAC GCCTCCGGGC CGGCCATGAC CGAGATCGGC GAGCAGCCGT GGGGGCGGGA
     GAAGGCCCTG CGGAGGCCCG GCCGGTACTG GCTCTAGCCG CTCGTCGGCA CCCCCGCCCT
1021 GTTCGCCCTG CGCGACCCGG CCGGCAACTG CGTGCACTTC GTGGCCGAGG AGCAGGACTG
     CAAGCGGGAC GCGCTGGGCC GGCCGTTGAC GCACGTGAAG CACCGGCTCC TCGTCCTGAC
1081 ATCATGATGA TATTATTTTA TCTTGTGCAA TGTAACATCA GAGATTTTGA GACACGGGCC
     TAGTACTACT ATAATAAAAT AGAACACGTT ACATTGTAGT CTCTAAAACT CTGTGCCCGG
1141 AGAGCTGCCA GGAAACAGCT ATGACCATGT AATACGACTC ACTATAGGGG ATATCAGCTG
     TCTCGACGGT CCTTTGTCGA TACTGGTACA TTATGCTGAG TGATATCCCC TATAGTCGAC
1201 GATGGCAAAT AATGATTTTA TTTTGACTGA TAGTGACCTG TTCGTTGCAA CACCGGTGCT
     CTACCGTTTA TTACTAAAAT AAAACTGACT ATCACTGGAC AAGCAACGTT GTGGCCACGA
1261 AGCGTATACC CGAAGTATGT CAAAAAGAGG TGTGCTATGA AGCAGCGTAT TACAGTGACA
     TCGCATATGG GCTTCATACA GTTTTTCTCC ACACGATACT TCGTCGCATA ATGTCACTGT
1321 GTTGACACGA ACACGTATCA GTTGCTCAAG GCATATATGA TGTCAATATC TCCGGTCTGG
     CAACTGTGCT TGTGCATAGT CAACGAGTTC CGTATATACT ACAGTTATAG AGGCCAGACC
1381 TAAGCACAAC CATGCAGAAT GAAGCCCGTC GTCTGCGTGC CGAACGCTGG AAAGCGGAAA
     ATTCGTGTTG GTACGTCTTA CTTCGGGCAG CAGACGCACG GCTTGCGACC TTTCGCCTTT
1441 ATCAGGAAGG GATGGCTGAG GTCGCCCGGT TTATTGAAAT GAACGGCTCT TTTGCTGACG
     TAGTCCTTCC CTACCGACTC CAGCGGGCCA AATAACTTTA CTTGCCGAGA AAACGACTGC
1501 AGAACGGGA CTGGTGAAAT GCAGTTTAAG GTTTACACCT ATAAAAGAGA GAGCCGTTAT
     TCTTGTCCCT GACCACTTTA CGTCAAATTC CAAATGTGGA TATTTTCTCT CTCGGCAATA
1561 CGTCTGTTTG TGGATGTACA GAGTGATATT ATTGACACGC CCGGGCGACG GATGGTGATC
     GCAGACAAAC ACCTACATGT CTCACTATAA TAACTGTGCG GGCCCGCTGC CTACCACTAG
1621 CCCCTGGCCA GTGCACGTCT GCTGTCAGAT AAAGTCTCCC GTGAACTTTA CCCGGTGGTG
     GGGGACCGGT CACGTGCAGA CGACAGTCTA TTTCAGAGGG CACTTGAAAT GGGCCACCAC
1681 CATATCGGGG ATGAAAGCTG GCGCATGATG ACCACCGATA TGGCCATGTC GCCGGTCTCC
     GTATAGCCCC TACTTTCGAC CGCGTACTAC TGGTGGCTAT ACCGGTCACA CGGCCAGAGG
1741 GTTATCGGGG AAGAAGTGGC TGATCTCAGC CGCCGCGAAA ATGACATCAA AAACGCCATT
     CAATAGCCCC TTCTTCACCG ACTAGAGTCG GCGGCGCTTT TACTGTAGTT TTTGCGGTAA
```

Fig. 44₁

```
                                                                  PstI
                                                                  ~~~~~~
1801 AACCTGATGT TCTGGGGAAT ATAAATGTCA GGCTCCCTTA TACACAGCCA GTCTGCAGGT
     TTGGACTACA AGACCCCTTA TATTTACAGT CCGAGGGAAT ATGTGTCGGT CAGACGTCCA
1861 CGACCATAGT GACTGGATAT GTTGTGTTTT ACAGTATTAT GTAGTCTGTT TTTTATGCAA
     GCTGGTATCA CTGACCTATA CAACACAAAA TGTCATAATA CATCAGACAA AAAATACGTT
1921 AATCTAATTT AATATATTGA TATTTATATC ATTTTACGTT TCTCGTTCAG CTTTCTTGTA
     TTAGATTAAA TTATATAACT ATAAATATAG TAAAATGCAA AGAGCAAGTC GAAAGAACAT
                                                    HindIII
                                                    ~~~~~~~
1981 CAAAGTGGTG ATAATTAATT AAGATCAGAT CCGGCTGCTA AGCTTGCGGC CGCATAATGC
     GTTTCACCAC TATTAATTAA TTCTAGTCTA GGCCGACGAT TCGAACGCCG GCGTATTACG
2041 TTAAGTCGAA CAGAAAGTAA TCGTATTGTA CACGGCCGCA TAATCGAAAT TAATACGACT
     AATTCAGCTT GTCTTTCATT AGCATAACAT GTGCCGGCGT ATTAGCTTTA ATTATGCTGA
2101 CACTATAGGG GAATTGTGAG CGGATAACAA TTCCCCATCT TAGTATATTA GTTAAGTATA
     GTGATATCCC CTTAACACTC GCCTATTGTT AAGGGGTAGA ATCATATAAT CAATTCATAT
2161 AGAAGGAGAT ATACATATGC CAGATCTCAA TTGGATATCG GCCGGCCACG CGATCGCTGA
     TCTTCCTCTA TATGTATACG GTCTAGAGTT AACCTATAGC CGGCCGGTGC GCTAGCGACT
2221 CGTCGGTACC CTCGAGTCTG GTAAAGAAAC CGCTGCTGCG AAATTTGAAC GCCAGCACAT
     GCAGCCATGG GAGCTCAGAC CATTTCTTTG GCGACGACGC TTTAAACTTG CGGTCGTGTA
                                    AvrII
                                    ~~~~~~~
2281 GGACTCGTCT ACTAGCGCAG CTTAATTAAC CTAGGCTGCT GCCACCGCTG AGCAATAACT
     CCTGAGCAGA TGATCGCGTC GAATTAATTG GATCCGACGA CGGTGGCGAC TCGTTATTGA
2341 AGCATAACCC CTTGGGGCCT CTAAACGGGT CTTGAGGGGT TTTTGCTGAA AACCTCAGGC
     TCGTATTGGG GAACCCCGGA GATTTGCCCA GAACTCCCCA AAAACGACTT TTGGAGTCCG
2401 ATTTGAGAAG CACACGGTCA CACTGCTTCC GGTAGTCAAT AAACCGGTAA ACCAGCAATA
     TAAACTCTTC GTGTGCCAGT GTGACGAAGG CCATCAGTTA TTTGGCCATT TGGTCGTTAT
2461 GACATAAGCG GCTATTTAAC GACCCTGCCC TGAACCGACG ACCGGGTCAT CGTGGCCGGA
     CTGTATTCGC CGATAAATTG CTGGGACGGG ACTTGGCTGC TGGCCCAGTA GCACCGGCCT
2521 TCTTGCGGCC CCTCGGCTTG AACGAATTGT TAGACATTAT TTGCCGACTA CCTTGGTGAT
     AGAACGCCGG GGAGCCGAAC TTGCTTAACA ATCTGTAATA AACGGCTGAT GGAACCACTA
2581 CTCGCCTTTC ACGTAGTGGA CAAATTCTTC CAACTGATCT GCGCGCGAGG CCAAGCGATC
     GAGCGGAAAG TGCATCACCT GTTTAAGAAG GTTGACTAGA CGCGCGCTCC GGTTCGCTAG
2641 TTCTTCTTGT CCAAGATAAG CCTGTCTAGC TTCAAGTATG ACGGGCTGAT ACTGGGCCGG
     AAGAAGAACA GGTTCTATTC GGACAGATCG AAGTTCATAC TGCCCGACTA TGACCCGGCC
2701 CAGGCGCTCC ATTGCCCAGT CGGCAGCGAC ATCCTTCGGC GCGATTTTGC CGGTTACTGC
     GTCCGCGAGG TAACGGGTCA GCCGTCGCTG TAGGAAGCCG CGCTAAAACG GCCAATGACG
2761 GCTGTACCAA ATGCGGGACA ACGTAAGCAC TACATTTCGC TCATCGCCAG CCCAGTCGGG
     CGACATGGTT TACGCCCTGT TGCATTCGTG ATGTAAAGCG AGTAGCGGTC GGGTCAGCCC
2821 CGGCGAGTTC CATAGCGTTA AGGTTTCATT TAGCGCCTCA AATAGATCGT GTTCAGGAAC
     GCCGCTCAAG GTATCGCAAT TCCAAAGTAA ATCGCGGAGT TTATCTAGCA CAAGTCCTTG
2881 CGGATCAAAG AGTTCCTCCG CCGCTGGACC TACCAAGGCA ACGCTATGTT CTCTTGCTTT
     GCCTAGTTTC TCAAGGAGGC GGCGACCTGG ATGGTTCCGT TGCGATACAA GAGAACGAAA
2941 TGTCAGCAAG ATAGCCAGAT CAATGTCGAT CGTGGCTGGC TCGAAGATAC CTGCAAGAAT
     ACAGTCGTTC TATCGGTCTA GTTACAGCTA GCACCGACCG AGCTTCTATG GACGTTCTTA
3001 GTCATTGCGC TGCCATTCTC CAAATTGCAG TTCGCGCTTA GCTGGATAAC GCCACGGAAT
     CAGTAACGCG ACGGTAAGAG GTTTAACGTC AAGCGCGAAT CGACCTATTG CGGTGCCTTA
3061 GATGTCGTCG TGCACAACAA TGGTGACTTC TACAGCGCGG AGAATCTCGC TCTCTCCAGG
     CTACAGCAGC ACGTGTTGTT ACCACTGAAG ATGTCGCGCC TCTTAGAGCG AGAGAGGTCC
3121 GGAAGCCGAA GTTTCCAAAA GGTCGTTGAT CCTCGATGTC CGCGTTGTTT CATCAAGCCT
     CCTTCGGCTT CAAAGGTTTT CCAGCAACTA GTTCGAGCCG GCGCAACAAA GTAGTTCGGA
3181 TACGGTCACC GTAACCAGCA AATCAATATC ACTGTGTGGC TTCAGGCCGC CATCCACTGC
     ATGCCAGTGG CATTGGTCGT TTAGTTATAG TGACACACCG AAGTCCGGCG GTAGGTGACG
3241 GGAGCCGTAC AAATGTACGG CCAGCAACGT CGGTTCGAGA TGGCGCTCGA TGACGCCAAC
     CCTCGGCATG TTTACATGCC GGTCGTTGCA GCCAAGCTCT ACCGCGAGCT ACTGCGGTTG
3301 TACCTCTGAT AGTTGAGTCG ATACTTCGGC GATCACCGCT TCCCTCATAC TCTTCCTTTT
     ATGGAGACTA TCAACTCAGC TATGAAGCCG CTAGTGGCGA AGGGAGTATG AGAAGGAAAA
3361 TCAATATTAT TGAAGCATTT ATCAGGGTTA TTGTCTCATG AGCGGATACA TATTTGAATG
     AGTTATAATA ACTTCGTAAA TAGTCCCAAT AACAGAGTAC TCGCCTATGT ATAAACTTAC
3421 TATTTAGAAA AATAAACAAA TAGGCTAGCTC ACTCGGTCGC TACGCTCCGG GCGTGAGACT
     ATAAATCTTT TTATTTGTTT ATCGATCGAG TGAGCCAGCA ATGCGAGGCC CGCACTCTGA
3481 GCGGCGGGCG CTGCGGACAC ATACAAAGTT ACCCACAGAT TCCGTGGATA AGCAGGGGAC
     CGCCGCCCGC GACGCCTGTG TATGTTTCAA TGGGTGTCTA AGGCACCTAT TCGTCCCCTG
3541 TAACATGTGA GGCAAAACAG CAGGGCCGCG CCGGTGGCGT TTTTCCTAG CTCCGCCCT
     ATTGTACACT CCGTTTTGTC GTCCCGGCGC GGCCACCGCA AAAGGTATC GAGGCGGGA
3601 CCTGCCAGAG TTCACATAAA CAGACGCTTT TCCGTGTGCAT CTGTGGGAGC CGTGAGGCTC
     GGACGGTCTC AAGTGTATTT GTCTGCGAAA AGGCACGTA GACACCCTCG GCACTCCGAG
3661 AACCATGAAT CTGACAGTAC GGGCGAAACC CGACAGGACT TAAAGATCCC ACCGTTTCC
     TTGGTACTTA GACTGTCATG CCCGCTTTGG GCTGTCCTGA ATTTCTAGGG GTGGCAAAGG
```

Fig. 44₂

```
3721  GGCGGGTCGC TCCCTCTTGC GCTCTCCTGT TCCGACCCTG CCGTTTACCG GATACCTGTT
      CCGCCCAGCG AGGGAGAACG CGAGAGGACA AGGCTGGGAC GGCAAATGGC CTATGGACAA
3781  CCGCCTTTCT CCCTTACGGG AAGTGTGGCG CTTTCTCATA GCTCACACAC TGGTATCTCG
      GGCGGAAAGA GGGAATGCCC TTCACACCGC GAAAGAGTAT CGAGTGTGTG ACCATAGAGC
3841  GCTCGGTGTA GGTCGTTCGC TCCAAGCTGG GCTGTAAGCA AGAACTCCCC GTTCAGCCCG
      CGAGCCACAT CCAGCAAGCG AGGTTCGACC CGACATTCGT TCTTGAGGGG CAAGTCGGGC
3901  ACTGCTGCGC CTTATCCGGT AACTGTTCAC TTGAGTCCAA CCCGGAAAAG CACGGTAAAA
      TGACGACGCG GAATAGGCCA TTGACAAGTG AACTCAGGTT GGGCCTTTTC GTGCCATTTT
3961  CGCCACTGGC AGCAGCCATT GGTAACTGGG AGTTCGCAGA GGATTTGTTT AGCTAAACAC
      GCGGTGACCG TCGTCGGTAA CCATTGACCC TCAAGCGTCT CCTAAACAAA TCGATTTGTG
4021  GCGGTTGCTC TTGAAGTGTG CGCCAAAGTC CGGCTACACT GGAAGGACAG ATTTGGTTGC
      CGCCAACGAG AACTTCACAC GCGGTTTCAG GCCGATGTGA CCTTCCTGTC TAAACCAACG
4081  TGTGCTCTGC GAAAGCCAGT TACCACGGTT AAGCAGTTCC CCAACTGACT TAACCTTCGA
      ACACGAGACG CTTTCGGTCA ATGGTGCCAA TTCGTCAAGG GGTTGACTGA ATTGGAAGCT
4141  TCAAACCACC TCCCCAGGTG GTTTTTTCGT TTACAGGGCA AAAGATTACG CGCAGAAAAA
      AGTTTGGTGG AGGGGTCCAC CAAAAAAGCA AATGTCCCGT TTTCTAATGC GCGTCTTTTT
4201  AAGGATCTCA AGAAGATCCT TTGATCTTTT CTACTGAACC GCTCTAGATT TCAGTGCAAT
      TTCCTAGAGT TCTTCTAGGA AACTAGAAAA GATGACTTGG CGAGATCTAA AGTCACGTTA
4261  TTATCTCTTC AAATGTAGCA CCTGAAGTCA GCCCCATACG ATATAAGTTG TAATTCTCAT
      AATAGAGAAG TTTACATCGT GGACTTCAGT CGGGGTATGC TATATTCAAC ATTAAGAGTA
4321  GTTAGTCATG CCCCGCGCCC ACCGGAAGGA GCTGACTGGG TTGAAGGCTC TCAAGGGCAT
      CAATCAGTAC GGGGCGCGGG TGGCCTTCCT CGACTGACCC AACTTCCGAG AGTTCCCGTA
4381  CGGTCGAGAT CCCGGTGCCT AATGAGTGAG CTAACTTACA TTAATTGCGT TGCGCTCACT
      GCCAGCTCTA GGGCCACGGA TTACTCACTC GATTGAATGT AATTAACGCA ACGCGAGTGA
4441  GCCCGCTTTC CAGTCGGGAA ACCTGTCGTG CCAGCTGCAT TAATGAATCG GCCAACGCGC
      CGGGCGAAAG GTCAGCCCTT TGGACAGCAC GGTCGACGTA ATTACTTAGC CGGTTGCGCG
4501  GGGGAGAGGC GGTTTGCGTA TTGGGCGCCA GGGTGGTTTT TCTTTTCACC AGTGAGACGG
      CCCCTCTCCG CCAAACGCAT AACCCGCGGT CCCACCAAAA AGAAAAGTGG TCACTCTGCC
4561  GCAACAGCTG ATTGCCCTTC ACCGCCTGGC CCTGAGAGAG TTGCAGCAAG CGGTCCACGC
      CGTTGTCGAC TAACGGGAAG TGGCGGACCG GGACTCTCTC AACGTCGTTC GCCAGGTGCG
4621  TGGTTTGCCC CAGCAGGCGA AAATCCTGTT TGATGGTGGT TAACGGCGGG ATATAACATG
      ACCAAACGGG GTCGTCCGCT TTTAGGACAA ACTACCACCA ATTGCCGCCC TATATTGTAC
4681  AGCTGTCTTC GGTATCGTCG TATCCCACTA CCGAGATGTC CGCACCAACG CGCAGCCCGG
      TCGACAGAAG CCATAGCAGC ATAGGGTGAT GGCTCTACAG GCGTGGTTGC GCGTCGGGCC
4741  ACTCGGTAAT GGCGCGCATT GCGCCCAGCG CCATCTGATC GTTGGCAACC AGCATCGCAG
      TGAGCCATTA CCGCGCGTAA CGCGGGTCGC GGTAGACTAG CAACCGTTGG TCGTAGCGTC
4801  TGGGAACGAT GCCCTCATTC AGCATTTGCA TGGTTTGTTG AAAACCGGAC ATGGCACTCC
      ACCCTTGCTA CGGGAGTAAG TCGTAAACGT ACCAAACAAC TTTTGGCCTG TACCGTGAGG
4861  AGTCGCCTTC CCGTTCCGCT ATCGGCTGAA TTTGATTGCG AGTGAGATAT TTATGCCAGC
      TCAGCGGAAG GGCAAGGCGA TAGCCGACTT AAACTAACGC TCACTCTATA AATACGGTCG
4921  CAGCCAGACG CAGACGCGCC GAGACAGAAC TTAATGGGCC CGCTAACAGC GCGATTTGCT
      GTCGGTCTGC GTCTGCGCGG CTCTGTCTTG AATTACCCGG GCGATTGTCG CGCTAAACGA
4981  GGTGACCCAA TGCGACCAGA TGCTCCACGC CCAGTCGCGT ACCGTCTTCA TGGGAGAAAA
      CCACTGGGTT ACGCTGGTCT ACGAGGTGCG GGTCAGCGCA TGGCAGAAGT ACCCTCTTTT
5041  TAATACTGTT GATGGGTGTC TGGTCAGAGA CATCAAGAAA TAACGCCGGA ACATTAGTGC
      ATTATGACAA CTACCCACAG ACCAGTCTCT GTAGTTCTTT ATTGCGGCCT TGTAATCACG
5101  AGGCAGCTTC CACAGCAATG GCATCCTGGT CATCCAGCGG ATAGTTAATG ATCAGCCCAC
      TCCGTCGAAG GTGTCGTTAC CGTAGGACCA GTAGGTCGCC TATCAATTAC TAGTCGGGTG
5161  TGACGCGTTG CGCGAGAAGA TTGTGCACCG CCGCTTTACA GGCTTCGACG CCGCTTCGTT
      ACTGCGCAAC GCGCTCTTCT AACACGTGGC GGCGAAATGT CCGAAGCTGC GGCGAAGCAA
5221  CTACCATCGA CACCACCACG CTGGCACCCA GTTGATCGGC GCGAGATTTA ATCGCCGCGA
      GATGGTAGCT GTGGTGGTGC GACCGTGGGT CAACTAGCCG CGCTCTAAAT TAGCGGCGCT
5281  CAATTTGCGA CGGCGCGTGC AGGGCCAGAC TGGAGGTGGC AACGCCAATC AGCAACGACT
      GTTAAACGCT GCCGCGCACG TCCCGGTCTG ACCTCCACCG TTGCGGTTAG TCGTTGCTGA
5341  GTTTGCCCGC CAGTTGTTGT GCCACGCGGT TGGGAATGTA ATTCAGCTCC GCCATCGCCG
      CAAACGGGCG GTCAACAACA CGGTGCGCCA ACCCTTACAT TAAGTCGAGG CGGTAGCGGC
5401  CTTCCACTTT TTCCCGCGTT TTCGCAGAAA CGTGGCTGGC CTGGTTCACC ACGCGGGAAA
      GAAGGTGAAA AAGGGCGCAA AAGCGTCTTT GCACCGACCG GACCAAGTGG TGCGCCCTTT
5461  CGGTCTGATA AGAGACACCG GCATACTCTG CGACATCGTA TAACGTTACT GGTTTCACAT
      GCCAGACTAT TCTCTGTGGC CGTATGAGAC GCTGTAGCAT ATTGCAATGA CCAAAGTGTA
5521  TCACCACCCT GAATTGACTC TCTTCCGGGC GCTATCATGC CATACCGCGA AAGGTTTTGC
      AGTGGTGGGA CTTAACTGAG AGAAGGCCCG CGATAGTACG GTATGGCGCT TTCCAAAACG
5581  GCCATTCGAT GGTGTCCGGG ATCTCGACGC TCTCCCTTAT GCGACT
      CGGTAAGCTA CCACAGGCCC TAGAGCTGCG AGAGGGAATA CGCTGA
```

Fig. 44$_3$

| Fig. 46₁ |
|---|
| Fig. 46₂ |
| Fig. 46₃ |

Fig. 46

```
         EcoNI
         ~~~~~~~~~~
   1  CCTGCATTAG GAAGCAGCCC AGTAGTAGGT TGAGGCCGTT GAGCACCGCC GCCGCAAGGA
      GGACGTAATC CTTCGTCGGG TCATCATCCA ACTCCGGCAA CTCGTGGCGG CGGCGTTCCT
  61  ATGGTGCATG CAAGGAGATG GCGCCCAACA GTCCCCCGGC CACGGGGCCT GCCACCATAC
      TACCACGTAC GTTCCTCTAC CGCGGGTTGT CAGGGGGCCG GTGCCCCGGA CGGTGGTATG
 121  CCACGCCGAA ACAAGCGCTC ATGAGCCCGA AGTGGCGAGC CCGATCTTCC CCATCGGTGA
      GGTGCGGCTT TGTTCGCGAG TACTCGGGCT TCACCGCTCG GGCTAGAAGG GGTAGCCACT
 181  TGTCGGCGAT ATAGGCGCCA GCAACCGCAC CTGTGGCGCC GGTGATGCCG GCCACGATGC
      ACAGCCGCTA TATCCGCGGT CGTTGGCGTG GACACCGCGG CCACTACGGC CGGTGCTACG
 241  GTCCGGCGTA GAGGATCGAG ATCTCGATCC CGCGAAATTA ATACGACTCA CTATAGGGGA
      CAGGCCGCAT CTCCTAGCTC TAGAGCTAGG GCGCTTTAAT TATGCTGAGT GATATCCCCT
 301  ATTGTGAGCG GATAACAATT CCCCTCTAGA AATAATTTTG TTTAACTTTA AGAAGGAGAT
      TAACACTCGC CTATTGTTAA GGGGAGATCT TTATTAAAAC AAATTGAAAT TCTTCCTCTA
 361  ATACATATGA AATACCTGCT GCCGACCGCT GCTGCTGGTC TGCTGCTCCT CGCTGCCCAG
      TATGTATACT TTATGGACGA CGGCTGGCGA CGACGACCAG ACGACGAGGA GCGACGGGTC
                                                        EcoRI
                                                        ~~~~~~~
           NcoI                   BamHI
           ~~~~~~                 ~~~~~~
 421  CCGGCGATGG CCATGGATAT CGGAATTAAT TCGGATCCGA ATTCGAGCTC GATCACAAGT
      GGCCGCTACC GGTACCTATA GCCTTAATTA AGCCTAGGCT TAAGCTCGAG CTAGTGTTCA
 481  TTGTACAAAA AAGCTGAACG AGAAACGTAA AATGATATAA ATATCAATAT ATTAAAATTAG
      AACATGTTTT TTCGACTTGC TCTTTGCATT TTACTATATT TATAGTTATA TAATTTAATC
 541  ATTTTGCATA AAAAACAGAC TACATAATAC TGTAAAACAC AACATATCCA GTCACTATGG
      TAAAACGTAT TTTTTGTCTG ATGTATTATG ACATTTTGTG TTGTATAGGT CAGTGATACC
 601  CGGCCGCCAC GTTAAGGGAT TTTGGTCATG ATCAGCACGT GTTGACAATT AATCATCGGC
      GCCGGCGGTG CAATTCCCTA AAACCAGTAC TAGTCGTGCA CAACTGTTAA TTAGTAGCCG
                                                                 NcoI
                                                                 ~~~~~~
 661  ATAGTATATC GGCATAGTAT AATACGACAA GGTGAGGAAC TAAACCATGG CCAAGTTGAC
      TATCATATAG CCGTATCATA TTATGCTGTT CCACTCCTTG ATTTGGTACC GGTTCAACTG
 721  CAGTGCCGTT CCGGTGCTCA CCGCGCGCGA CGTCGCCGGA GCGGTCGAGT TCTGGACCGA
      GTCACGGCAA GGCCACGAGT GGCGCGCGCT GCAGCGGCCT CGCCAGCTCA AGACCTGGCT
                Xma I
                ~~~~~~~
              Sma I
              ~~~~~~
 781  CCGGCTCGGG TTCTCCCGGG ACTTCGTGGA GGACGACTTC GCCGGTGTGG TCCGGGACGA
      GGCCGAGCCC AAGAGGGCCC TGAAGCACCT CCTGCTGAAG CGGCCACACC AGGCCCTGCT
 841  CGTGACCCTG TTCATCAGCG CGGTCCAGGA CCAGGTGGTG CCGGACAACA CCCTGGCCTG
      GCACTGGGAC AAGTAGTCGC GCCAGGTCCT GGTCCACCAC GGCCTGTTGT GGGACCGGAC
 901  GGTGTGGGTG CGCGGCCTGG ACGAGCTGTA CGCCGAGTGG TCGGAGGTCG TGTCCACGAA
      CCACACCCAC GCGCCGGACC TGCTCGACAT GCGGCTCACC AGCCTCCAGC ACAGGTGCTT
 961  CTTCCGGGAC GCCTCCGGGC CGGCCATGAC CGAGATCGGC GAGCAGCCGT GGGGGCGGGA
      GAAGGCCCTG CGGAGGCCCG GCCGGTACTG GCTCTAGCCG CTCGTCGGCA CCCCCGCCCT
1021  GTTCGCCCTG CGCGACCCGG CCGGCAACTG CGTGCACTTC GTGGCCGAGG AGCAGGACTG
      CAAGCGGGAC GCGCTGGGCC GGCCGTTGAC GCACGTGAAG CACCGGCTCC TCGTCCTGAC
1081  ATCATGATGA TATTATTTTA TCTTGTGCAA TGTAACATCA GAGATTTTGA GACACGGGCC
      TAGTACTACT ATAATAAAAT AGAACACGTT ACATTGTAGT CTCTAAAACT CTGTGCCCGG
1141  AGAGCTGCCA GGAAACAGCT ATGACCATGT AATACGACTC ACTATAGGGG ATATCAGCTG
      TCTCGACGGT CCTTTGTCGA TACTGGTACA TTATGCTGAG TGATATCCCC TATAGTCGAC
1201  GATGGCAAAT AATGATTTTA TTTTGACTGA TAGTGACCTG TTCGTTGCAA CACCGGTGCT
      CTACCGTTTA TTACTAAAAT AAAACTGACT ATCACTGGAC AAGCAACGTT GTGGCCACGA
1261  AGCGTATACC CGAAGTATGT CAAAAAGAGG TGTGCTATGA AGCAGCGTAT TACAGTGACA
      TCGCATATGG GCTTCATACA GTTTTTCTCC ACACGATACT TCGTCGCATA ATGTCACTGT
1321  GTTGACAGCG ACAGCTATCA GTTGCTCAAG GCATATATGA TGTCAATATC TCCGGTCTGG
      CAACTGTCGC TGTCGATAGT CAACGAGTTC CGTATATACT ACAGTTATAG AGGCCAGACC
1381  TAAGCACAAC CATGCAGAAT GAAGCCCGTC GTCTGCGTGC CGAACGCTGG AAAGCGGAAA
      ATTCGTGTTG GTACGTCTTA CTTCGGGCAG CAGACGCACG GCTTGCGACC TTTCGCCTTT
1441  ATCAGGAAGG GATGGCTGAG GTCGCCCGGT TTATTGAAAT GAACGGCTCT TTTGCTGACG
      TAGTCCTTCC CTACCGACTC CAGCGGGCCA AATAACTTTA CTTGCCGAGA AAACGACTGC
1501  AGAACAGGGA CTGGTGAAAT GCAGTTTAAG GTTTACACCT ATAAAGAGA GAGCCGTTAT
      TCTTGTCCCT GACCACTTTA CGTCAAATTC CAAATGTGGA TATTTTCTCT CTCGGCAATA
                                                       Xma I
                                                       ~~~~~~~
                                                     Sma I
                                                     ~~~~~~
1561  CGTCTGTTTG TGGATGTACA GAGTGATATT ATTGACACGC CCGGGCGACG GATGGTGATC
      GCAGACAAAC ACCTACATGT CTCACTATAA TAACTGTGCG GGCCCGCTGC CTACCACTAG
1621  CCCCTGCCCA GTGCACGTCT GCTGTCAGAT AAAGTCTCCC GTGAACTTTA CCCGGTGGTG
      GGGGACCGGT CACGTGCAGA CGACAGTCTA TTTCAGAGGG CACTTGAAAT GGGCCACCAC
1681  CATATCGGGG ATGAAAGCTG GCGCATGATG ACCACCGATA TGGCCAGTGT GCCGGTCTCC
```

Fig. 46₁

```
        GTATAGCCCC TACTTTCGAC CGCGTACTAC TGGTGGCTAT ACCGGTCACA CGGCCAGAGG
 1741   GTTATCGGGG AAGAAGTGGC TGATCTCAGC CGCCGCGAAA ATGACATCAA AAACGCCATT
        CAATAGCCCC TTCTTCACCG ACTAGAGTCG GCGGCGCTTT TACTGTAGTT TTTGCGGTAA
                                                                 PstI
                                                                 ~~~~~~
 1801   AACCTGATGT TCTGGGGAAT ATAAATGTCA GGCTCCCTTA TACACAGCCA GTCTGCAGGT
        TTGGACTACA AGACCCCTTA TATTTACAGT CCGAGGGAAT ATGTGTCGGT CAGACGTCCA
 1861   CGACCATAGT GACTGGATAT GTTGTGTTTT ACAGTATTAT GTAGTCTGTT TTTTATGCAA
        GCTGGTATCA CTGACCTATA CAACACAAAA TGTCATAATA CATCAGACAA AAAATACGTT
 1921   AATCTAATTT AATATATTGA TATTTATATC ATTTTACGTT TCTCGTTCAG CTTTCTTGTA
        TTAGATTAAA TTATATAACT ATAAATATAG TAAAATGCAA AGAGCAAGTC GAAAGAACAT
                                                    HindIII
                                                    ~~~~~~~
 1981   CAAAGTGGTG ATAATTAATT AAGATCAGAT CCGGCTGCTA AGCTTGCGGC CGCATAATGC
        GTTTCACCAC TATTAATTAA TTCTAGTCTA GGCCGACGAT TCGAACGCCG GCGTATTACG
 2041   TTAAGTCGAA CAGAAAGTAA TCGTATTGTA CACGGCCGCA TAATCGAAAT TAATACGACT
        AATTCAGCTT GTCTTTCATT AGCATAACAT GTGCCGGCGT ATTAGCTTTA ATTATGCTGA
 2101   CACTATAGGG GAATTGTGAG CGGATAACAA TTCCCCATCT TAGTATATTA GTTAAGTATA
        GTGATATCCC CTTAACACTC GCCTATTGTT AAGGGGTAGA ATCATATAAT CAATTCATAT
 2161   AGAAGGAGAT ATACATATGG CAGATCTCAA TTGGATATCG GCCGGCCACG CGATCGCTGA
        TCTTCCTCTA TATGTATACC GTCTAGAGTT AACCTATAGC CGGCCGGTGC GCTAGCGACT
 2221   CGTCGGTACC CTCGAGTCTG GTAAAGAAAC CGCTGCTGCG AAATTTGAAC GCCAGCACAT
        GCAGCCATGG GAGCTCAGAC CATTTCTTTG GCGACGACGC TTTAAACTTG CGGTCGTGTA
 2281   GGACTCGTCT ACTAGCGCAG CTTAATTAAC CTAGGCTGCT GCCACCGCTG AGCAATAACT
        CCTGAGCAGA TGATCGCGTC GAATTAATTG GATCCGACGA CGGTGGCGAC TCGTTATTGA
 2341   AGCATAACCC CTTGGGGCCT CTAAACGGGT CTTGAGGGGT TTTTTGCTGA AACCTCAGGC
        TCGTATTGGG GAACCCCGGA GATTTGCCCA GAACTCCCCA AAAAACGACT TTGGAGTCCG
 2401   ATTTGAGAAG CACACGGTCA CACTGCTTCC GGTAGTCAAT AAACCGGTAA ACCAGCAATA
        TAAACTCTTC GTGTGCCAGT GTGACGAAGG CCATCAGTTA TTTGGCCATT TGGTCGTTAT
 2461   GACATAAGCG GCTATTTAAC GACCCTGCCC TGAACCGACG ACAAGCTGAC GACCGGGTCT
        CTGTATTCGC CGATAAATTG CTGGGACGGG ACTTGGCTGC TGTTCGACTG CTGGCCCAGA
 2521   CCGCAAGTGG CACTTTTCGG GGAAATGTGC GCGGAACCCC TATTTGTTTA TTTTTCTAAA
        GGCGTTCACC GTGAAAAGCC CCTTTACACG CGCCTTGGGG ATAAACAAAT AAAAAGATTT
 2581   TACATTCAAA TATGTATCCG CTCATGAATT AATTCTTAGA AAAACTCATC GAGCATCAAA
        ATGTAAGTTT ATACATAGGC GAGTACTTAA TTAAGAATCT TTTTGAGTAG CTCGTAGTTT
 2641   TGAAACTGCA ATTTATTCAT ATCAGGATTA TCAATACCAT ATTTTTGAAA AAGCCGTTTC
        ACTTTGACGT TAAATAAGTA TAGTCCTAAT AGTTATGGTA TAAAAACTTT TTCGGCAAAG
 2701   TGTAATGAAG GAGAAAACTC ACCGAGGCAG TTCCATAGGA TGGCAAGATC CTGGTATCGG
        ACATTACTTC CTCTTTTGAG TGGCTCCGTC AAGGTATCCT ACCGTTCTAG GACCATAGCC
 2761   TCTGCGATTC CGACTCGTCC AACATCAATA CAACCTATTA ATTTCCCCTC GTCAAAAATA
        AGACGCTAAG GCTGAGCAGG TTGTAGTTAT GTTGGATAAT TAAAGGGGAG CAGTTTTTAT
 2821   AGGTTATCAA GTGAGAAATC ACCATGAGTG ACGACTGAAT CCGGTGAGAA TGGCAAAAGT
        TCCAATAGTT CACTCTTTAG TGGTACTCAC TGCTGACTTA GGCCACTCTT ACCGTTTTCA
 2881   TTATGCATTT CTTTCCAGAC TTGTTCAACA GGCCAGCCAT TACGCTCGTC ATCAAAATCA
        AATACGTAAA GAAAGGTCTG AACAAGTTGT CCGGTCGGTA ATGCGAGCAG TAGTTTTAGT
 2941   CTCGCATCAA CCAAACCGTT ATTCATTCGT GATTGCGCCT GAGCGAGACA AAATACGCGG
        GAGCGTAGTT GGTTTGGCAA TAAGTAAGCA CTAACGCGGA CTCGCTCTGC TTTATGCGCC
 3001   TCGCTGTTAA AAGGACAATT ACAAACAGGA ATCGAATGCA ACCGGCGCAG GAACACTGCC
        AGCGACAATT TTCCTGTTAA TGTTTGTCCT TAGCTTACGT TGGCCGCGTC CTTGTGACGG
                                            EcoNI
                                            ~~~~~~~~~~~
 3061   AGCGCATCAA CAATATTTTC ACCTGAATCA GGATATTCTT CTAATACCTG AATGCTGTT
        TCGCGTAGTT GTTATAAAAG TGGACTTAGT CCTATAAGAA GATTATGGAC CTTACGACAA
           XmaI
           ~~~~~~
           SmaI
           ~~~~~~
 3121   TTCCCGGGGA TCGCAGTGGT GAGTAACCAT GCATCATCAG GAGTACGGAT AAAATGCTTG
        AAGGGCCCCT AGCGTCACCA CTCATTGGTA CGTAGTAGTC CTCATGCCTA TTTTACGAAC
 3181   ATGGTCGGAA GAGGCATAAA TTCCGTCAGC CAGTTTAGTC TGACCATCTC ATCTGTAACA
        TACCAGCCTT CTCCGTATTT AAGGCAGTCG GTCAAATCAG ACTGGTAGAG TAGACATTGT 3241   TCATTGGCAA CGCTACCTTT GCCATGTTTC AGAAACAACT CTGGCGCATC GGGCTTCCCA
        AGTAACCGTT GCGATGGAAA CGGTACAAAG TCTTTGTTGA GACCGCGTAG CCCGAAGGGT
              ClaI
              ~~~~~~~
 3301   TACAATCGAT AGATTGTCGC ACCTGATTGC CGACATTAT CGCGAGCCCA TTTATACCCA
        ATGTTAGCTA TCTAACAGCG TGGACTAACG GCTGTAATA GCGCTCGGGT AAATATGGGT
 3361   TATAAATCAG CATCCATGTT GGAATTTAAT CGCGGCCTAG AGCAAGACGT TTCCCGTTGA
        ATATTTAGTC GTAGGTACAA CCTTAAATTA GCGCCGGATC TCGTTCTGCA AAGGGCAACT
 3421   ATATGGCTCA TACTCTTCCT TTTTCAATAT TATTGAAGCA TTTATCAGGG TTATTGTCTC
        TATACCGAGT ATGAGAAGGA AAAAGTTATA ATAACTTCGT AAATAGTCCC AATAACAGAG
 3481   ATGAGCGGAT ACATATTTGA ATGTATTTAG AAAAATAAAC AAATAGGCAT GCAGCGCTCT
```

```
   1  CCTGCATTAG GAAGCAGCCC AGTAGTAGGT TGAGGCCGTT GAGCACCGCC GCCGCAAGGA
      GGACGTAATC CTTCGTCGGG TCATCATCCA ACTCCGGCAA CTCGTGGCGG CGGCGTTCCT
  61  ATGGTGCATG CAAGGAGATG GCGCCCAACA GTCCCCCGGC CACGGGGCCT GCCACCATAC
      TACCACGTAC GTTCCTCTAC CGCGGGTTGT CAGGGGGCCG GTGCCCCGGA CGGTGGTATG
 121  CCACGCCGAA ACAAGCGCTC ATGAGCCCGA AGTGGCGAGC CCGATCTTCC CCATCGGTGA
      GGTGCGGCTT TGTTCGCGAG TACTCGGGCT TCACCGCTCG GGCTAGAAGG GGTAGCCACT
 181  TGTCGGCGAT ATAGGCGCCA GCAACCGCAC CTGTGGCGCC GGTGATGCCG GCCACGATGC
      ACAGCCGCTA TATCCGCGGT CGTTGGCGTG GACACCGCGG CCACTACGGC CGGTGCTACG
 241  GTCCGGCGTA GAGGATCGAG ATCTCGATCC CGCGAAATTA ATACGACTCA CTATAGGGGA
      CAGGCCGCAT CTCCTAGCTC TAGAGCTAGG GCGCTTTAAT TATGCTGAGT GATATCCCCT
 301  ATTGTGAGCG GATAACAATT CCCCTCTAGA AATAATTTTG TTTAACTTTA AGAAGGAGAT
      TAACACTCGC CTATTGTTAA GGGGAGATCT TTATTAAAAC AAATTGAAAT TCTTCCTCTA
 361  ATACATATGA AATACCTGCT GCCGACCGCT GCTGCTGGTC TGCTGCTCCT CGCTGCCCAG
      TATGTATACT TTATGGACGA CGGCTGGCGA CGACGACCAG ACGACGAGGA GCGACGGGTC
                                                       EcoRI
                                                       ~~~~~~
          NcoI                       BamHI      SacI
          ~~~~~~                     ~~~~~~     ~~~~~~
 421  CCGGCGATGG CCATGGATAT CGGAATTAAT TCGGATCCGA ATTCGAGCTC GATCACAAGT
      GGCCGCTACC GGTACCTATA GCCTTAATTA AGCCTAGGCT TAAGCTCGAG CTAGTGTTCA
 481  TTGTACAAAA AAGCTGAACG AGAAACGTAA AATGATATAA ATATCAATAT ATTAAATTAG
      AACATGTTTT TTCGACTTGC TCTTTGCATT TTACTATATT TATAGTTATA TAATTTAATC
 541  ATTTTGCATA AAAAACAGAC TACATAATAC TGTAAAACAC AACATATCCA GTCACTATGG
      TAAAACGTAT TTTTTGTCTG ATGTATTATG ACATTTTGTG TTGTATAGGT CAGTGATACC
 601  CGGCCGCCAC GTTAAGGGAT TTTGGTCATG ATCAGCACGT GTTGACAATT AATCATCGGC
      GCCGGCGGTG CAATTCCCTA AAACCAGTAC TAGTCGTGCA CAACTGTTAA TTAGTAGCCG
                                                        NcoI
                                                        ~~~~~~~
 661  ATAGTATATC GGCATAGTAT AATACGACAA GGTGAGGAAC TAAACCATGG CCAAGTTGAC
      TATCATATAG CCGTATCATA TTATGCTGTT CCACTCCTTG ATTTGGTACC GGTTCAACTG
 721  CAGTGCCGTT CCGGTGCTCA CCGCGCGCGA CGTCGCCGGA GCGGTCGAGT TCTGGACCGA
      GTCACGGCAA GGCCACGAGT GGCGCGCGCT GCAGCGGCCT CGCCAGCTCA AGACCTGGCT
 781  CCGGCTCGGG TTCTCCCGGG ACTTCGTGGA GGACGACTTC GCCGGTGTGG TCCGGGACGA
      GGCCGAGCCC AAGAGGGCCC TGAAGCACCT CCTGCTGAAG CGGCCACACC AGGCCCTGCT
 841  CGTGACCCTG TTCATCAGCG CGGTCAGGA CCAGGTGGTG CCGGACAACA CCCTGGCCTG
      GCACTGGGAC AAGTAGTCGC GCCAGGTCCT GGTCCACCAC GGCCTGTTGT GGGACCGGAC
 901  GGTGTGGGTG CGCGGCCTGG ACGAGCTGTA CGCCGAGTGG TCGAGGTCG TGTCCACGAA
      CCACACCCAC GCGCCGGACC TGCTCGACAT GCGGCTCACC AGCCTCCAGC ACAGGTGCTT
 961  CTTCCGGGAC GCCTCCGGGC CGGCCATGAC CGAGATCGGC GAGCAGCCGT GGGGGCGGGA
      GAAGGCCCTG CGGAGGCCCG GCCGGTACTG GCTCTAGCCG CTCGTCGGCA CCCCCGCCCT
1021  GTTCGCCCTG CGCGACCCGG CCGGCAACTG CGTGCACTTC GTGGCCGAGG AGCAGGACTG
      CAAGCGGGAC GCGCTGGGCC GGCCGTTGAC GCACGTGAAG CACCGGCTCC TCGTCCTGAC
1081  ATCATGATGA TATTATTTTA TCTTGTGCAA TGTAACATCA GAGATTTTGA GACACGGGCC
      TAGTACTACT ATAATAAAAT AGAACACGTT ACATTGTAGT CTCTAAAACT CTGTGCCCGG
1141  AGAGCTGCCA GGAAACAGCT ATGACCATGT AATACGACTC ACTATAGGGG ATATCAGCTG
      TCTCGACGGT CCTTTGTCGA TACTGGTACA TTATGCTGAG TGATATCCCC TATAGTCGAC
1201  GATGGCAAAT AATGATTTTA TTTTGACTGA TAGTGACCTG TTCGTTGCAA CACCGGTGCT
      CTACCGTTTA TTACTAAAAT AAAACTGACT ATCACTGGAC AAGCAACGTT GTGGCCACGA
1261  AGCGTATACC CGAAGTATGT CAAAAGAGG TGTGCTATGA AGCAGCGTAT TACAGTGACA
      TCGCATATGG GCTTCATACA GTTTTCTCC ACACGATACT TCGTCGCATA ATGTCACTGT
1321  GTTGACGCAG CGTACTATCA GTTGCTCAAG GCATATATGA TGTCAATATC TCCGGTCTGG
      CAACTGCGTC GCATGATAGT CAACGAGTTC CGTATATACT ACAGTTATAG AGGCCAGACC
1381  TAAGCACAAC CATGCAGAAT GAAGCCCGTC GTCTGCGTGC CGAACGCTGG AAAGCGGAAA
      ATTCGTGTTG GTACGTCTTA CTTCGGGCAG CAGACGCACG GCTTGCGACC TTTCGCCTTT
1441  ATCAGGAAGG GATGGCTGAG GTCGCCCGGT TATTGAAAT GAACGGCTCT TTTGCTGACG
      TAGTCCTTCC CTACCGACTC CAGCGGGCCA AATAACTTTA CTTGCCGAGA AAACGACTGC
1501  AGAACAGGGA CTGGTGAAAT GCAGTTTAAG GTTTACACCT ATAAAAGAGA GAGCCGTTAT
      TCTTGTCCCT GACCACTTTA CGTCAAATTC CAAATGTGGA TATTTTCTCT CTCGGCAATA
1561  CGTCTGTTTG TGGATGTACA GAGTGATATT ATTGACACGC CCGGGCGACG GATGGTGATC
      GCAGACAAAC ACCTACATGT CTCACTATAA TAACTGTGCG GGCCCGCTGC CTACCACTAG
1621  CCCCTGGCCA GTGCACGTCT GCTGTCAGAT AAAGTCTCCC GTGAACTTTA CCCGGTGGTG
      GGGGACCGGT CACGTGCAGA CGACAGTCTA TTTCAGAGGG CACTTGAAAT GGGCCACCAC
1681  CATATCGGGG ATGAAAGCTG GCGCATGATG ACCACCGATA TGGCCAGTGT GCCGGTCTCC
      GTATAGCCCC TACTTTCGAC CGCGTACTAC TGGTGGCTAT ACCGGTCACA CGGCCAGAGG
1741  GTTATCGGGG AAGAAGTGGC TGATCTCAGC CGCCCGCGAAA ATGACATCAA AAACGCCATT
      CAATAGCCCC TTCTTCACCG ACTAGAGTCG GCGGCGCTTT TACTGTAGTT TTTGCGGTAA
                                                                 PstI
                                                                 ~~~~~~
1801  AACCTGATGT TCTGGGGAAT ATAAATGTCA GGCTCCCTTA TACACAGCCA GTCTGCAGGT
      TTGGACTACA AGACCCCTTA TATTTACAGT CCGAGGGAAT ATGTGTCGGT CAGACGTCCA
```

Fig. 48₁

```
1861  CGACCATAGT GACTGGATAT GTTGTGTTTT ACAGTATTAT GTAGTCTGTT TTTTATGCAA
      GCTGGTATCA CTGACCTATA CAACACAAAA TGTCATAATA CATCAGACAA AAAATACGTT
1921  AATCTAATTT AATATATTGA TATTTATATC ATTTTACGTT TCTCGTTCAG CTTTCTTGTA
      TTAGATTAAA TTATATAACT ATAAATATAG TAAAATGCAA AGAGCAAGTC GAAAGAACAT
                                                     HindIII
                                                     ~~~~~~~
1981  CAAAGTGGTG ATAATTAATT AAGATCAGAT CCGGCTGCTA AGCTTGCGGC CGCATAATGC
      GTTTCACCAC TATTAATTAA TTCTAGTCTA GGCCGACGAT TCGAACGCCG GCGTATTACG
2041  TTAAGTCGAA CAGAAAGTAA TCGTATTGTA CACGGCCGCA TAATCGAAAT TAATACGACT
      AATTCAGCTT GTCTTTCATT AGCATAACAT GTGCCGGCGT ATTAGCTTTA ATTATGCTGA
2101  CACTATAGGG GAATTGTGAG CGGATAACAA TTCCCCATCT TAGTATATTA GTTAAGTATA
      GTGATATCCC CTTAACACTC GCCTATTGTT AAGGGGTAGA ATCATATAAT CAATTCATAT
2161  AGAAGGAGAT ATACATATGG CAGATCTCAA TTGGATATCG GCCGGCCACG CGATCGCTGA
      TCTTCCTCTA TATGTATACC GTCTAGAGTT AACCTATAGC CGGCCGGTGC GCTAGCGACT
2221  CGTCGGTACC CTCGAGTCTG GTAAAGAAAC CGCTGCTGCG AAATTTGAAC GCCAGCACAT
      GCAGCCATGG GAGCTCAGAC CATTTCTTTG GCGACGACGC TTTAAACTTG CGGTCGTGTA
2281  GGACTCGTCT ACTAGCGCAG CTTAATTAAC CTAGGCTGCT GCCACCGCTG AGCAATAACT
      CCTGAGCAGA TGATCGCGTC GAATTAATTG GATCCGACGA CGGTGGCGAC TCGTTATTGA
2341  AGCATAACCC CTTGGGGCCT CTAAACGGGT CTTGAGGGGT TTTTTGCTGA AACCTCAGGC
      TCGTATTGGG GAACCCCGGA GATTTGCCCA GAACTCCCCA AAAAACGACT TTGGAGTCCG
2401  ATTTGAGAAG CACACGGTCA CACTGCTTCC GGTAGTCAAT AAACCGGTAA ACCAGCAATA
      TAAACTCTTC GTGTGCCAGT GTGACGAAGG CCATCAGTTA TTTGGCCATT TGGTCGTTAT
2461  GACATAAGCG GCTATTTAAC GACCCTGCCC TGAACCGACG ACCGGGTCGA ATTTGCTTTC
      CTGTATTCGC CGATAAATTG CTGGGACGGG ACTTGGCTGC TGGCCCAGCT TAAACGAAAG
2521  GAATTTCTGC CATTCATCCG CTTATTATCA CTTATTCAGG CGTAGCACCA GGCGTTTAAG
      CTTAAAGACG GTAAGTAGGC GAATAATAGT GAATAAGTCC GCATCGTGGT CCGCAAATTC
2581  GGCACCAATA ACTGCCTTAA AAAAATTACG CCCCGCCCTG CCACTCATCG CAGTACTGTT
      CCGTGGTTAT TGACGGAATT TTTTTAATGC GGGGCGGGAC GGTGAGTAGC GTCATGACAA
2641  GTAATTCATT AAGCATTCTG CCGACATGGA AGCCATCACA GACGGCATGA TGAACCTGAA
      CATTAAGTAA TTCGTAAGAC GGCTGTACCT TCGGTAGTGT CTGCCGTACT ACTTGGACTT
2701  TCGCCAGCGG CATCAGCACC TTGTCGCCTT GCGTATAATA TTTGCCCATA GTGAAAACGG
      AGCGGTCGCC GTAGTCGTGG AACAGCGGAA CGCATATTAT AAACGGGTAT CACTTTTGCC
2761  GGGCGAAGAA GTTGTCCATA TTGGCCACGT TTAAATCAAA ACTGGTGAAA CTCACCCAGG
      CCCGCTTCTT CAACAGGTAT AACCGGTGCA AATTTAGTTT TGACCACTTT GAGTGGGTCC
2821  GATTGGCTGA GACGAAAAAC ATATTCTCAA TAAACCCTTT AGGGAAATAG GCCAGGTTTT
      CTAACCGACT GCTGCTTTTG TATAAGAGTT ATTTGGGAAA TCCCTTTATC CGGTCCAAAA
2881  CACCGTAACA CGCCACATCT TGCGAATATA TGTGTAGAAA CTGCCGGAAA TCGTCGTGGT
      GTGGCATTGT GCGGTGTAGA ACGCTTATAT ACACATCTTT GACGGCCTTT AGCAGCACCA
2941  ATTCACTCCA GAGCGATGAA AACGTTTCAG TTTGCTCATG GAAAACGGTG TAACAAGGGT
      TAAGTGAGGT CTCGCTACTT TTGCAAAGTC AAACGAGTAC CTTTTGCCAC ATTGTTCCCA
3001  GAACACTATC CCATATCACC AGCTCACCGT CTTTCATTGC CATACGGAAC TCCGGATGAG
      CTTGTGATAG GGTATAGTGG TCGAGTGGCA GAAAGTAACG GTATGCCTTG AGGCCTACTC
3061  CATTCATCAG GCGGGCAAGA ATGTGAATAA AGGCCGGATA AAACTTGTGC TTATTTTTCT
      GTAAGTAGTC CGCCCGTTCT TACACTTATT TCCGGCCTAT TTTGAACACG AATAAAAAGA
3121  TTACGGTCTT TAAAAAGGCC GTAATATCCA GCTGAACGGT CTGGTTATAG GTACATTGAG
      AATGCCAGAA ATTTTTCCGG CATTATAGGT CGACTTGCCA GACCAATATC CATGTAACTC
3181  CAACTGACTG AAATGCCTCA AAATGTTCTT TACGATGCCA TTGGGATATA TCAACGGTGG
      GTTGACTGAC TTTACGGAGT TTTACAAGAA ATGCTACGGT AACCCTATAT AGTTGCCACC
3241  TATATCCAGT GATTTTTTTC TCCATTTTAG CTTCCTTAGC TCCTGAAAAT CTCGATAACT
      ATATAGGTCA CTAAAAAAAG AGGTAAAATC GAAGGAATCG AGGACTTTTA GAGCTATTGA
3301  CAAAAAATAC GCCCGGTAGT GATCTTATTT CATTATGGTG AAAGTTGGAA CCTCTTACGT
      GTTTTTTATG CGGGCCATCA CTAGAATAAA GTAATACCAC TTTCAACCTT GGAGAATGCA
3361  GCCGATCAAC GTCTCATTTT CGCCAAAAGT TGGCCCAGGG CTTCCCGGTA TCAACAGGGA
      CGGCTAGTTG CAGAGTAAAA GCGGTTTTCA ACCGGGTCCC GAAGGGCCAT AGTTGTCCCT
3421  CACCAGGATT TATTTATTCT GCGAAGTGAT CTTCCGTCAC AGGTATTTAT TCGGCGCAAA
      GTGGTCCTAA ATAAATAAGA CGCTTCACTA GAAGGCAGTG TCCATAAATA AGCCGCGTTT
3481  GTGCGTCGGG TGATGCTGCC AACTTACTGA TTTAGTGTAT GATGGTGTTT TTGAGGTGCT
      CACGCAGCCC ACTACGACGG TTGAATGACT AAATCACATA CTACCACAAA AACTCCACGA
3541  CCAGTGGCTT CTGTTTCTAT CAGCTGTCCC TCCTGTTCAG CTACTGACGG GGTGGTGCGT
      GGTCACCGAA GACAAAGATA GTCGACAGGG AGGACAAGTC GATGACTGCC CCACCACGCA
3601  AACGGCAAAA GCACCGCCGG ACATCAGCGC TAGCGGAGTG TATACTGGCT TACTATGTTG
      TTGCCGTTTT CGTGGCGGCC TGTAGTCGCG ATCGCCTCAC ATATGACCGA ATGATACAAC
3661  GCACTGATGA GGGTGTCAGT GAAGTGCTTC ATGTGGCAGG AGAAAAAAGG CTGCACCGGT
      CGTGACTACT CCCACAGTCA CTTCACGAAG TACACCGTCC TCTTTTTTCC GACGTGGCCA
3721  GCGTCAGCAG AATATGTGAT ACAGGATATA TTCCGCTTCC TCGCTCACTG ACTCGCTACG
      CGCAGTCGTC TTATACACTA TGTCCTATAT AAGGCGAAGG AGCGAGTGAC TGAGCGATGC
3781  CTCGGTCGTT CGACTGCGGC GAGCGGAAAT GGCTTACGAA CGGGGCGGAG ATTTCCTGGA
      GAGCCAGCAA GCTGACGCCG CTCGCCTTTA CCGAATGCTT GCCCCGCCTC TAAAGGACCT
3841  AGATGCCAGG AAGATACTTA ACAGGGAAGT GAGAGGGCCG CGGCAAAGCC GTTTTTCCAT
```

Fig. 48$_2$

```
      TCTACGGTCC TTCTATGAAT TGTCCCTTCA CTCTCCCGGC GCCGTTTCGG CAAAAAGGTA
3901  AGGCTCCGCC CCCCTGACAA GCATCACGAA ATCTGACGCT CAAATCAGTG GTGGCGAAAC
      TCCGAGGCGG GGGGACTGTT CGTAGTGCTT TAGACTGCGA GTTTAGTCAC CACCGCTTTG
3961  CCGACAGGAC TATAAAGATA CCAGGCGTTT CCCCTGGCGG CTCCCTCGTG CGCTCTCCTG
      GGCTGTCCTG ATATTTCTAT GGTCCGCAAA GGGGACCGCC GAGGGAGCAC GCGAGAGGAC
4021  TTCCTGCCTT TCGGTTTACC GGTGTCATTC CGCTGTTATG GCCGCGTTTG TCTCATTCCA
      AAGGACGGAA AGCCAAATGG CCACAGTAAG GCGACAATAC CGGCGCAAAC AGAGTAAGGT
4081  CGCCTGACAC TCAGTTCCGG GTAGGCAGTT CGCTCCAAGC TGGACTGTAT GCACGAACCC
      GCGGACTGTG AGTCAAGGCC CATCCGTCAA GCGAGGTTCG ACCTGACATA CGTGCTTGGG
4141  CCCGTTCAGT CCGACCGCTG CGCCTTATCC GGTAACTATC GTCTTGAGTC CAACCCGGAA
      GGGCAAGTCA GGCTGGCGAC GCGGAATAGG CCATTGATAG CAGAACTCAG GTTGGGCCTT
4201  AGACATGCAA AAGCACCACT GGCAGCAGCC ACTGGTAATT GATTTAGACG AGTTAGTCTT
      TCTGTACGTT TTCGTGGTGA CCGTCGTCGG TGACCATTAA CTAAATCTCC TCAATCAGAA
4261  GAAGTCATGC GCCGGTTAAG GCTAAACTGA AAGGACAAGT TTTGGTGACT GCGCTCCTCC
      CTTCAGTACG CGGCCAATTC CGATTTGACT TTCCTGTTCA AAACCACTGA CGCGAGGAGG
4321  AAGCCAGTTA CCTCGGTTCA AAGAGTTGGT AGCTCAGAGA ACCTTCGAAA AACCGCCCTG
      TTCGGTCAAT GGAGCCAAGT TTCTCAACCA TCGAGTCTCT TGGAAGCTTT TTGGCGGGAC
4381  CAAGGCGGTT TTTTCGTTTT CAGAGCAAGA GATTACGCGC AGACCAAAAC GATCTCAAGA
      GTTCCGCCAA AAAAGCAAAA GTCTCGTTCT CTAATGCGCG TCTGGTTTTG CTAGAGTTCT
4441  AGATCATCTT ATTAATCAGA TAAAATATTT CTAGATTTCA GTGCAATTTA TCTCTTCAAA
      TCTAGTAGAA TAATTAGTCT ATTTTATAAA GATCTAAAGT CACGTTAAAT AGAGAAGTTT
4501  TGTAGCACCT GAAGTCAGCC CCATACGATA TAAGTTGTAA TTCTCATGTT AGTCATGCCC
      ACATCGTGGA CTTCAGTCGG GGTATGCTAT ATTCAACATT AAGAGTACAA TCAGTACGGG
4561  CGCGCCCACC GGAAGGAGCT GACTGGGTTG AAGGCTCTCA AGGGCATCGG TCGAGATCCC
      GCGCGGGTGG CCTTCCTCGA CTGACCCAAC TTCCGAGAGT TCCCGTAGCC AGCTCTAGGG
4621  GGTGCCTAAT GAGTGAGCTA ACTTACATTA ATTGCGTTGC GCTCACTGCC CGCTTTCCAG
      CCACGGATTA CTCACTCGAT TGAATGTAAT TAACGCAACG CGAGTGACGG GCGAAAGGTC
4681  TCGGGAAACC TGTCGTGCCA GCTGCATTAA TGAATCGGCC AACGCGCGGG GAGAGGCGGT
      AGCCCTTTGG ACAGCACGGT CGACGTAATT ACTTAGCCGG TTGCGCGCCC CTCTCCGCCA
4741  TTGCGTATTG GGCGCCAGGG TGGTTTTTCT TTTCACCAGT GAGACGGGCA ACAGCTGATT
      AACGCATAAC CCGCGGTCCC ACCAAAAGA AAAGTGGTCA CTCTGCCCGT TGTCGACTAA
4801  GCCCTTCACC GCCTGGCCCT GAGAGAGTTG CAGCAAGCGG TCCACGCTGG TTTGCCCCAG
      CGGGAAGTGG CGGACCGGGA CTCTCTCAAC GTCGTTCGCC AGGTGCGACC AAACGGGGTC
4861  CAGGCGAAAA TCCTGTTTGA TGGTGGTTAA CGGCGGGATA TAACATGAGC TGTCTTCGGT
      GTCCGCTTTT AGGACAAACT ACCACCAATT GCCGCCCTAT ATTGTACTCG ACAGAAGCCA
4921  ATCGTCGTAT CCCACTACCG AGATGTCCGC ACCAACGCGC AGCCCGGACT CGGTAATGGC
      TAGCAGCATA GGGTGATGGC TCTACAGGCG TGGTTGCGCG TCGGGCCTGA GCCATTACCG
4981  GCGCATTGCG CCCAGCGCCA TCTGATCGTT GGCAACCAGC ATCGCAGTGG GAACGATGCC
      CGCGTAACGC GGGTCGCGGT AGACTAGCAC CCGTTGGTCG TAGCGTCACC CTTGCTACGG
5041  CTCATTCAGC ATTTGCATGG TTTGTTGAAA ACCGGACATG GCACTCCAGT CGCCTTCCCG
      GAGTAAGTCG TAAACGTACC AAACAACTTT TGGCCTGTAC CGTGAGGTCA GCGGAAGGGC
5101  TTCCGCTATC GGCTGAATTT GATTGCGAGT GAGATATTTA TGCCAGCCAG CCAGACGCAG
      AAGGCGATAG CCGACTTAAA CTAACGCTCA CTCTATAAAT ACGGTCGGTC GGTCTGCGTC
5161  ACGCGCCGAG ACAGAACTTA ATGGGCCCGC TAACAGCGCG ATTTGCTGGT GACCCAATGC
      TGCGCGGCTC TGTCTTGAAT TACCCGGGCG ATTGTCGCGC TAAACGACCA CTGGGTTACG
5221  GACCAGATGC TCCACGCCCA GTCGCGTACC GTCTTCATGG GAGAAAATAA TACTGTTGAT
      CTGGTCTACG AGGTGCGGGT CAGCGCATGG CAGAAGTACC CTCTTTTATT ATGACAACTA
5281  GGGTGTCTGG TCAGAGACAT CAAGAAATAA CGCCGGAACA TTAGTGCAGG CAGCTTCCAC
      CCCACAGACC AGTCTCTGTA GTTCTTTATT GCGGCCTTGT AATCACGTCC GTCGAAGGTG
5341  AGCAATGGCA TCCTGGTCAT CCAGCGGATA GTTAATGATC AGCCCACTGA CGCGTTGCGC
      TCGTTACCGT AGGACCAGTA GGTCGCCTAT CAATTACTAG TCGGGTGACT GCGCAACGCG
5401  GAGAAGATTG TGCACCGCCG CTTTACAGGC TTCGACGCCC CTTCGTTCTA CCATCGACAC
      CTCTTCTAAC ACGTGGCGGC GAAATGTCCG AAGCTGCGGC GAAGCAAGAT GGTAGCTGTG
5461  CACCACGCTG GCACCCAGTT GATCGGCGCG AGATTAATC GCCGCGACAA TTTGCGACGG
      GTGGTGCGAC CGTGGGTCAA CTAGCCGCGC TCTAAATTAG CGGCGCTGTT AAACGCTGCC
5521  CGCGTCGCAG GCCAGACTGG AGGTGGCAAC GCCAATCAGC AACGACTGTT TGCCCGCCAG
      GCGCACGTCC GGTCTGACCT CCACCGTTG CGGTTAGTCG TTGCTGACAA ACGGGCGGTC
5581  TTGTTGTGCC ACGCGGTTGG GAATGTAATT CAGCTCCGCC ATCGCCGCTT CCACTTTTTC
      AACAACACGG TGCGCCAACC CTTACATTAA GTCGAGGCGG TAGCGGCGAA GGTGAAAAAG
5641  CCGCGTTTTC GCAGAAACGT GGCTGGCCTG GTTCACCACG CGGGAAACGG TCTGATAAGA
      GGCGCAAAAG CGTCTTTGCA CCGACCGGAC CAAGTGGTGC GCCCTTTGCC AGACTATTCT
5701  GACACCGGCA TACTCTGCGA CATCGTATAT CGTTACTGGT TTCACATTCA CCACCCTGAA
      CTGTGGCCGT ATGAGACGCT GTAGCATATT GCAATGACCA AAGTGTAAGT GGTGGGACTT
5761  TTGACTCTCT TCCGGGCGCT ATCATGCCAT ACCGCGAAAG GTTTTGCGCC ATTCGATGGT
      AACTGAGAGA AGGCCCGCGA TAGTACGGTA TGGCGCTTTC CAAAACGCGG TAAGCTACCA
5821  GTCCGGGATC TCGACGCTCT CCCTTATGCG ACT
      CAGGCCCTAG AGCTGCGAGA GGGAATACGC TGA
```

Fig. 48₃

| Fig. 50₁ |
|---|
| Fig. 50₂ |
| Fig. 50₃ |
| Fig. 50₄ |

Fig. 50

```
                EcoNI
                ~~~~~~~~~~
      1   CCTGCATTAG GAAGCAGCCC AGTAGTAGGT TGAGGCCGTT GAGCACCGCC GCCGCAAGGA
          GGACGTAATC CTTCGTCGGG TCATCATCCA ACTCCGGCAA CTCGTGGCGG CGGCGTTCCT
     61   ATGGTGCATG CAAGGAGATG GCGCCCAACA GTCCCCCGGC CACGGGGCCT GCCACCATAC
          TACCACGTAC GTTCCTCTAC CGCGGGTTGT CAGGGGCCG GTGCCCCGGA CGGTGGTATG
    121   CCACGCCGAA ACAAGCGCTC ATGAGCCCGA AGTGGCGAGC CCGATCTTCC CCATCGGTGA
          GGTGCGGCTT TGTTCGCGAG TACTCGGGCT TCACCGCTCG GGCTAGAAGG GGTAGCCACT
    181   TGTCGGCGAT ATAGGCGCCA GCAACCGCAC CTGTGGCGCC GGTGATGCCG GCCACGATGC
          ACAGCCGCTA TATCCGCGGT CGTTGGCGTG GACACCGCGG CCACTACGGC CGGTGCTACG
    241   GTCCGGCGTA GAGGATCGAG ATCTCGATCC CGCGAAATTA ATACGACTCA CTATAGGGGA
          CAGGCCGCAT CTCCTAGCTC TAGAGCTAGG GCGCTTTAAT TATGCTGAGT GATATCCCCT
    301   ATTGTGAGCG GATAACAATT CCCCTCTAGA AATAATTTTG TTTAACTTTA AGAAGGAGAT
          TAACACTCGC CTATTGTTAA GGGGAGATCT TTATTAAAAC AAATTGAAAT TCTTCCTCTA
    361   ATACATATGA AATACCTGCT GCCGACCGCT GCTGCTGGTC TGCTGCTCCT CGCTGCCCAG
          TATGTATACT TTATGGACGA CGGCTGGCGA CGACGACCAG ACGACGAGGA GCGACGGGTC
                                                       EcoRI
                                                       ~~~~~~~
              NcoI                    BamHI      SacI
              ~~~~~~                  ~~~~~~     ~~~~~~
    421   CCGGCGATGG CCATGGATAT CGGAATTAAT TCGGATCCGA ATTCGAGCTC GATCACAAGT
          GGCCGCTACC GGTACCTATA GCCTTAATTA AGCCTAGGCT TAAGCTCGAG CTAGTGTTCA
    481   TTGTACAAAA AAGCTGAACG AGAAACGTAA AATGATATAA ATATCAATAT ATTAAATTAG
          AACATGTTTT TTCGACTTGC TCTTTGCATT TTACTATATT TATAGTTATA TAATTTAATC
    541   ATTTTGCATA AAAAACAGAC TACATAATAC TGTAAAACAC AACATATCCA GTCACTATGG
          TAAAACGTAT TTTTTGTCTG ATGTATTATG ACATTTTGTG TTGTATAGGT CAGTGATACC
    601   CGGCCGCCAC GTTAAGGGAT TTTGGTCATG ATCAGCACGT GTTGACAATT AATCATCGGC
          GCCGGCGGTG CAATTCCCTA AAACCAGTAC TAGTCGTGCA CAACTGTTAA TTAGTAGCCG
                                                                   NcoI
                                                                   ~~~~~~~
    661   ATAGTATATC GGCATAGTAT AATACGACAA GGTGAGGAAC TAAACCATGG CCAAGTTGAC
          TATCATATAG CCGTATCATA TTATGCTGTT CCACTCCTTG ATTTGGTACC GGTTCAACTG
    721   CAGTGCCGTT CCGGTGCTCA CCGCGCGCGA CGTCGCCGGA GCGGTCGAGT CTGGACCGA
          GTCACGGCAA GGCCACGAGT GGCGCGCGCT GCAGCGGCCT CGCCAGCTCA AGACCTGGCT
              AvaI        AvaI
              ~~~~~~      ~~~~~~~
    781   CCGGCTCGGG TTCTCCCGGG ACTTCGTGGA GGACGACTTC GCCGGTGTGG TCCGGGACGA
          GGCCGAGCCC AAGAGGGCCC TGAAGCACCT CCTGCTGAAG CGGCCACACC AGGCCCTGCT
    841   CGTGACCCTG TTCATCAGCG CGGTCCAGGA CCAGGTGGTG CCGGACAACA CCCTGGCCTG
          GCACTGGGAC AAGTAGTCGC GCCAGGTCCT GGTCCACCAC GGCCTGTTGT GGGACCGGAC
    901   GGTGTGGGTG CGCGGCCTGG ACGAGCTGTA CGCCGAGTGG TCGGAGGTCG TGTCCACGAA
          CCACACCCAC GCGCCGGACC TGCTCGACAT GCGGCTCACC AGCCTCCAGC ACAGGTGCTT
    961   CTTCCGGGAC GCCTCCGGC CGGCCATGAC CGAGATCGGC GAGCAGCCGT GGGGCGGGA
          GAAGGCCCTG CGGAGGCCG GCCGGTACTG GCTCTAGCCG CTCGTCGGCA CCCCGCCCT
   1021   GTTCGCCCTG CGCGACCCGG CCGGCAACTG CGTGCACTTC GTGGCCGAGG AGCAGGACTG
          CAAGCGGGAC GCGCTGGGCC GGCCGTTGAC GCACGTGAAG CACCGGCTCC TCGTCCTGAC
   1081   ATCATGATGA TATTATTTTA TCTTGTGCAA TGTAACATCA GAGATTTTGA GACACGGGCC
          TAGTACTACT ATAATAAAAT AGAACACGTT ACATTGTAGT CTCTAAAACT CTGTGCCCGG
   1141   AGAGCTGCCA GGAAACAGCT ATGACCATGT AATACGACTC ACTATAGGGG ATATCAGCTG
          TCTCGACGGT CCTTTGTCGA TACTGGTACA TTATGCTGAG TGATATCCCC TATAGTCGAC
   1201   GATGGCAAAT AATGATTTTA TTTTGACTGA TAGTGACCTG TTCGTTGCAA CACCGGTGCT
          CTACCGTTTA TTACTAAAAT AAAACTGACT ATCACTGGAC AAGCAACGTT GTGGCCACGA
   1261   AGCGTATACC CGAAGTATGT CAAAAAGAGG TGTGCTATGA AGCAGCGTAT TACAGTGACA
          TCGCATATGG GCTTCATACA GTTTTTCTCC ACACGATACT TCGTCGCATA ATGTCACTGT
   1321   GTTGACAGCG ACAGCTATCA GTTGCTCAAG GCATATATGA TGTCAATATC TCCGGTCTGG
          CAACTGTCGC TGTCGATAGT CAACGAGTTC CGTATATACT ACAGTTATAG AGGCCAGACC
   1381   TAAGCACAAC CATGCAGAAT GAAGCCCGTC GTCTGCGTGC CGAACGCTGG AAAGCGGAAA
          ATTCGTGTTG GTACGTCTTA CTTCGGGCAG CAGACGCACG GCTTGCGACC TTTCGCCTTT
   1441   ATCAGGAAGG GATGGCTGAG GTCGCCCGGT TTATTGAAAT GAACGGCTCT TTTGCTGACG
          TAGTCCTTCC CTACCGACTC CAGCGGGCCA AATAACTTTA CTTGCCGAGA AAACGACTGC
   1501   AGAACAGGGA CTGGTGAAAT GCAGTTTAAG GTTTACACCT ATAAAAGAGA GAGCCGTTAT
          TCTTGTCCCT GACCACTTTA CGTCAAATTC CAAATGTGGA TATTTTCTCT CTCGGCAATA
                                                            AvaI
                                                            ~~~~~~~
   1561   CGTCTGTTTG TGGATGTACA GAGTGATATT ATTGACACGC CGGGCGACG GATGGTGATC
          GCAGACAAAC ACCTACATGT CTCACTATAA TAACTGTGCG GCCCGCTGC CTACCACTAG
   1621   CCCCTGGCCA GTGCACGTCT GCTGTCAGAT AAAGTCTCCC GTGAACTTTA CCCGGTGGTG
          GGGGACCGGT CACGTGCAGA CGACAGTCTA TTTCAGAGGG CACTTGAAAT GGGCCACCAC
   1681   CATATCGGGG ATGAAAGCTG GCGCATGATG ACCACCAGTG TGGCCAGTGT GCCGGTCTCC
          GTATAGCCCC TACTTTCGAC CGCGTACTAC TGGTGGTCAC ACCGGTCACA CGGCCAGAGG
   1741   GTTATCGGGG AAGAAGTGGC TGATCTCAGC CGCCGCGAAA ATGCATCAA AAACGCCATT
```

Fig. 50₁

```
              CAATAGCCCC TTCTTCACCG ACTAGAGTCG GCGGCGCTTT TACTGTAGTT TTTGCGGTAA
                                                                    PstI
                                                                    ~~~~~~
        1801  AACCTGATGT TCTGGGGAAT ATAAATGTCA GGCTCCCTTA TACACAGCCA GTCTGCAGGT
              TTGGACTACA AGACCCCTTA TATTTACAGT CCGAGGGAAT ATGTGTCGGT CAGACGTCCA
        1861  CGACCATAGT GACTGGATAT GTTGTGTTTT ACAGTATTAT GTAGTCTGTT TTTTATGCAA
              GCTGGTATCA CTGACCTATA CAACACAAAA TGTCATAATA CATCAGACAA AAAATACGTT
        1921  AATCTAATTT AATATATTGA TATTTATATC ATTTTACGTT TCTCGTTCAG CTTTCTTGTA
              TTAGATTAAA TTATATAACT ATAAATATAG TAAAATGCAA AGAGCAAGTC GAAAGAACAT
                                                             HindIII
                                                             ~~~~~~~
        1981  CAAAGTGGTG ATAATTAATT AAGATCAGAT CCGGCTGCTA AGCTTGCGGC CGCATAATGC
              GTTTCACCAC TATTAATTAA TTCTAGTCTA GGCCGACGAT TCGAACGCCG GCGTATTACG
        2041  TTAAGTCGAA CAGAAAGTAA TCGTATTGTA CACGGCCGCA TAATCGAAAT TAATACGACT
              AATTCAGCTT GTCTTTCATT AGCATAACAT GTGCCGGCGT ATTAGCTTTA ATTATGCTGA
        2101  CACTATAGGG GAATTGTGAG CGGATAACAA TTCCCCATCT TAGTATATTA GTTAAGTATA
              GTGATATCCC CTTAACACTC GCCTATTGTT AAGGGGTAGA ATCATATAAT CAATTCATAT
        2161  AGAAGGAGAT ATACATATGG CAGATCTCAA TTGGATATCG GCCGGCCACG CGATCGCTGA
              TCTTCCTCTA TATGTATACC GTCTAGAGTT AACCTATAGC CGGCCGGTGC GCTAGCGACT
                              AvaI
                              ~~~~~~
        2221  CGTCGGTACC CTCGAGTCTG GTAAAGAAAC CGCTGCTGCG AAATTTGAAC GCCAGCACAT
              GCAGCCATGG GAGCTCAGAC CATTTCTTTG GCGACGACGC TTTAAACTTG CGGTCGTGTA
                                       AvrII
                                       ~~~~~~~
        2281  GGACTCGTCT ACTAGCGCAG CTTAATTAAC CTAGGCTGCT GCCACCGCTG AGCAATAACT
              CCTGAGCAGA TGATCGCGTC GAATTAATTG GATCCGACGA CGGTGGCGAC TCGTTATTGA
        2341  AGCATAACCC CTTGGGGCCT CTAAACGGGT CTTGAGGGGT TTTTTGCTGA AAGGAGGAAC
              TCGTATTGGG GAACCCCGGA GATTTGCCCA GAACTCCCCA AAAAACGACT TTCCTCCTTG
        2401  TATATCCGGA TTGGCGAATG GGACGCGCCC TGTAGCGGCG CATTAAGCGC GGCGGGTGTG
              ATATAGGCCT AACCGCTTAC CCTGCGCGGG ACATCGCCGC GTAATTCGCG CCGCCCACAC
        2461  GTGGTTACGC GCAGCGTGAC CGCTACACTT GCCAGCGCCC TAGCGCCCGC TCCTTTCGCT
              CACCAATGCG CGTCGCACTG GCGATGTGAA CGGTCGCGGG ATCGCGGGCG AGGAAAGCGA
        2521  TTCTTCCCTT CCTTTCTCGC CACGTTCGCC GGCTTTCCCC GTCAAGCTCT AAATCGGGGG
              AAGAAGGGAA GGAAAGAGCG GTGCAAGCGG CCGAAGGGGG CAGTTCGAGA TTTAGCCCCC
        2581  CTCCCTTTAG GGTTCCGATT TAGTGCTTTA CGGCACCTCG ACCCCAAAAA ACTTGATTAG
              GAGGGAAATC CCAAGGCTAA ATCACGAAAT GCCGTGGAGC TGGGGTTTTT TGAACTAATC
        2641  GGTGATGGTT CACGTAGTGG GCCATCGCCC TGATGACGGT TTTTTCGCTT TTTGACGTTG
              CCACTACCAA GTGCATCACC CGGTAGCGGG ACTATCTGCC AAAAAGCGGG AAACTGCAAC
        2701  GAGTCCACGT TCTTTAATAG TGGACTCTTG TTCCAAACTG GAACAACACT CAACCCTATC
              CTCAGGTGCA AGAAATTATC ACCTGAGAAC AAGGTTTGAC CTTGTTGTGA GTTGGGATAG
        2761  TCGGTCTATT CTTTTGATTT ATAAGGGATT TTGCCGATTT CGGCCTATTG GTTAAAAAAT
              AGCCAGATAA GAAAACTAAA TATTCCCTAA AACGGCTAAA GCCGGATAAC CAATTTTTTA
        2821  GAGCTGATTT AACAAAAATT TAACGCGAAT TTTAACAAAA TATTAACGTT TACAATTTCT
              CTCGACTAAA TTGTTTTTAA ATTGCGCTTA AAATTGTTTT ATAATTGCAA ATGTTAAAGA
        2881  GGCGGCACGA TGGCATGAGA TTATCAAAAA GGATCTTCAC CTAGATCCTT TTAAATTAAA
              CCGCCGTGCT ACCGTACTCT AATAGTTTTT CCTAGAAGTG GATCTAGGAA AATTTAATTT
        2941  AATGAAGTTT TAAATCAATC TAAAGTATAT ATGAGTAAAC TTGGTCTGAC AGTTACCAAT
              TTACTTCAAA ATTTAGTTAG ATTTCATATA TACTCATTTG AACCAGACTG TCAATGGTTA
        3001  GCTTAATCAG TGAGGCACCT ATCTCAGCGA TCTGTCTATT TCGTTCATCC ATAGTTGCCT
              CGAATTAGTC ACTCCGTGGA TAGAGTCGCT AGACAGATAA AGCAAGTAGG TATCAACGGA
        3061  GACTCCCCGT CGTGTAGATA ACTACGATAC GGGAGGGCTT ACCATCTGGC CCCAGTGCTG
              CTGAGGGGCA GCACATCTAT TGATGCTATG CCCTCCCGAA TGGTAGACCG GGGTCACGAC
        3121  CAATGATACC GCGAGACCCA CGCTCACCGG CTCCAGATTT ATCAGCAATA AACCAGCCAG
              GTTACTATGG CGCTCTGGGT GCGAGTGGCC GAGGTCTAAA TAGTCGTTAT TTGGTCGGTC
        3181  CCGGAAGGGC CGAGCGCAGA AGTGGTCCTG CAACTTTATC CGCCTCCATC CAGTCTATTA
              GGCCTTCCCG GCTCGCGTCT TCACCAGGAC GTTGAAATAG GCGGAGGTAG GTCAGATAAT
        3241  ATTGTTGCCG GGAAGCTAGA GTAAGTAGTT CGCCAGTTAA TAGTTTGCGC AACGTTGTTG
              TAACAACGGC CCTTCGATCT CATTCATCAA GCGGTCAATT ATCAAACGCG TTGCAACAAC
        3301  CCATTGCTAC AGGCATCGTG GTGTCACGCT CGTCGTTTGG TATGGCTTCA TTCAGCTCCG
              GGTAACGATG TCCGTAGCAC CACAGTGCGA GCAGCAAACC ATACCGAAGT AAGTCGAGGC
        3361  GTTCCCAACG ATCAAGGCGA GTTACATGAT CCCCCATGTT GTGCAAAAAA GCGGTTAGCT
              CAAGGGTTGC TAGTTCCGCT CAATGTACTA GGGGGTACAA CACGTTTTTT CGCCAATCGA
        3421  CCTTCGGTCC TCCGATCGTT GTCAGAAGTA AGTTGGCCGC AGTGTTATCA CTCATGGTTA
              GGAAGCCAGG AGGCTAGCAA CAGTCTTCAT TCAACCGGCG TCACAATAGT GAGTACCAAT
        3481  TGGCAGCACT GCATAATTCT CTTACTGTCA TGCCATCCGT AAGATGCTTT TCTGTGACTG
              ACCGTCGTGA CGTATTAAGA GAATGACAGT ACGGTAGGCA TTCTACGAAA AGACACTGAC
        3541  GTGAGTACTC AACCAAGTCA TTCTGAGAAT AGTGTATGCG GCGACCGAGT TGCTCTTGCC
              CACTCATGAG TTGGTTCAGT AAGACTCTTA TCACATACGC CGCTGGCTCA ACGAGAACGG
        3601  CGGCGTCAAT ACGGGATAAT ACCGCGCCAC ATAGCAGAAC TTTAAAAGTG CTCATCATTG
              GCCGCAGTTA TGCCCTATTA TGGCGCGGTG TATCGTCTTG AAATTTTCAC GAGTAGTAAC
```

Fig. 50₂

```
3661  GAAAACGTTC TTCGGGGCGA AAACTCTCAA GGATCTTACC GCTGTTGAGA TCCAGTTCGA
      CTTTTGCAAG AAGCCCCGCT TTTGAGAGTT CCTAGAATGG CGACAACTCT AGGTCAAGCT
3721  TGTAACCCAC TCGTGCACCC AACTGATCTT CAGCATCTTT TACTTTCACC AGCGTTTCTG
      ACATTGGGTG AGCACGTGGG TTGACTAGAA GTCGTAGAAA ATGAAAGTGG TCGCAAAGAC
3781  GGTGAGCAAA AACAGGAAGG CAAAATGCCG CAAAAAAGGG AATAAGGGCG ACACGGAAAT
      CCACTCGTTT TTGTCCTTCC GTTTTACGGC GTTTTTTCCC TTATTCCCGC TGTGCCTTTA
3841  GTTGAATACT CATACTCTTC CTTTTTCAAT CATGATTGAA GCATTTATCA GGGTTATTGT
      CAACTTATGA GTATGAGAAG GAAAAAGTTA GTACTAACTT CGTAAATAGT CCCAATAACA
3901  CTCATGAGCG GATACATATT TGAATGTATT TAGAAAAATA AACAAATAGG TCATGACCAA
      GAGTACTCGC CTATGTATAA ACTTACATAA ATCTTTTTAT TTGTTTATCC AGTACTGGTT
3961  AATCCCTTAA CGTGAGTTTT CGTTCCACTG AGCGTCAGAC CCCGTAGAAA AGATCAAAGG
      TTAGGGAATT GCACTCAAAA GCAAGGTGAC TCGCAGTCTG GGGCATCTTT TCTAGTTTCC
4021  ATCTTCTTGA GATCCTTTTT TTCTGCGCGT AATCTGCTGC TTGCAAACAA AAAAACCACC
      TAGAAGAACT CTAGGAAAAA AAGACGCGCA TTAGACGACG AACGTTTGTT TTTTTGGTGG
4081  GCTACCAGCG GTGGTTTGTT TGCCGGATCA AGAGCTACCA ACTCTTTTTC CGAAGGTAAC
      CGATGGTCGC CACCAAACAA ACGGCCTAGT TCTCGATGGT TGAGAAAAAG GCTTCCATTG
4141  TGGCTTCAGC AGAGCGCAGA TACCAAATAC TGTCCTTCTA GTGTAGCCGT AGTTAGGCCA
      ACCGAAGTCG TCTCGCGTCT ATGGTTTATG ACAGGAAGAT CACATCGGCA TCAATCCGGT
4201  CCACTTCAAG AACTCTGTAG CACCGCCTAC ATACCTGCTC TGCTAATCC TGTTACCAGT
      GGTGAAGTTC TTGAGACATC GTGGCGGATG TATGGAGCGA GACGATTAGG ACAATGGTCA
4261  GGCTGCTGCC AGTGGCGATA AGTCGTGTCT TACCGGGTTG GACTCAAGAC GATAGTTACC
      CCGACGACGG TCACCGCTAT TCAGCACAGA ATGGCCCAAC CTGAGTTCTG CTATCAATGG
4321  GGATAAGGCG CAGCGGTCGG GCTGAACGGG GGGTTCGTGC ACACAGCCCA GCTTGGAGCG
      CCTATTCCGC GTCGCCAGCC CGACTTGCCC CCCAAGCACG TGTGTCGGGT CGAACCTCGC
4381  AACGACCTAC ACCGAACTGA GATACCTACA GCGTGAGCTA TGAGAAAGCG CCACGCTTCC
      TTGCTGGATG TGGCTTGACT CTATGGATGT CGCACTCGAT ACTCTTTCGC GGTGCGAAGG
4441  CGAAGGGAGA AAGGCGGACA GGTATCCGGT AAGCGGCAGG GTCGGAACAG GAGAGCGCAC
      GCTTCCCTCT TTCCGCCTGT CCATAGGCCA TTCGCCGTCC CAGCCTTGTC CTCTCGCGTG
4501  GAGGGAGCTT CCAGGGGGAA ACGCCTGGTA TCTTTATAGT CCTGTCGGGT TTCGCCACCT
      CTCCCTCGAA GGTCCCCCTT TGCGGACCAT AGAAATATCA GGACAGCCCA AAGCGGTGGA
4561  CTGACTTGAG CGTCGATTTT TGTGATGCTC GTCAGGGGGG CGGAGCCTAT GGAAAAACGC
      GACTGAACTC GCAGCTAAAA ACACTACGAG CAGTCCCCCC GCCTCGGATA CCTTTTTGCG
4621  CAGCAACGCG GCCTTTTTAC GGTTCCTGGC CTTTTGCTGG CCTTTTGCTC ACATGTTCTT
      GTCGTTGCGC CGGAAAAATG CCAAGGACGG GAAAACGACC GGAAAATGGAG TGTACAAGAA
4681  TCCTGCGTTA TCCCCTGATT CTGTGGATAA CCGTATTACC GCCTTTGAGT GAGCTGATAC
      AGGACGCAAT AGGGGACTAA GACACCTATT GGCATAATGG CGGAAACTCA CTCGACTATG
4741  CGCTCGCCGC AGCCGAACGA CCGAGCGCAG CGAGTCAGTG AGCGAGGAAG CGGAAGAGCG
      GCGAGCGGCG TCGGCTTGCT GGCTCGCGTC GCTCAGTCAC TCGCTCCTTC GCCTTCTCGC
4801  CCTGATGCGG TATTTTCTCC TTACGCATCT GTGCGGTATT TCACACCGCA TATATGGTGC
      GGACTACGCC ATAAAAGAGG AATGCGTAGA CACGCCATAA AGTGTGGCGT ATATACCACG
4861  ACTCTCAGTA CAATCTGCTC TGATGCCGCA TAGTTAAGCC AGTATACACT CCGCTATCGC
      TGAGAGTCAT GTTAGACGAG ACTACGGCGT ATCAATTCGG TCATATGTGA GGCGATAGCG
4921  TACGTGACTG GGTCATGGCT GCGCCCCGAC ACCCGCCAAC ACCCGCTGAC GCGCCCTGAC
      ATGCACTGAC CCAGTACCGA CGCGGGGCTG TGGGCGGTTG TGGGCGACTG CGCGGGACTG
4981  GGGCTTGTCT GCTCCCGGCA TCCGCTTACA GACAAGCTGT GACCGTCTCC GGGAGCTGCA
      CCCGAACAGA CGAGGGCCGT AGGCGAATGT CTGTTCGACA CTGGCAGAGG CCCTCGACGT
5041  TGTGTCAGAG GTTTTCACCG TCATCACCGA AACGCGCGAG GCAGCTGCGG TAAAGCTCAT
      ACACAGTCTC CAAAAGTGGC AGTAGTGGCT TTGCGCGCTC CGTCGACGCC ATTTCGAGTA
5101  CAGCGTGGTC GTGAAGCGAT TCACAGATGT CTGCCTGTTC ATCCGCGTCC AGCTCGTTGA
      GTCGCACCAG CACTTCGCTA AGTGTCTACA GACGGACAAG TAGGCGCAGG TCGAGCAACT
5161  GTTTCTCCAG AAGCGTTAAT GTCTGGCTTC TGATAAAGCG GGCCATGTTA AGGGCGGTTT
      CAAAGAGGTC TTCGCAATTA CAGACCGAAG ACTATTTCGC CCGGTACAAT TCCCGCCAAA
5221  TTTCCTGTTT GGTCACTGAT GCCTCCGTGT AAGGGGGATT TCTGTTCATG GGGGTAATGA
      AAAGGACAAA CCAGTGACTA CGGAGGCACA TTCCCCCTAA AGACAAGTAC CCCCATTACT
5281  TACCGATGAA ACGAGAGAGG ATGCTCACGA TACGGGTTAC TGATGATGAA CATGCCCGGT
      ATGGCTACTT TGCTCTCTCC TACGAGTGCT ATGCCCAATG ACTACTACTT GTACGGGCCA
5341  TACTGGAACG TTGTGAGGGT AAACAACTGG CGGTATGGAT GCGGCGGGAC CAGAGAAAAA
      ATGACCTTGC AACACTCCCA TTTGTTGACC GCCATACCTA CGCCGCCCTG GTCTCTTTTT
5401  TCACTCAGGG TCAATGCCAG CGCTTCGTTA ATACAGATGT AGGTGTTCCA CAGGGTAGCC
      AGTGAGTCCC AGTTACGGTC GCGAAGCAAT TATGTCTACA TCCACAAGGT GTCCCATCGG
5461  AGCAGCATCC TGCGATGCAG ATCCGGAACA TAATGGTGCA GGGCGCTGAC TTCCGCGTTT
      TCGTCGTAGG ACGCTACGTC TAGGCCTTGT ATTACCACGT CCCGCGACTG AAGGCGCAAA
5521  CCAGACTTTA CGAAACACGG AAACCGAAGA CCATTCATGT TGTTGCTCAG GTCGCAGACG
      GGTCTGAAAT GCTTTGTGCC TTTGGCTTCT GGTAAGTACA ACAACGAGTC CAGCGTCTGC
5581  TTTTGCAGCA GCAGTCGCTT CACGTTCGCT CGCGTATCGG TGATTCATTC TGCTAACCAG
      AAAACGTCGT CGTCAGCGAA GTGCAAGCGA GCGCATAGCC ACTAAGTAAG ACGATTGGTC
5641  TAAGGCAACC CCGCCAGCCT AGCCGGGTCC TCAACGCACA GAGCACGATC ATGCTAGTCA
      ATTCCGTTGG GGCGGTCGGA TCGGCCCAGG AGTTGCTGTC CTCGTGCTAG TACGATCAGT
```

Fig. 50₃

```
5701  TGCCCCGCGC CCACCGGAAG GAGCTGACTG GGTTGAAGGC TCTCAAGGGC ATCGGTCGAG
      ACGGGGCGCG GGTGGCCTTC CTCGACTGAC CCAACTTCCG AGAGTTCCCG TAGCCAGCTC
5761  ATCCCGGTGC CTAATGAGTG AGCTAACTTA CATTAATTGC GTTGCGCTCA CTGCCCGCTT
      TAGGGCCACG GATTACTCAC TCGATTGAAT GTAATTAACG CAACGCGAGT GACGGGCGAA
5821  TCCAGTCGGG AAACCTGTCG TGCCAGCTGC ATTAATGAAT CGGCCAACGC GCGGGGAGAG
      AGGTCAGCCC TTTGGACAGC ACGGTCGACG TAATTACTTA GCCGGTTGCG CGCCCCTCTC
5881  GCGGTTTGCG TATTGGGCGC CAGGGTGGTT TTTCTTTTCA CCAGTGAGAC GGGCAACAGC
      CGCCAAACGC ATAACCCGCG GTCCCACCAA AAAGAAAAGT GGTCACTCTG CCCGTTGTCG
5941  TGATTGCCCT TCACCGCCTG GCCCTGAGAG AGTTGCAGCA AGCGGTCCAC GCTGGTTTGC
      ACTAACGGGA AGTGGCGGAC CGGGACTCTC TCAACGTCGT TCGCCAGGTG CGACCAAACG
6001  CCCAGCAGGC GAAAATCCTG TTTGATGGTG GTTAACGGCG GGATATAACA TGAGCTGTCT
      GGGTCGTCCG CTTTTAGGAC AAACTACCAC CAATTGCCGC CCTATATTGT ACTCGACAGA
6061  TCGGTATCGT CGTATCCCAC TACCGAGATG TCCGCACCAA CGCGCAGCCC GGACTCGGTA
      AGCCATAGCA GCATAGGGTG ATGGCTCTAC AGGCGTGGTT GCGCGTCGGG CCTGAGCCAT
6121  ATGGCGCGCA TTGCGCCCAG CGCCATCTGA TCGTTGGCAA CCAGCATCGC AGTGGGAACG
      TACCGCGCGT AACGCGGGTC GCGGTAGACT AGCAACCGTT GGTCGTAGCG TCACCCTTGC
6181  ATGCCCTCAT TCAGCATTTG CATGGTTTGT TGAAAACCGG ACATGGCACT CCAGTCGCCT
      TACGGGAGTA AGTCGTAAAC GTACCAAACA ACTTTTGGCC TGTACCGTGA GGTCAGCGGA
6241  TCCCGTTCCG CTATCGGCTG AATTTGATTG CGAGTGAGAT ATTTATGCCA GCCAGCCAGA
      AGGGCAAGGC GATAGCCGAC TTAAACTAAC GCTCACTCTA TAAATACGGT CGGTCGGTCT
6301  CGCAGACGCG CCGAGACAGA ACTTAATGGG CCCGCTAACA GCGCGATTTG CTGGTGACCC
      GCGTCTGCGC GGCTCTGTCT TGAATTACCC GGGCGATTGT CGCGCTAAAC GACCACTGGG
6361  AATGCGACCA GATGCTCCAC GCCCAGTCGC GTACCGTCTT CATGGGAGAA AATAATACTG
      TTACGCTGGT CTACGAGGTG CGGGTCAGCG CATGGCAGAA GTACCCTCTT TTATTATGAC
6421  TTGATGGGTG TCTGGTCAGA GACATCAAGA ATAACGCCG GAACATTAGT GCAGGCAGCT
      AACTACCCAC AGACCAGTCT CTGTAGTTCT TTATTGCGGC CTTGTAATCA CGTCCGTCGA
6481  TCCACAGCAA TGGCATCCTG GTCATCCAGC GGATAGTTAA TGATCAGCCC ACTGACGCGT
      AGGTGTCGTT ACCGTAGGAC CAGTAGGTCG CCTATCAATT ACTAGTCGGG TGACTGCGCA
6541  TGCGCGAGAA GATTGTGCAC CGCCGCTTTA CAGGCTTCGA CGCCGCTTCG TTCTACCATC
      ACGCGCTCTT CTAACACGTG GCGGCGAAAT GTCCGAAGCT GCGGCGAAGC AAGATGGTAG
6601  GACACCACCA CGCTGGCACC CAGTTGATCG GCGCGAGATT TAATCGCCGC GACAATTTGC
      CTGTGGTGGT GCGACCGTGG GTCAACTAGC CGCGCTCTAA ATTAGCGGCG CTGTTAAACG
6661  GACGGCGCGT GCAGGGCCAG ACTGGAGGTG GCAACGCCAA TCAGCAACGA CTGTTTGCCC
      CTGCCGCGCA CGTCCCGGTC TGACCTCCAC CGTTGCGGTT AGTCGTTGCT GACAAACGGG
6721  GCCAGTTGTT GTGCCACGCG GTTGGGAATG TAATTCAGCT CCGCCATCGC CGCTTCCACT
      CGGTCAACAA CACGGTGCGC CAACCCTTAC ATTAAGTCGA GGCGGTAGCG GCGAAGGTGA
6781  TTTTCCCGCG TTTTCGCAGA AACGTGGCTG GCCTGGTTCA CCACGCGGGA AACGGTCTGA
      AAAAGGGCGC AAAAGCGTCT TTGCACCGAC CGGACCAAGT GGTGCGCCCT TTGCCAGACT
6841  TAAGAGACAC CGGCATACTC TGCGACATCG TATAACGTTA CTGGTTTCAC ATTCACCACC
      ATTCTCTGTG GCCGTATGAG ACGCTGTAGC ATATTGCAAT GACCAAAGTG TAAGTGGTGG
6901  CTGAATTGAC TCTCTTCCGG GCGCTATCAT GCCATACCGC GAAAGGTTTT GCGCCATTCG
      GACTTAACTG AGAGAAGGCC CGCGATAGTA CGGTATGGCG CTTTCCAAAA CGCGGTAAGC
6961  ATGGTGTCCG GGATCTCGAC GCTCTCCCTT ATGCGACT
      TACCACAGGC CCTAGAGCTG CGAGAGGGAA TACGCTGA
```

Fig. 50₄

| Fig. 52$_1$ |
|---|
| Fig. 52$_2$ |
| Fig. 52$_3$ |
| Fig. 52$_4$ |

Fig. 52 pDEST-CMZ1 sequence

```
   1  GGGGAATTGT GAGCGGATAA CAATTCCCCT GTAGAAATAA TTTTGTTTAA CTTTAATAAG
      CCCCTTAACA CTCGCCTATT GTTAAGGGGA CATCTTTATT AAAACAAATT GAAATTATTC
                                                              SacI
                                                              ~~~
  61  GAGATATACC ATGGGCAGCA GCCATCACCA TCATCACCAC AGCCAGGATC CGAATTCGAG
      CTCTATATGG TACCCGTCGT CGGTAGTGGT AGTAGTGGTG TCGGTCCTAG GCTTAAGCTC
      SacI
      ~~~
 121  CTCGGACCAT GATTACGCCA AGCTATCAAC TTTGTATAGA AAAGTTGAAC GAGAAACGTA
      GAGCCTGGTA CTAATGCGGT TCGATAGTTG AAACATATCT TTTCAACTTG CTCTTTGCAT
 181  AAATGATATA AATATCAATA TATTAAATTA GATTTTGCAT AAAAAACAGA CTACATAATA
      TTTACTATAT TTATAGTTAT ATAATTTAAT CTAAAACGTA TTTTTTGTCT GATGTATTAT
 241  CTGTAAAACA CAACATATCC AGTCACTATG GTCGACCTGC AGACTGGCTG TGTATAAGGG
      GACATTTTGT GTTGTATAGG TCAGTGATAC CAGCTGGACG TCTGACCGAC ACATATTCCC
 301  AGCCTGACAT TTATATTCCC CAGAACATCA GGTTAATGGC GTTTTTGATG TCATTTTCGC
      TCGGACTGTA AATATAAGGG GTCTTGTAGT CCAATTACCG CAAAAACTAC AGTAAAAGCG
 361  GGTGGCTGAG ATCAGCCACT TCTTCCCCGA TAACGGAGAC CGGCACACTG GCCATATCGG
      CCACCGACTC TAGTCGGTGA AGAAGGGGCT ATTGCCTCTG GCCGTGTGAC CGGTATAGCC
 421  TGGTCATCAT GCGCCAGCTT TCATCCCCGA TATGCACCAC CGGGTAAAGT TCACGGGGGA
      ACCAGTAGTA CGCGGTCGAA AGTAGGGGCT ATACGTGGTG GCCCATTTCA AGTGCCCCCT
 481  CTTTATCTGA CAGCAGACGT GCACTGGCCA GGGGGATCAC CATCCGTCGC CCGGGCGTGT
      GAAATAGACT GTCGTCTGCA CGTGACCGGT CCCCCTAGTG GTAGGCAGCG GGCCCGCACA
 541  CAATAATATC ACTCTGTACA TCCACAAACA GACGATAACG GCTCTCTCTT TTATAGGTGT
      GTTATTATAG TGAGACATGT AGGTGTTTGT CTGCTATTGC CGAGAGAGAA AATATCCACA
 601  AAACCTTAAA CTGCATTTCA CCGACCCCTG TTCTCGTCGG CAAAAGAGCC GTTCATTTCA
      TTTGGAATTT GACGTAAAGT GGCTGGGGAC AAGAGCAGCC GTTTTCTCGG CAAGTAAAGT
 661  ATAAACCGGG CGACCTCAGC CATCCCTTCC TGATTTTCCG CTTTCCAGCG TTCGGCACGC
      TATTTGGCCC GCTGGAGTCG GTAGGGAAGG ACTAAAAGGC GAAAGGTCGC AAGCCGTGCG
 721  AGACGACGGG CTTCATTCTG CATGGTTGTG CTTACCGAAC CGGAGATATT GACATCATAT
      TCTGCTGCCC GAAGTAAGAC GTACCAACAC GAATGGCTTG GCCTCTATAA CTGTAGTATA
 781  ATGCCTTGAG CAACTGATAG CTGTCGCTGT CAACTGTCAC TGTAATACGC TGCTTCATAG
      TACGGAACTC GTTGACTATC GACAGCGACA GTTGACAGTG ACATTATGCG ACGAAGTATC
 841  CATACCTCTT TTTGACATAC TTCGGGTATA CATATCAGTA TATATTCTTA TACCGCAAAA
      GTATGGAGAA AAACTGTATG AAGCCCATAT GTATAGTCAT ATATAAGAAT ATGGCGTTTT
 901  ATCAGCGCGC AAATACGCAT ACTGTTATCT GGCTTTTAGT AAGCCGGATC CTCTAGATTA
      TAGTCGCGCG TTTATGCGTA TGACAATAGA CCGAAAATCA TTCGGCCTAG GAGATCTAAT
 961  CGCCGACCCG TGCCACTCAT CGCAGTACTG TTGTAATTCA TTAAGCATTC TGCCGACATG
      GCGGGCTGGG CACGGTGAGTA GCGTCATGAC AACATTAAGT AATTCGTAAG ACGGCTGTAC
1021  GAAGCCATCA CAAACGGCAT GATGAACCTG AATCGCCAGC GGCATCAGCA CCTTGTCGCC
      CTTCGGTAGT GTTTGCCGTA CTACTTGGAC TTAGCGGTCG CCGTAGTCGT GGAACAGCGG
1081  TTGCGTATAA TATTTGCCCA TGGTGAAAAC GGGGGCGAAG AAGTTGTCCA TATTGGCCAC
      AACGCATATT ATAAACGGGT ACCACTTTTG CCCCCGCTTC TTCAACAGGT ATAACCGGTG
1141  GTTTAAATCA AAACTGGTGA AACTCACCCA GGGATTGGCT GAGACGAAAA ACATATTCTC
      CAAATTTAGT TTTGACCACT TTGAGTGGGT CCCTAACCGA CTCTGCTTTT TGTATAAGAG
1201  AATAAACCCT TTAGGGAAAT AGGCCAGGTT TTCACCGTAA CACGCCACAT CTTGCGAATA
      TTATTTGGGA AATCCCTTTA TCCGGTCCAA AAGTGGCATT GTGCGGTGTA GAACGCTTAT
1261  TATGTGTAGA AACTGCCGGA AATCGTCGTG GTATTCACTC CAGAGCGATG AAAACGTTTC
      ATACACATCT TTGACGGCCT TTAGCAGCAC CATAAGTGAG GTCTCGCTAC TTTTGCAAAG
1321  AGTTTGCTCA TGGAAAACGG TGTAACAAGG GTGAACACTA TCCCATATCA CCAGCTCACC
      TCAAACGAGT ACCTTTTGCC ACATTGTTCC CACTTGTGAT AGGGTATAGT GGTCGAGTGG
1381  GTCTTTCATT GCCATACGGA ATTCCGGATG AGCATTCATC AGGCGGGCAA GAATGTGAAT
      CAGAAAGTAA CGGTATGCCT TAAGGCCTAC TCGTAAGTAG TCCGCCCGTT CTTACACTTA
1441  AAAGGCCGGA TAAAACTTGT GCTTATTTTT CTTTACGGTC TTTAAAAAGG CCGTAATATC
      TTTCCGGCCT ATTTTGAACA CGAATAAAAA GAAATGCCAG AAATTTTTCC GGCATTATAG
1501  CAGCTGAACG GTCTGGTTAT AGGTACATTG AGCAACTGAC TGAAATGCCT CAAAATGTTC
      GTCGACTTGC CAGACCAATA TCCATGTAAC TCGTTGACTG ACTTTACGGA GTTTTACAAG
1561  TTTACGATGC CATTGGGATA TATCAACGGT GGTATATCCA GTGATTTTTT CTCCATTTTT
      AAATGCTACG GTAACCCTAT ATAGTTGCCA CCATATAGGT CACTAAAAAA GAGGTAAAA
1621  AGCTTCCTTA GCTCCTGAAA ATCTCGACGG ATCCTAACTC AAATCCACA CATTATACGA
      TCGAAGGAAT CGAGGACTTT TAGAGCTGCC TAGGATTGAG TTTAGGTGT GTAATATGCT
1681  GCCGGAAGCA TAAAGTGTAA AGCCTGGGGG TGCCTAATGC GGCCGCCATA GTGACTGGAT
      CGGCCTTCGT ATTTCACATT TCGGACCCCC ACGGATTACG CCGGCGGTAT CACTGACCTA
1741  ATGTTGTGTT TTACAGTATT ATGTAGTCTG TTTTTTATGC AAAATCTAAT TTAATATATT
      TACAACACAA AATGTCATAA TACATCAGAC AAAAAATACG TTTTAGATTA AATTATATAA
1801  GATATTTATA TCATTTTACG TTTCTCGTTC AACTTTATTA TACATAGTTG ATAATTCACT
      CTATAAATAT AGTAAAATGC AAAGAGCAAG TTGAAATAAT ATGTATCAAC TATTAAGTGA
1861  GGCCGTCGTT TTACAACGTC GTGACTGGGA AAACCCTGGC GTTACCCAAC TTAATCGCCT
```

Fig. 52$_1$

```
            CCGGCAGCAA AATGTTGCAG CACTGACCCT TTTGGGACCG CAATGGGTTG AATTAGCGGA
                HindIII
                ~~~~~~~
      1921  TGCAGCACAA GCTTGCGGCC GCATAATGCT TAAGTCGAAC AGAAAGTAAT CGTATTGTAC
            ACGTCGTGTT CGAACGCCGG CGTATTACGA ATTCAGCTTG TCTTTCATTA GCATAACATG
      1981  ACGGCCGCAT AATCGAAATT AATACGACTC ACTATAGGGG AATTGTGAGC GGATAACAAT
            TGCCGGCGTA TTAGCTTTAA TTATGCTGAG TGATATCCCC TTAACACTCG CCTATTGTTA
                                                            NdeI
                                                            ~~~~
      2041  TCCCCATCTT AGTATATTAG TTAAGTATAA GAAGGAGATA TACATATGGA TCACAAGTTT
            AGGGGTAGAA TCATATAATC AATTCATATT CTTCCTCTAT ATGTATACCT AGTGTTCAAA
      2101  GTACAAAAAA GCTGAACGAG AAACGTAAAA TGATATAAAT ATCAATATAT TAAATTAGAT
            CATGTTTTTT CGACTTGCTC TTTGCATTTT ACTATATTTA TAGTTATATA ATTTAATCTA
      2161  TTTGCATAAA AAACAGACTA CATAATACTG TAAAACACAA CATATCCAGT CACTATGGCG
            AAACGTATTT TTTGTCTGAT GTATTATGAC ATTTTGTGTT GTATAGGTCA GTGATACCGC
      2221  GCCGCCACGT TAAGGGATTT TGGTCATGAT CAGCACGTGT TGACAATTAA TCATCGGCAT
            CGGCGGTGCA ATTCCCTAAA ACCAGTACTA GTCGTGCACA ACTGTTAATT AGTAGCCGTA
      2281  AGTATATCGG CATAGTATAA TACGACAAGG TGAGGAACTA AACCATGGCC AAGTTGACCA
            TCATATAGCC GTATCATATT ATGCTGTTCC ACTCCTTGAT TTGGTACCGG TTCAACTGGT
      2341  GTGCCGTTCC GGTGCTCACC GCGCGCGACG TCGCCGGAGC GGTCGAGTTC TGGACCGACC
            CACGGCAAGG CCACGAGTGG CGCGCGCTGC AGCGGCCTCG CCAGCTCAAG ACCTGGCTGG
      2401  GGCTCGGGTT CTCCCGGGAC TTCGTGGAGG ACGACTTCGC CGGTGTGGTC CGGGACGACG
            CCGAGCCCAA GAGGGCCCTG AAGCACCTCC TGCTGAAGCG GCCACACCAG GCCCTGCTGC
      2461  TGACCCTGTT CATCAGCGCG GTCCAGGACC AGGTGGTGCC GGACAACACC CTGGCCTGGG
            ACTGGGACAA GTAGTCGCGC CAGGTCCTGG TCCACCACGG CCTGTTGTGG GACCGGACCC
      2521  TGTGGGTGCG CGGCCTGGAC GAGCTGTACG CCGAGTGGTC GGAGGTCGTG TCCACGAACT
            ACACCCACGC GCCGGACCTG CTCGACATGC GGCTCACCAG CCTCCAGCAC AGGTGCTTGA
      2581  TCCGGACGCC CTCCGGGCCG GCCATGACCG AGATCGGCGA GCAGCCGTGG GGGCGGGAGT
            AGGCCCTGCG GAGGCCCGGC CGGTACTGGC TCTAGCCGCT CGTCGGCACC CCCGCCCTCA
      2641  TCGCCCTGCG CGACCCGGCC GGCAACTGCG TGCACTTCGT GGCCGAGGAG CAGGACTGAT
            AGCGGGACGC GCTGGGCCGG CCGTTGACGC ACGTGAAGCA CCGGCTCCTC GTCCTGACTA
      2701  CATGATGATA TTATTTTATC TTGTGCAATG TAACATCAGA GATTTTGAGA CACGGGCCAG
            GTACTACTAT AATAAAATAG AACACGTTAC ATTGTAGTCT CTAAAACTCT GTGCCCGGTC
      2761  AGCTGCCAGG AAACAGCTAT GACCATGTAA TACGACTCAC TATAGGGGAT ATCGTCTGGA
            TCGACGGTCC TTTGTCGATA CTGGTACATT ATGCTGAGTG ATATCCCCTA TAGTCGACCT
      2821  TGGCAAATAA TGATTTTATT TTGACTGATA GTGACCTGTT CGTTGCAACA CCGGTGCTAG
            ACCGTTTATT ACTAAAATAA AACTGACTAT CACTGGACAA GCAACGTTGT GGCCACGATC
      2881  CGTATACCCG AAGTATGTCA AAAAGAGGTG TGCTATGAAG CAGCGTATTA CAGTGACAGT
            GCATATGGGC TTCATACAGT TTTTCTCCAC ACGATACTTC GTCGCATAAT GTCACTGTCA
      2941  TGACAGCGAC AGCTATCAGT TGCTCAAGGC ATATATGATG TCAATATCTC CGGTCTGGTA
            ACTGTCGCTG TCGATAGTCA ACGAGTTCCG TATATACTAC AGTTATAGAG GCCAGACCAT
      3001  AGCACAACCA TGCAGAATGA AGCCCGTCGT CTGCGTGCCG AACGCTGGAA ACGGAAAAT
            TCGTGTTGGT ACGTCTTACT TCGGGCAGCA GACGCACGGC TTGCGACCTT TCGCCTTTTA
      3061  CAGGAAGGGA TGGCTGAGGT CGCCCGGTTT ATTGAAATGA ACGGCTCTTT TGCTGACGAG
            GTCCTTCCCT ACCGACTCCA GCGGGCCAAA TAACTTTACT TGCCGAGAAA ACGACTGCTC
      3121  AACAGGGACT GGTGAAATGC AGTTTAAGGT TTACACCTAT AAAAGAGAGA GCCGTTATCG
            TTGTCCCTGA CCACTTTACG TCAAATTCCA AATGTGGATA TTTTCTCTCT CGGCAATAGC
      3181  TCTGTTTGTG GATGTACAGA GTGATATTGT TGACACGCCC GGGCGACGGA TGGTGATCCC
            AGACAAACAC CTACATGTCT CACTATAATA ACTGTGCGGG CCCGCTGCCT ACCACTAGGG
      3241  CCTGGCCAGT GCACGTCTGC TGTCAGATAA AGTCTCCCGT GAACTTTACC CGGTGGTGCA
            GGACCGGTCA CGTGCAGACG ACAGTCTATT TCAGAGGGCA CTTGAAATGG GCCACCACGT
      3301  TATCGGGGAT GAAAGCTGGC GCATGATGAC CACCGATATG GCCAGTGTGC CGGTCTCCGT
            ATAGCCCCTA CTTTCGACCG CGTACTACTG GTGGCTATAC CGGTCACACG GCCAGAGGCA
      3361  TATCGGGGAA GAAGTGGCTG ATCTCAGCCG CCGCGAAAAT GACATCAAAA ACGCCATTAA
            ATAGCCCCTT CTTCACCGAC TAGAGTCGGC GGCGCTTTTA CTGTAGTTTT TGCGGTAATT
      3421  CCTGATGTTC TGGGGAATAT AAATGTCAGG CTCCCTTATA CACAGCCAGT CTGCAGGTCG
            GGACTACAAG ACCCCTTATA TTTACAGTCC GAGGGAATAT GTGTCGGTCA GACGTCCAGC
      3481  ACCATAGTGA CTGGATATGT TGTGTTTTAC AGTATTATGT AGTCTGTTTT TTATGCAAAA
            TGGTATCACT GACCTATACA ACACAAAATG TCATAATACA TCAGACAAAA AATACGTTTT
      3541  TCTAATTTAA TATATTGATA TTTATATCAT TTTACGTTTC TCGTTCAGCT TTCTTGTACA
            AGATTAAATT ATATAACTAT AAATATAGTA AAATGCAAAG AGCAAGTCGA AAGAACATGT
                                                            KpnI
                                                            ~~~~~~~
      3601  AAGTGGTGAT AATTAATTAA GATCAGATCC GGCTGCTGGT ACCCTCGAGT CTGGTAAAGA
            TTCACCACTA TTAATTAATT CTAGTCTAGG CCGACGACCA TGGGAGCTCA GACCATTTCT
      3661  AACCGCTGCT GCGAAATTTG AACGCCAGCA CATGGACTCG TCTACTAGCG CAGCTTAATT
            TTGGCGACGA CGCTTTAAAC TTGCGGTCGT GTACCTGAGC AGATGATCGC GTCGAATTAA
                AvrII
                ~~~~~~
      3721  AACCTAGGCT GCTGCCACCG CTGAGCAATA ACTAGCATAA CCCCTTGGGG CCTCTAAACG
            TTGGATCCGA CGACGGTGGC GACTCGTTAT TGATCGTATT GGGGAACCCC GGAGATTTGC
      3781  GGTCTTGAGG GGTTTTTTGC TGAAACCTCA GGCATTTGAG AAGCACACGG TCACACTGCT
```

Fig. 52$_2$

```
      CCAGAACTCC CCAAAAAACG ACTTTGGAGT CCGTAAACTC TTCGTGTGCC AGTGTGACGA
3841  TCCGGTAGTC AATAAACCGG TAAACCAGCA ATAGACATAA GCGGCTATTT AACGACCCTG
      AGGCCATCAG TTATTTGGCC ATTTGGTCGT TATCTGTATT CGCCGATAAA TTGCTGGGAC
3901  CCCTGAACCG ACGACCGGGT CATCGTGGCC GGATCTTGCG GCCCCTCGGC TTGAACGAAT
      GGGACTTGGC TGCTGGCCCA GTAGCACCGG CCTAGAACGC CGGGGAGCCG AACTTGCTTA
3961  TGTTAGACAT TATTTGCCGA CTACCTTGGT GATCTCGCCT TTCACGTAGT GGACAAATTC
      ACAATCTGTA ATAAACGGCT GATGGAACCA CTAGAGCGGA AAGTGCATCA CCTGTTTAAG
4021  TTCCAACTGA TCTGCGCGCG AGGCCAAGCG ATCTTCTTCT TGTCCAAGAT AAGCCTGTCT
      AAGGTTGACT AGACGCGCGC TCCGGTTCGC TAGAAGAAGA ACAGGTTCTA TTCGGACAGA
4081  AGCTTCAAGT ATGACGGGCT GATACTGGGC CGGCAGGCGC TCCATTGCCC AGTCGGCAGC
      TCGAAGTTCA TACTGCCCGA CTATGACCCG GCCGTCCGCG AGGTAACGGG TCAGCCGTCG
4141  GACATCCTTC GGCGCGATTT TGCCGGTTAC TGCGCTGTAC CAAATGCGGG ACAACGTAAG
      CTGTAGGAAG CCGCGCTAAA ACGCCAATG ACGCGACATG GTTTACGCCC TGTTGCATTC
4201  CACTACATTT CGCTCATCGC CAGCCCAGTC GGGCGGCGAG TTCCATAGCG TTAAGGTTTC
      GTGATGTAAA GCGAGTAGCG GTCGGGTCAG CCCGCCGCTC AAGGTATCGC AATTCCAAAG
4261  ATTTAGCGCC TCAAATAGAT CCTGTTCAGG AACCGGATCA AAGAGTTCCT CCGCCGCTGG
      TAAATCGCGG AGTTTATCTA GGACAAGTCC TTGGCCTAGT TTCTCAAGGA GGCGGCGACC
4321  ACCTACCAAG GCAACGCTAT GTTCTCTTGC TTTTGTCAGC AAGATAGCCA GATCAATGTC
      TGGATGGTTC CGTTGCGATA CAAGAGAACG AAAACAGTCG TTCTATCGGT CTAGTTACAG
4381  GATCGTGGCT GGCTCGAAGA TACCTGCAAG AATGTCATTG CGCTGCCATT CTCCAAATTG
      CTAGCACCGA CCGAGCTTCT ATGGACGTTA TTACAGTAAC GCGACGGTAA GAGGTTTAAC
4441  CAGTTCGCGC TTAGCTGGAT AACGCCACGG AATGATGTCG TCGTGCACAA CAATGGTGAC
      GTCAAGCGCG AATCGACCTA TTGCGGTGCC TTACTACAGC AGCACGTGTT GTTACCACTG
4501  TTCTACAGCG CGGAGAATCT CGCTCTCTCC AGGGGAAGCC GAAGTTTCCA AAAGGTCGTT
      AAGATGTCGC GCCTCTTAGA GCGAGAGAGG TCCCCTTCGG CTTCAAAGGT TTTCCAGCAA
4561  GATCAAAGCT CGCCGCGTTG TTTCATCAAG CCTTACGGTC ACCGTAACCA GCAAATCAAT
      CTAGTTTCGA GCGGCGCAAC AAAGTAGTTC GGAATGCCAG TGGCATTGGT CGTTTAGTTA
4621  ATCACTGTGT GGCTTCAGGC CGCCATCCAC TGCGGAGCCG TACAAATGTA CGGCCAGCAA
      TAGTGACACA CCGAAGTCCG GCGGTAGGTG ACGCCTCGGC ATGTTTACAT GCCGGTCGTT
4681  CGTCGGTTCG AGATGGCGCT CGATGACGCC AACTACCTCT GATAGTTGAG TCGATACTTC
      GCAGCCAAGC TCTACCGCGA GCTACTGCGG TTGATGGAGA CTATCAACTC AGCTATGAAG
4741  GGCGATCACC GCTTCCCTCA TACTCTTCCT TTTTCAATAT TATTGAAGCA TTTATCAGGG
      CCGCTAGTGG CGAAGGGAGT ATGAGAAGGA AAAAGTTATA ATAACTTCGT AAATAGTCCC
4801  TTATTGTCTC ATGAGCGGAT ACATATTTGA ATGTATTTAG AAAAATAAAC AAATAGCTAG
      AATAACAGAG TACTCGCCTA TGTATAAACT TACATAAATC TTTTTATTTG TTTATCGATC
4861  CTCACTCGGT CGCTACGCTC CGGGCGTGAG ACTGCGGCGG GCGCTGCGGA CACATACAAA
      GAGTGAGCCA GCGATGCGAG GCCCGCACTC TGACGCCGCC CGCGACGCCT GTGTATGTTT
4921  GTTACCCACA GATTCCGTGG ATAAGCAGGG GACTAACATG TGAGGCAAAA CAGCAGGGCC
      CAATGGGTGT CTAAGGCACC TATTCGTCCC CTGATTGTAC ACTCCGTTTT GTCGTCCCGG
4981  GCGCCGGTGG CGTTTTTCCA TAGGCTCCGC CCTCCTGCCA GAGTTCACAT AAACAGACGC
      CGCGGCCACC GCAAAAAGGT ATCCGAGGCG GGAGGACGGT CTCAAGTGTA TTTGTCTGCG
5041  TTTTCCGGTG CATCTGTGGG AGCCGTGAGG CTCAACCATG AATCTGACAG TACGGGCGAA
      AAAAGGCCAC GTAGACACCC TCGGCACTCC GAGTTGGTAC TTAGACTGTC ATGCCCGCTT
5101  ACCCGACAGG ACTTAAAGAT CCCCACCCTT TCCGGCGGGT CGCTCCCTCC TGCGCTCTCC
      TGGGCTGTCC TGAATTTCTA GGGGTGGCAA AGGCCGCCCA GCGAGGGAGA ACGCGAGAGG
5161  TGTTCCGACC CTGCCGTTTA CCGGATACCT GTTCGCCCTT TCTCCCTTAC GGGAAGTGTG
      ACAAGGCTGG GACGGCAAAT GGCCTATGGA CAAGGCGGAA AGAGGGAATG CCCTTCACAC
5221  GCGCTTTCTC ATAGCTCACA CACTGGTATC TCGGCTCGGT GTAGGTCGTT CGCTCCAAGC
      CGCGAAAGAG TATCGAGTGT GTGACCATAG AGCCGAGCCA CATCCAGCAA GCGAGGTTCG
5281  TGGGCTGTAA GCAAGAACTC CCCGTTCACC CCGACTCTG CGCCTTATCC GGTAACTGTT
      ACCCGACATT CGTTCTTGAG GGGCAAGTCG GGCTGACGAC GCGGAATAGG CCATTGACAA
5341  CACTTGAGTC CAACCCGGAA AAGCACGGTA AAACGCCACT GGCAGCAGCC ATTGGTAACT
      GTGAACTCAG GTTGGGCCTT TTCGTGCCAT TTTGCGGTGA CCGTCGTCGG TAACCATTGA
5401  GGGAGTTCGC AGAGGATTTG TTTAGCTAAA CACGCGGTTG CTCTTGAAGT GTGCGCCAAA
      CCCTCAAGCG TCTCCTAAAC AAATCGATTT GTGCGCCAAC GAGAACTTCA CACGCGGTTT
5461  GTCCGGCTAC ACTGGAAGGA CAGATTTGGT TGCTGTGCTC TGCGAAAGCC AGTTACCACG
      CAGGCCGATG TGACCTTCCT GTCTAAACCA ACGACCAGG ACGCTTTCGG TCAATGGTGC
5521  GTTAAGCAGT TCCCCAACTG ACTTAACCTT CGATCAAACC ACCTCCCCAG GTGGTTTTTT
      CAATTCGTCA AGGGGTTGAC TGAATTGGAA GCTAGTTTGG TGGAGGGGTC CACCAAAAAA
5581  CGTTTACAGG GCAAAAGATT ACGCGCAGAA AAAAGGATC TCAAGAAGAT CCTTTGATCT
      GCAAATGTCC CGTTTTCTAA TGCGCGTCTT TTTTTCCTAG AGTTCTTCTA GGAAACTAGA
5641  TTTCTACTGA ACCGCTCTAG ATTTCAGTGC AATTTATCTC TTCAAATGTA GCACCTGAAG
      AAAGATGACT TGGCGAGATC TAAAGTCACG TTAAATAGAG AAGTTTACAT CGTGGACTTC
5701  TCAGCCCCAT ACGATATAAG TTGTAATTCT CATGTTAGTC ATGCCCCGCG CCCACCGGAA
      AGTCGGGGTA TGCTATATTC AACATTAAGA GTACAATCAG TACGGGGCGC GGGTGGCCTT
5761  GGAGCTGACT GGGTTGAAGG CTCTCAAGGG CATCGGTCGA GATCCCGGTG CCTAATGAGT
      CCTCGACTGA CCCAACTTCC GAGAGTTCCC GTAGCCAGCT CTAGGGCCAC GGATTACTCA
```

Fig. 52₃

```
5821  GAGCTAACTT ACATTAATTG CGTTGCGCTC ACTGCCCGCT TTCCAGTCGG GAAACCTGTC
      CTCGATTGAA TGTAATTAAC GCAACGCGAG TGACGGGCGA AAGGTCAGCC CTTTGGACAG
5881  GTGCCAGCTG CATTAATGAA TCGGCCAACG CGCGGGGAGA GGCGGTTTGC GTATTGGGCG
      CACGGTCGAC GTAATTACTT AGCCGGTTGC GCGCCCCTCT CCGCCAAACG CATAACCCGC
5941  CCAGGGTGGT TTTTCTTTTC ACCAGTGAGA CGGGCAACAG CTGATTGCCC TTCACCGCCT
      GGTCCCACCA AAAAGAAAAG TGGTCACTCT GCCCGTTGTC GACTAACGGG AAGTGGCGGA
6001  GGCCCTGAGA GAGTTGCAGC AAGCGGTCCA CGCTGGTTTG CCCCAGCAGG CGAAAATCCT
      CCGGGACTCT CTCAACGTCG TTCGCCAGGT GCGACCAAAC GGGGTCGTCC GCTTTTAGGA
6061  GTTTGATGGT GGTTAACGGC GGGATATAAC ATGAGCTGTC TTCGGTATCG TCGTATCCCA
      CAAACTACCA CCAATTGCCG CCCTATATTG TACTCGACAG AAGCCATAGC AGCATAGGGT
6121  CTACCGAGAT GTCCGCACCA ACGCGCAGCC CGGACTCGGT AATGGCGCGC ATTGCGCCCA
      GATGGCTCTA CAGGCGTGGT TGCGCGTCGG GCCTGAGCCA TTACCGCGCG TAACGCGGGT
6181  GCGCCATCTG ATCGTTGGCA ACCAGCATCG CAGTGGGAAC GATGCCCTCA TTCAGCATTT
      CGCGGTAGAC TAGCAACCGT TGGTCGTAGC GTCACCCTTG CTACGGGAGT AAGTCGTAAA
6241  GCATGGTTTG TTGAAAACCG GACATGGCAC TCCAGTCGCC TTCCCGTTCC GCTATCGGCT
      CGTACCAAAC AACTTTTGGC CTGTACCGTG AGGTCAGCGG AAGGGCAAGG CGATAGCCGA
6301  GAATTTGATT GCGAGTGAGA TATTTATGCC AGCCAGCCAG ACGCAGACGC GCCGAGACAG
      CTTAAACTAA CGCTCACTCT ATAAATACGG TCGGTCGGTC TGCGTCTGCG CGGCTCTGTC
6361  AACTTAATGG GCCCGCTAAC AGCGCGATTT GCTGGTGACC CAATGCGACC AGATGCTCCA
      TTGAATTACC CGGGCGATTG TCGCGCTAAA CGACCACTGG GTTACGCTGG TCTACGAGGT
6421  CGCCCAGTCG CGTACCGTCT TCATGGGAGA AAATAATACT GTTGATGGGT GTCTGGTCAG
      GCGGGTCAGC GCATGGCAGA AGTACCCTCT TTTATTATGA CAACTACCCA CAGACCAGTC
6481  AGACATCAAG AAATAACGCC GGAACATTAG TGCAGGCAGC TTCCACAGCA ATGGCATCCT
      TCTGTAGTTC TTTATTGCGG CCTTGTAATC ACGTCCGTCG AAGGTGTCGT TACCGTAGGA
6541  GGTCATCCAG CGGATAGTTA ATGATCAGCC CACTGACGCG TTGCGCGAGA AGATTGTGCA
      CCAGTAGGTC GCCTATCAAT TACTAGTCGG GTGACTGCGC AACGCGCTCT TCTAACACGT
6601  CCGCCGCTTT ACAGGCTTCG ACGCCGCTTC GTTCTACCAT CGACACCACC ACGCTGGCAC
      GGCGGCGAAA TGTCCGAAGC TGCGGCGAAG CAAGATGGTA GCTGTGGTGG TGCGACCGTG
6661  CCAGTTGATC GGCGCGAGAT TTAATCGCCG CGACAATTTG CGACGGCGCG TGCAGGGCCA
      GGTCAACTAG CCGCGCTCTA AATTAGCGGC GCTGTTAAAC GCTGCCGCGC ACGTCCCGGT
6721  GACTGGAGGT GGCAACGCCA ATCAGCAACG ACTGTTTGCC CGCCAGTTGT TGTGCCACGC
      CTGACCTCCA CCGTTGCGGT TAGTCGTTGC TGACAAACGG GCGGTCAACA ACACGGTGCG
6781  GGTTGGGAAT GTAATTCAGC TCCGCCATCG CCGCTTCCAC TTTTTCCCGC GTTTTCGCAG
      CCAACCCTTA CATTAAGTCG AGGCGGTAGC GGCGAAGGTG AAAAAGGGCG CAAAAGCGTC
6841  AAACGTGGCT GGCCTGGTTC ACCACGCGGG AAACGGTCTG ATAAGAGACA CCGGCATACT
      TTTGCACCGA CCGGACCAAG TGGTGCGCCC TTTGCCAGAC TATTCTCTGT GGCCGTATGA
6901  CTGCGACATC GTATAACGTT ACTGGTTTCA CATTCACCAC CCTGAATTGA CTCTCTTCCG
      GACGCTGTAG CATATTGCAA TGACCAAAGT GTAAGTGGTG GGACTTAACT GAGAGAAGGC
6961  GGCGCTATCA TGCCATACCG CGAAAGGTTT TGCGCCATTC GATGGTGTCC GGGATCTCGA
      CCGCGATAGT ACGGTATGGC GCTTTCCAAA ACGCGGTAAG CTACCACAGG CCCTAGAGCT
7021  CGCTCTCCCT TATGCGACTC CTGCATTAGG AAATTAATAC GACTCACTAT A
      GCGAGAGGGA ATACGCTGAG GACGTAATCC TTTAATTATG CTGAGTGATA T
```

Fig. 52₄

| Fig. $54_1$ |
|---|
| Fig. $54_2$ |
| Fig. $54_3$ |
| Fig. $54_4$ |
| Fig. $54_5$ |

Fig. 54

Sequence for pDEST-CMZc1

```
    1  GGGGAATTGT GAGCGGATAA CAATTCCCCT GTAGAAATAA TTTTGTTTAA CTTTAATAAG
       CCCCTTAACA CTCGCCTATT GTTAAGGGGA CATCTTTATT AAAACAAATT GAAATTATTC
                                                                   SacI
                                                                   ~~~
   61  GAGATATACC ATGGGCAGCA GCCATCACCA TCATCACCAC AGCCAGGATC CGAATTCGAG
       CTCTATATGG TACCCGTCGT CGGTAGTGGT AGTAGTGGTG TCGGTCCTAG GCTTAAGCTC
       SacI
       ~~~
  121  CTCGGACCAT GATTACGCCA AGCTATCAAC TTTGTATAGA AAAGTTGAAC GAGAAACGTA
       GAGCCTGGTA CTAATGCGGT TCGATAGTTG AAACATATCT TTTCAACTTG CTCTTTGCAT
  181  AAATGATATA AATATCAATA TATTAAATTA GATTTTGCAT AAAAAACAGA CTACATAATA
       TTTACTATAT TTATAGTTAT ATAATTTAAT CTAAAACGTA TTTTTTGTCT GATGTATTAT
  241  CTGTAAAACA CAACATATCC AGTCACTATG GTCGACCTGC AGACTGGCTG TGTATAAGGG
       GACATTTTGT GTTGTATAGG TCAGTGATAC CAGCTGGACG TCTGACCGAC ACATATTCCC
  301  AGCCTGACAT TTATATTCCC CAGAACATCA GGTTAATGGC GTTTTTGATG TCATTTTCGC
       TCGGACTGTA AATATAAGGG GTCTTGTAGT CCAATTACCG CAAAAACTAC AGTAAAAGCG
  361  GGTGGCTGAG ATCAGCCACT TCTTCCCCGA TAACGGAGAC CGGCACACTG GCCATATCGG
       CCACCGACTC TAGTCGGTGA AGAAGGGGCT ATTGCCTCTG GCCGTGTGAC CGGTATAGCC
  421  TGGTCATCAT GCGCCAGCTT TCATCCCCGA TATGCACCAC CGGGTAAAGT TCACGGGGGA
       ACCAGTAGTA CGCGGTCGAA AGTAGGGGCT ATACGTGGTG GCCCATTTCA AGTGCCCCCT
  481  CTTTATCTGA CAGCAGACGT GCACTGGCCA GGGGGATCAC CATCCGTCGC CCGGGCGTGT
       GAAATAGACT GTCGTCTGCA CGTGACCGGT CCCCCTAGTG GTAGGCAGCG GGCCCGCACA
  541  CAATAATATC ACTCTGTACA TCCACAAACA GACGATAACG GCTCTCTCTT TTATAGGTGT
       GTTATTATAG TGAGACATGT AGGTGTTTGT CTGCTATTGC CGAGAGAGAA AATATCCACA
  601  AAACCTTAAA CTGCATTTCA CCAGCCCCTG TTCTCGTCGG CAAAAGAGCC GTTCATTTCA
       TTTGGAATTT GACGTAAAGT GGTCGGGGAC AAGAGCAGCC GTTTTCTCGG CAAGTAAAGT
  661  ATAAACCGGG CGACCCTCAGC CATCCCTTCC TGATTTTCCG CTTTCCAGCG TTCGGCACGC
       TATTTGGCCC GCTGGAGTCG GTAGGGAAGG ACTAAAGGC GAAAGGTCGC AAGCCGTGCG
  721  AGACGACGGG CTTCATTCTG CATGGTTGTG CTTACCGAAC CGGAGATATT GACATCATAT
       TCTGCTGCCC GAAGTAAGAC GTACCAACAC GAATGGCTTG GCCTCTATAA CTGTAGTATA
  781  ATGCCTTGAG CAACTGATAG CTGTCGCTGT CAACTGTCAC TGTAATACGC TGCTTCATAG
       TACGGAACTC GTTGACTATC GACAGCGACA GTTGACAGTG ACATTATGCG ACGAAGTATC
  841  CATACCTCTT TTTGACATAC TTCGGGTATA CATATCATTA TATATTCTTA TACCGCAAAA
       GTATGGAGAA AAACTGTATG AAGCCCATAT GTATAGTCAT ATATAAGAAT ATGGCGTTTT
  901  ATCAGCGCGC AAATACGCAT ACTGTTATCT GGCTTTTAGT AAGCCGGATC CTCTAGATTA
       TAGTCGCGCG TTTATGCGTA TGACAATAGA CCGAAAATCA TTCGGCCTAG GAGATCTAAT
       SphI
       ~~~~~~
  961  GCATGCCTAC AGGAACAGGT GGTGGCGGCC CTCGGTGCGC TCGTACTGCT CCACGATGGT
       CGTACGGATG TCCTTGTCCA CCACCGCCGG GAGCCACGCG AGCATGACGA GGTGCTACCA
 1021  GTAGTCCTCG TTGTGGGAGG TGATGTCCAG CTTGGCGTCC ACGTAGTAGT AGCCGGGCAG
       CATCAGGAGC AACACCCTCC ACTACAGGTC GAACCGCAGG TGCATCATCA TCGGCCCGTC
 1081  CTGCACGGGC TTCTTGGCCA TGTAGATGGA CTTGAACTCC ACCAGGTAGT GGCCGCCGTC
       GACGTGCCCG AAGAACCGGT ACATCTACCT GAACTTGAGG TGGTCCATCA CCGGCGGCAG
 1141  CTTCAGCTTC AGGGCCTTGT GGGTCTCGCC CTTCAGCACG CCGTCGCGGG GGTACAGGCG
       GAAGTCGAAG TCCCGGAACA CCCAGAGCGG GAAGTCGTGC GGCAGCGCCC CCATGTCCGC
 1201  CTCCGTGGAG GCCTCCCAGC CCATGGTCTT CTTCTGCATC ACGGGGCCGT CGGAGGGGAA
       GAGCCACCTC CGGAGGGTCG GGTACCAGAA GAAGACGTAG TGCCCCGGCA GCCTCCCCTT
 1261  GTTCACGCCG ATGAACTTCA CCTTGTAGAT GAAGCCAGTG TCCTGCAGGG AGGAGTCCTG
       CAAGTGCGGC TACTTGAAGT GGAACATCTA CTTCGTCGCG AGGACGTCCC TCCTCAGGAC
 1321  GGTCACGGTC GCCACGCCGC CGTCCTCGAA GTTCATCACG CGCTCCCACT TGAAGCCCTC
       CCAGTGCCAG CGGTGCGGCG GCAGGAGCTT CAAGTAGTGC GCGAGGGTGA ACTTCGGGAG
 1381  GGGGAAGGAC AGCTTCTTGT AGTCGGGGAT GTCGGCGGGG TGCTTCACGT ACACCTTGGA
       CCCCTTCCTG TCGAAGAACA TCAGCCCCTA CAGCCGCCCC ACGAAGTGCA TGTGGAACCT
 1441  GCCGTACTGG AACTGGGGGG ACAGGATGTC CAGGGCGAAG GGCAGGGGGC CGCCCTTGGT
       CGGCATGACC TTGACCCCCC TGTCCTACAG GTCCCGCTTC CCGTCCCCCG GCGGGAACCA
 1501  CACCTTCAGC TTCACGGTGT TGTGGCCCTC GTAGGGGCGG CCCTCGCCCT CGCCCTCGAT
       GTGGAAGTCG AAGTGCCACA ACACCGGGAG CATCCCCGCC GGGAGCGGGA GCGGGAGCTA
 1561  CTCGAACTCG TGGCCGTTCA CGGTGCCCTC CATGCGCACC TTGAAGCGCA TGAACTCGGT
       GAGCTTGAGC ACCGGCAAGT GCCACGGGAG GTACGCGTGG AACTTCGCGT ACTTGAGCCA
                                                     SpeI
                                                     ~~~~~~~
 1621  GATGACGTTC TCGGAGGAGG CCATACTAGT CGCCCCGCCC TGCCACTCAT CGCAGTACTG
       CTACTGCAAG AGCCTCCTCC GGTATGATCA GCGGGGCGGG ACGGTGAGTA GCGTCATGAC
 1681  TTGTAATTCA TTAAGCATTC TGCCGACATG GAAGCCATCA CAAACGGCAT GATGAACCTG
       AACATTAAGT AATTCGTAAG ACGGCTGTAC CTTCGGTAGT GTTTGCCGTA CTACTTGGAC
 1741  AATCGCCAGC GGCATCAGCA CCTTGTCGCC TTGCGTATAA TATTTGCCCA TGGTGAAAAC
```

Fig. 54₁

```
      TTAGCGGTCG CCGTAGTCGT GGAACAGCGG AACGCATATT ATAAACGGGT ACCACTTTTG
1801  GGGGGCGAAG AAGTTGTCCA TATTGGCCAC GTTTAAATCA AAACTGGTGA AACTCACCCA
      CCCCCGCTTC TTCAACAGGT ATAACCGGTG CAAATTTAGT TTTGACCACT TTGAGTGGGT
1861  GGGATTGGCT GAGACGAAAA ACATATTCTC AATAAACCCT TTAGGGAAAT AGGCCAGGTT
      CCCTAACCGA CTCTGCTTTT TGTATAAGAG TTATTTGGGA AATCCCTTTA TCCGGTCCAA
1921  TTCACCGTAA CACGCCACAT CTTGCGAATA TATGTGTAGA AACTGCCGGA ATCGTCGTG
      AAGTGGCATT GTGCGGTGTA GAACGCTTAT ATACACATCT TTGACGGCCT TTAGCAGCAC
1981  GTATTCACTC CAGAGCGATG AAAACGTTTC AGTTTGCTCA TGGAAAACGG TGTAACAAGG
      CATAAGTGAG GTCTCGCTAC TTTTGCAAAG TCAAACGAGT ACCTTTTGCC ACATTGTTCC
2041  GTGAACACTA TCCCATATCA CCAGCTCACC GTCTTTCATT GCCATACGGA ATTCCGGATG
      CACTTGTGAT AGGGTATAGT GGTCGAGTGG CAGAAAGTAA CGGTATGCCT TAAGGCCTAC
2101  AGCATTCATC AGGCGGGCAA GAATGTGAAT AAAGGCCGGA TAAAACTTGT GCTTATTTTT
      TCGTAAGTAG TCCGCCCGTT CTTACACTTA TTTCCGGCCT ATTTTGAACA CGAATAAAAA
2161  CTTTACGGTC TTTAAAAAGG CCGTAATATC CAGCTGAACG GTCTGGTTAT AGGTACATTG
      GAAATGCCAG AAATTTTTCC GGCATTATAG GTCGACTTGC CAGACCAATA TCCATGTAAC
2221  AGCAACTGAC TGAAATGCCT CAAAATGTTC TTTACGATGC CATTGGGATA TATCAACGGT
      TCGTTGACTG ACTTTACGGA GTTTTACAAG AAATGCTACG GTAACCCTAT ATAGTTGCCA
2281  GGTATATCCA GTGATTTTTT TCTCCATTTT AGCTTCCTTA GCTCCTGAAA ATCTCGACGG
      CCATATAGGT CACTAAAAAA AGAGGTAAAA TCGAAGGAAT CGGAGGACTT TAGAGCTGCC
2341  ATCCTAACTC AAAATCCACA CATTATACGA GCCGAAGCA TAAAGTGTAA AGCCTGGGGG
      TAGGATTGAG TTTTAGGTGT GTAATATGCT CGGCCTTCGT ATTTCACATT TCGGACCCCC
2401  TGCCTAATGC GGCCGCCATA GTGACTGGAT ATGTTGTGTT TTACAGTATT ATGTAGTCTG
      ACGGATTACG CCGGCGGTAT CACTGACCTA TACAACACAA AATGTCATAA TACATCAGAC
2461  TTTTTTATGC AAAATCTAAT TTAATATATT TCATTTTACG TTTCTCGTTC
      AAAAAATACG TTTTAGATTA AATTATATAA CTATAAATAT AGTAAAATGC AAAGAGCAAG
2521  AACTTTATTA TACATAGTTG ATAATTCACT GGCCGTCGTT TTACAACGTC GTGACTGGGA
      TTGAAATAAT ATGTATCAAC TATTAAGTGA CCGGCAGCAA AATGTTGCAG CACTGACCCT
                                                      HindIII
                                                      ~~~~~~~
2581  AAACCCTGGC GTTACCCAAC TTAATCGCCT TGCAGCACAA GCTTGCGGCC GCATAATGCT
      TTTGGGACCG CAATGGGTTG AATTAGCGGA ACGTCGTGTT CGAACGCCGG CGTATTACGA
2641  TAAGTCGAAC AGAAAGTAAT CGTATTGTAC ACGGCCGCAT AATCGAAATT AATACGACTC
      ATTCAGCTTG TCTTTCATTA GCATAACATG TGCCGGCGTA TTAGCTTTAA TTATGCTGAG
2701  ACTATAGGGG AATTGTGAGC GGATAACAAT TCCCCATCTT AGTATATTAG TTAAGTATAA
      TGATATCCCC TTAACACTCG CCTATTGTTA AGGGGTAGAA TCATATAATC AATTCATATT
                 NdeI
                 ~~~~
2761  GAAGGAGATA TACATATGGA TCACAAGTTT GTACAAAAAA GCTGAACGAG AAACGTAAAA
      CTTCCTCTAT ATGTATACCT AGTGTTCAAA CATGTTTTTT CGACTTGCTC TTTGCATTTT
2821  TGATATAAAT ATCAATATAT TAAATTAGAT TTTGACAAAA AAACAGACTA CATATACTG
      ACTATATTTA TAGTTATATA ATTTAATCTA AAACTGTATTT TTTGTCTGAT GTATTATGAC
2881  TAAAACACAA CATATCCAGT CACTATGGCG GCCGCCACGT TAAGGGATTT TGGTCATGAT
      ATTTTGTGTT GTATAGGTCA GTGATACCGC CGGCGGTGCA ATTCCCTAAA ACCAGTACTA
2941  CAGCACGTGT TGACAATTAA TCATCGGCAT AGTATATCGG CATAGTATAA TACGACAAGG
      GTCGTGCACA ACTGTTAATT AGTAGCCGTA TCATATAGCC GTATCATATT ATGCTGTTCC
3001  TGAGGAACTA AACCATGGCC AAGTTGACCA GTGCCGTTCC GGTGCTCACC GCGCGCGACG
      ACTCCTTGAT TTGGTACCGG TTCAACTGGT CACGGCAAGG CCACGAGTGG CGCGCGCTGC
3061  TCGCCGGAGC GGTCGAGTTC TGGACCGACC GGCTCGGGTT CTCCCGGGAC TTCGTGGAGG
      AGCGGCCTCG CCAGCTCAAG ACCTGGCTGG CCGAGCCCAA GAGGGCCCTG AAGCACCTCC
3121  ACGACTTCGC CGGTGTGGTC CGGGACGACG TGACCCTGTT CATCAGCCGG GTCCAGGACC
      TGCTGAAGCG GCCACACCAG GCCCTGCTGC ACTGGGACAA GTAGTCGCGC CAGGTCCTGG
3181  AGGTGGTGCC GGACAACACC CTGGCCTGGG TGTGGGTGCG CGGCCTGGAC GAGCTGTACG
      TCCACCACGG CCTGTTGTGG GACCGGACCC ACACCCACGC GCCGGACCTG CTCGACATGC
3241  CCGAGTGGTC GGAGGTCGTG TCCACGAACT TCCGGGACGC CTCCGGGCCG GCCATGACCG
      GGCTCACCAG CCTCCAGCAC AGGTGCTTGA AGGCCCTGCG GAGGCCCGGC CGGTACTGGC
3301  AGATCGGCGA GCAGCCGTGG GGGCGGGAGT TCGCCCTGCG CGACCCGGCC GGCAACTGCG
      TCTAGCCGCT CGTCGGCACC CCCGCCCTCA AGCGGGACGC GCTGGGCCGG CCGTTGACGC
                                                  SpeI
                                                  ~~~~~~
3361  TGCACTTCGT GGCCGAGGAG CAGGACACTA GTATGAGTAA AGGAGAAGAA CTTTTCACTG
      ACGTGAAGCA CCGGCTCCTC GTCCTGTGAT CATACTCATT TCCTCTTCTT GAAAAGTGAC
3421  GAGTTGTCCC AATTCTTGTT GAATTAGATG GTGATGTTAA TGGGCACAAA TTTTCTGTCA
      CTCAACAGGG TTAAGAACAA CTTAATCTAC CACTACAATT ACCCGTGTTT AAAAGACAGT
3481  GTGGAGAGGG TGAAGGTGAT GCAACATACG GAAAACTTAC CCTTAAATTT ATTTGCACTA
      CACCTCTCCC ACTTCCACTA CGTTGTATGC CTTTTGAATG GGAATTTAAA TAAACGTGAT
3541  CTGGAAAACT ACCTGTTCCA TGGCCAACAC TTGTCACTAC TTTCTCTTAT GGTGTTCAAT
      GACCTTTTGA TGGACAAGGT ACCGGTTGTG AACAGTGATG AAAGAGAATA CCACAAGTTA
                                        NdeI
                                        ~~~~~~
3601  GCTTTTCCCG TTATCCGGAT CATATGAAAC GGCATGACTT TTTCAAGAGT GCCATGCCCG
      CGAAAAGGGC AATAGGCCTA GTATACTTTG CCGTACTGAA AAAGTTCTCA CGGTACGGGC
```

Fig. 54₂

```
3661 AAGGTTATGT ACAGGAACGC ACTATATCTT TCAAAGATGA CGGGAACTAC AAGACGCGTG
     TTCCAATACA TGTCCTTGCG TGATATAGAA AGTTTCTACT GCCCTTGATG TTCTGCGCAC
3721 CTGAAGTCAA GTTTGAAGGT GATACCCTTG TTAATCGTAT CGAGTTAAAA GGTATTGATT
     GACTTCAGTT CAAACTTCCA CTATGGGAAC AATTAGCATA GCTCAATTTT CCATAACTAA
3781 TTAAAGAAGA TGGAAACATT CTCGGACACA AACTCGAGTA CAACTATAAC TCACACAATG
     AATTTCTTCT ACCTTTGTAA GAGCCTGTGT TTGAGCTCAT GTTGATATTG AGTGTGTTAC
3841 TATACATCAC GGCAGACAAA CAAAGAATG GAATCAAAGC TAACTTCAAA ATTCGCCACA
     ATATGTAGTG CCGTCTGTTT GTTTCTTAC CTTAGTTTCG ATTGAAGTTT TAAGCGGTGT
3901 ACATTGAAGA TGGATCCGTT CAACTAGCAG ACCATTATCA ACAAAATACT CCAATTGGCG
     TGTAACTTCT ACCTAGGCAA GTTGATCGTC TGGTAATAGT TGTTTTATGA GGTTAACCGC
3961 ATGGCCCTGT CCTTTTACCA GACAACCATT ACCTGTCGAC ACAATCTGCC CTTTCGAAAG
     TACCGGGACA GGAAAATGGT CTGTTGGTAA TGGACAGCTG TGTTAGACGG GAAAGCTTTC
4021 ATCCCAACGA AAAGCGTGAC CACATGGTCC TTCTTGAGTT TGTAACTGCT GCTGGGATTA
     TAGGGTTGCT TTTCGCACTG GTGTACCAGG AAGAACTCAA ACATTGACGA CGACCCTAAT
                            SacI                SphI
                          ~~~~~~~              ~~~~~~~
4081 CACATGGCAT GGATGAGCTC TACAAATAAG CATGCTGATC ATGATGATAT TATTTTATCT
     GTGTACCGTA CCTACTCGAG ATGTTTATTC GTACGACTAG TACTACTATA ATAAAATAGA
4141 TGTGCAATGT AACATCAGAG ATTTTGAGAC ACGGGCCAGA GCTGCCAGGA AACAGCTATG
     ACACGTTACA TTGTAGTCTC TAAAACTCTG TGCCCGGTCT CGACGGTCCT TTGTCGATAC
4201 ACCATGTAAT ACGACTCACT ATAGGGGATA TCAGCTGGAT GGCAAATAAT GATTTTATTT
     TGGTACATTA TGCTGAGTGA TATCCCCTAT AGTCGACCTA CCGTTTATTA CTAAAATAAA
4261 TGACTGATAG TGACCTGTTC GTTGCAACAC CGGTGCTAGC GTATACCCGA AGTATGTCAA
     ACTGACTATC ACTGGACAAG CAACGTTGTG GCCACGATCG CATATGGGCT TCATACAGTT
4321 AAAGAGGTGT GCTATGAAGC AGCGTATTAC AGTGACAGTT GACAGCGACA GCTATCAGTT
     TTTCTCCACA CGATACTTCG TCGCATAATG TCACTGTCAA CTGTCGCTGT CGATAGTCAA
4381 GCTCAAGGCA TATATGATGT CAATATCTCC GGTCTGGTAA GCACAACCAT GCAGAATGAA
     CGAGTTCCGT ATATACTACA GTTATAGAGG CCAGACCATT CGTGTTGGTA CGTCTTACTT
4441 GCCCGTCGTC TGCGTGCCGA ACGCTGGAAA GCGGAAAATC AGGAAGGGAT GGCTGAGGTC
     CGGGCAGCAG ACGCACGGCT TGCGACCTTT CGCCTTTTAG TCCTTCCCTA CCGACTCCAG
4501 GCCCGGTTTA TTGAAATGAA CGGCTCTTTT GCTGACGAGA ACAGGGACTG GTGAAATGCA
     CGGGCCAAAT AACTTTACTT GCCGAGAAAA CGACTGCTCT TGTCCCTGAC CACTTTACGT
4561 GTTTAAGGTT TACACCTATA AAAGAGAGAG CCGTTATCGT CTGTTTGTGG ATGTACAGAG
     CAAATTCCAA ATGTGGATAT TTTCTCTCTC GGCAATAGCA GACAAACACC TACATGTCTC
4621 TGATATTATT GACACGCCCG GGGCACGGAT GGTGATCCCC CTGGCCAGTG CACGTCTGCT
     ACTATAATAA CTGTGCGGGC CCGCTGCCTA CCACTAGGGG GACCGGTCAC GTGCAGACGA
4681 GTCAGATAAA GTCTCCCGTG AACTTTACCC GGTGGTGCAT ATCGGGGATG AAAGCTGGCG
     CAGTCTATTT CAGAGGGCAC TTGAAATGGG CCACCACGTA TAGCCCCTAC TTTCGACCGC
4741 CATGATGACC ACCGATATGG CCAGTGTGCC GGTCTCCGTT ATCGGGGAAG AAGTGGCTGA
     GTACTACTGG TGGCTATACC GGTCACACGG CCAGAGGCAA TAGCCCCTTC TTCACCGACT
4801 TCTCAGCCGC CGCGAAAATG ACATCAAAAA CGCCATTAAC CTGATGTTCT GGGGAATATA
     AGAGTCGGCG GCGCTTTTAC TGTAGTTTTT GCGGTAATTG GACTACAAGA CCCCTTATAT
4861 AATGTCAGGC TCCCTTATAC ACAGCCAGTC TGCAGGTCGA CCATAGTGAC TGGATATGTT
     TTACAGTCCG AGGGAATATG TGTCGGTCAG ACGTCCAGCT GGTATCACTG ACCTATACAA
4921 GTGTTTTACA GTATTATGTA GTCTGTTTTT TATGCAAAAT CTAATTTAAT ATATTGATAT
     CACAAAATGT CATAATACAT CAGACAAAAA ATACGTTTTA GATTAAATTA TATAACTATA
4981 TTATATCATT TTACGTTTCT CGTTCAGCTT TCTTGTACAA AGTGGTGATA ATTAATTAAG
     AATATAGTAA AATGCAAAGA GCAAGTCGAA AGAACATGTT TCACCACTAT TAATTAATTC
                            KpnI
                          ~~~~~~~
5041 ATCAGATCCG GCTGCTGGTA CCCTCGAGTC TGGTAAAGAA ACCGCTGCTG CGAAATTTGA
     TAGTCTAGGC CGACGACCAT GGGAGCTCAG ACCATTTCTT TGGCGACGAC GCTTTAAACT
                                                 AvrII
                                               ~~~~~~~
5101 ACGCCAGCAC ATGGACTCGT CTACTAGCGC AGCTTAATTA ACCTAGGCTG CTGCCACCGC
     TGCGGTCGTG TACCTGAGCA GATGATCGCG TCGAATTAAT TGGATCCGAC GACGGTGGCG
5161 TGAGCAATAA CTAGCATAAC CCCTTGGGGC CTCTAAACGG GTCTTGAGGG GTTTTTTGCT
     ACTCGTTATT GATCGTATTG GGGAACCCCG GAGATTTGCC CAGAACTCCC CAAAAAACGA
5221 GAAACCTCAG GCATTTGAGA AGCACACGGT CACACTGCTT CCGGTAGTCA ATAAACCGGT
     CTTTGGAGTC CGTAAACTCT TCGTGTGCCA GTGTGACGAA GGCCATCAGT TATTTGGCCA
5281 AAACCAGCAA TAGACATAAG CGGCTATTTA ACGACCCTGC CCTGAACCGA CGACCGGGTC
     TTTGGTCGTT ATCTGTATTC GCCGATAAAT TGCTGGGACG GGACTTGGCT GCTGGCCCAG
5341 ATCGTGGCCG GATCTTGCGG CCCCTCGGCT TGAACGAATT GTTAGACATT ATTTGCCGAC
     TAGCACCGGC CTAGAACGCC GGGGAGCCGA ACTTGCTTAA CAATCTGTAA TAAACGGCTG
5401 TACCTTGGTG ATCTCGCCTT TCACGTAGTG GACAAATTCT TCCAACTGAT CTGCGCGCGA
     ATGGAACCAC TAGAGCGGAA AGTGCATCAC CTGTTTAAGA AGGTTGACTA GACGCGCGCT
5461 GGCCAAGCGA TCTTCTTCTT GTCCAAGATA AGCCTGTCTA GCTTCAAGTA TGACGGGCTG
     CCGGTTCGCT AGAAGAAGAA CAGGTTCTAT TCGGACAGAT CGAAGTTCAT ACTGCCCGAC
5521 ATACTGGGCC GGCAGGCGCT CCATTGCCCA GTCGGCAGCG ACATCCTTCG GCGCGATTTT
     TATGACCCGG CCGTCCGCGA GGTAACGGGT CAGCCGTCGC TGTAGGAAGC CGCGCTAAAA
```

Fig. 54₃

```
5581  GCCGGTTACT GCGCTGTACC AAATGCGGGA CAACGTAAGC ACTACATTTC GCTCATCGCC
      CGGCCAATGA CGCGACATGG TTTACGCCCT GTTGCATTCG TGATGTAAAG CGAGTAGCGG
5641  AGCCCAGTCG GGCGGCGAGT TCCATAGCGT TAAGGTTTCA TTTAGCGCCT CAAATAGATC
      TCGGGTCAGC CCGCCGCTCA AGGTATCGCA ATTCCAAAGT AAATCGCGGA GTTTATCTAG
5701  CTGTTCAGGA ACCGGATCAA AGAGTTCCTC CGCCGCTGGA CCTACCAAGG CAACGCTATG
      GACAAGTCCT TGGCCTAGTT TCTCAAGGAG GCGGCGACCT GGATGGTTCC GTTGCGATAC
5761  TTCTCTTGCT TTTGTCAGCA AGATAGCCAG ATCAATGTCG ATCGTGGCTG GCTCGAAGAT
      AAGAGAACGA AAACAGTCGT TCTATCGGTC TAGTTACAGC TAGCACCGAC CGAGCTTCTA
5821  ACCTGCAAGA ATGTCATTGC GCTGCCATTC TCCAAATTGC AGTTCGCGCT TAGCTGGATA
      TGGACGTTCT TACAGTAACG CGACGGTAAG AGGTTTAACG TCAAGCGCGA ATCGACCTAT
5881  ACGCCACGGA ATGATGTCGT CGTGCACAAC AATGGTGACT TCTACAGCGC GGAGAATCTC
      TGCGGTGCCT TACTACAGCA GCACGTGTTG TTACCACTGA AGATGTCGCG CCTCTTAGAG
5941  GCTCTCTCCA GGGGAAGCCG AAGTTTCCAA AAGGTCGTTG ATCAAAGCTC GCCGCGTTGT
      CGAGAGAGGT CCCCTTCGGC TTCAAAGGTT TTCCAGCAAC TAGTTTCGAG CGGCGCAACA
6001  TTCATCAAGC CTTACGGTCA CCGTAACCAG CAAATCAATA TCACTGTGTG GCTTCAGGCC
      AAGTAGTTCG GAATGCCAGT GGCATTGGTC GTTTAGTTAT AGTGACACAC CGAAGTCCGG
6061  GCCATCCACT GCGGAGCCGT ACAAATGTAC GGCCAGCAAC GTCGGTTCGA GATGGCGCTC
      CGGTAGGTGA CGCCTCGGCA TGTTTACATG CCGGTCGTTG CAGCCAAGCT CTACCGCGAG
6121  GATGACGCCA ACTACCTCTG ATAGTTGAGT CGATACTTCG GCGATCACCG CTTCCCTCAT
      CTACTGCGGT TGATGGAGAC TATCAACTCA GCTATGAAGC CGCTAGTGGC GAAGGGAGTA
6181  ACTCTTCCTT TTTCAATATT ATTGAAGCAT TTATCAGGGT TATTGTCTCA TGACGGGATA
      TGAGAAGGAA AAAGTTATAA TAACTTCGTA AATAGTCCCA ATAACAGAGT ACTCGCCTAT
6241  CATATTTGAA TGTATTTAGA AAAATAAACA AATAGCTAGC TCACTCGGTC GCTACGCTCC
      GTATAAACTT ACATAAATCT TTTTATTTGT TTATCGATCG AGTGAGCCAG CGATGCGAGG
6301  GGGCGTGAGA CTGCGGCGGG CGCTGCGGAC ACATACAAAG TTACCCACAG ATTCCGTGGA
      CCCGCACTCT GACGCCGCCC GCGACGCCTG TGTATGTTTC AATGGGTGTC TAAGGCACCT
6361  TAAGCAGGGG ACTAACATGT GAGGCAAAAC AGCAGGGCCG CGCCGGTGGC GTTTTTCCAT
      ATTCGTCCCC TGATTGTACA CTCCGTTTTG TCGTCCCGGC GCGGCCACCG CAAAAAGGTA
6421  AGGCTCCGCC CTCCTGCCAG AGTTCACATA AACAGACGCT TTTCCGGTGC ATCTGTGGGA
      TCCGAGGCGG GAGGACGGTC TCAAGTGTAT TTGTCTGCGA AAAGGCCACG TAGACACCCT
6481  GCCGTGAGGC TCAACCATGA ATCTGACAGT ACGGGCGAAA CCCGACAGGA CTTAAAGATC
      CGGCACTCCG AGTTGGTACT TAGACTGTCA TGCCCGCTTT GGGCTGTCCT GAATTTCTAG
6541  CCCACCGTTT CCGGCGGGTC GCTCCCTCTT GCGCTCTCCT GTTCCGACCC TGCCGTTTAC
      GGGTGGCAAA GGCCGCCCAG CGAGGGAGAA CGCGAGAGGA CAAGGCTGGG ACGGCAAATG
6601  CGGATACCTG TTCCGCCTTT CTCCCTTACG GGAAGTGTGG CGCTTTCTCA TAGCTCACAC
      GCCTATGGAC AAGGCGGAAA GAGGGAATGC CCTTCACACC GCGAAAGAGT ATCGAGTGTG
6661  ACTGGTATCT CGGCTCGGTG TAGGTCGTTC GCTCCAAGCT GGGCTGTAAG CAAGAACTCC
      TGACCATAGA GCCGAGCCAC ATCCGCAAG CGAGGTTCGA CCCGACATTC GTTCTTGAGG
6721  CCGTTCAGCC CGACTGCTGC GCCTTATCCG GTAACTGTTC ACTTGAGTCC AACCCGGAAA
      GGCAAGTCGG GCTGACGACG CGGAATAGGC CATTGACAAG TGAACTCAGG TTGGGCCTTT
6781  AGCACGGTAA AACGCCACTG GCAGCAGCCA TTGGTAACTG GGAGTTCGCA GAGGATTTGT
      TCGTGCCATT TTGCGGTGAC CGTCGTCGGT AACCATTGAC CCTCAAGCGT CTCCTAAACA
6841  TTAGCTAAAC ACGCGGTTGC TCTTGAAGTG TGCGCCAAAG TCCGGCTACA CTGGAAGGAC
      AATCGATTTG TGCGCCAACG AGAACTTCAC ACGCGGTTTC AGGCCGATGT GACCTTCCTG
6901  AGATTTGGTT GCTGTGCTCT GCGAAAGCCA GTTACCACGG TTAAGCAGTT CCCCAACTGA
      TCTAAACCAA CGACACGAGA CGCTTTCGGT CAATGGTGCC AATTCGTCAA GGGGTTGACT
6961  CTTAACCTTC GATCAAACCA CCTCCCCAGG TGGTTTTTTC GTTTACAGGG CAAAAGATTA
      GAATTGGAAG CTAGTTTGGT GGAGGGGTCC ACCAAAAAAG CAAATGTCCC GTTTTTCTAAT
7021  CGCGCAGAAA AAAAGGATCT CAAGAAGATC CTTTGATCTT TTCTACTGAA CCGCTCTAGA
      GCGCGTCTTT TTTTCCTAGA GTTCTTCTAG GAAACTAGAA AAGATGACTT GGCGAGATCT
7081  TTTCAGTGCA ATTTATCTCT TCAAATGTAG CACCTGAAGT CAGCCCCATA CGATATAAGT
      AAAGTCACGT TAAATAGAGA AGTTTACATC GTGGACTTCA GTCGGGGTAT GCTATATTCA
7141  TGTAATTCTC ATGTTAGTCA TGCCCCGCGC CCACCGGAAG GAGCGGACTG GGTTGAAGGC
      ACATTAAGAG TACAATCAGT ACGGGCGCG GGTGGCCTTC CTCGACTGAC CCAACTTCCG
7201  TCTCAAGGGC ATCGGTCGAG ATCCCGGTGC CTAATGAGTG AGCTAACTTA CATTAATTGC
      AGAGTTCCCG TAGCCAGCTC TAGGGCCACG GATTACTCAC TCGATTGAAT GTAATTAACG
7261  GTTGCGCTCA CTGCCCGCTT TCCAGTCGGG AAACCTGTCG TGCCAGCTGC ATTAATGAAT
      CAACGCGAGT GACGGGCGAA AGGTCAGCCC TTTGGACAGC ACGGTCGACG TAATTACTTA
7321  CGGCCAACGC GCGGGGAGAG GCGGTTTGCG TATTGGGCGC CAGGGTGGTT TTTCTTTTCA
      GCCGGTTGCG CGCCCCTCTC CGCCAAACGC ATAACCCGCG GTCCCACCAA AAAGAAAAGT
7381  CCAGTGAGAC GGGCAACAGC TGATTGCCCT TCACCGCCTG GCCCTGAGAG AGTTGCAGCA
      GGTCACTCTG CCCGTTGTCG ACTAACGGGA AGTGGCGGAC CGGGACTCTC TCAACGTCGT
7441  AGCGGTCCAC GCTGGTTTGC CCCAGCAGGC GAAAATCCTG TTTGATGGTG GTTAACGGCG
      TCGCCAGGTG CGACCAAACG GGGTCGTCCG CTTTTAGGAC AAACTACCAC CAATTGCCGC
7501  GGATATAACA TGAGCTGTCT TCGGTATCGT CGTATCCCAC TACCGAGATG TCCGCACCAA
      CCTATATTGT ACTCGACAGA AGCCATAGCA GCATAGGGTG ATGGCTCTAC AGGCGTGGTT
7561  CGCGCAGCCC GGACTCGGTA ATGGCGCGCA TTGCGCCCAG CGCCATCTGA TCGTTGGCAA
      GCGCGTCGGG CCTGAGCCAT TACCGCGCGT AACGCGGGTC GCGGTAGACT AGCAACCGTT
7621  CCAGCATCGC AGTGGGAACG ATGCCCTCAT TCAGCATTTG CATGGTTTGT TGAAAACCGG
      GGTCGTAGCG TCACCCTTGC TACGGGAGTA AGTCGTAAAC GTACCAAACA ACTTTTGGCC
7681  ACATGGCACT CCAGTCGCCT TCCCGTTCCG CTATCGGCTG AATTTGATTG CGAGTGAGAT
```

Fig. 54₄

```
            TGTACCGTGA GGTCAGCGGA AGGGCAAGGC GATAGCCGAC TTAAACTAAC GCTCACTCTA
7741 ATTTATGCCA GCCAGCCAGA CGCAGACGCG CCGAGACAGA ACTTAATGGG CCCGCTAACA
     TAAATACGGT CGGTCGGTCT GCGTCTGCGC GGCTCTGTCT TGAATTACCC GGGCGATTGT
7801 GCGCGATTTG CTGGTGACCC AATGCGACCA GATGCTCCAC GCCCAGTCGC GTACCGTCTT
     CGCGCTAAAC GACCACTGGG TTACGCTGGT CTACGAGGTG CGGGTCAGCG CATGGCAGAA
7861 CATGGGAGAA AATAATACTG TTGATGGGTG TCTGGTCAGA GACATCAAGA AATAACGCCG
     GTACCCTCTT TTATTATGAC AACTACCCAC AGACCAGTCT CTGTAGTTCT TTATTGCGGC
7921 GAACATTAGT GCAGGCAGCT TCCACAGCAA TGGCATCCTG GTCATCCAGC GGATAGTTAA
     CTTGTAATCA CGTCCGTCGA AGGTGTCGTT ACCGTAGGAC CAGTAGGTCG CCTATCAATT
7981 TGATCAGCCC ACTGACGCGT TGCGCGAGAA GATTGTGCAC CGCCGCTTTA CAGGCTTCGA
     ACTAGTCGGG TGACTGCGCA ACGCGCTCTT CTAACACGTG GCGGCGAAAT GTCCGAAGCT
8041 CGCCGCTTCG TTCTACCATC GACACCACCA CGCTGGCACC CAGTTGATCG GCGCGAGATT
     GCGGCGAAGC AAGATGGTAG CTGTGGTGGT GCGACCGTGG GTCAACTAGC CGCGCTCTAA
8101 TAATCGCCGC GACAATTTGC GACGGCGCGT GCAGGGCCAG ACTGGAGGTG GCAACGCCAA
     ATTAGCGGCG CTGTTAAACG CTGCCGCGCA CGTCCCGGTC TGACCTCCAC CGTTGCGGTT
8161 TCAGCAACGA CTGTTTGCCC GCCAGTTGTT GTGCCACGCG GTTGGGAATG TAATTCAGCT
     AGTCGTTGCT GACAAACGGG CGGTCAACAA CACGGTGCGC CAACCCTTAC ATTAAGTCGA
8221 CCGCCATCGC CGCTTCCACT TTTTCCCGCG TTTTCGCAGA AACGTGGCTG GCCTGGTTCA
     GGCGGTAGCG GCGAAGGTGA AAAAGGGCGC AAAAGCGTCT TTGCACCGAC CGGACCAAGT
8281 CCACGCGGGA AACGGTCTGA TAAGAGACAC CGGCATACTC TGCGACATCG TATAACGTTA
     GGTGCGCCCT TTGCCAGACT ATTCTCTGTG GCCGTATGAG ACGCTGTAGC ATATTGCAAT
8341 CTGGTTTCAC ATTCACCACC CTGAATTGAC TCTCTTCCGG GCGCTATCAT GCCATACCGC
     GACCAAAGTG TAAGTGGTGG GACTTAACTG AGAGAAGGCC CGCGATAGTA CGGTATGGCG
8401 GAAAGGTTTT GCGCCATTCG ATGGTGTCCG GGATCTCGAC GCTCTCCCTT ATGCGACTCC
     CTTTCCAAAA CGCGGTAAGC TACCACAGGC CCTAGAGCTG CGAGAGGGAA TACGCTGAGG
8461 TGCATTAGGA AATTAATACG ACTCACTATA
     ACGTAATCCT TTAATTATGC TGAGTGATAT
```

Fig. 54$_5$

SEQUENCE LISTING

<160> NUMBER OF SEQ ID NOS: 45

<210> SEQ ID NO 1
<211> LENGTH: 5334
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 1

| | | | | | |
|---|---|---|---|---|---|
| ggggaattgt | gagcggataa | caattcccct | gtagaaataa | ttttgtttaa | ctttaataag | 60 |
| gagatatacc | atggcacatc | accaccacca | tcacgtgggt | accggttcga | atgatgacga | 120 |
| cgacaaatca | acaagtttgt | acaaaaaagc | tgaacgagaa | acgtaaaatg | atataaatat | 180 |
| caatatatta | aattagattt | tgcataaaaa | acagactaca | taatactgta | aaacacaaca | 240 |
| tatccagtca | tattggcggc | cgcattaggc | accccaggct | ttacacttta | tgcttccggc | 300 |
| tcgtataatg | tgtggatttt | gagttaggat | ccgtcgagat | tttcaggagc | taaggaagct | 360 |
| aaaatggaga | aaaaaatcac | tggatatacc | accgttgata | tatcccaatg | gcatcgtaaa | 420 |
| gaacattttg | aggcatttca | gtcagttgct | caatgtacct | ataaccagac | cgttcagctg | 480 |
| gatattacgg | cctttttaaa | gaccgtaaag | aaaaataagc | acaagtttta | tccggccttt | 540 |
| attcacattc | ttgcccgcct | gatgaatgct | catccggaat | tccgtatggc | aatgaaagac | 600 |
| ggtgagctgg | tgatatggga | tagtgttcac | ccttgttaca | ccgttttcca | tgagcaaact | 660 |
| gaaacgtttt | catcgctctg | gagtgaatac | cacgacgatt | tccggcagtt | tctacacata | 720 |
| tattcgcaag | atgtggcgtg | ttacggtgaa | aacctggcct | atttccctaa | agggtttatt | 780 |
| gagaatatgt | ttttcgtctc | agccaatccc | tgggtgagtt | tcaccagttt | tgatttaaac | 840 |
| gtggccaata | tggacaactt | cttcgccccc | gttttcacca | tgggcaaata | ttatacgcaa | 900 |
| ggcgacaagg | tgctgatgcc | gctggcgatt | caggttcatc | atgccgtttg | tgatggcttc | 960 |
| catgtcggca | gaatgcttaa | tgaattacaa | cagtactgcg | atgagtggca | gggcggggcg | 1020 |
| taaagatctg | gatccggctt | actaaaagcc | agataacagt | atgcgtattt | gcgcgctgat | 1080 |
| ttttgcggta | taagaatata | tactgatatg | tatacccgaa | gtatgtcaaa | aagaggtatg | 1140 |
| ctatgaagca | gcgtattaca | gtgacagttg | acagcgacag | ctatcagttg | ctcaaggcat | 1200 |
| atatgatgtc | aatatctccg | gtctggtaag | cacaaccatg | cagaatgaag | cccgtcgtct | 1260 |
| gcgtgccgaa | cgctggaaag | cggaaaatca | ggaagggatg | gctgaggtcg | cccggtttat | 1320 |
| tgaaatgaac | ggctcttttg | ctgacgagaa | caggggctgg | tgaaatgcag | tttaaggttt | 1380 |
| acacctataa | aagagagagc | cgttatcgtc | tgtttgtgga | tgtacagagt | gatattattg | 1440 |
| acacgcccgg | gcgacggatg | gtgatccccc | tggccagtgc | acgtctgctg | tcagataaag | 1500 |
| tctcccgtga | actttacccg | gtggtgcata | tcggggatga | agctggcgc | atgatgacca | 1560 |
| ccgatatggc | cagtgtgccg | gtctccgtta | tcggggaaga | agtggctgat | ctcagccacc | 1620 |
| gcgaaaatga | catcaaaaac | gccattaacc | tgatgttctg | gggaatataa | atgtcaggct | 1680 |
| cccttataca | cagccagtct | gcaggtcgac | catagtgact | ggatatgttg | tgttttacag | 1740 |
| tattatgtag | tctgtttttt | atgcaaaatc | taatttaata | tattgatatt | tatatcattt | 1800 |
| tacgtttctc | gttcagcttt | cttgtacaaa | gtggttgatg | agtccggatc | ccaattggga | 1860 |
| gctcgtgtac | acggcgcgcc | tgcaggtcga | caagcttgcg | ccgcactcg | agtctggtaa | 1920 |

```
agaaaccgct gctgcgaaat ttgaacgcca gcacatggac tcgtctacta gcgcagctta   1980
attaacctag gctgctgcca ccgctgagca ataactagca taaccccttg gggcctctaa   2040
acgggtcttg aggggttttt tgctgaaacc tcaggcattt gagaagcaca cggtcacact   2100
gcttccggta gtcaataaac cggtaaacca gcaatagaca taagcggcta tttaacgacc   2160
ctgccctgaa ccgacgaccg ggtcatcgtg gccggatctt gcggcccctc ggcttgaacg   2220
aattgttaga cattatttgc cgactacctt ggtgatctcg cctttcacgt agtggacaaa   2280
ttcttccaac tgatctgcgc gcgaggccaa gcgatcttct tcttgtccaa gataagcctg   2340
tctagcttca gtatgacgg gctgatactg gccggcagg cgctccattg cccagtcggc     2400
agcgacatcc ttcggcgcga ttttgccggt tactgcgctg taccaaatgc gggacaacgt   2460
aagcactaca tttcgctcat cgccagccca gtcgggcggc gagttccata cgttaaggt    2520
ttcatttagc gcctcaaata gatcctgttc aggaaccgga tcaaagagtt cctccgccgc   2580
tggacctacc aaggcaacgc tatgttctct tgcttttgtc agcaagatag ccagatcaat   2640
gtcgatcgtg gctggctcga agatacctgc aagaatgtca ttgcgctgcc attctccaaa   2700
ttgcagttcg cgcttagctg ataacgcca cggaatgatg tcgtcgtgca caacaatggt    2760
gacttctaca gcgcggagaa tctcgctctc tccagggaa gccgaagttt ccaaaaggtc    2820
gttgatcaaa gctcgccgcg ttgtttcatc aagccttacg gtcaccgtaa ccagcaaatc   2880
aatatcactg tgtggcttca ggccgccatc cactgcggag ccgtacaaat gtacggccag   2940
caacgtcggt tcgagatggc gctcgatgac gccaactacc tctgatagtt gagtcgatac   3000
ttcggcgatc accgcttccc tcatactctt cctttttcaa tattattgaa gcatttatca   3060
gggttattgt ctcatgagcg gatacatatt tgaatgtatt tagaaaaata acaaatagc    3120
tagctcactc ggtcgctacg ctccgggcgt gagactgcgg cgggcgctgc ggacacatac   3180
aaagttaccc acagattccg tggataagca ggggactaac atgtgaggca aaacagcagg   3240
gccgcgccgg tggcgttttt ccataggctc cgccctcctg ccagagttca cataaacaga   3300
cgcttttccg gtgcatctgt gggagccgtg aggctcaacc atgaatctga cagtacgggc   3360
gaaacccgac aggacttaaa gatccccacc gtttccggcg ggtcgctccc tcttgcgctc   3420
tcctgttccg accctgccgt ttaccggata cctgttccgc cttctcccct tacgggaagt   3480
gtggcgcttt ctcatagctc acacactggt atctcggctc ggtgtaggtc gttcgctcca   3540
agctgggctg taagcaagaa ctccccgttc agcccgactg ctgcgcctta tccggtaact   3600
gttcacttga gtccaacccg gaaaagcacg gtaaaacgcc actggcagca gccattggta   3660
actgggagtt cgcagaggat tgttttagct aaacacgcgg ttgctcttga agtgtgcgcc   3720
aaagtccggc tacactggaa ggacagattt ggttgctgtg ctctgcgaaa gccagttacc   3780
acggttaagc agttccccaa ctgacttaac cttcgatcaa accacctccc caggtggttt   3840
tttcgtttac agggcaaaag attacgcgca gaaaaaagg atctcaagaa gatcctttga    3900
tcttttctac tgaaccgctc tagatttcag tgcaatttat ctcttcaaat gtagcacctg   3960
aagtcagccc catacgatat aagttgtaat tctcatgtta gtcatgcccc cgcccaccg    4020
gaaggagctg actgggttga aggctctcaa gggcatcggt cgagatcccg gtgcctaatg   4080
agtgagctaa cttacattaa ttgcgttgcg ctcactgccc gctttccagt cgggaaacct   4140
gtcgtgccag ctgcattaat gaatcggcca acgcgcgggg agaggcggtt tgcgtattgg   4200
gcgccagggt ggtttttctt ttcaccagtg agacgggcaa cagctgattg cccttcaccg   4260
cctggccctg agagagttgc agcaagcggt ccacgctggt ttgccccagc aggcgaaaat   4320
```

```
cctgtttgat ggtggttaac ggcgggatat aacatgagct gtcttcggta tcgtcgtatc    4380
ccactaccga gatgtccgca ccaacgcgca gcccggactc ggtaatggcg cgcattgcgc    4440
ccagcgccat ctgatcgttg caaccagca tcgcagtggg aacgatgccc tcattcagca    4500
tttgcatggt ttgttgaaaa ccggacatgg cactccagtc gccttcccgt tccgctatcg    4560
gctgaatttg attgcgagtg agatatttat gccagccagc cagacgcaga cgcgccgaga    4620
cagaacttaa tgggcccgct aacagcgcga tttgctggtg acccaatgcg accagatgct    4680
ccacgcccag tcgcgtaccg tcttcatggg agaaaataat actgttgatg ggtgtctggt    4740
cagagacatc aagaaataac gccggaacat tagtgcaggc agcttccaca gcaatggcat    4800
cctggtcatc cagcggatag ttaatgatca gcccactgac gcgttgcgcg agaagattgt    4860
gcaccgccgc tttacaggct tcgacgccgc ttcgttctac catcgacacc accacgctgg    4920
cacccagttg atcggcgcga gatttaatcg ccgcgacaat ttgcgacggc gcgtgcaggg    4980
ccagactgga ggtggcaacg ccaatcagca acgactgttt gcccgccagt tgttgtgcca    5040
cgcggttggg aatgtaattc agctccgcca tcgccgcttc cacttttttcc cgcgttttcg    5100 cagaaacgtg gctggcctgg ttcaccacgc gggaaacggt ctgataagag acaccggcat    5160
actctgcgac atcgtataac gttactggtt tcacattcac caccctgaat tgactctctt    5220
ccgggcgcta tcatgccata ccgcgaaagg ttttgcgcca ttcgatggtg tccgggatct    5280
cgacgctctc ccttatgcga ctcctgcatt aggaaattaa tacgactcac tata         5334

<210> SEQ ID NO 2
<211> LENGTH: 5230
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 2
ggggaattgt gagcggataa caattcccct gtagaaataa ttttgtttaa ctttaataag      60
gagatatacc atggcacatc accaccacca tcacgtgggt accggttcga atgatgacga     120
cgacaagagc tcgatcacaa gtttgtacaa aaaagctgaa cgagaaacgt aaaatgatat     180
aaatatcaat atattaaatt agattttgca taaaaaacag actacataat actgtaaaac     240
acaacatatc cagtcactat ggcggccgcc acgttaaggg attttggtca tgatcagcac     300
gtgttgacaa ttaatcatcg gcatagtata tcggcatagt ataatacgac aaggtgagga     360
actaaaccat ggccaagttg accagtgccg ttccggtgct caccgcgcgc gacgtcgccg     420
gagcggtcga gttctggacc gaccggctcg ggttctcccg ggacttcgtg gaggacgact     480
tcgccggtgt ggtccgggac gacgtgaccc tgttcatcag cgcggtccag gaccaggtgg     540
tgccggacaa caccctggcc tgggtgtggg tgcgcggcct ggacgagctg tacgccgagt     600
ggtcggaggt cgtgtccacg aacttccggg acgcctccgg ccggccatg accgagatcg     660 gcgagcagcc gtgggggcgg gagttcgccc tgcgcgaccc ggccggcaac tgcgtgcact     720
tcgtggccga ggagcaggac tgatcatgat gatattattt tatcttgtgc aatgtaacat     780
cagagatttt gagacacggg ccagagctgc aggaaacag ctatgaccat gtaatacgac     840
tcactatagg ggatatcagc tggatggcaa ataatgattt tattttgact gatagtgacc     900
tgttcgttgc aacaccggtg ctagcgtata cccgaagtat gtcaaaaaga ggtgtgctat     960
gaagcagcgt attacagtga cagttgacag cgacagctat cagttgctca aggcatatat    1020
```

-continued

```
gatgtcaata tctccggtct ggtaagcaca accatgcaga atgaagcccg tcgtctgcgt    1080
gccgaacgct ggaaagcgga aaatcaggaa gggatggctg aggtcgcccg gtttattgaa    1140
atgaacggct cttttgctga cgagaacagg gactggtgaa atgcagttta aggtttacac    1200
ctataaaaga gagagccgtt atcgtctgtt tgtggatgta cagagtgata ttattgacac    1260
gcccgggcga cggatggtga tcccctggc cagtgcacgt ctgctgtcag ataaagtctc     1320
ccgtgaactt tacccggtgg tgcatatcgg ggatgaaagc tggcgcatga tgaccaccga    1380
tatggccagt gtgccggtct ccgttatcgg ggaagaagtg gctgatctca gccgccgcga    1440
aaatgacatc aaaaacgcca ttaacctgat gttctgggga atataaatgt caggctccct    1500
tatacacagc cagtctgcag gtcgaccata gtgactggat atgttgtgtt ttacagtatt    1560
atgtagtctg ttttttatgc aaaatctaat ttaatatatt gatatttata tcattttacg    1620
tttctcgttc agctttcttg tacaaagtgg tgataattaa ttaagatcag atccggctgc    1680
taagcttgag tccggatccc aattgggagc tcgtgtacac ggcgcgcctg caggtcgaca    1740
agcttgcggc cgcactcgag tctggtaaag aaaccgctgc tgcgaaattt gaacgccagc    1800
acatggactc gtctactagc gcagcttaat taacctaggc tgctgccacc gctgagcaat    1860
aactagcata ccccttggg gcctctaaac gggtcttgag gggttttttg ctgaaacctc     1920
aggcatttga gaagcacacg gtcacactgc ttccggtagt caataaaccg gtaaaccagc    1980
aatagacata gcggctatt taacgaccct gccctgaacc gacgacaagc tgacgaccgg     2040
gtctccgcaa gtggcacttt tcggggaaat gtgcgcggaa ccctatttg tttattttc     2100
taaatacatt caaatatgta tccgctcatg aattaattct tagaaaaact catcgagcat    2160
caaatgaaac tgcaatttat tcatatcagg attatcaata ccatatttt gaaaaagccg     2220
tttctgtaat gaaggagaaa actcaccgag gcagttccat aggatggcaa gatcctggta    2280
tcggtctgcg attccgactc gtccaacatc aatacaacct attaatttcc cctcgtcaaa    2340
aataaggtta tcaagtgaga atcaccatg agtgacgact gaatccggtg agaatggcaa    2400
aagtttatgc atttctttcc agacttgttc aacaggccag ccattacgct cgtcatcaaa    2460
atcactcgca tcaaccaaac cgttattcat tcgtgattgc gcctgagcga acgaaatac     2520
gcggtcgctg ttaaaggac aattacaaac aggaatcgaa tgcaaccggc gcaggaacac    2580
tgccagcgca tcaacaatat tttcacctga atcaggatat tcttctaata cctggaatgc    2640
tgttttcccg gggatcgcag tggtgagtaa ccatgcatca tcaggagtac ggataaaatg    2700
cttgatggtc ggaagaggca taaattccgt cagccagttt agtctgacca tctcatctgt    2760
aacatcattg gcaacgctac ctttgccatg tttcagaaac aactctggcg catcgggctt    2820
cccatacaat cgatagattg tcgcacctga ttgcccgaca ttatcgcgag cccatttata    2880
cccatataaa tcagcatcca tgttggaatt taatcgcggc ctagagcaag acgtttcccg    2940
ttgaatatgg ctcatactct tccttttca atattattga agcatttatc agggttattg    3000
tctcatgagc ggatacatat ttgaatgtat ttagaaaaat aaacaaatag gcatgcagcg    3060
ctcttccgct tcctcgctca ctgactcgct acgctcggtc gttcgactgc ggcgagcggt    3120
gtcagctcac tcaaaagcgg taatacggtt atccacagaa tcaggggata agccggaaa    3180
gaacatgtga gcaaaaagca aagcaccgga agaagccaac gccgcaggcg ttttccata    3240
ggctccgccc cctgacgag catcacaaaa atcgacgctc aagccagagg tggcgaaacc    3300
cgacaggact ataaagatac caggcgtttc cccctggaag ctccctcgtg cgctctcctg    3360
```

```
ttccgaccct gccgcttacc ggatacctgt ccgcctttct cccttcggga agcgtggcgc   3420
tttctcatag ctcacgctgt tggtatctca gttcggtgta ggtcgttcgc tccaagctgg   3480
gctgtgtgca cgaacccccc gttcagcccg accgctgcgc cttatccggt aactatcgtc   3540
ttgagtccaa cccggtaaga cacgacttat cgccactggc agcagccatt ggtaactgat   3600
ttagaggact ttgtcttgaa gttatgcacc tgttaaggct aaactgaaag aacagatttt   3660
ggtgagtgcg gtcctccaac ccacttacct tggttcaaag agttggtagc tcagcgaacc   3720
ttgagaaaac caccgttggt agcggtggtt tttctttatt tatgagatga tgaatcaatc   3780
ggtctatcaa gtcaacgaac agctattccg ttactctaga tttcagtgca atttatctct   3840
tcaaatgtag cacctgaagt cagccccata cgatataagt tgtaattctc atgttagtca   3900
tgccccgcgc ccaccggaag gagctgactg ggttgaaggc tctcaagggc atcggtcgag   3960
atcccggtgc ctaatgagtg agctaactta cattaattgc gttgcgctca ctgcccgctt   4020
tccagtcggg aaacctgtcg tgccagctgc attaatgaat cggccaacgc gcggggagag   4080
gcggtttgcg tattgggcgc cagggtggtt tttcttttca ccagtgagac gggcaacagc   4140
tgattgccct tcaccgcctg gccctgagag agttgcagca agcggtccac gctggtttgc   4200
cccagcaggc gaaaatcctg tttgatggtg gttaacggcg gatataaca tgagctgtct   4260 tcggtatcgt cgtatcccac taccgagatg tccgcaccaa cgcgcagccc ggactcggta   4320
atggcgcgca ttgcgcccag cgccatctga tcgttggcaa ccagcatcgc agtgggaacg   4380
atgccctcat tcagcatttg catggtttgt tgaaaaccgg acatggcact ccagtcgcct   4440
tcccgttccg ctatcggctg aatttgattg cgagtgagat atttatgcca gccagccaga   4500
cgcagacgcg ccgagacaga acttaatggg cccgctaaca gcgcgatttg ctggtgaccc   4560
aatgcgacca gatgctccac gcccagtcgc gtaccgtctt catgggagaa ataatactg   4620 ttgatgggtg tctggtcaga gacatcaaga aataacgccg gaacattagt gcaggcagct   4680
tccacagcaa tggcatcctg gtcatccagc ggatagttaa tgatcagccc actgacgcgt   4740
tgcgcgagaa gattgtgcac cgccgcttta caggcttcga cgccgcttcg ttctaccatc   4800
gacaccacca cgctggcacc cagttgatcg gcgcgagatt taatcgccgc gacaatttgc   4860
gacggcgcgt gcagggccag actggaggtg caacgccaa tcagcaacga ctgtttgccc   4920
gccagttgtt gtgccacgcg gttgggaatg taattcagct ccgccatcgc cgcttccact   4980 tttcccgcg ttttcgcaga aacgtggctg gcctggttca ccacgcggga aacggtctga   5040
taagagacac cggcatactc tgcgacatcg tataacgtta ctggtttcac attcaccacc   5100
ctgaattgac tctcttccgg gcgctatcat gccataccgc gaaaggtttt gcgccattcg   5160
atggtgtccg gatctcgac gctctccctt atgcgactcc tgcattagga aattaatacg   5220
actcactata                                                           5230
```

<210> SEQ ID NO 3
<211> LENGTH: 5538
<212> TYPE: DNA
<213> ORGANISM: Artificial Sequence
<220> FEATURE:
<223> OTHER INFORMATION: Description of Artificial Sequence: Synthetic vector nucleotide sequence

<400> SEQUENCE: 3

```
ggggaattgt gagcggataa caattcccct gtagaaataa ttttgtttaa ctttaataag    60
gagatatacc atgggcagca gccatcacca tcatcaccac agccaggatc cgaattcgag   120
```

```
ctcgatcaca agtttgtaca aaaaagctga acgagaaacg taaaatgata taaatatcaa    180
tatattaaat tagattttgc ataaaaaaca gactacataa tactgtaaaa cacaacatat    240
ccagtcacta tggcggccgc cacgttaagg gattttggtc atgatcagca cgtgttgaca    300
attaatcatc ggcatagtat atcggcatag tataatacga caaggtgagg aactaaacca    360
tggccaagtt gaccagtgcc gttccggtgc tcaccgcgcg cgacgtcgcc ggagcggtcg    420
agttctggac cgaccggctc gggttctccc gggacttcgt ggaggacgac ttcgccggtg    480
tggtccggga cgacgtgacc ctgttcatca gcgcggtcca ggaccaggtg gtgccggaca    540
acaccctggc ctgggtgtgg gtgcgcgccc tggacgagct gtacgccgag tggtcggagg    600
tcgtgtccac gaacttccgg gacgcctccg ggccggccat gaccgagatc ggcgagcagc    660
cgtgggggcg ggagttcgcc ctgcgcgacc cggccggcaa ctgcgtgcac ttcgtggccg    720
aggagcagga ctgatcatga tgatattatt ttatcttgtg caatgtaaca tcagagattt    780
tgagacacgg gccagagctg ccaggaaaca gctatgacca tgtaatacga ctcactatag    840
gggatatcag ctggatggca ataatgatt ttattttgac tgatagtgac ctgttcgttg    900
caacaccggt gctagcgtat acccgaagta tgtcaaaaag aggtgtgcta tgaagcagcg    960
tattacagtg acagttgaca gcgacagcta tcagttgctc aaggcatata tgatgtcaat   1020
atctccggtc tggtaagcac aaccatgcag aatgaagccc gtcgtctgcg tgccgaacgc   1080
tggaaagcgg aaaatcagga agggatggct gaggtcgccc ggtttattga aatgaacggc   1140
tcttttgctg acgagaacag ggactggtga atgcagtttt aaggtttaca cctataaaag   1200
agagagccgt tatcgtctgt ttgtggatgt acagagtgat attattgaca cgcccgggcg   1260
acggatggta atcccctgg ccagtgcacg tctgctgtca gataaagtct cccgtgaact   1320
ttacccggtg gtgcatatcg gggatgaaag ctggcgcatg atgaccaccg atatggccag   1380
tgtgccggtc tccgttatcg gggaagaagt ggctgatctc agccgccgcg aaaatgacat   1440
caaaaacgcc attaacctga tgttctgggg aatataaatg tcaggctccc ttatacacag   1500
ccagtctgca ggtcgaccat agtgactgga tatgttgtgt tttacagtat tatgtagtct   1560
gttttttatg caaaatctaa tttaatatat tgatatttat atcatttac gtttctcgtt   1620 cagctttctt gtacaaagtg gtgataatta ttaagatca gatccggctg ctaagcttgc   1680
ggccgcataa tgcttaagtc gaacagaaag taatcgtatt gtacacggcc gcataatcga   1740
aattaatacg actcactata ggggaattgt gagcggataa caattcccca tcttagtata   1800
ttagttaagt ataagaagga gatatacata tggcagatct caattggata tcggccggcc   1860
acgcgatcgc tgacgtcggt accctcgagt ctggtaaaga accgctgct gcgaaatttg   1920 aacgccagca catggactcg tctactagcg cagcttaatt aacctaggct gctgccaccg   1980
ctgagcaata actagcataa ccccttgggg cctctaaacg gtcttgagg gttttttgc   2040 tgaaacctca ggcatttgag aagcacacgg tcacactgct tccggtagtc aataaaccgg   2100
taaaccagca atagacataa gcggctattt aacgaccctg ccctgaaccg acgaccgggt   2160
cgaatttgct ttcgaatttc tgccattcat ccgcttatta tcacttattc aggcgtagca   2220
ccaggcgttt aagggcacca ataactgcct taaaaaaatt acgccccgcc ctgccactca   2280
tcgcagtact gttgtaattc attaagcatt ctgccgacat ggaagccatc acagacggca   2340
tgatgaacct gaatcgccag cggcatcagc accttgtcgc cttgcgtata atatttgccc   2400
atagtgaaaa cggggggcgaa gaagttgtcc atattggcca cgtttaaatc aaaactggtg   2460
aaactcaccc agggattggc tgagacgaaa aacatattct caataaaccc tttagggaaa   2520
```

```
taggccaggt tttcaccgta acacgccaca tcttgcgaat atatgtgtag aaactgccgg   2580
aaatcgtcgt ggtattcact ccagagcgat gaaaacgttt cagtttgctc atggaaaacg   2640
gtgtaacaag ggtgaacact atcccatatc accagctcac cgtctttcat tgccatacgg   2700
aactccggat gagcattcat caggcgggca agaatgtgaa taaaggccgg ataaaacttg   2760
tgcttatttt tctttacggt cttttaaaaag gccgtaatat ccagctgaac ggtctggtta   2820
taggtacatt gagcaactga ctgaaatgcc tcaaaatgtt ctttacgatg ccattgggat   2880
atatcaacgg tggtatatcc agtgattttt ttctccattt tagcttcctt agctcctgaa   2940
aatctcgata actcaaaaaa tacgcccggt agtgatctta tttcattatg gtgaaagttg   3000
gaacctctta cgtgccgatc aacgtctcat tttcgccaaa agttggccca gggcttcccg   3060
gtatcaacag ggacaccagg atttatttat tctgcgaagt gatcttccgt cacaggtatt   3120
tattcggcgc aaagtgcgtc gggtgatgct gccaacttac tgatttagtg tatgatggtg   3180 ttttgaggt gctccagtgg cttctgtttc tatcagctgt ccctcctgtt cagctactga   3240
cggggtggtg cgtaacggca aaagcaccgc cggacatcag cgctagcgga gtgtatactg   3300
gcttactatg ttggcactga tgagggtgtc agtgaagtgc ttcatgtggc aggagaaaaa   3360
aggctgcacc ggtgcgtcag cagaatatgt gatacaggat atattccgct tcctcgctca   3420
ctgactcgct acgctcggtc gttcgactgc ggcgagcgga atggcttac gaacggggcg   3480 gagatttcct ggaagatgcc aggaagatac ttaacaggga agtgagaggg ccgcggcaaa   3540 gccgttttc cataggctcc gccccctga caagcatcac gaaatctgac gctcaaatca   3600
gtggtggcga aacccgacag gactataaag ataccaggcg tttcccctgg cggctccctc   3660
gtgcgctctc ctgttcctgc ctttcggttt accggtgtca ttccgctgtt atggccgcgt   3720
ttgtctcatt ccacgcctga cactcagttc cgggtaggca gttcgctcca agctggactg   3780
tatgcacgaa ccccccgttc agtccgaccg ctgcgcctta ccggtaact atcgtcttga   3840 gtccaacccg gaaagacatg caaaagcacc actggcagca gccactggta attgatttag   3900
aggagttagt cttgaagtca tgcgccggtt aaggctaaac tgaaaggaca gttttggtg   3960 actgcgctcc tccaagccag ttacctcggt tcaaagagtt ggtagctcag agaaccttcg   4020 aaaaccgcc ctgcaaggcg gttttttcgt tttcagagca agagattacg cgcagaccaa   4080
aacgatctca agaagatcat cttattaatc agataaaata tttctagatt tcagtgcaat   4140
ttatctcttc aaatgtagca cctgaagtca gccccatacg atataagttg taattctcat   4200
gttagtcatg ccccgcgccc accggaagga gctgactggg ttgaaggctc tcaagggcat   4260
cggtcgagat cccggtgcct aatgagtgag ctaacttaca ttaattgcgt tgcgctcact   4320
gcccgctttc cagtcgggaa acctgtcgtg ccagctgcat taatgaatcg gccaacgcgc   4380
ggggagaggc ggtttgcgta ttgggcgcca gggtggtttt tcttttcacc agtgagacgg   4440
gcaacagctg attgcccttc accgcctggc cctgagagag ttgcagcaag cggtccacgc   4500
tggtttgccc cagcaggcga aaatcctgtt tgatggtggt taacggcggg atataacatg   4560
agctgtcttc ggtatcgtcg tatcccacta ccgagatgtc cgcaccaacg cgcagcccgg   4620
actcggtaat ggcgcgcatt gcgcccagcg ccatctgatc gttggcaacc agcatcgcag   4680
tgggaacgat gccctcattc agcatttgca tggtttgttg aaaaccggac atggcactcc   4740
agtcgccttc ccgttccgct atcggctgaa tttgattgcg agtgagatat ttatgccagc   4800
cagccagacg cagacgcgcc gagacagaac ttaatgggcc cgctaacagc gcgatttgct   4860
```

```
ggtgacccaa tgcgaccaga tgctccacgc ccagtcgcgt accgtcttca tgggagaaaa    4920
taatactgtt gatgggtgtc tggtcagaga catcaagaaa taacgccgga acattagtgc    4980
aggcagcttc cacagcaatg gcatcctggt catccagcgg atagttaatg atcagcccac    5040
tgacgcgttg cgcgagaaga ttgtgcaccg ccgctttaca ggcttcgacg ccgcttcgtt    5100
ctaccatcga caccaccacg ctggcaccca gttgatcggc gcgagattta atcgccgcga    5160
caatttgcga cggcgcgtgc agggccagac tggaggtggc aacgccaatc agcaacgact    5220
gtttgcccgc cagttgttgt gccacgcggt tgggaatgta attcagctcc gccatcgccg    5280
cttccacttt ttcccgcgtt ttcgcagaaa cgtggctggc ctggttcacc acgcgggaaa    5340
cggtctgata agagacaccg gcatactctg cgacatcgta taacgttact ggtttcacat    5400
tcaccaccct gaattgactc tcttccgggc gctatcatgc cataccgcga aaggttttgc    5460
gccattcgat ggtgtccggg atctcgacgc tctcccttat gcgactcctg cattaggaaa    5520
ttaatacgac tcactata                                                 5538

<210> SEQ ID NO 4
<211> LENGTH: 1561
<212> TYPE: DNA
<213> ORGANISM: Artificial Sequence
<220> FEATURE:
<223> OTHER INFORMATION: Description of Artificial Sequence: Synthetic
      vector nucleotide sequence
<220> FEATURE:
<221> NAME/KEY: CDS
<222> LOCATION: (243)..(614)

<400> SEQUENCE: 4
gagctcgatc acaagtttgt acaaaaaagc tgaacgagaa acgtaaaatg atataaatat      60
caatatatta aattagattt tgcataaaaa acagactaca taatactgta aaacacaaca     120
tatccagtca ctatggcggc cgccacgtta agggattttg gtcatgatca gcacgtgttg     180
acaattaatc atcggcatag tatatcggca tagtataata cgacaaggtg aggaactaaa     240 cc atg gcc aag ttg acc agt gcc gtt ccg gtg ctc acc gcg cgc gac        287
   Met Ala Lys Leu Thr Ser Ala Val Pro Val Leu Thr Ala Arg Asp
   1               5                   10                  15 gtc gcc gga gcg gtc gag ttc tgg acc gac cgg ctc ggg ttc tcc cgg       335
Val Ala Gly Ala Val Glu Phe Trp Thr Asp Arg Leu Gly Phe Ser Arg
             20                  25                  30 gac ttc gtg gag gac gac ttc gcc ggt gtg gtc cgg gac gac gtg acc       383
Asp Phe Val Glu Asp Asp Phe Ala Gly Val Val Arg Asp Asp Val Thr
         35                  40                  45 ctg ttc atc agc gcg gtc cag gac cag gtg gtg ccg gac aac acc ctg       431
Leu Phe Ile Ser Ala Val Gln Asp Gln Val Val Pro Asp Asn Thr Leu
     50                  55                  60 gcc tgg gtg tgg gtg cgc ggc ctg gac gag ctg tac gcc gag tgg tcg       479
Ala Trp Val Trp Val Arg Gly Leu Asp Glu Leu Tyr Ala Glu Trp Ser
 65                  70                  75                  80 gag gtc gtg tcc acg aac ttc cgg gac gcc tcc ggg ccg gcc atg acc       527
Glu Val Val Ser Thr Asn Phe Arg Asp Ala Ser Gly Pro Ala Met Thr
                 85                  90                  95 gag atc ggc gag cag ccg tgg ggg cgg gag ttc gcc ctg cgc gac ccg       575
Glu Ile Gly Glu Gln Pro Trp Gly Arg Glu Phe Ala Leu Arg Asp Pro
            100                 105                 110 gcc ggc aac tgc gtg cac ttc gtg gcc gag gag cag gac tgatcatgat       624
Ala Gly Asn Cys Val His Phe Val Ala Glu Glu Gln Asp
        115                 120 gatattattt tatcttgtgc aatgtaacat cagagatttt gagacacggg ccagagctgc     684
```

-continued

| | |
|---|---|
| caggaaacag ctatgaccat gtaatacgac tcactatagg ggatatcagc tggatggcaa | 744 |
| ataatgattt tattttgact gatagtgacc tgttcgttgc aacaccggtg ctagcgtata | 804 |
| cccgaagtat gtcaaaaaga ggtgtgctat gaagcagcgt attacagtga cagttgacag | 864 |
| cgacagctat cagttgctca aggcatatat gatgtcaata tctccggtct ggtaagcaca | 924 |
| accatgcaga atgaagcccg tcgtctgcgt gccgaacgct ggaaagcgga aaatcaggaa | 984 |
| gggatggctg aggtcgcccg gtttattgaa atgaacggct cttttgctga cgagaacagg | 1044 |
| gactggtgaa atgcagttta aggtttacac ctataaaaga gagagccgtt atcgtctgtt | 1104 |
| tgtggatgta cagagtgata ttattgacac gcccgggcga cggatggtga tccccctggc | 1164 |
| cagtgcacgt ctgctgtcag ataaagtctc ccgtgaactt acccggtgg tgcatatcgg | 1224 |
| ggatgaaagc tggcgcatga tgaccaccga tatggccagt gtgccggtct ccgttatcgg | 1284 |
| ggaagaagtg gctgatctca gccgccgcga aaatgacatc aaaaacgcca ttaacctgat | 1344 |
| gttctgggga atataaatgt caggctccct tatacacagc cagtctgcag gtcgaccata | 1404 |
| gtgactggat atgttgtgtt ttacagtatt atgtagtctg ttttttatgc aaaatctaat | 1464 |
| ttaatatatt gatatttata tcattttacg tttctcgttc agctttcttg tacaaagtgg | 1524 |
| tgataattaa ttaagatcag atccggctgc taagctt | 1561 |

<210> SEQ ID NO 5
<211> LENGTH: 5567
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 5

| | |
|---|---|
| ggggaattgt gagcggataa caattcccct gtagaaataa ttttgtttaa ctttaataag | 60 |
| gagatatacc atgggcagca gccatcacca tcatcaccac agccaggatc cgaattcgag | 120 |
| ctcggaccat gattacgcca agctatcaac tttgtataga aagttgaac gagaaacgta | 180 |
| aaatgatata aatatcaata tattaaatta gattttgcat aaaaaacaga ctacataata | 240 |
| ctgtaaaaca caacatatcc agtcactatg gtcgacctgc agactggctg tgtataaggg | 300 |
| agcctgacat ttatattccc cagaacatca ggttaatggc gttttttgatg tcattttcgc | 360 |
| ggtggctgag atcagccact tcttccccga taacggagac cggcacactg gccatatcgg | 420 |
| tggtcatcat gcgccagctt tcatcccga tatgcaccac cgggtaaagt tcacggggga | 480 |
| ctttatctga cagcagacgt gcactggcca ggggatcac catccgtcgc ccgggcgtgt | 540 |
| caataatatc actctgtaca tccacaaaca gacgataacg ctctctctt ttataggtgt | 600 |
| aaaccttaaa ctgcatttca ccagcccctg ttctcgtcgg caaagagcc gttcatttca | 660 |
| ataaaccggg cgacctcagc catcccttcc tgattttccg ctttcagcg ttcggcacgc | 720 |
| agacgacggg cttcattctg catggttgtg cttaccgaac cggagatatt gacatcatat | 780 |
| atgccttgag caactgatag ctgtcgctgt caactgtcac tgtaatacgc tgcttcatag | 840 |
| catacctctt tttgacatac ttcgggtata catatcagta tatattctta taccgcaaaa | 900 |
| atcagcgcgc aaatacgcat actgttatct ggcttttagt aagccggatc tctagatta | 960 |
| cgccccgccc tgccactcat cgcagtactg ttgtaattca ttaagcattc tgccgacatg | 1020 |
| gaagccatca caaacggcat gatgaacctg aatcgccagc ggcatcagca ccttgtcgcc | 1080 |
| ttgcgtataa tatttgccca tggtgaaaac gggggcgaag aagttgtcca tattggccac | 1140 |

```
gtttaaatca aaactggtga aactcaccca gggattggct gagacgaaaa acatattctc    1200
aataaaccct ttagggaaat aggccaggtt ttcaccgtaa cacgccacat cttgcgaata    1260
tatgtgtaga aactgccgga aatcgtcgtg gtattcactc cagagcgatg aaaacgtttc    1320
agtttgctca tggaaaacgg tgtaacaagg gtgaacacta tcccatatca ccagctcacc    1380
gtctttcatt gccatacgga attccggatg agcattcatc aggcgggcaa gaatgtgaat    1440
aaaggccgga taaaacttgt gcttattttt ctttacggtc tttaaaaagg ccgtaatatc    1500
cagctgaacg gtctggttat aggtacattg agcaactgac tgaaatgcct caaaatgttc    1560
tttacgatgc cattgggata tatcaacggt ggtatatcca gtgatttttt tctccatttt    1620
agcttcctta gctcctgaaa atctcgacgc atcctaactc aaaatccaca cattatacga    1680
gccggaagca taaagtgtaa agcctggggg tgcctaatgc ggccgccata gtgactggat    1740
atgttgtgtt ttacagtatt atgtagtctg ttttttatgc aaaatctaat ttaatatatt    1800
gatatttata tcattttacg tttctcgttc aactttatta tacatagttg ataattcact    1860
ggccgtcgtt ttacaacgtc gtgactggga aaaccctggc gttacccaac ttaatcgcct    1920
tgcagcacaa gcttgcggcc gcataatgct taagtcgaac agaaagtaat cgtattgtac    1980
acggccgcat aatcgaaatt aatacgactc actatagggg aattgtgagc ggataacaat    2040
tccccatctt agtatattag ttaagtataa gaaggagata tacatatggc agatctcaat    2100
tggatatcgg ccggccacgc gatcgctgac gtcggtaccc tcgagtctgg taaagaaacc    2160
gctgctgcga aatttgaacg ccagcacatg gactcgtcta ctagcgcagc ttaattaacc    2220
taggctgctg ccaccgctga gcaataacta gcataacccc ttggggcctc taaacgggtc    2280
ttgagggggtt ttttgctgaa acctcaggca tttgagaagc acacggtcac actgcttccg    2340
gtagtcaata aaccggtaaa ccagcaatag acataagcgg ctatttaacg accctgccct    2400
gaaccgacga ccgggtcatc gtggccggat cttgcggccc ctcggcttga acgaattgtt    2460
agacattatt tgccgactac cttggtgatc tcgcctttca cgtagtggac aaattcttcc    2520
aactgatctg cgcgcgaggc caagcgatct tcttcttgtc caagataagc ctgtctagct    2580
tcaagtatga cgggctgata ctgggccggc aggcgctcca ttgcccagtc ggcagcgaca    2640
tccttcggcg cgattttgcc ggttactgcg ctgtaccaaa tgcgggacaa cgtaagcact    2700
acatttcgct catcgccagc ccagtcgggc ggcgagttcc atagcgttaa ggtttcattt    2760
agcgcctcaa atagatcctg ttcaggaacc ggatcaaaga gttcctccgc cgctggacct    2820
accaaggcaa cgctatgttc tcttgctttt gtcagcaaga tagccagatc aatgtcgatc    2880
gtggctggct cgaagatacc tgcaagaatg tcattgcgct gccattctcc aaattgcagt    2940
tcgcgcttag ctggataacg ccacggaatg atgtcgtcgt gcacaacaat ggtgacttct    3000
acagcgcgga gaatctcgct ctctccaggg gaagccgaag tttccaaaag gtcgttgatc    3060
aaagctcgcc gcgttgtttc atcaagcctt acggtcaccg taaccagcaa atcaatatca    3120
ctgtgtggct tcaggccgcc atccactgcg gagccgtaca aatgtacggc cagcaacgtc    3180
ggttcgagat ggcgctcgat gacgccaact acctctgata gttgagtcga tacttcggcg    3240
atcaccgctt ccctcatact cttcctttttt caatattatt gaagcattta tcagggttat    3300
tgtctcatga gcggatacat atttgaatgt atttagaaaa ataaacaaat agctagctca    3360
ctcggtcgct acgctccggg cgtgagactg cggcgggcgc tgcggacaca tacaaagtta    3420
cccacagatt ccgtggataa gcaggggact aacatgtgag gcaaaacagc agggccgcgc    3480
```

```
cggtggcgtt tttccatagg ctccgccctc ctgccagagt tcacataaac agacgctttt    3540
ccggtgcatc tgtgggagcc gtgaggctca accatgaatc tgacagtacg ggcgaaaccc    3600
gacaggactt aaagatcccc accgtttccg gcgggtcgct ccctcttgcg ctctcctgtt    3660
ccgaccctgc cgtttaccgg atacctgttc cgcctttctc ccttacggga agtgtggcgc    3720
tttctcatag ctcacacact ggtatctcgg ctcggtgtag gtcgttcgct ccaagctggg    3780
ctgtaagcaa gaactccccg ttcagcccga ctgctgcgcc ttatccggta actgttcact    3840
tgagtccaac ccggaaaagc acggtaaaac gccactggca gcagccattg gtaactggga    3900
gttcgcagag gatttgttta gctaaacacg cggttgctct tgaagtgtgc gccaaagtcc    3960
ggctacactg gaaggacaga tttggttgct gtgctctgcg aaagccagtt accacggtta    4020
agcagttccc caactgactt aaccttcgat caaaccacct ccccaggtgg ttttttcgtt    4080
tacagggcaa aagattacgc gcagaaaaaa aggatctcaa gaagatcctt tgatcttttc    4140
tactgaaccg ctctagattt cagtgcaatt tatctcttca aatgtagcac ctgaagtcag    4200
ccccatacga tataagttgt aattctcatg ttagtcatgc cccgcgccca ccggaaggag    4260
ctgactgggt tgaaggctct caagggcatc ggtcgagatc ccggtgccta atgagtgagc    4320
taacttacat taattgcgtt gcgctcactg cccgctttcc agtcgggaaa cctgtcgtgc    4380
cagctgcatt aatgaatcgg ccaacgcgcg gggagaggcg gtttgcgtat tgggcgccag    4440
ggtggttttt cttttcacca gtgagacggg caacagctga ttgcccttca ccgcctggcc    4500
ctgagagagt tgcagcaagc ggtccacgct ggtttgcccc agcaggcgaa aatcctgttt    4560
gatggtggtt aacggcggga tataacatga gctgtcttcg gtatcgtcgt atcccactac    4620
cgagatgtcc gcaccaacgc gcagcccgga ctcggtaatg gcgcgcattg cgcccagcgc    4680
catctgatcg ttggcaacca gcatcgcagt gggaacgatg ccctcattca gcatttgcat    4740
ggtttgttga aaaccggaca tggcactcca gtcgccttcc cgttccgcta tcggctgaat    4800
ttgattgcga gtgagatatt tatgccagcc agccagacgc agacgcgccg agacagaact    4860
taatgggccc gctaacagcg cgatttgctg gtgacccaat gcgaccagat gctccacgcc    4920
cagtcgcgta ccgtcttcat gggagaaaat aatactgttg atgggtgtct ggtcagagac    4980
atcaagaaat aacgccggaa cattagtgca ggcagcttcc acagcaatgg catcctggtc    5040
atccagcgga tagttaatga tcagcccact gacgcgttgc gcgagaagat tgtgcaccgc    5100
cgctttacag gcttcgacgc cgcttcgttc taccatcgac accaccacgc tggcacccag    5160
ttgatcggcg cgagatttaa tcgccgcgac aatttgcgac ggcgcgtgca gggccagact    5220
ggaggtggca acgccaatca gcaacgactg tttgcccgcc agttgttgtg ccacgcggtt    5280
gggaatgtaa ttcagctccg ccatcgccgc ttccactttt tcccgcgttt tcgcagaaac    5340
gtggctggcc tggttcacca cgcgggaaac ggtctgataa gagacaccgg catactctgc    5400
gacatcgtat aacgttactg gtttcacatt caccaccctg aattgactct cttccgggcg    5460
ctatcatgcc ataccgcgaa aggttttgcg ccattcgatg gtgtccggga tctcgacgct    5520
ctcccttatg cgactcctgc attaggaaat taatacgact cactata    5567
```

<210> SEQ ID NO 6
<211> LENGTH: 5615
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 6

```
ggggaattgt gagcggataa caattcccct gtagaaataa ttttgtttaa ctttaataag      60
gagatatacc atgggcagca gccatcacca tcatcaccac agccaggatc cgaattcgag     120
ctcggaccat gattacgcca agctatcaac tttgtataga aaagttgaac gagaaacgta     180
aaatgatata aatatcaata tattaaatta gattttgcat aaaaaacaga ctacataata     240
ctgtaaaaca caacatatcc agtcactatg gtcgacctgc agactggctg tgtataaggg     300
agcctgacat ttatattccc cagaacatca ggttaatggc gttttttgatg tcattttcgc    360
ggtggctgag atcagccact tcttccccga taacggagac cggcacactg gccatatcgg    420
tggtcatcat gcgccagctt tcatccccga tatgcaccac cgggtaaagt tcacggggga    480
ctttatctga cagcagacgt gcactggcca ggggatcac catccgtcgc ccgggcgtgt     540
caataatatc actctgtaca tccacaaaca gacgataacg gctctctctt ttataggtgt    600
aaaccttaaa ctgcatttca ccagccctg ttctcgtcgg caaagagcc gttcatttca     660
ataaaccggg cgacctcagc catcccttcc tgattttccg ctttccagcg ttcggcacgc    720
agacgacggg cttcattctg catggttgtg cttaccgaac cggagatatt gacatcatat    780
atgccttgag caactgatag ctgtcgctgt caactgtcac tgtaatacgc tgcttcatag    840
catacctctt tttgacatac ttcgggtata catatcagta tatattctta taccgcaaaa    900
atcagcgcgc aaatacgcat actgttatct ggcttttagt aagccggatc tctagatta     960
cgccccgccc tgccactcat cgcagtactg ttgtaattca ttaagcattc tgccgacatg   1020
gaagccatca caaacggcat gatgaacctg aatcgccagc ggcatcagca ccttgtcgcc   1080
ttgcgtataa tatttgccca tggtgaaaac ggggcgaag aagttgtcca tattggccac    1140
gtttaaatca aaactggtga aactcaccca gggattggct gagacgaaaa acatattctc   1200
aataaaccct ttagggaaat aggccaggtt ttcaccgtaa cacgccacat cttgcgaata   1260
tatgtgtaga aactgccgga atcgtcgtg gtattcactc cagagcgatg aaaacgtttc    1320
agtttgctca tggaaaacgg tgtaacaagg gtgaacacta tcccatatca ccagctcacc   1380
gtctttcatt gccatacgga attccggatg agcattcatc aggcgggcaa gaatgtgaat   1440
aaaggccgga taaacttgt gcttattttt ctttacggtc tttaaaaagg ccgtaatatc     1500
cagctgaacg gtctggttat aggtacattg agcaactgac tgaaatgcct caaaatgttc   1560
tttacgatgc cattgggata tatcaacggt ggtatatcca gtgatttttt tctccatttt   1620
agcttcctta gctcctgaaa atctcgacgg atcctaactc aaaatccaca cattatacga   1680
gccggaagca taagtgtaa agcctggggg tgcctaatgc ggccgccata gtgactggat   1740
atgttgtgtt ttacagtatt atgtagtctg ttttttatgc aaaatctaat ttaatatatt   1800
gatatttata tcatttttacg tttctcgttc aactttatta tacatagttg ataattcact   1860
ggccgtcgtt ttacaacgtc gtgactggga aaacctggc gttacccaac ttaatcgcct    1920
tgcagcacaa gcttgcggcc gcataatgct taagtcgaac agaaagtaat cgtattgtac   1980
acggccgcat aatcgaaatt aatacgactc actataggg aattgtgagc ggataacaat    2040
tccccatctt agtatattag ttaagtataa gaaggagata tacatatggc agatctcaat   2100
tggatatcgg ccgccacgc gatcgctgac gtcggtaccc tcgagtctgg taaagaaacc   2160
gctgctgcga aatttgaacg ccagcacatg gactcgtcta ctagcgcagc ttaattaacc   2220
taggctgctg ccaccgctga gcaataacta gcataacccc ttggggcctc taaacgggtc   2280
ttgagggggtt ttttgctgaa acctcaggca tttgagaagc acacggtcac actgcttccg   2340
```

```
gtagtcaata aaccggtaaa ccagcaatag acataagcgg ctatttaacg accctgccct   2400
gaaccgacga caagctgacg accgggtctc cgcaagtggc acttttcggg gaaatgtgcg   2460
cggaacccct atttgtttat ttttctaaat acattcaaat atgtatccgc tcatgaatta   2520
attcttagaa aaactcatcg agcatcaaat gaaactgcaa tttattcata tcaggattat   2580
caataccata tttttgaaaa agccgtttct gtaatgaagg agaaaactca ccgaggcagt   2640
tccataggat ggcaagatcc tggtatcggt ctgcgattcc gactcgtcca acatcaatac   2700
aacctattaa ttttcccctcg tcaaaaataa ggttatcaag tgagaaatca ccatgagtga   2760
cgactgaatc cggtgagaat ggcaaaagtt tatgcatttc tttccagact tgttcaacag   2820
gccagccatt acgctcgtca tcaaaatcac tcgcatcaac caaaccgtta ttcattcgtg   2880
attgcgcctg agcgagacga atacgcggt cgctgttaaa aggacaatta caaacaggaa   2940
tcgaatgcaa ccggcgcagg aacactgcca gcgcatcaac aatattttca cctgaatcag   3000
gatattcttc taatacctgg aatgctgttt tcccgggat cgcagtggtg agtaaccatg   3060
catcatcagg agtacggata aaatgcttga tggtcggaag aggcataaat tccgtcagcc   3120
agtttagtct gaccatctca tctgtaacat cattggcaac gctacctttg ccatgtttca   3180
gaaacaactc tggcgcatcg gcttcccat acaatcgata gattgtcgca cctgattgcc   3240
cgacattatc gcgagcccat ttatacccat ataaatcagc atccatgttg gaatttaatc   3300
gcggcctaga gcaagacgtt tcccgttgaa tatggctcat actcttcctt tttcaatatt   3360
attgaagcat ttatcagggt tattgtctca tgagcggata catatttgaa tgtatttaga   3420
aaaataaaca aataggcatg cagcgctctt ccgcttcctc gctcactgac tcgctacgct   3480
cggtcgttcg actgcggcga gcggtgtcag ctcactcaaa agcggtaata cggttatcca   3540
cagaatcagg ggataaagcc ggaaagaaca tgtgagcaaa aagcaaagca ccggaagaag   3600
ccaacgccgc aggcgttttt ccataggctc cgccccctg acgagcatca caaaaatcga   3660
cgctcaagcc agaggtggcg aaacccgaca ggactataaa gataccaggc gtttccccct   3720
ggaagctccc tcgtgcgctc tcctgttccg accctgccgc ttaccggata cctgtccgcc   3780
tttctccctt cgggaagcgt ggcgctttct catagctcac gctgttggta tctcagttcg   3840
gtgtaggtcg ttcgctccaa gctgggctgt gtgcacgaac ccccgttca gcccgaccgc   3900 tgcgccttat ccggtaacta tcgtcttgag tccaacccgg taagacacga cttatcgcca   3960
ctggcagcag ccattggtaa ctgatttaga ggactttgtc ttgaagttat gcacctgtta   4020
aggctaaact gaaagaacag attttggtga gtgcggtcct ccaacccact taccttggtt   4080
caaagagttg gtagctcagc gaaccttgag aaaaccaccg ttggtagcgg tggttttct   4140 ttatttatga gatgatgaat caatcggtct atcaagtcaa cgaacagcta ttccgttact   4200
ctagatttca gtgcaattta tctcttcaaa tgtagcacct gaagtcagcc ccatacgata   4260
taagttgtaa ttctcatgtt agtcatgccc cgcgcccacc ggaaggagct gactgggttg   4320
aaggctctca agggcatcgg tcgagatccc ggtgcctaat gagtgagcta acttacatta   4380
attgcgttgc gctcactgcc cgcttttcag tcgggaaacc tgtcgtgcca gctgcattaa   4440
tgaatcggcc aacgcgcggg gagaggcggt ttgcgtattg ggcgccaggg tggttttct   4500 tttcaccagt gagacgggca acagctgatt gcccttcacc gcctggccct gagagagttg   4560
cagcaagcgg tccacgctgg tttgccccag caggcgaaaa tcctgtttga tggtggttaa   4620
cggcgggata taacatgagc tgtcttcggt atcgtcgtat cccactaccg agatgtccgc   4680
```

```
accaacgcgc agcccggact cggtaatggc gcgcattgcg cccagcgcca tctgatcgtt      4740
ggcaaccagc atcgcagtgg gaacgatgcc ctcattcagc atttgcatgg tttgttgaaa      4800
accggacatg gcactccagt cgccttcccg ttccgctatc ggctgaattt gattgcgagt      4860
gagatattta tgccagccag ccagacgcag acgcgccgag acagaactta atgggcccgc      4920
taacagcgcg atttgctggt gacccaatgc gaccagatgc tccacgccca gtcgcgtacc      4980
gtcttcatgg gagaaaataa tactgttgat gggtgtctgg tcagagacat caagaaataa      5040
cgccggaaca ttagtgcagg cagcttccac agcaatggca tcctggtcat ccagcggata      5100
gttaatgatc agcccactga cgcgttgcgc gagaagattg tgcaccgccg ctttacaggc      5160
ttcgacgccg cttcgttcta ccatcgacac caccacgctg cacccagtt gatcggcgcg       5220 agatttaatc gccgcgacaa tttgcgacgg cgcgtgcagg gccagactgg aggtggcaac      5280
gccaatcagc aacgactgtt tgcccgccag ttgttgtgcc acgcggttgg gaatgtaatt      5340
cagctccgcc atcgccgctt ccactttttc ccgcgttttc gcagaaacgt ggctggcctg      5400
gttcaccacg cgggaaacgg tctgataaga gacaccggca tactctgcga catcgtataa      5460
cgttactggt ttcacattca ccaccctgaa ttgactctct tccgggcgct atcatgccat      5520
accgcgaaag gttttgcgcc attcgatggt gtccgggatc tcgacgctct cccttatgcg      5580
actcctgcat taggaaatta atacgactca ctata                                 5615

<210> SEQ ID NO 7
<211> LENGTH: 2449
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 7
gagctcgacc atgattacgc caagctatca actttgtata gaaaagttga acgagaaacg        60
taaaatgata taaatatcaa tatattaaat tagattttgc ataaaaaaca gactacataa       120
tactgtaaaa cacaacatat ccagtcacta tggtcgacct gcagactggc tgtgtataag       180
ggagcctgac atttatattc cccagaacat caggttaatg gcgttttga tgtcattttc        240 gcggtggctg agatcagcca cttcttcccc gataacggag accggcacac tggccatatc       300
ggtggtcatc atgcgccagc tttcatcccc gatatgcacc accgggtaaa gttcacgggg       360
gactttatct gacagcagac gtgcactggc caggggatc accatccgtc gcccgggcgt       420
gtcaataata tcactctgta catccacaaa cagacgataa cggctctctc ttttataggt       480
gtaaacctta aactgcattt caccagcccc tgttctcgtc ggcaaaagag ccgttcattt       540
caataaaccg ggcgacctca gccatccctt cctgattttc cgctttccag cgttcggcac       600
gcagacgacg gcttcattc tgcatggttg tgcttaccga accggagata ttgacatcat        660
atatgccttg agcaactgat agctgtcgct gtcaactgtc actgtaatac gctgcttcat       720 agcataccte ttttgacat acttcgggta tacatatcag tatatattct tataccgcaa       780
aaatcagcgc gcaaatacgc atactgttat ctggcttta gtaagccgga tcctctagag       840
acgcgatgga tatgttctgc caagggtgg tttgcgcatt cacagttctc gcaagaattt       900
gattggctcc aattcttgga gtggtgaatc cgttagcgag gtgccgccgg cttccattca       960
ggtcgaggtg gccggctcc atgcaccgcg acgcaacgcg gggaggcaga caaggtatag      1020
ggcggcgcct acaatccatg ccaacccgtt ccatgtgctc gccgaggcgg cataaatcgc      1080
```

-continued

```
cgtgacgatc agcggtccag tgatcgaagt taggctggta agagccgcga gcgatccttg    1140
aagctgtccc tgatggtcgt catctacctg cctggacagc atggcctgca acgcgggcat    1200
cccgatgccg ccggaagcga gaagaatcat aatggggaag ccatccagc ctcgcgtcgc     1260 gaacgccagc aagacgtagc ccagcgcgtc ggccgccatg ccggcgataa tggcctgctt    1320
ctcgccgaaa cgtttggtgg cgggaccagt gacgaaggct tgagcgaggg cgtgcaagat    1380
tccgaatacc gcaagcgaca ggccgatcat cgtcgcgctc cagcgaaagc ggtcctcgcc    1440
gaaaatgacc cagagcgctg ccggcacctg tcctacgagt tgcatgataa agaagacagt    1500
cataagtgcg gcgacgatag tcatgccccg cgcccaccgg aaggagctga ctgggttgaa    1560
ggctctcaag ggcatcggtc gacgctctcc cttatgcgac tcctgcatta ggaagcagcc    1620
cagtagtagg ttgaggccgt tgagcaccgc cgccgcaagg aatggtgcat gcaaggagat    1680
ggcgcccaac agtcccccgg ccacggggcc tgccaccata cccacgccga acaagcgct     1740 catgagcccg aagtgcgag cccgatcttc cccatcggtg atgtcggcga taggcgcc      1800 agcaaccgca cctgtggcgc cggtgatgcc ggccacgatg cgtccggcgt agaggatcca    1860
caggacgggt gtggtcgcca tgatcgcgta gtcgatagtg gctccaagta gcgaagcgag    1920
caggactggg cggcggccaa agcggtcgga cagtgctccg agaacgggtg cgcatagaaa    1980
ttgcatcaac gcatatagcg ctagcagcac gccatagtga ctggcgatgc tgtcggaatg    2040
gacgatatcc cgcaagaggc ccggcagtac cggcataacc aagcctatgc ctacagcatc    2100
cagggtgacg gtgccgagga tgacgatgag cgcattgtta gatttcatac acggtgcctg    2160
actgcgttag caatttaact gtgataaact accgcattaa agcttatcga tgataagctg    2220
tcaaacatga aagcggccg ccatagtgac tggatatgtt gtgttttaca gtattatgta     2280
gtctgttttt tatgcaaaat ctaatttaat atattgatat ttatatcatt ttacgtttct    2340
cgttcaactt tattatacat agttgataat tcactggccg tcgttttaca acgtcgtgac    2400
tgggaaaacc ctggcgttac ccaacttaat cgccttgcag cacaagctt                2449
```

<210> SEQ ID NO 8
<211> LENGTH: 6426
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 8

```
ggggaattgt gagcggataa caattcccct gtagaaataa ttttgtttaa ctttaataag     60
gagatatacc atgggcagca gccatcacca tcatcaccac agccaggatc cgaattcgag    120
ctcgaccatg attacgccaa gctatcaact ttgtatagaa aagttgaacg agaaacgtaa    180
aatgatataa atatcaatat attaaattag attttgcata aaaaacagac tacataatac    240
tgtaaaacac aacatatcca gtcactatgg tcgacctgca gactggctgt gtataaggga    300
gcctgacatt tatattcccc agaacatcag gttaatggcg ttttttgatgt cattttcgcg    360 gtggctgaga tcagccactt cttccccgat aacggagacc ggcacactgg ccatatcggt    420
ggtcatcatg cgccagcttt catccccgat atgcaccacc gggtaaagtt cacgggggac    480
tttatctgac agcagacgtg cactggccag ggggatcacc atccgtcgcc cgggcgtgtc    540
aataatatca ctctgtacat ccacaaacag acgataacgg ctctctcttt tataggtgta    600
aaccttaaac tgcatttcac cagcccctgt tctcgtcggc aaaagagccg ttcatttcaa    660
```

```
taaaccgggc gacctcagcc atcccttcct gattttccgc tttccagcgt tcggcacgca    720
gacgacgggc ttcattctgc atggttgtgc ttaccgaacc ggagatattg acatcatata    780
tgccttgagc aactgatagc tgtcgctgtc aactgtcact gtaatacgct gcttcatagc    840
atacctcttt ttgacatact tcgggtatac atatcagtat atattcttat accgcaaaaa    900
tcagcgcgca aatacgcata ctgttatctg gcttttagta agccggatcc tctagagacg    960
cgatggatat gttctgccaa gggttggttt gcgcattcac agttctccgc aagaattgat   1020
tggctccaat tcttggagtg gtgaatccgt tagcgaggtg ccgccggctt ccattcaggt   1080
cgaggtggcc cggctccatg caccgcgacg caacgcgggg aggcagacaa ggtatagggc   1140
ggcgcctaca atccatgcca acccgttcca tgtgctcgcc gaggcggcat aaatcgccgt   1200
gacgatcagc ggtccagtga tcgaagttag gctggtaaga gccgcgagcg atccttgaag   1260
ctgtccctga tggtcgtcat ctacctgcct ggacagcatg gcctgcaacg cgggcatccc   1320
gatgccgccg gaagcgagaa gaatcataat ggggaaggcc atccagcctc gcgtcgcgaa   1380
cgccagcaag acgtagccca gcgcgtcggc cgccatgccg gcgataatgg cctgcttctc   1440
gccgaaacgt ttggtggcgg gaccagtgac gaaggcttga gcgagggcgt gcaagattcc   1500
gaataccgca agcgacaggc cgatcatcgt cgcgctccag cgaaagcggt cctcgccgaa   1560
aatgacccag agcgctgccg gcacctgtcc tacgagttgc atgataaaga agacagtcat   1620
aagtgcggcg acgatagtca tgccccgcgc ccaccggaag gagctgactg ggttgaaggc   1680
tctcaagggc atcggtcgac gctctccctt atgcgactcc tgcattagga agcagcccag   1740
tagtaggttg aggccgttga gcaccgccgc cgcaaggaat ggtgcatgca aggagatggc   1800
gcccaacagt cccccggcca cggggcctgc caccataccc acgccgaaac aagcgctcat   1860
gagcccgaag tggcgagccc gatcttcccc atcggtgatg tcggcgatat aggcgccagc   1920
aaccgcacct gtggcgccgg tgatgccggc acgatgcgt ccggcgtaga ggatccacag   1980
gacgggtgtg gtcgccatga tcgcgtagtc gatagtggct ccaagtagcg aagcgagcag   2040
gactgggcgg cggccaaagc ggtcggacag tgctccgaga acgggtgcgc atagaaattg   2100
catcaacgca tatagcgcta gcagcacgcc atagtgactg gcgatgctgt cggaatggac   2160
gatatcccgc aagaggcccg gcagtaccgg cataaccaag cctatgccta cagcatccag   2220
ggtgacggtg ccgaggatga cgatgagcgc attgttagat tcatacacg gtgcctgact   2280
gcgttagcaa tttaactgtg ataaactacc gcattaaagc ttatcgatga taagctgtca   2340
aacatgagaa gcggccgcca tagtgactgg atatgttgtg ttttacagta ttatgtagtc   2400
tgttttttat gcaaaatcta atttaatata ttgatattta tatcatttta cgtttctcgt   2460
tcaactttat tatacatagt tgataattca ctggccgtcg ttttacaacg tcgtgactgg   2520
gaaaaccctg gcgttaccca acttaatcgc cttgcagcac aagcttgcgg ccgcataatg   2580
cttaagtcga acagaaagta atcgtattgt acacggccgc ataatcgaaa ttaatacgac   2640
tcactatagg ggaattgtga gcggataaca attcccccatc ttagtatatt agttaagtat   2700
aagaaggaga tatacatatg gcagatctca attggatatc ggccggccac gcgatcgctg   2760
acgtcggtac cctcgagtct ggtaaagaaa ccgctgctgc gaaatttgaa cgccagcaca   2820
tggactcgtc tactagcgca gcttaattaa cctaggctgc tgccaccgct gagcaataac   2880
tagcataacc ccttggggcc tctaaacggg tcttgagggg ttttttgctg aaacctcagg   2940
catttgagaa gcacacggtc acactgcttc cggtagtcaa taaaccggta accagcaat   3000
agacataagc ggctatttaa cgaccctgcc ctgaaccgac gaccgggtcg aatttgcttt   3060
```

```
cgaatttctg ccattcatcc gcttattatc acttattcag gcgtagcacc aggcgtttaa    3120
gggcaccaat aactgcctta aaaaaattac gccccgccct gccactcatc gcagtactgt    3180
tgtaattcat taagcattct gccgacatgg aagccatcac agacggcatg atgaacctga    3240
atcgccagcg gcatcagcac cttgtcgcct tgcgtataat atttgcccat agtgaaaacg    3300
ggggcgaaga agttgtccat attggccacg tttaaatcaa aactggtgaa actcacccag    3360
ggattggctg agacgaaaaa catattctca ataaaccctt tagggaaata ggccaggttt    3420
tcaccgtaac acgccacatc ttgcgaatat atgtgtagaa actgccggaa atcgtcgtgg    3480
tattcactcc agagcgatga aaacgtttca gtttgctcat ggaaaacggt gtaacaaggg    3540
tgaacactat cccatatcac cagctcaccg tctttcattg ccatacgaa ctccggatga    3600 gcattcatca ggcgggcaag aatgtgaata aaggccggat aaaacttgtg cttatttttc    3660
tttacggtct ttaaaaaggc cgtaaatatcc agctgaacgg tctggttata ggtacattga    3720
gcaactgact gaaatgcctc aaaatgttct ttacgatgcc attgggatat atcaacggtg    3780
gtatatccag tgatttttt ctccatttta gcttccttag ctcctgaaaa tctcgataac    3840
tcaaaaaata cgcccggtag tgatcttatt tcattatggt gaaagttgga acctcttacg    3900
tgccgatcaa cgtctcattt tcgccaaaag ttggcccagg gcttcccggt atcaacaggg    3960
acaccaggat ttatttattc tgcgaagtga tcttccgtca caggtattta ttcggcgcaa    4020
agtgcgtcgg gtgatgctgc caacttactg atttagtgta tgatggtgtt tttgaggtgc    4080
tccagtggct tctgtttcta tcagctgtcc ctcctgttca gctactgacg gggtggtgcg    4140
taacggcaaa agcaccgccg gacatcagcg ctagcggagt gtatactggc ttactatgtt    4200
ggcactgatg agggtgtcag tgaagtgctt catgtggcag gagaaaaaag gctgcaccgg    4260
tgcgtcagca gaatatgtga tacaggatat attccgcttc ctcgctcact gactcgctac    4320
gctcggtcgt tcgactgcgg cgagcggaaa tggcttacga acggggcgga gatttcctgg    4380
aagatgccag gaagatactt aacagggaag tgagagggcc gcggcaaagc cgttttttcca    4440 taggctccgc cccctgaca agcatcacga aatctgacgc tcaaatcagt ggtggcgaaa    4500
cccgacagga ctataaagat accaggcgtt tcccctggcg gctccctcgt gcgctctcct    4560
gttcctgcct ttcggtttac cggtgtcatt ccgctgttat ggccgcgttt gtctcattcc    4620
acgcctgaca ctcagttccg ggtaggcagt tcgctccaag ctggactgta tgcacgaacc    4680
ccccgttcag tccgaccgct gcgccttatc cggtaactat cgtcttgagt ccaacccgga    4740
aagacatgca aaagcaccac tggcagcagc cactggtaat tgatttagag gagttagtct    4800
tgaagtcatg cgccggttaa ggctaaactg aaaggacaag ttttggtgac tgcgctcctc    4860
caagccagtt acctcggttc aaagagttgg tagctcagag aaccttcgaa aaaccgccct    4920
gcaaggcggt tttttcgttt tcagagcaag agattacgcg cagaccaaaa cgatctcaag    4980
aagatcatct tattaatcag ataaaatatt tctagatttc agtgcaattt atctcttcaa    5040
atgtagcacc tgaagtcagc cccatacgat ataagttgta attctcatgt tagtcatgcc    5100
ccgcgcccac cggaaggagc tgactgggtt gaaggctctc aagggcatcg gtcgagatcc    5160
cggtgcctaa tgagtgagct aacttacatt aattgcgttg cgctcactgc ccgctttcca    5220
gtcgggaaac ctgtcgtgcc agctgcatta atgaatcggc caacgcgcgg ggagaggcgg    5280
tttgcgtatt gggcgccagg gtggtttttc ttttcaccag tgagacgggc aacagctgat    5340
tgcccttcac cgcctggccc tgagagagtt gcagcaagcg gtccacgctg gtttgccca    5400
```

-continued

```
gcaggcgaaa atcctgtttg atggtggtta acggcgggat ataacatgag ctgtcttcgg    5460
tatcgtcgta tcccactacc gagatgtccg caccaacgcg cagcccggac tcggtaatgg    5520
cgcgcattgc gcccagcgcc atctgatcgt tggcaaccag catcgcagtg ggaacgatgc    5580
cctcattcag catttgcatg gtttgttgaa accggacat ggcactccag tcgccttccc     5640
gttccgctat cggctgaatt tgattgcgag tgagatattt atgccagcca gccagacgca    5700
gacgcgccga gacagaactt aatgggcccg ctaacacgc gatttgctgg tgacccaatg     5760
cgaccagatg ctccacgccc agtcgcgtac cgtcttcatg ggagaaaata atactgttga    5820
tgggtgtctg gtcagagaca tcaagaaata acgccgaaac attagtgcag gcagcttcca    5880
cagcaatggc atcctggtca tccagcggat agttaatgat cagcccactg acgcgttgcg    5940
cgagaagatt gtgcaccgcc gctttacagg cttcgacgcc gcttcgttct accatcgaca    6000
ccaccacgct ggcacccagt tgatcggcgc gagatttaat cgccgcgaca atttgcgacg    6060
gcgcgtgcag ggccagactg gaggtggcaa cgccaatcag caacgactgt ttgcccgcca    6120
gttgttgtgc cacgcggttg ggaatgtaat tcagctccgc catcgccgct tccacttttt    6180
cccgcgtttt cgcagaaacg tggctggcct ggttcaccac gcgggaaacg gtctgataag    6240
agacaccggc atactctgcg acatcgtata acgttactgg tttcacattc accaccctga    6300
attgactctc ttccgggcgc tatcatgcca taccgcgaaa ggttttgcgc cattcgatgg    6360
tgtccgggat ctcgacgctc tcccttatgc gactcctgca ttaggaaatt aatacgactc    6420
actata                                                               6426

<210> SEQ ID NO 9
<211> LENGTH: 7206
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 9
ggggaattgt gagcggataa caattcccct ctagaaataa ttttgtttaa ctttaagaag      60
gagatatacc atgggcagca gccatcacca tcatcaccac agccaggatc cgaattcgag     120
ctcggaccat gattacgcca agctatcaac tttgtataga aaagttgaac gagaaacgta     180
aaatgatata aatatcaata tattaaatta gattttgcat aaaaaacaga ctacataata     240
ctgtaaaaca aacatatcc agtcactatg gtcgacctgc agactggctg tgtataaggg     300
agcctgacat ttatattccc cagaacatca ggttaatggc gtttttgatg tcattttcgc     360
ggtggctgag atcagccact tcttccccga taacggagac cggcacactg gccatatcgg     420
tggtcatcat gcgccagctt tcatccccga tatgcaccac cgggtaaagt tcacggggga    480
ctttatctga cagcagacgt gcactggcca ggggatacac catccgtcgc ccgggcgtgt    540
caataatatc actctgtaca tccacaaaca gacgataacg gctctctctt ttataggtgt    600
aaaccttaaa ctgcatttca ccagcccctg ttctcgtcgg caaaagagcc gttcatttca    660
ataaaccggg cgacctcagc catcccttcc tgattttccg ctttccagcg ttcggcacgc    720
agacgacggg cttcattctg catggttgtg cttaccgaac cggagatatt gacatcatat    780
atgccttgag caactgatag ctgtcgctgt caactgtcac tgtaatacgc tgcttcatag    840
catacctctt tttgacatac ttcgggtata catatcagta tatattctta taccgcaaaa    900
atcagcgcgc aaatacgcat actgttatct ggcttttagt aagccggatc ctctagatta    960
```

```
cgccccgccc tgccactcat cgcagtactg ttgtaattca ttaagcattc tgccgacatg   1020
gaagccatca caaacggcat gatgaacctg aatcgccagc ggcatcagca ccttgtcgcc   1080
ttgcgtataa tatttgccca tggtgaaaac gggggcgaag aagttgtcca tattggccac   1140
gtttaaatca aaactggtga aactcaccca gggattggct gagacgaaaa acatattctc   1200
aataaaccct ttagggaaat aggccaggtt ttcaccgtaa cacgccacat cttgcgaata   1260
tatgtgtaga aactgccgga aatcgtcgtg gtattcactc cagagcgatg aaaacgtttc   1320
agtttgctca tggaaaacgg tgtaacaagg gtgaacacta tcccatatca ccagctcacc   1380
gtctttcatt gccatacgga attccggatg agcattcatc aggcgggcaa gaatgtgaat   1440
aaaggccgga taaaacttgt gcttattttt ctttacggtc tttaaaaagg ccgtaatatc   1500
cagctgaacg gtctggttat aggtacattg agcaactgac tgaaatgcct caaaatgttc   1560
tttacgatgc cattgggata tatcaacggt ggtatatcca gtgatttttt tctccatttt   1620
agcttcctta gctcctgaaa atctcgacgg atcctaactc aaaatccaca cattatacga   1680
gccggaagca taaagtgtaa agcctggggg tgcctaatgc ggccgccata gtgactggat   1740
atgttgtgtt ttacagtatt atgtagtctg tttttttatgc aaaatctaat ttaatatatt   1800
gatatttata tcattttacg tttctcgttc aactttatta tacatagttg ataattcact   1860
ggccgtcgtt ttacaacgtc gtgactggga aaaccctggc gttacccaac ttaatcgcct   1920
tgcagcacaa gcttgcggcc gcataatgct taagtcgaac agaaagtaat cgtattgtac   1980
acggccgcat aatcgaaatt aatacgactc actataggg aattgtgagc ggataacaat   2040
tccccatctt agtatattag ttaagtataa gaaggagata tacatatggc agatctcaat   2100
tggatatcgg ccggccacgc gatcgctgac gtcggtaccc tcgagtctgg taaagaaacc   2160
gctgctgcga atttgaacg ccagcacatg gactcgtcta ctagcgcagc ttaattaacc   2220
taggctgctg ccaccgctga gcaataacta gcataacccc ttggggcctc taaacgggtc   2280
ttgaggggtt ttttgctgaa aggaggaact atatccggat tggcgaatgg gacgcgccct   2340
gtagcggcgc attaagcgcg gcgggtgtgg tggttacgcg cagcgtgacc gctacacttg   2400
ccagcgccct agcgcccgct cctttcgctt tcttcccttc ctttctcgcc acgttcgccg   2460
gctttccccg tcaagctcta aatcgggggc tccctttagg gttccgattt agtgctttac   2520
ggcacctcga ccccaaaaaa cttgattagg gtgatggttc acgtagtggg ccatcgccct   2580
gatagacggt ttttcgccct ttgacgttgg agtccacgtt ctttaatagt ggactcttgt   2640
tccaaactgg aacaacactc aaccctatct cggtctattc ttttgattta agggattt    2700 tgccgatttc ggcctattgg ttaaaaaatg agctgattta acaaaaattt aacgcgaatt   2760
ttaacaaaat attaacgttt acaatttctg gcggacgat ggcatgagat tatcaaaaag   2820
gatcttcacc tagatccttt taaattaaaa atgaagtttt aaatcaatct aaagtatata   2880
tgagtaaact tggtctgaca gttaccaatg cttaatcagt gaggcaccta tctcagcgat   2940
ctgtctattt cgttcatcca tagttgcctg actccccgtc gtgtagataa ctacgatacg   3000
ggagggctta ccatctggcc ccagtgctgc aatgataccg cgagacccac gctcaccggc   3060
tccagattta tcagcaataa accagccagc cggaagggcc gagcgcagaa gtggtcctgc   3120
aactttatcc gcctccatcc agtctattaa ttgttgccgg gaagctagag taagtagttc   3180
gccagttaat agtttgcgca acgttgttgc cattgctaca ggcatcgtgg tgtcacgctc   3240
gtcgtttggt atggcttcat tcagctccgg ttcccaacga tcaaggcgag ttacatgatc   3300
ccccatgttg tgcaaaaaag cggttagctc cttcggtcct ccgatcgttg tcagaagtaa   3360
```

```
gttggccgca gtgttatcac tcatggttat ggcagcactg cataattctc ttactgtcat    3420
gccatccgta agatgctttt ctgtgactgg tgagtactca accaagtcat tctgagaata    3480
gtgtatgcgg cgaccgagtt gctcttgccc ggcgtcaata cgggataata ccgcgccaca    3540
tagcagaact ttaaaagtgc tcatcattgg aaaacgttct cggggcgaa aactctcaag     3600 gatcttaccg ctgttgagat ccagttcgat gtaacccact cgtgcaccca actgatcttc    3660
agcatctttt actttcacca gcgtttctgg gtgagcaaaa acaggaaggc aaaatgccgc    3720
aaaaaaggga ataagggcga cacggaaatg ttgaatactc atactcttcc tttttcaatc    3780
atgattgaag catttatcag ggttattgtc tcatgagcgg atacatattt gaatgtattt    3840
agaaaaataa acaaataggt catgaccaaa atcccttaac gtgagttttc gttccactga    3900
gcgtcagacc ccgtagaaaa gatcaaagga tcttcttgag atcctttttt tctgcgcgta    3960
atctgctgct tgcaaacaaa aaaccaccg ctaccagcgg tggtttgttt gccggatcaa     4020
gagctaccaa ctcttttttcc gaaggtaact ggcttcagca gagcgcagat accaaatact    4080
gtccttctag tgtagccgta gttaggccac cacttcaaga actctgtagc accgcctaca    4140
tacctcgctc tgctaatcct gttaccagtg ctgctgcca gtggcgataa gtcgtgtctt     4200
accgggttgg actcaagacg atagttaccg gataaggcgc agcggtcggg ctgaacgggg    4260
ggttcgtgca cacagcccag cttggagcga acgacctaca ccgaactgag atacctacag    4320
cgtgagctat gagaaagcgc cacgcttccc gaagggagaa aggcggacag gtatccggta    4380
agcggcaggg tcggaacagg agagcgcacg agggagcttc cagggggaaa cgcctggtat    4440
ctttatagtc ctgtcgggtt tcgccacctc tgacttgagc gtcgatttt gtgatgctcg     4500 tcagggggc ggagcctatg gaaaaacgcc agcaacgcgg ccttttacg gttcctggcc      4560 ttttgctggc cttttgctca catgttcttt cctgcgttat cccctgattc tgtggataac    4620
cgtattaccg cctttgagtg agctgatacc gctcgccgca gccgaacgac cgagcgcagc    4680
gagtcagtga gcgaggaagc ggaagagcgc ctgatgcggt attttctcct tacgcatctg    4740
tgcggtattt cacaccgcat atatggtgca ctctcagtac aatctgctct gatgccgcat    4800
agttaagcca gtatacactc cgctatcgct acgtgactgg gtcatggctg cgccccgaca    4860
cccgccaaca cccgctgacg cgccctgacg ggcttgtctg ctcccggcat ccgcttacag    4920
acaagctgtg accgtctccg ggagctgcat gtgtcagagg ttttcaccgt catcaccgaa    4980
acgcgcgagg cagctgcggt aaagctcatc agcgtggtcg tgaagcgatt cacagatgtc    5040
tgcctgttca tccgcgtcca gctcgttgag tttctccaga agcgttaatg tctggcttct    5100
gataaagcgg gccatgttaa gggcggtttt ttcctgtttg gtcactgatg cctccgtgta    5160
agggggattt ctgttcatgg gggtaatgat accgatgaaa cgagagagga tgctcacgat    5220
acgggttact gatgatgaac atgcccggtt actggaacgt tgtgagggta acaactggc     5280 ggtatggatg cggcgggacc agagaaaaat cactcagggt caatgccagc gcttcgttaa    5340
tacagatgta ggtgttccac agggtagcca gcagcatcct gcgatgcaga tccggaacat    5400
aatggtgcag ggcgctgact ccgcgtttc cagactttac gaaacacgga aaccgaagac     5460
cattcatgtt gttgctcagg tcgcagacgt tttgcagcag cagtcgcttc acgttcgctc    5520
gcgtatcggt gattcattct gctaaccagt aaggcaaccc cgccagccta gccgggtcct    5580
caacgacagg agcacgatca tgctagtcat gccccgcgcc caccggaagg agctgactgg    5640
gttgaaggct ctcaagggca tcggtcgaga tcccggtgcc taatgagtga gctaacttac    5700
```

```
attaattgcg ttgcgctcac tgcccgcttt ccagtcggga aacctgtcgt gccagctgca    5760
ttaatgaatc ggccaacgcg cggggagagg cggtttgcgt attgggcgcc agggtggttt    5820
ttcttttcac cagtgagacg ggcaacagct gattgccctt caccgcctgg ccctgagaga    5880
gttgcagcaa gcggtccacg ctggtttgcc ccagcaggcg aaaatcctgt ttgatggtgg    5940
ttaacggcgg gatataacat gagctgtctt cggtatcgtc gtatcccact accgagatgt    6000
ccgcaccaac gcgcagcccg gactcggtaa tggcgcgcat tgcgcccagc gccatctgat    6060
cgttggcaac cagcatcgca gtgggaacga tgccctcatt cagcatttgc atggtttgtt    6120
gaaaaccgga catggcactc cagtcgcctt cccgttccgc tatcggctga atttgattgc    6180
gagtgagata tttatgccag ccagccagac gcagacgcgc cgagacagaa cttaatgggc    6240
ccgctaacag cgcgatttgc tggtgaccca atgcgaccag atgctccacg cccagtcgcg    6300
taccgtcttc atgggagaaa ataatactgt tgatgggtgt ctggtcagag acatcaagaa    6360
ataacgccgg aacattagtg caggcagctt ccacagcaat ggcatcctgg tcatccagcg    6420
gatagttaat gatcagccca ctgacgcgtt gcgcgagaag attgtgcacc gccgctttac    6480
aggcttcgac gccgcttcgt tctaccatcg acaccaccac gctggcaccc agttgatcgg    6540
cgcgagattt aatcgccgcg acaatttgcg acggcgcgtg cagggccaga ctggaggtgg    6600
caacgccaat cagcaacgac tgtttgcccg ccagttgttg tgccacgcgg ttgggaatgt    6660
aattcagctc cgccatcgcc gcttccactt tttcccgcgt tttcgcagaa acgtggctgg    6720
cctggttcac cacgcgggaa acggtctgat aagagacacc ggcatactct gcgacatcgt    6780
ataacgttac tggtttcaca ttcaccaccc tgaattgact ctcttccggg cgctatcatg    6840
ccataccgcg aaaggttttg cgccattcga tggtgtccgg gatctcgacg ctctccctta    6900
tgcgactcct gcattaggaa gcagcccagt agtaggttga ggccgttgag caccgccgcc    6960
gcaaggaatg gtgcatgcaa ggagatggcg cccaacagtc ccccggccac ggggcctgcc    7020 accatacccca cgccgaaaca gcgctcatg agcccgaagt ggcgagcccg atcttcccca    7080
tcggtgatgt cggcgatata ggcgccagca accgcacctg tggcgccggt gatgccggcc    7140
acgatgcgtc cggcgtagag gatcgagatc gatctcgatc ccgcgaaatt aatacgactc    7200
actata                                                              7206
```

<210> SEQ ID NO 10
<211> LENGTH: 5296
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 10

```
ggggaattgt gagcggataa caattcccct gtagaaataa ttttgtttaa ctttaataag      60
gagatatacc atgggcagca gccatcacca tcatcaccac agccaggatc cgaattcgag     120
ctcgatcaca agtttgtaca aaaaagctga acgagaaacg taaatgata taaatatcaa     180 tatattaaat tagattttgc ataaaaaaca gactacataa tactgtaaaa cacaacatat     240
ccagtcacta tggcggccgc cacgttaagg gattttggtc atgatcagca cgtgttgaca     300
attaatcatc ggcatagtat atcggcatag tataatacga caaggtgagg aactaaacca     360
tggccaagtt gaccagtgcc gttccggtgc tcaccgcgcg cgacgtcgcc ggagcggtcg     420
agttctggac cgaccggctc gggttctccc ggacttcgt ggaggacgac ttcgccggtg     480
```

-continued

```
tggtccggga cgacgtgacc ctgttcatca gcgcggtcca ggaccaggtg gtgccggaca      540
acaccctggc ctgggtgtgg gtgcgcggcc tggacgagct gtacgccgag tggtcggagg      600
tcgtgtccac gaacttccgg gacgcctccg ggccggccat gaccgagatc ggcgagcagc      660
cgtgggggcg ggagttcgcc ctgcgcgacc cggccggcaa ctgcgtgcac ttcgtggccg      720
aggagcagga ctgatcatga tgatattatt ttatcttgtg caatgtaaca tcagagattt      780
tgagacacgg gccagagctg ccaggaaaca gctatgacca tgtaatacga ctcactatag      840
gggatatcag ctggatggca ataatgatt ttattttgac tgatagtgac ctgttcgttg       900
caacaccggt gctagcgtat acccgaagta tgtcaaaaag aggtgtgcta tgaagcagcg      960
tattacagtg acagttgaca gcgacagcta tcagttgctc aaggcatata tgatgtcaat     1020
atctccggtc tggtaagcac aaccatgcag aatgaagccc gtcgtctgcg tgccgaacgc     1080
tggaaagcgg aaaatcagga agggatggct gaggtcgccc ggtttattga aatgaacggc     1140
tcttttgctg acgagaacag ggactggtga atgcagttt aaggtttaca cctataaaag      1200
agagagccgt tatcgtctgt ttgtggatgt acagagtgat attattgaca cgcccgggcg     1260
acggatggta atccccctgg ccagtgcacg tctgctgtca gataaagtct cccgtgaact     1320
ttacccggtg gtgcatatcg gggatgaaag ctggcgcatg atgaccaccg atatggccag     1380
tgtgccggtc tccgttatcg gggaagaagt ggctgatctc agccgccgcg aaaatgacat     1440
caaaaacgcc attaacctga tgttctgggg aatataaatg tcaggctccc ttatacacag     1500
ccagtctgca ggtcgaccat agtgactgga tatgttgtgt tttacagtat tatgtagtct     1560
gttttttatg caaaatctaa tttaatatat tgatatttat atcattttac gtttctcgtt     1620
cagctttctt gtacaaagtg gtgataatta attaagatca gatccggctg ctaagcttgg     1680
aattgttatc cgctcacaat tcctatagtg agtcgtatta cctaggctgc tgccaccgct     1740
gagcaataac tagcataacc ccttggggcc tctaaacggg tcttgagggg ttttttgctg     1800
aaacctcagg catttgagaa gcacacggtc acactgcttc cggtagtcaa taaaccggta     1860
aaccagcaat agacataagc ggctatttaa cgaccctgcc ctgaaccgac gaccgggtcg     1920
aatttgcttt cgaatttctg ccattcatcc gcttattatc acttattcag gcgtagcacc     1980
aggcgtttaa gggcaccaat aactgcctta aaaaaattac gccccgccct gccactcatc     2040
gcagtactgt tgtaattcat taagcattct gccgacatgg aagccatcac agacggcatg     2100
atgaacctga atcgccagcg gcatcagcac cttgtcgcct tgcgtataat atttgcccat     2160
agtgaaaacg ggggcgaaga agttgtccat attggccacg tttaaatcaa aactggtgaa     2220
actcacccag ggattggctg agacgaaaaa catattctca ataaaccctt tagggaaata     2280
ggccaggttt tcaccgtaac acgccacatc ttgcgaatat atgtgtagaa actgccggaa     2340
atcgtcgtgg tattcactcc agagcgatga aaacgtttca gtttgctcat ggaaaacggt     2400
gtaacaaggt gaacactat cccatatcac cagctcaccg tctttcattg ccatacggaa      2460
ctccggatga gcattcatca ggcgggcaag aatgtgaata aaggccggat aaaacttgtg     2520 cttattttc tttacggtct ttaaaaaggc cgtaatatcc agctgaacgg tctggttata     2580
ggtacattga gcaactgact gaaatgcctc aaaatgttct ttacgatgcc attgggatat     2640
atcaacggtg gtatatccag tgatttttt ctccatttta gcttccttag ctcctgaaaa     2700
tctcgataac tcaaaaaata cgcccggtag tgatcttatt tcattatggt gaaagttgga     2760
acctcttacg tgccgatcaa cgtctcattt tcgccaaaag ttggcccagg cttcccggt      2820 atcaacaggg acaccaggat ttatttattc tgcgaagtga tcttccgtca caggtattta     2880
```

-continued

```
ttcggcgcaa agtgcgtcgg gtgatgctgc caacttactg atttagtgta tgatggtgtt   2940
tttgaggtgc tccagtggct tctgtttcta tcagctgtcc ctcctgttca gctactgacg   3000
gggtggtgcg taacggcaaa agcaccgccg gacatcagcg ctagcggagt gtatactggc   3060
ttactatgtt ggcactgatg agggtgtcag tgaagtgctt catgtggcag agaaaaaag    3120
gctgcaccgg tgcgtcagca gaatatgtga tacaggatat attccgcttc ctcgctcact   3180
gactcgctac gctcggtcgt tcgactgcgg cgagcggaaa tggcttacga acggggcgga   3240
gatttcctgg aagatgccag gaagatactt aacaggaag tgagagggcc gcggcaaagc    3300
cgttttcca taggctccgc cccctgaca agcatcacga aatctgacgc tcaaatcagt     3360
ggtggcgaaa cccgacagga ctataaagat accaggcgtt tccctggcg gctccctcgt    3420
gcgctctcct gttcctgcct ttcggtttac cggtgtcatt ccgctgttat ggccgcgttt   3480
gtctcattcc acgcctgaca ctcagttccg ggtaggcagt tcgctccaag ctggactgta   3540
tgcacgaacc ccccgttcag tccgaccgct gcgccttatc cggtaactat cgtcttgagt   3600
ccaacccgga aagacatgca aaagcaccac tggcagcagc cactggtaat tgatttagag   3660
gagttagtct tgaagtcatg cgccggttaa ggctaaactg aaaggacaag ttttggtgac   3720
tgcgctcctc caagccagtt acctcggttc aaagagttgg tagctcagag aaccttcgaa   3780
aaaccgccct gcaaggcggt ttttcgttt tcagagcaag agattacgcg cagaccaaaa    3840
cgatctcaag aagatcatct tattaatcag ataaaatatt tctagatttc agtgcaattt   3900
atctcttcaa atgtagcacc tgaagtcagc cccatacgat ataagttgta attctcatgt   3960
tagtcatgcc ccgcgcccac cggaaggagc tgactgggtt gaaggctctc aagggcatcg   4020
gtcgagatcc cggtgcctaa tgagtgagct aacttacatt aattgcgttg cgctcactgc   4080
ccgctttcca gtcgggaaac ctgtcgtgcc agctgcatta atgaatcggc caacgcgcgg   4140
ggagaggcg tttgcgtatt gggcgccagg gtggttttc ttttcaccag tgagacgggc     4200
aacagctgat tgcccttcac cgcctggccc tgagagagtt gcagcaagcg tccacgctg    4260
gtttgcccca gcaggcgaaa atcctgtttg atggtggtta acggcgggat ataacatgag   4320
ctgtcttcgg tatcgtcgta tcccactacc gagatgtccg caccaacgcg cagcccggac   4380
tcggtaatgg cgcgcattgc gcccagcgcc atctgatcgt tggcaaccag catcgcagtg   4440
ggaacgatgc cctcattcag catttgcatg gtttgttgaa aaccggacat ggcactccag   4500
tcgccttccc gttccgctat cggctgaatt tgattgcgag tgagatattt atgccagcca   4560
gccagacgca gacgcgccga gacagaactt aatgggcccg ctaacagcgc gatttgctgg   4620
tgacccaatg cgaccagatg ctccacgccc agtcgcgtac cgtcttcatg ggagaaaata   4680
atactgttga tgggtgtctg gtcagagaca tcaagaaata acgccggaac attagtgcag   4740
gcagcttcca cagcaatggc atcctggtca tccagcggat agttaatgat cagcccactg   4800
acgcgttgcg cgagaagatt gtgcaccgcc gctttacagg cttcgacgcc gcttcgttct   4860
accatcgaca ccaccacgct ggcacccagt tgatcggcgc gagatttaat cgccgcgaca   4920
atttgcgacg gcgcgtgcag ggccagactg gaggtggcaa cgccaatcag caacgactgt   4980
ttgcccgcca gttgttgtgc cacgcggttg ggaatgtaat tcagctccgc catcgccgct   5040
tccacttttt cccgcgtttt cgcagaaacg tggctggcct ggttcaccac gcgggaaacg   5100
gtctgataag agacaccggc atactctgcg acatcgtata acgttactgg tttcacattc   5160
accaccctga attgactctc ttccgggcgc tatcatgcca taccgcgaaa ggttttgcgc   5220
```

```
cattcgatgg tgtccgggat ctcgacgctc tcccttatgc gactcctgca ttaggaaatt      5280
aatacgactc actata                                                      5296

<210> SEQ ID NO 11
<211> LENGTH: 5069
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 11
ggggaattgt gagcggataa caattcccct gtagaaataa ttttgtttaa ctttaataag        60
gagatatacc atgggcagca gccatcacca tcatcaccac agccaggatc cgaattcgag       120
ctcgatcaca gtttgtaca aaaaagctga acgagaaacg taaaatgata taaatatcaa       180
tatattaaat tagattttgc ataaaaaaca gactacataa tactgtaaaa cacaacatat       240
ccagtcacta tggcggccgc cacgttaagg gattttggtc atgatcagca cgtgttgaca       300
attaatcatc ggcatagtat atcggcatag tataatacga caaggtgagg aactaaacca       360
tggccaagtt gaccagtgcc gttccggtgc tcaccgcgcg cgacgtcgcc ggagcggtcg       420
agttctggac cgaccggctc gggttctccc gggacttcgt ggaggacgac ttcgccggtg       480
tggtcccgga cgacgtgacc ctgttcatca gcgcggtcca ggaccaggtg gtgccggaca       540
acaccctggc ctgggtgtgg gtgcgcggcc tggacgagct gtacgccgag tggtcggagg       600
tcgtgtccac gaacttccgg gacgcctccg ggccggccat gaccgagatc ggcgagcagc       660
cgtgggggcg ggagttcgcc ctgcgcgacc cggccggcaa ctgcgtgcac ttcgtggccg       720
aggagcagga ctgatcatga tgatattatt ttatcttgtg caatgtaaca tcagagattt       780
tgagacacgg gccagagctg ccaggaaaca gctatgacca tgtaatacga ctcactatag       840
gggatatcag ctgatggca ataatgatt ttatttgac tgatagtgac ctgttcgttg       900
caacaccggt gctagcgtat acccgaagta tgtcaaaaag aggtgtgcta tgaagcagcg       960
tattacagtg acagttgaca gcgacagcta tcagttgctc aaggcatata tgatgtcaat      1020
atctccggtc tggtaagcac aaccatgcag aatgaagccc gtcgtctgcg tgccgaacgc      1080
tggaaagcgg aaaatcagga agggatggct gaggtcgccc ggtttattga atgaacggc      1140 tcttttgctg acgagaacag ggactggtga atgcagtttt aaggtttaca cctataaaag      1200
agagagccgt tatcgtctgt ttgtggatgt acagagtgat attattgaca cgcccgggcg      1260
acggatggtg atccccctgg ccagtgcacg tctgctgtca gataaagtct cccgtgaact      1320
ttacccggtg gtgcatatcg gggatgaaag ctggcgcatg atgaccaccg atatggccag      1380
tgtgccggtc tccgttatcg gggaagaagt ggctgatctc agccgccgcg aaaatgacat      1440
caaaaacgcc attaacctga tgttctgggg aatatataatg tcaggctccc ttatacacag      1500
ccagtctgca ggtcgaccat agtgactgga tatgttgtgt tttacagtat tatgtagtct      1560
gttttttatg caaaatctaa tttaatatat tgatatttat atcattttac gtttctcgtt      1620
cagctttctt gtacaaagtg gtgataatta attaagatca gatccggctg ctaagcttgg      1680
aattgttatc cgctcacaat tcctatagtg agtcgtatta cctaggctgc tgccaccgct      1740
gagcaataac tagcataacc ccttggggcc tctaaacggg tcttgagggg ttttttgctg      1800
aaacctcagg catttgagaa gcacacggtc acactgcttc cggtagtcaa taaaccggta      1860
aaccagcaat agacataagc ggctatttaa cgaccctgcc ctgaaccgac gacccgggtca      1920
```

```
tcgtggccgg atcttgcggc ccctcggctt gaacgaattg ttagacatta tttgccgact    1980
accttggtga tctcgccttt cacgtagtgg acaaattctt ccaactgatc tgcgcgcgag    2040
gccaagcgat cttcttcttg tccaagataa gcctgtctag cttcaagtat gacgggctga    2100
tactgggccg gcaggcgctc cattgcccag tcggcagcga catccttcgg cgcgattttg    2160
ccggttactg cgctgtacca aatgcgggac aacgtaagca ctacatttcg ctcatcgcca    2220
gcccagtcgg gcggcgagtt ccatagcgtt aaggtttcat ttagcgcctc aaatagatcc    2280
tgttcaggaa ccggatcaaa gagttcctcc gccgctggac ctaccaaggc aacgctatgt    2340
tctcttgctt ttgtcagcaa gatagccaga tcaatgtcga tcgtggctgg ctcgaagata    2400
cctgcaagaa tgtcattgcg ctgccattct ccaaattgca gttcgcgctt agctggataa    2460
cgccacggaa tgatgtcgtc gtgcacaaca atggtgactt ctacagcgcg gagaatctcg    2520
ctctctccag gggaagccga agtttccaaa aggtcgttga tcaaagctcg ccgcgttgtt    2580
tcatcaagcc ttacggtcac cgtaaccagc aaatcaatat cactgtgtgg cttcaggccg    2640
ccatccactg cggagccgta caaatgtacg gccagcaacg tcggttcgag atggcgctcg    2700
atgacgccaa ctacctctga tagttgagtc gatacttcgg cgatcaccgc ttccctcata    2760
ctcttccttt ttcaatatta ttgaagcatt tatcagggtt attgtctcat gagcggatac    2820
atatttgaat gtatttagaa aaataaacaa atagctagct cactcggtcg ctacgctccg    2880
ggcgtgagac tgcggcgggc gctgcggaca catacaaagt tacccacaga ttccgtggat    2940
aagcagggga ctaacatgtg aggcaaaaca gcagggccgc gccggtggcg ttttccata    3000 ggctccgccc tcctgccaga gttcacataa acagacgctt ttccggtgca tctgtgggag    3060
ccgtgaggct caaccatgaa tctgacagta cgggcgaaac ccgacaggac ttaaagatcc    3120
ccaccgtttc cggcgggtcg ctccctcttg cgctctcctg ttccgaccct gccgtttacc    3180
ggatacctgt tccgcctttc tcccttacgg gaagtgtggc gctttctcat agctcacaca    3240
ctggtatctc ggctcggtgt aggtcgttcg ctccaagctg ggctgtaagc aagaactccc    3300
cgttcagccc gactgctgcg ccttatccgg taactgttca cttgagtcca acccggaaaa    3360
gcacggtaaa acgccactgg cagcagccat tggtaactgg gagttcgcag aggatttgtt    3420
tagctaaaca cgcggttgct cttgaagtgt gcgccaaagt ccggctacac tggaaggaca    3480
gatttggttg ctgtgctctg cgaaagccag ttaccacggt taagcagttc cccaactgac    3540
ttaaccttcg atcaaaccac ctccccaggt ggttttttcg tttacagggc aaaagattac    3600
gcgcagaaaa aaaggatctc aagaagatcc tttgatcttt tctactgaac cgctctagat    3660
ttcagtgcaa tttatctctt caaatgtagc acctgaagtc agccccatac gatataagtt    3720
gtaattctca tgttagtcat gccccgcgcc caccggaagg agctgactgg gttgaaggct    3780
ctcaagggca tcggtcgaga tcccggtgcc taatgagtga gctaacttac attaattgcg    3840
ttgcgctcac tgcccgcttt ccagtcggga acctgtcgt gccagctgca ttaatgaatc     3900
ggccaacgcg cggggagagg cggtttgcgt attgggcgcc agggtggttt tcttttcac    3960 cagtgagacg ggcaacagct gattgccctt caccgcctgg ccctgagaga gttgcagcaa    4020
gcggtccacg ctggtttgcc ccagcaggcg aaaatcctgt ttgatggtgg ttaacggcgg    4080
gatataacat gagctgtctt cggtatcgtc gtatcccact accgagatgt ccgcaccaac    4140
gcgcagcccg gactcggtaa tggcgcgcat tgcgcccagc gccatctgat cgttggcaac    4200
cagcatcgca gtgggaacga tgccctcatt cagcatttgc atggtttgtt gaaaaccgga    4260
catggcactc cagtcgcctt cccgttccgc tatcggctga atttgattgc gagtgagata    4320
```

| | |
|---|---|
| tttatgccag ccagccagac gcagacgcgc cgagacagaa cttaatgggc ccgctaacag | 4380 |
| cgcgatttgc tggtgaccca atgcgaccag atgctccacg cccagtcgcg taccgtcttc | 4440 |
| atgggagaaa ataatactgt tgatgggtgt ctggtcagag acatcaagaa ataacgccgg | 4500 |
| aacattagtg caggcagctt ccacagcaat ggcatcctgg tcatccagcg atagttaat | 4560 |
| gatcagccca ctgacgcgtt gcgcgagaag attgtgcacc gccgctttac aggcttcgac | 4620 |
| gccgcttcgt tctaccatcg acaccaccac gctggcaccc agttgatcgg cgcgagattt | 4680 |
| aatcgccgcg acaatttgcg acggcgcgtg cagggccaga ctggaggtgg caacgccaat | 4740 |
| cagcaacgac tgtttgcccg ccagttgttg tgccacgcgg ttgggaatgt aattcagctc | 4800 |
| cgccatcgcc gcttccactt tttcccgcgt tttcgcagaa acgtggctgg cctggttcac | 4860 |
| cacgcgggaa acggtctgat aagagacacc ggcatactct gcgacatcgt ataacgttac | 4920 |
| tggtttcaca ttcaccaccc tgaattgact ctcttccggg cgctatcatg ccataccgcg | 4980 |
| aaaggttttg cgccattcga tggtgtccgg gatctcgacg ctctccctta tgcgactcct | 5040 |
| gcattaggaa attaatacga ctcactata | 5069 |

<210> SEQ ID NO 12
<211> LENGTH: 5117
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 12

| | |
|---|---|
| ggggaattgt gagcggataa caattcccct gtagaaataa ttttgtttaa ctttaataag | 60 |
| gagatatacc atgggcagca gccatcacca tcatcaccac agccaggatc cgaattcgag | 120 |
| ctcgatcaca agtttgtaca aaaaagctga acgagaaacg taaaatgata taaatatcaa | 180 |
| tatattaaat tagattttgc ataaaaaaca gactacataa tactgtaaaa cacaacatat | 240 |
| ccagtcacta tggcggccgc cacgttaagg gattttggtc atgatcagca cgtgttgaca | 300 |
| attaatcatc ggcatagtat atcggcatag tataatacga caaggtgagg aactaaacca | 360 |
| tggccaagtt gaccagtgcc gttccggtgc tcaccgcgcg cgacgtcgcc ggagcggtcg | 420 |
| agttctggac cgaccggctc gggttctccc gggacttcgt ggaggacgac ttcgccggtg | 480 |
| tggtccggga cgacgtgacc ctgttcatca gcgcggtcca ggaccaggtg gtgccggaca | 540 |
| acaccctggc ctgggtgtgg gtgcgcgcc tggacgagct gtacgccgag tggtcggagg | 600 |
| tcgtgtccac gaacttccgg gacgcctccg ggccggccat gaccgagatc ggcgagcagc | 660 |
| cgtggggcg ggagttcgcc ctgcgcgacc cggccggcaa ctgcgtgcac ttcgtggccg | 720 |
| aggagcagga ctgatcatga tgatattatt ttatcttgtg caatgtaaca tcagagattt | 780 |
| tgagacacgg gccagagctg ccaggaaaca gctatgacca tgtaatacga ctcactatag | 840 |
| gggatatcag ctggatggca ataatgatt ttattttgac tgatagtgac ctgttcgttg | 900 |
| caacaccggt gctagcgtat acccgaagta tgtcaaaaag aggtgtgcta tgaagcagcg | 960 |
| tattacagtg acagttgaca gcgacagcta tcagttgctc aaggcatata tgatgtcaat | 1020 |
| atctccggtc tggtaagcac aaccatgcag aatgaagccc gtcgtctgcg tgccgaacgc | 1080 |
| tggaaagcgg aaaatcagga agggatggct gaggtcgccc ggtttattga aatgaacggc | 1140 |
| tcttttgctg acgagaacag ggactggtga aatgcagttt aaggtttaca cctataaaag | 1200 |
| agagagccgt tatcgtctgt tgtggatgt acagagtgat attattgaca cgcccgggcg | 1260 |

-continued

```
acggatggtg atccccctgg ccagtgcacg tctgctgtca gataaagtct cccgtgaact   1320
ttacccggtg gtgcatatcg gggatgaaag ctggcgcatg atgaccaccg atatggccag   1380
tgtgccggtc tccgttatcg gggaagaagt ggctgatctc agccgccgcg aaaatgacat   1440
caaaaacgcc attaacctga tgttctgggg aatataaatg tcaggctccc ttatacacag   1500
ccagtctgca ggtcgaccat agtgactgga tatgttgtgt tttacagtat tatgtagtct   1560
gttttttatg caaaatctaa tttaatatat tgatatttat atcatttttac gtttctcgtt   1620
cagctttctt gtacaaagtg gtgataatta attaagatca gatccggctg ctaagcttgg   1680
aattgttatc cgctcacaat tcctatagtg agtcgtatta cctaggctgc tgccaccgct   1740
gagcaataac tagcataacc ccttggggcc tctaaacggg tcttgagggg ttttttgctg   1800
aaacctcagg catttgagaa gcacacggtc acactgcttc cggtagtcaa taaaccggta   1860
aaccagcaat agacataagc ggctatttaa cgaccctgcc ctgaaccgac gacaagctga   1920
cgaccgggtc tccgcaagtg gcacttttcg gggaaatgtg cgcggaaccc ctatttgttt   1980
atttttctaa atacattcaa atatgtatcc gctcatgaat taattcttag aaaaactcat   2040
cgagcatcaa atgaaactgc aatttattca tatcaggatt atcaatacca tatttttgaa   2100
aaagccgttt ctgtaatgaa ggagaaaact caccgaggca gttccatagg atggcaagat   2160
cctggtatcg gtctgcgatt ccgactcgtc caacatcaat acaacctatt aatttcccct   2220
cgtcaaaaat aaggttatca agtgagaaat caccatgagt gacgactgaa tccggtgaga   2280
atggcaaaag tttatgcatt tctttccaga cttgttcaac aggccagcca ttacgctcgt   2340
catcaaaatc actcgcatca accaaaccgt tattcattcg tgattgcgcc tgagcgagac   2400
gaaatacgcg gtcgctgtta aaaggacaat tacaaacagg aatcgaatgc aaccggcgca   2460
ggaacactgc cagcgcatca acaatatttt cacctgaatc aggatattct tctaatacct   2520
ggaatgctgt tttcccgggg atcgcagtgg tgagtaacca tgcatcatca ggagtacgga   2580
taaaatgctt gatggtcgga agaggcataa attccgtcag ccagtttagt ctgaccatct   2640
catctgtaac atcattggca acgctacctt tgccatgttt cagaaacaac tctggcgcat   2700
cgggcttccc atacaatcga tagattgtcg cacctgattg cccgacatta tcgcgagccc   2760
atttataccc atataaatca gcatccatgt tggaatttaa tcgcggccta gagcaagacg   2820
tttcccgttg aatatggctc atactcttcc tttttcaata ttattgaagc atttatcagg   2880
gttattgtct catgagcgga tacatatttg aatgtattta gaaaaataaa caaataggca   2940
tgcagcgctc ttccgcttcc tcgctcactg actcgctacg ctcggtcgtt cgactgcggc   3000
gagcggtgtc agctcactca aaagcggtaa tacggttatc cacagaatca ggggataaag   3060
ccggaaagaa catgtgagca aaaagcaaag caccggaaga agccaacgcc gcaggcgttt   3120
ttccataggc tccgcccccc tgacgagcat cacaaaaatc gacgctcaag ccagaggtgg   3180
cgaaacccga caggactata agataccag gcgtttcccc ctggaagctc cctcgtgcgc   3240
tctcctgttc cgaccctgcc gcttaccgga tacctgtccg cctttctccc ttcgggaagc   3300
gtggcgcttt ctcatagctc acgctgttgg tatctcagtt cggtgtaggt cgttcgctcc   3360
aagctgggct gtgtgcacga accccccgtt cagcccgacc gctgcgcctt atccggtaac   3420
tatcgtcttg agtccaaccc ggtaagacac gacttatcgc cactggcagc agccattggt   3480
aactgattta gaggactttg tcttgaagtt atgcacctgt taaggctaaa ctgaaagaac   3540
agattttggt gagtgcggtc ctccaaccca cttaccttgg ttcaaagagt tggtagctca   3600
```

```
gcgaaccttg agaaaaccac cgttggtagc ggtggttttt ctttatttat gagatgatga   3660
atcaatcggt ctatcaagtc aacgaacagc tattccgtta ctctagattt cagtgcaatt   3720
tatctcttca aatgtagcac ctgaagtcag ccccatacga tataagttgt aattctcatg   3780
ttagtcatgc cccgcgccca ccggaaggag ctgactgggt tgaaggctct caagggcatc   3840
ggtcgagatc ccggtgccta atgagtgagc taacttacat taattgcgtt gcgctcactg   3900
cccgctttcc agtcgggaaa cctgtcgtgc cagctgcatt aatgaatcgg ccaacgcgcg   3960
gggagaggcg gtttgcgtat tgggcgccag gtggttttt ctttcacca gtgagacggg   4020 caacagctga ttgcccttca ccgcctggcc ctgagagagt tgcagcaagc ggtccacgct   4080
ggtttgcccc agcaggcgaa atcctgtttt gatggtggtt aacggcggga taacatga    4140 gctgtcttcg gtatcgtcgt atcccactac cgagatgtcc gcaccaacgc gcagcccgga   4200
ctcggtaatg gcgcgcattg cgcccagcgc catctgatcg ttggcaacca gcatcgcagt   4260
gggaacgatg ccctcattca gcatttgcat ggtttgttga aaaccggaca tggcactcca   4320
gtcgccttcc cgttccgcta tcggctgaat ttgattgcga gtgagatatt tatgccagcc   4380
agccagacgc agacgcgccg agacagaact taatgggccc gctaacgcg cgatttgctg    4440 gtgacccaat gcgaccagat gctccacgcc cagtcgcgta ccgtcttcat gggagaaaat   4500
aatactgttg atgggtgtct ggtcagagac atcaagaaat aacgccggaa cattagtgca   4560
ggcagcttcc acagcaatgg catcctggtc atccagcgga tagttaatga tcagcccact   4620
gacgcgttgc gcgagaagat tgtgcaccgc cgctttacag gcttcgacgc cgcttcgttc   4680
taccatcgac accaccacgc tggcacccag ttgatcggcg cgagatttaa tcgccgcgac   4740
aatttgcgac ggcgcgtgca gggccagact ggaggtggca acgccaatca gcaacgactg   4800
tttgcccgcc agttgttgtg ccacgcggtt gggaatgtaa ttcagctccg ccatcgccgc   4860
ttccactttt tcccgcgttt tcgcagaaac gtggctggcc tggttcacca cgcgggaaac   4920
ggtctgataa gagacaccgg catactctgc gacatcgtat aacgttactg gtttcacatt   4980
caccaccctg aattgactct cttccgggcg ctatcatgcc ataccgcgaa aggttttgcg   5040
ccattcgatg gtgtccggga tctcgacgct ctcccttatg cgactcctgc attaggaaat   5100
taatacgact cactata                                                  5117
```

<210> SEQ ID NO 13
<211> LENGTH: 6707
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 13

```
ggggaattgt gagcggataa caattcccct ctagaaataa ttttgtttaa ctttaagaag     60
gagatatacc atgggcagca gccatcacca tcatcaccac agccaggatc cgaattcgag    120
ctcgatcaca agtttgtaca aaaaagctga acgagaaacg taaatgata taaatatcaa    180 tatattaaat tagattttgc ataaaaaaca gactacataa tactgtaaaa cacaacatat    240
ccagtcacta tggcggccgc cacgttaagg gattttggtc atgatcagca cgtgttgaca    300
attaatcatc ggcatagtat atcggcatag tataatacga caaggtgagg aactaaacca    360
tggccaagtt gaccagtgcc gttccggtgc tcaccgcgcg cgacgtcgcc ggagcggtcg    420
agttctggac cgaccggctc gggttctccc gggacttcgt ggaggacgac ttcgccggtg    480
```

```
tggtccggga cgacgtgacc ctgttcatca gcgcggtcca ggaccaggtg gtgccggaca    540
acaccctggc ctgggtgtgg gtgcgcggcc tggacgagct gtacgccgag tggtcggagg    600
tcgtgtccac gaacttccgg gacgcctccg ggccggccat gaccgagatc ggcgagcagc    660
cgtggggcg ggagttcgcc ctgcgcgacc cggccggcaa ctgcgtgcac ttcgtggccg    720
aggagcagga ctgatcatga tgatattatt ttatcttgtg caatgtaaca tcagagattt    780
tgagacacgg gccagagctg ccaggaaaca gctatgacca tgtaatacga ctcactatag    840
gggatatcag ctggatggca ataatgatt ttattttgac tgatagtgac ctgttcgttg    900
cacaccggtg ctagcgtata cccgaagtat gtcaaaaaga ggtgtgctat gaagcagcgt    960
attacagtga cagttgacag cgacagctat cagttgctca aggcatatat gatgtcaata   1020
tctccggtct ggtaagcaca accatgcaga atgaagcccg tcgtctgcgt gccgaacgct   1080
ggaaagcgga aaatcaggaa gggatggctg aggtcgcccg gtttattgaa atgaacggct   1140
cttttgctga cgaaacagg gactggtgaa atgcagttta aggtttacac ctataaaaga   1200
gagagccgtt atcgtctgtt tgtggatgta cagagtgata ttattgacac gcccgggcga   1260
cggatggtga tcccctggc cagtgcacgt ctgctgtcag ataaagtctc ccgtgaactt   1320
tacccggtgg tgcatatcgg ggatgaaagc tggcgcatga tgaccaccga tatggccagt   1380
gtgccggtct ccgttatcgg ggaagaagtg gctgatctca gccgccgcga aaatgacatc   1440
aaaaacgcca ttaacctgat gttctgggga atataaatgt caggctccct tatacacagc   1500
cagtctgcag gtcgaccata gtgactggat atgttgtgtt ttacagtatt atgtagtctg   1560
ttttttatgc aaaatctaat ttaatatatt gatatttata tcattttacg tttctcgttc   1620
agctttcttg tacaaagtgg tgataattaa ttaagatcag atccggctgc taagcttgga   1680
attgttatcc gctcacaatt cctatagtga gtcgtattac ctaggctgct gccaccgctg   1740
agcaataact agcataaccc cttggggcct ctaaacgggt cttgaggggt ttttgctga   1800
aaggaggaac tatatccgga ttggcgaatg ggacgcgccc tgtagcggcg cattaagcgc   1860
ggcgggtgtg gtggttacgc gcagcgtgac cgctacactt gccagcgccc tagcgcccgc   1920
tcctttcgct ttcttccctt cctttctcgc cacgttcgcc ggctttcccc gtcaagctct   1980
aaatcggggg ctcccttag ggttccgatt tagtgcttta cggcacctcg accccaaaaa   2040
acttgattag ggtgatggtt cacgtagtgg gccatcgccc tgatagacgg ttttcgccc   2100
tttgacgttg gagtccacgt tctttaatag tggactcttg ttccaaactg gaacaacact   2160
caaccctatc tcggtctatt cttttgattt ataagggatt ttgccgattt cggcctattg   2220
gttaaaaaat gagctgattt aacaaaaatt taacgcgaat tttaacaaaa tattaacgtt   2280
tacaatttct ggcggcacga tggcatgaga ttatcaaaaa ggatcttcac ctagatcctt   2340
ttaaattaaa aatgaagttt taaatcaatc taaagtatat atgagtaaac ttggtctgac   2400
agttaccaat gcttaatcag tgaggcacct atctcagcga tctgtctatt tcgttcatcc   2460
atagttgcct gactccccgt cgtgtagata actacgatac gggagggctt accatctggc   2520
cccagtgctg caatgatacc gcgagaccca cgctcaccgg ctccagattt atcagcaata   2580
aaccagccag ccggaagggc cgagcgcaga agtggtcctg caactttatc cgcctccatc   2640
cagtctatta attgttgccg ggaagctaga gtaagtagtt cgccagttaa tagtttgcgc   2700
aacgttgttg ccattgctac aggcatcgtg gtgtcacgct cgtcgtttgg tatggcttca   2760
ttcagctccg gttcccaacg atcaaggcga gttacatgat cccccatgtt gtgcaaaaaa   2820
gcggttagct ccttcggtcc tccgatcgtt gtcagaagta agttggccgc agtgttatca   2880
```

```
ctcatggtta tggcagcact gcataattct cttactgtca tgccatccgt aagatgcttt    2940
tctgtgactg gtgagtactc aaccaagtca ttctgagaat agtgtatgcg gcgaccgagt    3000
tgctcttgcc cggcgtcaat acgggataat accgcgccac atagcagaac tttaaaagtg    3060
ctcatcattg gaaaacgttc ttcggggcga aaactctcaa ggatcttacc gctgttgaga    3120
tccagttcga tgtaacccac tcgtgcaccc aactgatctt cagcatcttt tactttcacc    3180
agcgtttctg ggtgagcaaa aacaggaagg caaaatgccg caaaaaaggg aataagggcg    3240
acacggaaat gttgaatact catactcttc cttttccaat catgattgaa gcatttatca    3300
gggttattgt ctcatgagcg gatacatatt tgaatgtatt tagaaaaata aacaaatagg    3360
tcatgaccaa aatcccttaa cgtgagtttt cgttccactg agcgtcagac cccgtagaaa    3420
agatcaaagg atcttcttga gatcctttt ttctgcgcgt aatctgctgc ttgcaaacaa    3480
aaaaaccacc gctaccagcg gtggtttgtt tgccggatca agagctacca actctttttc    3540
cgaaggtaac tggcttcagc agagcgcaga taccaaatac tgtccttcta gtgtagccgt    3600
agttaggcca ccacttcaag aactctgtag caccgcctac atacctcgct ctgctaatcc    3660
tgttaccagt ggctgctgcc agtggcgata agtcgtgtct taccgggttg gactcaagac    3720
gatagttacc ggataaggcg cagcggtcgg gctgaacggg gggttcgtgc acacagccca    3780
gcttggagcg aacgacctac accgaactga gatacctaca gcgtgagcta tgagaaagcg    3840
ccacgcttcc cgaagggaga aaggcggaca ggtatccggt aagcggcagg gtcggaacag    3900
gagagcgcac gagggagctt ccagggggaa acgcctggta tctttatagt cctgtcgggt    3960
ttcgccacct ctgacttgag cgtcgatttt tgtgatgctc gtcagggggg cggagcctat    4020
ggaaaaacgc cagcaacgcg gcctttttac ggttcctggc cttttgctgg ccttttgctc    4080
acatgttctt tcctgcgtta tcccctgatt ctgtggataa ccgtattacc gcctttgagt    4140
gagctgatac cgctcgccgc agccgaacga ccgagcgcag cgagtcagtg agcgaggaag    4200
cggaagagcg cctgatgcgg tattttctcc ttacgcatct gtgcggtatt tcacaccgca    4260
tatatggtgc actctcagta caatctgctc tgatgccgca tagttaagcc agtatacact    4320
ccgctatcgc tacgtgactg ggtcatggct gcgccccgac acccgccaac acccgctgac    4380
gcgccctgac gggcttgtct gctcccggca tccgcttaca gacaagctgt gaccgtctcc    4440
gggagctgca tgtgtcagag gttttcaccg tcatcaccga aacgcgcgag gcagctgcgg    4500
taaagctcat cagcgtggtc gtgaagcgat tcacagatgt ctgcctgttc atccgcgtcc    4560
agctcgttga gtttctccag aagcgttaat gtctggcttc tgataaagcg ggccatgtta    4620
agggcggttt tttcctgttt ggtcactgat gcctccgtgt aagggggatt tctgttcatg    4680
ggggtaatga taccgatgaa acgagagagg atgctcacga tacgggttac tgatgatgaa    4740
catgcccggt tactggaacg ttgtgagggt aaacaactgg cggtatggat gcggcgggac    4800
cagagaaaaa tcactcaggg tcaatgccag cgcttcgtta atacagatgt aggtgttcca    4860
cagggtagcc agcagcatcc tgcgatgcag atccggaaca taatggtgca gggcgctgac    4920
ttccgcgttt ccagacttta cgaaacacgg aaaccgaaga ccattcatgt tgttgctcag    4980
gtcgcagacg ttttgcagca gcagtcgctt cacgttcgct cgcgtatcgg tgattcattc    5040
tgctaaccag taaggcaacc ccgccagcct agccgggtcc tcaacgacag gagcacgatc    5100
atgctagtca tgccccgcgc ccaccggaag gagctgactg ggttgaaggc tctcaagggc    5160
atcggtcgag atcccggtgc ctaatgagtg agctaactta cattaattgc gttgcgctca    5220
```

```
ctgcccgctt tccagtcggg aaacctgtcg tgccagctgc attaatgaat cggccaacgc    5280
gcggggagag gcggtttgcg tattgggcgc caggtggtt tttcttttca ccagtgagac    5340
gggcaacagc tgattgccct tcaccgcctg gccctgagag agttgcagca agcggtccac    5400
gctggtttgc cccagcaggc gaaaatcctg tttgatggtg gttaacggcg ggatataaca    5460
tgagctgtct tcggtatcgt cgtatcccac taccgagatg tccgcaccaa cgcgcagccc    5520
ggactcggta atggcgcgca ttgcgcccag cgccatctga tcgttggcaa ccagcatcgc    5580
agtgggaacg atgccctcat tcagcatttg catggtttgt tgaaaaccgg acatggcact    5640
ccagtcgcct tcccgttccg ctatcggctg aatttgattg cgagtgagat atttatgcca    5700
gccagccaga cgcagacgcg ccgagacaga acttaatggg cccgctaaca gcgcgatttg    5760
ctggtgaccc aatgcgacca gatgctccac gcccagtcgc gtaccgtctt catgggagaa    5820
aataatactg ttgatgggtg tctggtcaga gacatcaaga ataacgccg gaacattagt    5880 gcaggcagct tccacagcaa tggcatcctg gtcatccagc ggatagttaa tgatcagccc    5940
actgacgcgt tgcgcgagaa gattgtgcac cgccgcttta caggcttcga cgccgcttcg    6000
ttctaccatc gacaccacca cgctggcacc cagttgatcg gcgcgagatt taatcgccgc    6060
gacaatttgc gacggcgcgt gcagggccag actggaggtg gcaacgccaa tcagcaacga    6120
ctgtttgccc gccagttgtt gtgccacgcg gttgggaatg taattcagct ccgccatcgc    6180
cgcttccact ttttcccgcg ttttcgcaga aacgtggctg gcctggttca ccacgcggga    6240
aacggtctga taagagacac cggcatactc tgcgacatcg tataacgtta ctggtttcac    6300
attcaccacc ctgaattgac tctcttccgg gcgctatcat gccataccgc gaaaggtttt    6360
gcgccattcg atggtgtccg ggatctcgac gctctccctt atgcgactcc tgcattagga    6420
agcagcccag tagtaggttg aggccgttga gcaccgccgc cgcaaggaat ggtgcatgca    6480
aggagatggc gcccaacagt cccccggcca cggggcctgc caccataccc acgccgaaac    6540
aagcgctcat gagcccgaag tggcgagccc gatcttcccc atcggtgatg tcggcgatat    6600
aggcgccagc aaccgcacct gtggcgccgg tgatgccggc cacgatgcgt ccggcgtaga    6660
ggatcgagat cgatctcgat cccgcgaaat taatacgact cactata           6707
```

<210> SEQ ID NO 14
<211> LENGTH: 5325
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 14

```
ggggaattgt gagcggataa caattcccct gtagaaataa ttttgtttaa ctttaataag     60
gagatatacc atgggcagca gccatcacca tcatcaccac agccaggatc cgaattcgag    120
ctcggaccat gattacgcca agctatcaac tttgtataga aagttgaac gagaaacgta    180 aaatgatata aatatcaata tattaaatta gattttgcat aaaaaacaga ctacataata    240
ctgtaaaaca caacatatcc agtcactatg gtcgacctgc agactggctg tgtataaggg    300
agcctgacat ttatattccc cagaacatca ggttaatggc gttttgatg tcattttcgc    360 ggtggctgag atcagccact tcttccccga taacggagac cggcacactg gccatatcgg    420
tggtcatcat gcgccagctt tcatcccga tatgcaccac cgggtaaagt tcacggggga    480
ctttatctga cagcagacgt gcactggcca ggggatcac catccgtcgc ccgggcgtgt    540
```

```
caataatatc actctgtaca tccacaaaca gacgataacg gctctctctt ttataggtgt    600
aaaccttaaa ctgcatttca ccagccctg ttctcgtcgg caaaagagcc gttcatttca    660
ataaaccggg cgacctcagc catcccttcc tgattttccg cttccagcg ttcggcacgc    720 agacgacggg cttcattctg catggttgtg cttaccgaac cggagatatt gacatcatat   780
atgccttgag caactgatag ctgtcgctgt caactgtcac tgtaatacgc tgcttcatag   840
catacctctt tttgacatac ttcgggtata catatcagta tatattctta taccgcaaaa   900
atcagcgcgc aaatacgcat actgttatct ggcttttagt aagccggatc ctctagatta   960
cgccccgccc tgccactcat cgcagtactg ttgtaattca ttaagcattc tgccgacatg  1020
gaagccatca caaacggcat gatgaacctg aatcgccagc ggcatcagca ccttgtcgcc  1080
ttgcgtataa tatttgccca tggtgaaaac ggggggcgaag aagttgtcca tattggccac 1140
gtttaaatca aaactggtga aactcaccca gggattggct gagacgaaaa acatattctc  1200
aataaaccct ttagggaaat aggccaggtt ttcaccgtaa cacgccacat cttgcgaata  1260
tatgtgtaga aactgccgga aatcgtcgtg gtattcactc cagagcgatg aaaacgtttc  1320
agtttgctca tggaaaacgg tgtaacaagg gtgaacacta tcccatatca ccagctcacc  1380
gtctttcatt gccatacgga attccggatg agcattcatc aggcgggcaa gaatgtgaat  1440
aaaggccgga taaaacttgt gcttattttt ctttacggtc tttaaaaagg ccgtaatatc  1500
cagctgaacg gtctggttat aggtacattg agcaactgac tgaaatgcct caaaatgttc  1560
tttacgatgc cattgggata tatcaacggt ggtatatcca gtgatttttt tctccatttt  1620
agcttcctta gctcctgaaa atctcgacgg atcctaactc aaaatccaca cattatacga  1680
gccggaagca taaagtgtaa agcctggggg tgcctaatgc ggccgccata gtgactggat  1740
atgttgtgtt ttacagtatt atgtagtctg ttttttatgc aaaatctaat ttaatatatt  1800
gatatttata tcattttacg tttctcgttc aactttatta tacatagttg ataattcact  1860
ggccgtcgtt ttacaacgtc gtgactggga aaaccctggc gttacccaac ttaatcgcct  1920
tgcagcacaa gcttggaatt gttatccgct cacaattcct atagtgagtc gtattaccta  1980
ggctgctgcc accgctgagc aataactagc ataacccctt ggggcctcta acgggtctt   2040 gaggggtttt ttgctgaaac ctcaggcatt tgagaagcac acggtcacac tgcttccggt  2100
agtcaataaa ccggtaaacc agcaatagac ataagcggct atttaacgac cctgccctga  2160
accgacgacc gggtcatcgt ggccggatct tgcggcccct cggcttgaac gaattgttag  2220
acattatttg ccgactacct tggtgatctc gcctttcacg tagtggacaa attcttccaa  2280
ctgatctgcg cgcgaggcca agcgatcttc ttcttgtcca agataagcct gtctagcttc  2340
aagtatgacg ggctgatact gggccggcag gcgctccatt gcccagtcgg cagcgacatc  2400
cttcggcgcg attttgccgg ttactgcgct gtaccaaatg cgggacaacg taagcactac  2460
atttcgctca tcgccagccc agtcgggcgg cgagttccat agcgttaagg tttcatttag  2520
cgcctcaaat agatcctgtt caggaaccgg atcaaagagt tcctccgccg ctggacctac  2580
caaggcaacg ctatgttctc ttgcttttgt cagcaagata gccagatcaa tgtcgatcgt  2640
ggctggctcg aagatacctg caagaatgtc attgcgctgc cattctccaa attgcagttc  2700
gcgcttagct ggataacgcc acggaatgat gtcgtcgtgc acaacaatgg tgacttctac  2760
agcgcggaga atctcgctct ctccagggga agccgaagtt ccaaaaggt cgttgatcaa   2820 agctcgccgc gttgtttcat caagccttac ggtcaccgta accagcaaat caatatcact  2880
gtgtggcttc aggccgccat ccactgcgga gccgtacaaa tgtacggcca gcaacgtcgg  2940
```

```
ttcgagatgg cgctcgatga cgccaactac ctctgatagt tgagtcgata cttcggcgat    3000
caccgcttcc ctcatactct tccttttca atattattga agcatttatc agggttattg    3060
tctcatgagc ggatacatat ttgaatgtat ttagaaaaat aaacaaatag ctagctcact    3120
cggtcgctac gctccgggcg tgagactgcg gcgggcgctg cggacacata caaagttacc    3180
cacagattcc gtggataagc aggggactaa catgtgaggc aaaacagcag ggccgcgccg    3240
gtggcgtttt tccataggct ccgccctcct gccagagttc acataaacag acgcttttcc    3300
ggtgcatctg tgggagccgt gaggctcaac catgaatctg acagtacggg cgaaacccga    3360
caggacttaa agatccccac cgtttccggc gggtcgctcc ctcttgcgct ctcctgttcc    3420
gaccctgccg tttaccggat acctgttccg ccttttctcc ttacgggaag tgtggcgctt    3480
tctcatagct cacacactgg tatctcggct cggtgtaggt cgttcgctcc aagctgggct    3540
gtaagcaaga actccccgtt cagcccgact gctgcgcctt atccggtaac tgttcacttg    3600
agtccaaccc ggaaaagcac ggtaaaacgc cactggcagc agccattggt aactgggagt    3660
tcgcagagga tttgtttagc taaacacgcg gttgctcttg aagtgtgcgc caaagtccgg    3720
ctacactgga aggacagatt tggttgctgt gctctgcgaa agccagttac cacggttaag    3780
cagttcccca actgacttaa ccttcgatca aaccacctcc ccaggtggtt ttttcgttta    3840
cagggcaaaa gattacgcgc agaaaaaaag gatctcaaga agatcctttg atcttttcta    3900
ctgaaccgct ctagatttca gtgcaattta tctcttcaaa tgtagcacct gaagtcagcc    3960
ccatacgata aagttgtaa ttctcatgtt agtcatgccc cgcgcccacc ggaaggagct    4020
gactgggttg aaggctctca agggcatcgg tcgagatccc ggtgcctaat gagtgagcta    4080
acttacatta attgcgttgc gctcactgcc cgctttccag tcgggaaacc tgtcgtgcca    4140
gctgcattaa tgaatcggcc aacgcgcggg gagaggcggt ttgcgtattg ggcgccaggg    4200 tggttttct tttcaccagt gagacgggca acagctgatt gcccttcacc gcctggccct    4260
gagagagttg cagcaagcgg tccacgctgg tttgccccag caggcgaaaa tcctgtttga    4320
tggtggttaa cggcgggata taacatgagc tgtcttcggt atcgtcgtat cccactaccg    4380
agatgtccgc accaacgcgc agcccggact cggtaatggc gcgcattgcg cccagcgcca    4440
tctgatcgtt ggcaaccagc atcgcagtgg gaacgatgcc ctcattcagc atttgcatgg    4500
tttgttgaaa accggacatg gcactccagt cgccttcccg ttccgctatc ggctgaattt    4560
gattgcgagt gagatattta tgccagccag ccagacgcag acgcgccgag acagaactta    4620
atgggcccgc taacagcgcg atttgctggt gacccaatgc gaccagatgc tccacgccca    4680
gtcgcgtacc gtcttcatgg gagaaaataa tactgttgat gggtgtctgg tcagagacat    4740
caagaaataa cgccggaaca ttagtgcagg cagcttccac agcaatggca tcctggtcat    4800
ccagcggata gttaatgatc agcccactga cgcgttgcgc gagaagattg tgcaccgccg    4860
ctttacaggc ttcgacgccg cttcgttcta ccatcgacac caccacgctg gcacccagtt    4920
gatcggcgcg agatttaatc gccgcgacaa tttgcgacgg cgcgtgcagg ccagactgg    4980 aggtggcaac gccaatcagc aacgactgtt tgcccgccag ttgttgtgcc acgcggttgg    5040
gaatgtaatt cagctccgcc atcgccgctt ccacttttc ccgcgttttc gcagaaacgt    5100
ggctggcctg gttcaccacg cgggaaacgg tctgataaga gacaccggca tactctgcga    5160
catcgtataa cgttactggt ttcacattca cacccctgaa ttgactctct tccgggcgct    5220
atcatgccat accgcgaaag gttttgcgcc attcgatggt gtccgggatc tcgacgctct    5280
```
cccttatgcg actcctgcat taggaaatta atacgactca ctata         5325

<210> SEQ ID NO 15
<211> LENGTH: 5373
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 15
ggggaattgt gagcggataa caattcccct gtagaaataa ttttgtttaa ctttaataag      60
gagatatacc atgggcagca gccatcacca tcatcaccac agccaggatc cgaattcgag     120
ctcggaccat gattacgcca agctatcaac tttgtataga aagttgaac gagaaacgta      180
aaatgatata aatatcaata tattaaatta gattttgcat aaaaaacaga ctacataata     240
ctgtaaaaca caacatatcc agtcactatg gtcgacctgc agactggctg tgtataaggg     300
agcctgacat ttatattccc cagaacatca ggttaatggc gttttttgatg tcattttcgc    360
ggtggctgag atcagccact tcttccccga taacggagac cggcacactg gccatatcgg    420
tggtcatcat gcgccagctt tcatcccga tatgcaccac cgggtaaagt tcacggggga    480
ctttatctga cagcagacgt gcactggcca ggggatcac catccgtcgc ccgggcgtgt     540
caataatatc actctgtaca tccacaaaca gacgataacg gctctctctt ttataggtgt    600
aaaccttaaa ctgcatttca ccagcccctg ttctcgtcgg caaaagagcc gttcatttca    660
ataaaccggg cgacctcagc catcccttcc tgattttccg ctttcagcg ttcggcacgc     720
agacgacggg cttcattctg catggttgtg cttaccgaac cggagatatt gacatcatat   780
atgccttgag caactgatag ctgtcgctgt caactgtcac tgtaatacgc tgcttcatag   840
catacctctt tttgacatac ttcgggtata catatcagta tatattctta taccgcaaaa    900
atcagcgcgc aaatacgcat actgttatct ggcttttagt aagccggatc ctctagatta  960
cgccccgccc tgccactcat cgcagtactg ttgtaattca ttaagcattc tgccgacatg  1020
gaagccatca caaacggcat gatgaacctg aatcgccagc ggcatcagca ccttgtcgcc  1080
ttgcgtataa tatttgccca tggtgaaaac gggggcgaag aagttgtcca tattggccac  1140
gtttaaatca aaactggtga aactcaccca gggattggct gagacgaaaa acatattctc  1200
aataaaccct ttagggaaat aggccaggtt ttcaccgtaa cacgccacat cttgcgaata  1260
tatgtgtaga aactgccgga atcgtcgtg tattcactc cagagcgatg aaaacgtttc   1320
agtttgctca tggaaaacgg tgtaacaagg gtgaacacta tcccatatca ccagctcacc  1380
gtctttcatt gccatacgga attccggatg agcattcatc aggcgggcaa gaatgtgaat  1440
aaaggccgga taaaacttgt gcttattttt ctttacggtc tttaaaaagg ccgtaatatc  1500
cagctgaacg gtctggttat aggtacattg agcaactgac tgaaatgcct caaaatgttc  1560
tttacgatgc cattgggata tatcaacggt ggtatatcca gtgatttttt tctccatttt  1620
agcttcctta gctcctgaaa atctcgacgg atcctaactc aaaatccaca cattatacga  1680
gccggaagca taaagtgtaa agcctggggg tgcctaatgc ggccgccata gtgactggat  1740
atgttgtgtt ttacagtatt atgtagtctg ttttttatgc aaaatctaat ttaatatatt  1800
gatatttata tcattttacg tttctcgttc aactttatta tacatagttg ataattcact  1860
ggccgtcgtt ttacaacgtc gtgactggga aaaccctggc gttacccaac ttaatcgcct  1920
tgcagcacaa gcttggaatt gttatccgct cacaattcct atagtgagtc gtattaccta  1980

```
ggctgctgcc accgctgagc aataactagc ataacccctt ggggcctcta acgggtctt      2040
gaggggtttt ttgctgaaac ctcaggcatt tgagaagcac acggtcacac tgcttccggt      2100
agtcaataaa ccggtaaacc agcaatagac ataagcggct atttaacgac cctgccctga      2160
accgacgaca agctgacgac cgggtctccg caagtggcac ttttcgggga aatgtgcgcg      2220
gaaccccctat ttgtttattt ttctaaatac attcaaatat gtatccgctc atgaattaat     2280
tcttagaaaa actcatcgag catcaaatga aactgcaatt tattccatatc aggattatca    2340
ataccatatt tttgaaaaag ccgtttctgt aatgaaggag aaaactcacc gaggcagttc     2400
cataggatgg caagatcctg gtatcggtct gcgattccga ctcgtccaac atcaatacaa     2460
cctattaatt tcccctcgtc aaaaataagg ttatcaagtg agaaatcacc atgagtgacg     2520
actgaatccg gtgagaatgg caaaagttta tgcatttctt tccagacttg ttcaacaggc     2580
cagccattac gctcgtcatc aaaatcactc gcatcaacca aaccgttatt cattcgtgat     2640
tgcgcctgag cgagacgaaa tacgcggtcg ctgttaaaag acaattaca aacaggaatc      2700
gaatgcaacc ggcgcaggaa cactgccagc gcatcaacaa tattttcacc tgaatcagga    2760
tattcttcta atacctggaa tgctgttttc ccggggatcg cagtggtgag taaccatgca    2820
tcatcaggag tacggataaa atgcttgatg gtcggaagag gcataaattc cgtcagccag    2880
tttagtctga ccatctcatc tgtaacatca ttggcaacgc tacctttgcc atgtttcaga    2940
aacaactctg gcgcatcggg cttcccatac aatcgataga ttgtcgcacc tgattgcccg    3000
acattatcgc gagcccattt atacccatat aaatcagcat ccatgttgga atttaatcgc    3060
ggcctagagc aagacgtttc ccgttgaata tggctcatac tcttcctttt tcaatattat    3120
tgaagcattt atcagggtta ttgtctcatg agcggataca tatttgaatg tatttagaaa    3180
aataaacaaa taggcatgca gcgctcttcc gcttcctcgc tcactgactc gctacgctcg    3240
gtcgttcgac tgcggcgagc ggtgtcagct cactcaaaag cggtaatacg gttatccaca    3300
gaatcagggg ataaagccgg aaagaacatg tgagcaaaaa gcaaagcacc ggaagaagcc    3360
aacgccgcag gcgttttttcc ataggctccg ccccccctgac gagcatcaca aaaatcgacg   3420
ctcaagccag aggtggcgaa acccgacagg actataaaga taccaggcgt ttccccctgg    3480
aagctccctc gtgcgctctc ctgttccgac cctgccgctt accggatacc tgtccgcctt    3540
tctcccttcg ggaagcgtgg cgctttctca tagctcacgc tgttggtatc tcagttcggt    3600
gtaggtcgtt cgctccaagc tgggctgtgt gcacgaaccc cccgttcagc ccgaccgctg    3660
cgccttatcc ggtaactatc gtcttgagtc aacccggta agacacgact tatcgccact    3720
ggcagcagcc attggtaact gatttagagg actttgtctt gaagttatgc acctgttaag    3780
gctaaactga agaacagat tttggtgagt gcggtcctcc aacccactta ccttggttca     3840
aagagttggt agctcagcga accttgagaa aaccaccgtt ggtagcggtg ttttttcttt    3900
atttatgaga tgatgaatca atcggtctat caagtcaacg aacagctatt ccgttactct    3960
agatttcagt gcaatttatc tcttcaaatg tagcacctga agtcagcccc atacgatata    4020
agttgtaatt ctcatgttag tcatgccccg cgcccaccgg aaggagctga ctgggttgaa    4080
ggctctcaag ggcatcggtc gagatcccgg tgcctaatga gtgagctaac ttacattaat    4140
tgcgttgcgc tcactgcccg ctttccagtc gggaaacctg tcgtgccagc tgcattaatg    4200
aatcggccaa cgcgcgggga gaggcggttt gcgtattggg cgccagggtg ttttttcttt    4260
tcaccagtga acgggcaac agctgattgc ccttcaccgc ctggccctga gagagttgca    4320
gcaagcggtc cacgctggtt tgccccagca ggcgaaaatc ctgtttgatg gtggttaacg    4380
```

```
gcgggatata acatgagctg tcttcggtat cgtcgtatcc cactaccgag atgtccgcac    4440
caacgcgcag cccggactcg gtaatggcgc gcattgcgcc cagcgccatc tgatcgttgg    4500
caaccagcat cgcagtggga acgatgccct cattcagcat ttgcatggtt tgttgaaaac    4560
cggacatggc actccagtcg ccttcccgtt ccgctatcgg ctgaatttga ttgcgagtga    4620
gatatttatg ccagccagcc agacgcagac gcgccgagac agaacttaat gggcccgcta    4680
acagcgcgat ttgctggtga cccaatgcga ccagatgctc cacgcccagt cgcgtaccgt    4740
cttcatggga gaaaataata ctgttgatgg gtgtctggtc agagacatca agaaataacg    4800
ccggaacatt agtgcaggca gcttccacag caatggcatc ctggtcatcc agcggatagt    4860
taatgatcag cccactgacg cgttgcgcga agattgtg caccgccgct ttacaggctt    4920
cgacgccgct tcgttctacc atcgacacca ccacgctggc acccagttga tcggcgcgag    4980
atttaatcgc cgcgacaatt tgcgacggcg cgtgcagggc cagactggag gtggcaacgc    5040
caatcagcaa cgactgtttg cccgccagtt gttgtgccac gcggttggga atgtaattca    5100
gctccgccat cgccgcttcc actttttccc gcgtttttcgc agaaacgtgg ctggcctggt    5160
tcaccacgcg ggaaacggtc tgataagaga caccggcata ctctgcgaca tcgtataacg    5220
ttactggttt cacattcacc accctgaatt gactctcttc cgggcgctat catgccatac    5280
cgcgaaaggt tttgcgccat tcgatggtgt ccgggatctc gacgctctcc cttatgcgac    5340
tcctgcatta ggaaattaat acgactcact ata                               5373

<210> SEQ ID NO 16
<211> LENGTH: 6964
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 16
ggggaattgt gagcggataa caattcccct ctagaaataa ttttgtttaa ctttaagaag      60
gagatatacc atgggcagca gccatcacca tcatcaccac agccaggatc cgaattcgag     120
ctcggaccat gattacgcca agctatcaac tttgtataga aagttgaac gagaaacgta     180 aaatgatata aatatcaata tattaaatta gattttgcat aaaaaacaga ctacataata     240
ctgtaaaaca caacatatcc agtcactatg gtcgacctgc agactggctg tgtataaggg     300
agcctgacat ttatattccc cagaacatca ggttaatggc gttttttgatg tcattttcgc     360 ggtggctgag atcagccact tcttccccga taacggagac cggcacactg gccatatcgg     420
tggtcatcat gcgccagctt tcatccccga tatgcaccac cgggtaaagt tcacgggga     480 ctttatctga cagcagacgt gcactggcca ggggatcac catccgtcgc ccgggcgtgt     540
caataatatc actctgtaca tccacaaaca gacgataacg ctctctctt ttataggtgt     600 aaaccttaaa ctgcatttca ccagcccctg ttctcgtcgg caaagagcc gttcatttca     660 ataaacgggg cgacctcagc catcccttcc tgatttttccg ctttcagcg ttcggcacgc     720 agacgacggg cttcattctg catggttgtg cttaccgaac cggagatatt gacatcatat     780
atgccttgag caactgatag ctgtcgctgt caactgtcac tgtaatacgc tgcttcatag     840
catacctctt tttgacatac ttcgggtata catatcagta tatattctta taccgcaaaa     900
atcagcgcgc aaatacgcat actgttatct ggcttttagt aagccggatc tctagatta     960 cgccccgccc tgccactcat cgcagtactg ttgtaattca ttaagcattc tgccgacatg    1020
```

-continued

```
gaagccatca caaacggcat gatgaacctg aatcgccagc ggcatcagca ccttgtcgcc    1080
ttgcgtataa tatttgccca tggtgaaaac gggggcgaag aagttgtcca tattggccac    1140
gtttaaatca aaactggtga aactcaccca gggattggct gagacgaaaa acatattctc    1200
aataaaccct ttagggaaat aggccaggtt ttcaccgtaa cacgccacat cttgcgaata    1260
tatgtgtaga aactgccgga aatcgtcgtg gtattcactc cagagcgatg aaaacgtttc    1320
agtttgctca tggaaaacgg tgtaacaagg gtgaacacta tcccatatca ccagctcacc    1380
gtctttcatt gccatacgga attccggatg agcattcatc aggcgggcaa gaatgtgaat    1440
aaaggccgga taaaacttgt gcttattttt ctttacggtc tttaaaaagg ccgtaatatc    1500
cagctgaacg gtctggttat aggtacattg agcaactgac tgaaatgcct caaaatgttc    1560
tttacgatgc cattgggata tatcaacggt ggtatatcca gtgatttttt tctccatttt    1620
agcttcctta gctcctgaaa atctcgacgg atcctaactc aaaatccaca cattatacga    1680
gccggaagca taaagtgtaa agcctggggg tgcctaatgc ggccgccata gtgactggat    1740
atgttgtgtt ttacagtatt atgtagtctg tttttatgc aaaatctaat ttaatatatt    1800
gatatttata tcattttacg tttctcgttc aactttatta tacatagttg ataattcact    1860
ggccgtcgtt ttacaacgtc gtgactggga aaaccctggc gttacccaac ttaatcgcct    1920
tgcagcacaa gcttggaatt gttatccgct cacaattcct atagtgagtc gtattaccta    1980
ggctgctgcc accgctgagc aataactagc ataaccccct ggggcctcta acgggtctt    2040
gagggggtttt ttgctgaaag gaggaactat atccggattg gcgaatggga cgcgccctgt    2100
agcggcgcat taagcgcggc gggtgtggtg gttacgcgca gcgtgaccgc tacacttgcc    2160
agcgccctag cgcccgctcc tttcgctttc ttcccttcct ttctcgccac gttcgccggc    2220
tttccccgtc aagctctaaa tcggggggctc cctttagggt tccgatttag tgctttacgg    2280
cacctcgacc ccaaaaaact tgattagggt gatggttcac gtagtgggcc atcgccctga    2340
tagacggttt ttcgcccttt gacgttggag tccacgttct ttaatagtgg actcttgttc    2400
caaactggaa caacactcaa ccctatctcg gtctattctt ttgatttata agggattttg    2460
ccgatttcgg cctattggtt aaaaaatgag ctgatttaac aaaaatttaa cgcgaatttt    2520
aacaaaatat taacgtttac aatttctggc ggcacgatgg catgagatta tcaaaaagga    2580
tcttcaccta gatcctttta aattaaaaat gaagttttaa atcaatctaa agtatatatg    2640
agtaaacttg gtctgacagt taccaatgct taatcagtga ggcacctatc tcagcgatct    2700
gtctatttcg ttcatccata gttgcctgac tccccgtcgt gtagataact acgatacggg    2760
agggcttacc atctggcccc agtgctgcaa tgataccgcg agaccacgc tcaccggctc     2820
cagatttatc agcaataaac cagccagccg gaagggccga gcgcagaagt ggtcctgcaa    2880
ctttatccgc ctccatccag tctattaatt gttgccggga agctagagta agtagttcgc    2940
cagttaatag tttgcgcaac gttgttgcca ttgctacagg catcgtggtg tcacgctcgt    3000
cgtttggtat ggcttcattc agctccggtt cccaacgatc aaggcgagtt acatgatccc    3060
ccatgttgtg caaaaaagcg gttagctcct tcggtcctcc gatcgttgtc agaagtaagt    3120
tggccgcagt gttatcactc atggttatgg cagcactgca taattctctt actgtcatgc    3180
catccgtaag atgcttttct gtgactggtg agtactcaac caagtcattc tgagaatagt    3240
gtatgcggcg accgagttgc tcttgcccgg cgtcaatacg ggataatacc gcgccacata    3300
gcagaacttt aaaagtgctc atcattggaa aacgttcttc ggggcgaaaa ctctcaagga    3360
```

```
tcttaccgct gttgagatcc agttcgatgt aacccactcg tgcacccaac tgatcttcag    3420
catcttttac tttcaccagc gtttctgggt gagcaaaaac aggaaggcaa aatgccgcaa    3480
aaaagggaat aagggcgaca cggaaatgtt gaatactcat actcttcctt tttcaatcat    3540
gattgaagca tttatcaggg ttattgtctc atgagcggat acatatttga atgtatttag    3600
aaaaataaac aaataggtca tgaccaaaat cccttaacgt gagttttcgt tccactgagc    3660
gtcagacccc gtagaaaaga tcaaaggatc ttcttgagat cctttttttc tgcgcgtaat    3720
ctgctgcttg caaacaaaaa aaccaccgct accagcggtg gtttgtttgc cggatcaaga    3780
gctaccaact ctttttccga aggtaactgg cttcagcaga gcgcagatac caaatactgt    3840
ccttctagtg tagccgtagt taggccacca cttcaagaac tctgtagcac cgcctacata    3900
cctcgctctg ctaatcctgt taccagtggc tgctgccagt ggcgataagt cgtgtcttac    3960
cgggttggac tcaagacgat agttaccgga taaggcgcag cggtcgggct gaacggggggg  4020 ttcgtgcaca cagcccagct tggagcgaac gacctacacc gaactgagat acctacagcg    4080
tgagctatga gaaagcgcca cgcttcccga agggagaaag gcggacaggt atccggtaag    4140
cggcagggtc ggaacaggag agcgcacgag ggagcttcca gggggaaacg cctggtatct    4200
ttatagtcct gtcgggtttc gccacctctg acttgagcgt cgatttttgt gatgctcgtc    4260
aggggggcgg agcctatgga aaaacgccag caacgcggcc ttttacggt tcctggcctt     4320 ttgctggcct tttgctcaca tgttctttcc tgcgttatcc cctgattctg tggataaccg    4380
tattaccgcc tttgagtgag ctgataccgc tcgccgcagc cgaacgaccg agcgcagcga    4440
gtcagtgagc gaggaagcgg aagagcgcct gatgcggtat tttctcctta cgcatctgtg    4500
cggtatttca caccgcatat atggtgcact ctcagtacaa tctgctctga tgccgcatag    4560
ttaagccagt atacactccg ctatcgctac gtgactgggt catggctgcg ccccgacacc    4620
cgccaacacc cgctgacgcg ccctgacggg cttgtctgct cccggcatcc gcttacagac    4680
aagctgtgac cgtctccggg agctgcatgt gtcagaggtt ttcaccgtca tcaccgaaac    4740
gcgcgaggca gctgcggtaa agctcatcag cgtggtcgtg aagcgattca cagatgtctg    4800
cctgttcatc cgcgtccagc tcgttgagtt tctccagaag cgttaatgtc tggcttctga    4860
taaagcgggc catgttaagg gcggttttt cctgtttggt cactgatgcc tccgtgtaag    4920
ggggatttct gttcatgggg gtaatgatac cgatgaaacg agagaggatg ctcacgatac    4980
gggttactga tgatgaacat gcccggttac tggaacgttg tgagggtaaa caactggcgg    5040 tatgatgcg gcgggaccag agaaaaatca ctcagggtca atgccagcgc ttcgttaata    5100
cagatgtagg tgttccacag ggtagccagc agcatcctgc gatgcagatc cggaacataa    5160
tggtgcaggg cgctgacttc cgcgtttcca gactttacga aacacggaaa ccgaagacca    5220
ttcatgttgt tgctcaggtc gcagacgttt gcagcagca gtcgcttcac gttcgctcgc    5280
gtatcggtga ttcattctgc taaccagtaa ggcaaccccg ccagcctagc cgggtcctca    5340
acgacaggag cacgatcatg ctagtcatgc cccgcgccca ccggaaggag ctgactgggt    5400
tgaaggctct caagggcatc ggtcgagatc ccggtgccta atgagtgagc taacttacat    5460
taattgcgtt gcgctcactg cccgctttcc agtcgggaaa cctgtcgtgc cagctgcatt    5520
aatgaatcgg ccaacgcgcg gggagaggcg gtttgcgtat tgggcgccag ggtggttttt    5580
cttttcacca gtgagacggg caacagctga ttgcccttca ccgcctggcc ctgagagagt    5640
tgcagcaagc ggtccacgct ggtttgcccc agcaggcgaa aatcctgttt gatggtggtt    5700
aacggcggga tataacatga gctgtcttcg gtatcgtcgt atcccactac cgagatgtcc    5760
```

```
gcaccaacgc gcagcccgga ctcggtaatg gcgcgcattg cgcccagcgc catctgatcg    5820
ttggcaacca gcatcgcagt gggaacgatg ccctcattca gcatttgcat ggtttgttga    5880
aaaccggaca tggcactcca gtcgccttcc cgttccgcta tcggctgaat ttgattgcga    5940
gtgagatatt tatgccagcc agccagacgc agacgcgccg agacagaact taatgggccc    6000
gctaacagcg cgatttgctg gtgacccaat gcgaccagat gctccacgcc cagtcgcgta    6060
ccgtcttcat gggagaaaat aatactgttg atgggtgtct ggtcagagac atcaagaaat    6120
aacgccggaa cattagtgca ggcagcttcc acagcaatgg catcctggtc atccagcgga    6180
tagttaatga tcagcccact gacgcgttgc gcgagaagat tgtgcaccgc cgctttacag    6240
gcttcgacgc cgcttcgttc taccatcgac accaccacgc tggcacccag ttgatcggcg    6300
cgagatttaa tcgccgcgac aatttgcgac ggcgcgtgca gggccagact ggaggtggca    6360
acgccaatca gcaacgactg tttgcccgcc agttgttgtg ccacgcggtt gggaatgtaa    6420
ttcagctccg ccatcgccgc ttccactttt tcccgcgttt tcgcagaaac gtggctggcc    6480
tggttcacca cgcgggaaac ggtctgataa gagacaccgg catactctgc gacatcgtat    6540
aacgttactg gtttcacatt caccaccctg aattgactct cttccgggcg ctatcatgcc    6600
ataccgcgaa aggttttgcg ccattcgatg gtgtccggga tctcgacgct ctcccttatg    6660
cgactcctgc attaggaagc agcccagtag taggttgagg ccgttgagca ccgccgccgc    6720
aaggaatggt gcatgcaagg agatggcgcc caacagtccc ccggccacgg ggcctgccac    6780
catacccacg ccgaaacaag cgctcatgag cccgaagtgg cgagcccgat cttccccatc    6840
ggtgatgtcg gcgatatagg cgccagcaac cgcacctgtg gcgccggtga tgccggccac    6900
gatgcgtccg gcgtagagga tcgagatcga tctcgatccc gcgaaattaa tacgactcac    6960
tata                                                                 6964
```

<210> SEQ ID NO 17
<211> LENGTH: 6902
<212> TYPE: DNA
<213> ORGANISM: Artificial Sequence
<220> FEATURE:
<223> OTHER INFORMATION: Description of Artificial Sequence: Synthetic vector nucleotide sequence

<400> SEQUENCE: 17

```
atccggatat agttcctcct ttcagcaaaa aaccccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttag    180
cagccggatc tgatcttaat taattatcac cactttgtac aagaaagctg aacgagaaac    240 gtaaatgat ataaatatca atatattaaa ttagattttg cataaaaaac agactacata    300
atactgtaaa acacaacata tccagtcact atggtcgacc tgcagactgg ctgtgtataa    360
gggagcctga catttatatt ccccagaaca tcaggttaat ggcgttttg atgtcatttt    420 cgcggcggct gagatcagcc acttcttccc cgataacgga gaccggcaca ctggccatat    480
cggtggtcat catgcgccag ctttcatccc cgatatgcac caccgggtaa agttcacggg    540
agactttatc tgacacgaga cgtgcactgg ccaggggggat caccatccgt cgcccgggcg    600
tgtcaataat atcactctgt acatccacaa acagacgata acggctctct cttttatagg    660
tgtaaacctt aaactgcatt tcaccagtcc ctgttctcgt cagcaaaaga gccgttcatt    720
tcaataaacc gggcgaccctc agccatccct tcctgatttt ccgctttcca gcgttcggca    780
```

```
cgcagacgac gggcttcatt ctgcatggtt gtgcttacca gaccggagat attgacatca    840
tatatgcctt gagcaactga tagctgtcgc tgtcaactgt cactgtaata cgctgcttca    900
tagcacacct cttttt gaca tacttcgggt atacgctagc accggtgttg caacgaacag    960
gtcactatca gtcaaaataa aatcattatt tgccatccag ctgatatccc ctatagtgag   1020
tcgtattaca tggtcatagc tgtttcctgg cagctctggc ccgtgtctca aaatctctga   1080
tgttacattg cacaagataa aataatatca tcatgatcag tcctgctcct cggccacgaa   1140
gtgcacgcag ttgccggccg ggtcgcgcag ggcgaactcc cgcccccacg gctgctcgcc   1200
gatctcggtc atggccggcc cggaggcgtc ccggaagttc gtggacacga cctccgacca   1260
ctcggcgtac agctcgtcca ggccgcgcac ccacacccag gccagggtgt tgtccggcac   1320
cacctggtcc tggaccgcgc tgatgaacag ggtcacgtcg tcccggacca caccggcgaa   1380
gtcgtcctcc acgaagtccc gggagaaccc gagccggtcg gtccagaact cgaccgctcc   1440
ggcgacgtcg cgcgcggtga gcaccggaac ggcactggtc aacttggcca tggtttagtt   1500
cctcaccttg tcgtattata ctatgccgat atactatgcc gatgattaat tgtcaacacg   1560
tgctgatcat gaccaaaatc ccttaacgtg gcggccgcca tagtgactgg atatgttgtg   1620
ttttacagta ttatgtagtc tgttttttat gcaaaatcta atttaatata ttgatattta   1680
tatcatttta cgtttctcgt tcagcttttt tgtacaaact tgtgatcgag ctcgaattcg   1740
gatccgaatt aattccgata tccatggcca tcgccggctg ggcagcgagg agcagcagac   1800
cagcagcagc ggtcggcagc aggtatttca tatgtatatc tccttcttaa agttaaacaa   1860
aattatttct agaggggaat tgttatccgc tcacaattcc cctatagtga gtcgtattaa   1920
tttcgcggga tcgagatctc gatcctctac gccgacgca tcgtggccgg catcaccggc   1980
gccacaggtg cggttgctgg cgcctatatc gccgacatca ccgatgggga agatcgggct   2040
cgccacttcg ggctcatgag cgcttgtttc ggcgtgggta tggtggcagg ccccgtggcc   2100
gggggactgt tgggcgccat ctccttgcat gcaccattcc ttgcggcggc ggtgctcaac   2160
ggcctcaacc tactactggg ctgcttccta atgcaggagt cgcataaggg agagcgtcga   2220
gatcccggac accatcgaat ggcgcaaaac ctttcgcggt atggcatgat agcgcccgga   2280
agagagtcaa ttcagggtgg tgaatgtgaa accagtaacg ttatacgatg tcgcagagta   2340
tgccggtgtc tcttatcaga ccgtttcccg cgtggtgaac caggccagcc acgtttctgc   2400
gaaaacgcgg gaaaagtgg aagcggcgat ggcggagctg aattacattc ccaaccgcgt   2460
ggcacaacaa ctggcgggca aacagtcgtt gctgattggc gttgccacct ccagtctggc   2520
cctgcacgcg ccgtcgcaaa ttgtcgcggc gattaaatct cgcgccgatc aactgggtgc   2580
cagcgtggtg gtgtcgatgg tagaacgaag cggcgtcgaa gcctgtaaag cggcggtgca   2640
caatcttctc gcgcaacgcg tcagtgggct gatcattaac tatccgctgg atgaccagga   2700
tgccattgct gtggaagctg cctgcactaa tgttccggcg ttatttcttg atgtctctga   2760
ccagacaccc atcaacagta ttattttctc ccatgaagac ggtacgcgac tgggcgtgga   2820
gcatctggtc gcattgggtc accagcaaat cgcgctgtta gcgggcccat taagttctgt   2880
ctcggcgcgt ctgcgtctgg ctggctggca taaatatctc actcgcaatc aaattcagcc   2940
gatagcggaa cgggaaggcg actggagtgc catgtccggt tttcaacaaa ccatgcaaat   3000
gctgaatgag ggcatcgttc ccactgcgat gctggttgcc aacgatcaga tggcgctggg   3060
cgcaatgcgc gccattaccg agtccgggct gcgcgttggt gcggatatct cggtagtggg   3120
```

```
atacgacgat accgaagaca gctcatgtta tatcccgccg ttaaccacca tcaaacagga    3180
ttttcgcctg ctggggcaaa ccagcgtgga ccgcttgctg caactctctc agggccaggc    3240
ggtgaagggc aatcagctgt tgcccgtctc actggtgaaa agaaaaacca ccctggcgcc    3300
caatacgcaa accgcctctc cccgcgcgtt ggccgattca ttaatgcagc tggcacgaca    3360
ggtttcccga ctggaaagcg ggcagtgagc gcaacgcaat taatgtaagt tagctcactc    3420
attaggcacc gggatctcga ccgatgccct tgagagcctt caacccagtc agctccttcc    3480
ggtgggcgcg gggcatgact atcgtcgccg cacttatgac tgtcttcttt atcatgcaac    3540
tcgtaggaca ggtgccggca gcgctctggg tcattttcgg cgaggaccgc tttcgctgga    3600
gcgcgacgat gatcggcctg tcgcttgcgg tattcggaat cttgcacgcc ctcgctcaag    3660
ccttcgtcac tggtcccgcc accaaacgtt tcggcgagaa gcaggccatt atcgccggca    3720
tggcggcccc acgggtgcgc atgatcgtgc tcctgtcgtt gaggacccgg ctaggctggc    3780
ggggttgcct tactgttag cagaatgaat accgatacg cgagcgaacg tgaagcgact    3840
gctgctgcaa aacgtctgcg acctgagcaa caacatgaat ggtcttcggt ttccgtgttt    3900
cgtaaagtct ggaaacgcgg aagtcagcgc cctgcaccat tatgttccgg atctgcatcg    3960
caggatgctg ctggctaccc tgtggaacac ctacatctgt attaacgaag cgctggcatt    4020 gacccctgagt gatttttctc tggtcccgcc gcatccatac cgccagttgt ttaccctcac    4080
aacgttccag taaccgggca tgttcatcat cagtaacccg tatcgtgagc atcctctctc    4140
gtttcatcgg tatcattacc cccatgaaca gaaatccccc ttacacggag gcatcagtga    4200
ccaaacagga aaaaaccgcc cttaacatgg cccgctttat cagaagccag acattaacgc    4260
ttctggagaa actcaacgag ctggacgcgg atgaacaggc agacatctgt gaatcgcttc    4320
acgaccacgc tgatgagctt taccgcagct gcctcgcgcg tttcggtgat gacggtgaaa    4380
acctctgaca catgcagctc ccggagacgg tcacagcttg tctgtaagcg gatgccggga    4440
gcagacaagc ccgtcagggc gcgtcagcgg gtgttggcgg gtgtcggggc gcagccatga    4500
cccagtcacg tagcgatagc ggagtgtata ctggcttaac tatgcggcat cagagcagat    4560
tgtactgaga gtgcaccata tatgcggtgt gaaataccgc acagatgcgt aaggagaaaa    4620
taccgcatca ggcgctcttc cgcttcctcg ctcactgact cgctgcgctc ggtcgttcgg    4680
ctgcggcgag cggtatcagc tcactcaaag gcggtaatac ggttatccac agaatcaggg    4740
gataacgcag gaaagaacat gtgagcaaaa ggccagcaaa aggccaggaa ccgtaaaaag    4800
gccgcgttgc tggcgttttt ccataggctc cgccccctg acgagcatca caaaatcga    4860 cgctcaagtc agaggtggcg aaacccgaca ggactataaa gataccaggc gtttcccct    4920 ggaagctccc tcgtgcgctc tcctgttccg accctgccgc ttaccggata cctgtccgcc    4980
tttctccctt cggaagcgt ggcgctttct catagctcac gctgtaggta tctcagttcg    5040
gtgtaggtcg ttcgctccaa gctgggctgt gtgcacgaac ccccgttca gcccgaccgc    5100 tgcgccttat ccggtaacta tcgtcttgag tccaacccgg taagacacga cttatcgcca    5160
ctggcagcag ccactggtaa caggattagc agagcgaggt atgtaggcgg tgctacagag    5220
ttcttgaagt ggtggcctaa ctacggctac actagaagga cagtatttgg tatctgcgct    5280
ctgctgaagc cagttacctt cggaaaaaga gttggtagc cttgatccgg caacaaacc    5340 accgctggta gcggtggttt ttttgtttgc aagcagcaga ttacgcgcag aaaaaaagga    5400
tctcaagaag atcctttgat cttttctacg gggtctgacg ctcagtggaa cgaaaactca    5460
cgttaaggga ttttggtcat gaacaataaa actgtctgct tacataaaca gtaatacaag    5520
```

```
gggtgttatg agccatattc aacgggaaac gtcttgctct aggccgcgat taaattccaa    5580
catggatgct gatttatatg ggtataaatg ggctcgcgat aatgtcgggc aatcaggtgc    5640
gacaatctat cgattgtatg ggaagcccga tgcgccagag ttgtttctga acatggcaa     5700 aggtagcgtt gccaatgatg ttacagatga gatggtcaga ctaaactggc tgacggaatt    5760
tatgcctctt ccgaccatca agcatttat ccgtactcct gatgatgcat ggttactcac     5820
cactgcgatc cccgggaaaa cagcattcca ggtattagaa gaatatcctg attcaggtga    5880
aaatattgtt gatgcgctgg cagtgttcct gcgccggttg cattcgattc ctgtttgtaa    5940
ttgtcctttt aacagcgatc gcgtatttcg tctcgctcag gcgcaatcac gaatgaataa    6000
cggtttggtt gatgcgagtg attttgatga cgagcgtaat ggctggcctg ttgaacaagt    6060
ctggaaagaa atgcataaac ttttgccatt ctcaccggat tcagtcgtca ctcatggtga    6120
tttctcactt gataaccta tttttgacga ggggaaatta ataggttgta ttgatgttgg     6180
acgagtcgga atcgcagacc gataccagga tcttgccatc ctatggaact gcctcggtga    6240
gttttctcct tcattacaga aacggctttt tcaaaaatat ggtattgata atcctgatat    6300
gaataaattg cagtttcatt tgatgctcga tgagttttt taagaattaa ttcatgagcg     6360
gatacatatt tgaatgtatt tagaaaaata acaaataggg gttccgcgc acatttcccc     6420 gaaaagtgcc acctgaaatt gtaaacgtta atattttgtt aaaattcgcg ttaaatttt     6480 gttaaatcag ctcatttttt aaccaatagg ccgaaatcgg caaaatccct tataaatcaa    6540
aagaatagac cgagataggg ttgagtgttg ttccagtttg gaacaagagt ccactattaa    6600
agaacgtgga ctccaacgtc aaagggcgaa aaaccgtcta tcagggcgat ggcccactac    6660
gtgaaccatc accctaatca agttttttgg ggtcgaggtg ccgtaaagca ctaaatcgga    6720
accctaaagg gagcccccga tttagagctt gacggggaaa gccggcgaac gtggcgagaa    6780
aggaagggaa gaaagcgaaa ggagcgggcg ctagggcgct ggcaagtgta gcggtcacgc    6840
tgcgcgtaac caccacaccc gccgcgctta atgcgccgct acagggcgcg tcccattcgc    6900
ca                                                                   6902
```

<210> SEQ ID NO 18
<211> LENGTH: 5626
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 18

```
cctgcattag gaagcagccc agtagtaggt tgaggccgtt gagcaccgcc gccgcaagga     60
atggtgcatg caaggagatg cgcccaaca gtcccccggc cacggggcct gccaccatac      120
ccacgccgaa acaagcgctc atgagcccga agtggcgagc cgatcttcc ccatcggtga     180 tgtcggcgat ataggcgcca gcaaccgcac ctgtggcgcc ggtgatgccg gccacgatgc    240
gtccggcgta gaggatcgag atctcgatcc cgcgaaatta atacgactca ctataggga     300 attgtgagcg gataacaatt cccctctaga aataattttg tttaacttta agaaggagat    360
atacatatga aatacctgct gccgaccgct gctgctggtc tgctgctcct cgctgcccag    420
ccggcgatgg ccatggatat cggaattaat tcggatccga attcgagctc gatcacaagt    480
ttgtacaaaa aagctgaacg agaaacgtaa aatgatataa atatcaatat attaaattag    540
attttgcata aaaaacagac tacataatac tgtaaaacac aacatatcca gtcactatgg    600
```

```
cggccgccac gttaagggat tttggtcatg atcagcacgt gttgacaatt aatcatcggc    660
atagtatatc ggcatagtat aatacgacaa ggtgaggaac taaaccatgg ccaagttgac    720
cagtgccgtt ccggtgctca ccgcgcgcga cgtcgccgga gcggtcgagt tctggaccga    780
ccggctcggg ttctcccggg acttcgtgga ggacgacttc gccggtgtgg tccgggacga    840
cgtgaccctg ttcatcagcg cggtccagga ccaggtggtg ccggacaaca ccctggcctg    900
ggtgtgggtg cgcggcctgg acgagctgta cgccgagtgg tcggaggtcg tgtccacgaa    960
cttccgggac gcctccgggc cggccatgac cgagatcggc gagcagccgt ggggcgggga   1020
gttcgccctg cgcgacccgg ccggcaactg cgtgcacttc gtggccgagg agcaggactg   1080
atcatgatga tattatttta tcttgtgcaa tgtaacatca gagattttga gacacgggcc   1140
agagctgcca ggaaacagct atgaccatgt aatacgactc actatagggg atatcagctg   1200
gatggcaaat aatgatttta ttttgactga tagtgacctg ttcgttgcaa caccggtgct   1260
agcgtatacc cgaagtatgt caaaaagagg tgtgctatga agcagcgtat tacagtgaca   1320
gttgacagcg acagctatca gttgctcaag gcatatatga tgtcaatatc ccggtctgg   1380 taagcacaac catgcagaat gaagcccgtc gtctgcgtgc cgaacgctgg aaagcggaaa   1440
atcaggaagg gatggctgag gtcgcccggt ttattgaaat gaacggctct tttgctgacg   1500
agaacaggga ctggtgaaat gcagtttaag gtttacacct ataaagaga gagccgttat   1560 cgtctgtttg tggatgtaca gagtgatatt attgacacgc ccgggcgacg gatggtgatc   1620
cccctggcca gtgcacgtct gctgtcagat aaagtctccc gtgaacttta cccggtggtg   1680
catatcgggg atgaaagctg gcgcatgatg accaccgata tggccagtgt gccggtctcc   1740
gttatcgggg aagaagtggc tgatctcagc cgccgcgaaa atgacatcaa aaacgccatt   1800
aacctgatgt tctggggaat ataaatgtca ggctccctta tacacagcca gtctgcaggt   1860
cgaccatagt gactggatat gttgtgtttt acagtattat gtagtctgtt ttttatgcaa   1920
aatctaattt aatatattga tatttatatc attttacgtt tctcgttcag ctttcttgta   1980
caaagtggta taattaatt aagatcagat ccggctgcta agcttgcggc cgcataatgc   2040
ttaagtcgaa cagaaagtaa tcgtattgta cacggccgca taatcgaaat taatacgact   2100
cactataggg gaattgtgag cggataacaa ttccccatct tagtatatta gttaagtata   2160
agaaggagat atacatatgg cagatctcaa ttggatatcg gccggccacg cgatcgctga   2220
cgtcggtacc ctcgagtctg gtaaagaaac cgctgctgcg aaatttgaac gccagcacat   2280
ggactcgtct actagcgcag cttaattaac ctaggctgct gccaccgctg agcaataact   2340
agcataaccc cttggggcct ctaaacgggt cttgaggggt ttttgctga acctcaggc    2400 atttgagaag cacacggtca cactgcttcc ggtagtcaat aaaccggtaa accagcaata   2460
gacataagcg ctatttaacg accctgccc tgaaccgacg accgggtcat cgtggccgga   2520
tcttgcggcc cctcggcttg aacgaattgt tagacattat ttgccgacta ccttggtgat   2580
ctcgcctttc acgtagtgga caattcttc caactgatct gcgcgcgagg ccaagcgatc   2640
ttcttcttgt ccaagataag cctgtctagc ttcaagtatg acgggctgat actgggccgg   2700
caggcgctcc attgcccagt cggcagcgac atccttcggc gcgattttgc cggttactgc   2760
gctgtaccaa atgcgggaca acgtaagcac tacatttcgc tcatcgccag cccagtcggg   2820
cggcgagttc catagcgtta aggtttcatt tagcgcctca aatagatcct gttcaggaac   2880
cggatcaaag agttcctccg ccgctggacc taccaaggca acgctatgtt ctcttgcttt   2940
```

```
tgtcagcaag atagccagat caatgtcgat cgtggctggc tcgaagatac ctgcaagaat    3000
gtcattgcgc tgccattctc caaattgcag ttcgcgctta gctggataac gccacggaat    3060
gatgtcgtcg tgcacaacaa tggtgacttc tacagcgcgg agaatctcgc tctctccagg    3120
ggaagccgaa gtttccaaaa ggtcgttgat caaagctcgc cgcgttgttt catcaagcct    3180
tacggtcacc gtaaccagca aatcaatatc actgtgtggc ttcaggccgc catccactgc    3240
ggagccgtac aaatgtacgg ccagcaacgt cggttcgaga tggcgctcga tgacgccaac    3300
tacctctgat agttgagtcg atacttcggc gatcaccgct cccctcatac tcttcctttt    3360
tcaatattat tgaagcattt atcagggtta ttgtctcatg agcggataca tatttgaatg    3420
tatttagaaa aataaacaaa tagctagctc actcggtcgc tacgctccgg cgtgagact    3480 gcggcgggcg ctgcggacac atacaaagtt acccacagat tccgtggata agcaggggac    3540
taacatgtga ggcaaaacag cagggccgcg ccggtggcgt ttttccatag gctccgccct    3600
cctgccagag ttcacataaa cagacgcttt tccggtgcat ctgtgggagc cgtgaggctc    3660
aaccatgaat ctgacagtac gggcgaaacc cgacaggact taaagatccc caccgtttcc    3720
ggcgggtcgc tccctcttgc gctctcctgt tccgaccctg ccgtttaccg gatacctgtt    3780
ccgcctttct cccttacggg aagtgtggcg ctttctcata gctcacacac tggtatctcg    3840
gctcggtgta ggtcgttcgc tccaagctgg gctgtaagca agaactcccc gttcagcccg    3900
actgctgcgc cttatccggt aactgttcac ttgagtccaa cccggaaaag cacggtaaaa    3960
cgccactggc agcagccatt ggtaactggg agttcgcaga ggatttgttt agctaaacac    4020
gcggttgctc ttgaagtgtg cgccaaagtc cggctacact ggaaggacag atttggttgc    4080
tgtgctctgc gaaagccagt taccacggtt aagcagttcc ccaactgact taaccttcga    4140
tcaaaccacc tccccaggtg gttttttcgt ttacagggca aaagattacg cgcagaaaaa    4200
aaggatctca agaagatcct ttgatctttt ctactgaacc gctctagatt tcagtgcaat    4260
ttatctcttc aaatgtagca cctgaagtca gccccatacg atataagttg taattctcat    4320
gttagtcatg ccccgcgccc accggaagga gctgactggg ttgaaggctc tcaagggcat    4380
cggtcgagat cccggtgcct aatgagtgag ctaacttaca ttaattgcgt tgcgctcact    4440
gcccgctttc cagtcgggaa acctgtcgtg ccagctgcat taatgaatcg gccaacgcgc    4500
ggggagaggc ggtttgcgta ttgggcgcca gggtggtttt tcttttcacc agtgagacgg    4560
gcaacagctg attgcccttc accgcctggc cctgagagag ttgcagcaag cggtccacgc    4620
tggtttgccc cagcaggcga aaatcctgtt tgatggtggt taacggcggg atataacatg    4680
agctgtcttc ggtatcgtcg tatcccacta ccgagatgtc cgcaccaacg cgcagcccgg    4740
actcggtaat ggcgcgcatt gcgcccagcg ccatctgatc gttggcaacc agcatcgcag    4800
tgggaacgat gccctcattc agcatttgca tggtttgttg aaaaccggac atggcactcc    4860
agtcgccttc ccgttccgct atcggctgaa tttgattgcg agtgagatat ttatgccagc    4920
cagccagacg cagacgcgcc gagacagaac ttaatgggcc cgctaacagc gcgatttgct    4980
ggtgacccaa tgcgaccaga tgctccacgc ccagtcgcgt accgtcttca tgggagaaaa    5040
taatactgtt gatgggtgtc tggtcagaga catcaagaaa taacgccgga acattagtgc    5100
aggcagcttc cacagcaatg gcatcctggt catccagcgg atagttaatg atcagcccac    5160
tgacgcgttg cgcgagaaga ttgtgcaccg ccgctttaca ggcttcgacg ccgcttcgtt    5220
ctaccatcga caccaccacg ctggcaccca gttgatcggc gcgagattta atcgccgcga    5280
caatttgcga cggcgcgtgc agggccagac tggaggtggc aacgccaatc agcaacgact    5340
```

-continued

```
gtttgcccgc cagttgttgt gccacgcggt tgggaatgta attcagctcc gccatcgccg    5400
cttccacttt ttcccgcgtt ttcgcagaaa cgtggctggc ctggttcacc acgcgggaaa    5460
cggtctgata agagacaccg gcatactctg cgacatcgta taacgttact ggtttcacat    5520
tcaccaccct gaattgactc tcttccgggc gctatcatgc cataccgcga aaggttttgc    5580
gccattcgat ggtgtccggg atctcgacgc tctcccttat gcgact                  5626
```

<210> SEQ ID NO 19
<211> LENGTH: 5674
<212> TYPE: DNA
<213> ORGANISM: Artificial Sequence
<220> FEATURE:
<223> OTHER INFORMATION: Description of Artificial Sequence: Synthetic vector nucleotide sequence

<400> SEQUENCE: 19

```
cctgcattag gaagcagccc agtagtaggt tgaggccgtt gagcaccgcc gccgcaagga      60
atggtgcatg caaggagatg gcgcccaaca gtccccggc cacggggcct gccaccatac     120
ccacgccgaa acaagcgctc atgagcccga agtggcgagc ccgatcttcc ccatcggtga    180
tgtcggcgat ataggcgcca gcaaccgcac ctgtggcgcc ggtgatgccg ccacgatgc     240 gtccggcgta gaggatcgag atctcgatcc cgcgaaatta atacgactca ctataggga     300 attgtgagcg gataacaatt cccctctaga aataattttg tttaacttta agaaggagat    360
atacatatga ataccctgct gccgaccgct gctgctggtc tgctgctcct cgctgcccag    420
ccggcgatgg ccatggatat cggaattaat tcggatccga attcgagctc gatcacaagt    480
ttgtacaaaa aagctgaacg agaaacgtaa atgatataa atatcaatat attaaattag    540
attttgcata aaaaacagac tacataatac tgtaaaacac aacatatcca gtcactatgg    600
cggccgccac gttaagggat tttggtcatg atcagcacgt gttgacaatt aatcatcggc    660
atagtatatc ggcatagtat aatacgacaa ggtgaggaac taaaccatgg ccaagttgac    720
cagtgccgtt ccggtgctca ccgcgcgcga cgtcgccgga gcggtcgagt tctggaccga    780
ccggctcggg ttctcccggg acttcgtgga ggacgacttc gccggtgtgg tccggacga    840 cgtgaccctg ttcatcagcg cggtccagga ccaggtggtg ccggacaaca ccctggcctg    900
ggtgtgggtg cgcggcctgg acgagctgta cgccgagtgg tcggaggtcg tgtccacgaa    960
cttccgggac gcctccggc cggccatgac cgagatcggc gagcagccgt ggggcgggga    1020
gttcgccctg cgcgacccgg ccggcaactg cgtgcacttc gtggccgagg agcaggactg    1080
atcatgatga tattatttta tcttgtgcaa tgtaacatca gagattttga gacacgggcc    1140
agagctgcca ggaaacagct atgaccatgt aatacgactc actatagggg atatcagctg    1200
gatggcaaat aatgatttta ttttgactga tagtgacctg ttcgttgcaa caccggtgct    1260
agcgtatacc cgaagtatgt caaaaagagg tgtgctatga gcagcgtat tacagtgaca    1320 gttgacagcg acagctatca gttgctcaag gcatatatga tgtcaatatc tccggtctgg    1380
taagcacaac catgcagaat gaagcccgtc gtctgcgtgc cgaacgctgg aaagcggaaa    1440
atcaggaagg gatggctgag gtcgcccggt ttattgaaat gaacggctct tttgctgacg    1500
agaacaggga ctggtgaaat gcagtttaag gtttacacct ataaaagaga gagccgttat    1560
cgtctgtttg tggatgtaca gagtgatatt attgacacgc ccgggcgacg gatggtgatc    1620
cccctgccca gtgcacgtct gctgtcagat aaagtctccc gtgaacttta cccggtggtg    1680
catatcgggg atgaaagctg gcgcatgatg accaccgata tggccagtgt gccggtctcc    1740
```

```
gttatcgggg aagaagtggc tgatctcagc cgccgcgaaa atgacatcaa aaacgccatt    1800
aacctgatgt tctggggaat ataaatgtca ggctccctta tacacagcca gtctgcaggt    1860
cgaccatagt gactggatat gttgtgtttt acagtattat gtagtctgtt ttttatgcaa    1920
aatctaattt aatatattga tatttatatc attttacgtt tctcgttcag ctttcttgta    1980
caaagtggtg ataattaatt aagatcagat ccggctgcta agcttgcggc cgcataatgc    2040
ttaagtcgaa cagaaagtaa tcgtattgta cacggccgca taatcgaaat taatacgact    2100
cactataggg gaattgtgag cggataacaa ttccccatct tagtatatta gttaagtata    2160
agaaggagat atacatatgg cagatctcaa ttggatatcg gccggccacg cgatcgctga    2220
cgtcggtacc ctcgagtctg gtaaagaaac cgctgctgcg aaatttgaac gccagcacat    2280
ggactcgtct actagcgcag cttaattaac ctaggctgct gccaccgctg agcaataact    2340
agcataaccc cttggggcct ctaaacgggt cttgaggggt tttttgctga aacctcaggc    2400
atttgagaag cacacggtca cactgcttcc ggtagtcaat aaaccggtaa accagcaata    2460
gacataagcg gctatttaac gaccctgccc tgaaccgacg acaagctgac gaccgggtct    2520
ccgcaagtgg cacttttcgg ggaaatgtgc gcggaacccc tatttgttta ttttttctaaa    2580 tacattcaaa tatgtatccg ctcatgaatt aattcttaga aaactcatc gagcatcaaa    2640 tgaaactgca atttattcat atcaggatta tcaataccat attttgaaa aagccgtttc    2700 tgtaatgaag gagaaaactc accgaggcag ttccatagga tggcaagatc ctggtatcgg    2760
tctgcgattc cgactcgtcc aacatcaata caacctatta atttccctc gtcaaaaata    2820 aggttatcaa gtgagaaatc accatgagtg acgactgaat ccggtgagaa tggcaaaagt    2880
ttatgcattt ctttccagac ttgttcaaca ggccagccat tacgctcgtc atcaaaatca    2940
ctcgcatcaa ccaaaccgtt attcattcgt gattgcgcct gagcgagacg aaatacgcgg    3000
tcgctgttaa aaggacaatt acaaacagga atcgaatgca accggcgcag gaacactgcc    3060
agcgcatcaa caatattttc acctgaatca ggatattctt ctaatacctg gaatgctgtt    3120
ttcccgggga tcgcagtggt gagtaaccat gcatcatcag gagtacggat aaaatgcttg    3180
atggtcggaa gaggcataaa ttccgtcagc cagtttagtc tgaccatctc atctgtaaca    3240
tcattggcaa cgctaccttt gccatgtttc agaaacaact ctggcgcatc gggcttccca    3300
tacaatcgat agattgtcgc acctgattgc ccgacattat cgcgagccca tttataccca    3360
tataaatcag catccatgtt ggaatttaat cgcggcctag agcaagacgt ttcccgttga    3420
atatggctca tactcttcct tttcaatat tattgaagca tttatcaggg ttattgtctc    3480
atgagcggat acatatttga atgtatttag aaaaataaac aaataggcat gcagcgctct    3540
tccgcttcct cgctcactga ctcgctacgc tcggtcgttc gactgcggcg agcggtgtca    3600
gctcactcaa aagcggtaat acggttatcc acagaatcag gggataaagc cggaaagaac    3660
atgtgagcaa aaagcaaagc accggaagaa gccaacgccg caggcgtttt tccataggct    3720
ccgcccccct gacgagcatc acaaaaatcg acgctcaagc cagaggtggc gaaacccgac    3780
aggactataa agataccagg cgtttccccc tggaagctcc ctcgtgcgct ctcctgttcc    3840
gaccctgccg cttaccggat acctgtccgc ctttctccct cgggaagcg tggcgctttc    3900 tcatagctca cgctgttggt atctcagttc ggtgtaggtc gttcgctcca agctgggctg    3960
tgtgcacgaa ccccccgttc agcccgaccg ctgcgcctta tccggtaact atcgtcttga    4020
gtccaacccg gtaagacacg acttatcgcc actggcagca gccattggta actgatttag    4080
```

| | |
|---|---|
| aggactttgt cttgaagtta tgcacctgtt aaggctaaac tgaaagaaca gattttggtg | 4140 |
| agtgcggtcc tccaacccac ttaccttggt tcaaagagtt ggtagctcag cgaaccttga | 4200 |
| gaaaaccacc gttggtagcg gtggttttc tttatttatg agatgatgaa tcaatcggtc | 4260 |
| tatcaagtca acgaacagct attccgttac tctagatttc agtgcaattt atctcttcaa | 4320 |
| atgtagcacc tgaagtcagc cccatacgat ataagttgta attctcatgt tagtcatgcc | 4380 |
| ccgcgcccac cggaaggagc tgactgggtt gaaggctctc aagggcatcg gtcgagatcc | 4440 |
| cggtgcctaa tgagtgagct aacttacatt aattgcgttg cgctcactgc ccgctttcca | 4500 |
| gtcgggaaac ctgtcgtgcc agctgcatta atgaatcggc caacgcgcgg ggagaggcgg | 4560 |
| tttgcgtatt gggcgccagg gtggtttttc ttttcaccag tgagacgggc aacagctgat | 4620 |
| tgcccttcac cgcctggccc tgagagagtt gcagcaagcg gtccacgctg gtttgcccca | 4680 |
| gcaggcgaaa atcctgtttg atggtggtta acggcgggat ataacatgag ctgtcttcgg | 4740 |
| tatcgtcgta tcccactacc gagatgtccg caccaacgcg cagcccggac tcggtaatgg | 4800 |
| cgcgcattgc gcccagcgcc atctgatcgt tggcaaccag catcgcagtg gaacgatgc | 4860 |
| cctcattcag catttgcatg gtttgttgaa aaccggacat ggcactccag tcgccttccc | 4920 |
| gttccgctat cggctgaatt tgattgcgag tgagatattt atgccagcca gcagacgca | 4980 |
| gacgcgccga gacagaactt aatgggcccg ctaacagcgc gatttgctgg tgacccaatg | 5040 |
| cgaccagatg ctccacgccc agtcgcgtac cgtcttcatg ggagaaaata atactgttga | 5100 |
| tgggtgtctg gtcagagaca tcaagaaata acgccgaac attagtgcag gcagcttcca | 5160 |
| cagcaatggc atcctggtca tccagcggat agttaatgat cagcccactg acgcgttgcg | 5220 |
| cgagaagatt gtgcaccgcc gctttacagg cttcgacgcc gcttcgttct accatcgaca | 5280 |
| ccaccacgct ggcacccagt tgatcggcgc gagatttaat cgccgcgaca atttgcgacg | 5340 |
| gcgcgtgcag ggccagactg gaggtggcaa cgccaatcag caacgactgt ttgcccgcca | 5400 |
| gttgttgtgc cacgcggttg ggaatgtaat tcagctccgc catcgccgct tccactttt | 5460 |
| cccgcgtttt cgcagaaacg tggctggcct ggttcaccac gcgggaaacg gtctgataag | 5520 |
| agacaccggc atactctgcg acatcgtata acgttactgg tttcacattc accaccctga | 5580 |
| attgactctc ttccgggcgc tatcatgcca taccgcgaaa ggttttgcgc cattcgatgg | 5640 |
| tgtccgggat ctcgacgctc tcccttatgc gact | 5674 |

<210> SEQ ID NO 20
<211> LENGTH: 5853
<212> TYPE: DNA
<213> ORGANISM: Artificial Sequence
<220> FEATURE:
<223> OTHER INFORMATION: Description of Artificial Sequence: Synthetic vector nucleotide sequence

<400> SEQUENCE: 20

| | |
|---|---|
| cctgcattag gaagcagccc agtagtaggt tgaggccgtt gagcaccgcc gccgcaagga | 60 |
| atggtgcatg caaggagatg cgcccaaca gtccccccggc cacggggcct gccaccatac | 120 |
| ccacgccgaa acaagcgctc atgagcccga agtggcgagc ccgatcttcc ccatcggtga | 180 |
| tgtcggcgat ataggcgcca gcaaccgcac ctgtggcgcc ggtgatgccg gccacgatgc | 240 |
| gtccggcgta gaggatcgag atctcgatcc cgcgaaatta atacgactca ctatagggga | 300 |
| attgtgagcg gataacaatt cccctctaga aataattttg tttaacttta agaaggagat | 360 |
| atacatatga aatacctgct gccgaccgct gctgctggtc tgctgctcct cgctgcccag | 420 |

-continued

```
ccggcgatgg ccatggatat cggaattaat tcggatccga attcgagctc gatcacaagt    480
ttgtacaaaa aagctgaacg agaaacgtaa aatgatataa atatcaatat attaaattag    540
attttgcata aaaaacagac tacataatac tgtaaaacac aacatatcca gtcactatgg    600
cggccgccac gttaagggat tttggtcatg atcagcacgt gttgacaatt aatcatcggc    660
atagtatatc ggcatagtat aatacgacaa ggtgaggaac taaaccatgg ccaagttgac    720
cagtgccgtt ccggtgctca ccgcgcgcga cgtcgccgga gcggtcgagt tctggaccga    780
ccggctcggg ttctcccggg acttcgtgga ggacgacttc gccggtgtgg tccgggacga    840
cgtgaccctg ttcatcagcg cggtccagga ccaggtggtg ccgacaaca ccctggcctg    900 ggtgtgggtg cgcggcctgg acgagctgta cgccgagtgg tcggaggtcg tgtccacgaa    960
cttccgggac gcctccgggc cggccatgac cgagatcggc gagcagccgt ggggcgggga    1020
gttcgccctg cgcgacccgg ccggcaactg cgtgcacttc gtggccgagg agcaggactg    1080
atcatgatga tattatttta tcttgtgcaa tgtaacatca gagattttga dacacgggcc    1140
agagctgcca ggaaacagct atgaccatgt aatacgactc actatagggg atatcagctg    1200
gatggcaaat aatgatttta ttttgactga tagtgacctg ttcgttgcaa caccggtgct    1260
agcgtatacc cgaagtatgt caaaaagagg tgtgctatga agcagcgtat tacagtgaca    1320
gttgacagcg acagctatca gttgctcaag gcatatatga tgtcaatatc tccggtctgg    1380
taagcacaac catgcagaat gaagcccgtc gtctgcgtgc cgaacgctgg aaagcggaaa    1440
atcaggaagg gatggctgag gtcgcccggt ttattgaaat gaacggctct tttgctgacg    1500
agaacaggga ctggtgaaat gcagtttaag gtttacacct ataaagaga gagccgttat    1560 cgtctgtttg tggatgtaca gagtgatatt attgacacgc ccgggcgacg datggtgatc    1620
cccctggcca gtgcacgtct gctgtcagat aaagtctccc gtgaacttta cccggtggtg    1680
catatcgggg atgaaagctg gcgcatgatg accaccgata tggccagtgt gccggtctcc    1740
gttatcgggg aagaagtggc tgatctcagc cgccgcgaaa atgacatcaa aaacgccatt    1800
aacctgatgt tctggggaat ataaatgtca ggctccctta tacacagcca gtctgcaggt    1860
cgaccatagt gactggatat gttgtgtttt acagtattat gtagtctgtt ttttatgcaa    1920
aatctaattt aatatattga tatttatatc attttacgtt tctcgttcag ctttcttgta    1980
caaagtggtg ataattaatt aagatcagat ccggctgcta agcttgcggc cgcataatgc    2040
ttaagtcgaa cagaaagtaa tcgtattgta cacggccgca taatcgaaat taatacgact    2100
cactataggg gaattgtgag cggataacaa ttccccatct tagtatatta gttaagtata    2160
agaaggagat atacatatgg cagatctcaa ttggatatcg gccggccacg cgatcgctga    2220
cgtcggtacc ctcgagtctg gtaaagaaac cgctgctgcg aaatttgaac gccagcacat    2280
ggactcgtct actagcgcag cttaattaac ctaggctgct gccaccgctg agcaataact    2340
agcataaccc cttggggcct ctaaacgggt cttgaggggt tttttgctga aacctcaggc    2400
atttgagaag cacacggtca cactgcttcc ggtagtcaat aaaccggtaa accagcaata    2460
gacataagcg gctatttaac gaccctgccc tgaaccgacg accgggtcga atttgctttc    2520
gaatttctgc cattcatccg cttattatca cttattcagg cgtagcacca ggcgtttaag    2580
ggcaccaata actgccttaa aaaaattacg ccccgccctg ccactcatcg cagtactgtt    2640
gtaattcatt aagcattctg ccgacatgga agccatcaca gacggcatga tgaacctgaa    2700
tcgccagcgg catcagcacc ttgtcgcctt gcgtataata tttgcccata gtgaaaacgg    2760
gggcgaagaa gttgtccata ttggccacgt ttaaatcaaa actggtgaaa ctcacccagg    2820
```

```
gattggctga gacgaaaaac atattctcaa taaacccttt agggaaatag gccaggtttt    2880
caccgtaaca cgccacatct tgcgaatata tgtgtagaaa ctgccggaaa tcgtcgtggt    2940
attcactcca gagcgatgaa aacgtttcag tttgctcatg gaaaacggtg taacaagggt    3000
gaacactatc ccatatcacc agctcaccgt ctttcattgc catacggaac tccggatgag    3060
cattcatcag gcgggcaaga atgtgaataa aggccggata aaacttgtgc ttattttct     3120 ttacggtctt taaaaaggcc gtaatatcca gctgaacggt ctggttatag gtacattgag    3180
caactgactg aaatgcctca aaatgttctt tacgatgcca tgggatata tcaacggtgg     3240 tatatccagt gatttttttc tccattttag cttccttagc tcctgaaaat ctcgataact    3300
caaaaaatac gcccggtagt gatcttattt cattatggtg aaagttggaa cctcttacgt    3360
gccgatcaac gtctcatttt cgccaaaagt tggcccaggg cttcccggta tcaacaggga    3420
caccaggatt tatttattct gcgaagtgat cttccgtcac aggtatttat tcggcgcaaa    3480
gtgcgtcggg tgatgctgcc aacttactga tttagtgtat gatggtgttt ttgaggtgct    3540
ccagtggctt ctgtttctat cagctgtccc tcctgttcag ctactgacgg ggtggtgcgt    3600
aacggcaaaa gcaccgccgg acatcagcgc tagcggagtg tatactggct tactatgttg    3660
gcactgatga gggtgtcagt gaagtgcttc atgtggcagg agaaaaaagg ctgcaccggt    3720
gcgtcagcag aatatgtgat acaggatata ttccgcttcc tcgctcactg actcgctacg    3780
ctcggtcgtt cgactgcggc gagcggaaat ggcttacgaa cggggcggag atttcctgga    3840
agatgccagg aagatactta acaggaagt gagagggccg cggcaaagcc gttttccat     3900 aggctccgcc cccctgacaa gcatcacgaa atctgacgct caaatcagtg gtggcgaaac    3960
ccgacaggac tataaagata ccaggcgttt cccctggcgg ctccctcgtg cgctctcctg    4020
ttcctgcctt tcggtttacc ggtgtcattc cgctgttatg gccgcgtttg tctcattcca    4080
cgcctgacac tcagttccgg gtaggcagtt cgctccaagc tggactgtat gcacgaaccc    4140
cccgttcagt ccgaccgctg cgccttatcc ggtaactatc gtcttgagtc caacccggaa    4200
agacatgcaa aagcaccact ggcagcagcc actggtaatt gatttagagg agttagtctt    4260
gaagtcatgc gccggttaag gctaaactga aaggacaagt tttggtgact gcgctcctcc    4320
aagccagtta cctcggttca aagagttggt agctcagaga accttcgaaa aaccgccctg    4380
caaggcggtt ttttcgtttt cagagcaaga gattacgcgc agaccaaaac gatctcaaga    4440
agatcatctt attaatcaga taaaatattt ctagatttca gtgcaattta tctcttcaaa    4500
tgtagcacct gaagtcagcc ccatacgata taagttgtaa ttctcatgtt agtcatgccc    4560
cgcgcccacc ggaaggagct gactgggttg aaggctctca agggcatcgg tcgagatccc    4620
ggtgcctaat gagtgagcta acttacatta attgcgttgc gctcactgcc cgctttccag    4680
tcggaaaacc tgtcgtgcca gctgcattaa tgaatcggcc aacgcgcggg gagaggcggt    4740
ttgcgtattg ggcgccaggg tggttttctt tttcaccagt gagacgggca acagctgatt    4800
gcccttcacc gcctggccct gagagagttg cagcaagcgg tccacgctgg tttgccccag    4860
caggcgaaaa tcctgtttga tggtggttaa cggcgggata acatgagc tgtcttcggt      4920 atcgtcgtat cccactaccg agatgtccgc accaacgcgc agcccggact cggtaatggc    4980
gcgcattgcg cccagcgcca tctgatcgtt ggcaaccagc atcgcagtgg gaacgatgcc    5040
ctcattcagc atttgcatgg tttgttgaaa accggacatg gcactccagt cgccttcccg    5100
ttccgctatc ggctgaattt gattgcgagt gagatattta tgccagccag ccagacgcag    5160
```

```
acgcgccgag acagaactta atgggcccgc taacagcgcg atttgctggt gacccaatgc    5220
gaccagatgc tccacgccca gtcgcgtacc gtcttcatgg gagaaaataa tactgttgat    5280
gggtgtctgg tcagagacat caagaaataa cgccggaaca ttagtgcagg cagcttccac    5340
agcaatggca tcctggtcat ccagcggata gttaatgatc agcccactga cgcgttgcgc    5400
gagaagattg tgcaccgccg ctttacaggc ttcgacgccg cttcgttcta ccatcgacac    5460
caccacgctg gcacccagtt gatcggcgcg agatttaatc gccgcgacaa tttgcgacgg    5520
cgcgtgcagg gccagactgg aggtggcaac gccaatcagc aacgactgtt tgcccgccag    5580
ttgttgtgcc acgcgttgg gaatgtaatt cagctccgcc atcgccgctt ccactttttc    5640
ccgcgttttc gcagaaacgt ggctggcctg gttcaccacg cgggaaacgg tctgataaga    5700
gacaccggca tactctgcga catcgtataa cgttactggt ttcacattca ccaccctgaa    5760
ttgactctct tccgggcgct atcatgccat accgcgaaag gttttgcgcc attcgatggt    5820
gtccgggatc tcgacgctct cccttatgcg act                                 5853
```

<210> SEQ ID NO 21
<211> LENGTH: 6998
<212> TYPE: DNA
<213> ORGANISM: Artificial Sequence
<220> FEATURE:
<223> OTHER INFORMATION: Description of Artificial Sequence: Synthetic
vector nucleotide sequence

<400> SEQUENCE: 21

```
cctgcattag gaagcagccc agtagtaggt tgaggccgtt gagcaccgcc gccgcaagga      60
atggtgcatg caaggagatg gcgcccaaca gtccccggc cacggggcct gccaccatac     120
ccacgccgaa acaagcgctc atgagcccga agtggcgagc ccgatcttcc ccatcggtga    180
tgtcggcgat ataggcgcca gcaaccgcac ctgtggcgcc ggtgatgccg gccacgatgc    240
gtccggcgta gaggatcgag atctcgatcc cgcgaaatta atacgactca ctatagggga    300
attgtgagcg gataacaatt cccctctaga ataattttgt ttaactttaa gaaggagat    360 atacatatga aatacctgct gccgaccgct gctgctggtc tgctgctcct cgctgcccag    420
ccggcgatgg ccatggatat cggaattaat tcggatccga attcgagctc gatcacaagt    480
ttgtacaaaa aagctgaacg agaaacgtaa atgatataa atatcaatat attaaattag    540
attttgcata aaaaacagac tacataatac tgtaaaacac aacatatcca gtcactatgg    600
cggccgccac gttaagggat tttggtcatg atcagcacgt gttgacaatt aatcatcggc    660
atagtatatc ggcatagtat aatacgacaa ggtgaggaac taaaccatgg ccaagttgac    720
cagtgccgtt ccggtgctca ccgcgcgcga cgtcgccgga gcggtcgagt tctggaccga    780
ccggctcggg ttctcccggg acttcgtgga ggacgacttc gccggtgtgg tccgggacga    840
cgtgaccctg ttcatcagcg cggtccagga ccaggtggtg ccggacaaca ccctggcctg    900
ggtgtgggtg cgcggcctgg acgagctgta cgccgagtgg tcggaggtcg tgtccacgaa    960
cttccgggac gcctccggc cggccatgac cgagatcggc gagcagccgt ggggcggga   1020 gttcgccctg cgcgacccgg ccggcaactg cgtgcacttc gtggccgagg agcaggactg   1080
atcatgatga tattatttta tcttgtgcaa tgtaacatca gagattttga dacacgggcc   1140
agagctgcca ggaaacagct atgaccatgt aatacgactc actataggg atatcagctg   1200 gatggcaaat aatgatttta ttttgactga tagtgacctg ttcgttgcaa caccggtgct   1260
agcgtatacc cgaagtatgt caaaagagg tgtgctatga agcagcgtat tacagtgaca   1320
```

```
gttgacagcg acagctatca gttgctcaag gcatatatga tgtcaatatc tccggtctgg   1380
taagcacaac catgcagaat gaagcccgtc gtctgcgtgc cgaacgctgg aaagcggaaa   1440
atcaggaagg gatggctgag gtcgcccggt ttattgaaat gaacggctct tttgctgacg   1500
agaacaggga ctggtgaaat gcagtttaag gtttacacct ataaagaga gagccgttat    1560 cgtctgtttg tggatgtaca gagtgatatt attgacacgc ccgggcgacg gatggtgatc   1620
cccctggcca gtgcacgtct gctgtcagat aaagtctccc gtgaacttta cccggtggtg   1680
catatcgggg atgaaagctg gcgcatgatg accaccgata tggccagtgt gccggtctcc   1740
gttatcgggg aagaagtggc tgatctcagc cgccgcgaaa atgacatcaa aaacgccatt   1800
aacctgatgt tctggggaat ataaatgtca ggctccctta tacacagcca gtctgcaggt   1860
cgaccatagt gactggatat gttgtgtttt acagtattat gtagtctgtt ttttatgcaa   1920
aatctaattt aatatattga tatttatatc attttacgtt tctcgttcag ctttcttgta   1980
caaagtggta ataattaatt aagatcagat ccggctgcta agcttgcggc cgcataatgc   2040
ttaagtcgaa cagaaagtaa tcgtattgta cacggccgca taatcgaaat taatacgact   2100
cactataggg gaattgtgag cggataacaa ttccccatct tagtatatta gttaagtata   2160
agaaggagat atacatatgg cagatctcaa ttggatatcg gccggccacg cgatcgctga   2220
cgtcggtacc ctcgagtctg gtaaagaaac cgctgctgcg aaatttgaac gccagcacat   2280
ggactcgtct actagcgcag cttaattaac ctaggctgct gccaccgctg agcaataact   2340
agcataaccc cttggggcct ctaaacgggt cttgaggggt tttttgctga aggaggaac    2400 tatatccgga ttggcgaatg ggacgcgccc tgtagcggcg cattaagcgc ggcgggtgtg   2460
gtggttacgc gcagcgtgac cgctacactt gccagcgccc tagcgcccgc tcctttcgct   2520
ttcttccctt cctttctcgc cacgttcgcc ggctttcccc gtcaagctct aaatcggggg   2580
ctccctttag ggttccgatt tagtgcttta cggcacctcg accccaaaaa acttgattag   2640
ggtgatggtt cacgtagtgg gccatcgccc tgatagacgg ttttcgccc tttgacgttg    2700 gagtccacgt tctttaatag tggactcttg ttccaaactg gaacaacact caaccctatc   2760
tcggtctatt cttttgattt ataagggatt ttgccgattt cggcctattg gttaaaaaat   2820
gagctgattt aacaaaaatt taacgcgaat tttaacaaaa tattaacgtt tacaatttct   2880
ggcggcacga tggcatgaga ttatcaaaaa ggatcttcac ctagatcctt ttaaattaaa   2940
aatgaagttt taaatcaatc taaagtatat atgagtaaac ttggtctgac agttaccaat   3000
gcttaatcag tgaggcacct atctcagcga tctgtctatt tcgttcatcc atagttgcct   3060
gactccccgt cgtgtagata actacgatac gggagggctt accatctggc cccagtgctg   3120
caatgatacc gcgagaccca cgctcaccgg ctccagattt atcagcaata aaccagccag   3180
ccggaagggc cgagcgcaga agtggtcctg caactttatc cgcctccatc cagtctatta   3240
attgttgccg ggaagctaga gtaagtagtt cgccagttaa tagtttgcgc aacgttgttg   3300
ccattgctac aggcatcgtg gtgtcacgct cgtcgtttgg tatggcttca ttcagctccg   3360
gttcccaacg atcaaggcga gttacatgat cccccatgtt gtgcaaaaaa gcggttagct   3420
ccttcggtcc tccgatcgtt gtcagaagta agttggccgc agtgttatca ctcatggtta   3480
tggcagcact gcataattct cttactgtca tgccatccgt aagatgcttt tctgtgactg   3540
gtgagtactc aaccaagtca ttctgagaat agtgtatgcg gcgaccgagt tgctcttgcc   3600
cggcgtcaat acgggataat accgcgccac atagcagaac tttaaaagtg ctcatcattg   3660
gaaaacgttc ttcggggcga aaactctcaa ggatcttacc gctgttgaga tccagttcga   3720
```

```
tgtaacccac tcgtgcaccc aactgatctt cagcatcttt tactttcacc agcgtttctg   3780
ggtgagcaaa acaggaagg caaaatgccg caaaaaggg aataagggcg acacggaaat    3840
gttgaatact catactcttc cttttcaat catgattgaa gcatttatca gggttattgt    3900
ctcatgagcg gatacatatt tgaatgtatt tagaaaaata aacaaatagg tcatgaccaa   3960
aatcccttaa cgtgagtttt cgttccactg agcgtcagac cccgtagaaa agatcaaagg   4020
atcttcttga gatcctttt ttctgcgcgt aatctgctgc ttgcaaacaa aaaaaccacc   4080
gctaccagcg gtggtttgtt tgccggatca agagctacca actctttttc cgaaggtaac   4140
tggcttcagc agagcgcaga taccaaatac tgtccttcta gtgtagccgt agttaggcca   4200
ccacttcaag aactctgtag caccgcctac atacctcgct ctgctaatcc tgttaccagt   4260
ggctgctgcc agtggcgata gtcgtgtct taccggggttg gactcaagac gatagttacc   4320
ggataaggcg cagcggtcgg gctgaacggg gggttcgtgc acacagccca gcttggagcg   4380
aacgacctac accgaactga gatacctaca gcgtgagcta tgagaaagcg ccacgcttcc   4440
cgaagggaga aaggcggaca ggtatccggt aagcggcagg gtcggaacag gagagcgcac   4500
gagggagctt ccaggggaa acgcctggta tctttatagt cctgtcgggt ttcgccacct   4560
ctgacttgag cgtcgatttt tgtgatgctc gtcagggggg cggagcctat ggaaaaacgc   4620
cagcaacgcg gccttttac ggttcctggc cttttgctgg ccttttgctc acatgttctt   4680
tcctgcgtta tccctgatt ctgtggataa ccgtattacc gcctttgagt gagctgatac   4740
cgctcgccgc agccgaacga ccgagcgcag cgagtcagtg agcgaggaag cggaagagcg   4800
cctgatgcgg tattttctcc ttacgcatct gtgcggtatt tcacaccgca tatatggtgc   4860
actctcagta caatctgctc tgatgccgca tagttaagcc agtatacact ccgctatcgc   4920
tacgtgactg ggtcatggct gcgccccgac acccgccaac acccgctgac gcgccctgac   4980
gggcttgtct gctcccggca tccgcttaca gacaagctgt gaccgtctcc gggagctgca   5040
tgtgtcagag gttttcaccg tcatcaccga aacgcgcgag gcagctgcgg taaagctcat   5100
cagcgtggtc gtgaagcgat tcacagatgt ctgcctgttc atccgcgtcc agctcgttga   5160
gtttctccag aagcgttaat gtctggcttc tgataaagcg ggccatgtta agggcggttt   5220
tttcctgttt ggtcactgat gcctccgtgt aagggggatt tctgttcatg ggggtaatga   5280
taccgatgaa acgagagagg atgctcacga tacgggttac tgatgatgaa catgcccggt   5340
tactggaacg ttgtgagggt aaacaactgg cggtatggat gcggcgggac cagagaaaaa   5400
tcactcaggg tcaatgccag cgcttcgtta atacagatgt aggtgttcca cagggtagcc   5460
agcagcatcc tgcgatgcag atccggaaca taatggtgca gggcgctgac ttccgcgttt   5520
ccagacttta cgaaacacgg aaaccgaaga ccattcatgt tgttgctcag gtcgcagacg   5580
ttttgcagca gcagtcgctt cacgttcgct cgcgtatcgg tgattcattc tgctaaccag   5640
taaggcaacc ccgccagcct agccgggtcc tcaacgacag gagcacgatc atgctagtca   5700
tgccccgcgc ccaccggaag gagctgactg ggttgaaggc tctcaagggc atcggtcgag   5760
atcccggtgc ctaatgagtg agctaactta cattaattgc gttgcgctca ctgcccgctt   5820
tccagtcggg aaacctgtcg tgccagctgc attaatgaat cggccaacgc gcggggagag   5880
gcggtttgcg tattgggcgc cagggtggtt tttcttttca ccagtgagac gggcaacagc   5940
tgattgccct tcaccgcctg gccctgagag agttgcagca agcggtccac gctggtttgc   6000
cccagcaggc gaaaatcctg tttgatggtg gttaacggcg ggatataaca tgagctgtct   6060
```

-continued

| | |
|---|---|
| tcggtatcgt cgtatcccac taccgagatg tccgcaccaa cgcgcagccc ggactcggta | 6120 |
| atggcgcgca ttgcgcccag cgccatctga tcgttggcaa ccagcatcgc agtgggaacg | 6180 |
| atgccctcat tcagcatttg catggtttgt tgaaaaccgg acatggcact ccagtcgcct | 6240 |
| tcccgttccg ctatcggctg aatttgattg cgagtgagat atttatgcca gccagccaga | 6300 |
| cgcagacgcg ccgagacaga acttaatggg cccgctaaca gcgcgatttg ctggtgaccc | 6360 |
| aatgcgacca gatgctccac gcccagtcgc gtaccgtctt catgggagaa ataatactg | 6420 |
| ttgatgggtg tctggtcaga gacatcaaga ataacgccg gaacattagt gcaggcagct | 6480 |
| tccacagcaa tggcatcctg gtcatccagc ggatagttaa tgatcagccc actgacgcgt | 6540 |
| tgcgcgagaa gattgtgcac cgccgcttta caggcttcga cgccgcttcg ttctaccatc | 6600 |
| gacaccacca cgctggcacc cagttgatcg gcgcgagatt taatcgccgc gacaatttgc | 6660 |
| gacggcgcgt gcagggccag actggaggtg gcaacgccaa tcagcaacga ctgtttgccc | 6720 |
| gccagttgtt gtgccacgcg gttgggaatg taattcagct ccgccatcgc cgcttccact | 6780 |
| ttttcccgcg ttttcgcaga aacgtggctg gcctggttca ccacgcggga aacggtctga | 6840 |
| taagagacac cggcatactc tgcgacatcg tataacgtta ctggtttcac attcaccacc | 6900 |
| ctgaattgac tctcttccgg gcgctatcat gccataccgc gaaaggtttt gcgccattcg | 6960 |
| atggtgtccg ggatctcgac gctctccctt atgcgact | 6998 |

<210> SEQ ID NO 22
<211> LENGTH: 7071
<212> TYPE: DNA
<213> ORGANISM: Artificial Sequence
<220> FEATURE:
<223> OTHER INFORMATION: Description of Artificial Sequence: Synthetic
      vector nucleotide sequence

<400> SEQUENCE: 22

| | |
|---|---|
| ggggaattgt gagcggataa caattcccct gtagaaataa ttttgtttaa ctttaataag | 60 |
| gagatatacc atgggcagca gccatcacca tcatcaccac agccaggatc cgaattcgag | 120 |
| ctcggaccat gattacgcca agctatcaac tttgtataga aaagttgaac gagaaacgta | 180 |
| aaatgatata aatatcaata tattaaatta gattttgcat aaaaaacaga ctacataata | 240 |
| ctgtaaaaca caacatatcc agtcactatg gtcgacctgc agactggctg tgtataaggg | 300 |
| agcctgacat ttatattccc cagaacatca ggttaatggc gttttgatg tcatttttcgc | 360 |
| ggtggctgag atcagccact tcttccccga taacggagac cggcacactg gccatatcgg | 420 |
| tggtcatcat gcgccagctt tcatccccga tatgcaccac cgggtaaagt tcacggggga | 480 |
| ctttatctga cagcagacgt gcactggcca ggggatcac catccgtcgc ccgggcgtgt | 540 |
| caataatatc actctgtaca tccacaaaca gacgataacg gctctctctt ttataggtgt | 600 |
| aaaccttaaa ctgcatttca ccagcccctg ttctcgtcgg caaaagagcc gttcatttca | 660 |
| ataaaccggg cgacctcagc catcccttcc tgatttccg ctttccagcg ttcggcacgc | 720 |
| agacgacggg cttcattctg catggttgtg cttaccgaac cggagatatt gacatcatat | 780 |
| atgccttgag caactgatag ctgtcgctgt caactgtcac tgtaatacgc tgcttcatag | 840 |
| catacctctt tttgacatac ttcgggtata catatcagta tatattctta taccgcaaaa | 900 |
| atcagcgcgc aaatacgcat actgttatct ggcttttagt aagccggatc tctctagatta | 960 |
| cgccccgccc tgccactcat cgcagtactg ttgtaattca ttaagcattc tgccgacatg | 1020 |
| gaagccatca caaacggcat gatgaacctg aatcgccagc ggcatcagca ccttgtcgcc | 1080 |

```
ttgcgtataa tatttgccca tggtgaaaac gggggcgaag aagttgtcca tattggccac    1140
gtttaaatca aaactggtga aactcaccca gggattggct gagacgaaaa acatattctc    1200
aataaaccct ttagggaaat aggccaggtt ttcaccgtaa cacgccacat cttgcgaata    1260
tatgtgtaga aactgccgga aatcgtcgtg gtattcactc cagagcgatg aaaacgtttc    1320
agtttgctca tggaaaacgg tgtaacaagg gtgaacacta tcccatatca ccagctcacc    1380
gtctttcatt gccatacgga attccggatg agcattcatc aggcgggcaa gaatgtgaat    1440
aaaggccgga taaaacttgt gcttattttt ctttacggtc tttaaaaagg ccgtaatatc    1500
cagctgaacg gtctggttat aggtacattg agcaactgac tgaaatgcct caaaatgttc    1560
tttacgatgc cattgggata tatcaacggt ggtatatcca gtgattttt tctccatttt     1620 agcttcctta gctcctgaaa atctcgacgg atcctaactc aaaatccaca cattatacga    1680
gccggaagca taaagtgtaa agcctggggg tgcctaatgc ggccgccata gtgactggat    1740
atgttgtgtt ttacagtatt atgtagtctg ttttttatgc aaaatctaat ttaatatatt    1800
gatatttata tcattttacg tttctcgttc aactttatta tacatagttg ataattcact    1860
ggccgtcgtt ttacaacgtc gtgactggga aaaccctggc gttacccaac ttaatcgcct    1920
tgcagcacaa gcttgcggcc gcataatgct taagtcgaac agaaagtaat cgtattgtac    1980
acggccgcat aatcgaaatt aatacgactc actatagggg aattgtgagc ggataacaat    2040
tccccatctt agtatattag ttaagtataa gaaggagata tacatatgga tcacaagttt    2100
gtacaaaaaa gctgaacgag aaacgtaaaa tgatataaat atcaatatat taaattagat    2160
tttgcataaa aaacagacta cataatactg taaaacacaa catatccagt cactatggcg    2220
gccgccacgt taagggattt tggtcatgat cagcacgtgt tgacaattaa tcatcggcat    2280
agtatatcgg catagtataa tacgacaagg tgaggaacta accatggcc aagttgacca    2340 gtgccgttcc ggtgctcacc gcgcgcgacg tcgccggagc ggtcgagttc tggaccgacc    2400
ggctcgggtt ctcccgggac ttcgtggagg acgacttcgc cggtgtggtc cgggacgacg    2460
tgaccctgtt catcagcgcg gtccaggacc aggtggtgcc ggacaacacc ctggcctggg    2520
tgtgggtgcg cggcctggac gagctgtacg ccgagtggtc ggaggtcgtg tccacgaact    2580
tccgggacgc ctccgggccg gccatgacc agatcggcga gcagccgtgg gggcgggagt    2640
tcgccctgcg cgacccggcc ggcaactgcg tgcacttcgt ggccgaggag caggactgat    2700
catgatgata ttattttatc ttgtgcaatg taacatcaga gattttgaga cacgggccag    2760
agctgccagg aaacagctat gaccatgtaa tacgactcac tatagggat atcagctgga    2820 tggcaaataa tgattttatt ttgactgata gtgacctgtt cgttgcaaca ccggtgctag    2880
cgtatacccg aagtatgtca aaagaggtg tgctatgaag cagcgtatta cagtgacagt    2940
tgacagcgac agctatcagt tgctcaaggc atatatgatg tcaatatctc cggtctggta    3000
agcacaacca tgcagaatga agcccgtcgt ctgcgtgccg aacgctggaa agcggaaaat    3060
caggaaggga tggctgaggt cgcccggttt attgaaatga acggctcttt tgctgacgag    3120 aacaggagact ggtgaaatgc agtttaaggt ttacacctat aaaagagaga gccgttatcg    3180
tctgtttgtg gatgtacaga gtgatattat tgacacgccc gggcgacgga tggtgatccc    3240
cctggccagt gcacgtctgc tgtcagataa agtctcccgt gaactttacc cggtggtgca    3300
tatcggggat gaaagctggc gcatgatgac caccgatatg ccagtgtgc cggtctccgt     3360 tatcggggaa gaagtggctg atctcagccg ccgcgaaaat gacatcaaaa acgccattaa    3420
cctgatgttc tggggaatat aaatgtcagg ctcccttata cacagccagt ctgcaggtcg    3480
```

```
accatagtga ctggatatgt tgtgttttac agtattatgt agtctgtttt ttatgcaaaa    3540
tctaatttaa tatattgata tttatatcat tttacgtttc tcgttcagct ttcttgtaca    3600
aagtggtgat aattaattaa gatcagatcc ggctgctggt accctcgagt ctggtaaaga    3660
aaccgctgct gcgaaatttg aacgccagca catggactcg tctactagcg cagcttaatt    3720
aacctaggct gctgccaccg ctgagcaata actagcataa cccccttgggg cctctaaacg    3780
ggtcttgagg ggttttttgc tgaaacctca ggcatttgag aagcacacgg tcacactgct    3840
tccggtagtc aataaaccgg taaaccagca atagacataa gcggctattt aacgaccctg    3900
ccctgaaccg acgaccgggt catcgtggcc ggatcttgcg gcccctcggc ttgaacgaat    3960
tgttagacat tatttgccga ctaccttggt gatctcgcct ttcacgtagt ggacaaattc    4020
ttccaactga tctgcgcgcg aggccaagcg atcttcttct tgtccaagat aagcctgtct    4080
agcttcaagt atgacgggct gatactgggc cggcaggcgc tccattgccc agtcggcagc    4140
gacatccttc ggcgcgattt tgccggttac tgcgctgtac caaatgcggg acaacgtaag    4200
cactacattt cgctcatcgc cagcccagtc gggcggcgag ttccatagcg ttaaggtttc    4260
atttagcgcc tcaaatagat cctgttcagg aaccggatca aagagttcct ccgccgctgg    4320
acctaccaag gcaacgctat gttctcttgc ttttgtcagc aagatagcca gatcaatgtc    4380
gatcgtggct ggctcgaaga tacctgcaag aatgtcattg cgctgccatt ctccaaattg    4440
cagttcgcgc ttagctggat aacgccacgg aatgatgtcg tcgtgcacaa caatggtgac    4500
ttctacagcg cggagaatct cgctctctcc aggggaagcc gaagtttcca aaaggtcgtt    4560
gatcaaagct cgccgcgttg tttcatcaag ccttacggtc accgtaacca gcaaatcaat    4620
atcactgtgt ggcttcaggc cgccatccac tgcggagccg tacaaatgta cggccagcaa    4680
cgtcggttcg agatggcgct cgatgacgcc aactacctct gatagttgag tcgatacttc    4740
ggcgatcacc gcttccctca tactcttcct ttttcaatat tattgaagca tttatcaggg    4800
ttattgtctc atgagcggat acatatttga atgtatttag aaaaataaac aaatagctag    4860
ctcactcggt cgctacgctc cgggcgtgag actgcgcgg gcgctgcgga cacatacaaa    4920
gttacccaca gattccgtgg ataagcaggg gactaacatg tgaggcaaaa cagcagggcc    4980
gcgccggtgg cgttttttcca taggctccgc cctcctgcca gagttcacat aaacagacgc    5040
ttttccggtg catctgtggg agccgtgagg ctcaaccatg aatctgacag tacgggcgaa    5100
acccgacagg acttaaagat ccccaccgtt tccggcgggt cgctccctct tgcgctctcc    5160
tgttccgacc ctgccgttta ccggatacct gttccgcctt tctcccttac gggaagtgtg    5220
gcgctttctc atagctcaca cactggtatc tcggctcggt gtaggtcgtt cgctccaagc    5280
tgggctgtaa gcaagaactc cccgttcagc ccgactgctg cgccttatcc ggtaactgtt    5340
cacttgagtc caacccggaa aagcacggta aaacgccact ggcagcagcc attggtaact    5400
gggagttcgc agaggatttg tttagctaaa cacgcggttg ctcttgaagt gtgcgccaaa    5460
gtccggctac actggaagga cagatttggt tgctgtgctc tgcgaaagcc agttaccacg    5520
gttaagcagt tccccaactg acttaacctt cgatcaaacc acctcccag gtggttttt    5580
cgtttacagg gcaaaagatt acgcgcagaa aaaaggatc tcaagaagat cctttgatct    5640
tttctactga accgctctag atttcagtgc aatttatctc ttcaaatgta gcacctgaag    5700
tcagccccat acgatataag ttgtaattct catgttagtc atgccccgcg cccaccggaa    5760
ggagctgact gggttgaagg ctctcaaggg catcggtcga gatcccggtg cctaatgagt    5820
```

| | |
|---|---|
| gagctaactt acattaattg cgttgcgctc actgcccgct ttccagtcgg gaaacctgtc | 5880 |
| gtgccagctg cattaatgaa tcggccaacg cgcggggaga ggcggtttgc gtattgggcg | 5940 |
| ccagggtggt ttttctttc accagtgaga cgggcaacag ctgattgccc ttcaccgcct | 6000 |
| ggccctgaga gagttgcagc aagcggtcca cgctggtttg ccccagcagg cgaaaatcct | 6060 |
| gtttgatggt ggttaacggc gggatataac atgagctgtc ttcggtatcg tcgtatccca | 6120 |
| ctaccgagat gtccgcacca acgcgcagcc cggactcggt aatggcgcgc attgcgccca | 6180 |
| gcgccatctg atcgttggca accagcatcg cagtgggaac gatgccctca ttcagcattt | 6240 |
| gcatggtttg ttgaaaaccg gacatggcac tccagtcgcc ttcccgttcc gctatcggct | 6300 |
| gaatttgatt gcgagtgaga tatttatgcc agccagccag acgcagacgc gccgagacag | 6360 |
| aacttaatgg gcccgctaac agcgcgattt gctggtgacc caatgcgacc agatgctcca | 6420 |
| cgcccagtcg cgtaccgtct tcatgggaga aaataatact gttgatgggt gtctggtcag | 6480 |
| agacatcaag aaataacgcc ggaacattag tgcaggcagc ttccacagca atggcatcct | 6540 |
| ggtcatccag cggatagtta atgatcagcc cactgacgcg ttgcgcgaga agattgtgca | 6600 |
| ccgccgcttt acaggcttcg acgccgcttc gttctaccat cgacaccacc acgctggcac | 6660 |
| ccagttgatc ggcgcgagat ttaatcgccg cgacaatttg cgacggcgcg tgcagggcca | 6720 |
| gactggaggt ggcaacgcca atcagcaacg actgtttgcc cgccagttgt tgtgccacgc | 6780 |
| ggttgggaat gtaattcagc tccgccatcg ccgcttccac tttttcccgc gttttcgcag | 6840 |
| aaacgtggct ggcctggttc accacgcggg aaacggtctg ataagagaca ccggcatact | 6900 |
| ctgcgacatc gtataacgtt actggtttca cattcaccac cctgaattga ctctcttccg | 6960 |
| ggcgctatca tgccataccg cgaaaggttt tgcgccattc gatggtgtcc gggatctcga | 7020 |
| cgctctccct tatgcgactc ctgcattagg aaattaatac gactcactat a | 7071 |

<210> SEQ ID NO 23
<211> LENGTH: 8490
<212> TYPE: DNA
<213> ORGANISM: Artificial Sequence
<220> FEATURE:
<223> OTHER INFORMATION: Description of Artificial Sequence: Synthetic
    vector nucleotide sequence

<400> SEQUENCE: 23

| | |
|---|---|
| ggggaattgt gagcggataa caattcccct gtagaaataa ttttgtttaa ctttaataag | 60 |
| gagatatacc atgggcagca gccatcacca tcatcaccac agccaggatc cgaattcgag | 120 |
| ctcggaccat gattacgcca agctatcaac tttgtataga aagttgaac gagaaacgta | 180 |
| aaatgatata aatatcaata tattaaatta gattttgcat aaaaaacaga ctacataata | 240 |
| ctgtaaaaca caacatatcc agtcactatg gtcgacctgc agactggctg tgtataaggg | 300 |
| agcctgacat ttatattccc cagaacatca ggttaatggc gttttgatg tcattttcgc | 360 |
| ggtggctgag atcagccact tcttccccga taacggagac cggcacactg gccatatcgg | 420 |
| tggtcatcat cgccagctt tcatcccga tatgcaccac cgggtaaagt tcacggggga | 480 |
| ctttatctga cagcagacgt gcactggcca gggggatcac catccgtcgc ccgggcgtgt | 540 |
| caataatatc actctgtaca tccacaaaca gacgataacg ctctctctt ttataggtgt | 600 |
| aaaccttaaa ctgcatttca ccagcccctg ttctcgtcgg caaagagcc gttcatttca | 660 |
| ataaaccggg cgacctcagc catcccttcc tgattttccg ctttccagcg ttcggcacgc | 720 |
| agacgacggg cttcattctg catggttgtg cttaccgaac cggagatatt gacatcatat | 780 |

```
atgccttgag caactgatag ctgtcgctgt caactgtcac tgtaatacgc tgcttcatag   840
catacctctt tttgacatac ttcgggtata catatcagta tatattctta taccgcaaaa   900
atcagcgcgc aaatacgcat actgttatct ggcttttagt aagccggatc ctctagatta   960
gcatgcctac aggaacaggt ggtggcggcc ctcggtgcgc tcgtactgct ccacgatggt  1020
gtagtcctcg ttgtgggagg tgatgtccag cttggcgtcc acgtagtagt agccgggcag  1080
ctgcacgggc ttcttggcca tgtagatgga cttgaactcc accaggtagt ggccgccgtc  1140
cttcagcttc agggccttgt gggtctcgcc cttcagcacg ccgtcgcggg ggtacaggcg  1200
ctcggtggag gcctcccagc ccatggtctt cttctgcatc acggggccgt cggaggggaa  1260
gttcacgccg atgaacttca ccttgtagat gaagcagccg tcctgcaggg aggagtcctg  1320
ggtcacggtc gccacgccgc cgtcctcgaa gttcatcacg cgctcccact gaagccctc   1380 ggggaaggac agcttcttgt agtcggggat gtcggcgggg tgcttcacgt acaccttgga  1440
gccgtactgg aactgggggg acaggatgtc ccaggcgaag ggcaggggggc cgcccttggt  1500 caccttcagc ttcacggtgt tgtggccctc gtaggggcgg ccctcgccct cgccctcgat  1560
ctcgaactcg tggccgttca cggtgccctc catgcgcacc ttgaagcgca tgaactcggt  1620
gatgacgttc tcggaggagg ccatactagt cgccccgccc tgccactcat cgcagtactg  1680
ttgtaattca ttaagcattc tgccgacatg gaagccatca caaacggcat gatgaacctg  1740
aatcgccagc ggcatcagca ccttgtcgcc ttgcgtataa tatttgccca tggtgaaaac  1800
gggggcgaag aagttgtcca tattggccac gtttaaatca aaactggtga aactcaccca  1860
gggattggct gagacgaaaa acatattctc aataaaccct ttagggaaat aggccaggtt  1920
ttcaccgtaa cacgccacat cttgcgaata tatgtgtaga aactgccgga atcgtcgtg   1980 gtattcactc cagagcgatg aaaacgtttc agtttgctca tggaaaacgg tgtaacaagg  2040
gtgaacacta tcccatatca ccagctcacc gtctttcatt gccatacgga attccggatg  2100
agcattcatc aggcgggcaa gaatgtgaat aaaggccgga taaaacttgt gcttattttt  2160
ctttacggtc tttaaaaagg ccgtaatatc cagctgaacg gtctggttat aggtacattg  2220
agcaactgac tgaaatgcct caaaatgttc tttacgatgc cattgggata tatcaacggt  2280
ggtatatcca gtgattttt tctccatttt agcttcctta gctcctgaaa atctcgacgg  2340
atcctaactc aaaatccaca cattatacga gccggaagca taaagtgtaa agcctggggg  2400
tgcctaatgc ggccgccata gtgactggat atgttgtgtt ttacagtatt atgtagtctg  2460
ttttttatgc aaaatctaat ttaatatatt gatatttata tcattttacg tttctcgttc  2520
aactttatta tacatagttg ataattcact ggccgtcgtt ttacaacgtc gtgactggga  2580
aaaccctggc gttaccccaac ttaatcgcct tgcagcacaa gcttgcggcc gcataatgct  2640
taagtcgaac agaaagtaat cgtattgtac acggccgcat aatcgaaatt aatacgactc  2700
actatagggg aattgtgagc ggataacaat tccccatctt agtatattag ttaagtataa  2760
gaaggagata tacatatgga tcacaagttt gtacaaaaaa gctgaacgag aaacgtaaaa  2820
tgatataaat atcaatatat taattagat tttgcataaa aaacagacta cataatactg  2880
taaaacacaa catatccagt cactatggcg gccgcacgt taagggattt tggtcatgat  2940
cagcacgtgt tgacaattaa tcatcggcat agtatatcgg catagtataa tacgacaagg  3000
tgaggaacta aaccatggcc aagttgacca gtgccgttcc ggtgctcacc gcgcgcgacg  3060
tcgccggagc ggtcgagttc tggaccgacc ggctcgggtt ctcccgggac ttcgtggagg  3120
acgacttcgc cggtgtggtc cgggacgacg tgaccctgtt catcagcgcg gtccaggacc  3180
```

```
aggtggtgcc ggacaacacc ctggcctggg tgtgggtgcg cggcctggac gagctgtacg    3240
ccgagtggtc ggaggtcgtg tccacgaact tccgggacgc ctccgggccg ccatgaccg     3300 agatcggcga gcagccgtgg gggcgggagt tcgccctgcg cgacccggcc ggcaactgcg    3360
tgcacttcgt ggccgaggag caggacacta gtatgagtaa aggagaagaa cttttcactg    3420
gagttgtccc aattcttgtt gaattagatg gtgatgttaa tgggcacaaa ttttctgtca    3480
gtggagaggg tgaaggtgat gcaacatacg gaaaacttac ccttaaattt atttgcacta    3540
ctggaaaact acctgttcca tggccaacac ttgtcactac tttctcttat ggtgttcaat    3600
gcttttcccg ttatccggat catatgaaac ggcatgactt tttcaagagt gccatgcccg    3660
aaggttatgt acaggaacgc actatatctt caaagatga cgggaactac aagacgcgtg    3720
ctgaagtcaa gtttgaaggt gatacccttg ttaatcgtat cgagttaaaa ggtattgatt    3780
ttaaagaaga tggaaacatt ctcggacaca aactcgagta caactataac tcacacaatg    3840
tatacatcac ggcagacaaa caaaagaatg gaatcaaagc taacttcaaa attcgccaca    3900
acattgaaga tggatccgtt caactagcag accattatca acaaaatact ccaattggcg    3960
atggccctgt ccttttacca gacaaccatt acctgtcgac acaatctgcc ctttcgaaag    4020
atcccaacga aaagcgtgac cacatggtcc ttcttgagtt tgtaactgct gctgggatta    4080
cacatggcat ggatgagctc tacaaataag catgctgatc atgatgatat tattttatct    4140
tgtgcaatgt aacatcagag attttgagac acgggccaga gctgccagga aacagctatg    4200
accatgtaat acgactcact ataggggata tcagctggat ggcaaataat gattttattt    4260
tgactgatag tgacctgttc gttgcaacac cggtgctagc gtatacccga agtatgtcaa    4320
aaagaggtgt gctatgaagc agcgtattac agtgacagtt gacagcgaca gctatcagtt    4380
gctcaaggca tatatgatgt caatatctcc ggtctggtaa gcacaaccat gcagaatgaa    4440
gcccgtcgtc tgcgtgccga acgctggaaa gcggaaaatc aggaagggat ggctgaggtc    4500
gcccggttta ttgaaatgaa cggctctttt gctgacgaga acagggactg gtgaaatgca    4560
gtttaaggtt tacacctata aaagagagag ccgttatcgt ctgtttgtgg atgtacagag    4620
tgatattatt gacacgcccg gcgacggat ggtgatcccc ctggccagtg cacgtctgct    4680
gtcagataaa gtctcccgtg aactttaccc ggtggtgcat atcggggatg aaagctggcg    4740
catgatgacc accgatatgg ccagtgtgcc ggtctccgtt atcggggaag aagtggctga    4800
tctcagccgc cgcgaaaatg acatcaaaaa cgccattaac ctgatgttct ggggaatata    4860
aatgtcaggc tcccttatac acagccagtc tgcaggtcga ccatagtgac tggatatgtt    4920
gtgttttaca gtattatgta gtctgttttt tatgcaaaat ctaatttaat atattgatat    4980
ttatatcatt ttacgtttct cgttcagctt tcttgtacaa agtggtgata attaattaag    5040
atcagatccg gctgctggta ccctcgagtc tggtaaagaa accgctgctg cgaaatttga    5100
acgccagcac atggactcgt ctactagcgc agcttaatta acctaggctg ctgccaccgc    5160
tgagcaataa ctagcataac cccttggggc ctctaaacgg gtcttgaggg gttttttgct    5220
gaaacctcag gcatttgaga agcacacggt cacactgctt ccggtagtca ataaaccggt    5280
aaaccagcaa tagacataag cggctattta acgaccctgc cctgaaccga cgaccgggtc    5340
atcgtggccg gatcttgcgg cccctcggct tgaacgaatt gttagacatt atttgccgac    5400
taccttggtg atctcgcctt tcacgtagtg gacaaattct tccaactgat ctgcgcgcga    5460
ggccaagcga tcttcttctt gtccaagata agcctgtcta gcttcaagta tgacgggctg    5520
```

```
atactgggcc ggcaggcgct ccattgccca gtcggcagcg acatccttcg gcgcgatttt   5580
gccggttact gcgctgtacc aaatgcggga caacgtaagc actacatttc gctcatcgcc   5640
agcccagtcg ggcggcgagt tccatagcgt taaggtttca tttagcgcct caaatagatc   5700
ctgttcagga accggatcaa agagttcctc cgccgctgga cctaccaagg caacgctatg   5760
ttctcttgct tttgtcagca agatagccag atcaatgtcg atcgtggctg gctcgaagat   5820
acctgcaaga atgtcattgc gctgccattc tccaaattgc agttcgcgct tagctggata   5880
acgccacgga atgatgtcgt cgtgcacaac aatggtgact tctacagcgc ggagaatctc   5940
gctctctcca ggggaagccg aagtttccaa aaggtcgttg atcaaagctc gccgcgttgt   6000
ttcatcaagc cttacggtca ccgtaaccag caaatcaata tcactgtgtg gcttcaggcc   6060
gccatccact gcggagccgt acaaatgtac ggccagcaac gtcggttcga gatggcgctc   6120
gatgacgcca actacctctg atagttgagt cgatacttcg gcgatcaccg cttccctcat   6180
actcttcctt tttcaatatt attgaagcat ttatcagggt tattgtctca tgagcggata   6240
catatttgaa tgtatttaga aaaataaaca aatagctagc tcactcggtc gctacgctcc   6300
gggcgtgaga ctgcggcggg cgctgcggac acatacaaag ttacccacag attccgtgga   6360
taagcagggg actaacatgt gaggcaaaac agcagggccg cgccggtggc gttttttccat  6420
aggctccgcc ctcctgccag agttcacata aacagacgct tttccggtgc atctgtggga   6480
gccgtgaggc tcaaccatga atctgacagt acgggcgaaa cccgacagga cttaaagatc   6540
cccaccgttt ccggcgggtc gctccctctt gcgctctcct gttccgaccc tgccgtttac   6600
cggatacctg ttccgccttt ctcccttacg ggaagtgtgg cgctttctca tagctcacac   6660
actggtatct cggctcggtg taggtcgttc gctccaagct gggctgtaag caagaactcc   6720
ccgttcagcc cgactgctgc gccttatccg gtaactgttc acttgagtcc aacccggaaa   6780
agcacggtaa aacgccactg gcagcagcca ttggtaactg ggagttcgca gaggatttgt   6840
ttagctaaac acgcggttgc tcttgaagtg tgcgccaaag tccggctaca ctggaaggac   6900
agatttggtt gctgtgctct gcgaaagcca gttaccacgg ttaagcagtt ccccaactga   6960
cttaaccttc gatcaaacca cctccccagg tggttttttc gtttacaggg caaaagatta   7020
cgcgcagaaa aaaaggatct caagaagatc ctttgatctt ttctactgaa ccgctctaga   7080
tttcagtgca atttatctct tcaaatgtag cacctgaagt cagccccata cgatataagt   7140
tgtaattctc atgttagtca tgccccgcgc ccaccggaag gagctgactg ggttgaaggc   7200
tctcaagggc atcggtcgag atcccggtgc ctaatgagtg agctaactta cattaattgc   7260
gttgcgctca ctgcccgctt tccagtcggg aaacctgtcg tgccagctgc attaatgaat   7320
cggccaacgc gcgggagag gcggtttgcg tattgggcgc caggtggtt tttcttttca    7380
ccagtgagac gggcaacagc tgattgccct tcaccgcctg gccctgagag agttgcagca   7440
agcggtccac gctggtttgc cccagcaggc gaaaatcctg tttgatggtg ttaacggcg    7500
ggatataaca tgagctgtct tcggtatcgt cgtatcccac taccgagatg tccgcaccaa   7560
cgcgcagccc ggactcggta atggcgcgca ttgcgcccag cgccatctga tcgttggcaa   7620
ccagcatcgc agtgggaacg atgccctcat tcagcatttg catggtttgt tgaaaaccgg   7680
acatggcact ccagtcgcct tcccgttccg ctatcggctg aatttgattg cgagtgagat   7740
atttatgcca gccagcagca gcagacgcg ccgagacaga acttaatggg cccgctaaca    7800
gcgcgatttg ctggtgaccc aatgcgacca gatgctccac gcccagtcgc gtaccgtctt   7860
catgggagaa aataatactg ttgatgggtg tctggtcaga gacatcaaga ataacgccg    7920
```

-continued

```
gaacattagt gcaggcagct tccacagcaa tggcatcctg gtcatccagc ggatagttaa    7980
tgatcagccc actgacgcgt tgcgcgagaa gattgtgcac cgccgcttta caggcttcga    8040
cgccgcttcg ttctaccatc gacaccacca cgctggcacc cagttgatcg gcgcgagatt    8100
taatcgccgc gacaatttgc gacggcgcgt gcagggccag actggaggtg caacgccaa     8160 tcagcaacga ctgtttgccc gccagttgtt gtgccacgcg gttgggaatg taattcagct    8220
ccgccatcgc cgcttccact ttttcccgcg ttttcgcaga aacgtggctg gcctggttca    8280
ccacgcggga acggtctga taagagacac cggcatactc tgcgacatcg tataacgtta    8340
ctggtttcac attcaccacc ctgaattgac tctcttccgg gcgctatcat gccataccgc    8400
gaaaggtttt gcgccattcg atggtgtccg ggatctcgac gctctccctt atgcgactcc    8460
tgcattagga aattaatacg actcactata                                    8490
```

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtttcttgcg gccgccacgt taagggattt tggtca                              36

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtttcttacc ggtgttgcaa cgaacaggtc act                                 33

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtttcttgag ctcgatcaca agtttgtaca aaaaagc                             37

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtttcttaag cttagcagcc ggatctgatc tta                                 33

<210> SEQ ID NO 28
<211> LENGTH: 25
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 28

Met Arg Ser Gly Ser His His His His His His Arg Ser Asp Ile Thr
1               5                   10                  15

Ser Leu Tyr Lys Lys Ala Glu Arg Glu
            20                  25

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Ala His His His His His His Val Gly Thr Gly Ser Asn Asp Asp
1               5                   10                  15

Asp Asp Lys Ser Thr Ser Leu Tyr Lys Lys Ala Glu Arg Glu
            20                  25                  30

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtttcttgcg gccgcttctc atgtttgaca gcttatcat                            39

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtttctttct agagacgcga tggatatgtt ctg                                  33

<210> SEQ ID NO 32
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctaggtaata cgactcacta taggaattgt gagcggataa caattcca                  48

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agcttggaat tgttatccgc tcacaattcc tatagtgagt cgtattac                  48
```

<210> SEQ ID NO 34
<211> LENGTH: 120
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cttacaagtt tgtacaaaaa agcaggctta cttcaggtag tgatgatcta tcaaacaaat      60
tatatgatca attttcagaa aaagtcagca aaagtttggt gaaggtggtg gagagctgca    120

<210> SEQ ID NO 35
<211> LENGTH: 120
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cttaccactt tgtacaagaa agctgggtgg gacggttgag acaaactgga gatggcatag      60
cgtattttac tacttcgagg tattcatctt gcagctctcc accaccttca cccaaacttt    120

<210> SEQ ID NO 36
<211> LENGTH: 120
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cttacaagtt tgtacaaaaa agcaggctta tggttctccg gccttcacac ggaattcctt      60
tccatccaaa tccaaatcga acttcggagc ctcatgcatt ggcttagcag tagcagccgc    120

<210> SEQ ID NO 37
<211> LENGTH: 119
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cttaccactt tgtacaagaa agctgggtgt atgaataccg tgtcgttgcc gtcaacaaag      60
ctgggccagg acaaccatca gattcgtctg cggctgctac tgctaagcca atgcatgag     119

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other

<400> SEQUENCE: 38 gacnnnngtc                                                            10

```
<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gacaagagtc                                                            10

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gacaaatcaa c                                                          11

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gttgatgagt c                                                          11

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gacaagagct c                                                          11

<210> SEQ ID NO 43
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aagcttgagt c                                                          11

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 44

His His His His His His
 1               5
```

```
<210> SEQ ID NO 45
<211> LENGTH: 124
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 45

Met Ala Lys Leu Thr Ser Ala Val Pro Val Leu Thr Ala Arg Asp Val
 1               5                  10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
            115                 120
```

VECTORS AND METHODS FOR HIGH THROUGHPUT CO-EXPRESSION

CONTINUING APPLICATION DATA

This application claims the benefit of U.S. Provisional Application Ser. No. 60/642,309, filed Jan. 7, 2005, U.S. Provisional Application Ser. No. 60/642,310, filed Jan. 7, 2005, and U.S. Provisional Application Ser. No. 60/756,028, titled "Vectors," filed Jan. 4, 2006, each of which is incorporated by reference herein.

GOVERNMENT FUNDING

The present invention was made with government support under Grant No. NIH GM062407, awarded by the National Institutes of Health. The Government has certain rights in this invention.

BACKGROUND

With the completion of the sequencing of the human genomes and genomes of other organisms including, for example, the genomes of a wide and rapidly expanding number of prokaryotes, yeast, rice, rat, and dog, increasing attention has focused on the characterization and function of proteins, the products of genes. See, for example, Celestino et al., Gen Mol. Res. 3:421-431, 2004; Nature 436:793-800, 2005; Toh et al., Nature 438:803-819, 2005; Collins et al., Nature 422:835-847, 2003; and Cherry et al., Nature 387(6632 Suppl):67-73, 1997. The availability of sequence data and the growing impact of structural biology on biomedical research have prompted international efforts to determine protein structures on a large scale. Structural genomics (also referred to as "SG") is a worldwide initiative aimed at determining a large number of protein structures in a high throughput mode (see, for example, Rost, Structure 6:259-63, 1998; and Stevens et al., Science 294:89-92, 2001). One such effort is the National Institutes of Health's Protein Structure Initiative, a large-scale, high-throughput (also referred to as "HTP") effort to determine the three-dimensional atomic-level structures of a broad range of protein. These structures will be made widely available for clinical and basic studies that will expand the knowledge of the role of proteins both in normal biological processes and in disease. Initiatives, such as the Protein Structure Initiative, focus on an important aspect of proteins: the three-dimensional structures of proteins. While gene sequencing projects identify and arrange all the nucleotide bases in an organism's genetic material, efforts such as the Protein Structure Initiative will harness this genetic information to help identify and group into "families" all the natural shapes that proteins can form. To examine a protein's role in health and disease, and to explore ways to control its action, researchers seek to decipher the protein's shape, or structure. This structure reveals the physical, chemical and electrical properties of the protein and provides clues about its role in the body. See, for example, Norvell and Machalek, Nat Struct Biol 7 Suppl:931, 2000; the worldwide web at nigms.nih.gov/psi/ and rcsb.org/pdb/strucgen.html#Worldwide; and "From Genes to Proteins: NIGMS Catalogs the Shapes of Life," NIH Record, February 2001.

In structural genomics-type high-throughput projects, thousands of genes must be inserted into expression vectors and it has become clear that protein expression and protein purification are limiting steps and a major expense. Traditional technologies of manipulating genes are too cumbersome and inefficient when one is dealing with more than a few genes at a time. See, for example, Rual et al., Curr Opin Chem Biol. 8(1):20-5, 2004.

While success rates for gene cloning are close to one hundred percent, only about twenty percent of targeted genes are successfully expressed and purified and an accurate crystal structure is obtained for only a fraction of those polypeptides that are expressed and purified. See, for example, Adams et al., Acc Chem Res 36:191-8, 2003; Brenner, Nat Struct Biol 7 Suppl:967-9, 2000; Brenner and Levitt, Protein Sci 9:197-200, 2000; Burley, Nat Struct Biol 7 Suppl:932-4, 2000; Chance et al., Biophysical Journal 82:454a-454a, 2002; Chayen, J Struct Funct Genomics 4:115-20, 2003; Lesley et al., Proc Natl Acad Sci USA 99:11664-9, 2002; and Christendat et al., Nat Struct Biol 7:903-9, 2000. Traditional technologies of manipulating genes are too cumbersome and inefficient when one is dealing with more than a few genes at a time. See, for example, Rual et al., Curr Opin Chem Biol. 8(1):20-5, 2004.

Current methodologies for determining protein structures are difficult and time-consuming. Thus, there is a need for products and methods that allow for the determination of protein structures in a low-cost and high-throughput manner.

SUMMARY OF THE INVENTION

The present invention includes expression vectors having a nucleotide sequence operably encoding a ccdB polypeptide flanked by att recombination recognition sequences, wherein the selectable marker for selection of the expression vector within a host cell is not ampicillin resistance.

In another aspect, the invention includes host cells having one or more expression vectors having a nucleotide sequence operably encoding a ccdB polypeptide flanked by att recombination recognition sequences, wherein the selectable marker for selection of the expression vector within a host cell is not ampicillin resistance.

In another aspect, the invention include methods for the expression of one or more polypeptides, the method including expressing at least one polypeptide by an expression vector having a nucleotide sequence operably encoding a ccdB polypeptide flanked by att recombination recognition sequences, wherein the selectable marker for selection of the expression vector within a host cell is not ampicillin resistance.

In another aspect, the invention includes methods for the co-expression of four or more polypeptides, the method including expressing at least one polypeptide by an expression vector having a nucleotide sequence operably encoding a ccdB polypeptide flanked by att recombination recognition sequences, wherein the selectable marker for selection of the expression vector within a host cell is not ampicillin resistance.

In another aspect, the invention includes methods of improving the solubility of one or more expressed polypeptides, the method including expressing at least one polypeptide by an expression vector having a nucleotide sequence operably encoding a ccdB polypeptide flanked by att recombination recognition sequences, wherein the selectable marker for selection of the expression vector within a host cell is not ampicillin resistance.

In another aspect, the invention includes the expression vector pDEST-C1, pDEST-C2, pDEST-C3, pDEST-CM1, pDEST-CM2, pDEST-CM3, pDEST-CM4, pDEST-CS, pDEST-CS1, pDEST-CS2, pDEST-CS3, pDEST-CS4, pDEST-CMZ1, or pDEST-CMZc1.

In another aspect, the invention includes host cells having one of more expression vectors selected from pDEST-C1, pDEST-C2, pDEST-C3, pDEST-CM1, pDEST-CM2, pDEST-CM3, pDEST-CM4, pDEST-CS, pDEST-CS1, pDEST-CS2, pDEST-CS3, pDEST-CS4, pDEST-CMZ1, and pDEST-CMZc1.

In another aspect, the invention includes polynucleotides having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the polynucleotide includes the G144704 cassette. In some embodiments, the G144704 cassette includes SEQ ID NO: 4, as shown in FIG. 9.

In another aspect, the invention includes expression vectors having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4, as shown in FIG. 9.

In another aspect, the invention includes host cells having an expression vector having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4, as shown in FIG. 9.

In another aspect, the invention includes methods for the expression of one or more polypeptides, the method including expressing at least one polypeptide by an expression vector having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4, as shown in FIG. 9.

In another aspect, the invention includes methods for the co-expression of four or more polypeptides, the method including expressing at least one polypeptide by an expression vector having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4, as shown in FIG. 9.

In another aspect, the invention includes methods of improving the solubility of one or more expressed polypeptides, the method including expressing at least one polypeptide by an expression vector having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4, as shown in FIG. 9.

In another aspect, the invention includes polynucleotides having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes expression vectors including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multi site includes SEQ ID NO: 7 shown in FIG. 21.

In another aspect, the invention includes a host cell including an expression vector including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes methods for the expression of one or more polypeptides, the method including expressing at least one polypeptide by an expression vector including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes methods for the co-expression of four or more polypeptides, the method including expressing at least one polypeptide by an expression vector including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes methods of improving the solubility of one or more expressed polypeptides, the method including expressing at least one polypeptide by an expression vector including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes RNA interference (RNAi) vectors including a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the polynucleotide includes a G144704 cassette. In some embodiments, the G144704 cassette includes SEQ ID NO: 4, as shown in FIG. 9.

In another aspect, the invention includes methods of producing one or more interfering RNA products, the method including expressing at least one interfering RNA product by an expression vector having a polynucleotide having a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide is flanked by attR1 and attR2 sites. In some embodiments, the expression vector includes a polynucleotide including a G144704 cassette. In some embodiments, the G144704 cassette includes SEQ ID NO: 4, as shown in FIG. 9.

In another aspect, the invention includes RNA interference (RNAi) vectors including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes methods of producing one or more interfering RNA products, the method including expressing at least one interfering RNA product by an expression vector including a polynucleotide having a nucleotide sequence operably encoding tetracycline resistance and a nucleotide sequence operably encoding a ccdB polypeptide, wherein the nucleotide sequence operably encoding tetracycline zeomycin resistance and the nucleotide sequence operably encoding a ccdB polypeptide is flanked by attR3 and attR4 sites. In some embodiments, the polynucleotide includes a tet Multisite. In some embodiments, the tet Multisite includes SEQ ID NO: 7 shown in FIG. 21.

In another aspect, the invention includes the RNAi vectors pRIPPER-1, pRIPPER-2, pRIPPER-3, pRIPPER-4, pRIPPER-II, pRIPPER-III, and pRIPPER-IV.

In another aspect, the invention includes methods of producing one or more interfering RNA products, the method including expressing at least one interfering RNA product by an expression vector selected form pRIPPER-1, pRIPPER-2, pRIPPER-3, pRIPPER-4, pRIPPER-II, pRIPPER-III, or pRIPPER-IV.

BRIEF DESCRIPTION OF THE FIGURES

FIG. 3 presents the nucleotide sequence of the pDEST-C1 vector (SEQ ID NO: 1).

FIG. 5 presents the nucleotide sequence of the pDEST-C2 vector (SEQ ID NO: 2).

FIG. 7 presents the nucleotide sequence of the pDEST-C3 vector (SEQ ID NO: 3).

FIG. 8A shows a map of the zeomycin cassette. FIG. 8B shows a map of the Gateway cassette. FIG. 8C shows a map of the G144704 cassette. FIG. 8D is a map of the G144704 cassette, indicating the location of various restriction enzyme sites.

Figure 9:
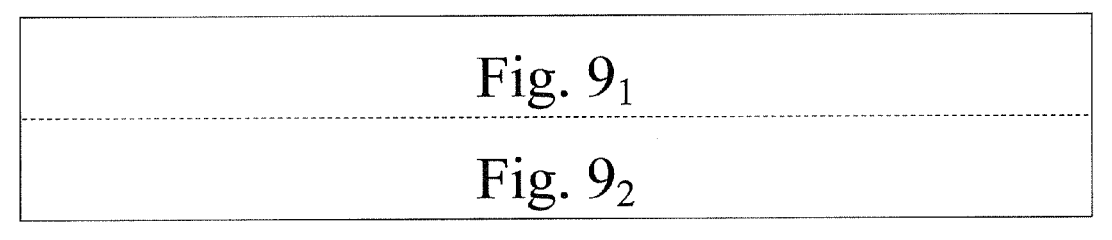

FIG. 9 shows the nucleotide sequence of the G144704 cassette (SEQ ID NO: 4). The nucleotide sequences of the attR1 and attR2 sites are shaded (Encoded protein disclosed as SEQ ID NO: 45).

FIG. 11A is an SDS-PAGE of the total cell extract of the recombinant expression experiments for each Clostrodium thermocellum JW-20 gene construct. The black arrows point to the bands that correspond to the proteins expressed in the cells. FIG. 11B is a chart identifying each of the lanes. Lanes 1 through 12 are cells with two different, randomly selected, genes expressed. Lanes 13-18 are the expression testing of those cells with only one expression construct, to monitor expression of the individual proteins. Lanes 19 and 20 show expression of three non-interacting proteins.

In FIG. 14A, lanes 1 and 8 are the molecular weight markers; lanes 2, 4, and 6 are the three soluble fractions that represent calmodulin hPMCA4b and co-expression of the two, respectively; lanes 3, 5 and 7 are the pellet fractions of the same growths, and lane 6 contains the soluble complex and this growth was further pursued to purification. FIG. 14B is the FPLC 280 nm chromatogram and SDS-PAGE of the indicated fraction in lane 9 showing a complex of the two proteins. Lane 10 is the same marker as lanes 1 and 8 in FIG. 14A.

FIG. 17 presents the nucleotide sequence of the pDEST-CM1 vector (SEQ ID NO: 5).

FIG. 19 presents the nucleotide sequence of the pDEST-CM2 vector (SEQ ID NO: 6).

FIG. 21 is the nucleotide sequence of the Multisite TetR cassette (SEQ ID NO: 7).

FIG. 23 show the nucleotide sequence of the pDEST-CM3 vector (SEQ ID NO: 8).

FIG. 25 presents the nucleotide sequence of the pDEST-CM4 vector (SEQ ID NO: 9).

FIG. 26A is the Gateway® cassette. FIG. 26B is the G144704 cassette. FIG. 26C is a Multisite® cassette.

FIG. 28 is the nucleotide sequence of the pRIPPER-3 vector (SEQ ID NO: 10).

FIG. 30 is the nucleotide sequence of the pRIPPER-1 vector (SEQ ID NO: 11).

FIG. 32 is the nucleotide sequence of the pRIPPER-2 vector (SEQ ID NO: 12).

FIG. 34 is the nucleotide sequence of the pRIPPER-4 vector (SEQ ID NO: 13).

FIG. 36 is the nucleotide sequence of the pRIPPER-II vector (SEQ ID NO: 14).

FIG. 38 is the nucleotide sequence of the pRIPPER-III vector (SEQ ID NO: 15).

FIG. 40 is the nucleotide sequence of the pRIPPER-IV vector (SEQ ID NO: 16).

FIG. 42 is the nucleotide sequence of the pDEST-CS vector (SEQ ID NO: 17).

FIG. 44 is the nucleotide sequence of the pDEST-C1 vector (SEQ ID NO: 18).

FIG. 46 is the nucleotide sequence of the pDEST-CS2 vector (SEQ ID NO: 19).

FIG. 48 is the nucleotide sequence of the pDEST-CS3 vector (SEQ ID NO: 20).

FIG. 50 is the nucleotide sequence of the pDEST-CS4 vector (SEQ ID NO: 21).

FIG. 52 is the nucleotide sequence of the pDEST-CMZ1 vector (SEQ ID NO: 22).

FIG. 54 is the nucleotide sequence of the pDEST-CMZc1 vector (SEQ ID NO: 23).

DETAILED DESCRIPTION OF ILLUSTRATIVE EMBODIMENTS OF THE INVENTION

Figure 1:
FIG. 1 is a schematic presenting the locations of the attR1 site, the attR2 site, the chloramphenical resistance gene, the ccdB gene and Primer 1 and Primer 2 in the Gateway Conversion Cassette for Reading Frame A, Reading Frame B and Reading Frame C.

The polynucleotides, vectors and methods of the present invention provide for the improved high throughput (HTP) expression of polypeptides and for the improved high throughput (HTP) expression of interfering RNAs.

The present invention includes vectors having a nucleotide sequence operably encoding a ccdB polypeptide flanked by att recombination recognition sequences, wherein the selectable marker for selection of the expression vector within a host cell is not resistance to the antibiotic ampicillin. Selectable markers for the expression vector within the host cell include, but are not limited to, kanamycin resistance, chloramphenicol resistance, streptomycin resistance, spectinomycin resistance, zeomycin resistance, carbenicillin resistance, tetracycline resistance, and rifampicin resistance. See, for example, Novagen 2004/2005 catalog and New England Biolabs 2005-06 Catalog. In some aspects, the present invention includes vectors having a nucleotide sequence operably encoding a ccdB polypeptide and operably encoding chloramphenicol resistance, wherein the nucleotide sequence is flanked by att recombination recognition sequences, and wherein the selectable marker for selection of the expression vector within a host cell is not ampicillin resistance. In some aspects of the present invention, the vector is an expression vector.

As used herein, the terms "polynucleotide" and "nucleotide sequence" refer to polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

As used herein, the terms "polypeptide," "peptide," and "protein" are used interchangeably herein to refer to polymers of amino acids of any length.

As used herein, a "vector" is a polynucleotide which transfers an inserted nucleic acid molecule into and/or between host cells. A vector may provide for the insertion of DNA or RNA into a cell, the replication of DNA or RNA, the transcription of the DNA or RNA, the translation of the DNA or RNA, and/or the processing of the translated polypeptide product. A vector may provide for more than one of the above functions. A vector may include an origin of replication, also referred to as an ori sequence or a replicon, which allows for replication of the polynucleotide in an appropriate host cell. See, for example, Novagen 2004/2005 catalog and New England Biolabs 2005-06 Catalog.

As used herein, an "expression vector" is a vector which, when introduced into an appropriate host cell, can be transcribed and translated into a polypeptide(s). An "expression system" usually connotes a suitable host cell comprised of an expression vector that can function to yield a desired expression product. An expression vector may include an origin of replication, which allows for replication of the polynucleotide in an appropriate host cell. Origins of replication include, but are not limited to the ColE1 replicon, the P15A replicon, the CloDF13 replicon, or the the RSD1030 replicon. An expression vector may include a promoter, including, for example, the T7lac promoter, that provides for protein expression in the host cell. See, for example, Novagen 2004/2005 catalog and New England Biolabs 2005-06 Catalog.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectively referred to as gene product.

The polynucleotides and vectors of the present invention take advantage of Gateway® technology. The Gateway® cloning system is an vitro site-specific recombination technology that takes advantage of the att site-specific recombination properties of bacteriophage lambda (Hartley et al., Genome Res. 10: 1788-1795, 2000; (Landy, Annu Rev Biochem 58:913-49, 1989; Sasaki et al., J. Biotechnol. 107, 233-243, 2004; U.S. Pat. Nos. 5,888,732, 6,143,557, 6,171,861, 6,270,969, 6,277,608, and 6,720,140; and the Gateway Technology manual Version E, updated Sep. 22, 2003; available on the worldwide web at invitrogen.con/content/sfs/manuals/gatewayman.pdf) to provide a rapid and efficient way to move a gene of interest between multiple vector systems.

Polynucleotides and vectors of the present invention include one or more att recombination recognition sequences. As used herein, att recombination recognition sequences include, but are not limited to attR1, attR2, attR3, and attR4, the sequences of which are well known, and include, but are not limited to, those described in the examples included herewith and those described in Landy, Annu Rev Biochem 58:913-49, 1989; Sasaki et al., J. Biotechnol. 107, 233-243, 2004; U.S. Pat. Nos. 5,888,732, 6,143,557, 6,171,861, 6,270, 969, 6,277,608, and 6,720,140; and the Gateway Technology manual Version E, updated Sep. 22, 2003; available on the worldwide web at invitrogen.com/content/sfs/manuals/gatewayman.pdf. The two recombination recognition sequences, attR1 and attR2 have been employed in the conventional gateway technology (Hartley et al., Genome Res. 10:1788-1795, 2000; (Landy, Annu Rev Biochem 58:913-49, 1989; Sasaki et al., J. Biotechnol. 107, 233-243, 2004; U.S. Pat. Nos. 5,888,732, 6,143,557, 6,171,861, 6,270,969, 6,277,608, and 6,720,140; and the Gateway Technology manual Version E, updated Sep. 22, 2003; available on the worldwide web at invitrogen.com/content/sfs/manuals/gatewayman.pdf). The recombination recognition sequences, attR3 and attR4, have been recently made available as MultiSite™ Gateway® Three-Fragment Vector Construction Kit from Invitrogen Corp.

Gateway® technology makes gene cloning simpler, more specific and faster than traditional methods of gene cloning based on restriction enzyme digestion and ligation. Gateway® technology allows for the rapid site specific exchange of target DNA between an entry vector (containing the initial clone of the target gene) and multiple expression vectors, via recombination. In order to allow for this versatility, the Gateway® system is characterized by a DNA sequence called the Gateway® cassette. This DNA sequence contains two recombination sites attR1 and attR2 along with genes that encode chloramphenicol resistance and the "control of cell death" polypeptide, also referred to herein as ccdB (Bernard et al., J. Mol. Biol. 234, 534-541, 1993). The ccdB polypeptide is lethal to Escherichia coli (Bernard and Couturier, Mol. Gen. Genet. 226:297-304, 1991). Nucleotide sequences encoding the ccdB polypeptide are well known in the art, and include those described in the examples included herewith. A Gateway cassette allows for the selection of recombinants, as only the desired recombinants will form colonies when transformed into E. coli.

In some aspects, polynucleotides and vectors of the present invention may have a Gateway® cassette, wherein a Gateway® cassette is a polynucleotide sequence containing the two recombination sites attR1 and attR2, along with a nucleotide sequence that operably encodes the gene product responsible for chloramphenicol resistance and the nucleotide sequence operably encoding a ccdB polypeptide. The two recombination sites, attR1 and attR2, may flank the nucleotide sequence encoding chloramphenicol resistance and the nucleotide sequence encoding a ccdB polypeptide. As used herein, a nucleotide sequence that "operably encodes" a polypeptide product with a given function includes all of the appropriate sequences necessary to result in the expression of the polypeptide product with the identified function, including, for example, coding sequences and regulatory sequences.

In some aspects, polynucleotides and vectors of the present invention may have a MultiSite™ Gateway® cassette, wherein a MultiSite™ Gateway® cassette is a polynucleotide sequence containing the two recombination sites attR3 and attR4, along with a nucleotide sequence that operably encodes the gene product responsible for chloramphenicol resistance and the nucleotide sequence operably encoding a ccdB polypeptide. The two recombination sites, attR3 and attR4, may flank the nucleotide sequence encoding chloramphenicol resistance and the nucleotide sequence encoding a ccdB polypeptide.

The present invention includes vectors having a nucleotide sequence operably encoding a ccdB polypeptide flanked by att recombination recognition sequences, wherein the selectable marker for selection of the expression vector within a host cell is not ampicillin resistance. Selectable markers for the expression vector within the host cell include, but are not limited to, kanamycin resistance, chloramphenicol resistance, streptomycin resistance, spectinomycin resistance, zeomycin resistance, carbenicillin resistance, tetracycline resistance, and rifampicin resistance. See, for example, Novagen 2004/2005 catalog and New England Biolabs 2005-06 Catalog. Of the more than fifty Gateway® expression vectors currently available, all encode ampicillin resistance, which is not desirable for an expression vector, due to high background problems when grown for over sixteen.

Vectors of the present invention include vectors in which the chloramphenicol resistance (chlR) gene in the Gateway® recombination cassette has been replaced with the Zeocin® resistance gene as a selective marker. Vectors of the present invention include vectors in which the technologies of the Gateway® site-specific recombination system is fused with the capacities of a multiple vector co-expression system, resulting is vectors that can express multiple proteins in a parallel manner in one E. coli strain.

A series of several vectors of the present invention, when compared to one another, may have differing replicons and resistance genes, allowing for the effective propagation, maintenance of the series of vectors in a single host cell.

The vectors of the present invention may be used in concert with any of the many available co-expression vectors, including, for example, the pET family of expression vectors (Novagen, Madison, Wis.). These vectors use a strong phage T7 promoter driven by the presence of lactose or a lactose analog (isopropyl-β-D-galactopyranoside, IPTG) to express the target protein. Other available co-expression vectors include pCDF, pRSF, and pACYC, which are compatible with pET (www.emdbiosciences.com). All four of these have compatible replication origins, and different antibiotic selection markers, so as many as all four can be stably maintained in the same *E. coli* cell. Thus, co-expression of up to four proteins in the same cell became possible. These vectors have been further modified (the pDUET series; see www.emdbiosciences.com) so that each vector contains two multiple cloning site, allowing for expression of up to eight different target genes simultaneously. However, while these vectors are well known, their use is limited due to the necessity of using classical restriction enzymes and ligation for cloning.

The vectors of the present invention combine aspects of co-expression vectors with the power of Gateway® technology. The vectors of the present invention may include one or more of the elements of such co-expression vectors, including, but not limited, one or more elements from a member of the pET family of vectors, the pDUET series of vectors, pCDF, pRSF, and pACYC.

The vectors of the present invention may include one or more additional elements, including, for example, elements encoding various fusion tags, fusion proteins, affinity tags, protease cleavage sites, expression signals, or promoters, including, for example, prokaryotic or eukaryotic promoters. Vectors may include, for example, an N-terminal 6×His tag (SEQ ID NO: 44) and/or an enterokinase cleavage site just before the attR1 recombination site. The vectors of the present invention may include any of the various nucleotide sequences that provide for the expression of native proteins, N- or C-terminally tagged proteins, secreted proteins, or proteins that are targeted to a subcellular location. The vectors of the present invention may include any of the various nucleotide sequences that provide a variety of promoters, poly-A addition signals, and/or elements for transient, stable and bicistronic expression.

The vectors of the present invention may include the appropriate promoters and/or origins of replication that allow for the expression of a polypeptide product in a range of host cells, including, but not limited to, bacterial host cells, including, for example, *E. coli*, yeast, insect cells, and mammalian cells.

Figure 2:
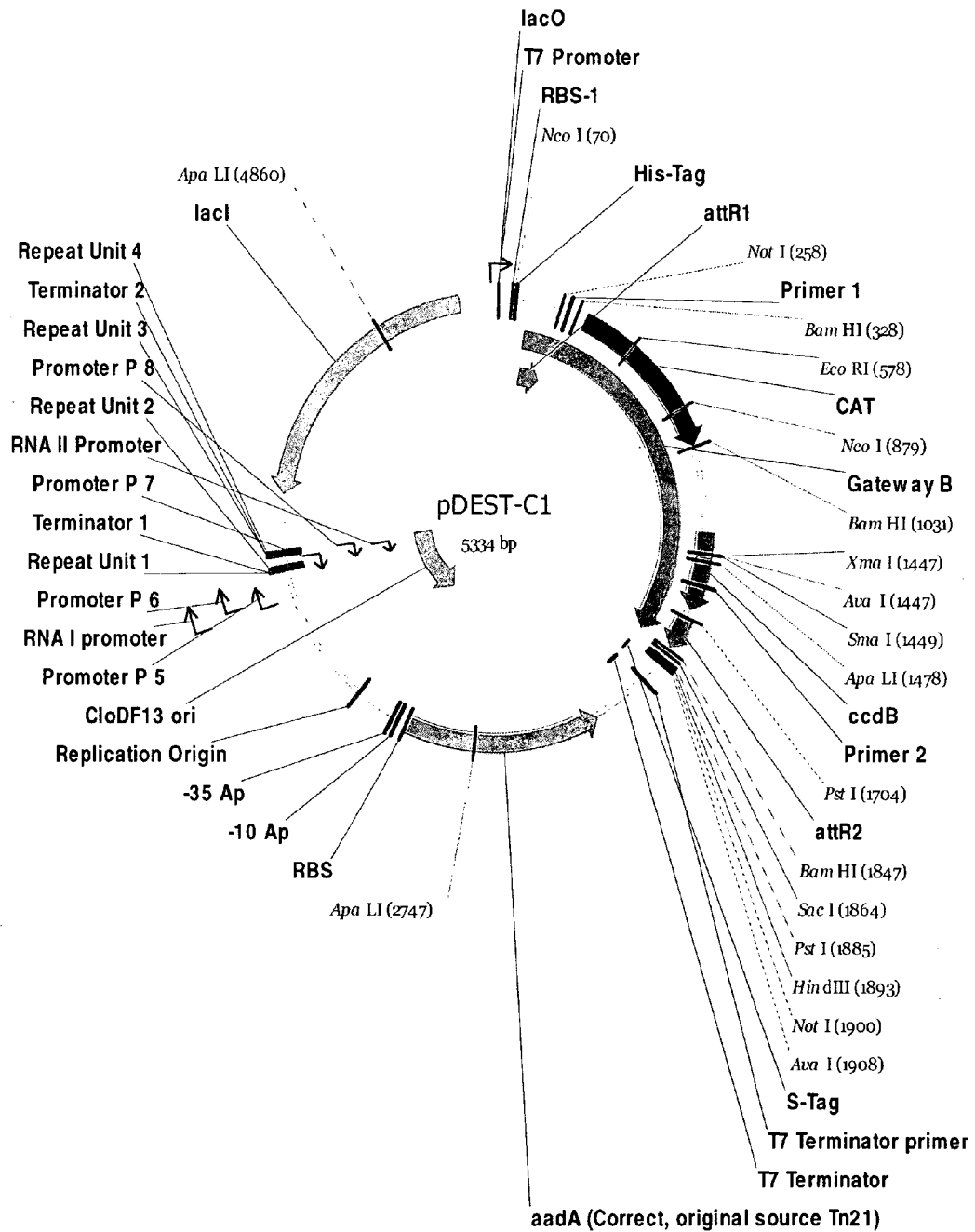
FIG. 2 shows a map of the pDEST-C1 vector.
Figure 3:
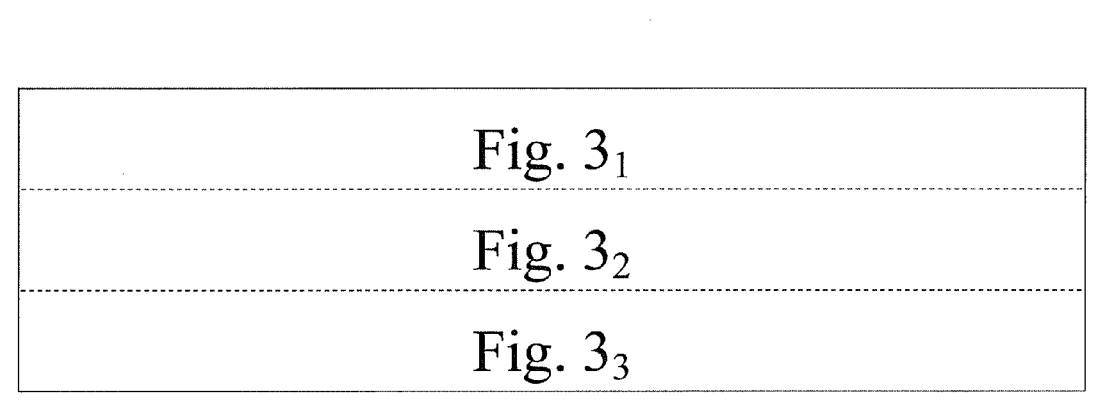

Vectors of the present invention include vectors having one or more of the elements shown in FIG. 2. An example of such a vector is the pDEST-C1 vector, the nucleotide sequence of which is shown in FIG. 3.

Figure 4:
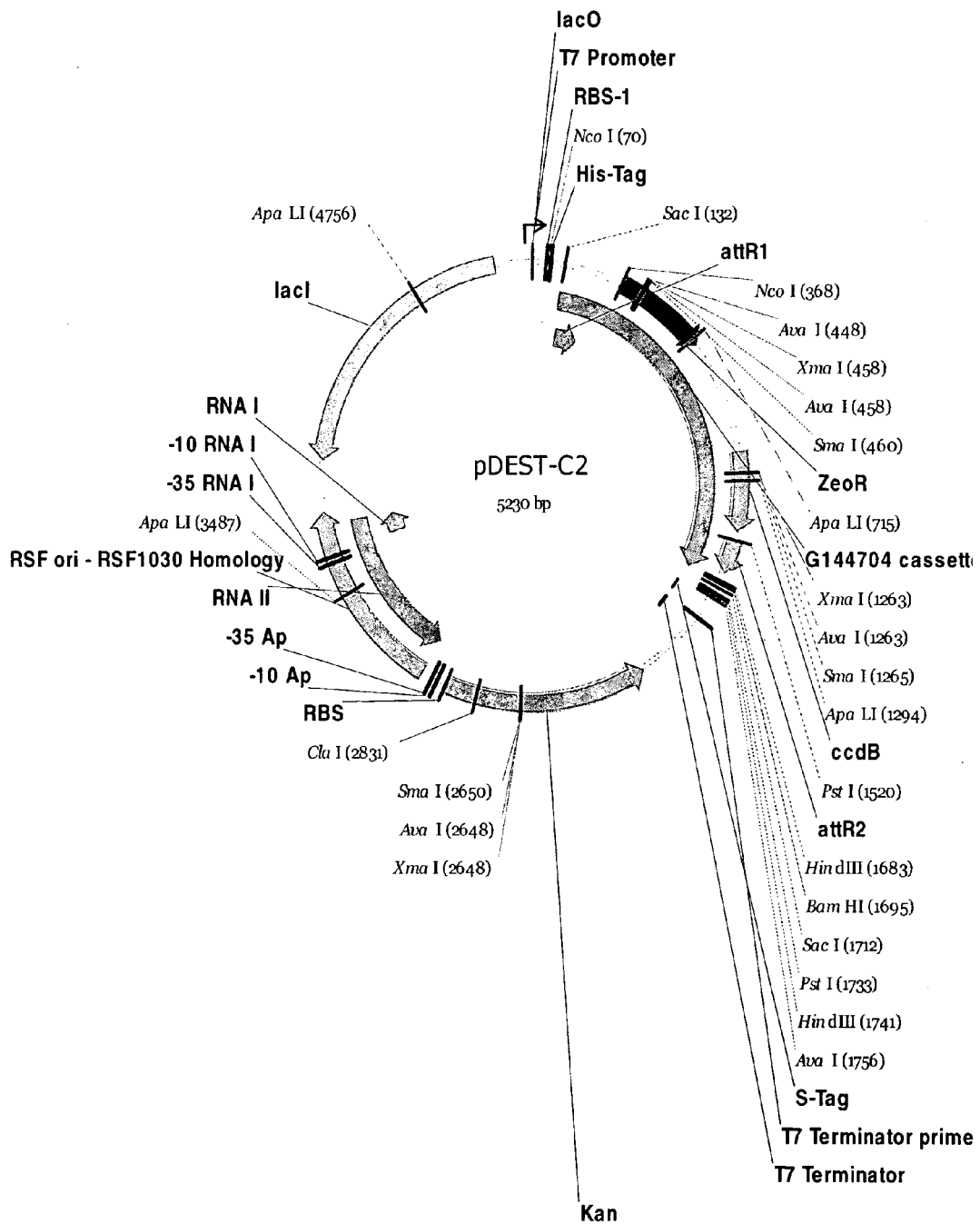
FIG. 4 shows a map of the pDEST-C2 vector.
Figure 5:
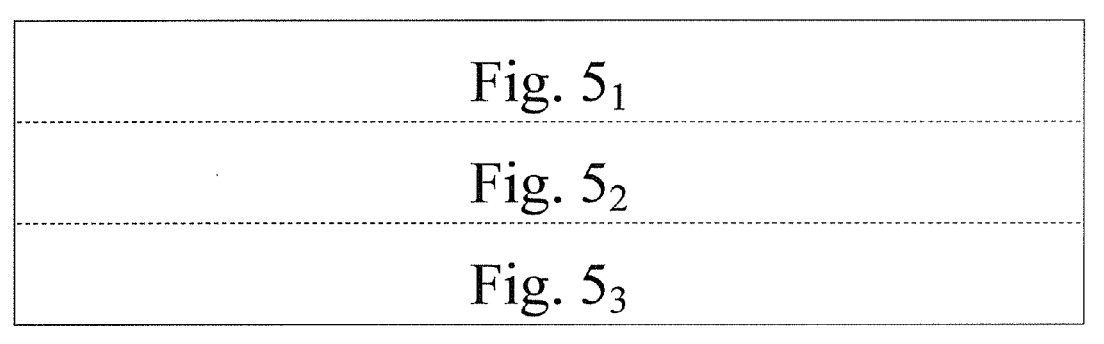

Vectors of the present invention include vectors having one or more of the elements shown in FIG. 4. An example of such a vector is the pDEST-C2 vector, the nucleotide sequence of which is shown in FIG. 5.

Figure 6:
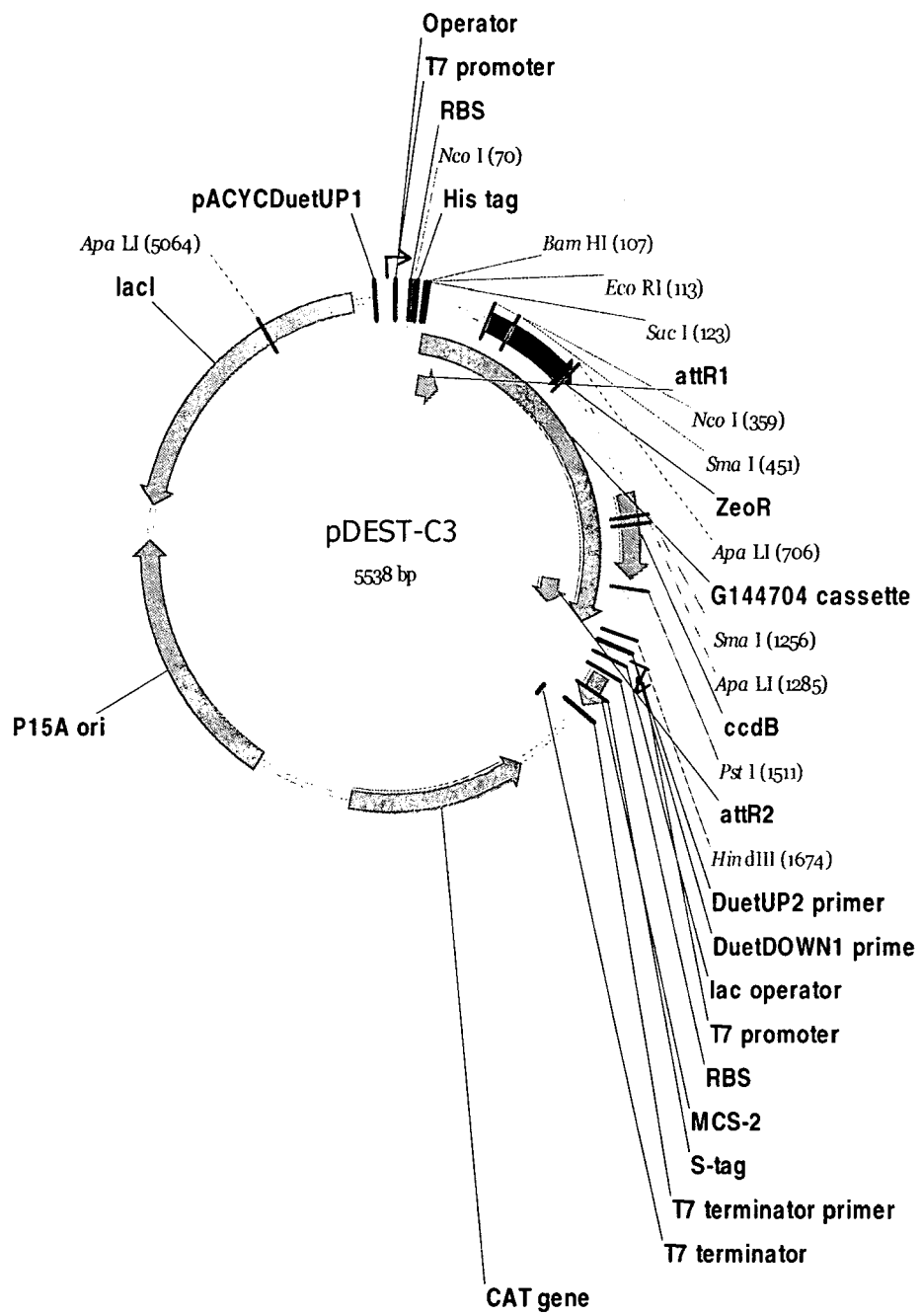
FIG. 6 shows a map of the pDEST-C3 vector.
Figure 7:
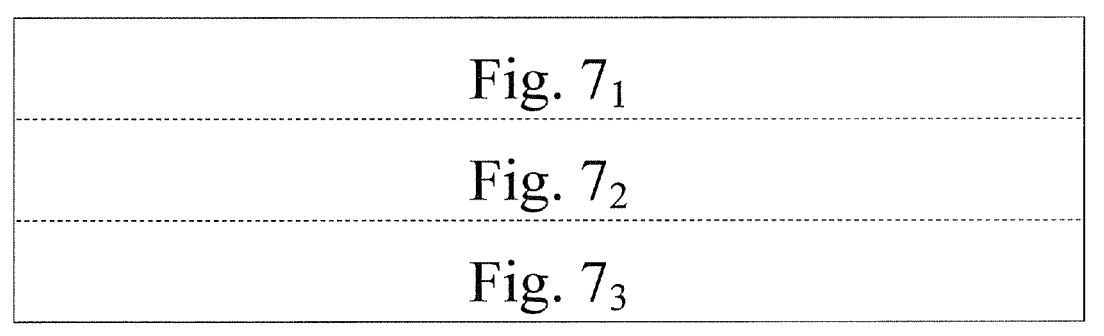

Vectors of the present invention include vectors having one or more of the elements shown in FIG. 6. An example of such a vector is the pDEST-C3 vector, the nucleotide sequence of which is shown in FIG. 7.

Figure 16:
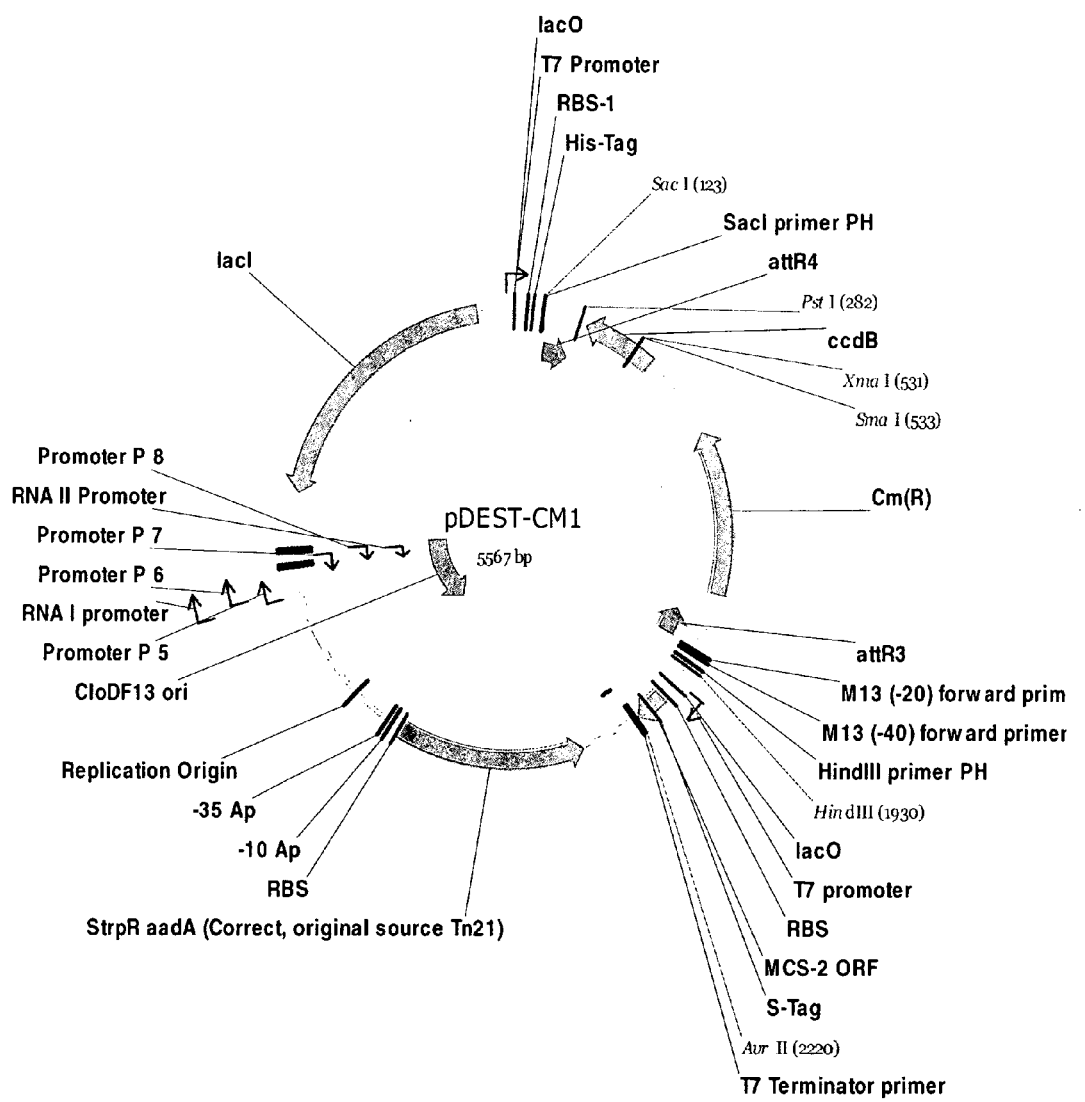
FIG. 16 shows a map of the pDEST-CM1 vector.
Figure 17:
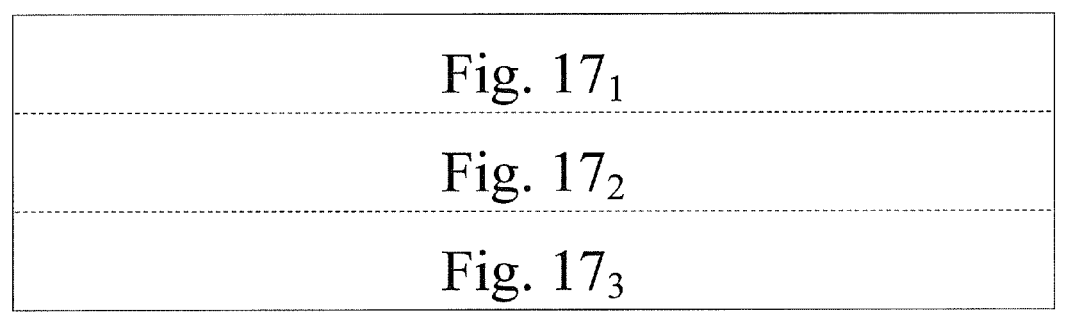

Vectors of the present invention include vectors having one or more of the elements shown in FIG. 16. An example of such a vector is the pDEST-CM1 vector, the nucleotide sequence of which is shown in FIG. 17.

Figure 18:
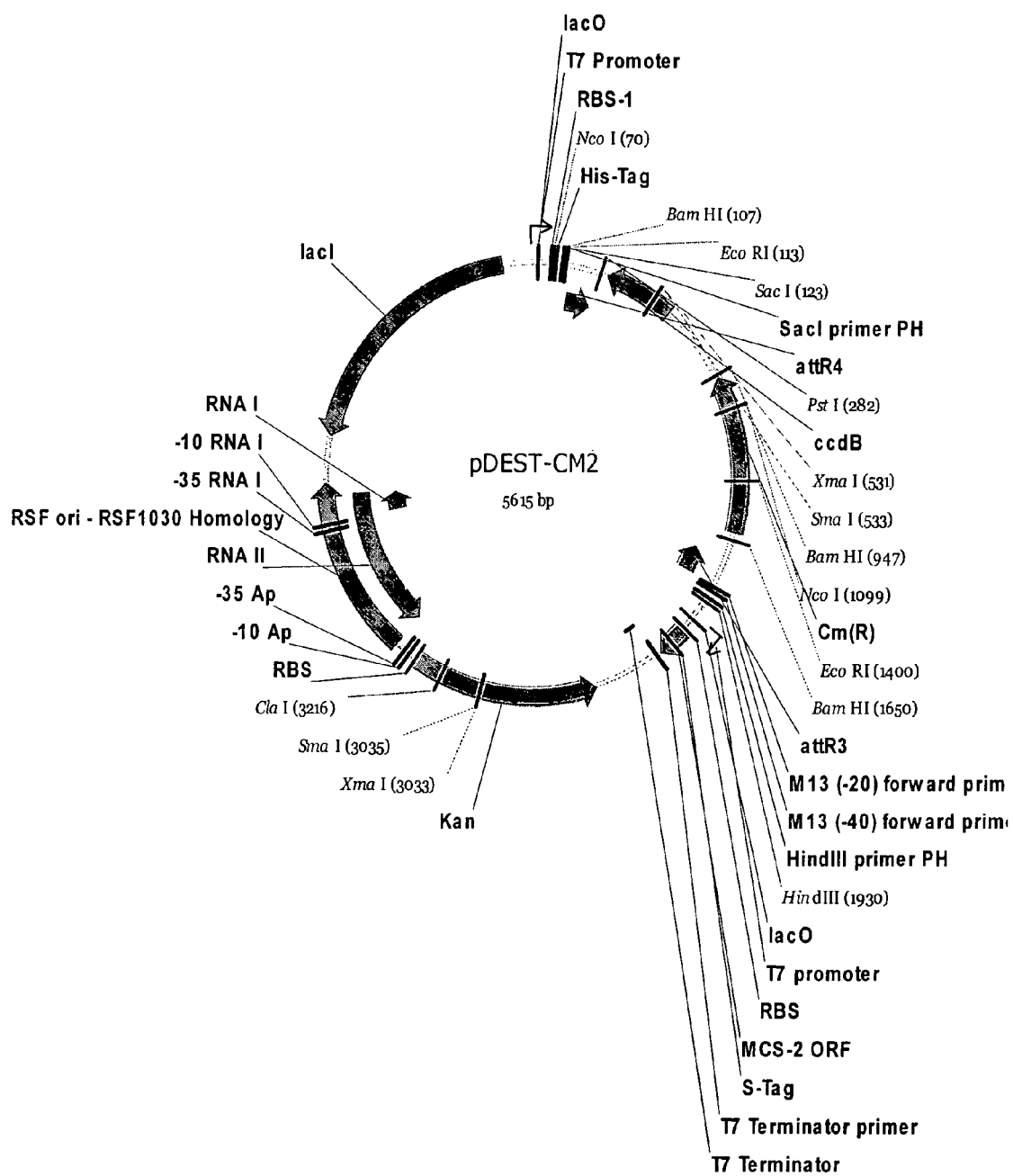
FIG. 18 shows a map of the pDESTCM-2 vector.
Figure 19:
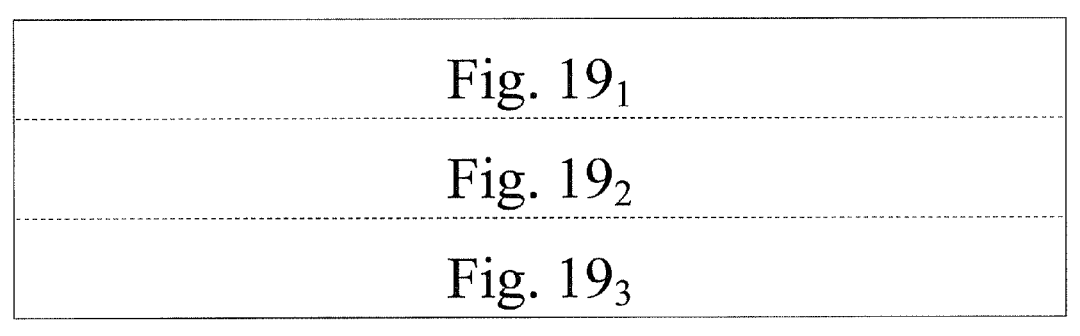

Vectors of the present invention include vectors having one or more of the elements shown in FIG. 18. An example of such a vector is the pDEST-CM2 vector, the nucleotide sequence of which is shown in FIG. 19.

Figure 22:
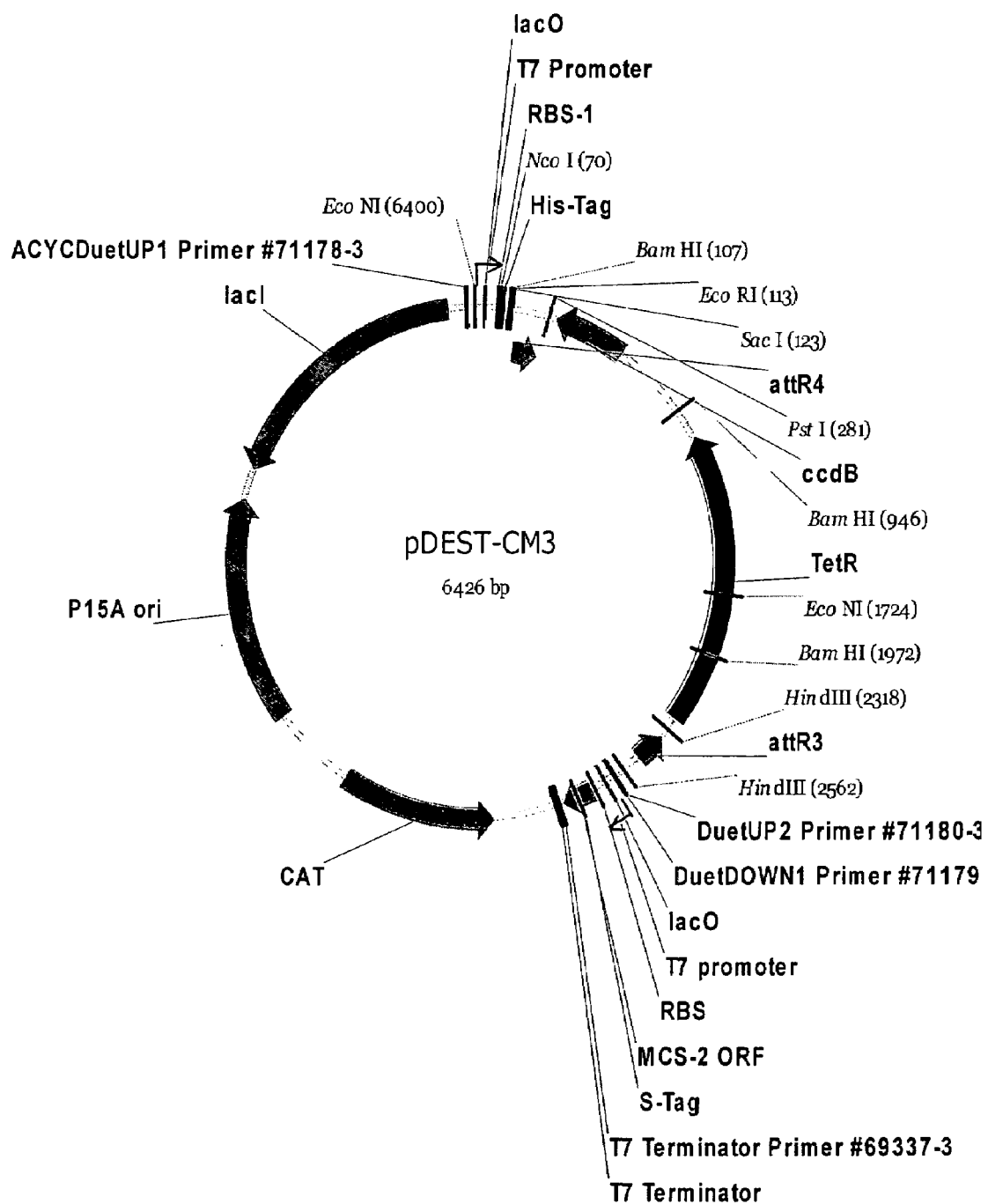
FIG. 22 shows a map of the pDEST-CM3 vector.
Figure 23:
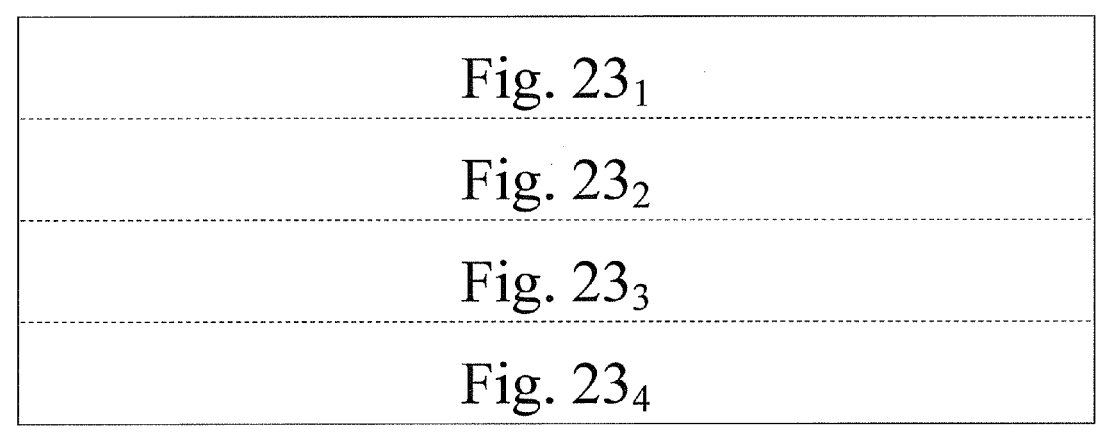

Vectors of the present invention include vectors having one or more of the elements shown in FIG. 22. An example of such a vector is the pDEST-CM3, the nucleotide sequence of which is shown in FIG. 23.

Figure 24:
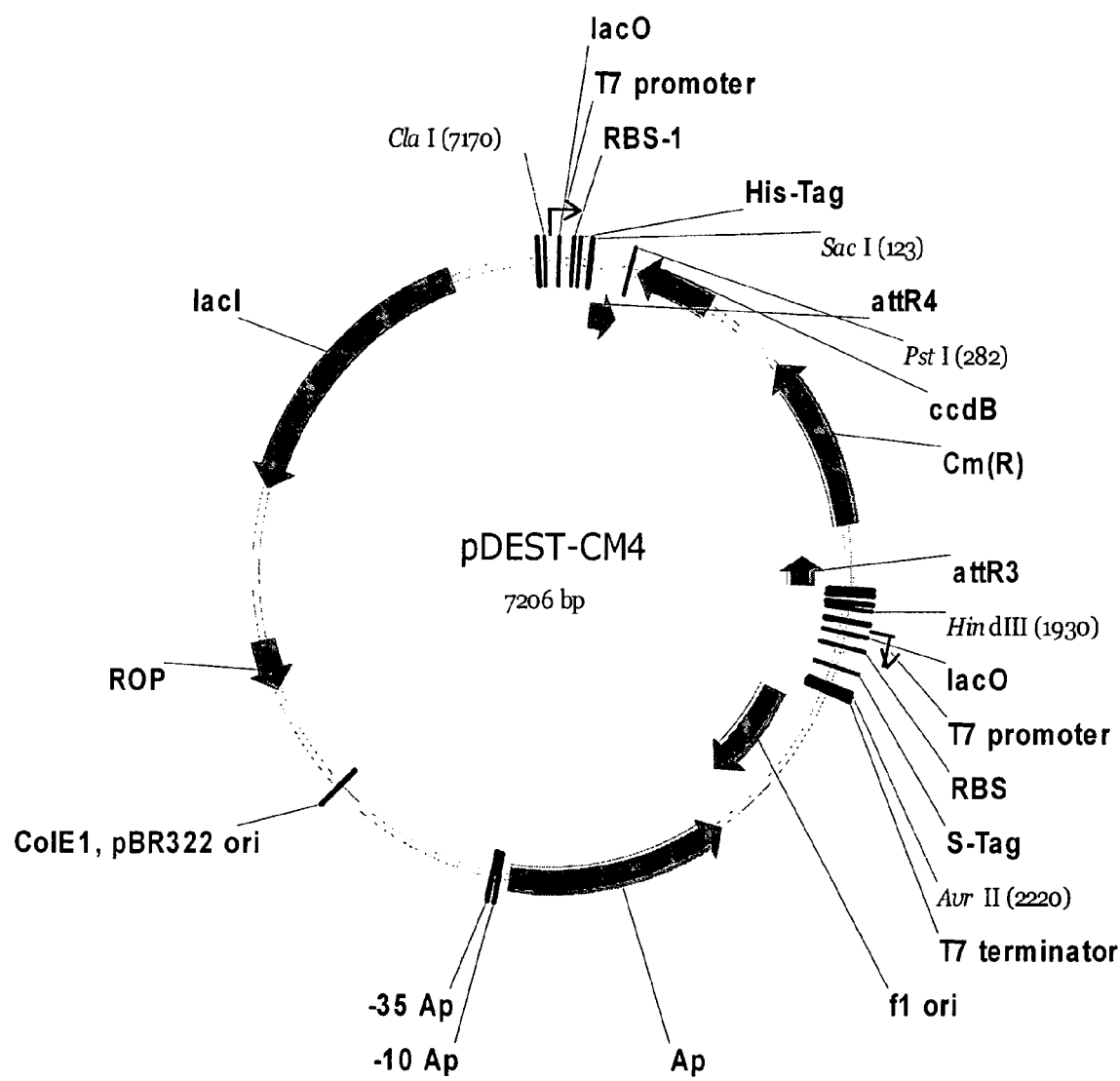
FIG. 24 shows a map of the pDEST-CM4 vector.
Figure 25:
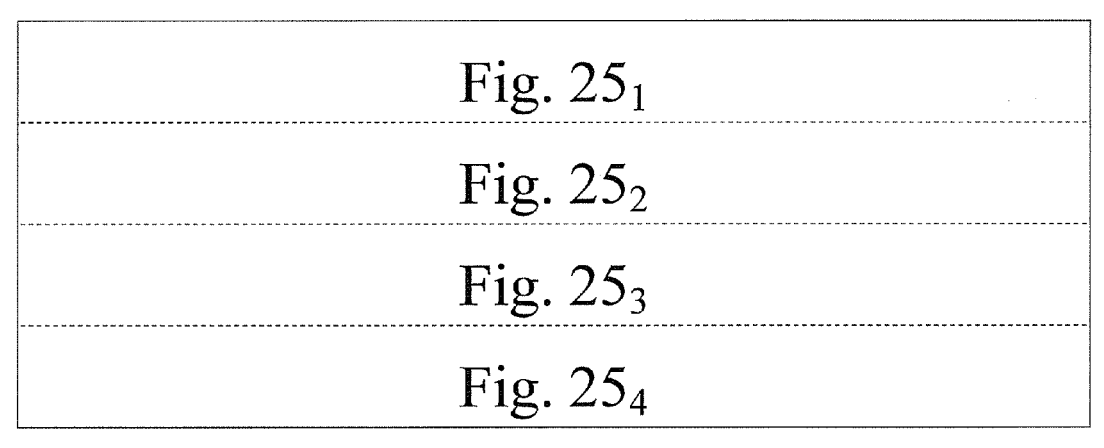

Vectors of the present invention include vectors having one or more of the elements shown in FIG. 24. An example of such a vector is the pDEST-CM4 vector, the nucleotide sequence of which is shown in FIG. 25.

Figure 41:
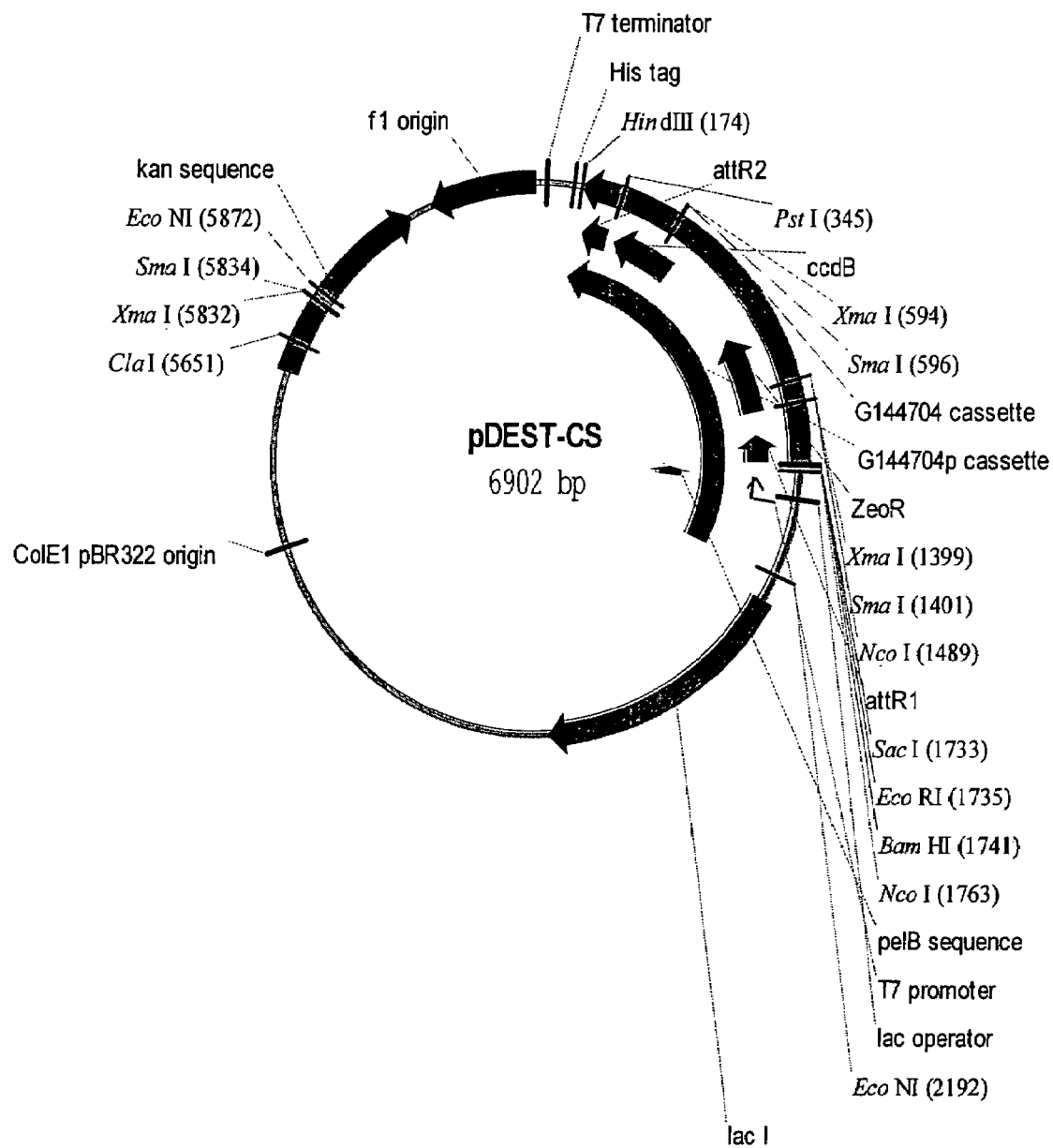
FIG. 41 is a map of the pDEST-CS.
Figure 42:
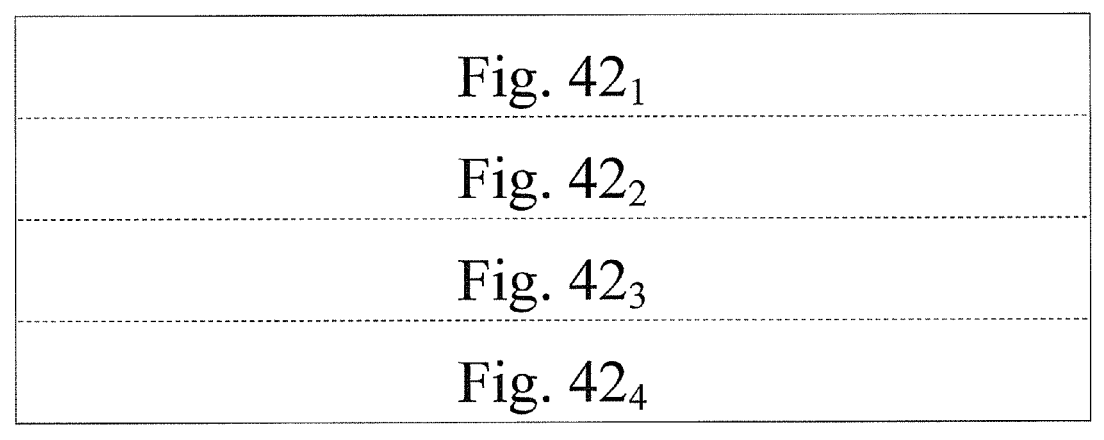

Vectors of the present invention include vectors having one or more of the elements shown in FIG. 41. An example of such a vector is the pDEST-CS vector, the nucleotide sequence of which is shown in FIG. 42.

Figure 43:
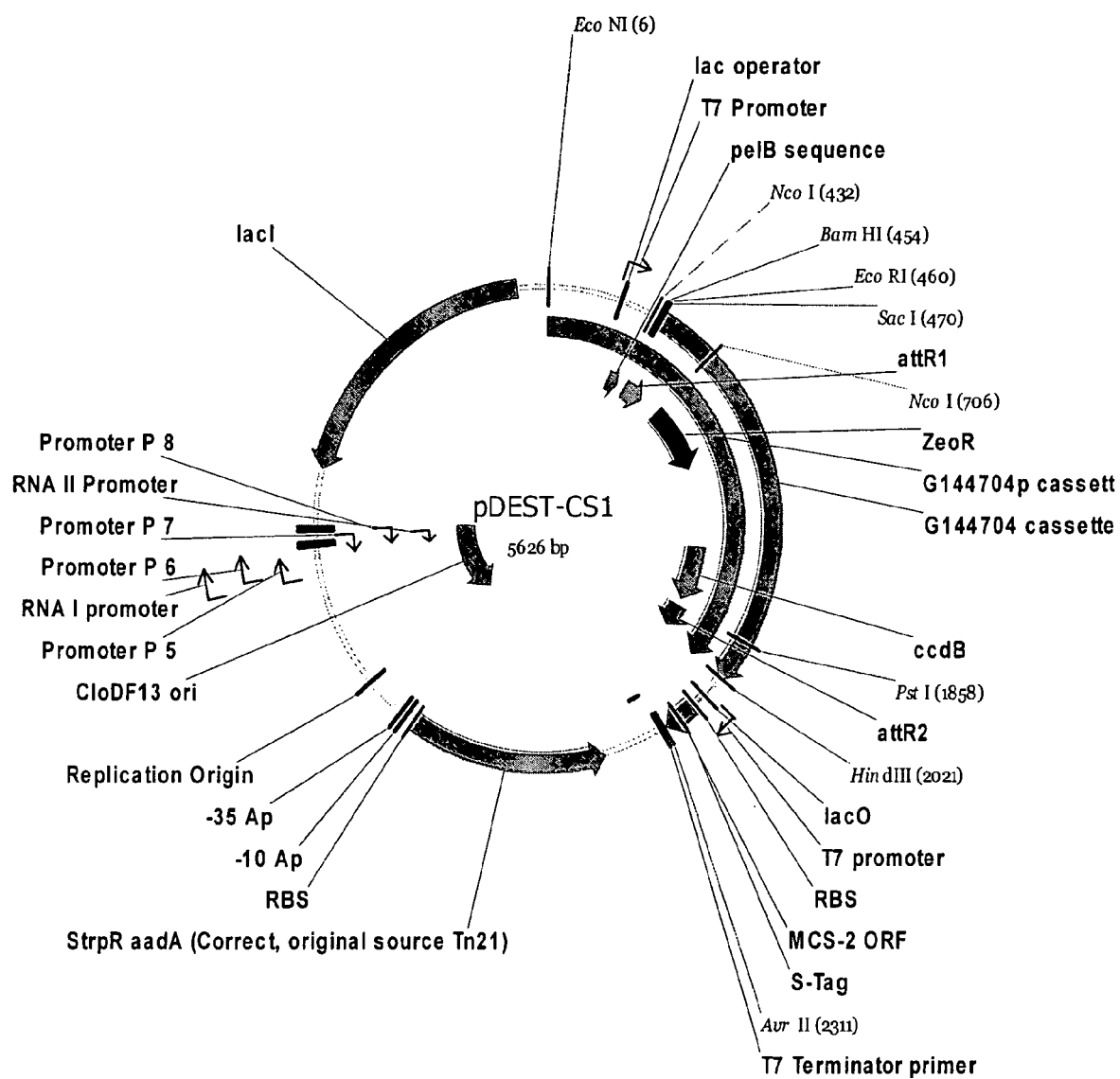
FIG. 43 is a map of the pDEST-CS1 vector.
Figure 44:
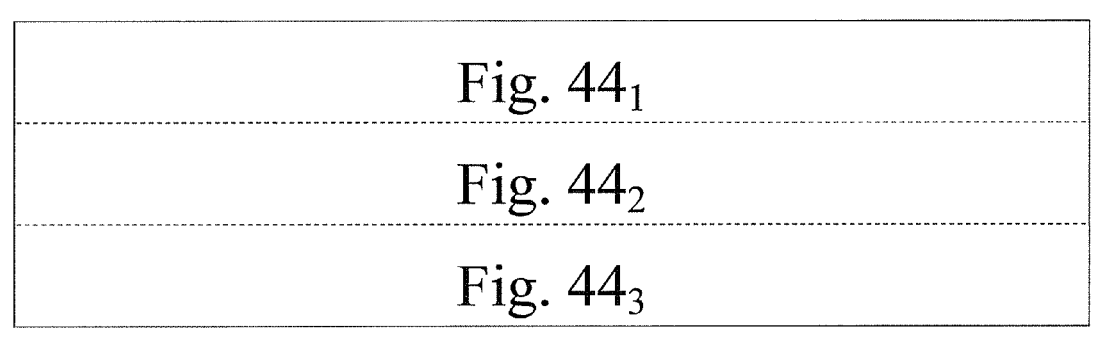

Vectors of the present invention include vectors having one or more of the elements shown in FIG. 43. An example of such a vector is the pDEST-CS1 vector, the nucleotide sequence of which is shown in FIG. 44.

Figure 45:
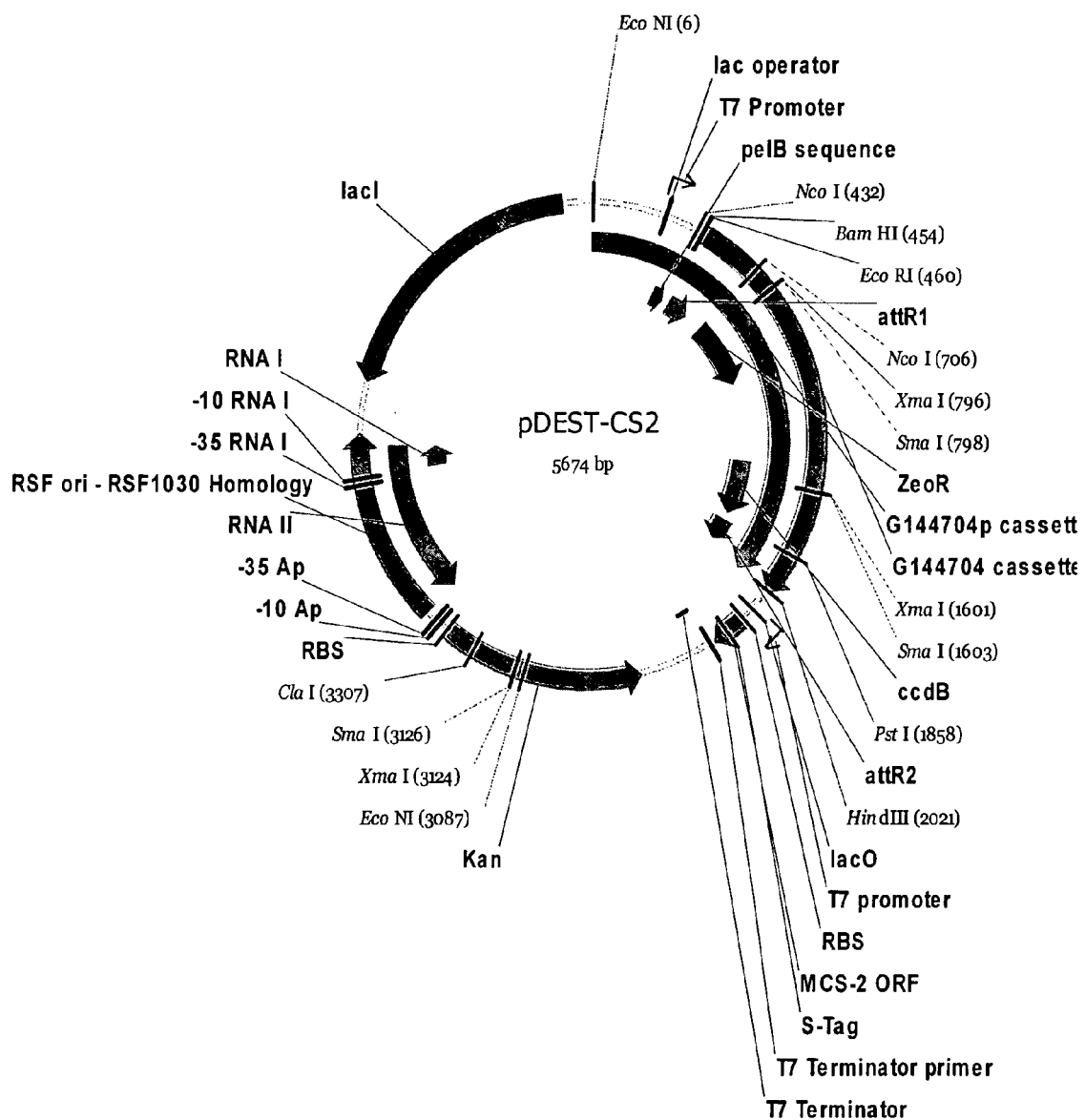
FIG. 45 is a map of the pDEST-CS2 vector.
Figure 46:
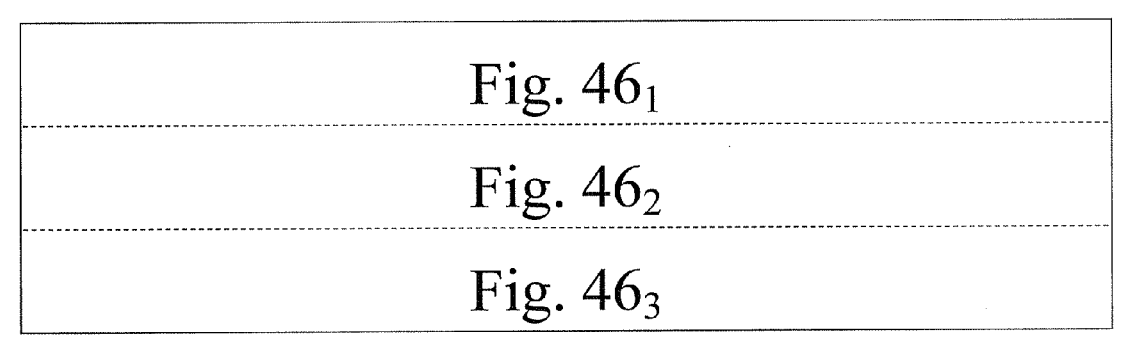

Vectors of the present invention include vectors having one or more of the elements shown in FIG. 45. An example of such a vector is the pDEST-CS2, the nucleotide sequence of which is shown in FIG. 46.

Figure 47:
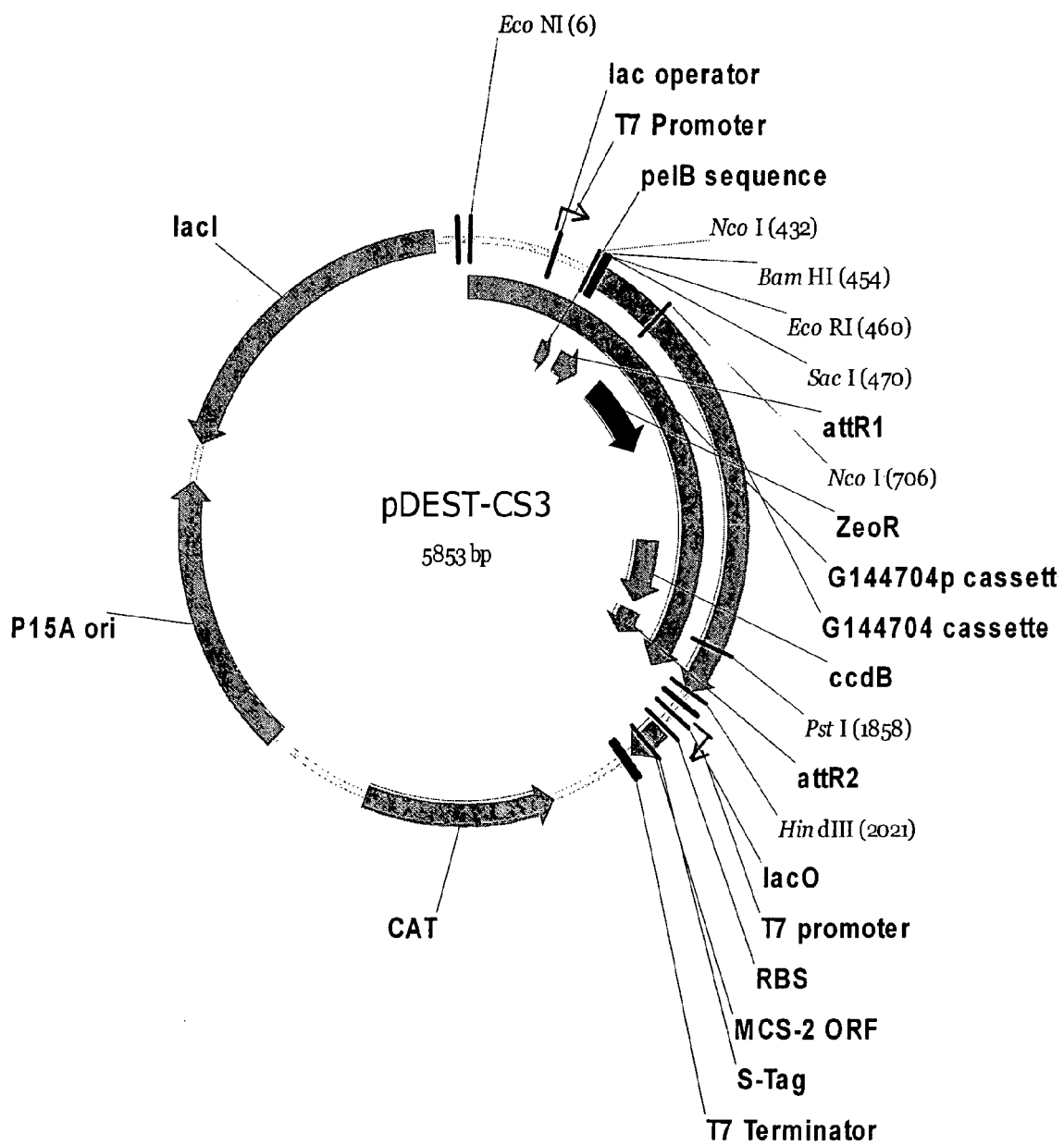
FIG. 47 is a map of the pDEST-CS3 vector.
Figure 48:
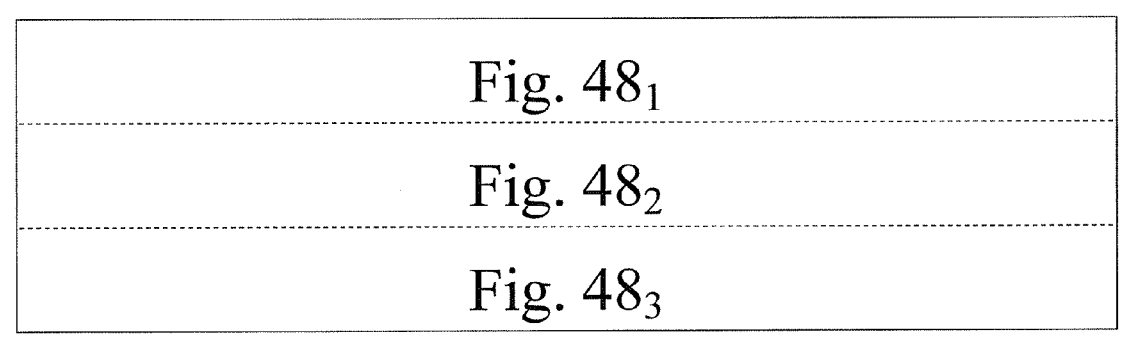

Vectors of the present invention include vectors having one or more of the elements shown in FIG. 47. An example of such a vector is the pDEST-CS3, the nucleotide sequence of which is shown in FIG. 48.

Figure 49:
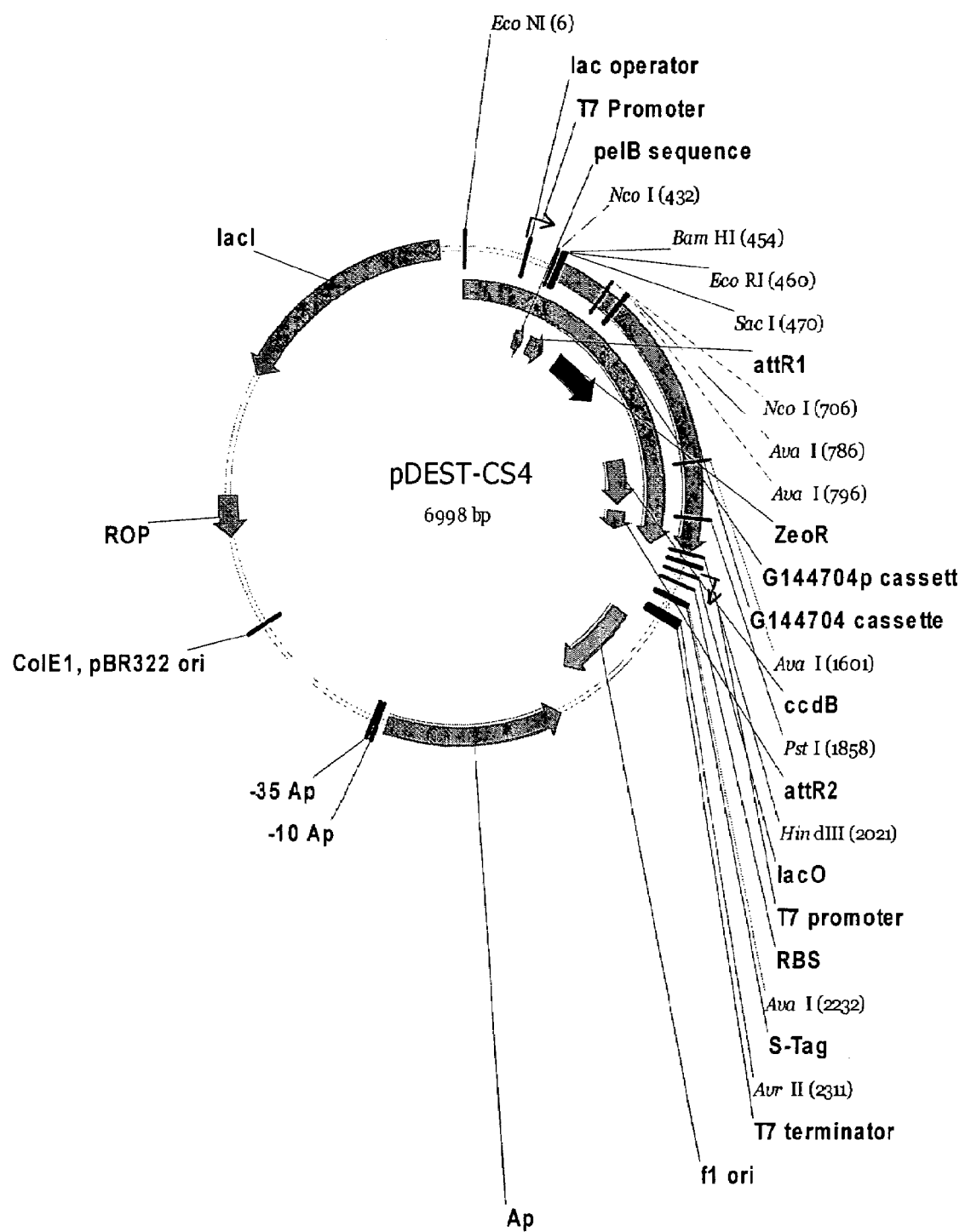
FIG. 49 is a map of the pDEST-CS4 vector.
Figure 50:
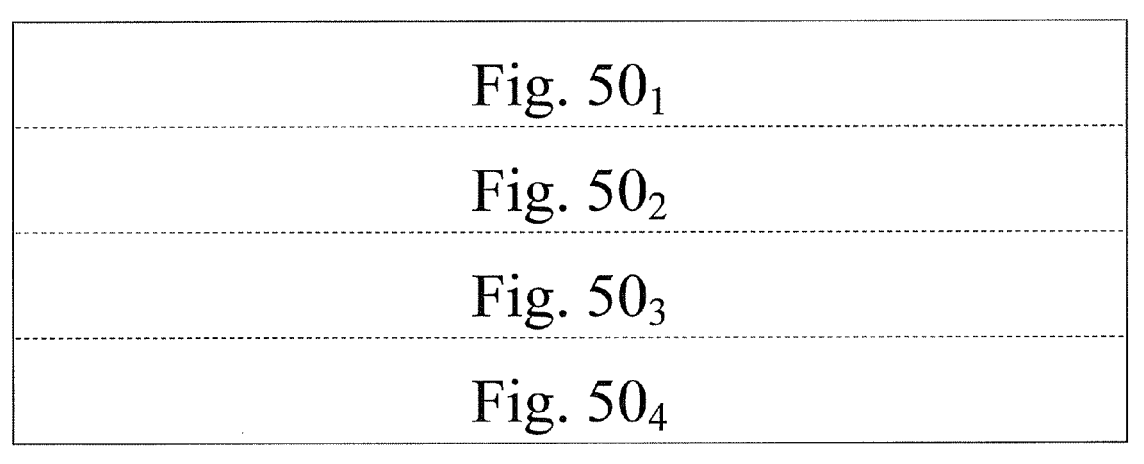

Vectors of the present invention include vectors having one or more of the elements shown in FIG. 49. An example of such a vector is the pDEST-CS4, the nucleotide sequence of which is shown in FIG. 50.

Figure 51:
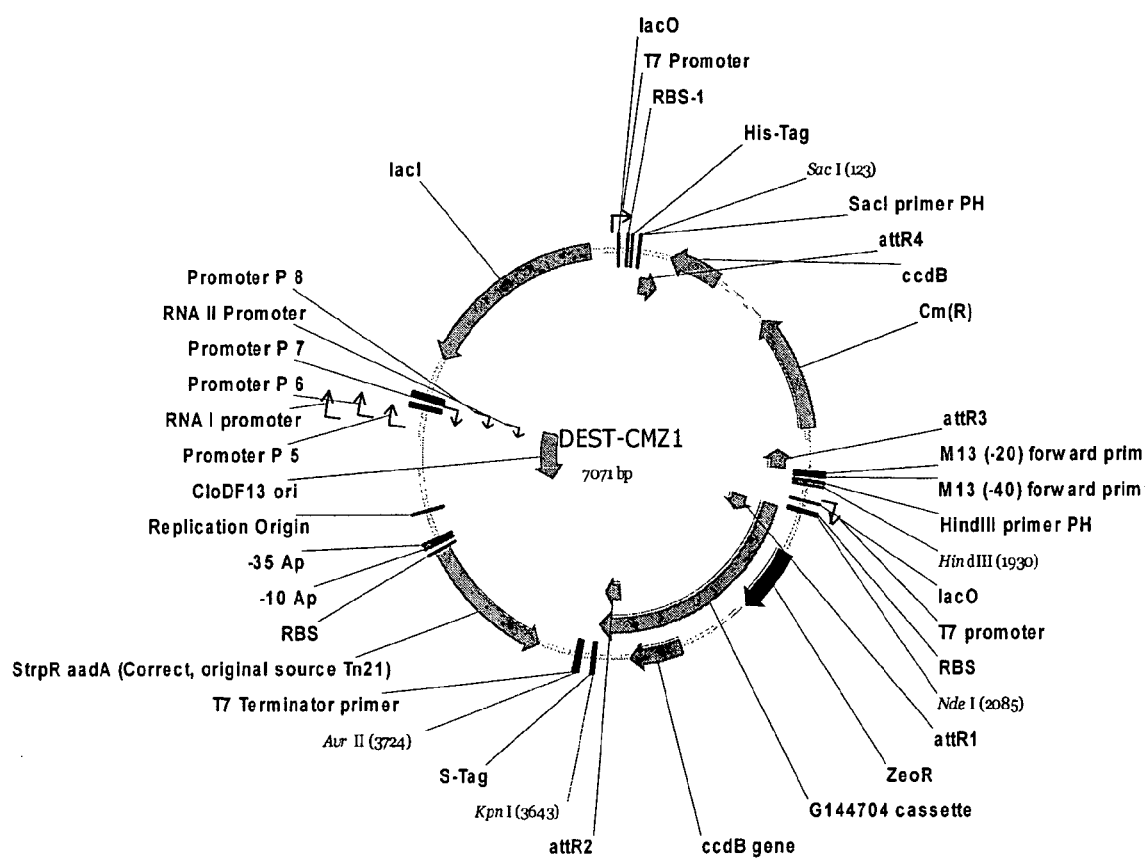
FIG. 51 is a map of the pDEST-CMZ1 vector.
Figure 52:
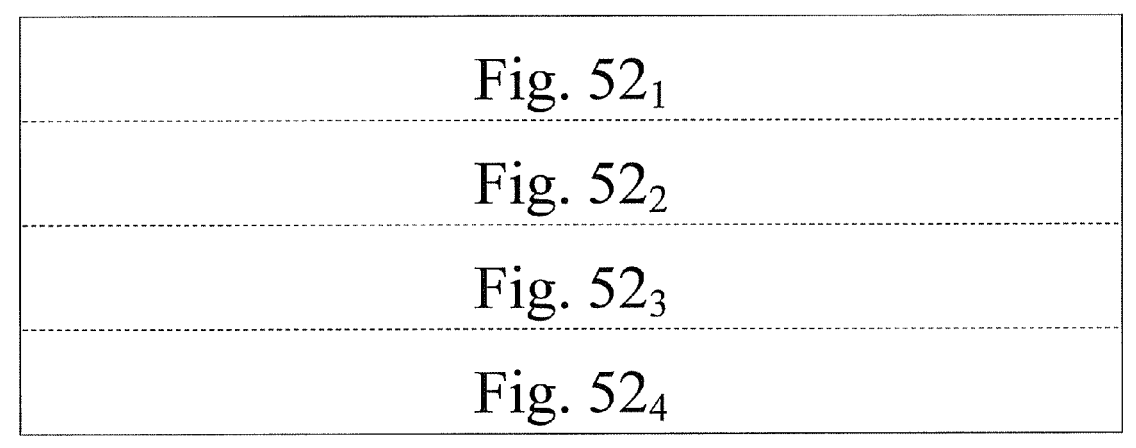

Vectors of the present invention include vectors having one or more of the elements shown in FIG. 51. An example of such a vector is the pDEST-CMZ1, the nucleotide sequence of which is shown in FIG. 52.

Figure 53:
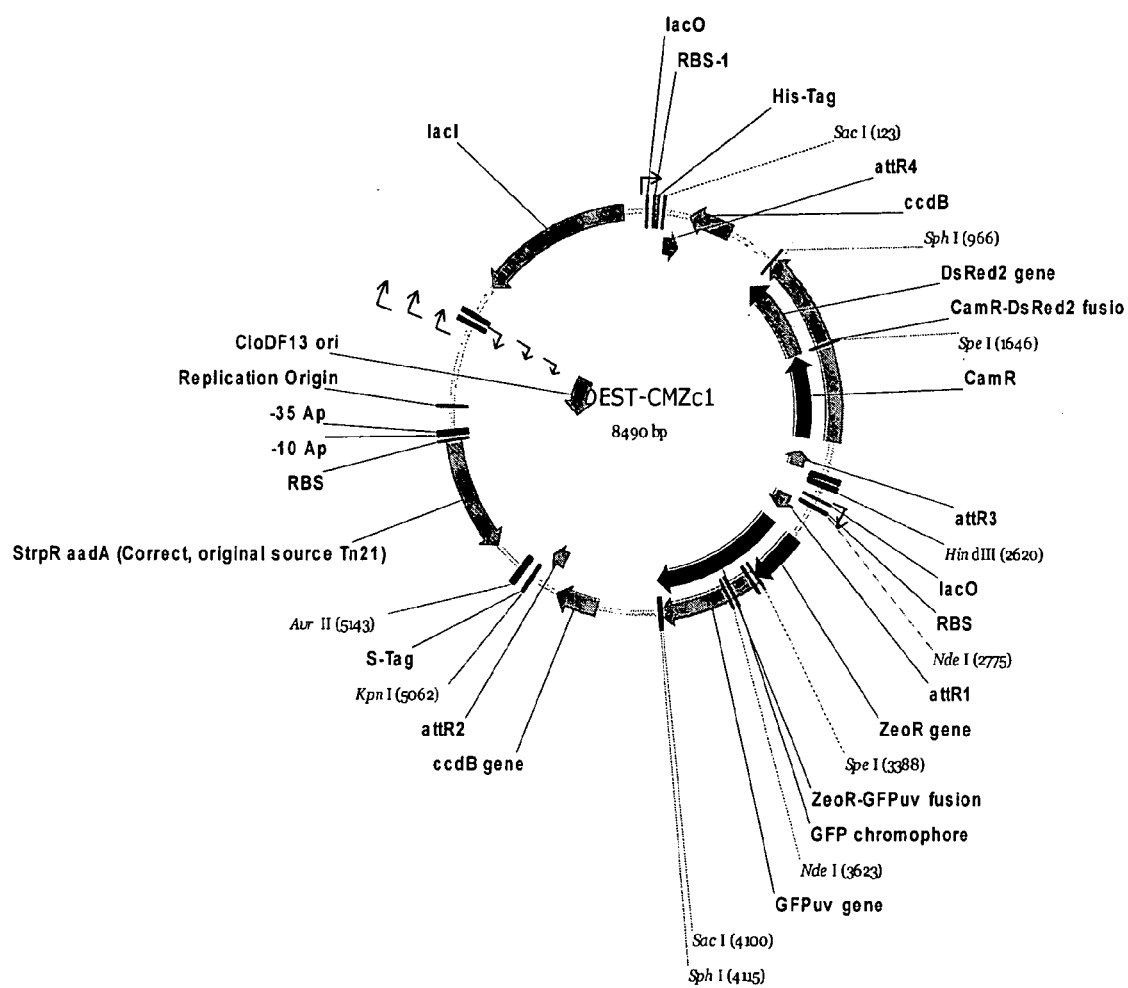
FIG. 53 is a map of the pDEST-CMc1 vector.
Figure 54:
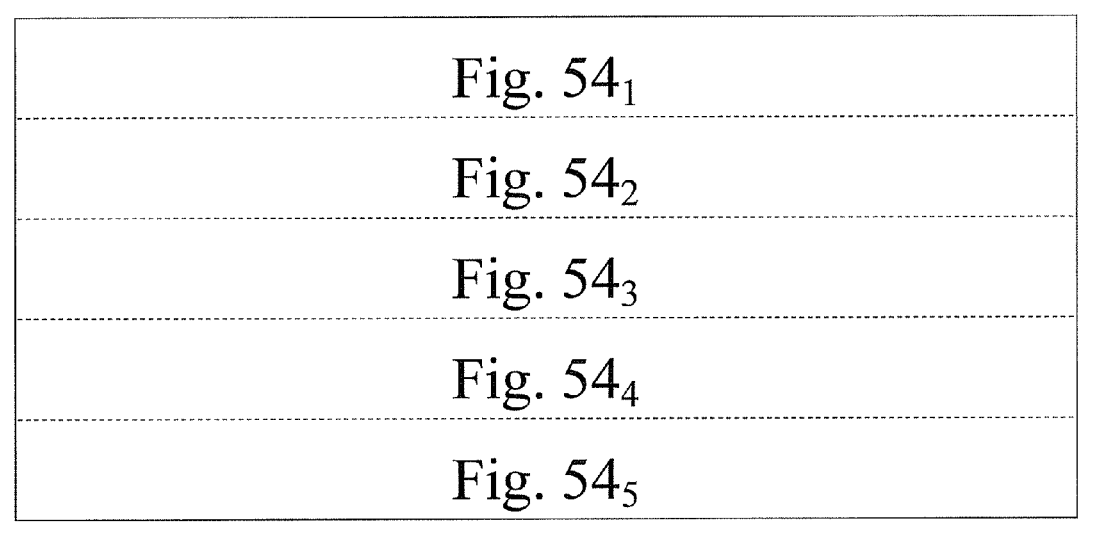

Vectors of the present invention include vectors having one or more of the elements shown in FIG. 53. An example of such a vector is the pDEST-CMc1, the nucleotide sequence of which is shown in FIG. 54.

The vectors of the present invention, when used together in the same cell, can express in a parallel manner multiple open reading frames ("ORFs"). As used herein, an ORF may include, for example, a polypeptide product, mRNA product, and an RNAi product. For example, up to two ORFs, two or more ORFs, up to three ORFs, three or more ORFs, up to four ORFs, four or more ORFs, up to six ORFs, six or more ORFs, up to eight ORFs, eight or more ORFs, up to ten ORFs, ten or more ORFs, up to twelve ORFs, twelve or more ORFs, up to sixteen ORFs, sixteen or more ORFs, up to twenty ORFs, twenty or more ORFs, up to twenty-two ORFs, twenty-two or more ORFs, up to twenty-four ORFs, twenty-four or more ORFs, up to twenty-eight ORFs, twenty-eight or more ORFs, up to thirty ORFs, thirty or more ORFs, up to thirty-two ORFs, thirty-two, or more ORFs may be expressed in a single host cell using a combination of the vectors of the present invention. Any combination of vectors of the present invention may be used in concert with any number of other available expression vectors to express multiple reading frames. The present invention also includes methods of expressing such ORFs using the one or more of the vectors of the present invention. The present invention also includes methods of expressing such ORFs using the one or more of the vectors of the present invention in combination with one or more additional expression vectors.

One, two, three, four, five, six, seven, eight, nine, ten, or more of the vectors described herein may be used in a single co-expression experiment. The vectors of the present invention may be used along with any number of currently available expression vectors and/or newly developed co-expression vectors. Examples of such vectors include, but are not limited to, those reported in the scientific literature and the many commercially available expression vectors, including those marketed, for example, Invitrogen, Novagen (Novagen 2004/2005 Catalog), Promega (Promega 2005 Life Sciences Catalog), Stratagene (Strategene 2005-06 Catalog)and New England Biolabs (2006 NEB catalog).

The expression vectors of the present invention may be used to for the expression of one or more polypeptides. The polypeptide may be homologous to the host cell, which includes, for example, proteins or peptides that are naturally encoded by the host cell, from a native DNA sequence, or a substitution, deletion, and/or insertion variant thereof. The polypeptide may also be heterologous to the host cell, expressed on a heterologous nucleic acid sequence, which includes, for example, proteins and peptides that are not naturally expressed by the host cell, proteins and peptides that are naturally expressed or encoded by the host cell, and substitutions, deletions, and/or insertion variants of proteins and peptides that are naturally expressed or encoded by the host cell. The protein or peptide may be a fusion protein, comprising two or more polypeptides that are synthesized from a nucleic acid molecule encoding both polypeptides under the control of a single set of translational control elements. The fusion protein may include a linker peptide situated between the polypeptides.

A DNA molecule encoding the polypeptide may be prepared using well known recombinant DNA technology methods such as those set forth in Sambrook et al. (Molecular Cloning: A Laboratory Manual, Cold Spring Harbor Laboratory Press, Cold Spring Harbor, N.Y., 2001) and/or Ausubel et al., eds, (Current Protocols in Molecular Biology, Green Publishing Assoc., Inc. John Wiley & Sons, Inc., N.Y., 1994).

Insertion (also referred to as "transformation" or "transfection") of a vector of the present invention into the selected host cell may be accomplished using any of a variety of methods. The method selected will in part be a function of the type of host cell to be used. These methods and other suitable methods are well known to the skilled artisan. Transformation of a bacterial host with the vector of the present invention may be accomplished using any of a variety of methods. For example, any of the methods described in the examples herein, and any of the well known methods such as those set forth, for example, in Sambrook et al., *Molecular Cloning: A Laboratory Manual*, Cold Spring Harbor Laboratory Press, 1989, may be used. Methods that may be used include, for example, such methods as calcium phosphate precipitation or electroporation. Likewise, transfection of the vectors of the present invention into mammalian cells may be accomplished using any of the many known methods. For example, transfection into mammalian cells may be accomplished using Lipofectamine™ (Invitrogen Corp) according to the supplier's instructions.

Any of a variety of host-expression vector systems may be used to express the protein or peptide. These include, but are not limited to, microorganisms such as bacteria, yeast, insect cell systems, plant cell systems, or animal cell systems, including, for example, any of a variety of murine and human cells systems. The co-expression systems of the present invention may be used to express therapeutic proteins, including protein complexes, including, for example antibodies.

The vectors of the present invention provide many innovations, including, but not limited to the following. Cconstructs may be created in the same reaction and plated on different antibiotic supplemented plates. Each of these vectors can be used by itself, which allows for their use as a conventional expression vector. The throughput of expression screening is increased by testing up to four non-interacting ORFs' expression/solubility in the same cells. The vectors of the present invention can be used in methods of solubilizing proteins through soluble complex expression. The vectors of the present invention may be used in methods of high throughput (HTP) expression of already known protein complexes. And, the vectors of the present invention are compatible with the existing Gateway cloning system via the well-known L/R reaction.

In some aspects, polynucleotides and vectors of the of the present invention may include a cassette, wherein the cassette is a polynucleotide sequence containing the two recombination sites, for example attR1 and attR2 or attR3 and attR4, along with a nucleotide sequence that operably encodes the ccdB polypeptide. The two recombination sites flank the nucleotide sequence encoding encoding a ccdB polypeptide. This cassette may also include a nucleotide sequence that operably encodes a selectable marker other than chloramphenicol resistance, including for example, zeocin resistance. Zeocin™, a registered trademark of Cayla, is the commercial name of a formulation containing Phleomycin D1, an antibiotic of the bleomycin family (also called the phleomycin family). The ble gene encodes zeocin antibiotic resistance, conferring resistance to an antibiotic of the phleomycin family (U.S. Pat. Nos. 5,021,344 and 5,118,620). In the nucleotides and vectors of the present invention, the efficiency of the Gateway® recombination reaction is not affected by the insertion of the Zeocin gene between the att recombination recognition sites.

The present invention includes a polynucleotide, also referred to herein as a "cassette," wherein the cassette has a nucleotide sequence operably encoding zeomycin resistance and a nucleotide sequence operably encoding a ccdB polypeptide, wherein the nucleotide sequence operably encoding zeomycin resistance and the nucleotide sequence operably encoding a ccdB polypeptide are flanked by attR sites, including, for example, attR1 and attR2 or attR3 and attR4 recombinant recognition sites. An example of such a cassette is a cassette including one or more of the elements shown in FIGS. 8C and 8D. An example of such a cassette is the G144704 cassette, the nucleotide sequence of which is shown in FIG. 9. Another example of such a cassette is a cassette having one or more of the elements shown in FIG. 20. An example of such a cassette is the Multisite TetR cassette, the nucleotide sequence of which is shown in FIG. 21.

Vectors of the present invention allow for the tandem expression of more than one polypeptide product from a single co-expression vector. See, also, Sone et al. (Multi-gene gateway clone design for expression of multiple heterologous genes in living cells: Modular construction of multiple cDNA expression elements using recombinant cloning, "J Biotechnol. 2005 Jun. 24 (doi: 10,1016/jbiotec.2005.02.02 1)).

The present invention also includes methods of improving the solubility of expressed polypeptides by co-expressing more than one polypeptide using one or more of the vectors described herein. The vectors described herein may be used in concert with additional, available expression vectors in such methods of improving the solubility of one or more expressed polypeptides. The solubility of an expressed polypeptide can be determined using standard methods known in the art, including any of the methods described in the examples included herewith. For example, host cells may be collected three to twenty hours after induction and the cells are lysed. Cell lysis may be accomplished using physical methods such as homogenization, sonication, French press, microfluidizer, or the like, or by using chemical methods such as treatment of the cells with EDTA and a detergent (see Falconer et al., Biotechnol. Bioengin. 53:453-458 [1997]) or by taking advantage of the lytic activities of some bacteriophage proteins (Crabtree, S. & Cronan, J. E., J. Bact., 1984, 158:354-356). In some cases, it may be advantageous to combine more than one technique.

Expression of and mRNA or polypeptide product by a vector of the present invention may be assayed by any of a wide variety of methods, including any of those described herein.

Additionally, for example, fluorescent proteins with different excitation and emission wavelengths can be used to label a target product of a cDNA or to be expressed solely. Examples of such fluorescent proteins include, for example, EGFP (BD Biosciences Clontech Inc.; GenBank accession no.: U55763) (Cormack et al., Gene 173:33-38, 1996; Zhang et al., Biochem. Biophys. Res. Commun. 227:707-711, 1996), Venus (EYFP-F46L/F64L/M153T/V163A/S175G) (Nagai et al., Nat. Biotechnol. 20:87-90, 2002), SECFP (ECFP-K27R/N165H) (Zhang et al., Proc. Natl. Acad. Sci. U.S.A. 98:14997-15002, 2001), DsRed2 (BD Biosciences Clontech Inc.) (Matz et al., Nat. Biotechnol. 17:969-973, 1999; Terskikh et al., J. Biol. Chem. 277:7633-7636.2002) and mRFP1 (GenBank accession no.: AF506027) (Campbell et al., Proc. Natl. Acad. Sci. U.S.A. 99:7877-7882, 2002).

The present invention includes nucleotides and vectors for use in producing interfering RNA molecules for use in RNA interference (RNAi) studies. RNA is a biological process that involves sequence-specific mRNA degradation that is mediated by short interfering RNA (siRNA) molecules generated from the cleavage of dsRNA homologous to the gene targeted for silencing. The mechanism of RNAi-mediated specific gene silencing was first discovered in C. elegans and has also been found in other organisms, including Drosophila, hydra, zebrafish, and trypanasomes.

While the exact mechanism behind RNA interference is still not entirely understood, it appears that a dsRNA is processed into 20-25 nucleotide short interfering RNAs (siRNAs) by an Rnase III-like enzyme called Dicer. The siRNAs assemble into endoribonuclease-containing complexes known as RNA-induced silencing complexes (RISCs). The siRNA strands are then unwound to form activated RISCs, and the siRNA strands subsequently guide the RISCs to complementary RNA molecules, where they cleave and destroy the cognate RNA (discussed in Bass, B., Nature 411: 428-429 (2001) and Sharp, P. A., Genes Dev. 15:485-490 (2001)). Although the phenomenon of RNAi was first characterized in C. elegans and Drosophila, RNAi has also been demonstrated to work in mammalian cells (Wianny, F. and Zernica-Goetz, M., (2000), Natrue Cell Biology Vol 2., 70-75.

Accordingly, the invention includes both novel methods and compositions for reducing nonspecific suppression and novel methods and compositions for performing RNAi to reduce expression of target genes.

Nucleotides and vectors of the present invention for use in RNAi may include any of the various nucleotides, vectors, cassettes and elements described herein.

The RNAi vectors of the present invention may be used in any of the many available RNAi systems. For example, the RNAi vectors of the present invention may used to produce an interfering RNA product in the worm Cerenohabditis elegans (C. elegans). For example, worms may be fed with bacteria transformed with one or more vectors of the present invention. Currently available methods of RNAi allow for only gene to be studied at a time. The vectors of the present invention provide HTP RNAi vectors and provide for the large scale RNAi investigation of multiple genes at a time, for example, up to four, up to eight, up to ten, up to twelve, up to sixteen, up to twenty, up to twenty-four, up to twenty-eight, or up to thirty-two genes at one time.

Figure 27:
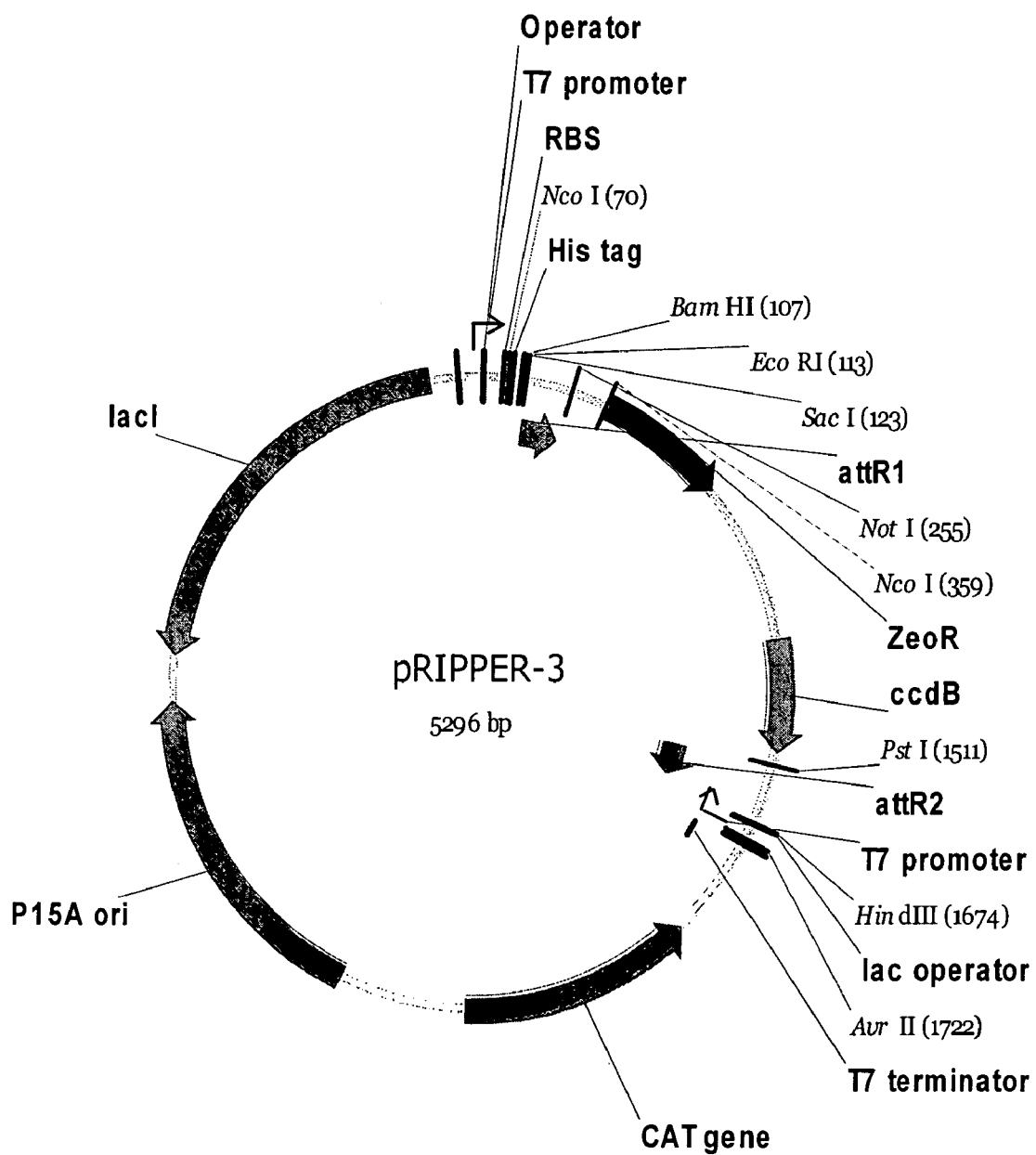
FIG. 27 is a map of the pRIPPER-3 vector.
Figure 28:
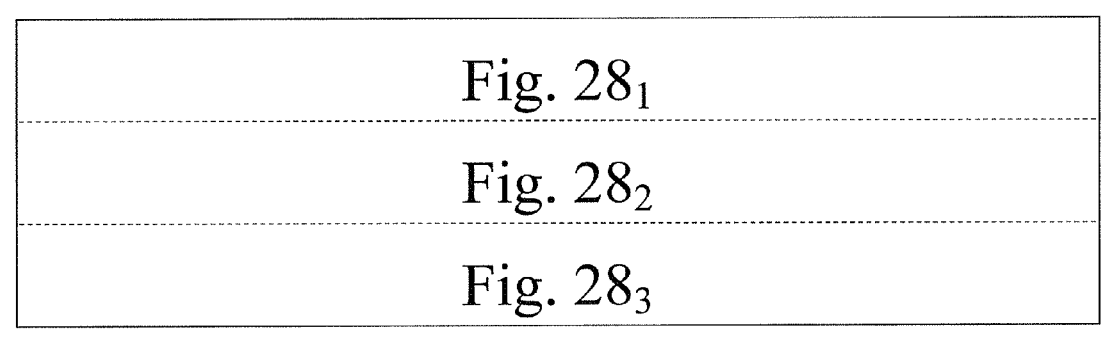

RNAi vectors of the present invention include vectors having one or more of the elements shown in FIG. 27. An example of such a vector is the pRIPPER-3 vector, the nucleotide sequence of which is shown in FIG. 28.

Figure 29:
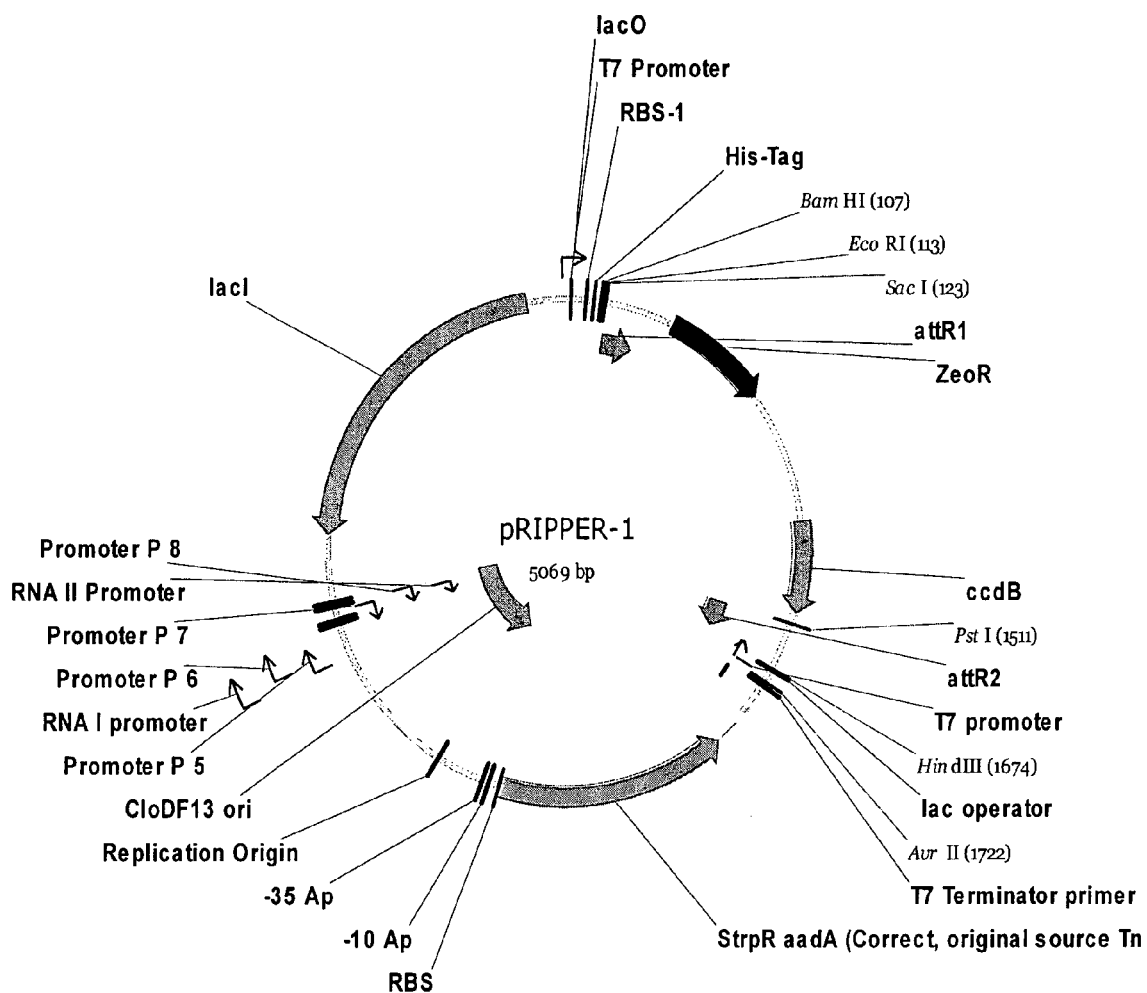
FIG. 29 is a map of the pRIPPER-1 vector.
Figure 30:
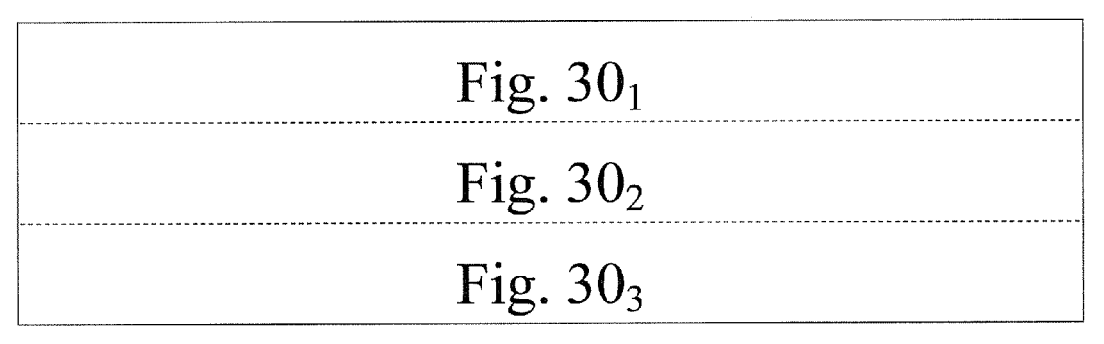

RNAi vectors of the present invention include vectors having one or more of the elements shown in FIG. 29. An example of such a vector is the pRIPPER-1 vector, the nucleotide sequence of which is shown in FIG. 30.

Figure 31:
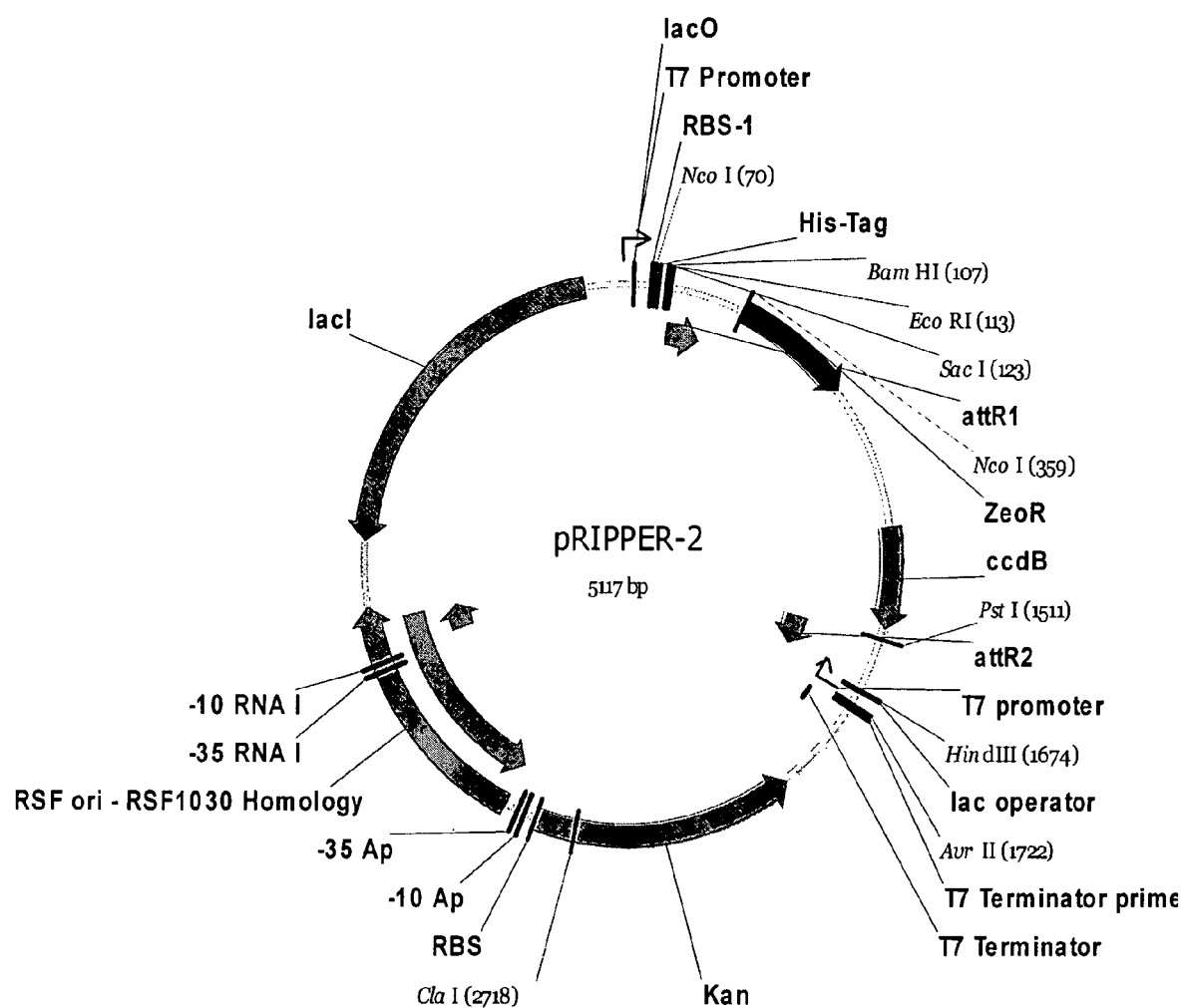
FIG. 31 is the map of the pRIPPER-2 vector.
Figure 32:
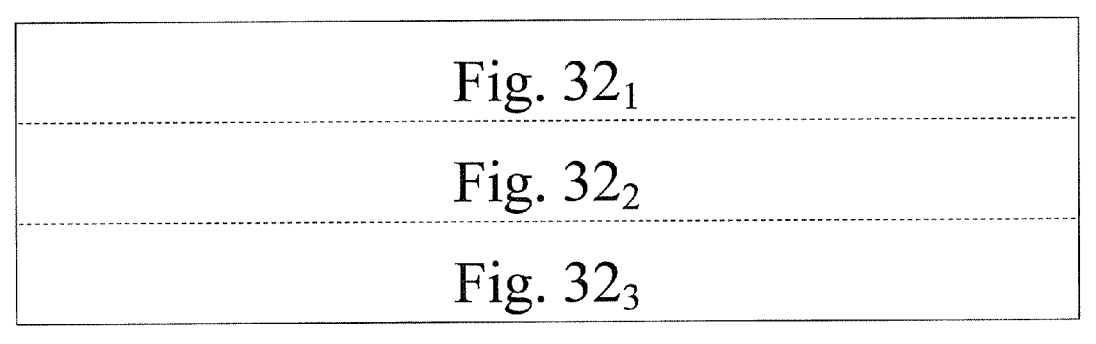

RNAi vectors of the present invention include vectors having one or more of the elements shown in FIG. 31. An example of such a vector is the pRIPPER-2 vector, the nucleotide sequence of which is shown in FIG. 32.

Figure 33:
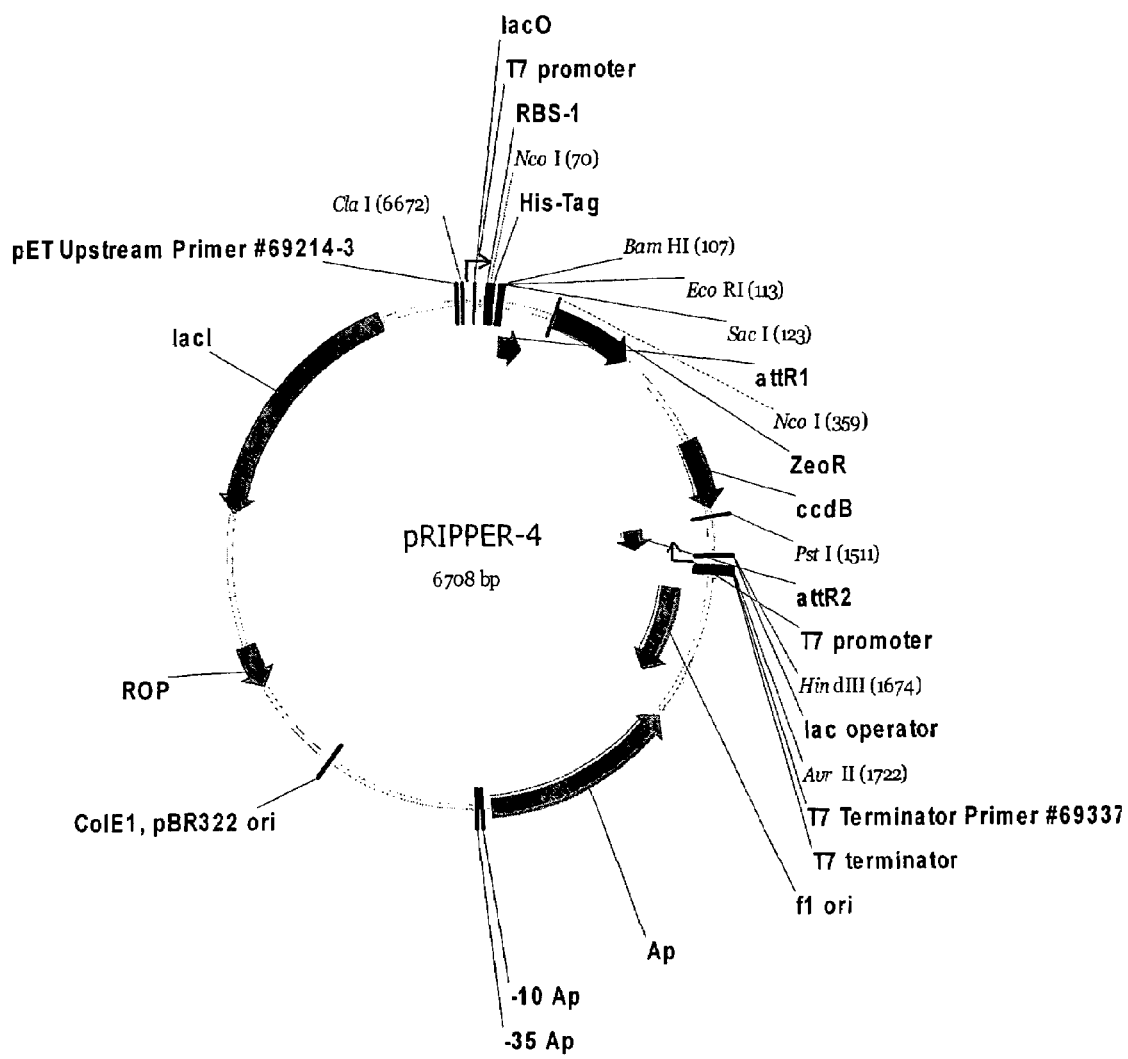
FIG. 33 is the map of the pRIPPER-4 vector.
Figure 34:
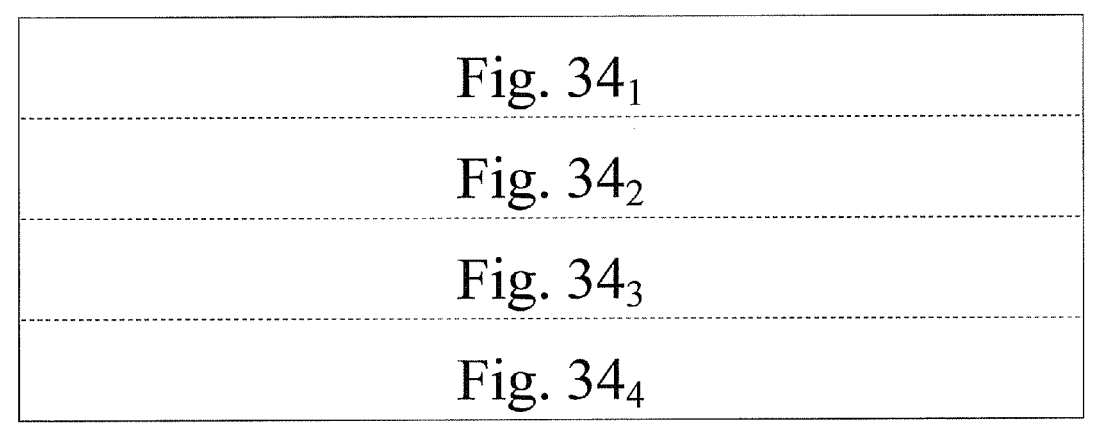

RNAi vectors of the present invention include vectors having one or more of the elements shown in FIG. 33. An example of such a vector is the pRIPPER-4 vector, the nucleotide sequence of which is shown in FIG. 34.

Figure 35:
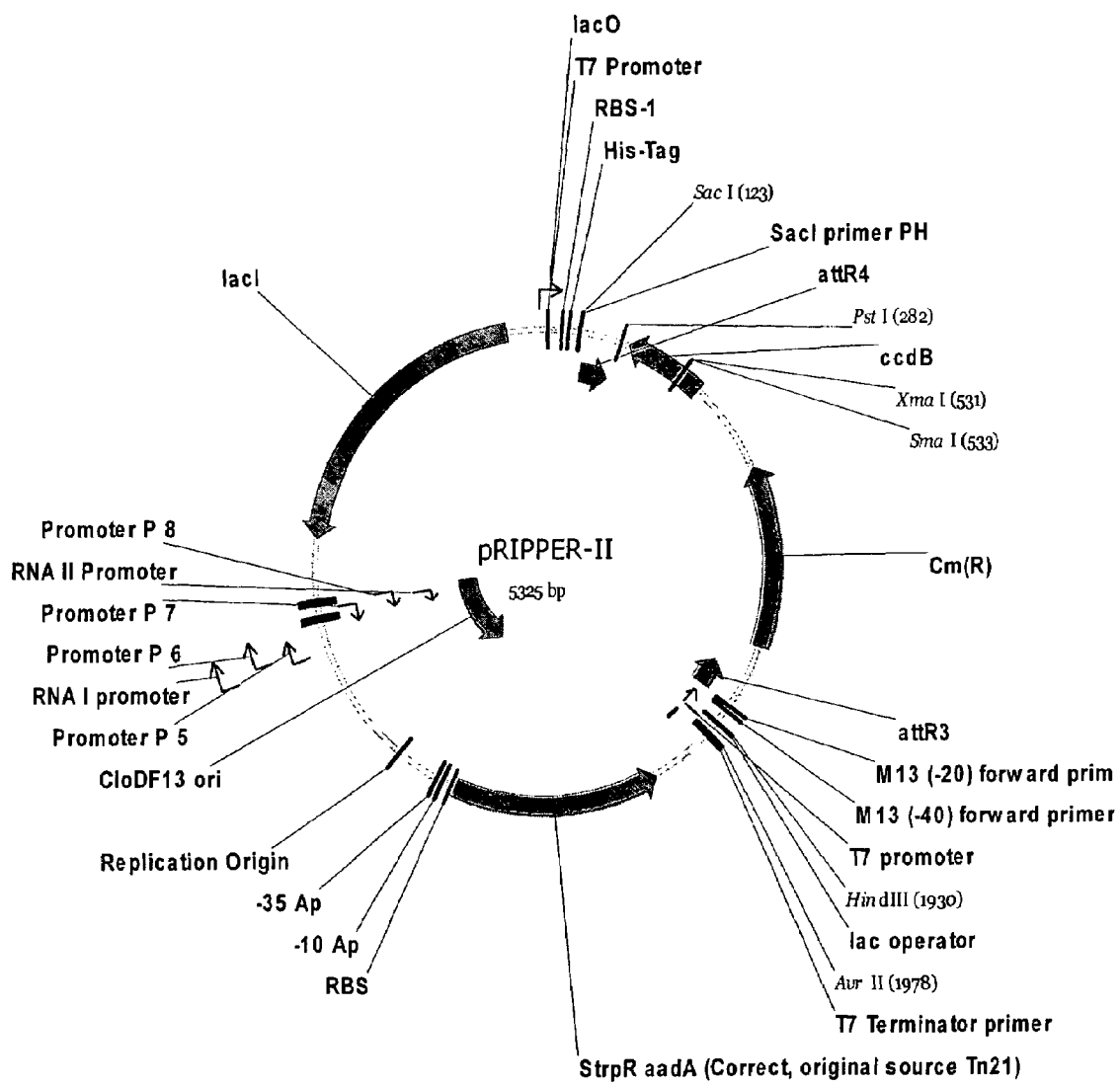
FIG. 35 is a map of the pRIPPER-II vector.
Figure 36:
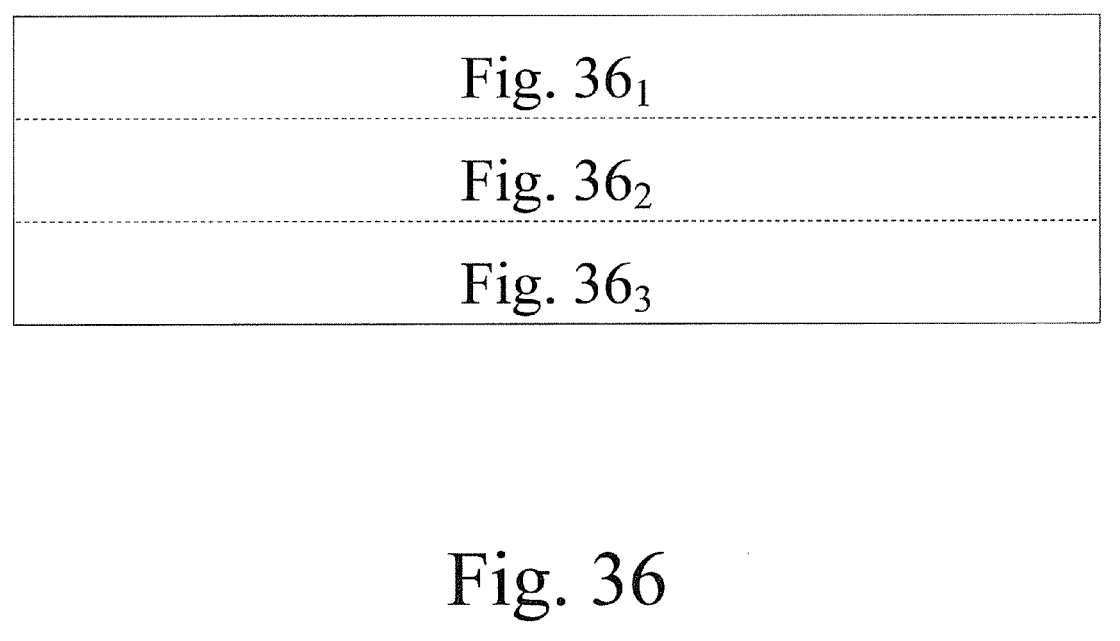

RNAi vectors of the present invention include vectors having one or more of the elements shown in FIG. 35. An example of such a vector is the pRIPPER-II vector, the nucleotide sequence of which is shown in FIG. 36.

Figure 37:
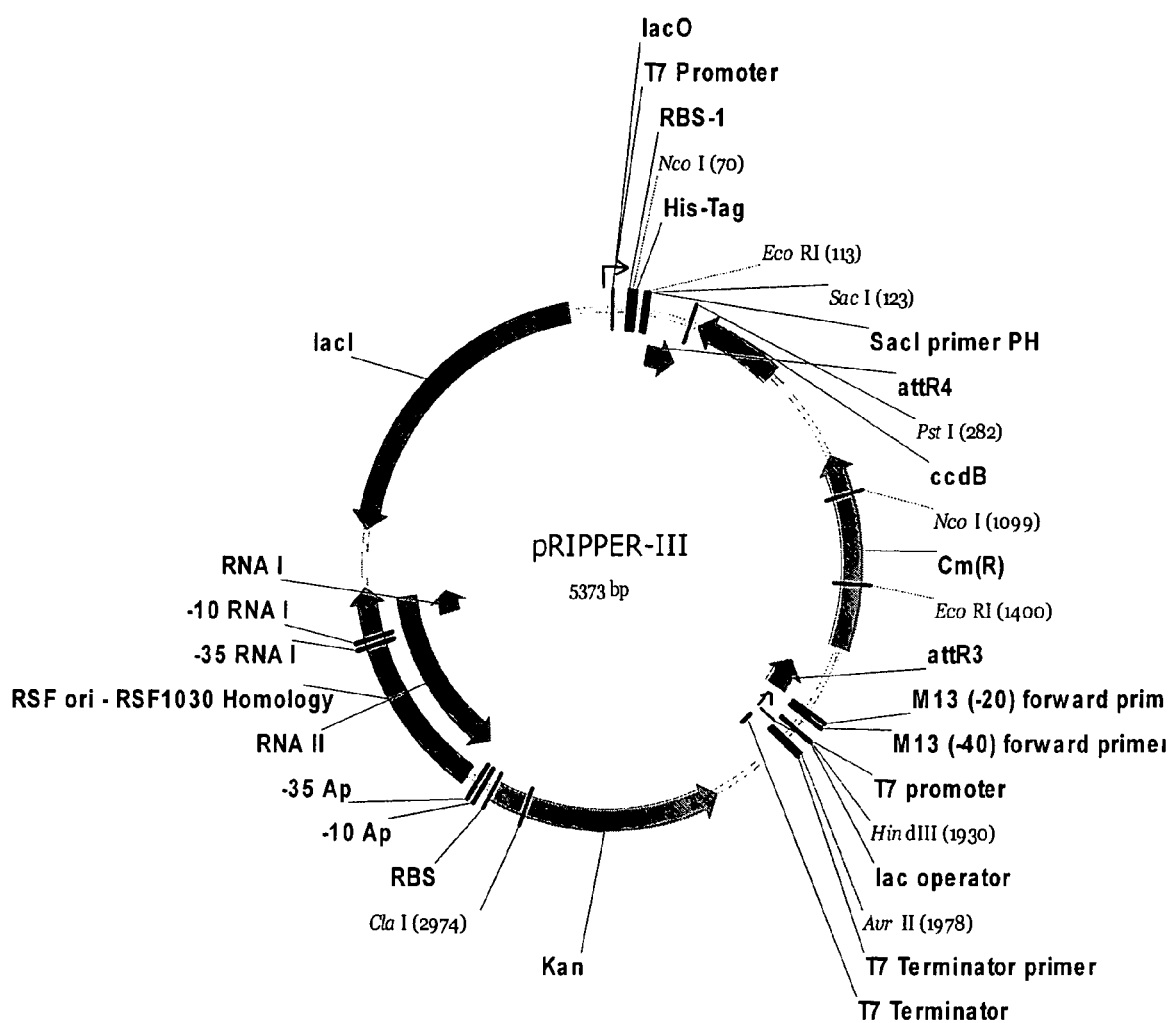
FIG. 37 is a map of the pRIPPER-III vector.
Figure 38:
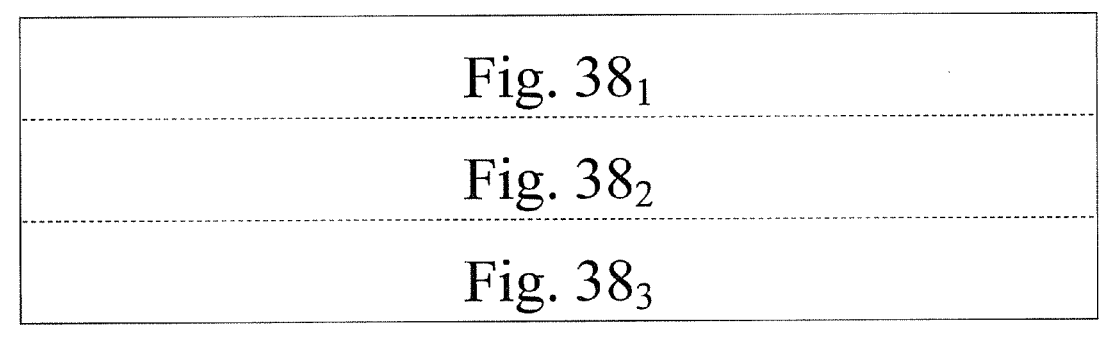

RNAi vectors of the present invention include vectors having one or more of the elements shown in FIG. 37. An example of such a vector is the pRIPPER-IV vector, the nucleotide sequence of which is shown in FIG. 38.

Figure 39:
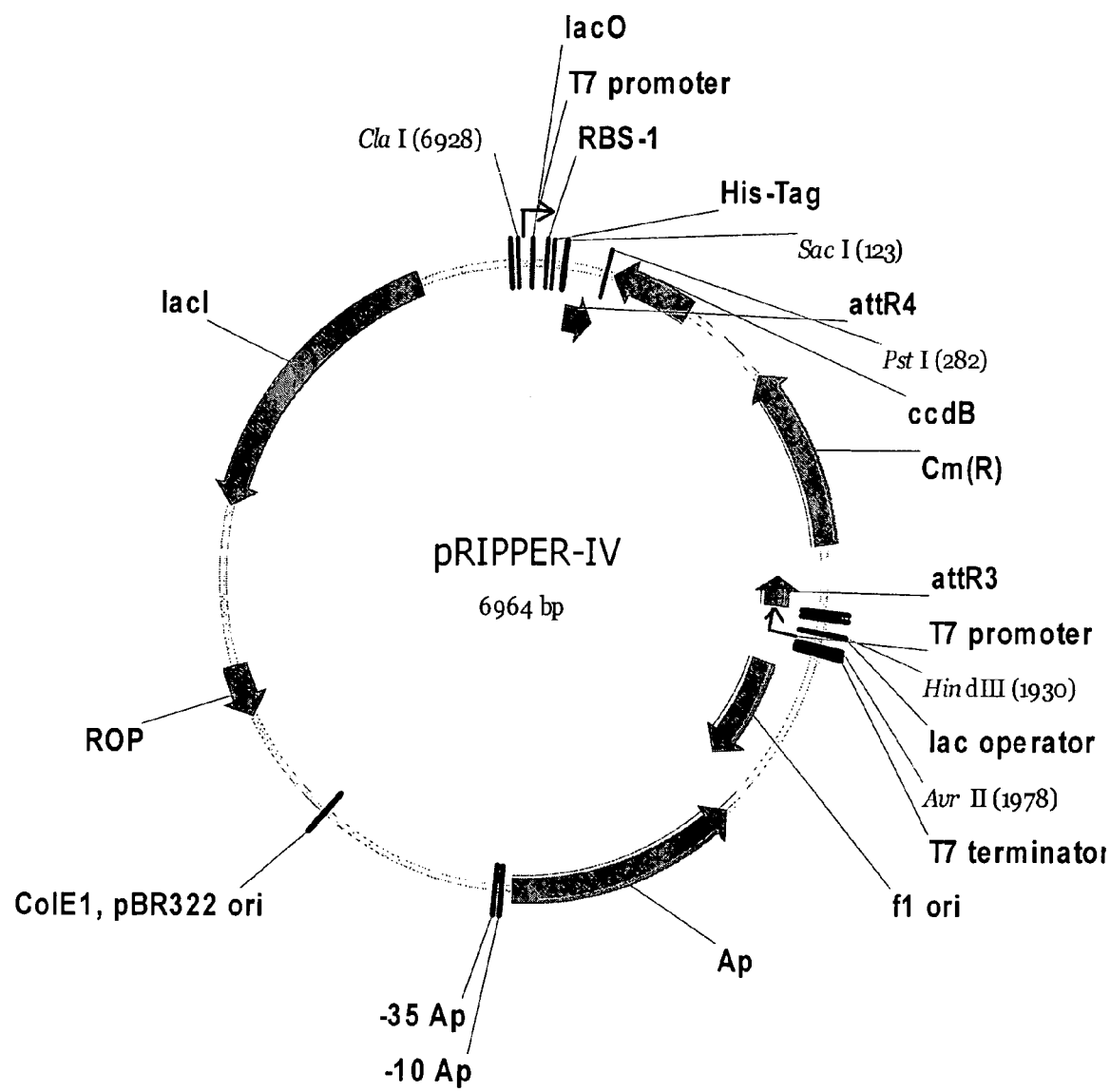
FIG. 39 is a map of the pRIPPER-IV vector.
Figure 40:
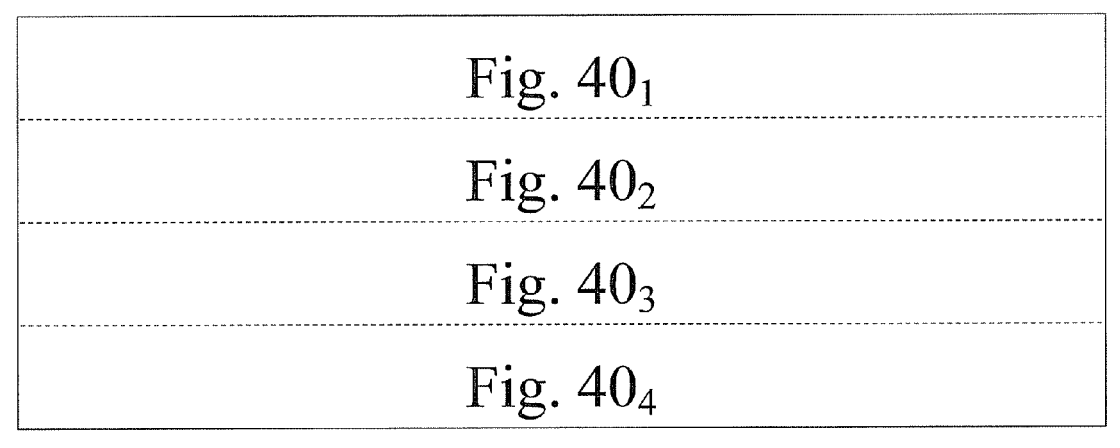

RNAi vectors of the present invention include vectors having one or more of the elements shown in FIG. 39. An example of such a vector is the pRIPPER-IV vector, the nucleotide sequence of which is shown in FIG. 40.

The present invention also includes methods of producing one or more interfering RNAs using one or more of the vectors described herein. The present invention also includes methods of inhibiting the expression of a gene, thereby inhibiting gene function, in a host cell or animal model system, including, for example, C. elegans and transgeneic animals, such as transgenic mice, by expressing one or more interfering RNAs in the host cell or animal model system using the vectors described herein. Methods for producing and assaying the effect of interfering RNAs produced by the vectors described herein may be by any of the many available methods. See, for example, materials available on the world wide web at ambion.com/techlib/resources/RNAi/; "RNAi" A "How To" for New Users" TechNotes 11(5), Ambion, 2006; or "RNA Interference and Gene Silencing—History and Overview," Ambion, May 20, 2002.

The vectors and method of the present invention may be used to lower production costs by allowing the use of parallel gene expression, the simultaneous expression of multiple proteins in the same cell. For example, multiple vector constructs, for example, four, sixteen, or thirty-two constructs, may be in a single expression experiment. For example, four constructs, each containing an affinity tag with a varying cleavage site can be used and four different trials can be carried out simultaneously in one experiment and therefore greatly increases protein expression and screening efficiency.

The vectors and methods of the present invention also allow for the use of different antibiotic resistance encoding vectors in addition to the Ampicillin resistance encoding pDEST vectors currently in use. Furthermore, the vectors and methods of the present invention allow for the co-expression of soluble multiple-protein complexes and for RNAi studies of certain organisms where many genes are turned on/off simultaneously. The vectors and method of the present invention will facilitate large scale operations in protein production. The vectors and method of the present invention provide for the co-expression of stable protein complexes. The vectors and method of the present invention may be used for the co-expression of endogenous and/or exogenous proteins. The vectors and method of the present invention may be used for the expression of secreted, intracellular and/or periplasmic polypeptides.

The vectors and methods of the present invention also allow for parallel gene expression and target salvaging at the gene level. Recombinant expression is a technique of choice for the synthesis of proteins of interest for structural genomics ("SG") studies. However, based on the recent structural genomics initiatives' data, less than one half of attempted open reading frames are expressed solubly and a fraction of these actually become structures (Liu et al., Acta Crystallogr D Biol Crystallogr 61(Pt 6):679-84, 2005). The total cost and speed of the structural determinations can be deciding factors in efficiency of SG studies. When a protein does not express, or is expressed, but insoluble, using the standard recombinant protocols, then multiple approaches have to be attempted, including co-expression with potential partners (Shen et al., Proteome Sci, 3(1):3, 2005). Proteins in their native environment exist as part of complexes, bound by other, specific proteins with weak, non-covalent interactions (Sorensen and Mortensen, J Biotechnol 115(2):113-28, 2005). Soluble proteins have been shown to solubilize other, previously insoluble, proteins (Sorensen and Mortensen, J Biotechnol 115(2):113-28, 2005). The vectors and methods of the present invention allow for screening multiple proteins (and their interactions) in the same cell and can be used to facilitate the expression of proteins that are known essential parts of a stable protein-complex and to individual, non-interacting proteins.

Since many proteins are tightly bound subunits of multi-protein complexes in vivo (Wang and Chong, Proc Natl Acad Sci USA 100:478-483, 2003) co-expression of multiple target proteins is a tool for successful heterologous protein expression. It has been shown for genes that are in a stable complex in the native host, that co-expression can improve their solubility and expression yield (Bernard and Couturier, Mol. Gen. Genet. 226:297-304, 1991; Li et al., Proc Natl Acad Sci USA 94:2278-2283, 1997; and Henricksen et al., J Biol Chem, 269:11121-11132 1994). Using the vectors and methods of the present invention, genes may be co-expressed either on the same expression vector from the same promoter, or using multiple, compatible vectors each containing one target gene.

The polynucleotides and vectors of the present invention can be used in methods to perform rapid and convenient construction of many different types of expression clones carrying multiple cDNAs on a single vector for their simultaneous introduction into cells.

The polynucleotides and vectors of the present invention can be used in methods of co-expression that allow for the parallel expression of multiple proteins that are essential subunits of stable protein complexes. In most of these protein partners are difficult to identify, and once they are known, other questions arise, which requires the creation of new constructs and attempting new complexes. Addressing such question using conventional technologies is laborious and time consuming. The vectors and methods of the present invention allow such questions to be addressed in a single reaction. With the vectors and methods of the present invention, one can mix and match any proteins in a potential complex easily in hours not weeks.

Many, if not most proteins in living cells exist as part of complexes, bound by a large number of weak, non-covalent interactions. The expression of a protein in the absence of a partner protein required for it to fold properly, or for stabilization, will in most cases lead to an insoluble (incorrectly folded) product, or degradation of the target protein by the cell's normal recycling systems. The vectors and methods of the present invention provide for parallel expression of multiple proteins that form a soluble and stable complex.

The vectors and methods of the present invention may be used to simultaneously and stoichiometrically introduce multiple heterologous genes into a single living cell and has many applications in proteomic research. For example, the vectors and methods of the present invention may be in used in study of pathways, cascades, multi-unit functional protein complexes, receptor-ligand interactions and the like.

The present invention is illustrated by the following examples. It is to be understood that the particular examples, materials, amounts, and procedures are to be interpreted broadly in accordance with the scope and spirit of the invention as set forth herein.

EXAMPLES

Example 1

Vectors for High Throughput (HTP) Recombinant Co-expression of Genes in E. coli

To develop vectors for use in high-throughput co-expression methods, various commercially available co-expression vectors were modified to make them compatible for use in the Gateways® system, marketed by Invitrogen. The nucleic acid sequences encompassing the att recombination sites of the Gateway® system were transferred into each of the commercially available co-expression vectors pCDF-1b (Novagen catalog no. 71330-3), pRSF-1b (Novagen catalog no. 1363-3), and pACYCDuet™-1 (Novagen catalog no. 71147-3). The new vector constructs are called pDEST-C1, pDEST-C2, and pDEST-C3, respectively. The development of the pDEST-C3 vector is discussed in more detail in Example 2. The nucleotide sequence of vectors obtained from Novagen and Invitrogen is available online, for example at invitrogen.com and novagen.com.

Invitrogen's Gateway® technology allows one to quickly shuttle a cloned insert between various vectors systems, such as cloning vectors and expression vectors. The Gateway® system utilizes phage lambda site-specific att recombination sites to make cloning simpler, more specific, and faster in comparison to traditional methods utilizing restriction enzyme digestion and ligation. As marketed, the Gateway® system is suitable for the expression of only single proteins, not the co-expression of multiple proteins. The nucleic acid sequence encompassing the att recombination site is also referred to as the Gateway® cloning cassette and includes the two recombination recognitions sequences, a gene encoding chloramphenicol resistance, and the ccdB gene.

A commercially available Gateway® conversion kit (Invitrogen, catalog #118280) was used for the initial conversion of the pCDF-1b and pRSF-1b vectors to derive the pDEST-C1 and pDEST-C2 vectors. Development of the pDEST-C3 vector required a modification of the commercially available Gateway® cassette, replacing a chloramphenicol resistance gene with a gene encoding zeocin resistance. This modified cassette, called the G144704 cassette, is discussed in more detail in Example 2.

The Gateway® conversion kit includes three different versions of the Gateway® cassette, representing reading frame A, reading frame B, and reading Frame C.1 (see FIG. 1). Gateway® cassette reading frame B was used in the construction of the pDEST-C1, pDEST-C2, and pDEST-C3 vectors. FIG. 1 presents the locations of the attR1 site, attR2 site, chloramphenicol resistance gene, ccdB gene and Prime 1 and Primer 2 for Gateway Conversion Cassettes for Reading Frame A, Reading Frame B and Reading Frame C.1. Procedures were as described in more detail in Invitrogen Life Technologies Instruction Manual Gateway® Vector Conversion System with One Shot® ccdB Survival™ Competent Cells (Catalog no. 11828-029, Version A, 14 Jun. 2004, 25-0748, Invitrogen Life Technologies).

The PshAI restriction site present in both the pCDF-1b and pRSF-1b vectors was used for the insertion of the Gateway® cassette. The restriction enzyme PshA1 recognizes the nucleotide sequence GACNN|NNGTC (SEQ ID NO: 38). For the pDEST-C1 vector, the PshA1 recognition sequence in the pCDF-1b vector is 5'-GACAA|GAGTC-3' (SEQ ID NO: 39) and the resultant sequence after the insertion of the Gateway cassette is 5'-GACAAATCAAC . . . GTTGATGAGTC-3' (SEQ ID NOS 40 & 41). For the pDEST-C2 vector, the PshA1 recognition sequence in the pRSF-1b vector is 5'-GACAA|GAGTC-3' (SEQ ID NO: 39) and the resultant sequence after the insertion of the Gateway cassette is 5'-GACAAGAGCTC . . . AAGCTTGAGTC-3' (SEQ ID NOS 42 & 43).

The pDEST-C1 vector was selected for by growth of on streptomycin and chloramphenicol. The pDEST-C2 vector was selected for by growth on kanamycin and chloramphenicol. The orientation of the insert was verified by digestion with PstI. A proper insert results in a PstI fragment of about 500 basepairs on an agarose gel. Plasmids showing the correct digestion pattern on an agarose gel were sequenced to ensure that the destination vector was created in the proper reading frame.

FIG. 2 is a map of the pDEST-C1 vector. FIG. 3 presents the nucleotide sequence of the pDEST-C1 vector. FIG. 4 is a map of the pDEST-C2 vector. FIG. 5 presents the nucleotide sequence of the pDEST-C2 vector.

Example 2

A Zeocin Resistant Gateway Technology Cassette

Currently available co-expression vectors do not include a vector with resistance to the antibiotic zeocin as a selectable marker. In this example, a co-expression vector containing both the Gateway® cloning cassette and zeocin resistance was created by replacing the chloramphenicol gene within a Gateway® cassette with the gene encoding zeocin resistance. The resultant modified Gateway® cassette is called the G144704 Zeocin resistant Gateway® Cassette. The G144704 Zeocin resistant Gateway® Cassette was inserted into Novagen's pACYCDuet™-1 expression vector. The resultant zeomycin resistant co-expression vector was named pDEST-C3. FIG. 6 is a map of the pDEST-C3 vector. FIG. 7 presents the nucleotide sequence of the pDEST-C3 vector.

Figures 8A, 8B, 8C, 8D:
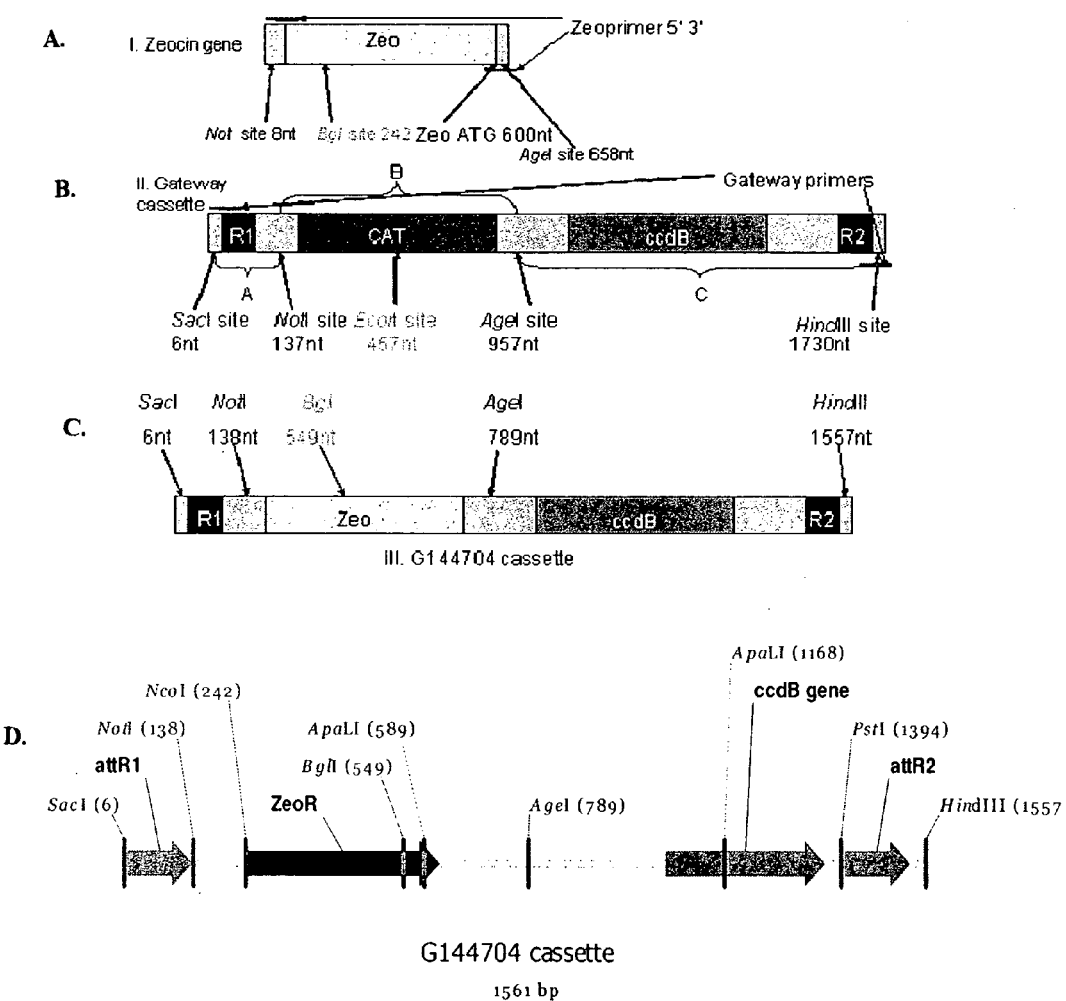
FIGS. 8A-8D show maps of the zeomycin gene, the Gateway cassette, and the G144704 cassette.

The gene encoding zeocin resistance, shown in FIG. 8A, was obtained from the pDONR-Zeo vector (Invitrogen catalog no. 12535-035). The nucleotide sequence of the pDONOR-Zeo vector is available online at novagen.com.

Zeocin is an antibiotic that is an effective selection reagent in *E. coli* (Drocourt et al., Nucleic Acids Res. 18:4009, 1990). Analysis of the commercially available pDONOR-Zeo vector sequence with the New England Biolab's NEBcutter software (Vincze et al., Nucleic Acids Res. 31:3688-3691, 2003) identified the 510 nucleotide long zeomycin gene and upstream regulatory sequences of approximately 58 nucleotides (FIG. 8A). This sequence is cut by the restriction enzyme BglI at nucleotide 242. A set of primers was designed for amplification of this region by PCR which also contained a 5' NotI site and a 3' AgeI site (restriction enzymes that flank the CAT gene within a Gateway cassette (see FIG. 8B). The 5' Zeocin gene primer used was 5'-GTT TCT TGC GGC CGC CAC GTT AAG GGA TTT TGG TCA-3' (SEQ ID NO: 24) and the 3' Zeocin gene primer used was 5'-GTT TCT TAC CGG TGT TGC AAC GAA CAG GTC ACT-3' (SEQ ID NO: 25).

The expression vector pDEST160 (Invitrogen) was used as the source for the Gateway DNA sequences (FIG. 8B) for amplification by PCR. The sequence was analyzed for restriction enzyme recognition sites. The enzymes SacI and HindIII, on the 5' and 3' ends, respectively, where identified as restriction enzymes that do not cut within the cassette and, thus, allow the cloning of the cassette into the new expression vector pACYC (Novagen, San Diego, Calif.). The restriction enzymes NotI and AgeI were selected as enzymes that cut the cassette at specific locations, allowing for the removal of the CAT gene from the Gateway cassette and replacement with the Zeo gene.

Polymerase chain reaction (PCR) was used to amplify this template. Primers used in the amplification of the Gateway cassette were designed with SacI and HindIII sites on the 5' and 3' ends, respectively. The Gateway cassette 5' primer was 5'-GTT TCT TGA GCT CGAT CAC AAG TTT GTA CAA AAA AGC-3' (SEQ ID NO: 26) and the Gateway cassette 3' primer was 5'-GTT TCT TAA GCT TAG CAG CCG GAT CTG ATC TTA-3' (SEQ ID NO: 27).

After PCR amplification of both the Gateway cassette, the resultant PCR products were digested with the enzymes indicated in FIG. 8B by the enzymes SacI and HindIII. The cassette had to be further digested with the restriction enzyme EcoRI, as fragments B and C in FIG. 8B are indistinguishable on a gel with sizes 820 and 773 nucleotides, respectively. Cutting fragment B with EcoRI, into a 500 nucleotide and a 320 nucleotide fragment, facilitated the accurate identification and isolation of fragments A and C. Fragment A and Fragment C were purified from agarose gels using standard techniques (see, for example, Sambrook et al., *Molecular Cloning: A Laboratory Manual*, Cold Spring Harbor Laboratory Press, 1989).

Fragment A and Fragment C (FIG. 8B) along with the digested Zeo PCR product were purified and mixed with the vector pACYC (digested with SacI and HindIII and gel-purified) and T4 DNA ligase. The ligation reaction was incubated overnight at 13° C. and transformed into a strain of *E. coli* called ccdB survival cells on plates containing both zeocin and chloramphenicol. Colonies were picked and grown up for plasmid DNA isolation. Each of the plasmids were digested with SacI, HindIII and BglI, since BglI cuts the Zeo gene, but it does not cut the commercially available Gateway cassette or pACYC. SacI and HindIII separate the plasmid and the newly inserted fragment. The correct digestion pattern as well, as correct molecular weight, were observed on agarose gel, confirming success of the new construct.

FIG. 8A shows a schematic of the cassette modification. Each site is labeled with the nucleotide number where the respective sites end. FIG. 8A shows the Zeocin gene as amplified for this experiment containing all regulatory regions. FIG. 8B shows the original Gateway cassette as amplified for this experiment. FIGS. 8C and 8D show the G144704 cassette. The G144704 cassette is also referred to herein "GatewayZeoPH." The strategy discussed above will be used to create additional co-expression vectors encoding tetracycline resistance. In FIG. 8B, the capital letters A, B, and C represent the three fragments of the original Gateway cassette when cleaved by enzymes listed in black. Fragments A and C are retained throughout the experiments. R1 and R2 represent the attR1 attR2 sites respectively. Each of the genes are represented by the following abbreviations: Zeo, zeocin resistance gene; CAT, chloramphenicol acetyl transferase (chloramphenicol resistance gene); ccdB, encodes a protein that stabilizes gyrase covalent intermediates and is lethal for *E. coli* cells not containing the ccdA gene (Bernard and Couturier, Mol. Gen. Genet. 226:297-304, 1991; and Salmon et al., Mol. Gen. Genet. 244:530-538, 1994).

Sequencing of the three plasmid clones confirmed the construct. The sequence of the G144704 cassette is shown in FIG. 9. Both the orientation and DNA sequence of the new cassette has been confirmed by DNA sequencing. This plasmid was designated pDEST-C3. Using the new destination vector pDEST-C3, a number of genes have been tested for expression of the correct molecular weight proteins.

The plasmid pDEST-C3 was then utilized in a L/R recombination reaction to test that the recombination sites were intact and that genes could be cloned into the Gateway R1 R2 cassette. The efficiency of the reaction was not affected by the insertion of the Zeocin gene between the recombination sites. To date, six different genes have been tested for expression of the correct molecular weight proteins using this destination vector.

The pDEST-C3 vector, along with the pDESt-C1 and pDEST-C2 vectors described in Example 1, are three new Gateway® compatible expression/destination vectors that, when used in combination with one of the many currently available co-expression vectors allows for the expression in a parallel manner up to four genes. Each of the pDEST-C1, pDEST-C2, and pDEST-C3 vectors can also be used individually, as a conventional expression vector. Each of the vectors can be maintained individually. Each of these vectors can be further modified to include various fusion tags/proteins, protease cleavage sites, expression signals. The plasmids presently have an N-terminal 6×His tag (SEQ ID NO: 44) and pDEST-C1 and pDEST-C2 have an enterokinase cleavage site just before the attR1 recombination site.

Example 3

Expression of Son Proteins

The vectors of the present invention were used to simultaneously express various Shewanella oneidensis ("Son") polypeptides; Son-3961, Son-0433, Son-1358, Son-1350, and Son-2015. The Son-3961 polypeptide was expressed in the pDEST-15G vector; Son-0433 polypeptide was expressed in the pDEST-C3 vector; Son-1358 polypeptide was expressed in the pDEST-C2 vector; Son-1350 polypeptide was expressed in the pDEST-C1 vector; and Son-2015 was expressed in the pDEST-15 vector.

Figure 10:
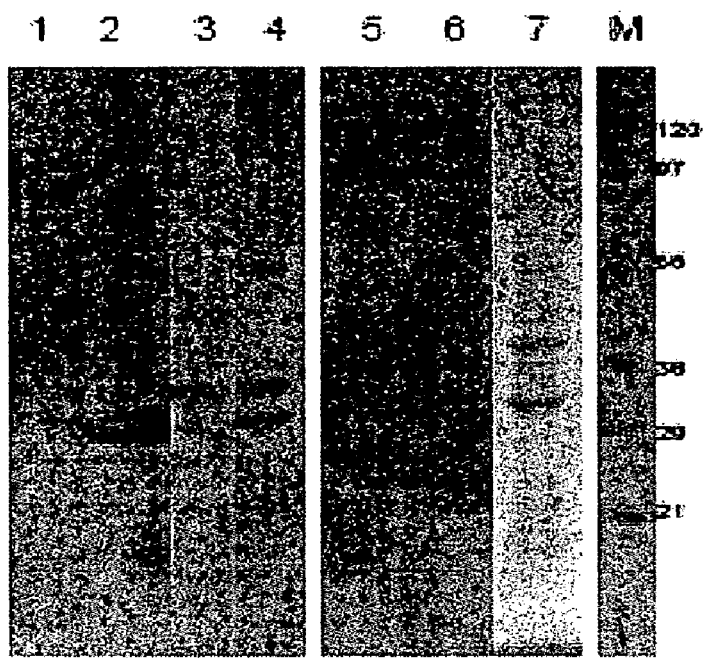
FIG. 10 show a SDS-PAGE demonstrating expression of various *Shewanella oneidensis* ("Son") polypeptides. Lane 1 shows expression of Son-3961. Lane 2 shows expression of Son-0433. Lane 3 shows expression of Son-1358. Lane 4 shows parallel expression of Son-3961, Son-0433 and Son-1358. Lane 5 shows expression of Son-1350. Lane 6 shows expression of Son-2015. Lane 7 shows parallel expression of Son-1350 and Son-2015. Lane "M" is molecular weight markers.

The respective plasmids were transformed into BL21 (DE3) cells (Stratagene, La Jolla, Calif.) and the cells were grown in LB media and induced with 1 mM IPTG at OD of 0.6. The cells were then allowed to grow for four hours. Cells were harvested by spinning at 13,000 RPM for 1 minute and the resulting pellet was then run on an SDS-PAGE gel. The results are shown in FIG. 10. Lane 1 shows the expression of Son-3961. Lane 2 shows the expression of Son-0433. Lane 3 shows the expression of Son-1358. Lane 4 shows the parallel expression of Son-396 1, Son-0433 and Son-1358. Lane 5 shows the expression of Son-1350. Lane 6 shows expression of Son-2015. Each of the four constructs created contains an affinity tag with varying cleavage sites. Thus, up to four different trials (see FIG. 10, lanes 4 and 7) can be carried out simultaneously in one experiment and therefore may greatly increase protein expression and screening efficiency.

Example 4

Expression of Clostrodium thermocellum JW-20 Polypeptides

Materials and Methods

For expression studies, genes cloned lab from the organism Clostrodium thermocellum JW-20 were expressed using the pDEST-C1, pDEST-C2, and pDEST-C3 vectors. Entry vectors were created with the use of pDONR-221 (kanamycin resistance) or pDONR-Zeo (Zeocin® resistance). The L/R recombination reaction was used to insert six genes into the R1-R2 sites of each of the vectors. These individual vectors were then transformed into Mach-1 E. coli cells (Invitrogen). After plasmid DNA was purified and the size of the DNA was confirmed by agarose gel electrophoresis, E. coli BL21 (DE3) cells were transformed with each of the vectors at the same time and plated on media supplemented with the appropriate antibiotics. These gene targets were chosen as proteins which had been expressed and purified successfully in earlier experiments. They were grown in one milliliter small scale test cultures overnight in LB medium. The cells were then induced with 2 mM IPTG for 5 five hours and the total cell and soluble fractions, where applicable were run on a gel. Soluble fraction of cells was achieved by incubating the cell pellet with five mg/ml lysozyme for fifteen minutes at room temperature.

Figure 12:
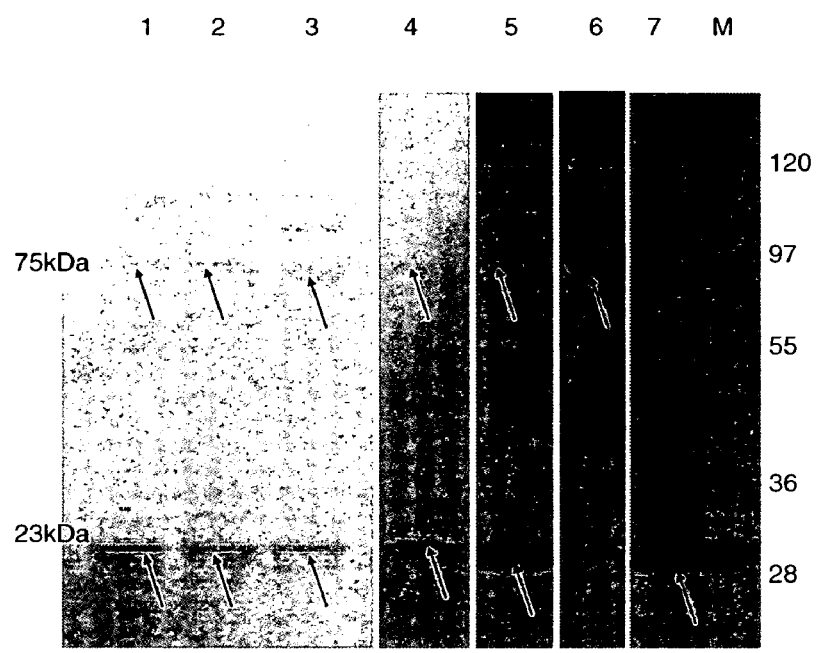
FIG. 12 shows the co-expression of a stable protein complex for Son0433 and Son1284. Lanes 1-3 show consecutive fractions from gel-filtration. Lane 4 shows the elution from the NiNTA, 6×HIS (SEQ ID NO: 44) affinity column. Lanes 5-7 show total cell extracts; Lane 5 shows the co-expression of Son0433 and Son1284; Lanes 7 and 6 show the single expression experiments of Son0433 and Son1284, respectively.

For studies on the purification of protein complexes, cloned genes from the organism Shewanella oneidensis (Son) were provided Dr. Jizhong Zhou from Oak Ridge National Labs. The genes Son0433 (also called Regulator of Sigma Factor D) and Son1284 (also called Sigma Factor D) were cloned into pDEST 221. These clones were then inserted into each of the vectors (Son1284 into pDEST-C3 and Son 0433 into DEST C1) and the colonies were grown in defined PA 0.5 G media overnight. These two proteins (Son0433 and Son1284) were identified as a complex by Database of Interacting Proteins. These cultures were then inoculated into 5 L of PASM 5052 media that is self inducing and was labeled with Seleno-Methionine. The cultured were grown at 30 degrees celsius for sixteen hours. The cells were harvested by centrifugation and the cells were lysed by sonication in 50 mM HEPES buffer pH 7.6/500 mM NaCl. Both of the proteins were purified by their individual 6×HIS tags (SEQ ID NO: 44), in the same solution by one step elution with 400 mM imidazole. The eluted sample was then passed through a Superdex 75 column in 100 mM NaCl, 50 mM HEPES pH 7.6, 1 mM DTT. FIG. 12 shows the fractions from the purification, showing that the proteins formed a complex.

mRNA detection. E. coli BL21(DE3) cells containing the gene Pfu-89099 cloned into the entry clones pDEST-C1, pDEST-C2, pDEST-C3 and pET15G were grown overnight with the appropriate antibiotics and induced with 3 mM IPTG for six hours. Total RNA was isolated with the RNeasy kit from Qiagen (Valencia, Calif.) and was run on a 1.0% agarose gel. The amount of RNA was quantitated with the intensity of the band detected in the gel.

Results

Compatibility with existing system. The new vectors pDEST-C1, pDEST-C2, and pDEST-C3 are compatible with the existing Gateway cloning system via the well-known L/R reaction. The efficiency of the reaction was not affected by the insertion of the zeocin gene between the recombination sites. The proteins expressed are all the correct molecular weight with 2 shown in experiments below. Both the orientation and DNA sequence of the new cassette has been confirmed by DNA sequencing. The most widely used entry vectors used today encode kanamycin resistance. If these vectors are used, they can make the isolation of correct destination vectors from the L/R reaction with pDEST-C2 difficult and not HTP. The use of pDONR-Zeo is recommended for the use of these vectors, since other antibiotic resistance markers can interfere with the cloning into any of the four vectors.

Parallel screening of genes. In the 2×2×2 matrix shown in FIG. 11, all of the genes made their predicted protein product. The expression of two vectors at the same time is cost effective and convenient. With transformation of the third and fourth vectors, a reduced antibiotic concentration resulted in improved DNA quality. There is no apparent difference in growth rate when using any combination of the vectors used. The proteins are expressed in a similar manner in all cases, but the amount of the protein made is different in each case.

Figure 11:
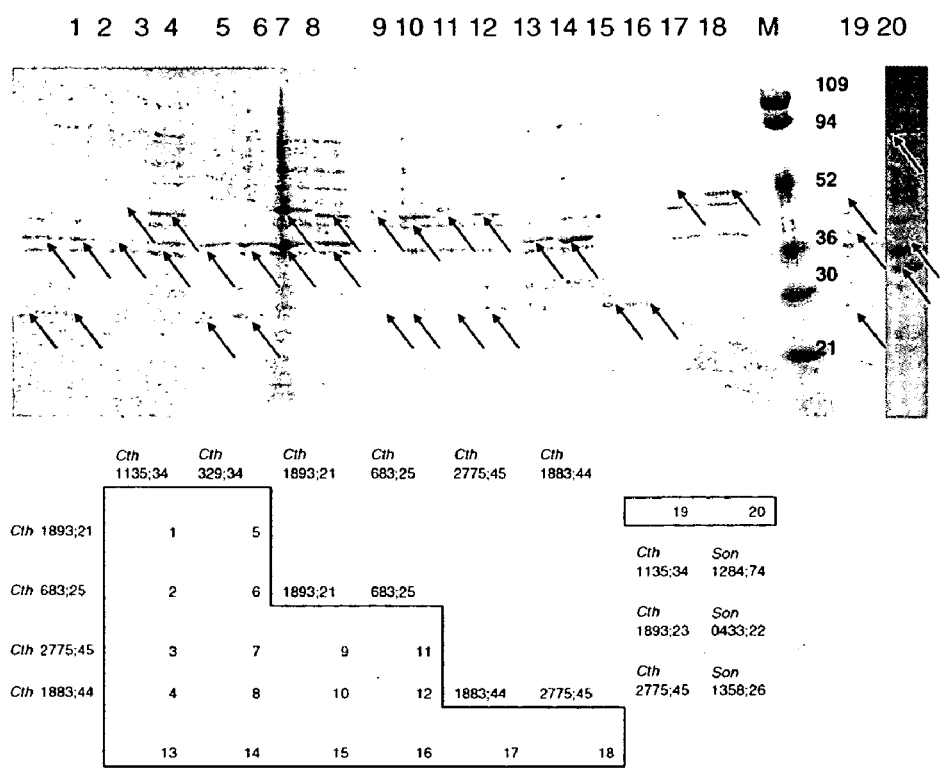
FIGS. 11A and 11B show the co-expression of *Clostrodium thermocellum* JW-20 gene construct in pDEST-C1-C3 vectors.

Each vector/protein construct was also expressed individually (FIG. 11). All individual expression experiments show expression of the proteins in a similar way as the parallel expression studies. This shows that our system is compatible with the previously established Gateway® system.

FIG. 11A is an SDS-PAGE of the total cell extract for each *Clostrodium thermocellum* JW-20 gene construct. The black arrows point to the bands that correspond to the proteins expressed in the cells. FIG. 11B is a chart identifying each of the lanes. Lanes 1 through 12 are cells with two different, randomly selected, genes expressed. Lanes 13-18 are the expression testing of those cells with only one expression construct, to monitor expression of the individual proteins. Lanes 19 and 20 are the two lanes, where three non-interacting proteins are expressed.

Parallel expression for purification. The experiments illustrate that the expression system can produce the desired protein. The data shows that varying combinations of ORFs can be expressed in parallel, in the same cell, without inhibiting each others' expression. Since these proteins are also soluble as observed during single expression experiments, the purification of all of the soluble proteins is possible, especially if the proteins expressed together have large difference in molecular weight, or only three vectors are used together. pDEST-C1 and pDEST-C2 contain an enterokinase cleavage site which can also be used for cleavage of the tag, while pDEST-C3 does not. All Gateway® compatible clones in our collection have a Tobacco Etch Virus (TEV) protease cleavage site between the gene and the recombination sequence for a final processing step. This ensures that the protein attempted for crystallization will have the native sequence, without any extra amino acids. All constructs are optimized for structural biological experiments, so when the protein is fully processed only 2 N-terminal glycines are extra to the native sequence.

Co-expression of a stable protein complex. Gateway® compatible HTP protein complex expression is the power of the present invention. Expressing more than one protein at the same time to form a stable protein complex is shown in this example. When the newly developed co-expression or parallel expression system is used, these experiments now can be carried out in a HTP manner, or with the use of all of the resources available with Gateway® compatible clones. The two genes used in here, Son0433 (Regulator of Sigma Factor D (rsd)) and Son1284 (Sigma Factor D (rpoD)), were co-expressed in culture and they co-purified in gel filtration, in the same fraction. The proteins expressed separately before the co-expression studies and the total yield of protein during co-expression was comparable, although the expression level of Son0433 was slightly affected (see a comparison of lanes 5, 6, and 7 in FIG. 12). The expression level for Son 1284 seemed to have decreased in this case. The interaction between these two proteins was not investigated. The separation of the two proteins was not possible in this co-expression experiment, due to their seemingly stable interaction with each other. Only the smaller molecular weight protein (Son 0433), due to its excess concentration compared to (Son1284) could be isolated from the mixture, by filtering the solution through a 50 kDa MW cutoff concentrator.

FIG. 12 shows the co-expression of a stable protein complex. Proteases were a problem with rpoD; the effect of proteolysis on rpoD can be seen in lane 3 of FIG. 12. Lanes 1-3 of FIG. 12 were the consecutive fractions from gel-filtration through a Superdex 75 (Amersham, Piscataway, N.J.). Lane 4 of FIG. 12 is the elution from the NiNTA, 6×HIS (SEQ ID NO: 44) affinity column. Lanes 5 through 7 are the total cell gels, with Lane 5 showing the co-expression of Son0433 and Son1284. Lanes 7 and 6 are the single expression experiments of Son0433 and Son 1284 respectively. These results for the Son0433 and Son1284 proteins are also shown in lanes 1-4 of FIG. 10.

This example facilitates the parallel expression of proteins that are essential parts of a stable protein complex. In most of these protein partners are difficult to identify, and once they are known, other questions arise, which requires the creation of new constructs and new complexes. These second set of experiments, or sub-cloning, used to be laborious and time consuming. The true power of this system lies here, since with these novel vectors, scientists now can mix and match any proteins in a potential complex easily in hours not weeks. The parallel expression testing or the parallel expression of non-interacting proteins is an added benefit, which was not anticipated. Beyond those benefits already listed, some of the other potentials of this system is that the use of expression vectors that encode for antibiotics other than ampicillin are preferred for protein expression, especially when the cells have to be grown for long times, for increased time of induction. With the vectors of the present invention, a drastic reduction of cell mass is observed, when compared to non-ampicillin resistance encoding vectors in defined media. The effects of defined media on the expression is important, since labeling of each protein with seleno-mnethionine allows for the HTP structure determination of each protein. Using currently available vectors in concert with the vectors of the present example, the amount of cells has increased.

Example 5

Parallel Gene Expression and Target Salvaging at Gene Level

This example demonstrates that three Gateway® compatible coexpression vectors, pDEST-C1, pDEST-C2, and pDEST-C3, when used together, along with a commercially available expression vector, in the same cell, can express in a parallel manner up to four ORFs.

Materials and Methods

Expression testing. The genes for all ORFs shown were cloned from the organism Clostrodium thermocellum JW-20. Entry vectors were created with the use of pDONR-221 (kanamycin resistance) or pDONR-Zeo (Zeocin® resistance). The L/R recombination reaction was used to insert six ORFs into the R1-R2 sites of each of the vectors. These individual vectors were then transformed into Mach-1 *E. coli* cells (Invitrogen). After plasmid DNA was purified the size of the DNA was confirmed by agarose gel electrophoresis and *E. coli* BL21 (DE3) cells were transformed with each of the vectors at the same time and plated on media supplemented with the appropriate antibiotics. These ORFs were chosen randomly from proteins that had been expressed and purified successfully in earlier experiments. They were grown in one milliliter small scale test cultures overnight in LB medium. The cells were then induced with 2 mM IPTG for five hours and the total cell and soluble fractions, where applicable were run on a gel. Soluble fraction of cells was achieved by incubating the cell pellet with five mg/ml lysozyme for fifteen minutes at room temperature.

Solubilization and Purification of a protein complex. The human Plasma Membrane Calcium ATPase C-terminal tail was cloned by Hua Yang. This ninety amino acid 10.5 kDa protein was truncated to amino acid 1055 through 1142. This construct was predicted to have secondary structure by JPRED (Cuff et al., Bioinformatics 14:892-3, 1998). The PCR product was cloned into pDONR-Zeo vector. The hPMCA construct was then inserted into pDEST-C1. The Calmodulin construct was supplied by Dr. Jeffrey Urbauer in a pET 15 plasmid. The two vectors were then co-transformed into BL21-DE3 cells. These cultures were then inoculated into five liters of PASM 5052 media, a self inducing media labeled with seleno-methionine. The cultures were grown at 30° C. for sixteen hours. The cells were harvested by centrifugation at 4000 g and were lysed by sonication in 50 mM HEPES buffer pH 7.6 500 mM NaCl. Both of the proteins were purified by their individual 6×HIS tags (SEQ ID NO: 44), in the same solution by one step elution with 400 mM imidazole. The eluted sample was then passed through a Superdex 75 column in 100 mM NaCl, 50 mM HEPES pH 7.6, 1 mM DTT.

Results

Compatibility with existing system. The new vectors pDEST-Cx described here are compatible with the existing Gateway® cloning system via the well-known L/R reaction. The efficiency of the reaction was not noticeably affected by the insertion of the Zeocin® gene between the recombination sites. The proteins expressed are all the correct molecular weight. Both the orientation and DNA sequence of the new DESTination vectors has been confirmed by DNA sequencing. The most widely used entry vectors encode kanamycin resistance which is not productive when using the pDEST-C1-C3 vectors. The use of pDONR-Zeo is recommended use as a pDONR vector, since other antibiotic resistance markers can interfere with each of the four vectors.

Figure 13:
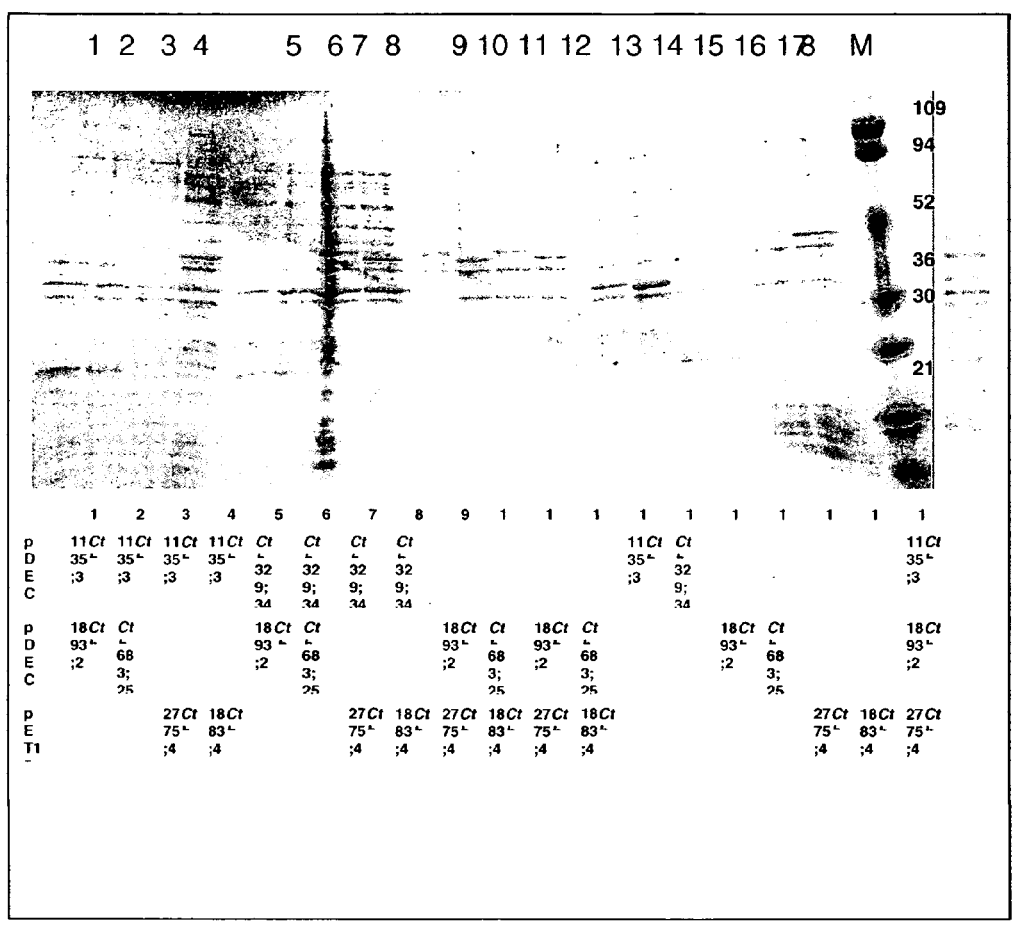
FIG. 13 shows parallel expression of non-interacting proteins in the same cell. Lanes 13-18 are the expression studies of single genes per cell. Lanes 1-12 are the expression tests of two genes per cell. Lane 19 is the parallel expression of three genes.

Parallel screening of genes. In the 2×2×2 matrix shown in FIG. 13, all of the genes made their predicted protein product. The expression of two vectors at the same time is the most cost effective and convenient method used here with cell yields similar as those cells expressing each construct individually. Transformation with the third and fourth vectors demonstrates a reduced success rate, but this can be overcome by reducing the concentration of the antibiotics. Nonetheless each non-interacting, co-expressed protein, was made in this system as they were when expressed individually FIG. 13. The same expression profile are seen for the co-expression of three proteins. The proteins were all known to be soluble prior to expression and the soluble cell fractions were loaded onto the gel in FIG. 13. FIG. 13 shows parallel expression of non-interacting proteins in the same cell. Lanes 13-18 are the expression studies of single genes per cell. Lanes 1-12 are the expression tests of 2 genes per cell. Lane 19 is the parallel expression of three genes. The results from this co-expression experiment are also presented in FIG. 11.

Figure 14:
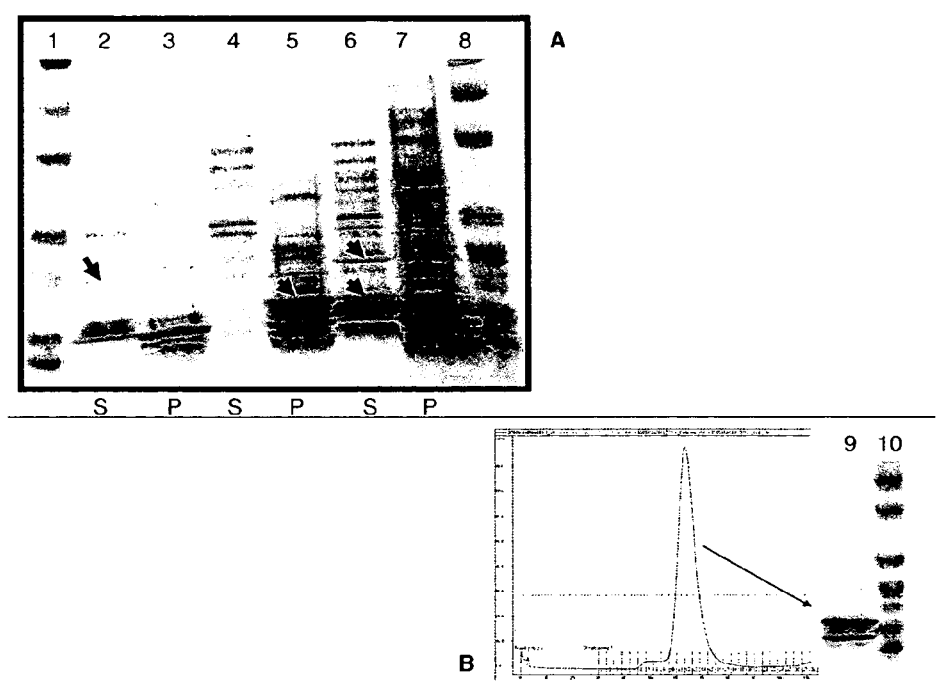
FIGS. 14A and 14B show improved recombinant protein solubility with co-expression of the two individual proteins, calmodulin and the human Plasma Membrane Calcium ATPase C-terminal calmodulin binding domain (hPMCA4b).

Improving protein solubility with co-expression of a protein complex. The protein complexes expressed are of greater use than just co-expression of already soluble proteins. Co-expression of previously insoluble protein with soluble, well expressing partner has been known to improve solubility. In this experiment, the insoluble human Plasma Membrane Calcium ATPase isoform 4b's (hPMCA4b) C-terminal tail was used as the insoluble protein. Previous work has shown that this part of the protein insoluble (see FIG. 13, lane 5) and it has been identified as the Calmodulin Binding Domain of the protein (Kessler et al., Biochemistry 31:11785-92, 1992). This insoluble protein was co-expressed, using our vectors, with Calmodulin, a soluble protein. These two proteins have been known to interact (Elshorst et al., Biochemistry 38:12320-32, 1999). Upon their co-expression, as shown in FIG. 14A, the two proteins are co-expressed and the previously insoluble C-terminal fragment of hPMCA4b is now soluble and in a complex with Calmodulin. This complex can also be purified together as shown by lane 9 of FIG. 14B.

Improving recombinant protein solubility with coexpression. The expression testing of the two individual proteins, calmodulin and the human Plasma Membrane Calcium ATPase C-terminal calmodulin binding domain (hPMCA4b) is shown in FIGS. 14A and 14B. The hPMCA protein was truncated for structural studies. The amino acids used here are from 1055 through 1145. This construct is the JPRED predicted structured part of the hPMCA (Cuff et al., Bioinformatics 14:892-3, 1998. In FIG. 14A, lanes 1 and 8 are the molecular weight markers; lanes 2, 4, and 6 are the three soluble fractions that represent calmodulin hPMCA4b and co-expression of the two, respectively; lanes 3, 5 and 7 are the pellet fractions of the same growths; lane 6 contains the soluble complex and this growth was further pursued to purification. FIG., 14B show the FPLC 280 nm chromatogram and the SDS-PAGE of the indicated fraction in lane 9 showing a complex of the two proteins. Lane 10 is the same marker as lanes 1 and 8 of FIG. 13.

The pDEST-C1, pDEST-C2, and pDEST-C3 coexpression vectors present at least five new innovations. One, all four of these constructs are created with the same reaction and plated on four different antibiotic supplemented plates. Two, each of these vectors can also be used by itself, which allows for their use as just a conventional expression vector. Three, increasing the throughput of expression screening by testing up to four non-interacting ORFs' expression/solubility in the same cells. Four, they are new tools for solubilizing proteins through soluble complex expression. And, five, HTP Expression of already known protein complexes. The use of parallel processing at the screening and expression level enables the structural genomics community to express, in an HTP manner, protein-protein complexes and cut costs by increasing expression efficiency of non-interacting soluble proteins.

Example 6

Copy Number and Increased Protein Solubility

Currently available recombinant protein expression system, based on very efficient and fast RNA polymerases, such as T7 polymerase, used in the DE3 cell lines are very powerful and widely used. However, the benefit of the increased efficiency with this expression system presents problems. The overabundance of the recombinant transcript causes the cells to translate the transcript faster than the protein can be folded. This folding inefficiency then interferes with soluble protein expression.

A solution for this problem with protein expression is to use the vectors of the present invention to manipulate the copy number of the vectors that encode the recombinant proteins. The vectors pDEST-C1, pDEST-C2, and pDEST-C3 have different replicons which results in different numbers of copies in the cell. This characteristic facilitates their use as co-expression vectors.

Previously, the protein PF1955 from the organism *Pyrococcus furiosus* was expressed and its structure determined. This effort took two years to accomplish, since the protein was not soluble. The vector pDEST527 was used to express this protein for refolding studies. The present example demonstrates that the PF1955 protein can be expressed in a complex or by itself, when using a vector with a lower copy number that that of pDEST527. The results are shown in FIG. 15, a SDS-PAGE gel of the expression experiment.

Figure 15:
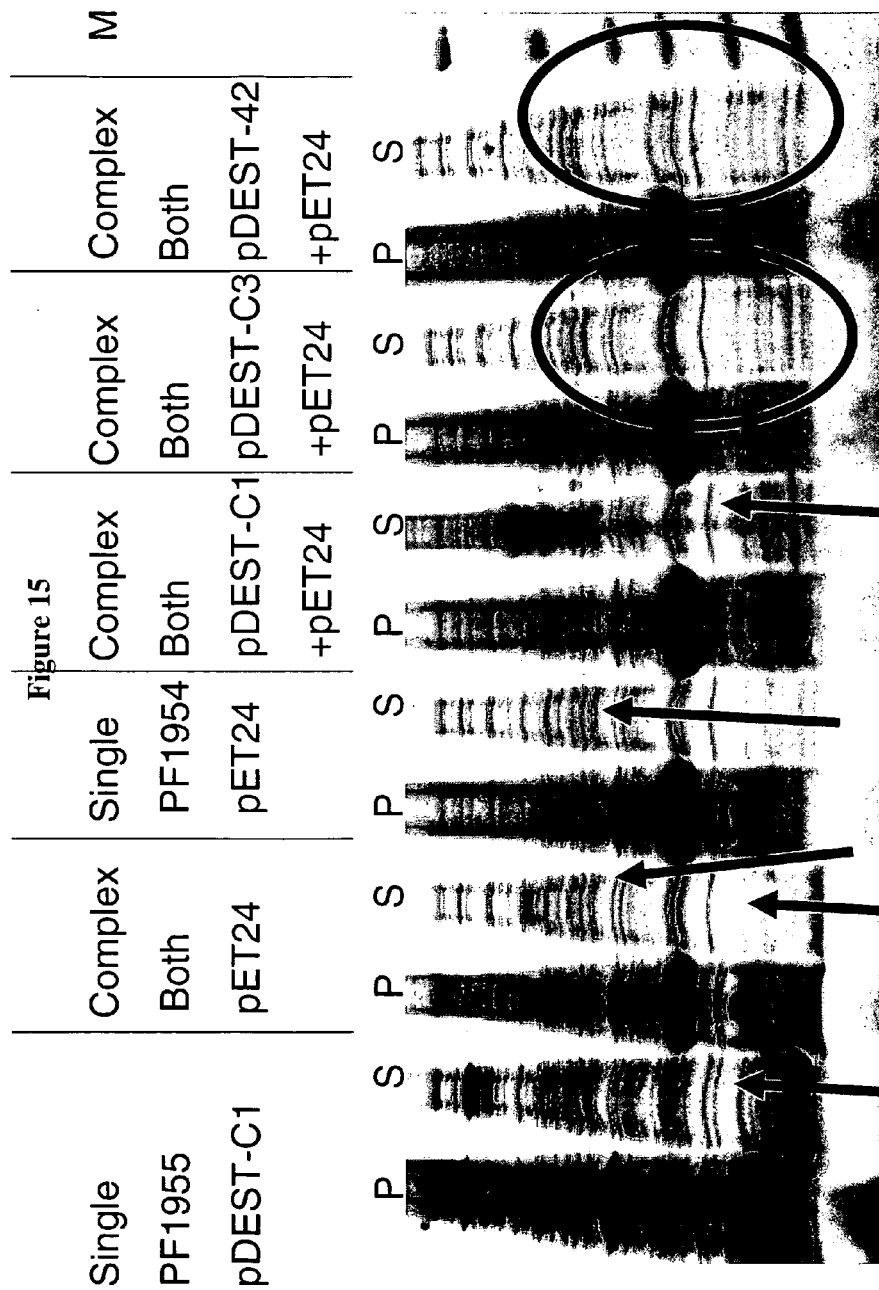
FIG. 15 is an SDS-PAGE gel showing expression of the PF194 and PF1955 proteins. Each pair of lanes shows total cell fraction ("P") and soluble ("S") fraction, side by side. "M" represents molecular size markers (6×His tag disclosed as SEQ ID NO: 44).

In FIG. 15, every pair of lanes show total cell fraction ("P") and soluble ("S") fraction side by side. Lanes 1 and 2 show expression of PF1955 protein in the vector pDEST-C1. Lanes 1 and 2 show that in the PF1955 protein is soluble when expressed in the pDEST-C1 vector. Lanes 3 and 4 of FIG. 15 show expression of the PF1955 and PF1954 proteins, each cloned into the pET24 vector. These two genes are structured in the same operon in the genome of *Pyrococcus furiosus*. Lanes 3 and 4 demonstrate expression of the complex using traditional methods of protein complex expression. Lanes 5 and 6 show expressions of the PF1954 protein in the pET24 vector. Lanes 7 and 8 show expression of the PF1955 protein in the pDEST-C1 vector and expression of the PF1954 protein in the pET24 vector. An expression pattern similar to the control was observed. Lanes 9 and 10 show expression of PF1955 protein in the pDEST-C3 vector and expression of the PF1954 protein in the pET24 vector. Little expression was observed. Lanes 11 and 12 show expression of the PF1955 protein in the pDEST42 vector and expression of the PF1954 protein in the pET24 vector. Both the plasmids have the same replicon, but different antibiotics resistances. These lanes show no expression of either protein from the complex, suggesting that plasmid copy number has an effect of recombinant protein expression. Lane "M" represents molecular size markers.

In the experiments of this example, the pDEST-527 vector has the 6HIS tag (SEQ ID NO: 44) of Met R S G S H H H H H H R S D I T S L Y K K A E R E (SEQ ID NO: 28) while the pDEST-C1 vector has 6HIS tag (SEQ ID NO: 44) of Met A H H H H H H V G T G S N D D D D K S T S L Y K K A E R E (SEQ ID NO: 29). The difference in HIS tags is five amino acids, encoding an enterokinase cleavage site. The pDEST-527 vector has a copy number of 40 copies per cell and the pDEST-C1 vector has a copy number of 20-40 copies per cell.

This example demonstrates that the use of an alternate copy number vector alone can improve solubility. This example also shows that different copy number plasmids, when used together, can efficiently form a complex of two proteins (PF1954 and PF1955) that interact on protein level.

Example 7 pDEST-CM Vectors

The additional vectors pDEST-CM1, pDEST-CM2, pDEST-CM3, and pDEST-CM4 were developed. To develop these vectors, the commercially available Multisite Gateway®. Three-Fragment cassette, pDEST R4-R3 (Invitrogen, catalog #12537-023) was introduced into the commercially available vectors pCDF-Duet1 (Novagen catalog #71340-3), pRSF-Duet1 (Novagen catalog #71341-3), pACYC-Duet1 (Novagen catalog #71147-3), and pET-Duet 1 (EMD Biosciences, catalog #71146-3). The nucleotide sequence of vectors obtained from Novagen and Invitrogen is available online, for example at invitrogen.com and novagen.com.

Modification of the pCDF-Duet1 vector resulted in the pDEST-CM1 vector. FIG. 16 shows a map of the pDEST-CM1 and FIG. 17 presents the nucleotide sequence of the pDEST-CM1 vector. pDEST-CM1 was created by amplifying the Gateway® Multisite cassette from pDESTR4-R3 and adding SacI and HindIII sites to the 5' and 3' ends, respectively. This construct was then ligated to similarly digested pCDF-Duet1, to create pDEST-CM1. The nucleotide sequence of the pCDF-Duet1 vector is available online, for example at novagen.com.

Modification of the pRSF-Duet1 vector resulted in the pDEST-CM2 vector. FIG. 18 shows a map of the pDESTCM-2 vector and FIG. 19 presents the nucleotide sequence of the pDEST-CM2 vector. pDEST-CM2 was created by amplifying the Gateway® Multisite cassette from pDESTR4-R3 and adding SacI and HindIII sites to the 5' and 3' ends, respectively. This construct was then ligated to similarly digested pRSF-Duet1, to create pDEST-CM1. The nucleotide sequence of the pRSF-Duet1 vector is available online, for example at novagen.com.

Modification of the pACYC-Duet1 vector resulted in the pDEST-CM3 vector. To construct the pDEST-CM3 vector, a tetracycline resistance multisite cassette (TetR multisite cassette) was first created by amplifying the multisite cassette from the pDEST R4-R3 vector by PCR with the same primers used for the creation of the pDEST-CM1, pDEST-CM2, and pDEST-CM4 vectors. The tetracycline resistance (TetR) gene was amplified from the plasmid pBR322 (Promega #D1511) using as a 5' primer:
GTTTCTTGCGGCCGCTTCTCATGTTTGA-CAGCTTATCAT (SEQ ID NO: 30) (creating a recognition site for the restriction enzyme NotI) and as a 3' primer: GTTTCTTTCTAGAGACGCGATGGATATGTTCTG (SEQ ID NO: 31) (creating a recognition site for the restriction enzyme XbaI).

The two PCR reactions then were then cleaved with enzymes from New England Biolabs using standard protocols. The Multisite PCR product was digested with HindIII, SacI, NotI and XbaI, creating two fragments of interest; a 834 bp SacI-XbaI fragment and a 208 bp NotI-HindIII fragment. Fragments were gel purified using standard methods. The TetR gene PCR product was digested with NotI and XbaI and ligated to the two remaining fragments of the Multisite cassette, replacing the CamR gene with the TetR gene between the NotI and XbaI sites. This was simultaneously ligated to HindIII, SacI digested pACYCDuet-1 to create pDEST-CM3 (See FIG. 20). Note this cannot be moved out using EcoNI and HindIII as the other Multisite cassette constructs were made due to internal EcoNI and HindIII sites in this construct.

Figure 20:
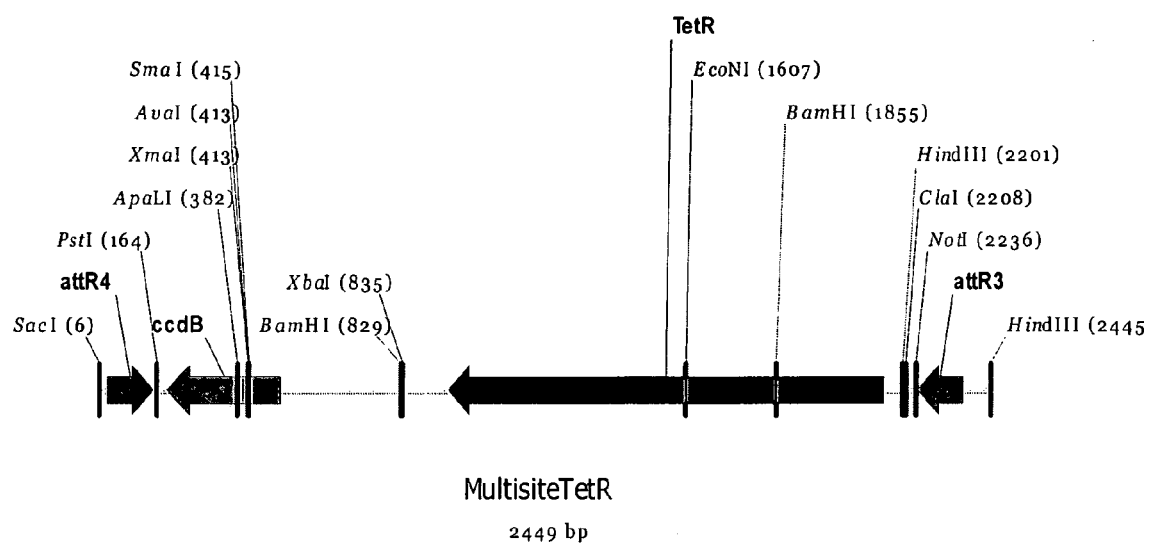
FIG. 20 shows a map of the Multisite TetR cassette.
Figure 21:
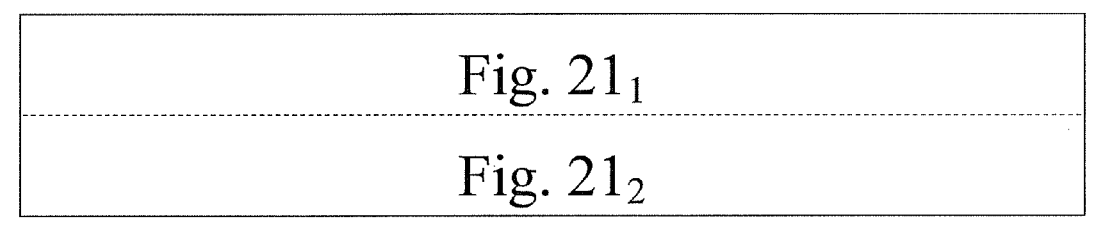

FIG. 20 shows a map of the Multisite TetR cassette. FIG. 21 is the nucleotide sequence of the Multisite TetR cassette (SEQ ID NO: 7).

FIG. 22 shows a map of the pDEST-CM3 vector. FIG. 23 is the nucleotide sequence of the pDEST-C3 vector (SEQ ID NO: 8)

Modification of the pET-Duet 1 vector resulted in the pDEST-CM4 vector. FIG. 24 shows a map of the pDEST-CM4 and FIG. 25 presents the nucleotide sequence of the pDEST-CM4 vector. The pDEST-CM4 vector was created by amplifying the Gateway Multisite cassette from pDESTR4-R3 and adding SacI and HindIII sites to the 5' and 3' ends, respectively. This was then ligated to similarly digested pET-Duet1.

The pDEST-CM1, pDEST-CM2, pDEST-CM3, and pDEST-CM4 vectors were produced following the procedures described in Example 1 for the development of the pDEST-C1, pDEST-C2, and pDEST-C3 vectors. A Multisite Gateway® cassette with SacI and HindIII ends was cloned into the first multicloning site of each pDUET vector.

The pDEST-CM series vectors will allow the simultaneous expression of up to sixteen genes, twelve cloned by recombination into the Multisite, and four cloned by standard techniques into the second multiple cloning site on each vector.

Example 8

High Throughput RNAi Co-interference

Figure 26:
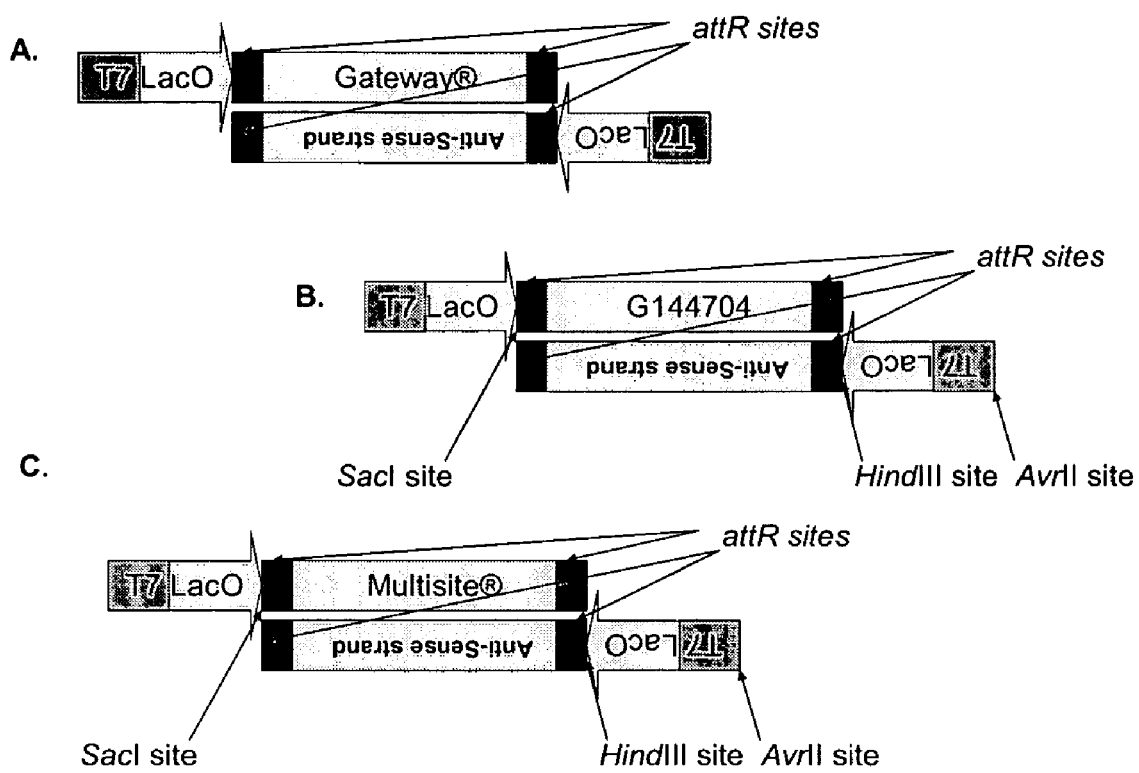
FIGS. 26A-26C show the various cassettes used in the construction of the pRIPPER vectors.

Current RNA-mediated interference (RNAi) assays study one gene at a time. Current RNAi vectors rely on T7 promoters and Lac operator sequences. To allow for the analysis of multiple genes simultaneously, this example presents five new vectors for use in methods of high throughput RNAi co-interference. These five vectors are pRIPPER-1, pRIPPER-2, pRIPPER-3, pRIPPER-II, and pRIPPER-III. Each of these high throughput RNAi vectors contains two T7 promoters ("T7") and two Lac Operator sequences ("LacO") pointing towards the Gateway® cassette from both sides (See FIG. 26A). The vectors also have an antibiotic resistance gene and an origin of replication.

Each of the new vectors pRIPPER-1, pRIPPER-2, and pRIPPER-3 contain a Zeocin-labeled Gateway® cassette G144704 flanked by two T7 promoters and Lac Operator sequences (see FIG. 26B) pointing at the Gateway® sequences. This DNA cassette is from the pC3-DEST vector, described in more detail in Example 2. The 3' end of this Gateway® cassette contains a HindIII restriction site that is the end of the site. This sequence is followed by a second T7 promoter and open reading frame with multiple cloning site and S-tag™, followed by an AvrII site. All of these sequences are removed in order to reduce background by digestion with the two restriction enzymes AvrII and HindIII. Further downstream, a T7 terminator is retained.

To create the pRIPPER-3 vector, the pDEST-C3 vector (as described in more detail in Example 2) was altered to remove a multiple cloning site, an S-tag™ and an AvrII restriction site by digestion with the two restriction enzymes AvrII and HindIII. Then a second T7 promoter and a second Lac operator were added. The T7 promoter and Lac operator were added by ligating in the short double stranded synthetic oligonucleotide sequence formed by 5' CTAGGTAATACGACTCAC-TATAGGAATTGTGAGCGGATAACAATTCCA 3' (SEQ ID NO: 32) and 3'CATTATGCTGAGTGATATCCTTAA-CACTCGCCTATTGTTAAGGTTCGA 5' (SEQ ID NO: 33). The sequence of the T7 promoter is shown in bold. The underlined sequence is the Lac Operator sequence. The proper sequence overhang needed for the AvrII enzyme recognition sequence to be complete and the sequence of the HindIII enzyme recognition sequence required for ligation are formed by the double stranded product. This sequence was synthetically created at Integrated DNA Technologies (Coralville, Iowa).

The G144704 cassette was modified by inserting a copy of the T7 promoter LacO operator in reverse orientation relative to the upstream promoter into the HindIII-AvrII sites of pDEST-C3, creating pRIPPER-3, and the novel G144704ri cassette (with a reversed-orientation promoter) surrounded by SacI and AvrII sites. This G144704ri cassette was then removed from pRIPPER-3 by digestion with SacI-AvrII, and ligated into similarly digested pCDFDuet-1, pRSFDuet-1, and pETDuet-1 to create pRIPPER-1, pRIPPER-2, and pRIPPER-4 respectively.

A map of the pRIPPER-3 vector is shown in FIG. 27 and the nucleotide sequence of the pRIPPER-3 vector (SEQ ID NO: 10) is shown in FIG. 28.

To create the pRIPPER-1 vector, a large fragment of the pRIPPER-3 vector was inserted into Novagen's pCDF-Duet™-1 vector (catalog no. 71340-3). Specifically, the sequence from between the SacI site (5' site of pC3-DEST Zeo labeled Gateway® cassette) and the AvrII site in vector pRIPPER-3 were moved into the pCDF-DUET, creating pRIPPER-1. Clones with correct digestion pattern with AvrII, HindIII and SacI were sequenced to ensure correct sequence. A map of the pRIPPER-1 vector is shown in FIG. 29 and the nucleotide sequence of the pRIPPER-1 vector (SEQ ID NO: 11) is shown in FIG. 30.

To create the pRIPPER-2 vector, this same fragment of the pRIPPER-3 vector was inserted into Novagen's pRSF-Duet™-1 vector (catalog no. 71341-3). A map of the pRIPPER-2 vector is shown in FIG. 31 and the nucleotide sequence of the pRIPPER-2 vector (SEQ ID NO: 12) is shown in FIG. 32.

To create the pRIPPER-4 vector, this same fragment of the pRIPPER-3 vector was inserted into the pETDuet-1 vector (Novagen). A map of the pRIPPER-4 vector is shown in FIG. 33 and the nucleotide sequence of the pRIPPER-2 vector (SEQ ID NO: 13) is shown in FIG. 34.

To create the pRIPPER-II vector, the Multisite® Gateway® Cassette from Invitrogen's pDEST™ R4-R3 vector (catalog no. 12537-023) was amplified using polymerase chain reaction (PCR) and ligated into the pCDFDuet vector, using SacI and HindIII (yielding the pDEST-CM1 vector described in Example 4) followed by the insertion of an additional T7 promoter and Lac operator. The T7 promotor and lac operator sequences were inserted into the HindIII/ AvrII sites of pDEST-CM1, creating pRIPPER-II. The pRIPPER-II vector is streptomycin Str(R)) and chloramphenicol resistant (Cm(R)). A map of the pRIPPER-II vector is shown in FIG. 35 and the nucleotide sequence of the pRIPPER-II vector (SEQ ID NO: 14) is shown in FIG. 36.

To create the pRIPPER-III and pRIPPER-IV vectors, the pRIPPER-II vector sequence between the ScaI and AvrII restriction sites was ligated into the pRSFDuet-1 and pET-Duet™-1 (Novagen catalog no. 71146-3) vectors, respectively. A map of the pRIPPER-III vector is shown in FIG. 37 and the nucleotide sequence of the pRIPPER-III vector (SEQ ID NO: 15) is shown in FIG. 38. A map of the pRIPPER-IV vector is shown in FIG. 39 and the nucleotide sequence of the pRIPPER-IV vector (SEQ ID NO: 16) is shown in FIG. 40.

Example 9

RNAi Vectors in Functional Assays

The RNAi vectors of the present invention may be utilized in any of the various methods of functional genomic analysis. For example, the RNAi vectors of the present invention may be used in assays utlizing *Caenorhabditis elegans*, including the assays described by Gonczy et al. (Gonczy et al., Nature 408(6810):331-6, 2000). For example, the RNAi vectors of the present invention will be used interfere with the expression of the Eri-1 and Rrf-3 genes in *C. elegans*. The RNAi vectors of the present invention will also be used interfere with the expression of the Lin-1 and Unc-22 proteins in *C. elegans*, genes which give the worms a multi-vulva phenotype and a stumpy phenotype, respectively. These phenotypes are recalcitrant to regular RNAi methods. The RNAi vectors of the present invention will also be used interfere with the expression Green Fluorescent Protein (GFP) and Red Fluorescent Protein in *C. elegans*. With the experiments outlined above, the RNAi vectors of the present invention will also be used interfere with the expression of at least six different proteins in a single *C. elegans* organism. The RNAi vectors of the present invention will also be used interfere with the expression of additional genes and phenotypes in *C. elegans*. These will show that the RNAi vectors of the present invention can be used to interfere with the expression of a large number of genes at the same time. Additional genes may include Lin-15A and lin-35 (which together give a synthetic multi-vulva phenotype), Dpy-10 (giving a dumpy phenotype), Zyg-11 (sterile phenotype) and an ORF called F33H2.8 in wormbase (giving an uncoordinated phenotype).

Example 10

Interference of URF3 and UNC-22 in *C. elegans* with pRIIPER Vector Constructs

*C. elegans* strains used in this example (strain CF1827 with GFP expression in the intestine and strain GR1373, a Eri-1 mutation no phenotype that enables increased RNAi response) were from the Caenorhabditis Genetics Center, University of Minnesota. Worms were incubated with *E. coli* cells that were purchased for feeding the worm, *C. elegans*. This strain of *E. coli*, was acquired from Open biosystems (pn RCE1182-9366364 feeding clone pL4440-DEST for ORF T07A9.5 (Eri-1) in *E. coli* strain HT115 (DE3)). The above strain of bacteria was than made competent and transformed with plasmids pRIPPER 1-Rrf-3, pRIPPER-2 Unc-22. These bacterial strains were then grown with appropriate antibiotics in liquid media and were induced with 2 mM IPTG for two hours and plated on LB plates supplemented with the appropriate antibiotics and 2 mM IPTG. The above listed worms were then plated onto the bacteria and allowed to grow for two days. Observation showed that the twitching phenotype that is associated with the Unc-22 gene's RNAi-mediated induction of the twitching phenotype. Results were observed for four worms in the GR1373 strain of worms and for one worm that does not lay the eggs is the CF1827 strain.

The RNAi constructs were made by PCRing the following primers together in the absence of any template. The primers contain the attB sequences (capitalized) and sequences that are complimentary to each other (underlined). These primers were then cycled in the PCR machine for five cycles to create the constructs used in the subsequent cloning reactions using pDONR Zeo as the DONR vector and pRIPPER 1 and pRIPPER 2 as destination vectors.

The RRF3 primers used were as follows:
5' CTTACAAGTTTGTACAAAAAAGCAGGCTTA cttcaggtag tgatgatcta tcaaacaaat tatatgatca attttcagaa aaagtcagca aaagtttggtgaaggtggtggagagctgca 3' (SEQ ID NO: 34) and
5' CTTACCACTTTGTACAAGAAAGCTGGGTG ggacggttga gacaaactgg agatggcata gcgtatttta ctacttcgag gtattcatct tgcagctctccaccaccttcacccaaactt 3' (SEQ ID NO: 35).

The UNC-22 primers used were as follows:
5' CTTACAAGTTTGTACAAAAAAGCAGGCTTA tggttctccg gccttcacac ggaattcctt tccatccaaa tccaaatcga acttcggagc ctcatgcattggcttagcagtagcagccgc 3' (SEQ ID NO: 36) and
5' CTTACCACTTTGTACAAGAAAGCTGGGTG tatgaatacc gtgtcgttgc cgtcaacaaa gctgggccag gacaaccatc agattcgtct gcggctgctactgctaagccaatgcatgag 3' (SEQ ID NO: 37).

Example 11 pDEST-CS Vectors

The PDEST-CS series of vectors (pDEST-CS, pDEST-CS1, pDEST-CS2, pDEST-CS3, and pDEST-CS4) allows for the co-expression of secreted proteins. The pDEST-SC vector was created by removing the G114704 cassette from pDEST-C3 using SacI and HindIII and ligating it to similarly digested pET-26b(+) (Novagen catalog #70774-3). PDEST-CS contains the G144704p cassette as an EcoNI and HindIII fragment containing the G144704 cassette fused to the pelB sequence of pET-26b(+). This results in a vector which will create a fusion of the pelB sequence to the N-terminal of target proteins, which can target proteins for secretion into the periplasmic space in *Escherichia coli*. This vector is created to provide the G144704 cassette. The pDEST-CS1-4 family of vectors is then created by digestion of pDEST-CS with EcoNI and HindIII, and ligating the fragment containing the G144704p cassette to similarly digested DUET series plasmids. FIG. 41 is a map of the pDEST-CS. FIG. 42 is the nucleotide sequence of the pDEST-CS vector (SEQ ID NO: 17).

The pDEST-CS1 vector was created by removing the G114704p cassette from pDEST-CS using EcoNI and HindIII and ligating it to similarly digested pCDFDuet-1. FIG. 43 is a map of the pDEST-CS1 vector. FIG. 44 is the nucleotide sequence of the pDEST-C1 vector (SEQ ID NO: 18).

The pDEST-CS2 vector will be created by removing the GI14704p cassette from pDEST-CS using EcoNI and HindIII and ligating it to similarly digested pRSFDuet-1. There is a second EcoNIsite in the middle of the KanR gene. However, this simply means the construct will be made by a limiting digestion (a standard technique where limiting amounts of enzyme are used to give only partially digested plasmid) using a low concentration of EcoNI. Correct constructs will be selected for by KanR. If the EcoNI in the KanR gene is cut, then no colony will result. FIG. 45 is a map of the pDEST-CS2 vector. FIG. 46 is the expected nucleotide sequence of the pDEST-CS2 vector (SEQ ID NO: 19).

The pDEST-CS3 vector will be created by removing the G114704p cassette from pDEST-CS using EcoNI and HindIII, and ligating it to similarly digested pACYCDuet-1. FIG. 47 is a map of the pDEST-C3 vector. FIG. 48 is the expected nucleotide sequence of the pDEST-C3 vector (SEQ ID NO: 20).

The pDEST-CS4 vector will be created by removing the G114704p cassette from pDEST-CS using EcoNI and HindIII, and ligating it to similarly digested pETDuet-1. FIG. 49 is a map of the pDEST-C4 vector. FIG. 50 is the expected nucleotide sequence of the pDEST-CS4 vector (SEQ ID NO: 21).

Example 12 pDEST-CMZ (pSYZYGY) Family of Vectors
Containing Both G144704 and Multisite Cassettes Modification of the pDEST-CM family of vectors to include the G144704 Gateway ZeoR cassette in the second multiple cloning site will be done as follows. The pDEST-CM1, pDEST-CM2, and pDEST-CM4 vectors contain the Gateway Multisite cassette in the first multiple cloning site (MCS) of each of the available Novagen DUET vectors, pCDFDuet-1, pRSFDuet-1, and pETDuet-1, respectively, and the Gateway Multisite TetR cassette in pACYCDuet-1 (CM3). However, each of these vectors has a second multiple cloning site, accessible only by standard restriction enzyme/ligation cloning. The second MCS on each of these vectors will be replaced with the G144704 cassette, allowing Gateway recombination cloning at this site as well. Note that the recombination sites of the G144704 and Multisite differ, so that as long as the recombination reactions are performed separately, both are possible. This will be performed in a manner very similar to that described for the initial construction of the pDEST-C series of vectors. This will create a set of four vectors, pDEST-CMZ1, pDEST-CMZ2, pDEST-CMZ3, and pDEST-CMZ4 also referred to as the 'pSYZYGY' family, each with a total of four possible Gateway recombination sites, for a grand total of sixteen co-expressible proteins. This will be done by amplifying the G144704 cassette using primers that add NdeI and KpnI restriction sites to the 5' and 3' ends respectively. This will be digested with these two enzymes, and then ligated directly to each of the similarly digested pDEST-CM1-4 vectors, creating pDEST-CMZ1-4. An example map of the proposed pDEST-CMZ1 is shown below. The other three vectors will be constructed in precisely the same manner, insertion of the same cassette at the NdeI and KpnI sites on those vectors.

A map of the pDEST-CMZ1 vector is shown in FIG. 51. The expected nucleotide sequence of the pDEST-CMZ1 vector is shown in FIG. 52.

Example 13 pDEST-CMZc (pSYZYGYc) Family Containing Both G144704 and Multisite Cassettes Tagged with GFP and RFP To create the pDEST-CMc series of vectors, the G144704 cassette will be modified to include a green fluorescent protein (GFP) marker and the Gateway Multisite cassette will be modified to include a red fluorescent protein (RFP) marker.

PCR will be used to amplify pDEST-C3 at the 3' end of the ZeoR gene using primers abutting at their 3' ends, which will amplify the entire vector to create a linear plasmid with SpeI and SphI restriction sites artificially added on (SpeI on the 3' end of the ZeoR gene), followed by digestion with these enzymes to create sticky ends. Next, the green fluorescent protein (GFPuv) encoding gene from the commercially available plasmid pGFPuv (BD Biosciences/Clontech #632312) will be amplified with primers that SpeI and SphI restriction sites to the 5' and 3' ends of the PCR product respectively. After digestion with these enzymes, it will be ligated to the similarly digested pDEST-C3 to create pDEST-C3g. The primers will be designed such that the GFPuv encoding gene will be fused in frame with the ZeoR gene, creating a gene fusion. These are all standard molecular biology protocols. This vector will contain the new G144704g cassette, which will have all the same characteristics of the parent G144704 cassette (ZeoR, ccdB, Gateway R1 and R2 recombination sites), but additionally will express the GFPuv protein as a fusion with the ZeoR protein. This will result in colonies with a green fluorescent color when grown in the appropriate ccdA host strain in the presence of Zeocin.

In a similar manner, the gene (DsRed2) encoding the red fluorescent protein (RFP) will be amplified from the commercially available plasmid pDsRed2 (BD Biosciences/Clontech #632404), and cloned into the Gateway Multisite cassette as a 3' fusion with the CamR gene, to create the MultisiteR cassette, which will result in red colonies.

A third construct will be made in a similar manner, fusing the RFP encoding gene to the 3' end of the TetR gene in the Multisite TetR cassette, the only difference being that the restriction enzymes used will be SpeI and XbaI, due to the presence of an SphI site in the TetR gene, creating the Multisite TetRr cassette.

These constructs will allow for a fluorescent screen for the first step of recombination. The current selection for successful recombination, the loss of the ccdB gene in the cassette, will not work when there are two copies of this lethal gene. In the pDEST-CMZ1-4 family of vectors, which will contain two different Gateway cassettes (G144704 and Multisite), each with a ccdB gene, one can use either the ZeoR or CamR marker on the G144704 or Multisite cassette respectively to screen for recombination at one cassette or the other, but this is a two step process requiring growth of colonies under non-selective conditions, followed by replica plating and screening for colonies which have lost the marker of interest. The utility of this insertion of the GFPuv and RFP markers into the G144704g and MultisiteR cassettes respectively will reduce this selection process to one step. Colonies which have lost the color of interest, and thus contain plasmids which have successfully recombined at the desired position, can be screened directly, and moved on to the next recombination event. The G144704g cassette will be used to replace the G144704 cassettes in the second multiple cloning sites of the four pDEST-CMZ family of vectors, and the MultisiteR will replace the Multisite cassette (Multisite TetRr will replace the Multisite TetR in pDEST-CMZ3) in the other recombination site of these four vectors. This will create the pDEST-CMZc1-4 family of vectors (or 'pSYZYGYc family), with colored markers ('c') for recombination screening.

A representative map of a pDEST-CMZc1 vector is shown in FIG. 53. The expected nucleotide sequence of a pDEST-CMZc1 vector is shown in FIG. 54.

Example 14

Expression of Multiple Genes in a Single Vector

The vectors of the pDEST-C series, the pDEST-CS series, and the pRIPPER series can be further modified to allow the co-expression of up to five unique proteins for each vector, allowing the expression of up to sixteen different genes, when the vectors of the present invention are used in concert with the available vectors (pDEST, pL4440, pET). In turn, the SYZYGY vectors of the present invention can be used for the co-expression of up to thirty-two proteins or, when used in RNAi, to silence thirty-two genes, since these vectors unite the traditional Gateway® and Multisite® methods into one plasmid. See also, Sone et. al. (Multi-gene gateway clone design for expression of multiple heterologous genes in living cells: Modular construction of multiple cDNA expression elements using recombinant cloning," J Biotechnol. 2005 Jun. 24 (doi:10,1016/jbiotec.2005.02.021)) which describes methods for the insertion of up to five unique DNA fragments into the B1 B2 sites of a single Gateway® vector.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A polynucleotide comprising a first nucleotide sequence operably encoding zeomycin resistance and a second nucleotide sequence operably encoding a ccdB polypeptide, wherein the first nucleotide sequence and the second nucleotide sequence are flanked within the same attR1 and attR2 sites, and wherein the polynucleotide comprises a G144704 cassette having SEQ ID NO:4.

2. The polynucleotide of claim 1, wherein the polynucleotide is selected from the group consisting of pDEST-C1 (SEQ ID NO:1), pDEST-C2 (SEQ ID NO:2), pDEST-C3 (SEQ ID NO:3), pDEST-CS (SEQ ID NO:17), pDEST-CS1 (SEQ ID NO:18), pDEST-CS2 (SEQ ID NO:19), pDEST-CS3 (SEQ ID NO:20), pDEST-CS4 (SEQ ID NO:21), pDEST-CMZ1 (SEQ ID NO:22), and pDEST-CMZc1 (SEQ ID NO:23).

3. An expression vector comprising the polynucleotide of claim 1.

4. A host cell comprising the expression vector of claim 3.

5. A polynucleotide comprising a first nucleotide sequence operably encoding tetracycline resistance and a second nucleotide sequence operably encoding a ccdB polypeptide, wherein the first nucleotide sequence and the second nucleotide sequence are flanked within the same attR3 and attR4 sites, and wherein the polynucleotide comprises a tet Multisite having SEQ ID NO: 7.

6. The polynucleotide of claim 5 wherein the polynucleotide is selected from the group consisting of pDEST-CM1 (SEQ ID NO:5), pDEST-CM2 (SEQ ID NO:6), pDEST-CM3 (SEQ ID NO:8), pDEST-CM4 (SEQ ID NO:9), pDEST-CMZ1 (SEQ ID NO:22), and pDEST-CMZc1 (SEQ ID NO:23).

7. An expression vector comprising the polynucleotide of claim 5.

8. A host cell comprising the expression vector of claim 7.

9. An RNA interference (RNAi) vector comprising the polynucleotide of claim 1.

10. An RNA interference (RNAi) vector comprising the polynucleotide of claim 5.

11. An RNAi vector selected from the group consisting of pRIPPER-1 (SEQ ID NO:11), pRIPPER-2 (SEQ ID NO:12), pRIPPER-3 (SEQ ID NO:10), pRIPPER-4 (SEQ ID NO:13), pRIPPER-II (SEQ ID NO:14), pRIPPER-III (SEQ ID NO:15), and pRIPPER-IV (SEQ ID NO:16).

12. A method of producing one or more interfering RNA products, the method comprising expressing at least one interfering RNA product by an RNAi vector of claim 11.

13. A host cell comprising the RNAi vector of claim 11.

14. The RNA interference (RNAi) vector of claim 9, wherein the RNAi vector is selected from the group consisting of pRIPPER-1 (SEQ ID NO:11), pRIPPER-2 (SEQ ID NO:12), pRIPPER-3 (SEQ ID NO:10), and pRIPPER-4 (SEQ ID NO:13).

15. The RNA interference (RNAi) vector of claim 10, wherein the RNAi vector is selected from the group consisting of pRIPPER-II (SEQ ID NO:14), pRIPPER-III (SEQ ID NO: 15), and pRIPPER-IV (SEQ ID NO:16).

16. An RNA interference (RNAi) vector comprising a polynucleotide cassette, the polynucleotide cassette comprising a nucleotide sequence operably encoding zeomycin resistance and a nucleotide sequence operably encoding a ccdB polypeptide, wherein the polynucleotide cassette is flanked by attR1 and attR2 sites, and wherein the polynucleotide cassette comprises a G144704 cassette having SEQ ID NO: 4.

17. An RNA interference (RNAi) vector of claim 16, wherein the RNAi vector is selected from the group consisting of pRIPPER-1 (SEQ ID NO:11), pRIPPER-2 (SEQ ID NO:12), pRIPPER-3 (SEQ ID NO:10), and pRIPPER-4 (SEQ ID NO:13).

18. The RNA interference (RNAi) vector of claim 16, wherein the G144704 cassette having SEQ ID NO: 4 is flanked on either end by a T7 promoter and a Lac Operator sequence.

19. An RNA interference (RNAi) vector comprising a polynucleotide cassette, the polynucleotide cassette comprising a nucleotide sequence operably encoding tetracycline resistance and a nucleotide sequence operably encoding a ccdB polypeptide, wherein the polynucleotide cassette is flanked by attR3 and attR4 sites, and wherein the polynucleotide cassette flanked by attR3 and attR4 sites comprises a tet Multisite having SEQ ID NO: 7.

20. An RNA interference (RNAi) vector of claim 19, wherein the RNAi vector is selected from the group consisting of pRIPPER-II (SEQ ID NO:14), pRIPPER-III (SEQ ID NO: 15), and pRIPPER-IV (SEQ ID NO:16).

21. The RNA interference (RNAi) vector of claim 19, wherein the tet Multisite having SEQ ID NO: 7 is flanked on either end by a T7 promoter and a Lac Operator (LacO) sequence.

* * * * *

UNITED STATES PATENT AND TRADEMARK OFFICE
CERTIFICATE OF CORRECTION

| | | |
|---|---|---|
| PATENT NO. | : 7,582,475 B2 | Page 1 of 1 |
| APPLICATION NO. | : 11/327200 | |
| DATED | : September 1, 2009 | |
| INVENTOR(S) | : Horanyi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Signed and Sealed this

Fourteenth Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,582,475 B2  
APPLICATION NO. : 11/327200  
DATED : September 1, 2009  
INVENTOR(S) : Horanyi et al.

Page 1 of 1

It is certified that error appears in the above-identified patent and that said Letters Patent is hereby corrected as shown below:

In the Specification

Column 1, line 13, under GOVERNMENT FUNDING

Please delete
"The present invention was made with government support under Grant No. NIH GM062407, awarded by the National Institutes of Health. The Government has certain rights in this invention"

And insert
--This invention was made with government support under Grant No. GM062407 awarded by the National Institutes of Health. The government has certain rights in this invention.--

Signed and Sealed this  
Twenty-sixth Day of January, 2016

Michelle K. Lee  
*Director of the United States Patent and Trademark Office*